United States Patent
Hata et al.

(10) Patent No.: US 9,725,442 B2
(45) Date of Patent: Aug. 8, 2017

(54) HETEROCYCLIC DERIVATIVE HAVING PGD2 RECEPTOR ANTAGONIST ACTIVITY

(71) Applicant: Shionogi & Co., Ltd., Osaka-shi, Osaka (JP)

(72) Inventors: Kayoko Hata, Toyonaka (JP); Manami Masuda, Toyonaka (JP); Hiromi Nakai, Toyonaka (JP); Daisuke Taniyama, Toyonaka (JP); Hiroyuki Tobinaga, Toyonaka (JP); Yoshio Hato, Sapporo (JP); Motohiro Fujiu, Toyonaka (JP)

(73) Assignee: SHIONOGI & CO., LTD., Osaka (JP)

( * ) Notice: Subject to any disclaimer, the term of this patent is extended or adjusted under 35 U.S.C. 154(b) by 319 days.

(21) Appl. No.: 14/351,234

(22) PCT Filed: Oct. 24, 2012

(86) PCT No.: PCT/JP2012/077393
§ 371 (c)(1),
(2) Date: Apr. 11, 2014

(87) PCT Pub. No.: WO2013/061977
PCT Pub. Date: May 2, 2013

(65) Prior Publication Data
US 2014/0275074 A1 Sep. 18, 2014

(30) Foreign Application Priority Data
Oct. 25, 2011 (JP) ................................ 2011-233965

(51) Int. Cl.
*A61K 31/535* (2006.01)
*C07D 413/14* (2006.01)
*C07D 401/14* (2006.01)
*C07D 401/04* (2006.01)
*C07D 403/04* (2006.01)
*C07D 403/14* (2006.01)
*C07D 451/04* (2006.01)

(52) U.S. Cl.
CPC ......... *C07D 413/14* (2013.01); *C07D 401/04* (2013.01); *C07D 401/14* (2013.01); *C07D 403/04* (2013.01); *C07D 403/14* (2013.01); *C07D 451/04* (2013.01)

(58) Field of Classification Search
CPC .. C07D 401/04; C07D 401/14; C07D 403/04; C07D 403/14; C07D 413/14; C07D 451/04
USPC .... 514/234.5, 338, 364, 381, 397, 403, 404, 514/406
See application file for complete search history.

(56) References Cited

U.S. PATENT DOCUMENTS

| 7,842,692 B2 * | 11/2010 | Kugimiya | ............ C07D 471/04 514/234.5 |
| 8,143,285 B2 * | 3/2012 | Kugimiya | ............ C07D 401/04 514/323 |
| 2005/0096376 A1 | 5/2005 | Sundermann et al. | |
| 2009/0030014 A1 | 1/2009 | Kugimiya et al. | |
| 2009/0105274 A1 * | 4/2009 | Kugimiya | ............ C07D 401/04 514/254.09 |

FOREIGN PATENT DOCUMENTS

| EP | 1505061 A1 | 2/2005 |
| EP | 1911759 A1 | 4/2008 |
| EP | 1932839 A1 | 6/2008 |
| EP | 1939175 A1 | 7/2008 |
| EP | 2423190 A1 | 2/2012 |
| WO | WO 03/097598 A1 | 11/2003 |
| WO | WO 2005/019208 A1 | 3/2005 |
| WO | WO 2005/123731 A2 | 12/2005 |
| WO | WO 2006/034419 A2 | 3/2006 |
| WO | WO 2007/010964 A1 | 1/2007 |
| WO | WO 2007/010965 A1 | 1/2007 |
| WO | WO 2007/029629 A1 | 3/2007 |
| WO | WO 2007/037187 A1 | 4/2007 |

OTHER PUBLICATIONS

Coleman et al., "VIII. International Union of Pharmacology Classification of Prostanoid Receptors: Properties, Distribution, and Structure of the Receptors and Their Subtypes", Pharmacological Reviews, vol. 46, No. 2, 1994, pp. 205-229.
International Preliminary Report on Patentability and English translation of Written Opinion of the International Searching Authority for International Application No, PCT/JP2012/077393 dated May 8, 2014 (Forms PCT/IB/338, PCT/IB/373, and PCT/ISA/237).
Saczewski et al., "Synthesis, structure and antiaggregatory effects of some N-(4,5-dihydro-1H-imidazol-2-yl)indoles", IL Farmaco, vol. 55, 2000, pp. 56-64.

* cited by examiner

*Primary Examiner* — My-Chau T Tran
(74) *Attorney, Agent, or Firm* — Birch, Stewart, Kolasch & Birch, LLP

(57) ABSTRACT

The present invention is related to a compound represented by formula (I),

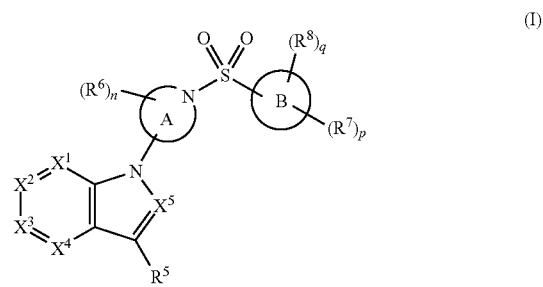

wherein $X^1$, $X^2$, $X^3$, $X^4$, $X^5$, $R^5$, $R^6$, $R^7$, $R^8$, n, p, q, ring A and ring B are as described in the specification, or a pharmaceutically acceptable salt thereof.

24 Claims, No Drawings

HETEROCYCLIC DERIVATIVE HAVING PGD2 RECEPTOR ANTAGONIST ACTIVITY

TECHNICAL FIELD

This invention relates to heterocyclic derivatives having PGD2 receptor antagonistic activity and a medicinal use thereof.

BACKGROUND ART

Prostaglandin D2 (PGD2) is a metabolic product of arachidonic acid through PGG2 and PGH2, and known to have various potent physiological activities. For example, in Non-Patent Document 1 it is described that PGD2 is involved in sleeping and secretion of hormones in central nervous system, and in inhibiting activity of platelet aggregation, contraction of bronchial smooth muscle, vasodilation and constriction of a blood vessel etc. in peripheral system. Moreover, PGD2 is considered to be involved in forming pathological condition of an allergic disease such as bronchial asthma since it is a major metabolic product of arachidonic acid produced from a mast cell, and has a potent bronchoconstricting effect, causing an increase of vascular permeability and migration of inflammatory cell such as eosinophils.

A DP receptor (also called DPI receptor) or CRTH2 receptor (also called DP2 receptor) is known as a receptor of PGD2 but these are completely different receptors. WO2007/029629 (Patent Document 1) discloses indazole compounds etc. having DP receptor antagonistic activity but does not describe the compounds as having CRTH2 receptor antagonistic activity. Similarly, WO2007/010964 (Patent Document 2) discloses indole derivatives having DP receptor antagonistic activity, and WO2007/010965 (Patent Document 3) discloses azaindole derivatives having DP receptor antagonistic activity, but neither document describes the indole or azaindole derivatives as having CRTH2 receptor antagonistic activity.

On the other hand, WO2003/097598 (Patent Document 4) discloses indazole compounds having CRTH2 receptor antagonistic activity but does not describe the compounds as having DP receptor antagonistic activity. Similarly, WO2005/123731 (Patent Document 5) discloses azaindole derivatives having CRTH2 receptor antagonistic activity, and WO2006/034419 (Patent Document 6) discloses indole derivatives having CRTH2 receptor antagonistic activity, but neither document describes the azaindole nor indole derivatives as having DP receptor antagonistic activity.

Furthermore, WO2005/019208 (Patent Document 7) discloses indole derivatives having noradrenaline re-uptake inhibiting activity, and Non-Patent Document 2 discloses indole derivatives having anti-platelet aggregation activity.

PRIOR ART REFERENCES

Patent Document

[Patent Document 1] International Publication No. 2007/029629 pamphlet
[Patent Document 2] International Publication No. 2007/010964 pamphlet
[Patent Document 3] International Publication No. 2007/010965 pamphlet
[Patent Document 4] International Publication No. 2003/097598 pamphlet
[Patent Document 5] International Publication No. 2005/123731 pamphlet
[Patent Document 6] International Publication No. 2006/034419 pamphlet
[Patent Document 7] International Publication No. 2005/019208 pamphlet

Non-Patent Document

[Non-patent document 1] Pharmacol. Rev., 1994, 46, p. 205-229
[Non-patent document 2] Farmaco, 2000, 55(1), p. 56-64

DISCLOSURE OF INVENTION

Problem to be Solved

The present invention provides heterocyclic derivatives having DP receptor antagonistic activity, CRTH2 receptor antagonistic activity, and/or antagonistic activities against both the DP receptor and the CRTH2 receptor. The present invention also provides a pharmaceutical composition containing the said compounds. The said pharmaceutical composition is useful as a therapeutic agent for allergic diseases.

Means for Solving Problem

The present inventors found that the following heterocyclic derivatives have strong DP receptor antagonistic activity, CRTH2 receptor antagonistic activity, and/or antagonistic activities against both the DP receptor and the CRTH2 receptor. The present inventors also found that the pharmaceutical composition containing the following heterocyclic derivatives is effective as a therapeutic agent for allergic diseases.

The present invention relates to the following 1) to 22).
1) A compound of general formula (I);

[Chemical Formula 1]

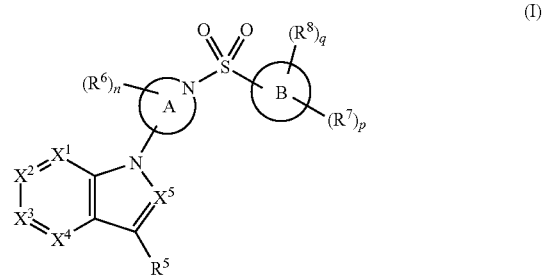

wherein ring A is a nitrogen-containing non-aromatic heterocycle or a nitrogen-containing aromatic heterocycle;
ring B is an aromatic carbocycle, a non-aromatic carbocycle, an aromatic heterocycle or a non-aromatic heterocycle;
—$X^1$═ is —N═ or —C($R^1$)═;
—$X^2$═ is —N═ or —C($R^2$)═;
—$X^3$═ is —N═ or —C($R^3$)═;
—$X^4$═ is —N═ or —C($R^4$)═;
—$X^5$═ is —N═ or —C($R^{12}$)═;
wherein the number of "—N═" on the ring in —$X^1$═, —$X^2$═, —$X^3$═ and —$X^4$═ is 0, 1 or 2;
$R^1$, $R^2$, $R^3$ and $R^4$ are each independently a hydrogen atom, halogen, cyano, substituted or unsubstituted alkyl, substituted or unsubstituted alkyloxy, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl; or two groups selected from $R^1$, $R^2$, $R^3$ and $R^4$ which are attached to neighboring ring constituent carbon atoms are taken together to form substituted or unsubstituted alkylene which may be intervened with one or two heteroatom(s);

$R^{12}$ is a hydrogen atom or substituted or unsubstituted alkyl;

$R^5$ is formula: -L-$R^9$, wherein $R^9$ is carboxy, alkyloxycarbonyl or a carboxy equivalent;

-L- is substituted or unsubstituted alkylene, substituted or unsubstituted alkenylene, or substituted or unsubstituted alkynylene;

$R^6$ is each independently halogen, hydroxy, carboxy, formyl, formyloxy, sulfanyl, sulfino, sulfo, thioformyl, thiocarboxy, dithiocarboxy, cyano, nitro, nitroso, azido, amidino, guanidino, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted alkenylcarbonyl, substituted or unsubstituted alkynylcarbonyl, substituted or unsubstituted amino, substituted or unsubstituted alkylsulfonyl, substituted or unsubstituted alkenylsulfonyl, substituted or unsubstituted alkynylsulfonyl, substituted or unsubstituted imino, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted alkylsulfanyl, substituted or unsubstituted alkenylsulfanyl, substituted or unsubstituted alkynylsulfanyl, substituted or unsubstituted alkylsulfinyl, substituted or unsubstituted alkenylsulfinyl, substituted or unsubstituted alkynylsulfinyl, substituted or unsubstituted carbamoyl, substituted or unsubstituted sulfamoyl, substituted or unsubstituted aromatic carbocyclyl, substituted or unsubstituted non-aromatic carbocyclyl, substituted or unsubstituted aromatic heterocyclyl, or unsubstituted non-aromatic heterocyclyl, substituted or unsubstituted aromatic carbocyclyl oxy, substituted or unsubstituted non-aromatic carbocyclyl oxy, substituted or unsubstituted aromatic heterocyclyl oxy, substituted or unsubstituted non-aromatic heterocyclyl oxy, substituted or unsubstituted aromatic carbocyclyl carbonyl, substituted or unsubstituted non-aromatic carbocyclyl carbonyl, substituted or unsubstituted aromatic heterocyclyl carbonyl, substituted or unsubstituted non-aromatic heterocyclyl carbonyl, substituted or unsubstituted aromatic carbocyclyl oxycarbonyl, substituted or unsubstituted non-aromatic carbocyclyl oxycarbonyl, substituted or unsubstituted aromatic heterocyclyl oxycarbonyl, substituted or unsubstituted non-aromatic heterocyclyl oxycarbonyl, substituted or unsubstituted aromatic carbocyclyl sulfanyl, substituted or unsubstituted non-aromatic carbocyclyl sulfanyl, substituted or unsubstituted aromatic heterocyclyl sulfanyl, substituted or unsubstituted non-aromatic heterocyclyl sulfanyl, substituted or unsubstituted aromatic carbocyclyl sulfonyl, substituted or unsubstituted non-aromatic carbocyclyl sulfonyl, substituted or unsubstituted aromatic heterocyclyl sulfonyl, or substituted or unsubstituted non-aromatic heterocyclyl sulfonyl; or two of $R^6$ attached to the same ring constituent carbon atom are taken together to form a carbocycle containing the above ring constituent carbon atom, a heterocycle containing the above ring constituent carbon atom, oxo, or the formula =$CR^{6a}R^{6b}$, wherein $R^{6a}$ and $R^{6b}$ are each independently a hydrogen atom, halogen, cyano, or substituted or unsubstituted alkyl; or two of $R^6$ attached to the different ring constituent carbon atoms are taken together to form substituted or unsubstituted alkylene which may be intervened with one or two heteroatom(s);

$R^7$ is halogen, substituted or unsubstituted alkyl, substituted or unsubstituted alkyloxy, substituted or unsubstituted non-aromatic carbocyclyl, substituted or unsubstituted aromatic carbocyclyl oxy or substituted or unsubstituted non-aromatic carbocyclyl oxy;

$R^8$ is each independently halogen, hydroxy, carboxy, formyl, formyloxy, sulfanyl, sulfino, sulfo, thioformyl, thiocarboxy, dithiocarboxy, cyano, nitro, nitroso, azido, amidino, guanidino, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted alkenylcarbonyl, substituted or unsubstituted alkynylcarbonyl, substituted or unsubstituted amino, substituted or unsubstituted alkylsulfonyl, substituted or unsubstituted alkenylsulfonyl, substituted or unsubstituted alkynylsulfonyl, substituted or unsubstituted imino, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted alkylsulfanyl, substituted or unsubstituted alkenylsulfanyl, substituted or unsubstituted alkynylsulfanyl, substituted or unsubstituted alkylsulfinyl, substituted or unsubstituted alkenylsulfinyl, substituted or unsubstituted alkynylsulfinyl, substituted or unsubstituted carbamoyl, substituted or unsubstituted sulfamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyl oxy, substituted or unsubstituted non-aromatic carbocyclyl oxy, substituted or unsubstituted aromatic heterocyclyl oxy, substituted or unsubstituted non-aromatic heterocyclyl oxy, substituted or unsubstituted aromatic carbocyclyl carbonyl, substituted or unsubstituted non-aromatic carbocyclyl carbonyl, substituted or unsubstituted aromatic heterocyclyl carbonyl, substituted or unsubstituted non-aromatic heterocyclyl carbonyl, substituted or unsubstituted aromatic carbocyclyl oxycarbonyl, substituted or unsubstituted non-aromatic carbocyclyl oxycarbonyl, substituted or unsubstituted aromatic heterocyclyl oxycarbonyl, substituted or unsubstituted non-aromatic heterocyclyl oxycarbonyl, substituted or unsubstituted aromatic carbocyclyl sulfanyl, substituted or unsubstituted non-aromatic carbocyclyl sulfanyl, substituted or unsubstituted aromatic heterocyclyl sulfanyl, substituted or unsubstituted non-aromatic heterocyclyl sulfanyl, substituted or unsubstituted aromatic carbocyclyl sulfonyl, substituted or unsubstituted non-aromatic carbocyclyl sulfonyl, substituted or unsubstituted aromatic heterocyclyl sulfonyl, or substituted or unsubstituted non-aromatic heterocyclyl sulfonyl;

n is 0, 1, 2 or 3;

q is 0, 1, 2 or 3; and p is 0 or 1, with the proviso that when the ring A is a ring represented by the formula:

[Chemical Formula 2]

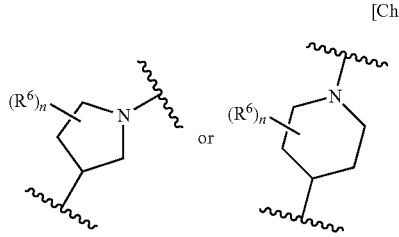

then n is 1, 2 or 3, or a pharmaceutically acceptable salt thereof.

2) The compound according to 1), wherein the ring A is the formula:

[Chemical Formula 3]

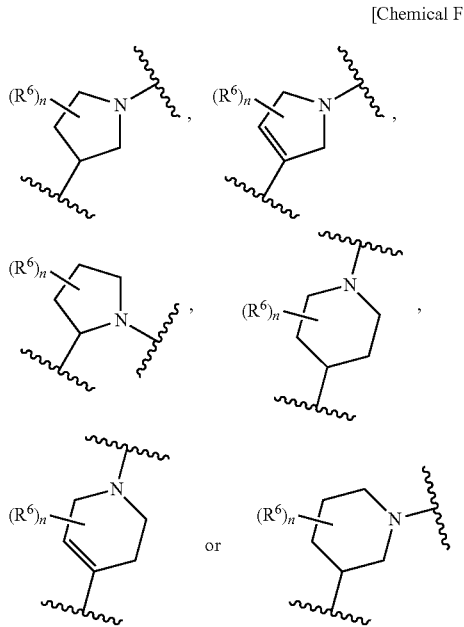

wherein $R^6$ and n are as defined in 1);

—$X^1$=$X^2$—$X^3$=$X^4$— is —C($R^1$)=C($R^2$)—C($R^3$)=C($R^4$)—, —N=C($R^2$)—C($R^3$)=C($R^4$)—, —C($R^1$)=N—C($R^3$)=C($R^4$)—, —C($R^2$)=C($R^2$)—N=C($R^4$)—, or —C($R^2$)=C($R^2$)—C($R^3$)=N—;

$R^5$ is the formula: -L-$R^9$, wherein $R^9$ is carboxy;

-L- is substituted or unsubstituted C1-C3 alkylene; and the formula:

[Chemical Formula 4]

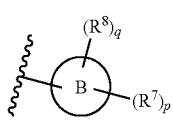

is the formula:

[Chemical Formula 5]

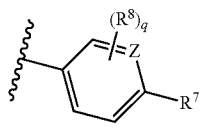

wherein $R^7$, $R^8$ and q are as defined in 1);

—Z= is —C($R^{10}$)= or —N=;

$R^{10}$ is a hydrogen atom, halogen, hydroxy, carboxy, formyl, formyloxy, sulfanyl, sulfino, sulfo, thioformyl, thiocarboxy, dithiocarboxy, cyano, nitro, nitroso, azido, amidino, guanidino, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted alkenylcarbonyl, substituted or unsubstituted alkynylcarbonyl, substituted or unsubstituted amino, substituted or unsubstituted alkylsulfonyl, substituted or unsubstituted alkenylsulfonyl, substituted or unsubstituted alkynylsulfonyl, substituted or unsubstituted imino, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted alkylsulfanyl, substituted or unsubstituted alkenylsulfanyl, substituted or unsubstituted alkynylsulfanyl, substituted or unsubstituted alkylsulfinyl, substituted or unsubstituted alkenylsulfinyl, substituted or unsubstituted alkynylsulfinyl, substituted or unsubstituted carbamoyl, substituted or unsubstituted sulfamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyl oxy, substituted or unsubstituted non-aromatic carbocyclyl oxy, substituted or unsubstituted aromatic heterocyclyl oxy, substituted or unsubstituted non-aromatic heterocyclyl oxy, substituted or unsubstituted aromatic carbocyclyl carbonyl, substituted or unsubstituted non-aromatic carbocyclyl carbonyl, substituted or unsubstituted aromatic heterocyclyl carbonyl, substituted or unsubstituted non-aromatic heterocyclyl carbonyl, substituted or unsubstituted aromatic carbocyclyl oxycarbonyl, substituted or unsubstituted non-aromatic carbocyclyl oxycarbonyl, substituted or unsubstituted aromatic heterocyclyl oxycarbonyl, substituted or unsubstituted non-aromatic heterocyclyl oxycarbonyl, substituted or unsubstituted aromatic carbocyclyl sulfanyl, substituted or unsubstituted non-aromatic carbocyclyl sulfanyl, substituted or unsubstituted aromatic heterocyclyl sulfanyl, substituted or unsubstituted non-aromatic heterocyclyl sulfanyl, substituted or unsubstituted aromatic carbocyclyl sulfonyl, substituted or unsubstituted non-aromatic carbocyclyl sulfonyl, substituted or unsubstituted aromatic heterocyclyl sulfonyl, or substituted or unsubstituted non-aromatic heterocyclyl sulfonyl, or a pharmaceutically acceptable salt thereof.

3) The compound according to 1) or 2), wherein —X$^1$=X$^2$—X$^3$=X$^4$— is —C(R$^1$)=C(R$^2$)—C(R$^3$)=C(R$^4$)—, or a pharmaceutically acceptable salt thereof.

4) The compound according to any one of 1) to 3), wherein —X$^5$= is —N=, or a pharmaceutically acceptable salt thereof.

5) The compound according to any one of 1) to 3), wherein —X$^5$= is —C(R$^{12}$)=, or a pharmaceutically acceptable salt thereof.

6) The compound according to any one of 1) to 5), wherein R$^1$, R$^2$, R$^3$ and R$^4$ are each independently a hydrogen atom, halogen, or substituted or unsubstituted alkyl, or a pharmaceutically acceptable salt thereof.

7) The compound according to any one of 1) to 6), wherein R$^6$ is independently halogen, hydroxy, cyano, substituted or unsubstituted alkyl, substituted or unsubstituted alkenyl, substituted or unsubstituted alkyloxy, substituted or unsubstituted carbamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted non-aromatic carbocyclyl oxy, or substituted or unsubstituted non-aromatic heterocyclyl oxy; or two of R$^6$ attached to the same ring constituent carbon atom are taken together to form a carbocycle containing the above ring constituent carbon atom, a heterocycle containing the above ring constituent carbon atom, oxo, or the formula: =CR$^{6a}$R$^{6b}$, wherein R$^{6a}$ and R$^{6b}$ are a hydrogen atom, halogen, cyano, or substituted or unsubstituted alkyl; or two of R$^6$ attached to the a different ring constituent carbon atoms are taken together to form substituted or unsubstituted alkylene which may be intervened with one or two heteroatom(s), or a pharmaceutically acceptable salt thereof.

8) The compound according to any one of 1) to 7), wherein the ring A is the formula:

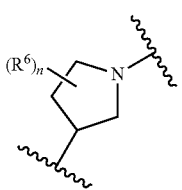

[Chemical Formula 6]

wherein R$^6$ is as defined in 1) and n is 1 or 2, or a pharmaceutically acceptable salt thereof.

9) The compound according to any one of 1) to 8), wherein p is 1 and R$^7$ is halogen, substituted or unsubstituted alkyloxy, or substituted or unsubstituted non-aromatic carbocyclyl, or a pharmaceutically acceptable salt thereof.

10) The compound according to any one of 1) to 9), wherein q is 0, or a pharmaceutically acceptable salt thereof.

11) The compound according to any one of 1) to 9), wherein q is 1 and R$^8$ is halogen or cyano, or a pharmaceutically acceptable salt thereof.

12) The compound according to any one of 1) to 11), wherein —X$^1$=X$^2$—X$^3$=X$^4$— is —C(R$^1$)=C(R$^2$)—C(R$^3$)=C(R$^4$)—, R$^1$ and R$^4$ are a hydrogen atom, and R$^2$ and R$^3$ are each independently a hydrogen atom, halogen or methyl, or a pharmaceutically acceptable salt thereof.

13) A pharmaceutical composition comprising the compound of any one of 1) to 12) or a pharmaceutically acceptable salt thereof.

14) The pharmaceutical composition according to 13) for inhibiting a DP receptor and/or a CRTH2 receptor.

15) The pharmaceutical composition according to 14), which is a therapeutic agent for allergy.

16) The pharmaceutical composition according to 14), wherein a therapeutic agent for allergy is allergic rhinitis.

17) A method for treating or preventing a disease related to a DP receptor and/or a CRTH2 receptor characterized by administration of the compound according to any one of 1) to 12) or a pharmaceutically acceptable salt thereof.

18) The method according to 17), wherein the disease related to a DP receptor and/or a CRTH2 receptor is allergic rhinitis.

19) A compound of any one of 1) to 12) or a pharmaceutically acceptable salt thereof for treating or preventing a disease related to a DP receptor and/or a CRTH2 receptor.

20) The compound or a pharmaceutically acceptable salt thereof according to 19) wherein the disease related to a DP receptor and/or a CRTH2 receptor is allergic rhinitis.

21) Use of a compound of any one of 1) to 12) or a pharmaceutically acceptable salt thereof in manufacture of a medicament for treating or preventing a disease related to a DP receptor and/or a CRTH2 receptor.

22) The use according to 21), wherein the disease related to a DP receptor and/or a CRTH2 receptor is allergic rhinitis.

The present invention also relates to the following 1') to 20').

1') A compound of general formula (Ia):

[Chemical Formula 7]

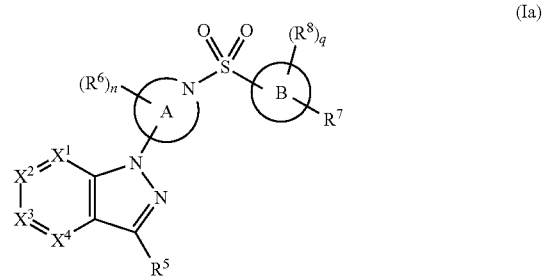

(Ia)

wherein:
ring A is a nitrogen-containing non-aromatic heterocycle or a nitrogen-containing aromatic heterocycle;
ring B is an aromatic carbocycle or an aromatic heterocycle;
—X$^1$= is —N= or —C(R$^1$)=;
—X$^2$= is —N= or —C(R$^2$)=;
—X$^3$= is —N= or —C(R$^3$)=;
—X$^4$= is —N= or —C(R$^4$)=;
wherein the number of "—N=" on the ring in —X$^1$=, —X$^2$=, —X$^3$= and —X$^4$= is 0, 1 or 2;
R$^1$, R$^2$, R$^3$ and R$^4$ are each independently a hydrogen atom, halogen, cyano, substituted or unsubstituted alkyl, substituted or unsubstituted alkyloxy; or
two groups selected from R$^1$ to R$^4$ which are attached to neighboring ring constituent carbon atoms are taken together to form substituted or unsubstituted alkylene which may be intervened with one or two heteroatom(s);
R$^5$ is the formula: -L-R$^9$,
wherein R$^9$ is carboxy or a carboxy equivalent;
-L- is substituted or unsubstituted alkylene, substituted or unsubstituted alkenylene, or substituted or unsubstituted alkynylene;

R⁶ is each independently halogen, hydroxy, carboxy, formyl, formyloxy, sulfanyl, sulfino, sulfo, thioformyl, thiocarboxy, dithiocarboxy, cyano, nitro, nitroso, azido, amidino, guanidino, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted alkenylcarbonyl, substituted or unsubstituted alkynylcarbonyl, substituted or unsubstituted amino, substituted or unsubstituted alkylsulfonyl, substituted or unsubstituted alkenylsulfonyl, substituted or unsubstituted alkynylsulfonyl, substituted or unsubstituted imino, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted alkylsulfanyl, substituted or unsubstituted alkenylsulfanyl, substituted or unsubstituted alkynylsulfanyl, substituted or unsubstituted alkylsulfinyl, substituted or unsubstituted alkenylsulfinyl, substituted or unsubstituted alkynylsulfinyl, substituted or unsubstituted carbamoyl, substituted or unsubstituted sulfamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyl oxy, substituted or unsubstituted non-aromatic carbocyclyl oxy, substituted or unsubstituted aromatic heterocyclyl oxy, substituted or unsubstituted non-aromatic heterocyclyl oxy, substituted or unsubstituted aromatic carbocyclyl carbonyl, substituted or unsubstituted non-aromatic carbocyclyl carbonyl, substituted or unsubstituted aromatic heterocyclyl carbonyl, substituted or unsubstituted non-aromatic heterocyclyl carbonyl, substituted or unsubstituted aromatic carbocyclyl oxycarbonyl, substituted or unsubstituted non-aromatic carbocyclyl oxycarbonyl, substituted or unsubstituted aromatic heterocyclyl oxycarbonyl, substituted or unsubstituted non-aromatic heterocyclyl oxycarbonyl, substituted or unsubstituted aromatic carbocyclyl sulfanyl, substituted or unsubstituted non-aromatic carbocyclyl sulfanyl, substituted or unsubstituted aromatic heterocyclyl sulfanyl, substituted or unsubstituted non-aromatic heterocyclyl sulfanyl, substituted or unsubstituted aromatic carbocyclyl sulfonyl, substituted or unsubstituted non-aromatic carbocyclyl sulfonyl, substituted or unsubstituted aromatic heterocyclyl sulfonyl, or substituted or unsubstituted non-aromatic heterocyclyl sulfonyl; or two of R⁶ attached to the same ring constituent carbon atom are taken together to form a carbocycle containing the above ring constituent carbon atom, a heterocycle containing the above ring constituent carbon atom, oxo, or the formula: =CR⁶ᵃR⁶ᵇ, wherein R⁶ᵃ and R⁶ᵇ are each independently a hydrogen atom, halogen, cyano, or substituted or unsubstituted alkyl; or two of R⁶ attached to the different ring constituent carbon atoms are taken together to form substituted or unsubstituted alkylene;

R⁷ is halogen, substituted or unsubstituted alkyl, substituted or unsubstituted alkyloxy, substituted or unsubstituted non-aromatic carbocyclyl or substituted or unsubstituted non-aromatic carbocyclyl oxy;

R⁸ is each independently halogen, hydroxy, carboxy, formyl, formyloxy, sulfanyl, sulfino, sulfo, thioformyl, thiocarboxy, dithiocarboxy, cyano, nitro, nitroso, azido, amidino, guanidino, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted alkenylcarbonyl, substituted or unsubstituted alkynylcarbonyl, substituted or unsubstituted amino, substituted or unsubstituted alkylsulfonyl, substituted or unsubstituted alkenylsulfonyl, substituted or unsubstituted alkynylsulfonyl, substituted or unsubstituted imino, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted alkylsulfanyl, substituted or unsubstituted alkenylsulfanyl, substituted or unsubstituted alkynylsulfanyl, substituted or unsubstituted alkylsulfinyl, substituted or unsubstituted alkenylsulfinyl, substituted or unsubstituted alkynylsulfinyl, substituted or unsubstituted carbamoyl, substituted or unsubstituted sulfamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyl oxy, substituted or unsubstituted non-aromatic carbocyclyl oxy, substituted or unsubstituted aromatic heterocyclyl oxy, substituted or unsubstituted non-aromatic heterocyclyl oxy, substituted or unsubstituted aromatic carbocyclyl carbonyl, substituted or unsubstituted non-aromatic carbocyclyl carbonyl, substituted or unsubstituted aromatic heterocyclyl carbonyl, substituted or unsubstituted non-aromatic heterocyclyl carbonyl, substituted or unsubstituted aromatic carbocyclyl oxycarbonyl, substituted or unsubstituted non-aromatic carbocyclyl oxycarbonyl, substituted or unsubstituted aromatic heterocyclyl oxycarbonyl, substituted or unsubstituted non-aromatic heterocyclyl oxycarbonyl, substituted or unsubstituted aromatic carbocyclyl sulfanyl, substituted or unsubstituted non-aromatic carbocyclyl sulfanyl, substituted or unsubstituted aromatic heterocyclyl sulfanyl, substituted or unsubstituted non-aromatic heterocyclyl sulfanyl, substituted or unsubstituted aromatic carbocyclyl sulfonyl, substituted or unsubstituted non-aromatic carbocyclyl sulfonyl, substituted or unsubstituted aromatic heterocyclyl sulfonyl, or substituted or unsubstituted non-aromatic heterocyclyl sulfonyl;

n is 0, 1, 2 or 3; and q is 0, 1, 2 or 3; and with the proviso that when the ring A is a ring represented by the formula:

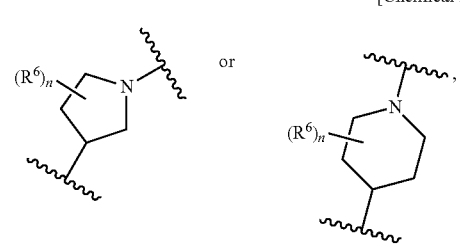

[Chemical Formula 8]

then n is 1, 2 or 3, or a pharmaceutically acceptable salt thereof.

2') The compound according to 1'), wherein the ring A is the formula:

[Chemical Formula 9]

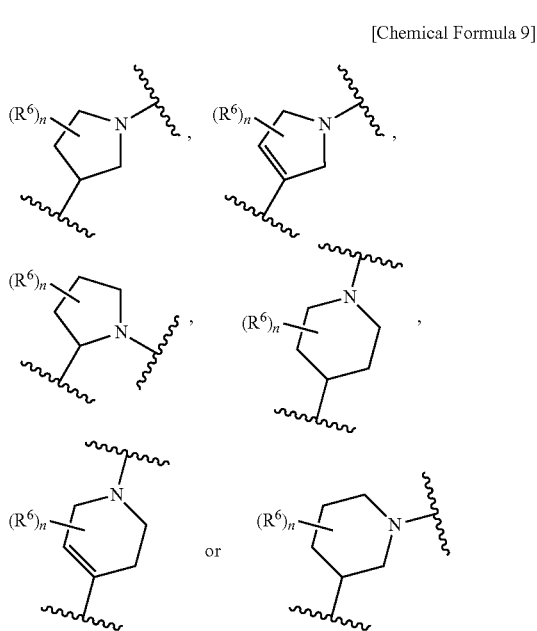

wherein R⁶ and n are as defined in 1');
—X¹═X²—X³═X⁴— is —C(R¹)═C(R²)—C(R³)═C(R⁴)—, —N═C(R²)—C(R³)═C(R⁴)—, —C(R¹)═N—C(R³)═C(R⁴)—, —C(R¹)═C(R²)—N═C(R⁴)—, or —C(R¹)═C(R²)—C(R³)═N—;
R⁵ is the formula: -L-R⁹,
wherein R⁹ is carboxy;
-L- is substituted or unsubstituted C1-C3 alkylene; and
the formula:

[Chemical Formula 10]

is the formula:

[Chemical Formula 11]

wherein R⁷, R⁸ and q are as defined in 1');
—Z═ is —C(R¹⁰)═ or —N═;
R¹⁰ is a a hydrogen atom, halogen, hydroxy, carboxy, formyl, formyloxy, sulfanyl, sulfino, sulfo, thioformyl, thiocarboxy, dithiocarboxy, cyano, nitro, nitroso, azido, amidino, guanidino, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted alkenylcarbonyl, substituted or unsubstituted alkynylcarbonyl, substituted or unsubstituted amino, substituted or unsubstituted alkylsulfonyl, substituted or unsubstituted alkenylsulfonyl, substituted or unsubstituted alkynylsulfonyl, substituted or unsubstituted imino, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted alkylsulfanyl, substituted or unsubstituted alkenylsulfanyl, substituted or unsubstituted alkynylsulfanyl, substituted or unsubstituted alkylsulfinyl, substituted or unsubstituted alkenylsulfinyl, substituted or unsubstituted alkynylsulfinyl, substituted or unsubstituted carbamoyl, substituted or unsubstituted sulfamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyl oxy, substituted or unsubstituted non-aromatic carbocyclyl oxy, substituted or unsubstituted aromatic heterocyclyl oxy, substituted or unsubstituted non-aromatic heterocyclyl oxy, substituted or unsubstituted aromatic carbocyclyl carbonyl, substituted or unsubstituted non-aromatic carbocyclyl carbonyl, substituted or unsubstituted aromatic heterocyclyl carbonyl, substituted or unsubstituted non-aromatic heterocyclyl carbonyl, substituted or unsubstituted aromatic carbocyclyl oxycarbonyl, substituted or unsubstituted non-aromatic carbocyclyl oxycarbonyl, substituted or unsubstituted aromatic heterocyclyl oxycarbonyl, substituted or unsubstituted non-aromatic heterocyclyl oxycarbonyl, substituted or unsubstituted aromatic carbocyclyl sulfanyl, substituted or unsubstituted non-aromatic carbocyclyl sulfanyl, substituted or unsubstituted aromatic heterocyclyl sulfanyl, substituted or unsubstituted non-aromatic heterocyclyl sulfanyl, substituted or unsubstituted aromatic carbocyclyl sulfonyl, substituted or unsubstituted non-aromatic carbocyclyl sulfonyl, substituted or unsubstituted aromatic heterocyclyl sulfonyl, or substituted or unsubstituted non-aromatic heterocyclyl sulfonyl, or a pharmaceutically acceptable salt thereof.

3') The compound according to 1') or 2'), wherein —X¹═X²—X³═X⁴— is —C(R¹)═C(R²)—C(R³)═C(R⁴)—, or a pharmaceutically acceptable salt thereof.

4') The compound according to any one of 1') to 3'), wherein R¹, R², R³ and R⁴ are each independently a hydrogen atom, halogen, or substituted or unsubstituted alkyl, or a pharmaceutically acceptable salt thereof.

5') The compound according to any one of 1') to 4'), wherein R⁶ is each independently halogen, hydroxy, cyano, substituted or unsubstituted alkyl, substituted or unsubstituted alkenyl, substituted or unsubstituted alkyloxy, substituted or unsubstituted carbamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted non-aromatic carbocyclyl oxy, substituted or unsubstituted non-aromatic heterocyclyl oxy; or
two of R⁶ attached to the same ring constituent carbon atom are taken together to form a carbocycle containing the above ring constituent carbon atom, a heterocycle containing the above ring constituent carbon atom, oxo, or the formula: ═CR⁶ᵃR⁶ᵇ, wherein R⁶ᵃ and R⁶ᵇ are a hydrogen atom, halogen, cyano, or substituted or unsubstituted alkyl, or a pharmaceutically acceptable salt thereof.

6') The compound according to any one of 1') to 4'), wherein the ring A is the formula:

[Chemical Formula 12]

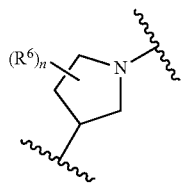

wherein $R^6$ is as defined in 1') and n is 1 or 2, or a pharmaceutically acceptable salt thereof.

7') The compound according to any one of 1') to 6'), wherein $R^7$ is halogen, substituted or unsubstituted alkyloxy, or substituted or unsubstituted non-aromatic carbocyclyl, or a pharmaceutically acceptable salt thereof.

8') The compound according to any one of 1') to 7'), wherein q is 0, or a pharmaceutically acceptable salt thereof.

9') The compound according to any one of 1') to 8'), wherein q is 0 and —Z═ is —N═, or a pharmaceutically acceptable salt thereof.

10') The compound according to any one of 1') to 7'), wherein q is 1 and $R^8$ is halogen or cyano, or a pharmaceutically acceptable salt thereof.

11') The compound according to any one of 1') to 10'), wherein —$X^1$═$X^2$—$X^3$═$X^4$— is —C($R^1$)═C($R^2$)—C($R^3$)═C($R^4$)—;

$R^1$, $R^2$, $R^3$ and $R^4$ are each independently a hydrogen atom;

the ring A is the formula:

[Chemical Formula 13]

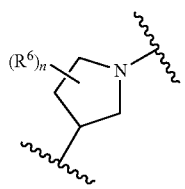

wherein $R^6$ is each independently halogen, cyano, substituted or unsubstituted alkyl, substituted or unsubstituted alkenyl, substituted or unsubstituted alkyloxy, substituted or unsubstituted non-aromatic carbocyclyl, substituted or unsubstituted aromatic heterocyclyl, substituted or unsubstituted non-aromatic heterocyclyl, substituted or unsubstituted non-aromatic carbocyclyl oxy, substituted or unsubstituted non-aromatic heterocyclyl oxy;

n is 1 or 2, or a pharmaceutically acceptable salt thereof.

12') The compound according to any one of 1'), 2') and 5') to 11'), wherein —$X^1$═$X^2$—$X^3$═$X^4$— is —C($R^1$)═C($R^2$)═C($R^3$)═C($R^4$)—;

$R^1$ and $R^4$ are a hydrogen atom;

$R^2$ and $R^3$ are each independently a hydrogen atom, halogen or methyl, or a pharmaceutically acceptable salt thereof.

13') A pharmaceutical composition comprising the compound of any one of 1') to 12'), or a pharmaceutically acceptable salt thereof.

14') The pharmaceutical composition according to 13'), which is a DP receptor antagonist and/or a CRTH2 receptor antagonist.

15') The pharmaceutical composition according to 14'), which is a therapeutic agent for allergy.

16') The pharmaceutical composition according to 14'), wherein a therapeutic agent for allergy is a medicine for asthma.

17') A method for treating or preventing a disease related to a DP receptor and/or a CRTH2 receptor characterized by administration of the compound according to any one of 1') to 12') or a pharmaceutically acceptable salt thereof.

18') The method according to 17'), wherein the disease related to a DP receptor and/or a CRTH2 receptor is asthma.

19') A compound of any one of 1') to 12') or a pharmaceutically acceptable salt thereof for treating or preventing a disease related to a DP receptor and/or a CRTH2 receptor.

20') The compound or a pharmaceutically acceptable salt thereof according to 19'), wherein the disease related to a DP receptor and/or a CRTH2 receptor is asthma.

Effect of the Invention

Each meaning of terms used herein is described below. Both when used alone and in combination with another word, each term is used in the same meaning.

MODE FOR CARRYING OUT THE INVENTION

The term of "halogen" includes a fluorine atom, a chlorine atom, a bromine atom and an iodine atom. A fluorine atom, a chlorine atom and a bromine atom are preferable.

The term of "hetero atom" includes an oxygen atom, a sulfur atom and a nitrogen atom.

The term of "alkyl" includes a linear or branched hydrocarbon group having 1 to 15 carbon atom(s), preferably 1 to 10 carbon atom(s), more preferably 1 to 6 carbon atom(s), further preferably 1 to 4 carbon atom(s). For example, methyl, ethyl, n-propyl, isopropyl, n-butyl, isobutyl, sec-butyl, tert-butyl, n-pentyl, isopentyl, neo-pentyl, n-hexyl, isohexyl, n-heptyl, isoheptyl, n-octyl, isooctyl, n-nonyl, n-decyl and the like are exemplified.

In one embodiment of "alkyl", methyl, ethyl, n-propyl, isopropyl, n-butyl, isobutyl, sec-butyl, tert-butyl and n-pentyl are exemplified. In another embodiment, methyl, ethyl, n-propyl, isopropyl and tert-butyl are exemplified.

The term of "alkenyl" includes a linear or branched hydrocarbon group having 2 to 15 carbon atoms, preferably 2 to 10 carbon atoms, more preferably 2 to 6 carbon atoms, further preferably 2 to 4 carbon atoms, and one or more double bond(s) at any available position. For example, vinyl, allyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl, decenyl, undecenyl, dodecenyl, tridecenyl, tetradecenyl, pentadecenyl and the like are exemplified.

In one embodiment of "alkenyl", vinyl, allyl, propenyl, isopropenyl and butenyl are exemplified.

The term of "alkynyl" includes a linear or branched hydrocarbon group having 2 to 10 carbon atoms, preferably 2 to 8 carbon atoms, more preferably 2 to 6 carbon atoms, further preferably 2 to 4 carbon atoms, and one or more triple bond(s) at any available position. For example, ethynyl, propynyl, butynyl, pentynyl, hexynyl, heptynyl, octynyl, nonynyl, decynyl and the like are exemplified. These may have further a double bond at any available position.

The term of "alkylene" includes a linear divalent hydrocarbon group having 1 to 8 carbon atom(s), preferably 1 to 6 carbon atom(s), more preferably 1 to 4 carbon atom(s). For example, methylene, ethylene, propylene and the like are exemplified.

The term of "alkenylene" includes a linear divalent hydrocarbon group having 2 to 8 carbon atoms, preferably 2 to 6 carbon atoms, more preferably 2 to 4 carbon atoms, and one or more double bond(s) at any available position. For example, vinylene, propenylene, butenylene, pentenylene and the like are exemplified.

The term of "alkynylene" includes a linear divalent hydrocarbon group having 2 to 8 carbon atoms, preferably 2 to 6 carbon atoms, more preferably 2 to 4 carbon atoms, and one or more triple bond(s) at any available position. For example, ethynylene, propynylene, butynylene, pentynylene, hexynylene and the like are exemplified.

The term of "aromatic carbocycle" includes a cyclic aromatic hydrocarbon which is monocyclic, or two or more rings. For example, benzene ring, naphthalene ring, anthracene ring, phenanthrene ring and the like are exemplified.

In one embodiment of "aromatic carbocycle", benzene ring and naphthalene ring are exemplified. In another embodiment, benzene ring is exemplified.

The term of "aromatic carbocyclyl" includes a cyclic aromatic hydrocarbon group which is monocyclic, or two or more rings. For example, phenyl, naphthyl, anthryl, phenanthryl and the like are exemplified.

In one embodiment of "aromatic carbocyclyl", phenyl, 1-naphthyl, 2-naphthyl are exemplified. In another embodiment, phenyl is exemplified.

The term of "non-aromatic carbocycle" includes a cyclic saturated hydrocarbon or a cyclic non-aromatic unsaturated hydrocarbon which is monocyclic, or two or more rings. A "non-aromatic carbocycle" of two or more rings includes a fused ring wherein a non-aromatic mono-carbocycle or a non-aromatic carbocycle of two or more rings is fused with a ring of the above "aromatic carbocycle".

In addition, the "non-aromatic carbocycle" also includes a ring having a bridge or a ring to form a spiro ring as follows:

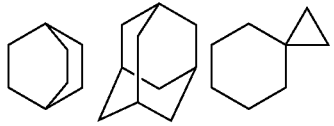

[Chemical Formula 14]

As a monocyclic non-aromatic carbocycle, 3 to 16 carbon atoms is preferred, more preferably 3 to 12 carbon atoms, further preferably 3 to 8 carbon atoms. For example, cyclopropane, cyclobutane, cyclopentane, cyclohexane, cycloheptane, cyclooctane, cyclononane, cyclodecane, cyclopropene, cyclobutene, cyclopentene, cyclohexene, cycloheptene, cyclohexadiene and the like are exemplified.

As a non-aromatic carbocycle of two or more rings, for example, indane, indene, acenaphthalene, tetrahydronaphthalene, fluorene and the like are exemplified.

The term of "non-aromatic carbocyclyl" includes a cyclic saturated hydrocarbon group or a cyclic non-aromatic unsaturated hydrocarbon group which is monocyclic, or two or more rings. A "non-aromatic carbocyclyl" of two or more rings includes a fused ring wherein a non-aromatic carbocycle of monocyclic, or two or more rings is fused with a ring of the above "aromatic carbocycle".

In addition, the "non-aromatic carbocyclyl" also includes a cyclic group having a bridge or a cyclic group to form a spiro ring as follows:

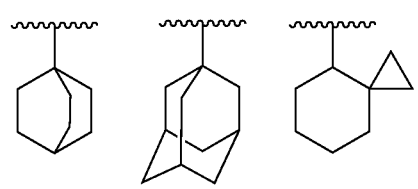

[Chemical Formula 15]

As a monocyclic non-aromatic carbocyclyl, 3 to 16 carbon atoms is preferred, more preferably 3 to 12 carbon atoms, further preferably 3 to 8 carbon atoms. For example, cyclopropyl, cyclobutyl, cyclopentyl, cyclohexyl, cycloheptyl, cyclooctyl, cyclononyl, cyclodecyl, cyclopropenyl, cyclobutenyl, cyclopentenyl, cyclohexenyl, cycloheptenyl, cyclohexadienyl and the like are exemplified.

As a non-aromatic carbocyclyl of two or more rings, for example, indanyl, indenyl, acenaphthyl, tetrahydronaphthyl, fluorenyl and the like are exemplified.

The term of "aromatic heterocycle" includes an aromatic ring which is monocyclic, or two or more rings, containing one or more the same or different of heteroatom(s) independently selected from oxygen, sulfur and nitrogen atom(s) in the ring.

An "aromatic heterocycle" of two or more rings includes a fused ring wherein an aromatic heterocycle of monocyclic, or two or more rings is fused with a ring of the above "aromatic carbocycle".

As a monocyclic aromatic heterocycle, a 5- to 8-membered ring is preferred, more preferably 5- to 6-membered. For example, pyrrole, imidazole, pyrazole, pyridine, pyridazine, pyrimidine, pyrazine, triazole, triazine, tetrazole, furan, thiophene, isoxazole, oxazole, oxadiazole, isothiazole, thiazole, thiadiazole and the like are exemplified.

As a bicyclic aromatic heterocycle, for example, indoline, isoindoline, indazorin, indolizine, quinoline, isoquinoline, cinnoline, phthalazine, quinazoline, naphthyridine, quinoxaline, purine, pteridine, benzimidazole, benzisoxazole, benzoxazole, benzoxadiazole, benzisothiazole, benzothiazole, benzothiadiazole, benzofuran, isobenzofuran, benzothiophene, benzotriazoie, imidazopyridine, triazolopyridine, imidazothiazole, pyrazinopyridazine, oxazolopyridine, thiazolopyridine and the like are exemplified.

As an aromatic heterocycle of three or more rings, for example, carbazole, acridine, xanthene, phenothiazine, phenoxathiin, phenoxazine, dibenzofuran and the like are exemplified.

The term of "aromatic heterocyclyl" includes an aromatic cyclic group which is monocyclic, or two or more rings, containing one or more the same or different of heteroatom(s) independently selected from oxygen, sulfur and nitrogen atom(s) in the ring.

An "aromatic heterocyclyl" of two or more rings includes a fused ring wherein an aromatic heterocyclyl of monocyclic, or two or more rings is fused with a ring of the above "aromatic carbocyclyl".

As a monocyclic aromatic heterocyclyl, a 5- to 8-membered ring is preferred, more preferably 5- to 6-membered. For example, pyrrolyl, imidazolyl, pyrazolyl, pyridyl, pyridazinyl, pyrimidinyl, pyrazinyl, triazolyl, triazinyl, tetrazolyl, furyl, thienyl, isoxazolyl, oxazolyl, oxadiazolyl, isothiazolyl, thiazolyl, thiadiazolyl and the like are exemplified.

As a bicyclic aromatic heterocyclyl, for example, indolyl, isoindolyl, indazolyl, indolizinyl, quinolinyl, isoquinolinyl, cinnolinyl, phthalazinyl, quinazolinyl, naphthyridinyl, quinoxalinyl, purinyl, pteridinyl, benzimidazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, imidazopyridyl, triazolopyridyl, imidazothiazolyl, pyrazinopyridazinyl, oxazolopyridyl, thiazolopyridyl and the like are exemplified.

As an aromatic heterocyclyl of three or more rings, for example, carbazolyl, acridinyl, xanthenyl, phenothiazinyl, phenoxathiinyl, phenoxazinyl, dibenzofuryl and the like are exemplified.

The term of "non-aromatic heterocycle" includes a cyclic non-aromatic ring which is monocyclic, or two or more rings, containing one or more the same or different of heteroatom(s) independently selected from oxygen, sulfur and nitrogen atom(s) in the ring.

A "non-aromatic heterocycle" of two or more rings includes a fused ring wherein a non-aromatic heterocycle of monocyclic, or two or more ring(s) is fused with a ring of the above "aromatic carbocycle", "non-aromatic carbocycle" and/or "aromatic heterocycle".

In addition, the "non-aromatic heterocycle" also includes a ring having a bridge or a ring to form a spiro ring as follows:

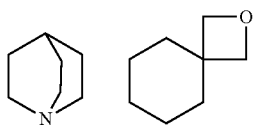

[Chemical Formula 16]

As a monocyclic non-aromatic heterocycle, a 3- to 8-membered ring is preferred, more preferably 5- to 6-membered. For example, dioxane, thiirane, oxirane, oxetane, oxathiolane, azetidine, thiane, thiazolidine, pyrrolidine, pyrroline, imidazolidine, imidazoline, pyrazolidine, pyrazoline, piperidine, piperazine, morpholine, thiomorpholine, dihydropyridine, tetrahydropyridine, tetrahydrofuran, tetrahydropyran, dihydrothiazoline, tetrahydrothiazoline, tetrahydroisothiazoline, dihydrooxazine, hexahydroazepine, tetrahydrodiazepine, tetrahydropyridazine, hexahydropyrimidine, dioxolane, dioxazine, aziridine, dioxoline, oxepane, thiolane, thiazine and the like are exemplified.

As a non-aromatic heterocycle of two or more rings, for example, indoline, isoindoline, chroman, isochroman and the like are exemplified.

The term of "non-aromatic heterocyclyl" includes a non-aromatic cyclic group which is monocyclic, or two or more rings, containing one or more the same or different of heteroatom(s) independently selected from oxygen, sulfur and nitrogen atoms.

A "non-aromatic heterocyclyl" of two or more rings includes a fused ring wherein a non-aromatic heterocyclyl of monocyclic, or two or more rings is fused with a ring of the above "aromatic carbocyclyl", "non-aromatic carbocyclyl" and/or "aromatic heterocyclyl".

In addition, the "non-aromatic heterocyclyl" also includes a cyclic group having a bridge or a cyclic group to form a spiro ring as follows:

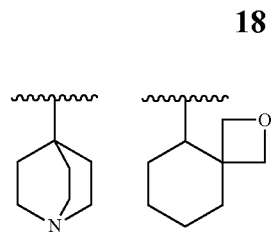

[Chemical Formula 17]

As a monocyclic non-aromatic heterocyclyl, a 3- to 8-membered ring is preferred, more preferably 5- to 6-membered. For example, dioxanyl, thiiranyl, oxiranyl, oxetanyl, oxathiolanyl, azetidinyl, thianyl, thiazolidinyl, pyrrolidinyl, pyrrolinyl, imidazolidinyl, imidazolinyl, pyrazolidinyl, pyrazolinyl, piperidyl, piperazinyl, morpholinyl, morpholino, thiomorpholinyl, thiomorpholino, dihydropyridyl, tetrahydropyridyl, tetrahydrofuryl, tetrahydropyranyl, dihydrothiazolyl, tetrahydrothiazolyl, tetrahydroisothiazolyl, dihydrooxazinyl, hexahydroazepinyl, tetrahydrodiazepinyl, tetrahydropyridazinyl, hexahydropyrimidinyl, dioxolanyl, dioxazinyl, aziridinyl, dioxolinyl, oxepanyl, thiolanyl, thiinyl, thiazinyl and the like are exemplified.

As a non-aromatic heterocyclyl of two or more rings, for example, indolinyl, isoindolinyl, chromanyl, isochromanyl and the like are exemplified.

The term of "hydroxyalkyl" includes a group wherein hydrogen atom(s) attached to one or more carbon atom(s) of above "alkyl" is (are) replaced with one or more hydroxy group(s). For example, hydroxymethy, 1-hydroxyethyl, 2-hydroxyethyl, 1-hydroxypropyl, 2-hydroxypropyl, 1,2-dihydroxyethyl and the like are exemplified.

In one embodiment of "hydroxyalkyl", hydroxymethyl is exemplified.

The term of "alkyloxy" includes a group wherein an oxygen atom is substituted with one above "alkyl". For example, methyloxy, ethyloxy, n-propyloxy, isopropyloxy, n-butyloxy, tert-butyloxy, isobutyloxy, sec-butyloxy, pentyloxy, isopentyloxy, hexyloxy and the like are exemplified.

In one embodiment of "alkyloxy", methyloxy, ethyloxy, n-propyloxy, isopropyloxy and tert-butyloxy are exemplified.

The term of "alkenyloxy" includes a group wherein an oxygen atom is substituted with one above "alkenyl". For example, vinyloxy, allyloxy, 1-propenyloxy, 2-butenyloxy, 2-pentenyloxy, 2-hexenyloxy, 2-heptenyloxy, 2-octenyloxy and the like are exemplified.

The term of "alkynyloxy" includes a group wherein an oxygen atom is substituted with one above "alkynyl". For example, ethynyloxy, 1-propynyloxy, 2-propynyloxy, 2-butynyloxy, 2-pentynyloxy, 2-hexynyloxy, 2-heptynyloxy, 2-octynyloxy and the like are exemplified.

The term of "haloalkyl" includes a group wherein hydrogen atom(s) attached to one or more carbon atom(s) of above "alkyl" is (are) replaced with one or more above "halogen". For example, monofluoromethyl, monofluoroethyl, monofluoropropyl, 2,2,3,3,3-pentafluoropropyl, monochloromethyl, trifluoromethyl, trichloromethyl, 2,2,2-trifluoroethyl, 2,2,2-trichloroethyl, 1,2-dibromoethyl, 1,1,1-trifluoropropan-2-yl and the like are exemplified.

In one embodiment of "haloalkyl", trifluoromethyl and trichloromethyl are exemplified.

The term of "haloalkyloxy" includes a group wherein an oxygen atom is substituted with one above "haloalkyl". For example, monofluoromethyloxy, monofluoroethyloxy, trifluoromethyloxy, trichloromethyloxy, trifluoroethyloxy, trichloroethyloxy and the like are exemplified.

In one embodiment of "haloalkyloxy", trifluoromethyloxy and trichloromethyloxy are exemplified.

The term of "alkyloxyalkyl" includes a group wherein above "alkyl" is substituted with above "alkyloxy". For example, methyloxymethyl, methyloxyethyl, ethyloxymethyl and the like are exemplified.

The term of "alkyloxyalkyloxy" includes a group wherein above "alkyloxy" is substituted with above "alkyloxy". For example, methyloxymethyloxy, methyloxyethyloxy, ethyloxymethyloxy, ethyloxyethyloxy and the like are exemplified.

The term of "alkylcarbonyl" includes a group wherein a carbonyl is substituted with one above "alkyl". For example, methylcarbonyl, ethylcarbonyl, n-propylcarbonyl, isopropylcarbonyl, tert-butylcarbonyl, isobutylcarbonyl, sec-butylcarbonyl, pentylcarbonyl, isopentylcarbonyl, hexylcarbonyl and the like are exemplified.

In one embodiment of "alkylcarbonyl", methylcarbonyl, ethylcarbonyl and n-propylcarbonyl are exemplified.

The term of "alkenylcarbonyl" includes a group wherein a carbonyl is substituted with one above "alkenyl". For example, ethylenylcarbonyl, propenylcarbonyl, butenylcarbonyl and the like are exemplified.

The term of "alkynylcarbonyl" includes a group wherein a carbonyl is substituted with one above "alkynyl". For example, ethynylcarbonyl, propynylcarbonyl butynylcarbonyl and the like are exemplified.

The term of "monoalkylamino" includes a group wherein a hydrogen atom attached to a nitrogen atom of an amino group is replaced with above "alkyl". For example, methylamino, ethylamino, isopropylamino and the like are exemplified.

In one embodiment of "monoalkylamino", methylamino and ethylamino are exemplified.

The term of "dialkylamino" includes a group wherein two hydrogen atoms attached to a nitrogen atom of an amino group are replaced with two above "alkyl". These two alkyl groups may be the same or different. For example, dimethylamino, diethylamino, N,N-diisopropylamino, N-methyl-N-ethylamino, N-isopropyl-N-ethylamino and the like are exemplified.

In one embodiment of "dialkylamino", dimethylamino and diethylamino are exemplified.

The term of "alkylsulfonyl" includes a group wherein a sulfonyl is substituted with one above "alkyl". For example, methylsulfonyl, ethylsulfonyl, propylsulfonyl, isopropylsulfonyl, tert-butylsulfonyl, isobutylsulfonyl, sec-butylsulfonyl and the like are exemplified.

In one embodiment of "alkylsulfonyl", methylsulfonyl and ethylsulfonyl are exemplified.

The term of "alkenylsulfonyl" includes a group wherein a sulfonyl is substituted with one above "alkenyl". For example, ethylenylsulfonyl, propenylsulfonyl, butenylsulfonyl and the like are exemplified.

The term of "alkynylsulfonyl" includes a group wherein a sulfonyl is substituted with one above "alkynyl". For example, ethynylsulfonyl, propynylsulfonyl, butynylsulfonyl and the like are exemplified.

The term of "alkylcarbonylamino" includes a group wherein a hydrogen atom attached to a nitrogen atom of an amino group is replaced with above "alkylcarbonyl". For example, methylcarbonylamino, ethylcarbonylamino, propylcarbonylamino, isopropylcarbonylamino, tert-butylcarbonylamino, isobutylcarbonylamino, sec-butylcarbonylamino and the like are exemplified.

In one embodiment of "alkylcarbonylamino", methylcarbonylamino and ethylcarbonylamino are exemplified.

The term of "alkylsulfonylamino" includes a group wherein a hydrogen atom attached to a nitrogen atom of an amino group is replaced with above "alkylsulfonyl". For example, methylsulfonylamino, ethylsulfonylamino, propylsulfonylamino, isopropylsulfonylamino, tert-butylsulfonylamino, isobutylsulfonylamino, sec-butylsulfonylamino and the like are exemplified.

In one embodiment of "alkylsulfonylamino", methylsulfonylamino and ethylsulfonylamino are exemplified.

The term of "alkylimino" includes a group wherein a hydrogen atom attached to a nitrogen atom of an imino group is replaced with above "alkyl". For example, methylimino, ethylimino, n-propylimino, isopropylimino and the like are exemplified.

The term of "alkenylimino" includes a group wherein a hydrogen atom attached to a nitrogen atom of an imino group is replaced with above "alkenyl". For example, ethylenylimino, propenylimino and the like are exemplified.

The term of "alkynylimino" includes a group wherein a hydrogen atom attached to a nitrogen atom of an imino group is replaced with above "alkynyl". For example, ethynylimino, propynylimino and the like are exemplified.

The term of "alkylcarbonylimino" includes a group wherein a hydrogen atom attached to a nitrogen atom of an imino group is replaced with above "alkylcarbonyl". For example, methylcarbonylimino, ethylcarbonylimino, n-propylcarbonylimino, isopropylcarbonylimino and the like are exemplified.

The term of "alkenylcarbonylimino" includes a group wherein a hydrogen atom attached to a nitrogen atom of an imino group is replaced with above "alkenylcarbonyl". For example, ethylenylcarbonylimino, propenylcarbonylimino and the like are exemplified.

The term of "alkynylcarbonylimino" includes a group wherein a hydrogen atom attached to a nitrogen atom of an imino group is replaced with above "alkynylcarbonyl". For example, ethynylcarbonylimino, propynylcarbonylimino and the like are exemplified.

The term of "alkyloxyimino" includes a group wherein a hydrogen atom attached to a nitrogen atom of an imino group is replaced with above "alkyloxy". For example, methyloxyimino, ethyloxyimino, n-propyloxyimino, isopropyloxyimino and the like are exemplified.

The term of "alkenyloxyimino" includes a group wherein a hydrogen atom attached to a nitrogen atom of an imino group is replaced with above "alkenyloxy". For example, ethylenyloxyimino, propenyloxyimino and the like are exemplified.

The term of "alkynyloxyimino" includes a group wherein a hydrogen atom attached to a nitrogen atom of an imino group is replaced with above "alkynyloxy". For example, ethynyloxyimino, propynyloxyimino and the like are exemplified.

The term of "alkylcarbonyloxy" includes a group wherein an oxygen atom is substituted with one above "alkylcarbonyl". For example, methylcarbonyloxy, ethylcarbonyloxy, propylcarbonyloxy, isopropylcarbonyloxy, tert-butylcarbonyloxy, isobutylcarbonyloxy, sec-butylcarbonyloxy and the like are exemplified.

In one embodiment of "alkylcarbonyloxy", methylcarbonyloxy and ethylcarbonyloxy are exemplified.

The term of "alkenylcarbonyloxy" includes a group wherein an oxygen atom is substituted with one above "alkenylcarbonyl". For example, ethylenylcarbonyloxy, propenylcarbonyloxy and the like are exemplified.

The term of "alkynylcarbonyloxy" includes a group wherein an oxygen atom is substituted with one above "alkynylcarbonyl". For example, ethynylcarbonyloxy, propynylcarbonyloxy and the like are exemplified.

The term of "alkyloxycarbonyl" includes a group wherein a carbonyl is substituted with one above "alkyloxy". For example, methyloxycarbonyl, ethyloxycarbonyl, propyloxycarbonyl, isopropyloxycarbonyl, tert-butyloxycarbonyl, isobutyloxycarbonyl, sec-butyloxycarbonyl, pentyloxycarbonyl, isopentyloxycarbonyl, hexyloxycarbonyl and the like are exemplified.

In one embodiment of "alkyloxycarbonyl", methyloxycarbonyl, ethyloxycarbonyl and propyloxycarbonyl are exemplified.

The term of "alkenyloxycarbonyl" includes a group wherein a carbonyl is substituted with one above "alkenyloxy". For example, ethylenyloxycarbonyl, propenyloxycarbonyl, butenyloxycarbonyl and the like are exemplified.

The term of "alkynyloxycarbonyl" includes a group wherein a carbonyl is substituted with one above "alkynyloxy". For example, ethynyloxycarbonyl, propynyloxycarbonyl butynyloxyarbonyl and the like are exemplified.

The term of "alkylsulfanyl" includes a group wherein a hydrogen atom attached to a sulfur atom of a sulfanyl is replaced with one above "alkyl". For example, methylsulfanyl, ethylsulfanyl, n-propylsulfanyl, isopropylsulfanyl, tert-butylsulfanyl, isobutylsulfanyl and the like are exemplified.

The term of "alkenylsulfanyl" includes a group wherein a hydrogen atom attached to a sulfur atom of sulfanyl is replaced with one above "alkenyl". For example, ethylenylsulfanyl, propenylsulfanyl, butenylsulfanyl and the like are exemplified.

The term of "alkynylsulfanyl" includes a group wherein a hydrogen atom attached to a sulfur atom of sulfanyl is replaced with one above "alkynyl". For example, ethynylsulfanyl, propynylsulfanyl, butynylsulfanyl and the like are exemplified.

The term of "alkylsulfinyl" includes a group wherein a sulfinyl is substituted with one above "alkyl". For example, methylsulfinyl, ethylsulfinyl, n-propylsulfinyl, isopropylsulfinyl and the like are exemplified.

The term of "alkenylsulfinyl" includes a group wherein a sulfinyl is substituted with one above "alkenyl". For example, ethylenylsulfinyl, propenylsulfinyl, butenylsulfinyl and the like are exemplified.

The term of "alkynylsulfinyl" includes a group in which a sulfinyl is substituted with one above "alkynyl". For example, ethynylsulfinyl, propynylsulfinyl butynylsulfinyl and the like are exemplified.

The term of "monoalkylcarbamoyl" includes a group wherein a hydrogen atom attached to a nitrogen atom of a carbamoyl group is replaced with above "alkyl". For example, methylcarbamoyl, ethylcarbamoyl, n-propylcarbamoyl, isopropylcarbamoyl and the like are exemplified.

The term of "dialkylcarbamoyl" includes a group wherein two hydrogen atoms attached to a nitrogen atom of a carbamoyl group are replaced with two above "alkyl". These two alkyl groups may be the same or different. For example, dimethylcarbamoyl, diethylcarbamoyl, N-methyl-N-ethylcarbamoyl and the like are exemplified.

The term of "monoalkylsulfamoyl" includes a group wherein a hydrogen atom attached to a nitrogen atom of a sulfamoyl is replaced with one above "alkyl". For example, methylsulfamoyl, ethylsulfamoyl, n-propylsulfamoyl, isopropylsulfamoyl and the like are exemplified.

The term of "dialkylsulfamoyl" includes a group wherein two hydrogen atoms attached to a nitrogen atom of a sulfamoyl are replaced with two above "alkyl". These two alkyl groups may be the same or different. For example, N,N-dimethylcarbamoyl, N,N-diethylcarbamoyl, N-methyl-N-ethylcarbamoyl and the like are exemplified.

The term of "trialkylsilyl" includes a group wherein a silicon atom is substituted with three above "alkyl". These three alkyl groups may be the same or different. For example, trimethylsilyl, triethylsilyl, tert-butyldimethylsilyl and the like are exemplified.

The alkyl portion of "aromatic carbocyclyl alkyl", "non-aromatic carbocyclyl alkyl", "aromatic heterocyclyl alkyl" and "non-aromatic heterocyclyl alkyl", "aromatic carbocyclyl alkyloxy", "non-aromatic carbocyclyl alkyloxy", "aromatic heterocyclyl alkyloxy" and"non-aromatic heterocyclyl alkyloxy", "aromatic carbocyclyl alkyloxycarbonyl", "non-aromatic carbocyclyl alkyloxycarbonyl", "aromatic heterocyclyl alkyloxycarbonyl" and"non-aromatic heterocyclyl alkyloxycarbonyl", "aromatic carbocyclyl alkyloxyalkyl", "non-aromatic carbocyclyl alkyloxyalkyl", "aromatic heterocyclyl alkyloxyalkyl" and"non-aromatic heterocyclyl alkyloxyalkyl", and "aromatic carbocyclyl alkylamino", "non-aromatic carbocyclyl alkylamino", "aromatic heterocyclyl alkylamino" and"non-aromatic heterocyclyl alkylamino" means the aforementioned "alkyl".

The term of "aromatic carbocyclyl alkyl" includes an alkyl substituted with one or more above "aromatic carbocyclyl". Examples thereof include such as benzyl, phenethyl, phenylpropynyl, benzhydryl, trityl, naphthylmethyl and a group of the formula of

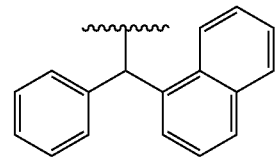

[Chemical Formula 18]

In one embodiment of "aromatic carbocyclyl alkyl", benzyl, phenethyl and benzhydryl are exemplified.

The term of "non-aromatic carbocyclyl alkyl" includes an alkyl substituted with one or more above "non-aromatic carbocyclyl". Also, "non-aromatic carbocyclyl alkyl" includes a "non-aromatic carbocyclyl alkyl" wherein the alkyl portion thereof is substituted with one or more above "aromatic carbocyclyl". Examples thereof include such as cyclopropylmethyl, cyclobutylmethyl, cyclopentylmethyl, cyclohexylmethyl and a group of the formula of

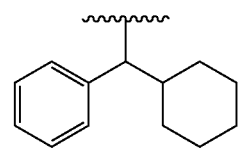

[Chemical Formula 19]

The term of "aromatic heterocyclyl alkyl" includes an alkyl substituted with one or more above "aromatic heterocyclyl". Also, "aromatic heterocyclyl alkyl" includes an "aromatic heterocyclyl alkyl" wherein the alkyl portion thereof is substituted with one or more above "aromatic carbocyclyl", and/or "non-aromatic carbocyclyl". Examples thereof include such as pyridylmethyl, furanylmethyl, imidazolylmethyl, indolylmethyl, benzothiophenylmethyl, oxazolylmethyl, isoxazolylmethyl, thiazolylmethyl, isothiazolylmethyl, pyrazolylmethyl, isopyrazolylmethyl, pyrrolidinylmethyl, benzoxazolylmethyl and groups of the formula of

[Chemical Formula 20]

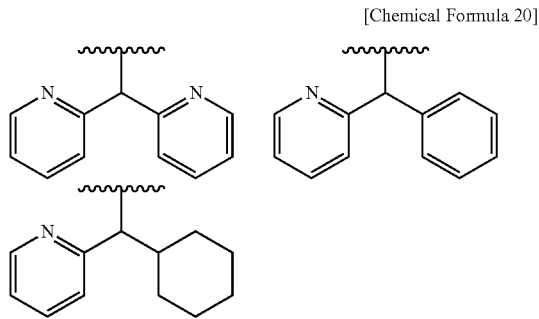

The term of "non-aromatic heterocyclyl alkyl" includes an alkyl substituted with one or more above "non-aromatic heterocyclyl". Also, "non-aromatic heterocyclyl alkyl" includes a "non-aromatic heterocyclyl alkyl" wherein the alkyl portion thereof is substituted with one or more above "aromatic carbocyclyl", "non-aromatic carbocyclyl" and/or "aromatic heterocyclyl". Examples thereof include such as tetrahydropyranylmethyl, morpholinylmethyl, morpholinylethyl, piperidinylmethyl, piperazinylmethyl and groups of the formula of

[Chemical Formula 21]

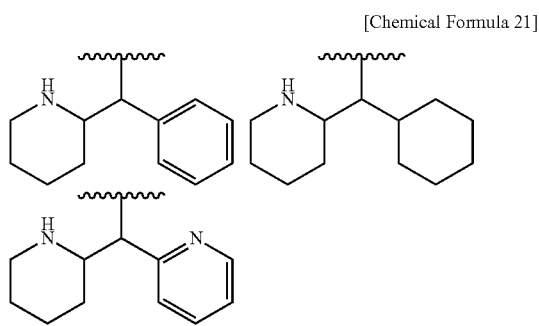

The term of "aromatic carbocyclyl alkyloxy" includes an alkyloxy substituted with one or more above "aromatic carbocyclyl". Examples thereof include such as benzyloxy, phenethyloxy, phenylpropynyloxy, benzhydryloxy, trityloxy, naphthylmethyloxy and a group of the formula of

[Chemical Formula 22]

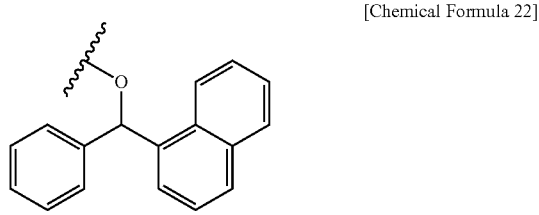 [SMILES: *OC(c1ccccc1)c1cccc2ccccc12]

The term of "non-aromatic carbocyclyl alkyloxy" includes an alkyloxy substituted with one or more above "non-aromatic carbocyclyl". Also, "non-aromatic carbocyclyl alkyloxy" includes a "non-aromatic carbocyclyl alkyloxy" wherein the alkyl portion thereof is substituted with one or more above "aromatic carbocyclyl". Examples thereof include such as cyclopropylmethyloxy, cyclobutylmethyloxy, cyclopentylmethyloxy, cyclohexylmethyloxy and a group of the formula of

[Chemical Formula 23]

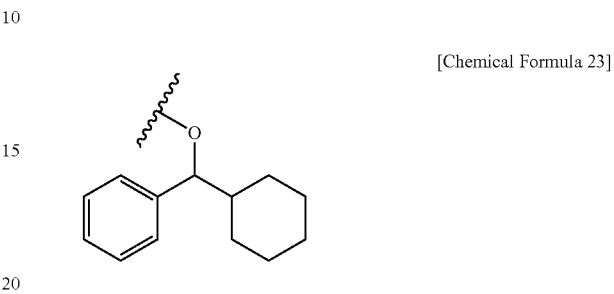

The term of "aromatic heterocyclyl alkyloxy" includes an alkyloxy substituted with one or more above "aromatic heterocyclyl". Also, "aromatic heterocyclyl alkyloxy" includes an "aromatic heterocyclyl alkyloxy" wherein the alkyl portion thereof is substituted with one or more above "aromatic carbocyclyl", and/or "non-aromatic carbocyclyl". Examples thereof include such as pyridylmethyloxy, furanylmethyloxy, imidazolylmethyloxy, indolylmethyloxy, benzothiophenylmethyloxy, oxazolylmethyloxy, isoxazolylmethyloxy, thiazolylmethyloxy, isothiazolylmethyloxy, pyrazolylmethyloxy, isopyrazolylmethyloxy, pyrrolidinylmethyloxy, benzoxazolylmethyloxy and groups of the formula of

[Chemical Formula 24]

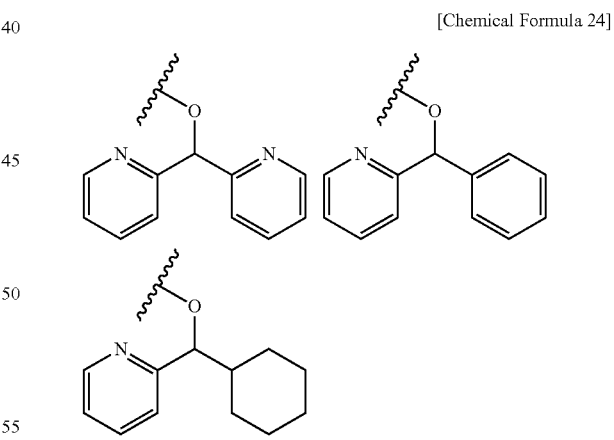

The term of "non-aromatic heterocyclyl alkyloxy" includes an alkyloxy substituted with one or more above "non-aromatic heterocyclyl". Also, "non-aromatic heterocyclyl alkyloxy" includes a "non-aromatic heterocyclyl alkyloxy" wherein the alkyl portion thereof is substituted with one or more above "aromatic carbocyclyl", "non-aromatic carbocyclyl" and/or "aromatic heterocyclyl". Examples thereof include such as tetrahydropyranylmethyloxy, morpholinylmethyloxy, morpholinylethyloxy, piperidinylmethyloxy, piperazinylmethyloxy and groups of the formula of

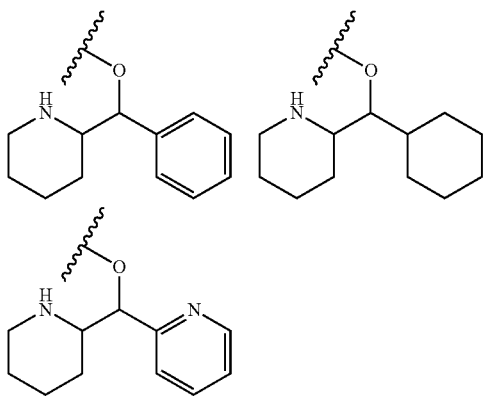

The term of "aromatic carbocyclyl alkyloxycarbonyl" includes an alkyloxycarbonyl substituted with one or more above "aromatic carbocyclyl". Examples thereof include such as benzyloxycarbonyl, phenethyloxycarbonyl, phenylpropynyloxycarbonyl, benzhydryloxycarbonyl, trityloxycarbonyl, naphthylmethyloxycarbonyl and a group of the formula of

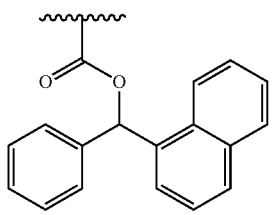

The term of "non-aromatic carbocyclyl alkyloxycarbonyl" includes an alkyloxycarbonyl substituted with one or more above "non-aromatic carbocyclyl". Also, "non-aromatic carbocyclyl alkyloxycarbonyl" includes a "non-aromatic carbocyclyl alkyloxycarbonyl" wherein the alkyl portion thereof is substituted with one or more above "aromatic carbocyclyl". Examples thereof include such as cyclopropylmethyloxycarbonyl, cyclobutylmethyloxycarbonyl, cyclopentylmethyloxycarbonyl, cyclohexylmethyloxycarbonyl and a group of the formula of

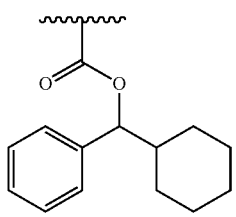

The term of "aromatic heterocyclyl alkyloxycarbonyl" includes an alkyloxycarbonyl substituted with one or more above "aromatic heterocyclyl". Also, "aromatic heterocyclyl alkyloxycarbonyl" includes an "aromatic heterocyclyl alkyloxycarbonyl" wherein the alkyl portion thereof is substituted with one or more above "aromatic carbocyclyl", and/or "non-aromatic carbocyclyl". Examples thereof include such as pyridylmethyloxycarbonyl, furanylmethyloxycarbonyl, imidazolylmethyloxycarbonyl, indolylmethyloxycarbonyl, benzothiophenylmethyloxycarbonyl, oxazolylmethyloxycarbonyl, isoxazolylmethyloxycarbonyl, thiazolylmethyloxycarbonyl, isothiazolylmethyloxycarbonyl, pyrazolylmethyloxycarbonyl, isopyrazolylmethyloxycarbonyl, pyrrolidinylmethyloxycarbonyl, benzoxazolylmethyloxycarbonyl and groups of the formula of

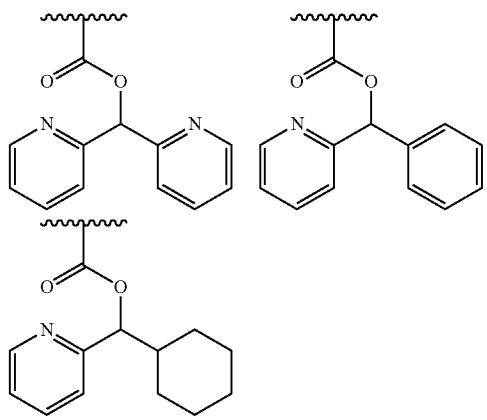

The term of "non-aromatic heterocyclyl alkyloxycarbonyl" includes an alkyloxycarbonyl substituted with one or more above "non-aromatic heterocyclyl". Also, "non-aromatic heterocyclyl alkyloxycarbonyl" includes a "non-aromatic heterocyclyl alkyloxycarbonyl" wherein the alkyl portion thereof is substituted with one or more above "aromatic carbocyclyl", "non-aromatic carbocyclyl" and/or "aromatic heterocyclyl". Examples thereof include such as tetrahydropyranylmethyloxycarbonyl, morpholinylmethyloxycarbonyl, morpholinylethyloxycarbonyl, piperidinylmethyloxycarbonyl, piperazinylmethyloxycarbonyl and groups of the formula of

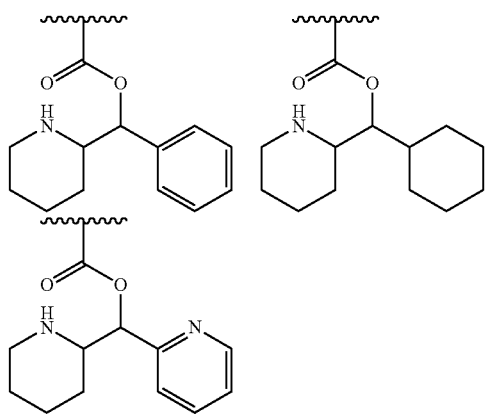

The term of "aromatic carbocyclyl alkyloxyalkyl" includes an alkyloxyalkyl substituted with one or more above "aromatic carbocyclyl". Examples thereof include such as benzyloxymethyl, phenethyloxymethyl, phenylpropynyloxymethyl, benzhydryloxymethyl, trityloxymethyl, nap hthylmethyloxymethyl and a group of the formula of

[Chemical Formula 30]

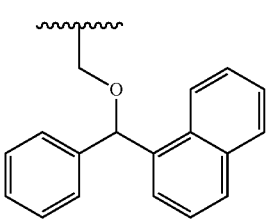

The term of "non-aromatic carbocyclyl alkyloxyalkyl" includes an alkyloxyalkyl substituted with one or more above "non-aromatic carbocyclyl". Also, "non-aromatic carbocyclyl alkyloxyalkyl" includes a "non-aromatic carbocyclyl alkyloxyalkyl" wherein the alkyl portion attached to a non-aromatic carbocycle is substituted with one or more above "aromatic carbocyclyl". Examples thereof include such as cyclopropylmethyloxymethyl, cyclobutylmethyloxymethyl, cyclopentylmethyloxymethyl, cyclohexylmethyloxymethyl and a group of the formula of

[Chemical Formula 31]

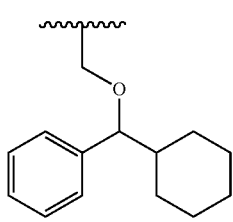

The term of "aromatic heterocyclyl alkyloxyalkyl" includes an alkyloxyalkyl substituted with one or more above "aromatic heterocyclyl". Also, "aromatic heterocyclyl alkyloxyalkyl" includes an "aromatic heterocyclyl alkyloxyalkyl" wherein the alkyl portion attached to aromatic heterocycle is substituted with one or more above "aromatic carbocyclyl" and/or "non-aromatic carbocyclyl". Examples thereof include such as pyridylmethyloxymethyl, furanylmethyloxymethyl, imidazolylmethyloxymethyl, indolylmethyloxymethyl, benzothiophenylmethyloxymethyl, oxazolylmethyloxymethyl, isoxazolylmethyloxymethyl, thiazolylmethyloxymethyl, isothiazolylmethyloxymethyl, pyrazolylmethyloxymethyl, isopyrazolylmethyloxymethyl, pyrrolidinylmethyloxymethyl, benzoxazolylmethyloxymethyl and groups of the formula of

[Chemical Formula 32]

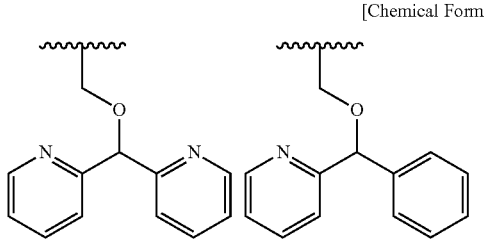

-continued

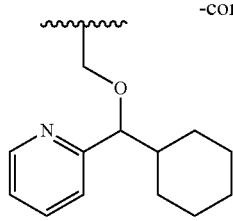

The term of "non-aromatic heterocyclyl alkyloxyalkyl" includes an alkyloxyalkyl substituted with one or more above "non-aromatic heterocyclyl". Also, "non-aromatic heterocyclyl alkyloxyalkyl" includes a "non-aromatic heterocyclyl alkyloxyalkyl" wherein the alkyl portion attached to non-aromatic heterocycle is substituted with one or more above "aromatic carbocyclyl", "non-aromatic carbocyclyl" and/or "aromatic heterocyclyl". Examples thereof include such as tetrahydropyranylmethyloxymethyl, morpholinylmethyloxymethyl, morpholinylethyloxymethyl, piperidinylmethyloxymethyl, piperazinylmethyloxymethyl and groups of the formula of

[Chemical Formula 33]

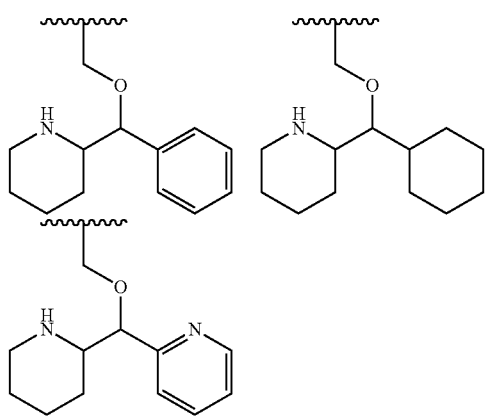

The term of "aromatic carbocyclyl alkylamino" includes a group wherein one or two hydrogen atom(s) attached to a nitrogen atom of an amino group is replaced with above "aromatic carbocyclyl alkyl". For example, benzylamino, phenethylamino, phenylpropynylamino, benzhydrylamino, tritylamino, naphthylmethylamino, dibenzylamino and the like are exemplified.

The term of "non-aromatic carbocyclyl alkylamino" includes a group wherein one or two hydrogen atom(s) attached to a nitrogen atom of an amino group is replaced with above "non-aromatic carbocyclyl alkyl". For example, cyclopropylmethylamino, cyclobutylmethylamino, cyclopentylmethylamino, cyclohexylmethylamino and the like are exemplified.

The term of "aromatic heterocyclyl alkylamino" includes a group wherein one or two hydrogen atom(s) attached to a nitrogen atom of an amino group is replaced with above "aromatic heterocyclyl alkyl". For example, pyridylmethylamino, furanylmethylamino, imidazolylmethylamino, indolylmethylamino, benzothiophenylmethylamino, oxazolylmethylamino, isoxazolylmethylamino, thiazolylmethylamino, isothiazolylmethylamino, pyrazolylmethylamino, isopyrazolylmethylamino, pyrrolidinylmethylamino, benzoxazolylmethylamino and the like are exemplified.

The term of "non-aromatic heterocyclyl alkylamino" includes a group wherein one or two hydrogen atom(s) attached to a nitrogen atom of an amino group is replaced with above "non-aromatic heterocyclyl alkyl". For example, tetrahydropyranylmethylamino, morpholinylethylamino, piperidinylmethylamino, piperazinylmethyamino and the like are exemplified.

The "aromatic carbocycle" portion of "aromatic carbocyclyl oxy", "aromatic carbocyclyl carbonyl", "aromatic carbocyclyl oxycarbonyl", "aromatic carbocyclyl sulfanyl" and "aromatic carbocyclyl sulfonyl" means the aforementioned "aromatic carbocyclyl".

The term of "aromatic carbocyclyl oxy" includes a group wherein an oxygen atom is substituted with one above "aromatic carbocycle". For example, phenyloxy, naphthyloxy and the like are exemplified.

The term of "aromatic carbocyclyl carbonyl" includes a group wherein a carbonyl is substituted with one above "aromatic carbocycle". For example, phenylcarbonyl, naphthylcarbonyl and the like are exemplified.

The term of "aromatic carbocyclyl oxycarbonyl" includes a group wherein a carbonyl is substituted with one above "aromatic carbocyclyl oxy". For example, phenyloxycarbonyl, naphthyloxycarbonyl and the like are exemplified.

The term of "aromatic carbocyclyl sulfanyl" includes a group wherein a hydrogen atom attached to a sulfur atom of a sulfanyl is replaced with one above "aromatic carbocycle". For example, phenylsulfanyl, naphthylsulfanyl and the like are exemplified.

The term of "aromatic carbocyclyl sulfonyl" includes a group wherein a sulfonyl is substituted with one above "aromatic carbocycle". For example, phenylsulfonyl, naphthylsulfonyl and the like are exemplified.

The "non-aromatic carbocycle" portion of "non-aromatic carbocyclyl oxy", "non-aromatic carbocyclyl carbonyl", "non-aromatic carbocyclyl oxycarbonyl", "non-aromatic carbocyclyl sulfanyl" and "non-aromatic carbocyclyl sulfonyl" means the aforementioned "non-aromatic carbocyclyl".

The term of "non-aromatic carbocyclyl oxy" includes a group wherein an oxygen atom is substituted with one above "non-aromatic carbocycle". For example, cyclopropyloxy, cyclohexyloxy, cyclohexenyloxy and the like are exemplified.

The term of "non-aromatic carbocyclyl carbonyl" includes a group wherein a carbonyl is substituted with one above "non-aromatic carbocycle". For example, cyclopropylcarbonyl, cyclohexylcarbonyl, cyclohexenylcarbonyl and the like are exemplified.

The term of "non-aromatic carbocyclyl oxycarbonyl" includes a group wherein a carbonyl is substituted with one above "non-aromatic carbocyclyl oxy". For example, cyclopropyloxycarbonyl, cyclohexyloxycarbonyl, cyclohexenyloxycarbonyl and the like are exemplified.

The term of "non-aromatic carbocyclyl sulfanyl" includes a group wherein a hydrogen atom attached to a sulfur atom of a sulfanyl is replaced with one above "non-aromatic carbocycle". For example, cyclopropylsulfonyl, cyclohexylsulfanyl, cyclohexenylsulfanyl and the like are exemplified.

The term of "non-aromatic carbocyclyl sulfonyl" includes a group wherein a sulfonyl is substituted with one above "non-aromatic carbocycle". For example, cyclopropylsulfonyl, cyclohexylsulfonyl, cyclohexenylsulfonyl and the like are exemplified.

The "aromatic heterocycle" portion of "aromatic heterocyclyl oxy", "aromatic heterocyclyl carbonyl", "aromatic heterocyclyl oxycarbonyl", "aromatic heterocyclyl sulfanyl" and "aromatic heterocyclyl sulfonyl" means the aforementioned "aromatic heterocyclyl".

The term of "aromatic heterocyclyl oxy" includes a group wherein an oxygen atom is substituted with one above "aromatic heterocycle". For example, pyridyloxy, oxazolyloxy and the like are exemplified.

The term of "aromatic heterocyclyl carbonyl" includes a group wherein a carbonyl is substituted with one above "aromatic heterocycle". For example, pyridylcarbonyl, oxazolylcarbonyl and the like are exemplified.

The term of "aromatic heterocyclyl oxycarbonyl" includes a group wherein a carbonyl is substituted with one above "aromatic heterocyclyl oxy". For example, pyridyloxycarbonyl, oxazolyloxycarbonyl and the like are exemplified.

The term of "aromatic heterocyclyl sulfanyl" includes a group wherein a hydrogen atom attached to a sulfur atom of a sulfanyl is replaced with one above "aromatic heterocycle". For example, pyridylsulfanyl, oxazolylsulfanyl and the like are exemplified.

The term of "aromatic heterocyclyl sulfonyl" includes a group wherein a sulfonyl is substituted with one above "aromatic heterocycle". For example, pyridylsulfonyl, oxazolylsulfonyl and the like are exemplified.

The "non-aromatic heterocycle" portion of "non-aromatic heterocyclyl oxy", "non-aromatic heterocyclyl carbonyl", "non-aromatic heterocyclyl oxycarbonyl", "non-aromatic heterocyclyl sulfanyl" and "non-aromatic heterocyclyl sulfonyl" means the aforementioned "non-aromatic heterocyclyl".

The term of "non-aromatic heterocyclyl oxy" includes a group wherein an oxygen atom is substituted with one above "non-aromatic heterocycle". For example, piperidinyloxy, tetrahydrofuryloxy and the like are exemplified.

The term of "non-aromatic heterocyclyl carbonyl" includes a group wherein a carbonyl is substituted with one above "non-aromatic heterocycle". For example, piperidinylcarbonyl, tetrahydrofurylcarbonyl and the like are exemplified.

The term of "non-aromatic heterocyclyl oxycarbonyl" includes a group wherein a carbonyl is substituted with one above "non-aromatic heterocyclyl oxy". For example, piperidinyloxycarbonyl, tetrahydrofuryloxycarbonyl and the like are exemplified.

The term of "non-aromatic heterocyclyl sulfanyl" includes a group wherein a hydrogen atom attached to a sulfur atom of a sulfanyl is replaced with one above "non-aromatic heterocycle". For example, piperidinylsulfanyl, tetrahydrofurylsulfanyl and the like are exemplified.

The term of "non-aromatic heterocyclyl sulfonyl" includes a group wherein a sulfonyl is substituted with one above "non-aromatic heterocycle". For example, piperidinylsulfonyl, tetrahydrofurylsulfonyl and the like are exemplified.

The substituents of "substituted or unsubstituted alkyl", "substituted or unsubstituted alkenyl", "substituted or unsubstituted alkynyl", "substituted or unsubstituted alkyloxy", "substituted or unsubstituted alkenyloxy", "substituted or unsubstituted alkynyloxy", "substituted or unsubstituted alkylcarbonyl", "substituted or unsubstituted alkenylcarbonyl", "substituted or unsubstituted alkynylcarbonyl", "substituted or unsubstituted alkylsulfonyl", "substituted or unsubstituted alkenylsulfonyl", "substituted or unsubstituted alkynylsulfonyl", "substituted or unsubstituted alkylcarbonyloxy", "substituted or unsubstituted alkenylcarbonyloxy", "substituted or unsubstituted alkynylcarbonyloxy", "substituted or unsubstituted alkyloxycarbonyl", "substituted or unsubstituted alkenyloxycarbonyl", "substituted or unsubstituted alkynyloxycarbonyl", "substituted or unsubstituted alkylsulfanyl", "substituted or unsubstituted alkenylsulfanyl", "substituted or unsubstituted alkynylsulfanyl", "substituted or unsubstituted alkylsulfinyl", "substituted or unsubstituted alkenylsulfinyl", and "substituted or unsubstituted alkynylsulfinyl" include the group as follows. A carbon atom at any possible position(s) can be substituted with one or more substituent(s) selected from the following group.

Substituent: halogen, hydroxy, carboxy, amino, imino, hydroxyamino, hydroxyimino, formyl, carbamoyl, sulfamoyl, sulfanyl, sulfino, sulfo, thioformyl, thiocarboxy, dithiocarboxy, thiocarbamoyl, cyano, nitro, azido, hydrazino, ureido, amidino, guanidino, trialkylsilyl, alkyloxy optionally substituted with substituent group A, alkenyloxy, alkynyloxy, haloalkyloxy, alkylcarbonyl optionally substituted with a halogen at 1 to 3 position(s), alkenylcarbonyl optionally substituted with a halogen at 1 to 3 position(s), alkynylcarbonyl optionally substituted with a halogen at 1 to 3 position(s), monoalkylamino optionally substituted with substituent group B, dialkylamino optionally substituted with substituent group B, alkylsulfonyl optionally substituted with a halogen at 1 to 3 position(s), alkenylsulfonyl, alkynylsulfonyl, alkylcarbonylamino optionally substituted with a halogen at 1 to 3 position(s), alkylsulfonylamino optionally substituted with a halogen at 1 to 3 position(s), alkylimino optionally substituted with a halogen at 1 to 3 position(s), alkenylimino, alkynylimino, alkylcarbonylimino, alkenylcarbonylimino, alkynylcarbonylimino, alkyloxyimino optionally substituted with substituent group C, alkenyloxyimino, alkynyloxyimino, alkylcarbonyloxy, alkenylcarbonyloxy, alkynylcarbonyloxy, alkyloxycarbonyl, alkenyloxycarbonyl, alkynyloxycarbonyl, alkylsulfanyl, alkenylsulfanyl, alkynylsulfanyl, monoalkylcarbamoyl optionally substituted with substituent group D, dialkylcarbamoyl optionally substituted with substituent group D, monoalkylsulfamoyl optionally substituted with substituent group D, dialkylsulfamoyl optionally substituted with substituent group D, aromatic carbocyclyl optionally substituted with substituent group E, non-aromatic carbocyclyl, aromatic heterocyclyl optionally substituted with substituent group E, non-aromatic heterocyclyl, aromatic carbocyclyl oxy optionally substituted with substituent group E, non-aromatic carbocyclyl oxy, aromatic heterocyclyl oxy optionally substituted with substituent group E, non-aromatic heterocyclyl oxy, aromatic carbocyclyl carbonyl optionally substituted with substituent group E, non-aromatic carbocyclyl carbonyl, aromatic heterocyclyl carbonyl optionally substituted with substituent group E, non-aromatic heterocyclyl carbonyl, aromatic carbocyclyl oxycarbonyl optionally substituted with substituent group E, non-aromatic carbocyclyl oxycarbonyl, aromatic heterocyclyl oxycarbonyl optionally substituted with substituent group E, non-aromatic heterocyclyl oxycarbonyl, aromatic carbocyclyl alkyloxy optionally substituted with substituent group E, non-aromatic carbocyclyl alkyloxy, aromatic heterocyclyl alkyloxy optionally substituted with substituent group E, non-aromatic heterocyclyl alkyloxy, aromatic carbocyclyl alkyloxycarbonyl optionally substituted with substituent group E, non-aromatic carbocyclyl alkyloxycarbonyl, aromatic heterocyclyl alkyloxycarbonyl optionally substituted with substituent group E, non-aromatic heterocyclyl alkyloxycarbonyl, aromatic carbocyclyl alkylamino optionally substituted with substituent group E, non-aromatic carbocyclyl alkylamino, aromatic heterocyclyl alkylamino optionally substituted with substituent group E, non-aromatic heterocyclyl alkylamino, aromatic carbocyclyl sulfanyl optionally substituted with substituent group E, non-aromatic carbocyclyl sulfanyl, aromatic heterocyclyl sulfanyl optionally substituted with substituent group E, non-aromatic heterocyclyl sulfanyl, aromatic carbocyclyl sulfonyl optionally substituted with substituent group E, non-aromatic carbocyclyl sulfonyl, aromatic heterocyclyl sulfonyl optionally substituted with substituent group E, and non-aromatic heterocyclyl sulfonyl.

Substituent group A is comprised of hydroxyl, alkyloxy, haloalkyloxy, alkyloxyalkyloxy, aromatic carbocyclyl oxy and aromatic heterocyclyl oxy.

Substituent group B is comprised of halogen, hydroxyl, carboxy, sulfanyl, cyano, alkyloxy, non-aromatic carbocyclyl oxy and non-aromatic heterocyclyl oxy.

Substituent group C is comprised of halogen, hydroxyl, carboxy, carbamoyl, alkyloxy, monoalkylamino, dialkylamino, monoalkylcarbamoyl, and dialkylcarbamoyl.

Substituent group D is comprised of halogen, hydroxyl, cyano, non-aromatic carbocyclyl and non-aromatic heterocyclyl.

Substituent group E is comprised of halogen, hydroxyl, amino, carbamoyl, cyano, nitro, alkyl, haloalkyl, alkyloxy, haloalkyloxy, monoalkylamino, dialkylamino, alkylsulfonyl and haloalkylsulfonyl.

Substituent group F is comprised of halogen, hydroxyl, amino, alkyl, haloalkyl, alkyloxy and haloalkyloxy.

The term of ""R" optionally substituted with substituent group A" includes "R" can be substituted with same or different substituent(s) selected from substituent group A at one or more position(s). In one embodiment, "R" optionally substituted with same or different substituent(s) selected from substituent group A at 1 to 6 position(s) is included. In another embodiment, "R" optionally substituted with same or different substituent(s) selected from substituent group A at 1 to 3 position(s) is included.

The term of ""R" optionally substituted with substituent group B", ""R" optionally substituted with substituent group C", ""R" optionally substituted with substituent group D", ""R" optionally substituted with substituent group E", and ""R" optionally substituted with substituent group F" are as defined in the above.

The term of "substituted or unsubstituted amino" includes an amino optionally substituted with the following substituent group G at one or two position(s).

Substituent group G is comprised of hydroxyl, cyano, alkyl, haloalkyl, alkylcarbonyl, haloalkylcarbonyl, alkylsulfonyl, haloalkylsulfonyl, alkylcarbamoyl, aromatic carbocyclyl optionally substituted with substituent group E, non-aromatic carbocyclyl optionally substituted with substituent group E, aromatic heterocyclyl optionally substituted with substituent group E, non-aromatic heterocyclyl optionally substituted with substituent group E, aromatic carbocyclyl alkyl optionally substituted with substituent group E, non-aromatic carbocyclyl alkyl optionally substituted with substituent group E, aromatic heterocyclyl alkyl optionally substituted with substituent group E, non-aromatic heterocyclyl alkyl optionally substituted with substituent group E, aromatic carbocyclyl carbonyl optionally substituted with substituent group E, non-aromatic carbocyclyl carbonyl optionally substituted with substituent group E, aromatic heterocyclyl carbonyl optionally substituted with substituent group E, non-aromatic heterocyclyl carbonyl optionally substituted with substituent group E, aromatic carbocyclyl carbamoyl optionally substituted with substituent group E, non-aromatic carbocyclyl carbamoyl optionally substituted with substituent group E, aromatic heterocyclyl carbamoyl optionally substituted with substituent group E and non-aromatic heterocyclyl carbamoyl optionally substituted with substituent group E.

In one embodiment of "substituted or unsubstituted amino", amino, methylamino, dimethylamino, ethylamino, diethylamino, ethylmethylamino, cyclopropylamino, cyclohexylamino, benzylamino, acetylamino, benzoylamino, methylsulfonylamino, tetrahydropyranylamino, tetrahydrofuranylamino, morpholinoamino, morpholinylamino, piperidinylamino, piperazinylamino and the like are exemplified. In another embodiment, amino, methylamino, dimethylamino, ethylmethylamino, diethylamino, acetylamino, methylsulfonylamino, tetrahydropyranylamino, tetrahydrofuranylamino, morpholinoamino, piperidinylamino and the like are exemplified.

The term of "substituted or unsubstituted imino" includes an imino optionally substituted with the following substituent group H at one position.

Substituent group G is comprised of hydroxy, alkyl, alkenyl, alkynyl, haloalkyl, haloalkenyl, haloalkynyl, alkyloxy, alkenyloxy, alkynyloxy, haloalkyloxy, haloalkenyloxy, haloalkynyloxy, alkylcarbonyl, alkenylcarbonyl, alkynylcarbonyl, haloalkylcarbonyl, haloalkenylcarbonyl, haloalkynylcarbonyl, amino, alkylamino, haloalkylamino, aromatic carbocyclyl optionally substituted with substituent group E, non-aromatic carbocyclyl optionally substituted with substituent group E, aromatic heterocyclyl optionally substituted with substituent group E and non-aromatic heterocyclyl optionally substituted with substituent group E.

In one embodiment of "substituted or unsubstituted imino", imino, methylimino, ethylimino, cyclopropylimino, cyclohexylimino, acetylimino, tetrahydropyranylimino, tetrahydrofuranylimino, morpholinoimino, morpholinylimino, piperidinylimino, piperazinylimino and the like are exemplified.

The term of "substituted or unsubstituted carbamoyl" includes a carbamoyl optionally substituted with the following substituent group I at one or two position(s).

Substituent group I is comprised of hydroxyl, cyano, amino, alkylamino, alkyl, haloalkyl, hydroxyalkyl, alkylcarbonyl, alkylsulfonyl, aromatic carbocyclyl optionally substituted with substituent group E, non-aromatic carbocyclyl optionally substituted with substituent group E, aromatic heterocyclyl optionally substituted with substituent group E, non-aromatic heterocyclyl optionally substituted with substituent group E, aromatic carbocyclyl alkyl optionally substituted with substituent group E, non-aromatic carbocyclyl alkyl optionally substituted with substituent group E, aromatic heterocyclyl alkyl optionally substituted with substituent group E, non-aromatic heterocyclyl alkyl optionally substituted with substituent group E.

In one embodiment of "substituted or unsubstituted carbamoyl", carbamoyl, N-methylcarbamoyl, N,N-dimethylcarbamoyl, N-ethyl-N-methylcarbamoyl, N,N-diethylcarbamoyl, N-n-propylaminocarbamoyl, N-isopropylcarbamoyl, N-morpholinocarbamoyl, N-tetrahydrofuranylcarbamoyl, N-piperidylcarbamoyl, N-tetrahydropyranylcarbamoyl, N-benzylcarbamoyl, N-acetylcarbamoyl, N-methylsulfonylcarbamoyl, N-(2,2,2-trifluoroethyl)carbamoyl, N-(2-hydroxy-1-methylethyl) carbamoyl and the like are exemplified. In another embodiment, carbamoyl, N-methylcarbamoyl, N,N-dimethylcarbamoyl, N-n-propylaminocarbamoyl, N-isopropylcarbamoyl, N-morpholinocarbamoyl, N-tetrahydrofuranylcarbamoyl, N-piperidylcarbamoyl, N-tetrahydropyranylcarbamoyl, N-methylsulfonylcarbamoyl, N-(2,2,2-trifluoroethyl)carbamoyl, N-(2-hydroxy-1-methylethyl)carbamoyl and the like are exemplified.

The term of "substituted or unsubstituted sulfamoyl" includes a sulfamoyl optionally substituted with the above substituent group I at one or two position(s).

In one embodiment of "substituted or unsubstituted sulfamoyl", sulfamoyl, N-methylsulfamoyl, N,N-dimethylsulfamoyl, N-ethyl-N-methylsulfamoyl, N,N-diethylsulfamoyl, N-n-propylaminosulfamoyl, N-isopropylsulfamoyl, N-morpholinosulfamoyl, N-tetrahydrofuranylsulfamoyl, N-piperidylsulfamoyl, N-tetrahydropyranylsulfamoyl, N-benzylsulfamoyl, N-acetylsulfamoyl, N-methylsulfonylsulfamoyl and the like are exemplified. In another embodiment, sulfamoyl, N-methylsulfamoyl, N,N-dimethylsulfamoyl, N-n-propylaminosulfamoyl, N-isopropylsulfamoyl, N-morpholinosulfamoyl, N-tetrahydrofuranylsulfamoyl, N-piperidylsulfamoyl, N-tetrahydropyranylsulfamoyl, N-methylsulfonylsulfamoyl and the like are exemplified.

The substituents on "aromatic carbocycle", "non-aromatic carbocycle", "aromatic heterocycle" and "non-aromatic heterocycle" of "substituted or unsubstituted aromatic carbocyclyl", "substituted or unsubstituted non-aromatic carbocyclyl", "substituted or unsubstituted aromatic heterocyclyl", "substituted or unsubstituted non-aromatic heterocyclyl", "substituted or unsubstituted aromatic carbocyclyl oxy", "substituted or unsubstituted non-aromatic carbocyclyl oxy", "substituted or unsubstituted aromatic heterocyclyl oxy", "substituted or unsubstituted non-aromatic heterocyclyl oxy", "substituted or unsubstituted aromatic carbocyclyl carbonyl", "substituted or unsubstituted non-aromatic carbocyclyl carbonyl", "substituted or unsubstituted aromatic heterocyclyl carbonyl", "substituted or unsubstituted non-aromatic heterocyclyl carbonyl", "substituted or unsubstituted aromatic carbocyclyl oxycarbonyl", "substituted or unsubstituted non-aromatic carbocyclyl oxycarbonyl", "substituted or unsubstituted aromatic heterocyclyl oxycarbonyl", "substituted or unsubstituted non-aromatic heterocyclyl oxycarbonyl", "substituted or unsubstituted aromatic carbocyclyl sulfanyl", "substituted or unsubstituted non-aromatic carbocyclyl sulfanyl", "substituted or unsubstituted aromatic heterocyclyl sulfanyl", "substituted or unsubstituted non-aromatic heterocyclyl sulfanyl", "substituted or unsubstituted aromatic carbocyclyl sulfonyl", "substituted or unsubstituted non-aromatic carbocyclyl sulfonyl", "substituted or unsubstituted aromatic heterocyclyl sulfonyl", and "substituted or unsubstituted non-aromatic heterocyclyl sulfonyl" include the group as follows. An atom at any possible position(s) on the ring can be substituted with one or more substituent(s) selected from the following group.

Substituent: halogen, hydroxy, carboxy, amino, imino, hydroxyamino, hydroxyimino, formyl, carbamoyl, sulfamoyl, sulfanyl, sulfino, sulfo, thioformyl, thiocarboxy, dithiocarboxy, thiocarbamoyl, cyano, nitro, azido, hydrazino, ureido, amidino, guanidino, trialkylsilyl, oxo, alkyl, alkenyl, alkynyl, haloalkyl, hydroxyalkyl, alkyloxy, alkenyloxy, alkynyloxy, haloalkyloxy, alkyloxyalkyl optionally substituted with a halogen at 1 to 3 position(s), alkyloxyalkyloxy optionally substituted with a halogen at 1 to 3 position(s), alkylcarbonyl optionally substituted with a halogen at 1 to 3 position(s), alkenylcarbonyl optionally substituted with a halogen at 1 to 3 position(s), alkynylcarbonyl optionally substituted with a halogen at 1 to 3 position(s), monoalkylamino optionally substituted with substituent group B, dialkylamino optionally substituted with substituent group B, alkylsulfonyl optionally substituted with a halogen at 1 to 3 position(s), alkenylsulfonyl, alkynylsulfonyl, alkylcarbonylamino optionally substituted with a halogen at 1 to 3 position(s), alkylsulfonylamino optionally substituted with a halogen at 1 to 3 position(s), alkylimino optionally substituted with a halogen at 1 to 3 position(s), alkenylimino, alkynylimino, alkylcarbonylimino, alkenylcarbonylimino, alkynylcarbonylimino, alkyloxyimino optionally substituted with substituent group C, alkenyloxyimino, alkynyloxyimino, alkylcarbonyloxy, alkenylcarbonyloxy, alkynylcarbonyloxy, alkyloxycarbonyl, alkenyloxycarbonyl, alkynyloxycarbonyl, alkylsulfanyl, alkenylsulfanyl, alkynylsulfanyl, monoalkylcarbamoyl optionally substituted with substituent group D, dialkylcarbamoyl optionally substituted with substituent group D, monoalkylsulfamoyl optionally substituted with substituent group D and dialkylsulfamoyl optionally substituted with substituent group D.

The substituents of "substituted or unsubstituted alkylene", "substituted or unsubstituted alkenylene" and "substituted or unsubstituted alkynylene" are as defined in the above substituents on the ring.

A "substituted or unsubstituted non-aromatic carbocyclyl" and "substituted or unsubstituted non-aromatic heterocyclyl" can be substituted with "oxo". A group wherein two hydrogen atoms attached to a carbon atom are replaced with oxo as follows is included:

[Chemical Formula 34]

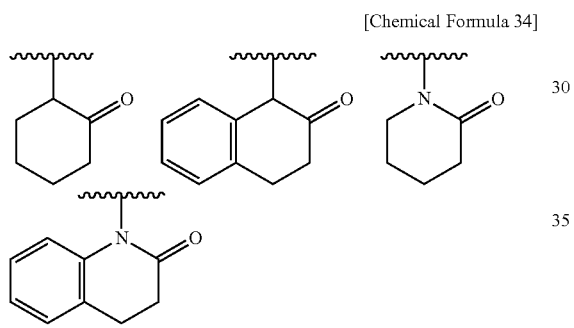

The "non-aromatic carbocycle" and "non-aromatic heterocycle" portion of above "substituted or unsubstituted non-aromatic carbocyclyl oxy", "substituted or unsubstituted non-aromatic heterocyclyl oxy", "substituted or unsubstituted non-aromatic carbocyclyl carbonyl", "substituted or unsubstituted non-aromatic heterocyclyl carbonyl", "substituted or unsubstituted non-aromatic carbocyclyl oxycarbonyl", "substituted or unsubstituted non-aromatic heterocyclyl oxycarbonyl", "substituted or unsubstituted non-aromatic carbocyclyl sulfanyl", "substituted or unsubstituted non-aromatic heterocyclyl sulfanyl", "substituted or unsubstituted non-aromatic carbocyclyl sulfonyl" and "substituted or unsubstituted non-aromatic heterocyclyl sulfonyl" can be substituted with "oxo" as defined above.

The term of "alkylene which may be intervened with one or two heteroatom(s)" of "substituted or unsubstituted alkylene which may be intervened with one or two heteroatom(s)" includes a linear alkylene having one to six carbon atom(s), optionally containing one or two oxygen atom(s), sulfur atom(s) and/or a nitrogen atom(s). For example, —CH$_2$O—, —OCH$_2$—, —CH$_2$CH$_2$O—, —OCH$_2$CH$_2$—, —CH$_2$OCH$_2$—, —CH$_2$S—, —SCH$_2$—, —CH$_2$CH$_2$S—, —SCH$_2$CH$_2$—, —CH$_2$CH$_2$OCH$_2$CH$_2$—, —OCH$_2$CH$_2$O—, —OCH$_2$O—, —NHCH$_2$—, —NHCH$_2$CH$_2$CH$_2$— and the like are exemplified.

The substituents of "substituted or unsubstituted alkylene which may be intervened with one or two heteroatom(s)" include halogen, hydroxyl, alkyl, haloalkyl, alkyloxy, haloalkyloxy and the like. Further, heteroatom(s) intervened with an alkylene may be substituted with the above substituent(s).

The term of "C1-C3 alkylene" includes a linear alkylene having one to three carbon atom(s), and for example, —CH$_2$—, —CH$_2$CH$_2$— and —CH$_2$CH$_2$CH$_2$— are exemplified.

The substituents of "substituted or unsubstituted C1-C3 alkylene" include halogen, hydroxyl, alkyl, haloalkyl, alkyloxy, haloalkyloxy, non-aromatic carbocycle and the like.

The term of "nitrogen-containing non-aromatic heterocycle" includes a 3- to 8-membered non-aromatic heterocycle containing one or more nitrogen atom(s) in the ring. Examples thereof include such as a ring of the formula of

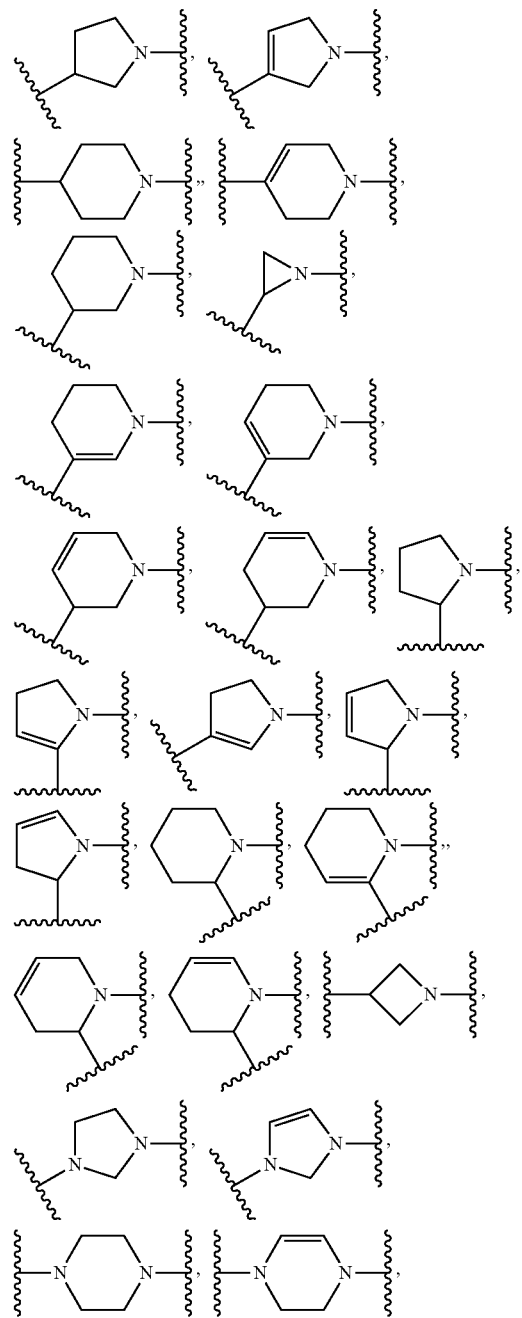

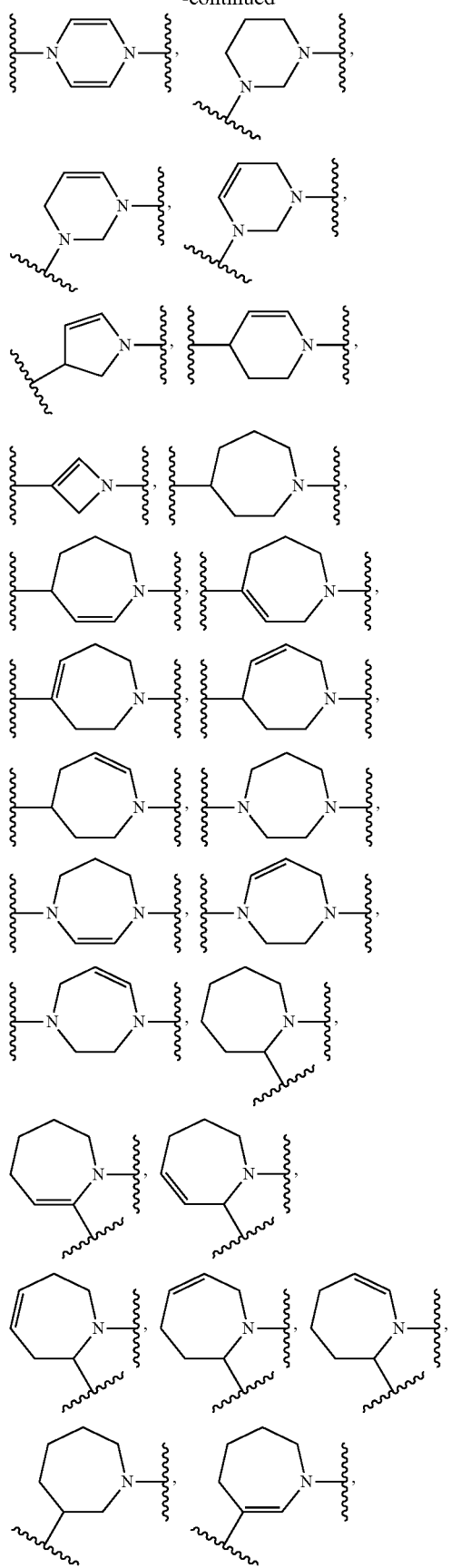
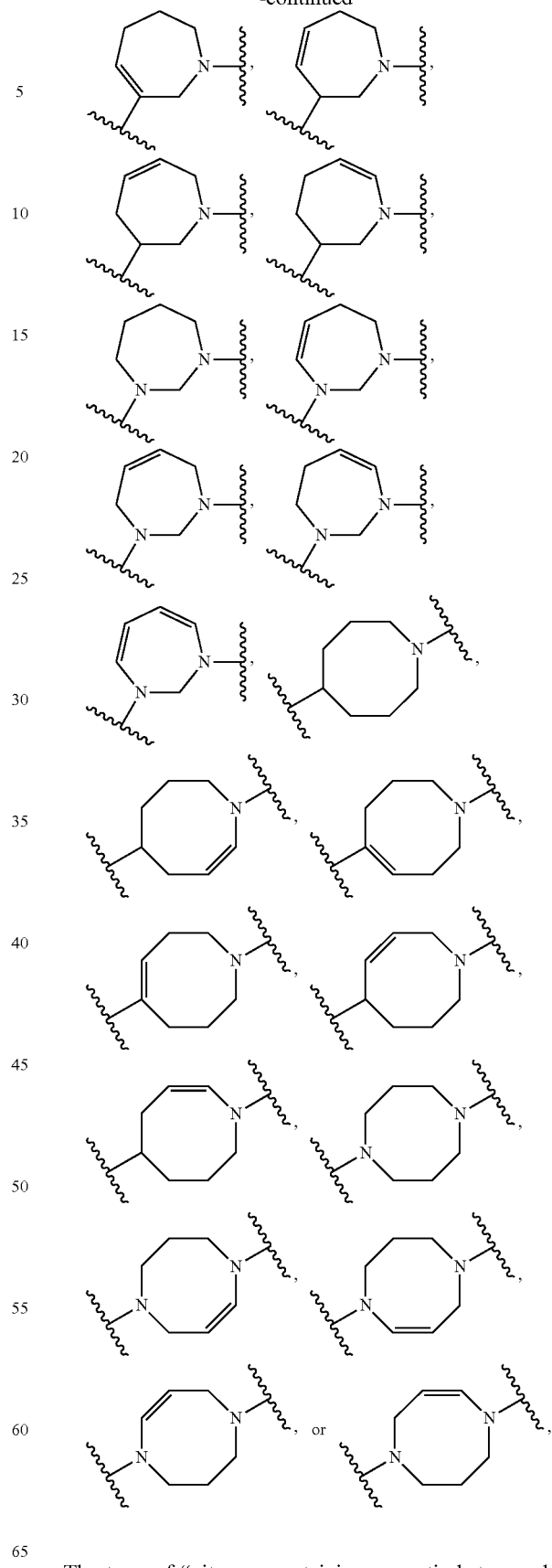
The term of "nitrogen-containing aromatic heterocycle" includes a 5- to 8-membered aromatic heterocycle containing one or more nitrogen atom(s) in the ring. In some instances, the heterocycle contains further an oxygen atom and/or a sulfur atom in the ring. For example, pyrrolyl(e.g., 1-pyrrolyl, 2-pyrrolyl, 3-pyrrolyl), imidazolyl(e.g., 2-imidazolyl, 4-imidazolyl), pyrazolyl (e.g., 1-pyrazolyl, 3-pyrazolyl), isothiazolyl(e.g., 3-isothiazolyl), isoxazolyl(e.g., 3-isoxazolyl), oxazolyl(e.g., 2-oxazolyl), thiazolyl(e.g., 2-thiazolyl), pyridyl(e.g., 2-pyridyl, 3-pyridyl, 4-pyridyl), pyrazinyl(e.g., 2-pyrazinyl), pyrimidinyl(e.g., 2-pyrimidinyl, 4-pyrimidinyl), pyridazinyl(e.g., 3-pyridazinyl), tetrazolyl(e.g., 1H-tetrazolyl), oxadiazolyl(e.g., 1,3,4-oxadiazolyl) and thiadiazolyl (e.g., 1,3,4-thiadiazolyl) and the like are exemplified.

The term of "carbocycle" includes the above "aromatic carbocycle" and "non-aromatic carbocycle".

In one embodiment of "carbocycle", a 3- to 6-membered non-aromatic carbocycle is exemplified. In another embodiment, cyclopropane and cyclobutane and the like are exemplified.

The term of "heterocycle" includes the above "aromatic heterocycle" and "non-aromatic heterocycle".

In one embodiment of "heterocycle", a 3- to 6-membered non-aromatic heterocycle is exemplified. In another embodiment, oxirane and oxetane and the like are exemplified.

The term of "carboxy equivalent" means a biological equivalent and includes substituents having the same polar effect as a carboxy group. Examples thereof include such as —CONHCN, —CONHSO$_2$Me, —CONHOH, —CONHOMe, —CONHOt-Bu, —CONHOCH$_2$Ph, —SO$_3$H, —SO$_2$NH$_2$, —SO$_2$NHMe, —NHCONH$_2$, —NHCONMe$_2$, —P(=O)(OH)$_2$, —P(=O)(OH)(OEt), —P(=O)(OH)NH$_2$, —P(=O)(OH)NHMe, —CONHSO$_2$Ph, —SO$_2$NHCOMe, —SO$_2$NHCOPh, and the formulae of:

[Chemical Formula 36]

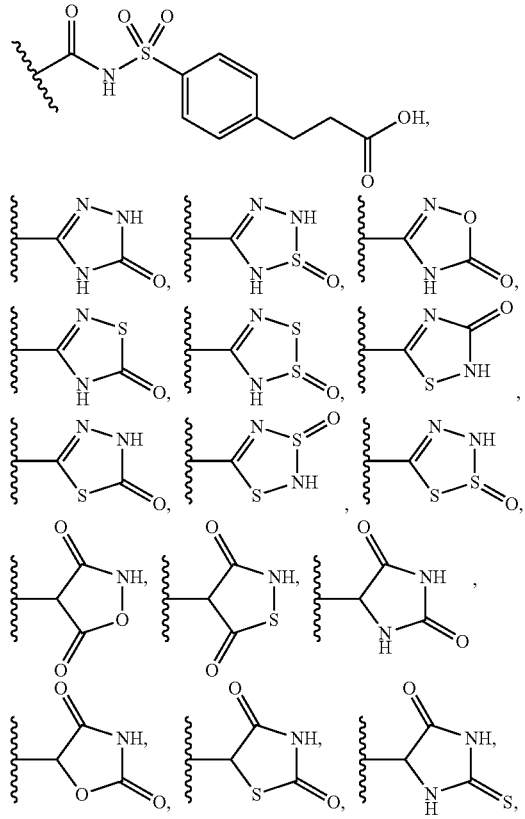

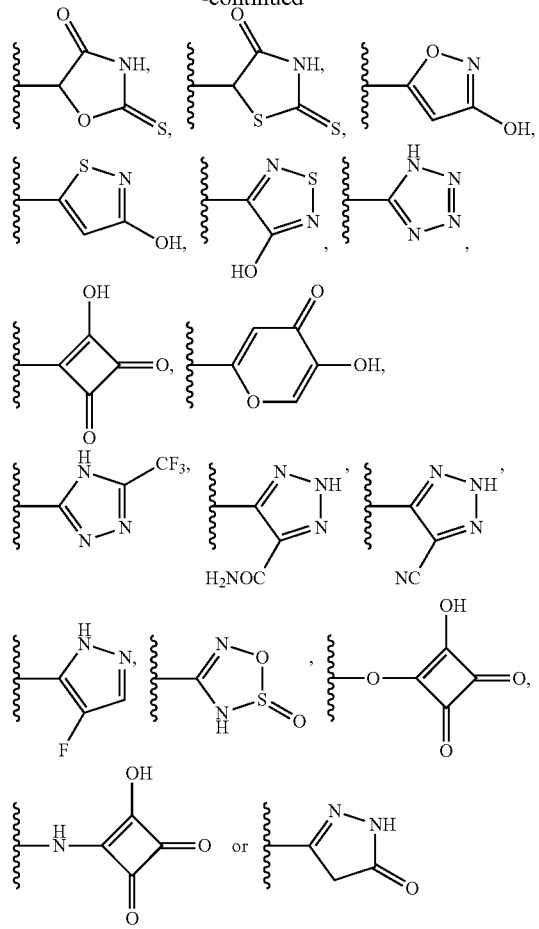

In one embodiment of "carboxy equivalent", —CONHCN, —CONHSO$_2$Me, —CONHOH, —SO$_3$H and the formulae of

[Chemical Formula 37]

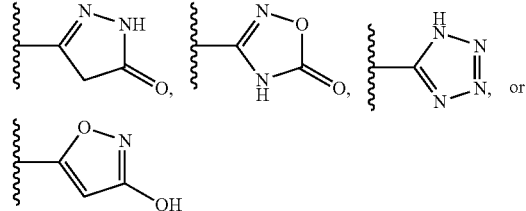

are exemplified.

In one embodiment of "carboxy equivalent", —CONHCN, —CONHSO$_2$Me, —CONHOH and the formula of

[Chemical Formula 38]

are exemplified.

In the compounds represented by the formula (I), one embodiment of "—$X^1$=$X^2$—$X^3$=$X^4$—", —$X^5$=, $R^1$, $R^2$, $R^3$, $R^4$, $R^5$, $R^6$, $R^7$, $R^8$, $R^{10}$, -L-, n, p, q, the ring A, and the ring B are shown below.

In one embodiment, "—$X^1$=$X^2$—$X^3$=$X^4$—" is —C($R^1$)=C($R^2$)—C($R^3$)=C($R^4$)—, —N=C($R^2$)—C($R^3$)=C($R^4$)—, —C($R^1$)=N—C($R^3$)=C($R^4$)—, —C($R^1$)=C($R^2$)—N=C($R^4$)—, —C($R^1$)=C($R^2$)—C($R^3$)=N—, —N=C($R^2$)—N=C($R^4$)—, —N=C($R^2$)—C($R^3$)=N—, —C($R^1$)=N—N=C($R^4$)—, —C($R^1$)=N—C($R^3$)=N— or —C($R^1$)=C($R^2$)—N=N—.

In some embodiment, "—$X^1$=$X^2$—$X^3$=$X^4$-" is —C($R^1$)=C($R^2$)—C($R^3$)=C($R^4$)—, —N=C($R^2$)—C($R^3$)=C($R^4$)—, —C($R^1$)=N—C($R^3$)=C($R^4$)—, —C($R^1$)=C($R^2$)—N=C($R^4$)— or —C($R^1$)=C($R^2$)—C($R^3$)=N—

In another embodiment, "—$X^1$=$X^2$—$X^3$=$X^4$—" is —C($R^1$)=C($R^2$)—C($R^3$)=C($R^4$)—.

In one embodiment, "—$X^5$=" is —N= or —C($R^{12}$)=.

In some embodiment, "—$X^5$=" is —N=.

In another embodiment, "—$X^5$=" is —C(H)= or —C(CH$_3$)=.

In one embodiment, "$R^1$" is a hydrogen atom, halogen, substituted or unsubstituted alkyl, or substituted or unsubstituted alkyloxy.

In some embodiment, "R" is a hydrogen atom or halogen.

In another embodiment, "$R^1$" is a hydrogen atom.

In $R^1$, the substituents of "substituted or unsubstituted alkyl" or "substituted or unsubstituted alkyloxy" include halogen.

In one embodiment, "$R^2$" is a hydrogen atom, halogen, cyano, substituted or unsubstituted alkyl, substituted or unsubstituted alkyloxy, substituted or unsubstituted non-aromatic carbocyclyl, substituted or unsubstituted aromatic heterocyclyl, or substituted or unsubstituted non-aromatic heterocyclyl.

In some embodiment, "$R^2$" is a hydrogen atom, halogen, or substituted or unsubstituted alkyl.

In another embodiment, "$R^2$" is a hydrogen atom, halogen or methyl.

In $R^2$, the substituents of "substituted or unsubstituted alkyl" or "substituted or unsubstituted alkyloxy" include halogen.

In $R^2$, the substituents of "substituted or unsubstituted non-aromatic carbocyclyl", "substituted or unsubstituted aromatic heterocyclyl" or "substituted or unsubstituted non-aromatic heterocyclyl" include alkyl.

In one embodiment, "$R^3$" is a hydrogen atom, halogen, cyano, substituted or unsubstituted alkyl, or substituted or unsubstituted alkyloxy.

In some embodiment, "$R^3$" is a hydrogen atom, halogen, or substituted or unsubstituted alkyl.

In another embodiment, "$R^3$" is a hydrogen atom or halogen.

In $R^3$, the substituents of "substituted or unsubstituted alkyl" or "substituted or unsubstituted alkyloxy" include halogen.

In one embodiment, "$R^4$" is a hydrogen atom, halogen, cyano, substituted or unsubstituted alkyl, or substituted or unsubstituted alkyloxy.

In some embodiment, "$R^4$" is a hydrogen atom or halogen.

In another embodiment, "$R^4$" is a hydrogen atom.

In $R^4$, the substituents of "substituted or unsubstituted alkyl" or "substituted or unsubstituted alkyloxy" include halogen.

In one embodiment, $R^6$ is halogen, hydroxy, cyano, substituted or unsubstituted alkyl, substituted or unsubstituted alkenyl, substituted or unsubstituted alkyloxy, substituted or unsubstituted carbamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted non-aromatic carbocyclyl oxy, or substituted or unsubstituted non-aromatic heterocyclyl oxy;

two of $R^6$ attached to the same ring constituent carbon atom are taken together to form a carbocycle containing the above ring constituent carbon atom, a heterocycle containing the above ring constituent carbon atom, oxo, or the formula: =C$R^{6a}R^{6b}$, wherein $R^{6a}$ and $R^{6b}$ are each independently a hydrogen atom, halogen, or substituted or unsubstituted alkyl; or two of $R^6$ attached to the different ring constituent carbon atoms are taken together to form substituted or unsubstituted alkylene which may be intervened with one or two heteroatom(s).

In some embodiment, $R^6$ is halogen, hydroxy, cyano, substituted or unsubstituted alkyl, substituted or unsubstituted alkenyl, substituted or unsubstituted alkyloxy, substituted or unsubstituted non-aromatic carbocyclyl, substituted or unsubstituted non-aromatic heterocyclyl, substituted or unsubstituted non-aromatic carbocyclyl oxy, or substituted or unsubstituted non-aromatic heterocyclyl oxy; two of $R^6$ attached to the same ring constituent carbon atom are taken together to form a carbocycle containing the above ring constituent carbon atom or a heterocycle containing the above ring constituent carbon atom; or two of $R^6$ attached to the different ring constituent carbon atoms are taken together to form substituted or unsubstituted alkylene which may be intervened with one or two heteroatom(s).

In some embodiment, $R^6$ is halogen, hydroxy, cyano, substituted or unsubstituted alkyl, substituted or unsubstituted alkenyl, substituted or unsubstituted non-aromatic carbocyclyl, substituted or unsubstituted non-aromatic heterocyclyl, or substituted or unsubstituted non-aromatic carbocyclyl oxy.

In some embodiment, $R^6$ is halogen, cyano, or substituted or unsubstituted alkyl.

In $R^6$, the substituents of "substituted or unsubstituted alkyl", "substituted or unsubstituted alkenyl", "substituted or unsubstituted alkyloxy", "substituted or unsubstituted carbamoyl", "substituted or unsubstituted aromatic carbocyclyl", "substituted or unsubstituted non-aromatic carbocyclyl", "substituted or unsubstituted aromatic heterocyclyl", "substituted or unsubstituted non-aromatic heterocyclyl", "substituted or unsubstituted non-aromatic carbocyclyl oxy", or "substituted or unsubstituted non-aromatic heterocyclyl oxy" include halogen, hydroxy, cyano, alkenyl, alkyloxy, haloalkyloxy, alkylimino optionally substituted with a halogen, alkyloxyimino optionally substituted with substituent group C, or aromatic heterocyclyl.

In some embodiment, the above substituents of $R^6$ include halogen, hydroxy, cyano, alkenyl, alkyloxyimino optionally substituted with substituent group C, or aromatic heterocyclyl.

In some embodiment, the above substituents of $R^6$ include halogen or cyano.

In some embodiment, $R^6$ is a fluorine atom or methyl.

In some embodiment, $R^6$ is methyl.

In one embodiment, $R^7$ is halogen, substituted or unsubstituted alkyloxy, substituted or unsubstituted non-aromatic carbocyclyl, or substituted or unsubstituted non-aromatic carbocyclyl oxy.

In some embodiment, $R^7$ is substituted or unsubstituted alkyloxy, or substituted or unsubstituted non-aromatic carbocyclyl.

In another embodiment, $R^7$ is substituted or unsubstituted alkyloxy.

In $R^7$, the substituents of "substituted or unsubstituted alkyloxy", "substituted or unsubstituted non-aromatic carbocyclyl", or "substituted or unsubstituted non-aromatic carbocyclyl oxy" include halogen.

In some embodiment, $R^7$ is methyloxy, ethyloxy, isopropyloxy, difluoromethyloxy, or cyclopropyl.

In some embodiment, $R^7$ is ethyloxy, isopropyloxy or difluoromethyloxy.

In one embodiment, $R^8$ is halogen, cyano, amino, substituted or unsubstituted alkyl, substituted or unsubstituted alkenyl, substituted or unsubstituted alkynyl, or substituted or unsubstituted alkyloxy.

In some embodiment, $R^8$ is halogen, cyano, or substituted or unsubstituted alkyl.

In some embodiment, $R^8$ is halogen or cyano.

In $R^8$, the substituents of "substituted or unsubstituted alkyl", "substituted or unsubstituted alkenyl", "substituted or unsubstituted alkynyl" or "substituted or unsubstituted alkyloxy" include halogen.

In one embodiment, $R^9$ is carboxy.

In one embodiment, $R^{10}$ is a hydrogen atom, halogen, cyano, substituted or unsubstituted alkyl, or substituted or unsubstituted alkyloxy.

In some embodiment, $R^{10}$ is a hydrogen atom, halogen, cyano, or substituted or unsubstituted alkyl.

In some embodiment, $R^{10}$ is a hydrogen atom, halogen or cyano.

In another embodiment, $R^{10}$ is a hydrogen atom.

In $R^{10}$, the substituents of "substituted or unsubstituted alkyl" or "substituted or unsubstituted alkyloxy" include halogen.

In one embodiment, n is 1 or 2.
In another embodiment, n is 1.
In one embodiment, p is 1.
In one embodiment, q is 0 or 1.
In one embodiment, -L- is substituted or unsubstituted methylene, or substituted or unsubstituted ethylene.
In some embodiment, -L- is methylene.
In -L-, the substituents of "substituted or unsubstituted methylene" or "substituted or unsubstituted ethylene" include halogen, hydroxy, alkyl, alkyloxy, haloalkyloxy or non-aromatic carbocycle.

In one embodiment, the ring A is the formula:

[Chemical Formula 39]

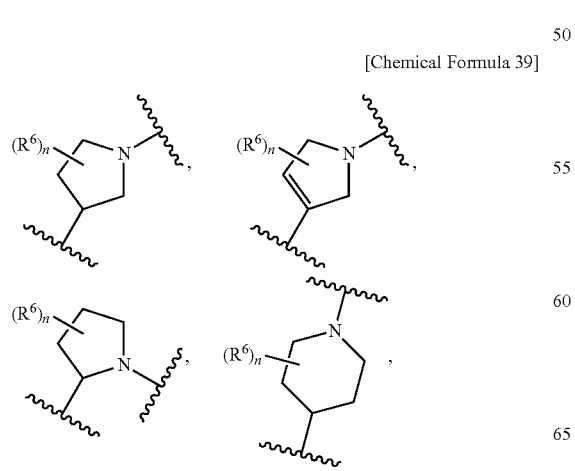

-continued

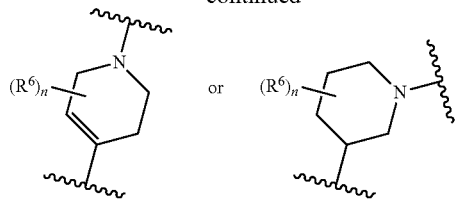

wherein $R^6$ and n are as defined in above 1).
In some embodiment, the ring A is the formula:

[Chemical Formula 40]

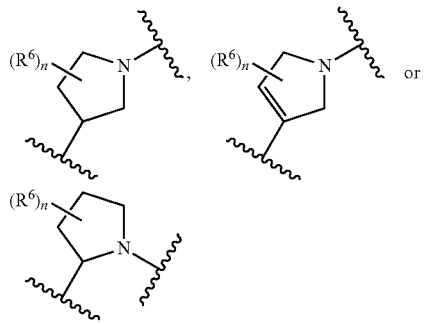

wherein $R^6$ and n are as defined in above 1).
In some embodiment, the ring A is the formula:

[Chemical Formula 41]

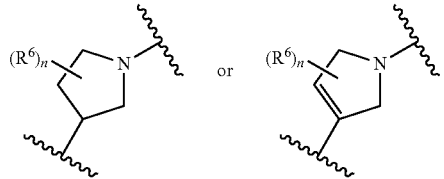

wherein $R^6$ and n are as defined above 1).
In some embodiment, the ring A is the formula:

[Chemical Formula 42]

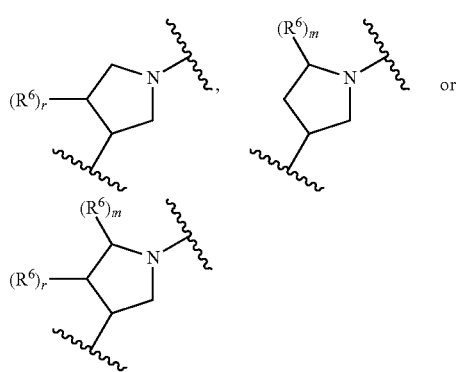

wherein $R^6$ is as defined above; r and m are each independently 0, 1, or 2; r+m≤3.
In some embodiment, the ring B represented by the formula:

[Chemical Formula 43]
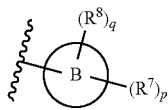
wherein R⁷, R⁸, p and q are as defined in above 1), is a group represented by the formula:
[Chemical Formula 44]
(b-1) 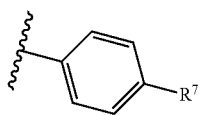
(b-2) 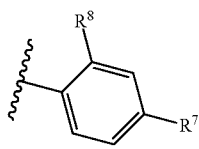
(b-3) 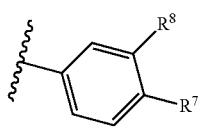
(b-4) 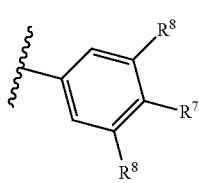
(b-5) 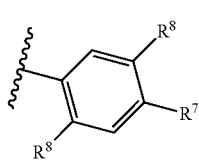
(b-6) 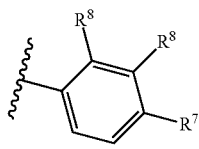
(b-7) 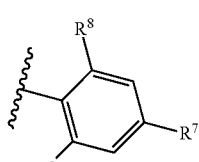
(b-8) 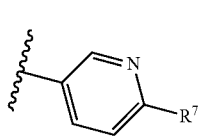
(b-9) 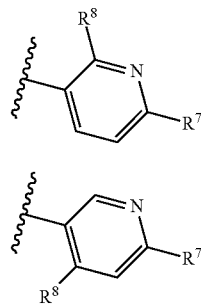
(b-10) 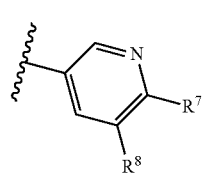
(b-11) 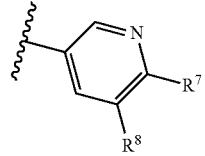
(b-12) 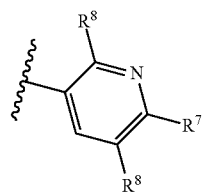
(b-13) 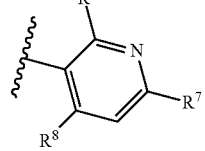
(b-14) 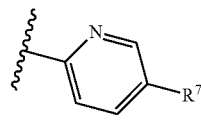
(b-15) 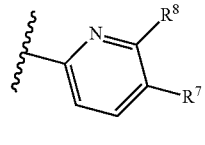
(b-16) 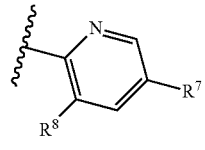
(b-17) 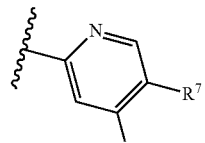
(b-18) 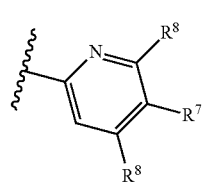

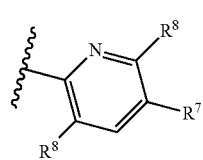
(b-19)
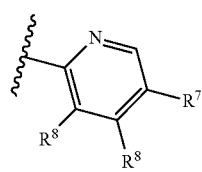
(b-20)
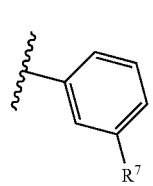
(b-21)
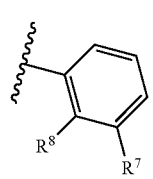
(b-22)
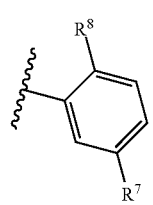
(b-23)
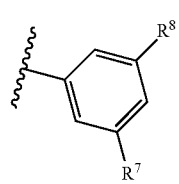
(b-24)
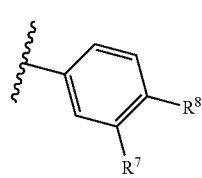
(b-25)
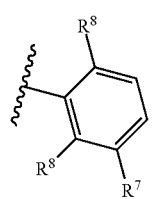
(b-26)
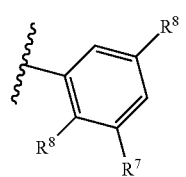
(b-27)
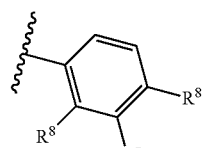
(b-28)
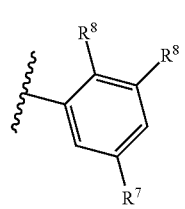
(b-29)
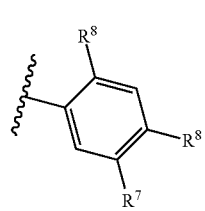
(b-30)
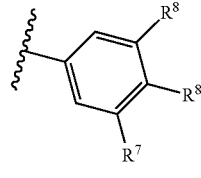
(b-31)
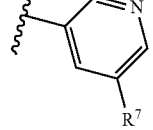
(b-32)
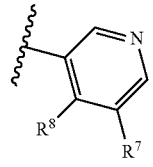
(b-33)
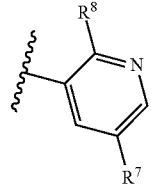
(b-34)
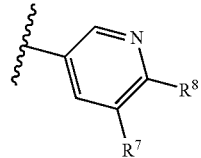
(b-35)

-continued
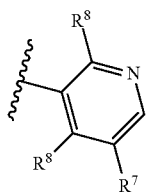
(b-36)
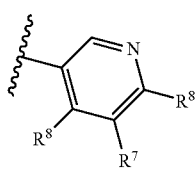
(b-37)
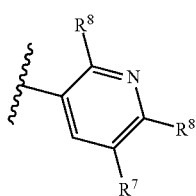
(b-38)
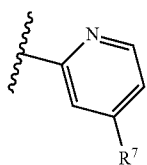
(b-39)
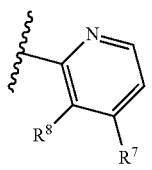
(b-40)
[Chemical Formula 45]
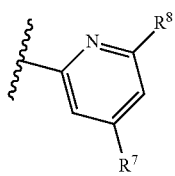
(b-41)
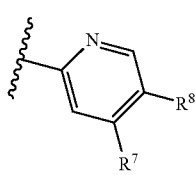
(b-42)
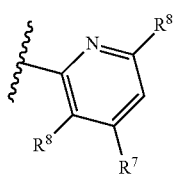
(b-43)
-continued
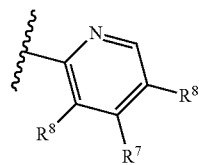
(b-44)
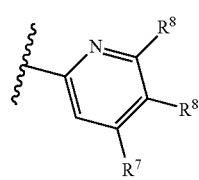
(b-45)
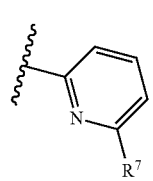
(b-46)
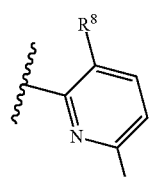
(b-47)
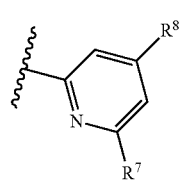
(b-48)
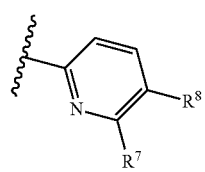
(b-49)
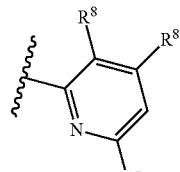
(b-50)
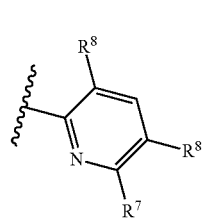
(b-51)

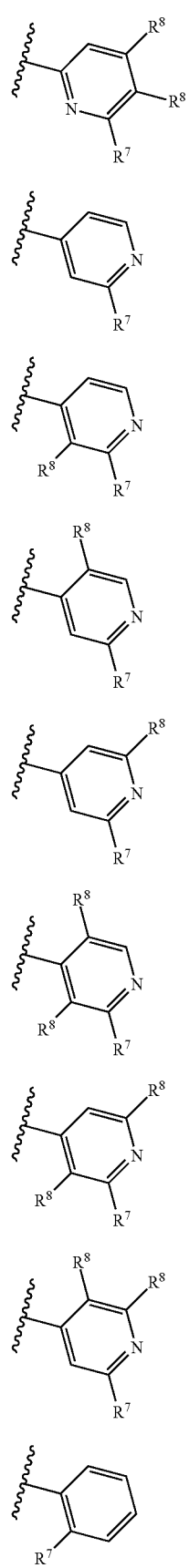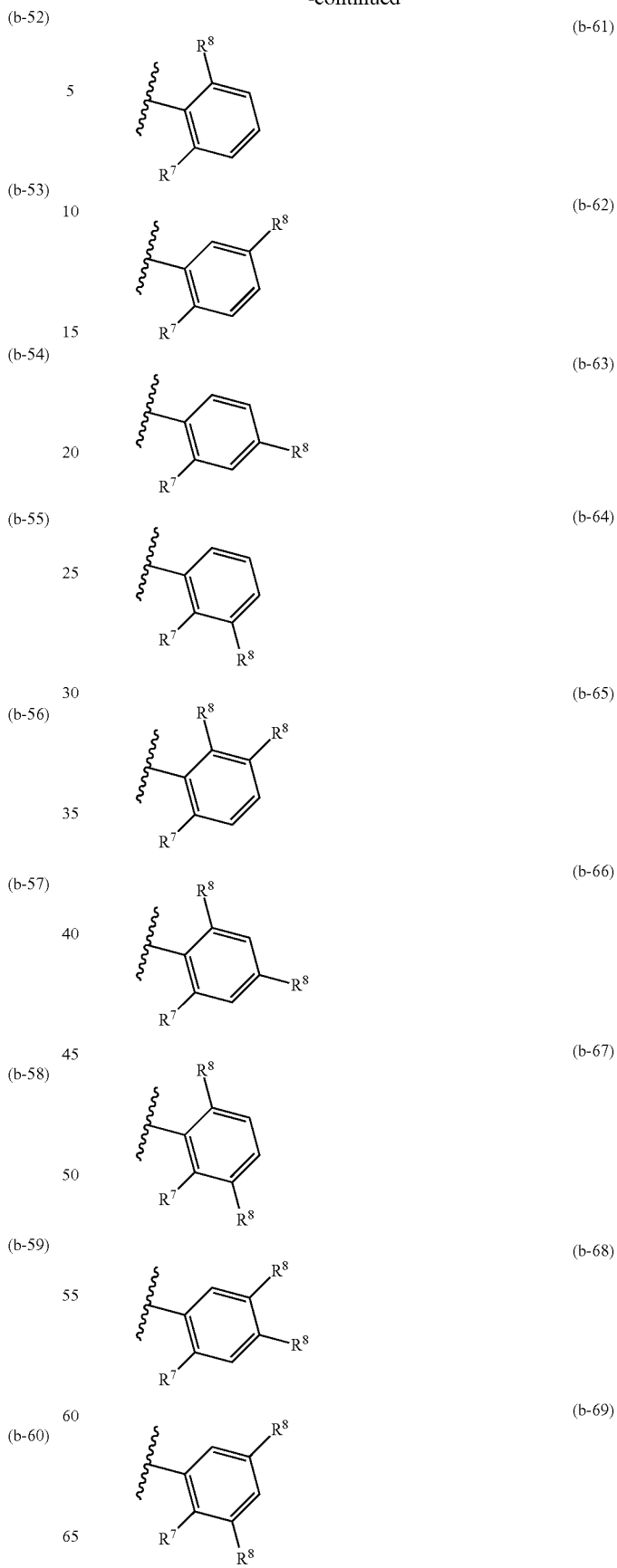

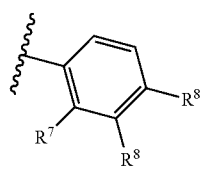 (b-70)
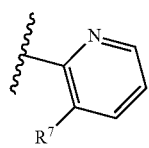 (b-71)
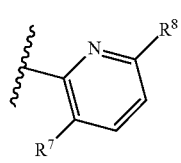 (b-72)
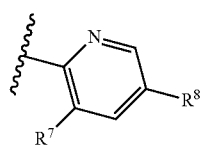 (b-73)
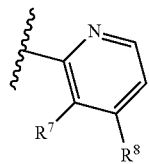 (b-74)
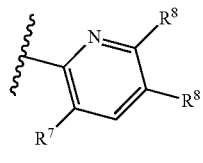 (b-75)
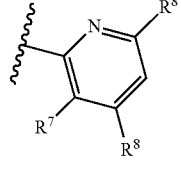 (b-76)
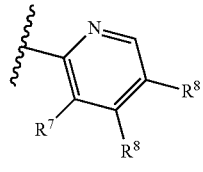 (b-77)
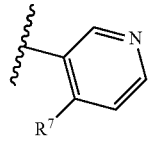 (b-78)
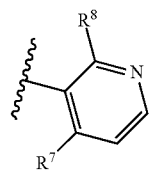 (b-79)
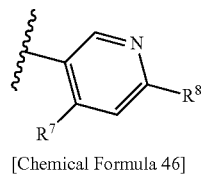 (b-80)
[Chemical Formula 46]
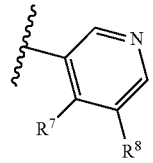 (b-81)
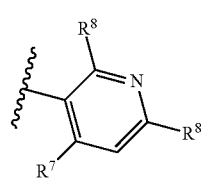 (b-82)
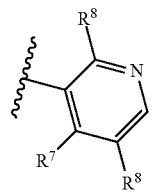 (b-83)
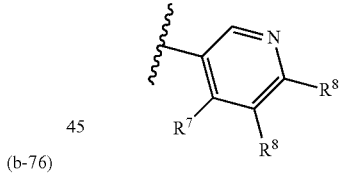 (b-84)
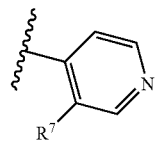 (b-85)
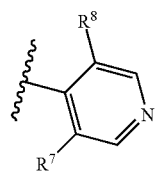 (b-86)
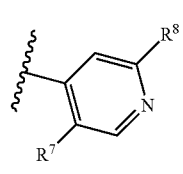 (b-87)

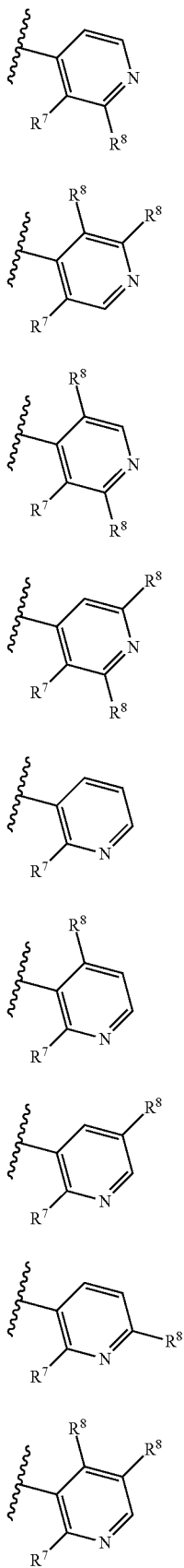
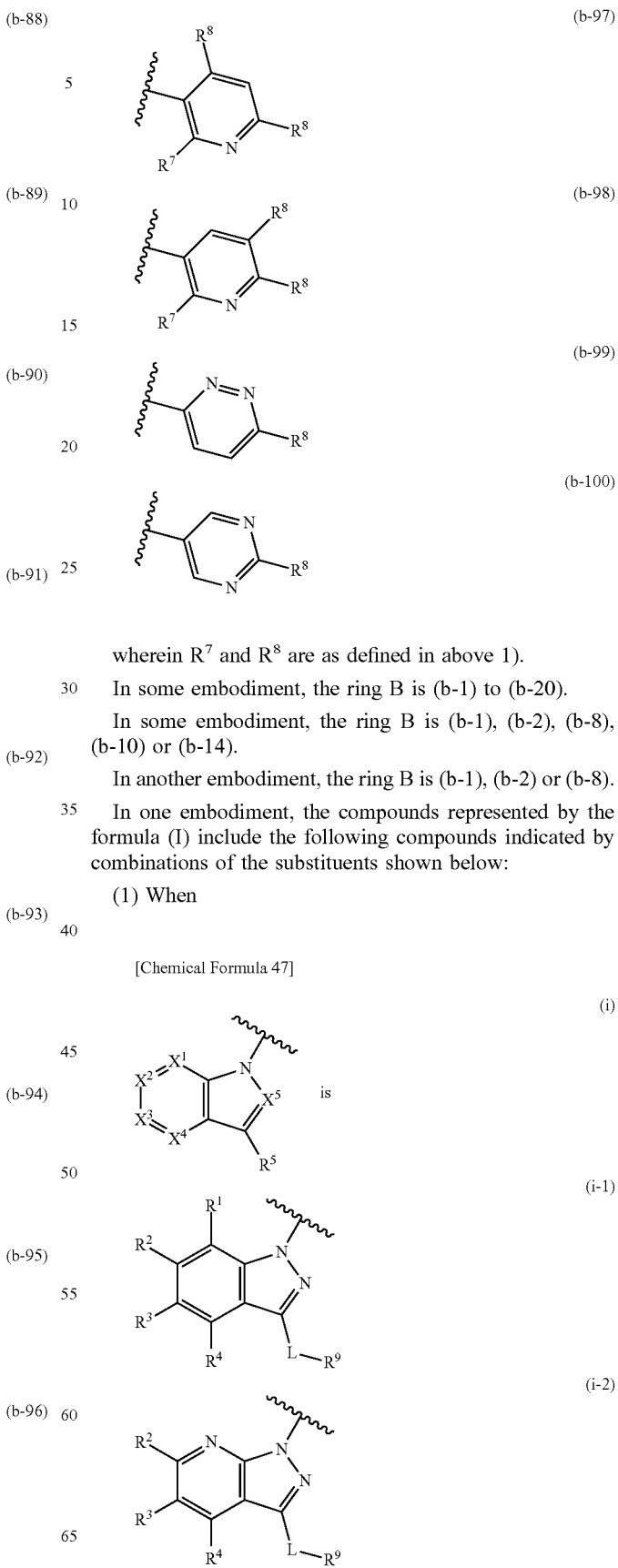
wherein $R^7$ and $R^8$ are as defined in above 1).
In some embodiment, the ring B is (b-1) to (b-20).
In some embodiment, the ring B is (b-1), (b-2), (b-8), (b-10) or (b-14).
In another embodiment, the ring B is (b-1), (b-2) or (b-8).
In one embodiment, the compounds represented by the formula (I) include the following compounds indicated by combinations of the substituents shown below:
(1) When
[Chemical Formula 47]

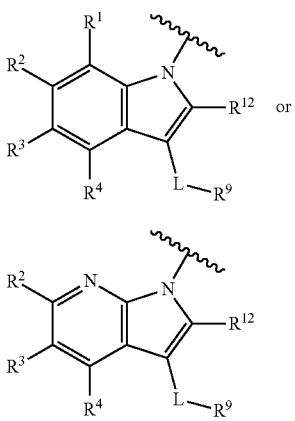

wherein, $R^1$ is a hydrogen atom or halogen; $R^2$ and $R^3$ are each independently a hydrogen atom, halogen, or substituted or unsubstituted alkyl; $R^4$ is a hydrogen atom; -L- is substituted or unsubstituted methylene; $R^9$ is carboxy; $R^{12}$ is a hydrogen atom or methyl, a compound wherein (i) is (i-1) (hereinafter referred to as I-1);

a compound wherein (i) is (i-2) (hereinafter referred to as I-2);

a compound wherein (i) is (i-3) (hereinafter referred to as I-3);

a compound wherein (i) id (i-4) (hereinafter referred to as I-4);

(2) When the ring A is

[Chemical Formula 48]

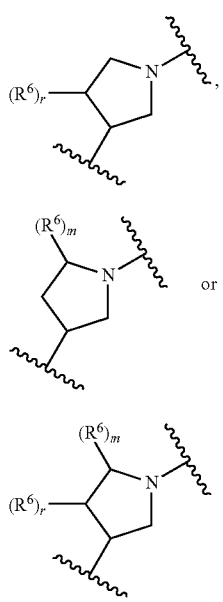

wherein, $R^6$ is as defined in above 1); m and r are each independently 1 or 2, and m+r is 1, 2, or 3, a compound wherein the ring A is (a-1), (a-2), or (a-3) (hereinafter referred to as A-1);

a compound wherein ring A is (a-1) or (a-2) (hereinafter referred to as A-2);

(3) a compound wherein $R^6$ is each independently halogen, hydroxy, cyano, substituted or unsubstituted alkyl, substituted or unsubstituted alkenyl, substituted or unsubstituted alkyloxy, substituted or unsubstituted non-aromatic carbocyclyl, substituted or unsubstituted non-aromatic heterocyclyl, substituted or unsubstituted non-aromatic carbocyclyl oxy, or substituted or unsubstituted non-aromatic heterocyclyl oxy; or two of $R^6$ attached to the same ring constituent carbon atom are taken together to form a carbocycle containing the above ring constituent carbon atom, a heterocycle containing the above ring constituent carbon atom, oxo, or the formula: $=CR^{6a}R^{6b}$, wherein $R^{6a}$ and $R^{6b}$ are a hydrogen atom, cyano, halogen, or substituted or unsubstituted alkyl; or two of $R^6$ attached to the different ring constituent carbon atoms are taken together to form substituted or unsubstituted alkylene which may be intervened with one or two heteroatom(s) (hereinafter referred to as R6-1);

a compound wherein $R^6$ is each independently halogen, hydroxy, cyano, substituted or unsubstituted alkyl, substituted or unsubstituted alkenyl, substituted or unsubstituted non-aromatic carbocyclyl, substituted or unsubstituted non-aromatic heterocyclyl, substituted or unsubstituted non-aromatic carbocyclyl oxy, or substituted or unsubstituted non-aromatic heterocyclyl oxy; or two of $R^6$ attached to the same ring constituent carbon atom are taken together to form a carbocycle containing the above ring constituent carbon atom, a heterocycle containing the above ring constituent carbon atom, or the formula: $=CR^{6a}R^{6b}$, wherein $R^{6a}$ and $R^{6b}$ are a hydrogen atom, halogen, or substituted or unsubstituted alkyl; or two of $R^6$ attached to the different ring constituent carbon atoms are taken together to form substituted or unsubstituted alkylene which may be intervened with one or two heteroatom(s) (hereinafter referred to as R6-2);

a compound wherein $R^6$ is each independently halogen, cyano, or substituted or unsubstituted alkyl (hereinafter referred to as R6-3);

a compound wherein $R^6$ is each independently halogen, cyano, or methyl (hereinafter referred to as R6-4);

(4) a compound wherein the ring B is (b-1), (b-2) or (b-8) (hereinafter referred to as B-1);

a compound wherein the ring B is (b-1) or (b-8) (hereinafter referred to as B-2);

(5) a compound wherein $R^7$ is halogen, substituted or unsubstituted alkyloxy, or substituted or unsubstituted non-aromatic carbocyclyl (hereinafter referred to as R7-1);

a compound wherein $R^7$ is substituted or unsubstituted alkyloxy, or substituted or unsubstituted non-aromatic carbocyclyl (hereinafter referred to as R7-2);

(6) a compound wherein $R^8$ is each independently halogen, cyano, nitro, amino, substituted or unsubstituted alkyl, substituted or unsubstituted alkenyl, substituted or unsubstituted alkynyl, or substituted or unsubstituted alkyloxy (hereinafter referred to as R8-1);

a compound wherein $R^8$ is each independently halogen, cyano, substituted or unsubstituted alkyl, or substituted or unsubstituted alkyloxy (hereinafter referred to as R8-2);

a compound wherein $R^8$ is each independently halogen or cyano (hereinafter referred to as R8-3); and compounds wherein the combinations of i, the ring A, $R^6$, the ring B, $R^7$ and $R^8$ (I, A, $R^6$, B, $R^7$, $R^8$) are as shown below:

(I, A, R6, B, R7, R8)=(I-1, A-1, R6-1, B-1, R7-1, R8-1), (I-1, A-1, R6-1, B-1, R7-1, R8-2), (I-1, A-1, R6-1, B-1, R7-1, R8-3), (I-1, A-1, R6-1, B-1, R7-2, R8-1), (I-1, A-1, R6-1, B-1, R7-2, R8-2), (I-1, A-1, R6-1, B-1, R7-2, R8-3), (I-1, A-1, R6-1, B-2, R7-1, R8-1), (I-1, A-1, R6-1, B-2, R7-1, R8-2), (I-1, A-1, R6-1, B-2, R7-1, R8-3), (I-1, A-1, R6-1, B-2, R7-2, R8-1), (I-1, A-1, R6-1, B-2, R7-2, R8-2), (I-1, A-1, R6-1, B-2, R7-2, R8-3), (I-1, A-1, R6-2, B-1, R7-1, R8-1), (I-1, A-1, R6-2, B-1, R7-1, R8-2), (I-1, A-1, R6-2, B-1, R7-1, R8-3), (I-1, A-1, R6-2, B-1, R7-2, R8-1), (I-1, A-1, R6-2, B-1, R7-2, R8-2), (I-1, A-1, R6-2, B-1, R7-2, R8-3), (I-1, A-1, R6-2, B-2, R7-1, R8-1), (I-1, A-1, R6-2, B-2, R7-1, R8-2), (I-1, A-1, R6-2, B-2, R7-1, R8-3), (I-1, A-1, R6-2, B-2, R7-2, R8-1), (I-1, A-1, R6-2, B-2, R7-2, R8-2), (I-1, A-1, R6-2, B-2, R7-2, R8-3), (I-1, A-1, R6-3, B-1, R7-1, R8-1), (I-1, A-1, R6-3, B-1, R7-1, R8-2), (I-1, A-1, R6-3, B-1, R7-1, R8-3), (I-1, A-1, R6-3, B-1, R7-2, R8-1), (I-1, A-1, R6-3, B-1, R7-2, R8-2), (I-1, A-1, R6-3, B-1, R7-2, R8-3), (I-1, A-1, R6-3, B-2, R7-1, R8-1), (I-1, A-1, R6-3, B-2, R7-1, R8-2), (I-1, A-1, R6-3, B-2, R7-1, R8-3), (I-1, A-1, R6-3, B-2, R7-2, R8-1), (I-1, A-1, R6-3, B-2, R7-2, R8-2), (I-1, A-1, R6-3, B-2, R7-2, R8-3), (I-1, A-1, R6-4, B-1, R7-1, R8-1), (I-1, A-1, R6-4, B-1, R7-1, R8-2), (I-1, A-1, R6-4, B-1, R7-1, R8-3), (I-1, A-1, R6-4, B-1, R7-2, R8-1), (I-1, A-1, R6-4, B-1, R7-2, R8-2), (I-1, A-1, R6-4, B-1, R7-2, R8-3), (I-1, A-1, R6-4, B-2, R7-1, R8-1), (I-1, A-1, R6-4, B-2, R7-1, R8-2), (I-1, A-1, R6-4, B-2, R7-1, R8-3), (I-1, A-1, R6-4, B-2, R7-2, R8-1), (I-1, A-1, R6-4, B-2, R7-2, R8-2), (I-1, A-1, R6-4, B-2, R7-2, R8-3), (I-1, A-2, R6-1, B-1, R7-1, R8-1), (I-1, A-2, R6-1, B-1, R7-1, R8-2), (I-1, A-2, R6-1, B-1, R7-1, R8-3), (I-1, A-2, R6-1, B-1, R7-2, R8-1), (I-1, A-2, R6-1, B-1, R7-2, R8-2), (I-1, A-2, R6-1, B-1, R7-2, R8-3), (I-1, A-2, R6-1, B-2, R7-1, R8-1), (I-1, A-2, R6-1, B-2, R7-1, R8-2), (I-1, A-2, R6-1, B-2, R7-1, R8-3), (I-1, A-2, R6-1, B-2, R7-2, R8-1), (I-1, A-2, R6-1, B-2, R7-2, R8-2), (I-1, A-2, R6-1, B-2, R7-2, R8-3), (I-1, A-2, R6-2, B-1, R7-1, R8-1), (I-1, A-2, R6-2, B-1, R7-1, R8-2), (I-1, A-2, R6-2, B-1, R7-1, R8-3), (I-1, A-2, R6-2, B-1, R7-2, R8-1), (I-1, A-2, R6-2, B-1, R7-2, R8-2), (I-1, A-2, R6-2, B-1, R7-2, R8-3), (I-1, A-2, R6-2, B-2, R7-1, R8-1), (I-1, A-2, R6-2, B-2, R7-1, R8-2), (I-1, A-2, R6-2, B-2, R7-1, R8-3), (I-1, A-2, R6-2, B-2, R7-2, R8-1), (I-1, A-2, R6-2, B-2, R7-2, R8-2), (I-1, A-2, R6-2, B-2, R7-2, R8-3), (I-1, A-2, R6-3, B-1, R7-1, R8-1), (I-1, A-2, R6-3, B-1, R7-1, R8-2), (I-1, A-2, R6-3, B-1, R7-1, R8-3), (I-1, A-2, R6-3, B-1, R7-2, R8-1), (I-1, A-2, R6-3, B-1, R7-2, R8-2), (I-1, A-2, R6-3, B-1, R7-2, R8-3), (I-1, A-2, R6-3, B-2, R7-1, R8-1), (I-1, A-2, R6-3, B-2, R7-1, R8-2), (I-1, A-2, R6-3, B-2, R7-1, R8-3), (I-1, A-2, R6-3, B-2, R7-2, R8-1), (I-1, A-2, R6-3, B-2, R7-2, R8-2), (I-1, A-2, R6-3, B-2, R7-2, R8-3), (I-1, A-2, R6-4, B-1, R7-1, R8-1), (I-1, A-2, R6-4, B-1, R7-1, R8-2), (I-1, A-2, R6-4, B-1, R7-1, R8-3), (I-1, A-2, R6-4, B-1, R7-2, R8-1), (I-1, A-2, R6-4, B-1, R7-2, R8-2), (I-1, A-2, R6-4, B-1, R7-2, R8-3), (I-1, A-2, R6-4, B-2, R7-1, R8-1), (I-1, A-2, R6-4, B-2, R7-1, R8-2), (I-1, A-2, R6-4, B-2, R7-1, R8-3), (I-1, A-2, R6-4, B-2, R7-2, R8-1), (I-1, A-2, R6-4, B-2, R7-2, R8-2), (I-1, A-2, R6-4, B-2, R7-2, R8-3), (I-2, A-1, R6-1, B-1, R7-1, R8-1), (I-2, A-1, R6-1, B-1, R7-1, R8-2), (I-2, A-1, R6-1, B-1, R7-1, R8-3), (I-2, A-1, R6-1, B-1, R7-2, R8-1), (I-2, A-1, R6-1, B-1, R7-2, R8-2), (I-2, A-1, R6-1, B-1, R7-2, R8-3), (I-2, A-1, R6-1, B-2, R7-1, R8-1), (I-2, A-1, R6-1, B-2, R7-1, R8-2), (I-2, A-1, R6-1, B-2, R7-1, R8-3), (I-2, A-1, R6-1, B-2, R7-2, R8-1), (I-2, A-1, R6-1, B-2, R7-2, R8-2), (I-2, A-1, R6-1, B-2, R7-2, R8-3), (I-2, A-1, R6-2, B-1, R7-1, R8-1), (I-2, A-1, R6-2, B-1, R7-1, R8-2), (I-2, A-1, R6-2, B-1, R7-1, R8-3), (I-2, A-1, R6-2, B-1, R7-2, R8-1), (I-2, A-1, R6-2, B-1, R7-2, R8-2), (I-2, A-1, R6-2, B-1, R7-2, R8-3), (I-2, A-1, R6-2, B-2, R7-1, R8-1), (I-2, A-1, R6-2, B-2, R7-1, R8-2), (I-2, A-1, R6-2, B-2, R7-1, R8-3), (I-2, A-1, R6-2, B-2, R7-2, R8-1), (I-2, A-1, R6-2, B-2, R7-2, R8-2), (I-2, A-1, R6-2, B-2, R7-2, R8-3), (I-2, A-1, R6-3, B-1, R7-1, R8-1), (I-2, A-1, R6-3, B-1, R7-1, R8-2), (I-2, A-1, R6-3, B-1, R7-1, R8-3), (I-2, A-1, R6-3, B-1, R7-2, R8-1), (I-2, A-1, R6-3, B-1, R7-2, R8-2), (I-2, A-1, R6-3, B-1, R7-2, R8-3), (I-2, A-1, R6-3, B-2, R7-1, R8-1), (I-2, A-1, R6-3, B-2, R7-1, R8-2), (I-2, A-1, R6-3, B-2, R7-1, R8-3), (I-2, A-1, R6-3, B-2, R7-2, R8-1), (I-2, A-1, R6-3, B-2, R7-2, R8-2), (I-2, A-1, R6-3, B-2, R7-2, R8-3), (I-2, A-1, R6-4, B-1, R7-1, R8-1), (I-2, A-1, R6-4, B-1, R7-1, R8-2), (I-2, A-1, R6-4, B-1, R7-1, R8-3), (I-2, A-1, R6-4, B-1, R7-2, R8-1), (I-2, A-1, R6-4, B-1, R7-2, R8-2), (I-2, A-1, R6-4, B-1, R7-2, R8-3), (I-2, A-1, R6-4, B-2, R7-1, R8-1), (I-2, A-1, R6-4, B-2, R7-1, R8-2), (I-2, A-1, R6-4, B-2, R7-1, R8-3), (I-2, A-1, R6-4, B-2, R7-2, R8-1), (I-2, A-1, R6-4, B-2, R7-2, R8-2), (I-2, A-1, R6-4, B-2, R7-2, R8-3), (I-2, A-2, R6-1, B-1, R7-1, R8-1), (I-2, A-2, R6-1, B-1, R7-1, R8-2), (I-2, A-2, R6-1, B-1, R7-1, R8-3), (I-2, A-2, R6-1, B-1, R7-2, R8-1), (I-2, A-2, R6-1, B-1, R7-2, R8-2), (I-2, A-2, R6-1, B-1, R7-2, R8-3), (I-2, A-2, R6-1, B-2, R7-1, R8-1), (I-2, A-2, R6-1, B-2, R7-1, R8-2), (I-2, A-2, R6-1, B-2, R7-1, R8-3), (I-2, A-2, R6-1, B-2, R7-2, R8-1), (I-2, A-2, R6-1, B-2, R7-2, R8-2), (I-2, A-2, R6-1, B-2, R7-2, R8-3), (I-2, A-2, R6-2, B-1, R7-1, R8-1), (I-2, A-2, R6-2, B-1, R7-1, R8-2), (I-2, A-2, R6-2, B-1, R7-1, R8-3), (I-2, A-2, R6-2, B-1, R7-2, R8-1), (I-2, A-2, R6-2, B-1, R7-2, R8-2), (I-2, A-2, R6-2, B-1, R7-2, R8-3), (I-2, A-2, R6-2, B-2, R7-1, R8-1), (I-2, A-2, R6-2, B-2, R7-1, R8-2), (I-2, A-2, R6-2, B-2, R7-1, R8-3), (I-2, A-2, R6-2, B-2, R7-2, R8-1), (I-2, A-2, R6-2, B-2, R7-2, R8-2), (I-2, A-2, R6-2, B-2, R7-2, R8-3), (I-2, A-2, R6-3, B-1, R7-1, R8-1), (I-2, A-2, R6-3, B-1, R7-1, R8-2), (I-2, A-2, R6-3, B-1, R7-1, R8-3), (I-2, A-2, R6-3, B-1, R7-2, R8-1), (I-2, A-2, R6-3, B-1, R7-2, R8-2), (I-2, A-2, R6-3, B-1, R7-2, R8-3), (I-2, A-2, R6-3, B-2, R7-1, R8-1), (I-2, A-2, R6-3, B-2, R7-1, R8-2), (I-2, A-2, R6-3, B-2, R7-1, R8-3), (I-2, A-2, R6-3, B-2, R7-2, R8-1), (I-2, A-2, R6-3, B-2, R7-2, R8-2), (I-2, A-2, R6-3, B-2, R7-2, R8-3), (I-2, A-2, R6-4, B-1, R7-1, R8-1), (I-2, A-2, R6-4, B-1, R7-1, R8-2), (I-2, A-2, R6-4, B-1, R7-1, R8-3), (I-2, A-2, R6-4, B-1, R7-2, R8-1), (I-2, A-2, R6-4, B-1, R7-2, R8-2), (I-2, A-2, R6-4, B-1, R7-2, R8-3), (I-2, A-2, R6-4, B-2, R7-1, R8-1), (I-2, A-2, R6-4, B-2, R7-1, R8-2), (I-2, A-2, R6-4, B-2, R7-1, R8-3), (I-2, A-2, R6-4, B-2, R7-2, R8-1), (I-2, A-2, R6-4, B-2, R7-2, R8-2), (I-2, A-2, R6-4, B-2, R7-2, R8-3), (I-3, A-1, R6-1, B-1, R7-1, R8-1), (I-3, A-1, R6-1, B-1, R7-1, R8-2), (I-3, A-1, R6-1, B-1, R7-1, R8-3), (I-3, A-1, R6-1, B-1, R7-2, R8-1), (I-3, A-1, R6-1, B-1, R7-2, R8-2), (I-3, A-1, R6-1, B-1, R7-2, R8-3), (I-3, A-1, R6-1, B-2, R7-1, R8-1), (I-3, A-1, R6-1, B-2, R7-1, R8-2), (I-3, A-1, R6-1, B-2, R7-1, R8-3), (I-3, A-1, R6-1, B-2, R7-2, R8-1), (I-3, A-1, R6-1, B-2, R7-2, R8-2), (I-3, A-1, R6-1, B-2, R7-2, R8-3), (I-3, A-1, R6-2, B-1, R7-1, R8-1), (I-3, A-1, R6-2, B-1, R7-1, R8-2), (I-3, A-1, R6-2, B-1, R7-1, R8-3), (I-3, A-1, R6-2, B-1, R7-2, R8-1), (I-3, A-1, R6-2, B-1, R7-2, R8-2), (I-3, A-1, R6-2, B-1, R7-2, R8-3), (I-3, A-1, R6-2, B-2, R7-1, R8-1), (I-3, A-1, R6-2, B-2, R7-1, R8-2), (I-3, A-1, R6-2, B-2, R7-1, R8-3), (I-3, A-1, R6-2, B-2, R7-2, R8-1), (I-3, A-1, R6-2, B-2, R7-2, R8-2), (I-3, A-1, R6-2, B-2, R7-2, R8-3), (I-3, A-1, R6-3, B-1, R7-1, R8-1), (I-3, A-1, R6-3, B-1, R7-1, R8-2), (I-3, A-1, R6-3, B-1, R7-1, R8-3), (I-3, A-1, R6-3, B-1, R7-2, R8-1), (I-3, A-1, R6-3, B-1, R7-2, R8-2), (I-3, A-1, R6-3, B-1, R7-2, R8-3), (I-3, A-1, R6-3, B-2, R7-1, R8-1), (I-3, A-1, R6-3, B-2, R7-1, R8-2), (I-3, A-1, R6-3, B-2, R7-1, R8-3), (I-3, A-1, R6-3, B-2, R7-2, R8-1), (I-3, A-1, R6-3, B-2, R7-2, R8-2), (I-3, A-1, R6-3, B-2, R7-2, R8-3), (I-3, A-1, R6-4, B-1, R7-1, R8-1), (I-3, A-1,

R6-4, B-1, R7-1, R8-2), (I-3, A-1, R6-4, B-1, R7-1, R8-3), (I-3, A-1, R6-4, B-1, R7-2, R8-1), (I-3, A-1, R6-4, B-1, R7-2, R8-2), (I-3, A-1, R6-4, B-1, R7-2, R8-3), (I-3, A-1, R6-4, B-2, R7-1, R8-1), (I-3, A-1, R6-4, B-2, R7-1, R8-2), (I-3, A-1, R6-4, B-2, R7-1, R8-3), (I-3, A-1, R6-4, B-2, R7-2, R8-1), (I-3, A-1, R6-4, B-2, R7-2, R8-2), (I-3, A-1, R6-4, B-2, R7-2, R8-3), (I-3, A-2, R6-1, B-1, R7-1, R8-1), (I-3, A-2, R6-1, B-1, R7-1, R8-2), (I-3, A-2, R6-1, B-1, R7-1, R8-3), (I-3, A-2, R6-1, B-1, R7-2, R8-1), (I-3, A-2, R6-1, B-1, R7-2, R8-2), (I-3, A-2, R6-1, B-1, R7-2, R8-3), (I-3, A-2, R6-1, B-2, R7-1, R8-1), (I-3, A-2, R6-1, B-2, R7-1, R8-2), (I-3, A-2, R6-1, B-2, R7-1, R8-3), (I-3, A-2, R6-1, B-2, R7-2, R8-1), (I-3, A-2, R6-1, B-2, R7-2, R8-2), (I-3, A-2, R6-1, B-2, R7-2, R8-3), (I-3, A-2, R6-2, B-1, R7-1, R8-1), (I-3, A-2, R6-2, B-1, R7-1, R8-2), (I-3, A-2, R6-2, B-1, R7-1, R8-3), (I-3, A-2, R6-2, B-1, R7-2, R8-1), (I-3, A-2, R6-2, B-1, R7-2, R8-2), (I-3, A-2, R6-2, B-1, R7-2, R8-3), (I-3, A-2, R6-2, B-2, R7-1, R8-1), (I-3, A-2, R6-2, B-2, R7-1, R8-2), (I-3, A-2, R6-2, B-2, R7-1, R8-3), (I-3, A-2, R6-2, B-2, R7-2, R8-1), (I-3, A-2, R6-2, B-2, R7-2, R8-2), (I-3, A-2, R6-2, B-2, R7-2, R8-3), (I-3, A-2, R6-3, B-1, R7-1, R8-1), (I-3, A-2, R6-3, B-1, R7-1, R8-2), (I-3, A-2, R6-3, B-1, R7-1, R8-3), (I-3, A-2, R6-3, B-1, R7-2, R8-1), (I-3, A-2, R6-3, B-1, R7-2, R8-2), (I-3, A-2, R6-3, B-1, R7-2, R8-3), (I-3, A-2, R6-3, B-2, R7-1, R8-1), (I-3, A-2, R6-3, B-2, R7-1, R8-2), (I-3, A-2, R6-3, B-2, R7-1, R8-3), (I-3, A-2, R6-3, B-2, R7-2, R8-1), (I-3, A-2, R6-3, B-2, R7-2, R8-2), (I-3, A-2, R6-3, B-2, R7-2, R8-3), (I-3, A-2, R6-4, B-1, R7-1, R8-1), (I-3, A-2, R6-4, B-1, R7-1, R8-2), (I-3, A-2, R6-4, B-1, R7-1, R8-3), (I-3, A-2, R6-4, B-1, R7-2, R8-1), (I-3, A-2, R6-4, B-1, R7-2, R8-2), (I-3, A-2, R6-4, B-1, R7-2, R8-3), (I-3, A-2, R6-4, B-2, R7-1, R8-1), (I-3, A-2, R6-4, B-2, R7-1, R8-2), (I-3, A-2, R6-4, B-2, R7-1, R8-3), (I-3, A-2, R6-4, B-2, R7-2, R8-1), (I-3, A-2, R6-4, B-2, R7-2, R8-2), (I-3, A-2, R6-4, B-2, R7-2, R8-3), (I-4, A-1, R6-1, B-1, R7-1, R8-1), (I-4, A-1, R6-1, B-1, R7-1, R8-2), (I-4, A-1, R6-1, B-1, R7-1, R8-3), (I-4, A-1, R6-1, B-1, R7-2, R8-1), (I-4, A-1, R6-1, B-1, R7-2, R8-2), (I-4, A-1, R6-1, B-1, R7-2, R8-3), (I-4, A-1, R6-1, B-2, R7-1, R8-1), (I-4, A-1, R6-1, B-2, R7-1, R8-2), (I-4, A-1, R6-1, B-2, R7-1, R8-3), (I-4, A-1, R6-1, B-2, R7-2, R8-1), (I-4, A-1, R6-1, B-2, R7-2, R8-2), (I-4, A-1, R6-1, B-2, R7-2, R8-3), (I-4, A-1, R6-2, B-1, R7-1, R8-1), (I-4, A-1, R6-2, B-1, R7-1, R8-2), (I-4, A-1, R6-2, B-1, R7-1, R8-3), (I-4, A-1, R6-2, B-1, R7-2, R8-1), (I-4, A-1, R6-2, B-1, R7-2, R8-2), (I-4, A-1, R6-2, B-1, R7-2, R8-3), (I-4, A-1, R6-2, B-2, R7-1, R8-1), (I-4, A-1, R6-2, B-2, R7-1, R8-2), (I-4, A-1, R6-2, B-2, R7-1, R8-3), (I-4, A-1, R6-2, B-2, R7-2, R8-1), (I-4, A-1, R6-2, B-2, R7-2, R8-2), (I-4, A-1, R6-2, B-2, R7-2, R8-3), (I-4, A-1, R6-3, B-1, R7-1, R8-1), (I-4, A-1, R6-3, B-1, R7-1, R8-2), (I-4, A-1, R6-3, B-1, R7-1, R8-3), (I-4, A-1, R6-3, B-1, R7-2, R8-1), (I-4, A-1, R6-3, B-1, R7-2, R8-2), (I-4, A-1, R6-3, B-1, R7-2, R8-3), (I-4, A-1, R6-3, B-2, R7-1, R8-1), (I-4, A-1, R6-3, B-2, R7-1, R8-2), (I-4, A-1, R6-3, B-2, R7-1, R8-3), (I-4, A-1, R6-3, B-2, R7-2, R8-1), (I-4, A-1, R6-3, B-2, R7-2, R8-2), (I-4, A-1, R6-3, B-2, R7-2, R8-3), (I-4, A-1, R6-4, B-1, R7-1, R8-1), (I-4, A-1, R6-4, B-1, R7-1, R8-2), (I-4, A-1, R6-4, B-1, R7-1, R8-3), (I-4, A-1, R6-4, B-1, R7-2, R8-1), (I-4, A-1, R6-4, B-1, R7-2, R8-2), (I-4, A-1, R6-4, B-1, R7-2, R8-3), (I-4, A-1, R6-4, B-2, R7-1, R8-1), (I-4, A-1, R6-4, B-2, R7-1, R8-2), (I-4, A-1, R6-4, B-2, R7-1, R8-3), (I-4, A-1, R6-4, B-2, R7-2, R8-1), (I-4, A-1, R6-4, B-2, R7-2, R8-2), (I-4, A-1, R6-4, B-2, R7-2, R8-3), (I-4, A-2, R6-1, B-1, R7-1, R8-1), (I-4, A-2, R6-1, B-1, R7-1, R8-2), (I-4, A-2, R6-1, B-1, R7-1, R8-3), (I-4, A-2, R6-1, B-1, R7-2, R8-1), (I-4, A-2, R6-1, B-1, R7-2, R8-2), (I-4, A-2, R6-1, B-1, R7-2, R8-3), (I-4, A-2, R6-1, B-2, R7-1, R8-1), (I-4, A-2, R6-1, B-2, R7-1, R8-2), (I-4, A-2, R6-1, B-2, R7-1, R8-3), (I-4, A-2, R6-1, B-2, R7-2, R8-1), (I-4, A-2, R6-1, B-2, R7-2, R8-2), (I-4, A-2, R6-1, B-2, R7-2, R8-3), (I-4, A-2, R6-2, B-1, R7-1, R8-1), (I-4, A-2, R6-2, B-1, R7-1, R8-2), (I-4, A-2, R6-2, B-1, R7-1, R8-3), (I-4, A-2, R6-2, B-1, R7-2, R8-1), (I-4, A-2, R6-2, B-1, R7-2, R8-2), (I-4, A-2, R6-2, B-1, R7-2, R8-3), (I-4, A-2, R6-2, B-2, R7-1, R8-1), (I-4, A-2, R6-2, B-2, R7-1, R8-2), (I-4, A-2, R6-2, B-2, R7-1, R8-3), (I-4, A-2, R6-2, B-2, R7-2, R8-1), (I-4, A-2, R6-2, B-2, R7-2, R8-2), (I-4, A-2, R6-2, B-2, R7-2, R8-3), (I-4, A-2, R6-3, B-1, R7-1, R8-1), (I-4, A-2, R6-3, B-1, R7-1, R8-2), (I-4, A-2, R6-3, B-1, R7-1, R8-3), (I-4, A-2, R6-3, B-1, R7-2, R8-1), (I-4, A-2, R6-3, B-1, R7-2, R8-2), (I-4, A-2, R6-3, B-1, R7-2, R8-3), (I-4, A-2, R6-3, B-2, R7-1, R8-1), (I-4, A-2, R6-3, B-2, R7-1, R8-2), (I-4, A-2, R6-3, B-2, R7-1, R8-3), (I-4, A-2, R6-3, B-2, R7-2, R8-1), (I-4, A-2, R6-3, B-2, R7-2, R8-2), (I-4, A-2, R6-3, B-2, R7-2, R8-3), (I-4, A-2, R6-4, B-1, R7-1, R8-1), (I-4, A-2, R6-4, B-1, R7-1, R8-2), (I-4, A-2, R6-4, B-1, R7-1, R8-3), (I-4, A-2, R6-4, B-1, R7-2, R8-1), (I-4, A-2, R6-4, B-1, R7-2, R8-2), (I-4, A-2, R6-4, B-1, R7-2, R8-3), (I-4, A-2, R6-4, B-2, R7-1, R8-1), (I-4, A-2, R6-4, B-2, R7-1, R8-2), (I-4, A-2, R6-4, B-2, R7-1, R8-3), (I-4, A-2, R6-4, B-2, R7-2, R8-1), (I-4, A-2, R6-4, B-2, R7-2, R8-2), (I-4, A-2, R6-4, B-2, R7-2, R8-3).

In one embodiment, the compounds represented by the formula (Ia) include the following compounds indicated by combinations of the substituents shown below:

(1) When

[Chemical Formula 49]

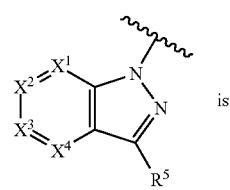

is

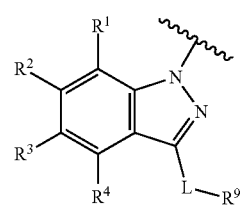

wherein, $R^1$ is a hydrogen atom or halogen; $R^2$ and $R^3$ are each independently a hydrogen atom, halogen, or substituted or unsubstituted alkyl; $R^4$ is a hydrogen atom; -L- is substituted or unsubstituted methylene; $R^9$ is carboxy, a compound wherein (i) is (i-1) (hereinafter referred to as I-1);

(2) When the ring A is

[Chemical Formula 50]

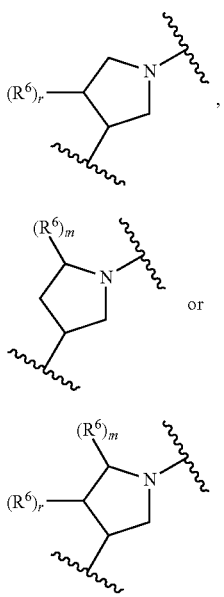

wherein, $R^6$ is as defined in above 1); m and r are independently 1 or 2, and m+r is 1, 2, or 3, a compound wherein the ring A is (a-1), (a-2), or (a-3) (hereinafter referred to as A-1);

a compound wherein ring A is (a-1) or (a-2) (hereinafter referred to as A-2);

(3) a compound wherein $R^6$ is each independently halogen, hydroxy, cyano, substituted or unsubstituted alkyl, substituted or unsubstituted alkenyl, substituted or unsubstituted alkyloxy, substituted or unsubstituted non-aromatic carbocyclyl, substituted or unsubstituted non-aromatic heterocyclyl, substituted or unsubstituted non-aromatic carbocyclyl oxy, or substituted or unsubstituted non-aromatic heterocyclyl oxy; or two of $R^6$ attached to the same ring constituent carbon atom are taken together to form a carbocycle containing the above ring constituent carbon atom, a heterocycle containing the above ring constituent carbon atom, oxo, or the formula: $=CR^{6a}R^{6b}$, wherein $R^{6a}$ and $R^{6b}$ are a hydrogen atom, cyano, halogen, or substituted or unsubstituted alkyl (hereinafter referred to as R6-1);

a compound wherein $R^6$ is each independently halogen, hydroxy, cyano, substituted or unsubstituted alkyl, substituted or unsubstituted alkenyl, substituted or unsubstituted non-aromatic carbocyclyl, substituted or unsubstituted non-aromatic heterocyclyl, substituted or unsubstituted non-aromatic carbocyclyl oxy, or substituted or unsubstituted non-aromatic heterocyclyl oxy; or two of $R^6$ attached to the same ring constituent carbon atom are taken together to form a carbocycle containing the above ring constituent carbon atom, a heterocycle containing the above ring constituent carbon atom, or the formula: $=CR^{6a}R^{6b}$, wherein $R^{6a}$ and $R^{6b}$ are a hydrogen atom, halogen, or substituted or unsubstituted alkyl (hereinafter referred to as R6-2);

a compound wherein $R^6$ is each independently halogen, cyano, or substituted or unsubstituted alkyl (hereinafter referred to as R6-3);

(4) a compound wherein the ring B is (b-1), (b-2) or (b-8) (hereinafter referred to as B-1);

a compound wherein the ring B is (b-1) or (b-8) (hereinafter referred to as B-2);

(5) a compound wherein q is 0 (hereinafter referred to as R8-1);

a compound wherein q is 1 and $R^8$ is halogen, cyano, substituted or unsubstituted alky, or substituted or unsubstituted alkyloxy (hereinafter referred to as R8-2);

a compound wherein q is 1 and $R^8$ is halogen or cyano (hereinafter referred to as R8-3);

compounds wherein the combinations of i, the ring A, $R^6$, the ring B and $R^8$ (I, A, $R^6$, B, $R^8$) are as shown below:

(I, A, R6, B, R8)=(I-1, A-1, R6-1, B-1, R8-1), (I-1, A-1, R6-1, B-1, R8-2), (I-1, A-1, R6-1, B-1, R8-3), (I-1, A-1, R6-1, B-2, R8-1), (I-1, A-1, R6-1, B-2, R8-2), (I-1, A-1, R6-1, B-2, R8-3), (I-1, A-1, R6-2, B-1, R8-1), (I-1, A-1, R6-2, B-1, R8-2), (I-1, A-1, R6-2, B- 1, R8-3), (I-1, A-1, R6-2, B-2, R8-1), (I-1, A-1, R6-2, B-2, R8-2), (I-1, A-1, R6-2, B-2, R8-3), (I-1, A-1, R6-3, B-1, R8-1), (I-1, A-1, R6-3, B-1, R8-2), (I-1, A-1, R6-3, B-1, R8-3), (I-1, A-1, R6-3, B-2, R8-1), (I-1, A-1, R6-3, B-2, R8-2), (I-1, A-1, R6-3, B-2, R8-3), (I-2, A-1, R6-1, B-1, R8-1), (I-2, A-1, R6-1, B-1, R8-2), (I-2, A-1, R6-1, B-1, R8-3), (I-2, A-1, R6-1, B-2, R8-1), (I-2, A-1, R6-1, B-2, R8-2), (I-2, A-1, R6-1, B-2, R8-3), (I-2, A-1, R6-2, B-1, R8-1), (I-2, A-1, R6-2, B-1, R8-2), (I-2, A-1, R6-2, B-1, R8-3), (I-2, A-1, R6-2, B-2, R8-1), (I-2, A-1, R6-2, B-2, R8-2), (I-2, A-1, R6-2, B-2, R8-3), (I-2, A-1, R6-3, B-1, R8-1), (I-2, A-1, R6-3, B-1, R8-2), (I-2, A-1, R6-3, B-1, R8-3), (I-2, A-1, R6-3, B-2, R8-1), (I-2, A-1, R6-3, B-2, R8-2), (I-2, A-1, R6-3, B-2, R8-3).

The compounds according to the present invention are characterized by the fact that they have DP receptor antagonistic activity, CRTH2 receptor antagonistic activity, and/or, antagonistic activity against both the DP receptor and CRTH2 receptor.

In another embodiment, the compounds according to the present invention are characterized by the fact that the compounds have high CRTH2 receptor antagonistic activity by introducing at least one $R^6$ in the ring A in formula (I).

The compounds represented by formula (I) are not limited to specific isomers but include all possible isomers (e.g., keto-enol isomers, imine-enamine isomers, diastereoisomers, enantiomers, rotamers, etc.), racemates, or mixtures thereof.

One or more hydrogen, carbon, and/or other atoms in the compounds represented by the formula (I) may be replaced with isotopes of hydrogen, carbon, and/or other atoms respectively. Examples of isotopes include hydrogen, carbon, nitrogen, oxygen, phosphorus, sulfur, fluorine, iodine and chlorine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{123}I$ and $^{36}Cl$ respectively. The compounds represented by the formula (I) include the compounds replaced with these isotopes. The compounds replaced with the above isotopes are useful as medicines and include all of radiolabeled compounds of the compound represented by the formula (I). A "method of radiolabeling" in the manufacture of "radiolabeled compounds" is encompassed by the present invention, and is useful for studies on metabolized drug pharmacokinetics and studies on binding assay, and/or a diagnostic tool.

A radiolabeled compound of the compounds represented by the formula (I) can be prepared using a well-known method in the relevant technical field. For example, a tritium-labeled compound of formula (I) can be prepared by introducing a tritium to a certain compound of formula (I), through a catalytic dehalogenation reaction using a tritium. This method comprise reacting with an appropriately-halogenated precursor of the compound of formula (I) with tritium gas in the presence of an appropriate catalyst, such as Pd/C, and in the presence or absent of a base. For another appropriate method of preparing a tritium-labeled compound, the document: Isotopes in the Physical and Biomedical Sciences, Vol. 1, Labeled Compounds (Part A), Chapter 6 (1987) can be referred to. A $^{14}$C-labeled compound can be prepared by using a raw material having $^{14}$C.

The pharmaceutically acceptable salts of the compounds represented by the formula (I) include for example salts with alkaline metal (e.g., lithium, sodium and potassium), alkaline earth metal (e.g., calcium and barium), magnesium, transition metal (e.g., zinc and iron), ammonia, organic bases (e.g., trimethylamine, triethylamine, dicyclohexylamine, ethanolamine, diethanolamine, triethanolamine, meglumine, ethylenediamine, pyridine, picoline, quinoline) and amino acids, or salts with inorganic acids (e.g., hydrochloric acid, sulfuric acid, nitric acid, carbonic acid, hydrobromic acid, phosphoric acid and hydroiodic acid) and organic acids (e.g., formic acid, acetic acid, propionic acid, trifluoroacetic acid, citric acid, lactic acid, tartaric acid, oxalic acid, maleic acid, fumaric acid, mandelic acid, glutaric acid, malic acid, benzoic acid, phthalic acid, ascorbic acid, benzenesulfonic acid, p-toluenesulfonic acid, methanesulfonic acid, ethanesulfonic acid). Salts with hydrochloric acid, sulfuric acid, phosphoric acid, tartaric acid, methanesulfonic acid and the like are exemplified. These salts can be formed by the usual method.

The compounds of the present invention represented by formula (I) or pharmaceutically acceptable salts thereof may form solvates (e.g., hydrates etc.) and/or crystal polymorphs. The present invention encompasses those various solvates and crystal polymorphs. "Solvates" may be those wherein any numbers of solvent molecules (e.g., water molecules etc.) are coordinated with the compounds represented by formula (I). When the compounds represented by formula (I) or pharmaceutically acceptable salts thereof are allowed to stand in the atmosphere, the compounds may absorb water, resulting in attachment of adsorbed water or formation of hydrates. Recrystallization of the compounds represented by formula (I) or pharmaceutically acceptable salts thereof may produce crystal polymorphs.

The compounds of the present invention represented by formula (I) or pharmaceutically acceptable salts thereof may form prodrugs. The present invention also encompasses such various prodrugs. Prodrugs are derivatives of the compounds of the present invention that have chemically or metabolically degradable groups and are compounds that are converted to the pharmaceutically active compounds of the present invention through solvolysis or under physiological conditions in vivo. Prodrugs include compounds that are converted to the compounds represented by formula (I) through enzymatic oxidation, reduction, hydrolysis and the like under physiological conditions in vivo and compounds that are converted to the compounds represented by formula (I) through hydrolysis by gastric acid and the like. Methods for selecting and preparing suitable prodrug derivatives are described, for example, in the Design of Prodrugs, Elsevier, Amsterdam 1985. Prodrugs themselves may be active compounds.

When the compounds represented by formula (I) or pharmaceutically acceptable salts thereof have hydroxyl, prodrugs include acyloxy derivatives and sulfonyloxy derivatives that are prepared by for example reacting compounds having hydroxyl with suitable acyl halide, suitable acid anhydride, suitable sulfonyl chloride, suitable sulfonyl anhydride, and mixed anhydride or with a condensing agent. For example, $CH_3COO$—, $C_2H_5COO$—, tert-BuCOO—, $C_{15}H_{31}COO$—, PhCOO—, (m-NaOOCPh)COO—, NaOOCCH$_2$CH$_2$COO—, CH$_3$CH(NH$_2$)COO—, CH$_2$N(CH$_3$)$_2$COO—, CH$_3$SO$_3$—, CH$_3$CH$_2$SO$_3$—, CF$_3$SO$_3$—, CH$_2$FSO$_3$CF$_3$CH$_2$SO$_3$, p-CH$_3$O—PhSO$_3$—, PhSO$_3$—, p-CH$_3$PhSO$_3$ and the like are exemplified.

(The General Synthetic Methods for the Compounds of the Present Invention)

For example, the compounds represented by the formula (I) in the present invention can be prepared by the general synthetic methods described below. The methods for extraction, purification, and the like may be carried out by using the usual method for the experiments of organic chemistry.

The compounds of the present invention can be synthesized in consideration of the condition of the known methods in the art.

The compounds of the present invention can be prepared by the method A, B or C set forth below. In addition, a racemate or an optical isomer is included in structural formulae of (I), (III) to (XVII), (VIIIa) to (VIIIe) and (Ia) to (If).

Method A is set forth below,

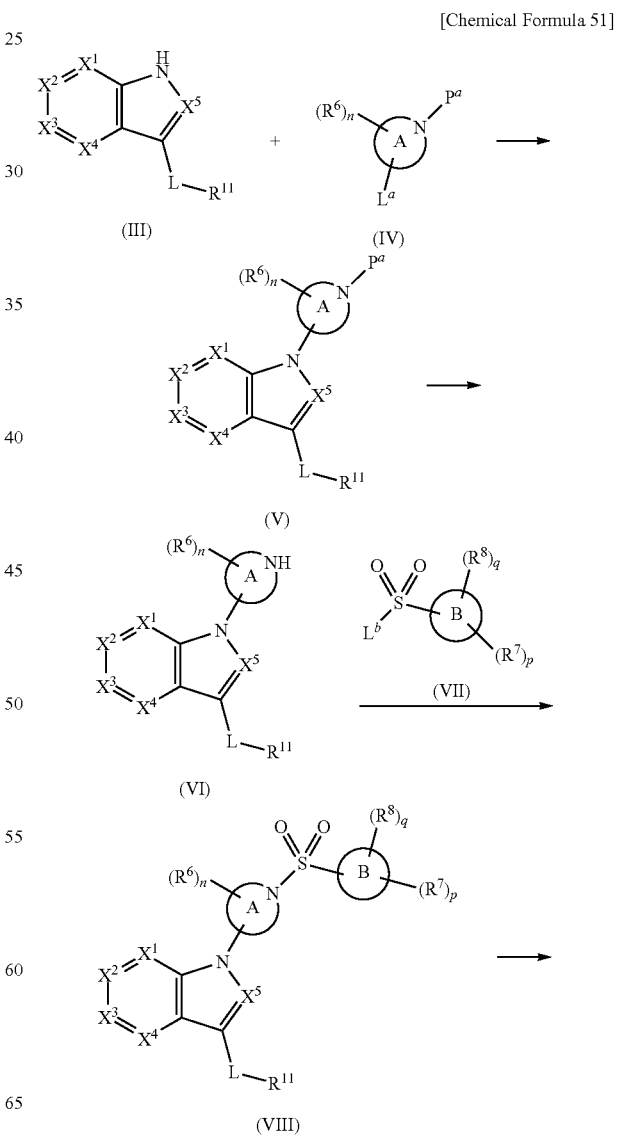

[Chemical Formula 51]

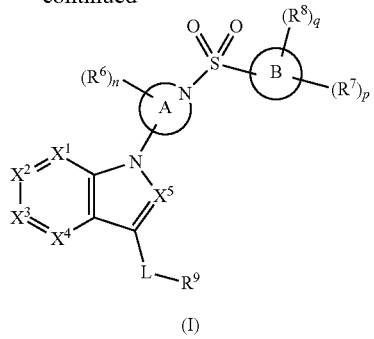

(I)

wherein Ring A, Ring B, $X^1$, $X^2$, $X^3$, $X^4$, $X^5$, $R^6$, $R^7$, $R^8$, $R^9$, $R^{11}$, L, n, p and q are as defined in above 1); $R^{11}$ is ester; $L^a$ is a leaving group such as halogen and the like or hydroxy; $L^b$ is halogen; and $P^a$ is a protecting group of amine.

Step 1

When $L^a$ of the compound represented by the formula (IV) is a hydroxy group, the compounds can be changed to a sulfonyl derivative, and the derivative can be condensed with the compound represented by the formula (III) to give the compound represented by the formula (V).

The sulfonyl derivative can be synthesized by the reaction of the compound represented by the formula (IV) with a sulfonylation agent in the presence of a base such as triethylamine, pyridine and the like.

As the sulfonylation agent, methanesulfonyl chloride, p-toluenesulphonyl chloride and the like are exemplified. The sulfonilation agent can be used 1 to 5 equivalent(s) per equivalent of the compound represented by the formula (IV).

As the reaction temperature, −80° C. to 50° C. is exemplified. Preferably, −20° C. to 20° C. is exemplified.

As the reaction time, 0.1 to 24 hour(s) is exemplified. Preferably, 0.5 to 12 hour(s) is exemplified.

As the reaction solvent, acetonitrile, THF, toluene, dichloromethane and the like can be used.

The compound represented by the formula (IV) or the sulfonyl derivative can be used from 1 to 5 equivalent(s) per equivalent of the compound represented by the formula (III) in the condensation reaction. This reaction may be carried out in the presence of 1 to 5 equivalent(s) of the base per equivalent of the compound represented by the formula (III).

As the base, sodium hydride, potassium carbonate, sodium carbonate, potassium hydrogen carbonate, sodium hydrogen carbonate, potassium hydroxide, sodium hydroxide, cesium carbonate, cesium hydroxide and the like are exemplified.

As the reaction temperature, 0° C. to 150° C. is exemplified. Preferably, 20° C. to 120° C. is exemplified. This reaction may be carried out under microwave irradiation at appropriate temperature, if necessary.

As the reaction time, 5 minutes to 48 hour(s) is exemplified. Preferably, 3 to 12 hours is exemplified.

As the reaction solvent, THF, DMF, DMA, DMSO, water and the like are exemplified. The mixed solvents of the above solvents can also be used.

Step 2

The compound represented by the formula (VI) can be synthesized by the deprotection reaction of the compound represented by the formula (V) under acidic conditions or under hydrogenation conditions.

[Acidic Conditions]

As the acid, hydrochloric acid-ethyl acetate, hydrochloric acid-methanol, hydrochloric acid-dioxane, sulfuric acid, formic acid, trifluoroacetic acid and the like are exemplified. As Lewis acid, iodotrimethylsilane, $BBr_3$, AlC13, $BF_3$ ($Et_2O$) and the like are exemplified. The acid can be used 1 to 20 mole equivalent(s) per equivalent of the compound represented by the formula (V).

As the reaction temperature, 0° C. to 60° C. is exemplified. Preferably, 0° C. to 20° C. is exemplified.

As the reaction time, 0.5 to 48 hour(s) is exemplified.

As the reaction solvent, ethyl acetate, dichloromethane, THF, methanol, ethanol, water, acetone, acetonitrile, DMF, dioxane and the like are exemplified. The mixed solvents of the above solvents can also be used.

[Hydrogenation Conditions]

The compound represented by the formula (V) can be hydrogenated in the presence of Pd-Carbon under hydrogen gas to give the compound represented by the formula (VI).

As the pressure of hydrogen, 1 to 50 pressure(s) is exemplified. Cyclohexene, 1,4-cyclohexadiene, formic acid, ammonium formate and the like can be used as a hydrogen source.

As the reaction temperature, 0° C. to 40° C. is exemplified. Preferably, 10° C. to 30° C. is exemplified.

As the reaction time, 0.5 to 12 hour(s) is exemplified. Preferably, 1 to 6 hour(s) is exemplified.

As the reaction solvent, methanol, ethanol, water, THF, ethyl acetate and the like are exemplified. The mixed solvents of the above solvents can also be used.

Step 3

The compound represented by the formula (VIII) or the compound represented by the formula (I) can be synthesized by the condensation reaction of the compound represented by the formula (VI) and the compound represented by the formula (VII)

The compound represented by the formula (VII) can be used 0.8 to 2 equivalent(s) per equivalent of the compound represented by the formula (VI). This reaction may be carried out in the presence of 1 to 5 equivalent(s) of the base per equivalent of the compound represented by the formula (VII).

As the base, triethylamine, diisopropylethylamine, pyridine, potassium carbonate, sodium carbonate, cesium carbonate, potassium hydrogen carbonate, sodium hydrogencarbonate and the like are exemplified.

As the reaction temperature, 0° C. to 150° C. is exemplified. Preferably, 0° C. to 30° C. is exemplified.

As the reaction time, 5 minutes to 48 hour(s) is exemplified. Preferably, 5 minutes to 1 hour is exemplified.

As the reaction solvent, ethyl acetate, dichloromethane, THF, DMF, DMSO, water and the like are exemplified. The mixed solvents of the above solvents can also be used.

Step 4

The compound represented by the formula (I) can be synthesized by the hydrolysis of the compound represented by the formula (VIII) under basic conditions, if necessary.

The base can be used 1 to 5 equivalent(s) per equivalent of the compound represented by the formula (VIII).

As the base, lithium hydroxide, potassium hydroxide, sodium hydroxide, barium hydroxide and the like are exemplified.

As the reaction temperature, 0° C. to 150° C. is exemplified. Preferably, 0° C. to 25° C. is exemplified.

As the reaction time, 5 minutes to 48 hour(s) is exemplified. Preferably, 5 minutes to 2 hour(s) is exemplified.

As the reaction solvent, THF, methanol, ethanol, isopropanol, DMF, DMSO, water and the like are exemplified. The mixed solvents of the above solvents can also be used.

The aimed compound represented by the formula (V), (VI) or (I) in each step can be purified by the usual method such as column chromatography, recrystallization and the like, if necessary.

Method B is set forth below,

[Chemical Formula 52]

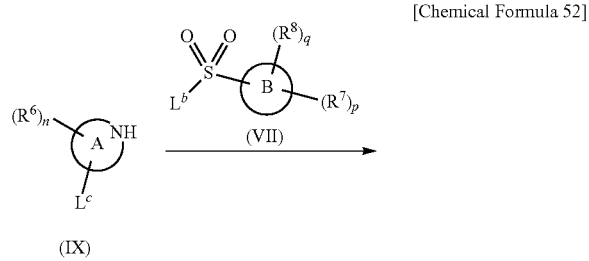

(IX)

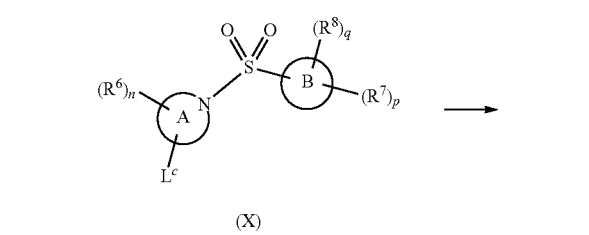

(X)

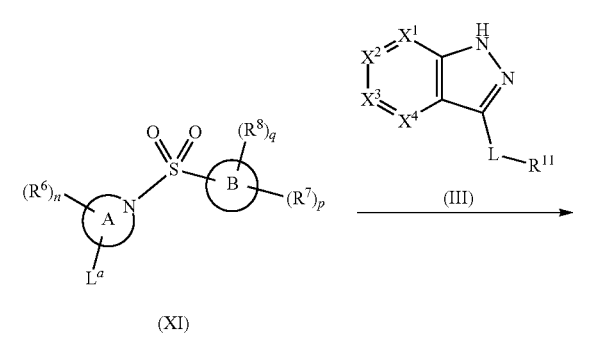

(VIII)

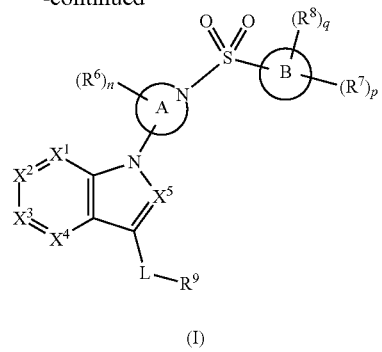

(I)

wherein Ring A, Ring B, $X^1$, $X^2$, $X^3$, $X^4$, $X^5$, $R^6$, $R^7$, $R^8$, $R^9$, $R^{11}$, L, n, p, q and $L^b$ are as defined above; $L^a$ is hydroxy or a leaving group such as halogen, p-toluenesulfonyloxy and the like; $L^c$ is halogen or $OP^b$ wherein $P^b$ is a protective group of hydroxy.

Step 1

The compound represented by the formula (X) can be synthesized by the condensation reaction of the compound represented by the formula (IX) and the compound represented by the formula (VII).

The compound represented by the formula (IX) can be used 0.8 to 2 equivalent(s) per equivalent of the compound represented by the formula (VII). This reaction may be carried out in the presence of 1 to 5 equivalent(s) of the base per equivalent of the compound represented by the formula (VII).

As the base, triethylamine, diisopropylethylamine, pyridine, potassium carbonate, sodium carbonate, cesium carbonate, potassium hydrogen carbonate, sodium hydrogen carbonate and the like are exemplified.

As the reaction temperature, 0° C. to 150° C. is exemplified. Preferably, 0° C. to 30° C. is exemplified.

As the reaction time, 5 minutes to 48 hour(s) is exemplified. Preferably, 5 minutes to 1 hour is exemplified.

As the reaction solvent, ethyl acetate, dichloromethane, THF, DMF, DMSO, water and the like are exemplified. The mixed solvents of the above solvents can also be used.

Step 2

Step 2 is carried out as needed.

The compound represented by the formula (XI) can be synthesized by the deprotection reaction of the compound represented by the formula (X) under basic conditions or under hydrogenation conditions.

[Basic Conditions]

The base can be used 1 to 5 equivalent(s) per equivalent of the compound represented by the formula (X).

As the base, lithium hydroxide, potassium hydroxide, sodium hydroxide and the like are exemplified.

As the reaction temperature, 0° C. to 150° C. is exemplified. Preferably, 0° C. to 30° C. is exemplified.

As the reaction time, 5 minutes to 48 hour(s) is exemplified. Preferably, 5 minutes to 2 hour(s) is exemplified.

As the reaction solvent, THF, methanol, DMF, DMSO, water and the like are exemplified. The mixed solvents of the above solvents can also be used.

[Hydrogenation Conditions]

The compound represented by the formula (X) can be hydrogenated in the presence of Pd(OH)$_2$ under hydrogen gas to give the compound represented by the formula (XI).

As the pressure of hydrogen, 1 to 50 pressure(s) is exemplified. Cyclohexene, 1,4-cyclohexadiene, formic acid, ammonium formate and the like can be used as a hydrogen source.

As the reaction temperature, 0° C. to 40° C. is exemplified. Preferably, 10° C. to 30° C. is exemplified.

As the reaction time, 0.5 to 12 hour(s) is exemplified. Preferably, 1 to 6 hour(s) is exemplified.

As the reaction solvent, methanol, ethanol, water, THF, ethyl acetate, acetic acid and the like are exemplified. The mixed solvents of the above solvents can also be used.

Step 3

When $L^a$ of the compound represented by the formula (XI) is a hydroxy group, the compounds can be changed to a sulfonyl derivative, and the derivative can be condensed with the compound represented by the formula (III) to give the compound represented by the formula (VIII) or the compound represented by the formula (I).

The sulfonyl derivative can be synthesized by the reaction of the compound represented by the formula (XI) of which $L^a$ is a hydroxy group with a sulfonylation agent in the presence of a base such as triethylamine, pyridine and the like.

As the sulfonylation agent, methanesulfonyl chloride, p-toluenesulphonyl chloride and the like are exemplified. The sulfonilation agent can be used 1 to 5 equivalent(s) per equivalent of the compound represented by the formula (XI).

As the reaction temperature, −80° C. to 50° C. is exemplified. Preferably, −20° C. to 20° C. is exemplified.

As the reaction time, 0.1 to 24 hour(s) is exemplified. Preferably, 0.5 to 12 hour(s) is exemplified.

As the reaction solvent, acetonitrile, THF, toluene, dichloromethane and the like can be used.

The compound represented by the formula (XI) or the sulfonyl derivative can be used from 1 to 5 equivalent(s) per equivalent of the compound represented by the formula (III) in the condensation reaction. This reaction may be carried out in the presence of 1 to 5 equivalent(s) of the base per equivalent of the compound represented by the formula (III).

As the base, sodium hydride, potassium carbonate, sodium carbonate, potassium hydrogen carbonate, sodium hydrogen carbonate, potassium hydroxide, sodium hydroxide, cesium carbonate, cesium hydroxide and the like are exemplified.

As the reaction temperature, 0° C. to 150° C. is exemplified. Preferably, 20° C. to 120° C. is exemplified. This reaction may be carried out under microwave irradiation at appropriate temperature, if necessary.

As the reaction time, 5 minutes to 48 hour(s) is exemplified. Preferably, 3 to 12 hours is exemplified.

As the reaction solvent, THF, DMF, DMA, DMSO, water and the like are exemplified. The mixed solvents of the above solvents can also be used.

Step 4

This reaction can be carried out in a similar manner as described in Step 4 of Method A.

The aimed compound represented by the formulae (X), (XI) or (I) in each step can be purified by the usual method such as column chromatography, recrystallization and the like, if necessary.

Method C is set forth below,

[Chemical Formula 53]

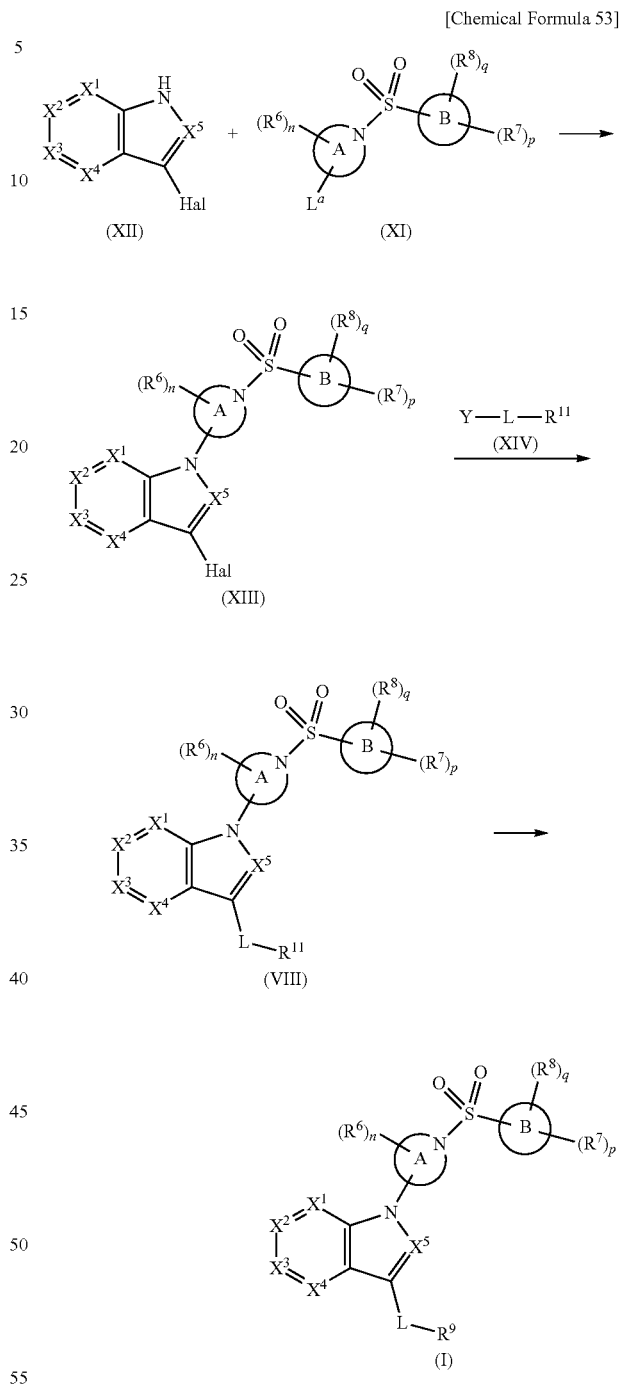

wherein Ring A, Ring B, $X^1$, $X^2$, $X^3$, $X^4$, $X^5$, $R^6$, $R^7$, $R^8$, $R^9$, $R^{11}$, L, n, p, q and $L^a$ are as defined above; Hal is halogen; Y is tributyltin, trimethyltin, Zn-Hal, boronic acid or boronate.

Step 1

In a similar manner to that described in Step 3 of Method B, the compound represented by the formula (XIII) can be synthesized by the condensation reaction of the compound represented by the formula (XI) and the compound represented by the formula (XII).

Step 2

The compound represented by the formula (VIII) can be synthesized by the coupling reaction of the compound represented by the formula (XIII) and the compound represented by the formula (XIV) in the presence of a metal catalyst and a base.

As the metal catalyst, palladium acetate, bis(dibenzylideneacetone)palladium, tetrakis(triphenylphosphine)palladium, bis(triphenylphosphine)palladium(II) dichloride, bis(tri-tert-butylphosphine)palladium and the like are exemplified. The catalyst can be used 0.001 to 0.5 mole equivalent per equivalent of the compound represented by the formula (XIII).

As the base, lithium hydroxide, sodium hydroxide, potassium hydroxide, potassium tert-butoxide, sodium tert-butoxide, sodium carbonate, potassium carbonate, sodium hydrogen carbonate, sodium phosphate, sodium hydrogen phosphate, potassium phosphate, potassium hydrogen phosphate and the like are exemplified. The base can be used 1 to 10 mole equivalent(s) per equivalent of the compound represented by the formula (XIII).

The compound represented by the formula (XIV) can be used 1 to 10 mole equivalent(s) per equivalent of the compound represented by the formula (XIII).

As the reaction temperature, 20° C. to the reflux temperature of the solvent is exemplified. This reaction may be carried out under microwave irradiation at appropriate temperature, as needed.

As the reaction time, 0.1 to 48 hour(s) is exemplified. Preferably, 0.5 to 12 hour(s) is exemplified.

As the reaction solvent, THF, toluene, DMF, dioxane, water and the like are exemplified. The mixed solvents of the above solvents can also be used.

Step 3

This reaction can be carried out in a similar manner as described in Step 4 of Methods A and B.

As the compound represented by the formula (III), a commercial product can be used or the compound can be synthesized. The synthetic method for the compound represented by the formula (III) is exemplified with reference to, but not limited to, the following method. The structure of the formula (III) includes a racemic compound and an optically active compound.

[Chemical Formula 54]

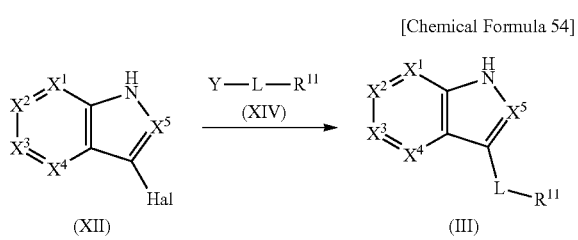

wherein $X^1$, $X^2$, $X^3$, $X^1$, $X^5$, $R^{11}$, L, Hal and Y are as defined above.

In a similar manner to that described in Step 2 of Method C, the compound represented by the formula (III) can be synthesized from the compound represented by the formula (XII).

As the compound represented by the formula (XVII), a commercial product can be used or the compound can be synthesized. The synthetic methods for the compound represented by the formula (XVII) is exemplified with reference to, but not limited to the following methods.

[Chemical Formula 55]

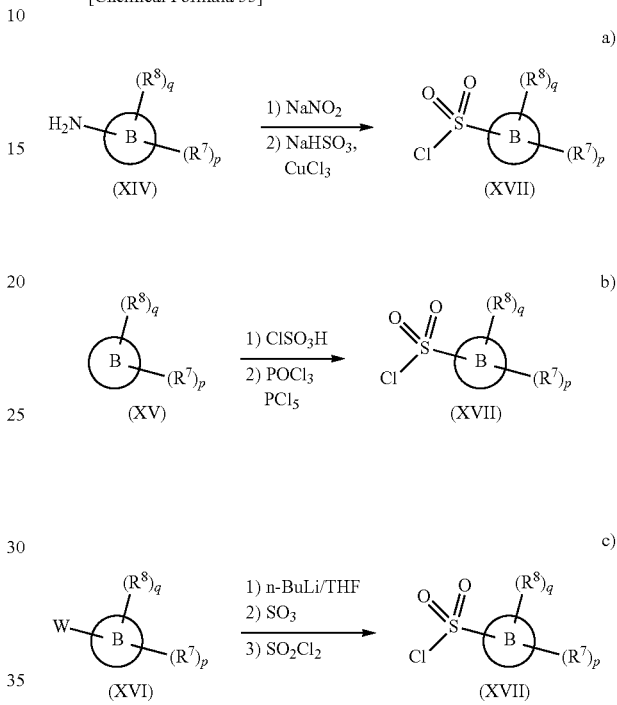

wherein Ring B, $R^7$, $R^8$ and q are as defined in above 1); W is halogen.

a) The compound represented by the formula (XV) can be 1) diazotized by sodium nitrite, and then, 2) the resulting compound can be reacted with sodium sulfite and copper chloride to give the compound represented by the formula (VII).

b) The compound represented by the formula (XVI) can be 1) sulfonated by ClSO$_3$H, and then, 2) a hydroxy group of the resulting compound can be chlorinated by POCl$_3$ or PCl$_5$ to give the compound represented by the formula VII)

c) The compound represented by the formula (XVII) can be 1) lithiated by n-BuLi, and then, 2) the resulting compound can be sulfonyllithiated by SO$_2$, and finally, 3) the resulting compound can be reacted with SO$_2$Cl$_2$ to give the compound represented by the formula (VII). As W, bromine or iodine is preferable.

Each substituents of $R^1$, $R^2$, $R^3$, $R^4$, $R^6$, $R^7$, $R^8$, $R^9$, $R^{10}$ or $R^{12}$ in the compound represented by the formula (I) is changed to another functional group according to the well know methods in the art. For example, the each substituent can be changed to another functional group by the following methods.

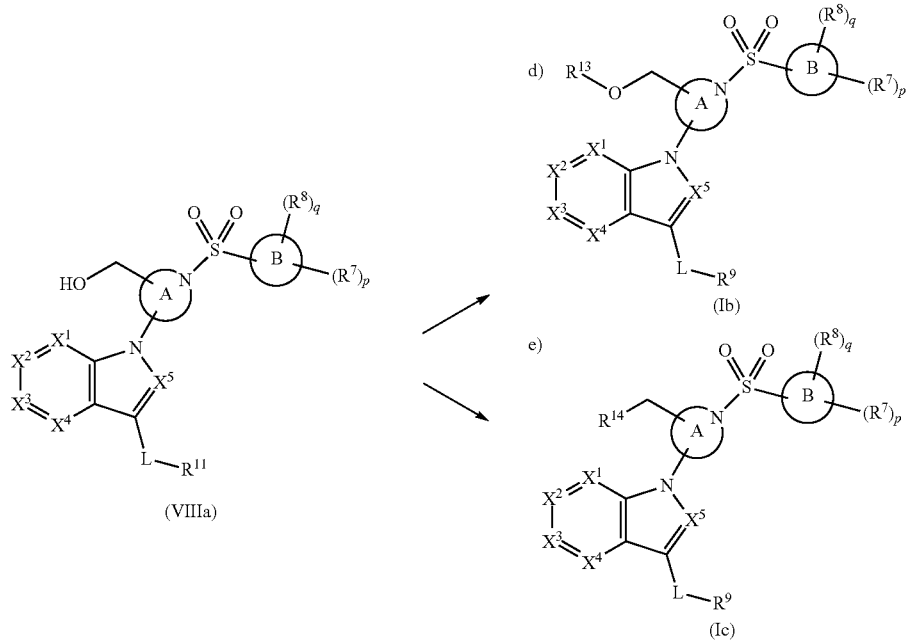

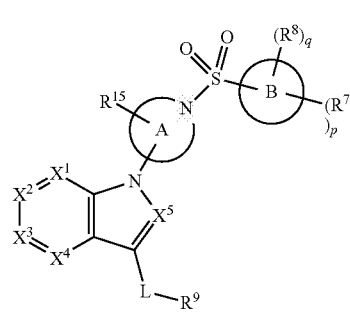

wherein Ring A, Ring B, $X^1$, $X^2$, $X^3$, $X^4$, $X^5$, $R^7$, $R^8$, $R^9$, $R^{11}$, L, p, and q are as defined above; $R^{13}$ is substituted or unsubstituted alkyl, substituted or unsubstituted alkenyl, substituted or unsubstituted alkynyl, a substituted or unsubstituted aromatic carbocyclyl, a substituted or unsubstituted non-aromatic carbocyclyl, a substituted or unsubstituted aromatic heterocyclyl, or a substituted or unsubstituted non-aromatic heterocyclyl; $R^{13}$ is halogen, cyano, substituted or unsubstituted amino, a substituted or unsubstituted aromatic heterocyclyl, a substituted or unsubstituted non-aromatic heterocyclyl or —$OR^{13}$.

d) The compound represented by the formula (VIIIa) can be alkylated by the known method, and then, the resulting compound can be hydrolyzed to give the compound represented by the formula (Ib).

e) The hydroxy group of the compound represented by the formula (VIIIa) can be changed to a leaving group, if needed, and then, the resulting compound can be reacted with a variety of nucleophilic agent, and can be hydrolyzed to give the compound represented by the formula (Ic).

wherein Ring A, Ring B, $X^1$, $X^2$, $X^3$, $X^4$, $X^5$, $R^7$, $R^8$, $R^9$, $R^{11}$, L, p, and q are as defined above; $R^{15}$ is substituted or unsubstituted aromatic heterocyclyl.

f) The carboxy group of the compound represented by the formula (VIIIb) can be changed to another functional group according to the known method, and then, the resulting compound can be hydrolyzed to give the compound represented by the formula (Id).

[Chemical Formula 57]

f)

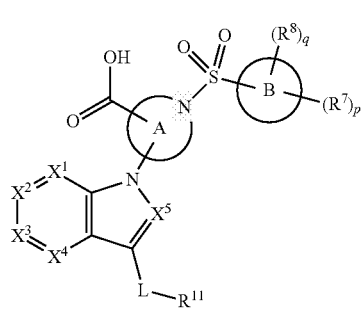

(VIIIb)

[Chemical Formula 58]

g)

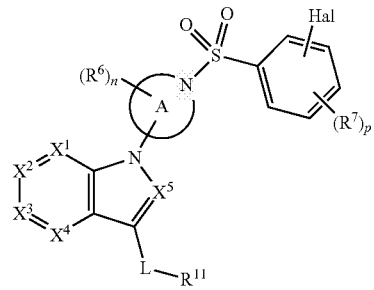

(VIIIc)

-continued

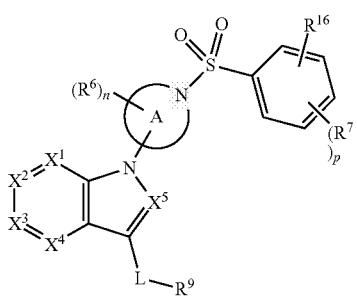

(Ie)

wherein Ring A, $X^1$, $X^2$, $X^3$, $X^4$, $X^5$, $R^6$, $R^7$, $R^9$, $R^{11}$, L, p and Hal are as defined above; $R^{16}$ is, cyano, substituted or unsubstituted alkenyl, substituted or unsubstituted alkynyl, substituted or unsubstituted amino, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl.

g) The compound represented by the formula (VIIIc) can be subjected to a coupling reaction with a metal catalyst, and the resulting compound can be hydrolyzed to give the compound represented by the formula (Ie).

[Chemical Formula 59]

h)

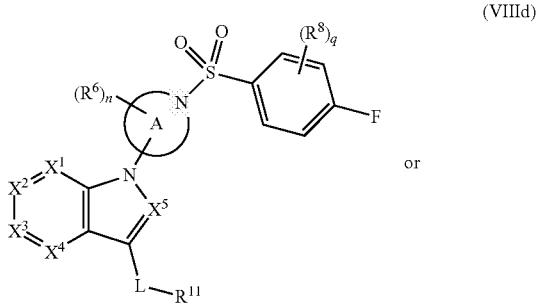

(VIIId)

or

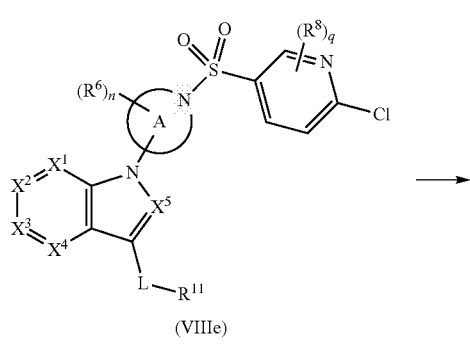

(VIIIe)

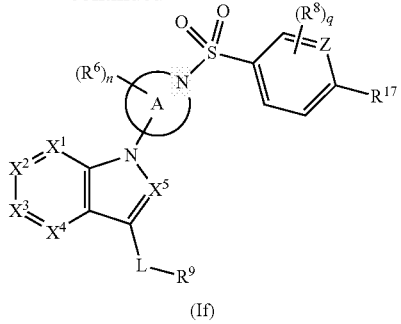

(If)

wherein Ring A, $X^1$, $X^2$, $X^3$, $X^4$, $X^5$, $R^6$, $R^8$, $R^9$, $R^{11}$, L and q are as defined above; $R^{17}$ is substituted or unsubstituted alkyloxy or substituted or unsubstituted non-aromatic carbocyclyl oxy.

h) The compound represented by the formulae (VIIId) or (VIIIe) can be reacted with $R^{17}H$ under basic conditions, and, the resulting compound can be hydrolyzed to give the compound represented by the formula (If).

The compounds of the present invention show a PGD2 receptor (a DP receptor and/or a CRTH2 receptor) antagonistic activity. Accordingly, the compounds of the present invention can be used as a therapeutic agent for preventing and/or treating allergic diseases such as asthma, allergic rhinitis, allergic dermatitis, allergic conjunctivitis, food allergy and the like; systemic mastocytosis; systemic disorder of mastcell-activation; lung emphysema; chronic bronchitis; chronic obstructive lung disease; skin disorder characterized by pruritus such as atopic dermatitis and hives; diseases occurring secondarily due to behavior accompanied by pruritus such as cataract and retinal detachment; brain damages such as cerebrovascular disorder, degenerative brain disorder and demyelinating disease; sleep-waking disorder; Churg-Strauss syndrome; papular dermatitis such as filariasis; vasculitis; polyarteritis; cutaneous eosoiophilic granuloma; autoimmune diseases such as multiple sclerosis and transplant rejection; eosoiophilic pneumonopathy; histiocytosis; pneumonia; aspergillosis; pleurisy; sarcoidosis; pulmonary fibrosis; eosinophilia; skin flush such as face flush by nicotinic acid; filariasis; schistosomiasis; trichinelliasis; coccidioidomycosis; tuberculosis; bronchial cancer; lymphoma; Hodgkin's disease and the like.

The compounds of the present invention not only have PGD2 receptor antagonistic activity but also are useful as a medicine and have any or all of the following excellent characteristics:

a) The compounds are a weak inhibitor of CYP enzymes (e.g., CYP1A2, CYP2C9, CYP2C19, CYP2D6, and CYP3A4).

b) The compounds demonstrate good pharmacokinetics, such as a high bioavailability and moderate clearance.

c) The compounds have a high metabolic stability.

d) The compounds have no irreversible inhibitory action against CYP enzymes (such as CYP3A4) when the concentration is within the range described in the present specification as the measurement conditions.

e) The compounds have no mutagenicity.

f) The compounds are associated with a low cardiovascular risk.

g) The compounds have a high solubility.

h) The compounds are highly selective for PGD2 receptors (DP receptors and/or CRTH2 receptors).

For the purpose of treating the above-mentioned diseases in humans, the compounds of the present invention may be administered orally as a powder, a granule, tablets, capsules, pills, a liquid and the like or parenterally as an injection, suppositories, a percutaneous drug, an inhalant and the like. The effective doses of the present compounds may be mixed with excipients suitable for the dosage form, such as fillers, binders, humectants, disintegrators, and lubricants, as appropriate, to form pharmaceutical preparations. For preparing an injection, sterilization is performed with a suitable carrier.

The pharmaceutical compositions according to the present invention can be administered either orally or parenterally. For oral administration, commonly used dosage forms, such as tablets, granule, powder, and capsules, may be prepared according to conventional methods. For parenteral administration, any commonly used dosage form, such as an injection, may be suitably used. The compounds according to the present invention can be suitably used as oral preparations because of their high oral absorbability.

The effective doses of the compounds of the present invention can be mixed with various pharmaceutical excipients suitable for the dosage form, such as fillers, binders, disintegrators, and lubricants, as appropriate, to form pharmaceutical compositions.

The dose depends on the condition of the disease, administration route, or age or weight of the patient. The usual oral dose for adults is 0.1 to 100 mg/kg per day, preferably 1 to 20 mg/kg per day.

The dose of the pharmaceutical composition of the present invention is preferably determined on the basis of the age and weight of the patient, type and severity of the disease, administration route and the like. The usual oral dose for adults is in the range of 0.05 to 100 mg/kg per day, preferably 0.1 to 10 mg/kg per day. The parenteral dose for adults significantly varies depending on the administration route but is usually in the range of 0.005 to 10 mg/kg per day, preferably 0.01 to 1 mg/kg per day. The dose may be administered once daily or may be divided into multiple daily doses.

The compounds of the present invention may be used in combination with other drugs and the like (hereinafter abbreviated as combination drugs) in order to increase the effect of the compounds, decrease the dose of the compounds and the like. In the case of treating inflammatory diseases including allergy, the compound can be used combined with or in a coupled formulation with leukotriene receptor antagonist (e.g., montelukast sodium, zafirlukast, pranlukast hydrate, leukotriene B4 receptor antagonist); leukotriene synthesis inhibitor (e.g., zileuton); PDE IV inhibitor (e.g., theophylline, cilomilast, roflumilast); corticosteroid (e.g., prednisolone, fluticasone, budesonide, ciclesonide); β2-agonist (e.g., salbutamol, salmeterol, formoterol); anti IgE antibody (e.g., omalizumab); histamine H1 receptor antagonist (e.g., chlorpheniramine, loratadine, cetirizine); immunosuppressant (e.g., tacrolimus, cyclosporin); thromboxane A2 receptor antagonist (e.g., ramatroban); chemokine receptor (especially CCR-1, CCR-2, CCR-3) antagonist, other prostanoid receptor antagonist (e.g., DP1 antagonist, CRTH2 antagonist); adhesion molecule antagonist (e.g., VLA-4 antagonist); cytokine antagonist (e.g., anti-IL-4 antibody, anti-IL-3 antibody); Non-steroidal anti-inflammatory agent (propionic acid derivative such as ibuprofen, ketoprofen and naproxen and the like; acetic acid derivative such as indomethacin, diclofenac and the like; salicylic acid such as acetyl salicylic acid and the like; cyclooxigenase-2 inhibitor such as celecoxib, etoricoxib and the like). Further, uses combined with or in a coupled formulation with antitussive agent (e.g., codeine, hydrocodein and the like), cholesterol lowering agent (e.g., lovastatin, simvastatin, fluvastatin, rosuvastatin and the like), anticholinergic drug (e.g., tiotropium, ipratropium, flutropium, oxitropium and the like) are also possible. The timing for the administration of the compounds of the present invention and concomitant drugs is not limited: the administration of the compounds of the present invention and concomitant drugs may be administered to the subject to be treated concurrently or with a time lag. The compounds of the present invention and concomitant drugs may be administered as 2 or more types of drug products containing respective active ingredients or as a single drug product containing all active ingredients.

The dose for combination drugs may be appropriately selected in reference to the clinical dose. The compounding ratio of the compounds of the present invention and combination drugs may be appropriately selected depending on the subject to be treated, administration route, disease to be treated, symptoms, combination of the drugs and the like. For administration in humans, for example, 1 part by weight of the compounds of the present invention may be used in combination with 0.01 to 100 parts by weight of concomitant drugs.

The present invention will be described in more detail with reference to, but not limited to, the following Reference Examples, Examples and Test Examples.

In this description, meaning of each abbreviation is as follows:

Ac: Acetyl
Bn: Benzyl
Boc: tert-Butoxycarbonyl
Bu: Butyl
DAST: N,N-Diethylaminosulfur trifluoride
DCC: N,N'-dicyclohexyl carbodiimide
DEAD: diethyl azodicarboxylate
DIPEA: diisopropylethylamine
DMA: N,N-Dimethylacetamide
DMAP: 4-Dimethylaminopyridine
DME: Dimethoxyethane
DMF: N,N-Dimethylformamide
DMSO: Dimethylsulfoxide
EDC: 1-Ethyl-3-(3-Dimethylaminopropyl)carbodiimide
Et: Ethyl
HATU: O-(7-Azabenzotriazol-1-yl)-1,1,3,3-tetramethyluronium hexafluorophosphate
HOBt: 1-Hydroxybenzotriazole
i-Pr: Isopropyl
Me: Methyl
Ms: Methanesulphonyl
n-Bu: n-Butyl
i-Pr: i-Propyl
Pd(OH)$_2$: Palladium hydroxide
PdCl$_2$ (dppf): [1,1'-Bis(diphenylphosphino)ferrocene]palladium(II)dichloride
Pd$_2$(dba)$_3$ Tris(dibenzylideneacetone)dipalladium
TBS: tert-Butyldimethylsilyl
t-Bu: tert-Butyl
THF: Tetrahydrofuran
Tr: Trityl
Ts: para-Toluenesulfonyl Moreover, "wedge-shaped" and "dashed line" mean configuration. The compounds with "Abs" in the chemical structure means the absolute configuration of the compounds are identified, and the compounds without "Abs" in the chemical structure means the relative configuration of the compounds are identified but not the absolute configuration of the compounds. The compound with "Rac" in the chemical structure means that the compound is racemic compound.

NMR analysis of each Reference Examples and Examples was performed by 300 MHz using DMSO-$d_6$ or CDCl$_3$.

"RT" in tables means retention time in LC/MS: liquid column chromatography/mass analysis and these are measured under the conditions as mentioned below:

[Condition A]
Column: XBridge C18 (5 μm, i.d.4.6×50 mm) (Waters)
Flow rate: 3 mL/min
UV detection wavelength: 254 nm
Mobile phases: [A] is 0.1% formic acid solution, and [B] is 0.1% formic acid in acetonitrile solvent.
Gradient: linear gradient of 10% to 100% solvent [B] for 3 minutes was performed, and 100% solvent [B] was maintained for 1 minute.

[Condition B]
Column: Shim-pack XR-ODS (2.2 μm, i.d.50×3.0 mm) (Shimadzu)
Flow rate: 1.6 mL/min
UV detection wavelength: 254 nm
Mobile phases: [A] is 0.1% formic acid solution, and [B] is 0.1% formic acid in acetonitrile solvent.
Gradient: linear gradient of 10% to 100% solvent [B] for 3 minutes was performed, and 100% solvent [B] was maintained for 0.5 minute.

[Condition C]
Column: Gemini-NX (5 μm, i.d. 4.6×50 mm) (Phenomenex)
Flow rate: 3 mL/min
UV detection wavelength: 254 nm
Mobile phases: [A] is 0.1% formic acid solution, and [B] is 0.1% formic acid in methanol solvent.
Gradient: linear gradient of 5% to 100% solvent [B] for 3.5 minutes was performed, and 100% solvent [B] was maintained for 0.5 minute.

[Condition P]
Column: ACQUITY UPLC® (1.7 μm, i.d.2.1×50 mm) (Waters)
Flow rate: 0.8 mL/min
UV detection wavelength: 254 nm
Mobile phases: [A] is 0.1% formic acid solution, and [B] is 0.1% formic acid in acetonitrile solvent.
Gradient: linear gradient of 10% to 100% solvent [B] for 3 minutes was performed, and 100% solvent [B] was maintained for 0.5 minute.

REFERENCE EXAMPLE 1

[Chemical Formula 60]

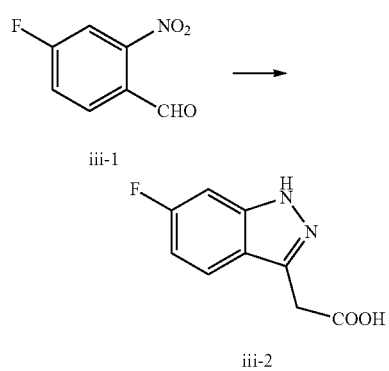

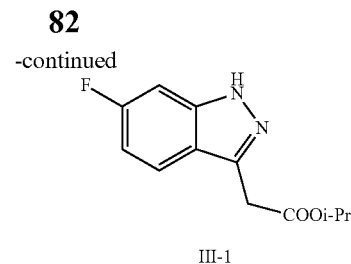

III-1

Step 1
Compound iii-2 was synthesized from Compound iii-1 in a similar manner as described in Journal of Medicinal Chemistry, 1992, Vol. 35, No. 12, p. 2155-2162.

$^1$H-NMR (DMSO-$d_6$) δ: 6.97 (1H, m), 7.27 (1H, d, J=9.60 Hz), 7.75 (1H, dd, J=8.59, 5.05 Hz), 12.70 (2H, brs).

Step 2
Compound iii-2 was reacted with isopropyl alcohol to obtain Compound III-1 in a similar manner as described in the above document.

$^1$H-NMR (CDCl$_3$) δ: 1.24 (6H, d, J=6.32 Hz), 3.97 (2H, s), 5.06 (1H, qq, J=6.32, 6.32 Hz), 6.94 (1H, td, J=9.00, 2.11 Hz), 7.08 (1H, dd, J=9.06, 2.11 Hz), 7.68 (1H, dd, J=8.52, 5.22 Hz), 9.92 (1H, s).

The following indazole isopropyl acetate derivatives were synthesized by the method in a similar manner to the above.

[Chemical Formula 61]

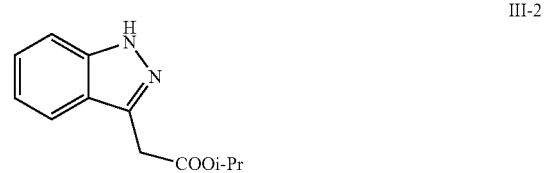

III-2

III-3

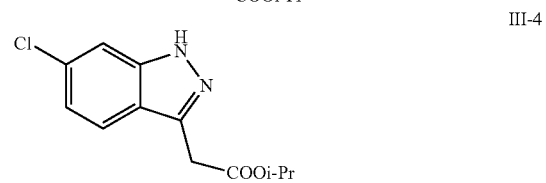

III-4

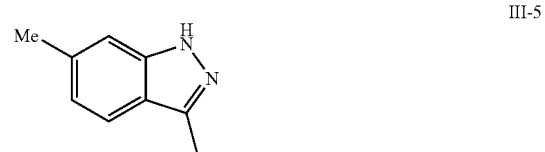

III-5

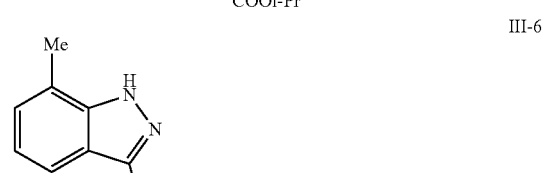

III-6

Compound III-2

¹H-NMR (CDCl3) δ: 7.73 (1H, d, J=8.1 Hz), 7.46-7.35 (2H, m), 7.17 (1H, t, J=7.4 Hz), 5.10-5.01 (1H, m), 4.00 (2H, s), 1.23 (6H, d, J=6.3 Hz).

Compound III-3

¹H-NMR (CDCl3) δ: 7.86 (1H, d, J=8.6 Hz), 7.76 (1H, s), 7.40 (1H, d, J=8.7 Hz), 5.10-5.02 (1H, m), 4.03 (2H, s), 1.24 (6H, d, J=6.2 Hz).

Compound III-4

¹H-NMR (CDCl₃) δ: 7.62 (1H, d, J=8.54 Hz), 7.47 (1H, s), 7.08 (1H, d, J=8.85 Hz), 5.03 (1H, t, J=6.33 Hz), 3.96 (2H, s), 1.22 (6H, d, J=6.41 Hz).

Compound III-5

¹H-NMR (CDCl₃) δ: 7.60 (1H, d, J=8.2 Hz), 7.20 (1H, s), 6.99 (1H, d, J=8.2 Hz), 5.09-5.00 (1H, m), 3.96 (2H, s), 2.48 (3H, s), 1.23 (6H, d, J=6.3 Hz).

Compound III-6

¹H-NMR (CDCl₃) δ: 9.78 (1H, s), 7.56 (1H, d, J=7.9 Hz), 7.17-7.14 (2H, m), 7.08 (2H, t, J=7.5 Hz), 5.12-4.99 (1H, m), 3.99 (2H, s), 2.53 (3H, s), 1.23 (7H, d, J=6.2 Hz).

REFERENCE EXAMPLE 2

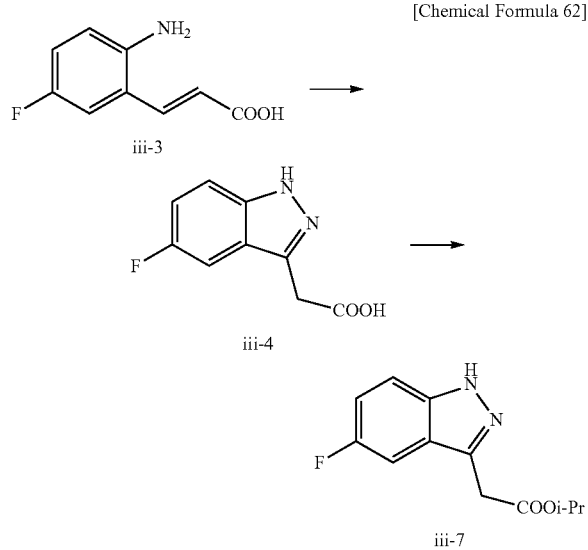

Compound iii-4 was synthesized from Compound iii-3 in a similar manner as described in U.S. Pat. No. 4,008,070, and was used in the next step without purification. The obtained compound was reacted with isopropylalcohol in a similar manner as described in Reference Example 1, Step 2 to give Compound III-7.

¹H-NMR (CDCl₃) δ: 10.04 (1H, brs), 7.41-7.34 (2H, m), 7.16 (1H, td, J=8.9, 2.4 Hz), 5.11-5.02 (1H, m), 3.97 (2H, s), 1.25 (6H, d, J=6.3 Hz).

The following indazole acetate derivatives were synthesized by the method in a similar manner to the above.

[Chemical Formula 63]

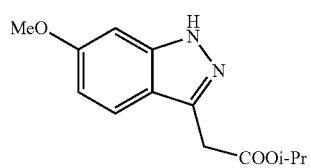

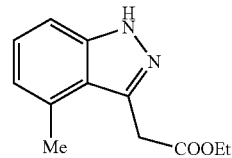

Compound III-8

¹H-NMR (CDCl₃) δ: 9.70 (1H, br s), 7.59 (1H, d, J=9.4 Hz), 6.84-6.80 (2H, m), 5.10-5.02 (1H, m), 3.94 (2H, s), 3.87 (3H, s), 1.23 (6H, d, J=6.3 Hz).

Compound III-9

¹H-NMR (CDCl₃) δ: 9.92 (1H, brs), 7.30-7.22 (2H, m), 6.89 (1H, d, J=6.2 Hz), 4.21 (2H, q, J=7.1 Hz), 4.14 (2H, s), 2.65 (3H, s), 1.26 (3H, t, J=7.11 Hz).

REFERENCE EXAMPLE 3

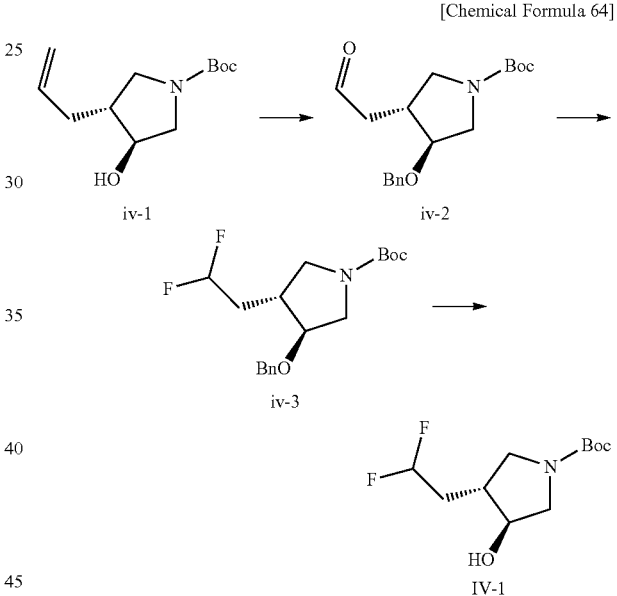

Step 1

In a similar manner as described in Acta Chemica Scandinavica, 1998, 52, 1214, Compound iv-1 (170 mg, 0.748 mmol) was dissolved in DMF (2 mL), and 60% sodium hydride (35.9 mg, 0.897 mmol) was added to the reaction mixture under ice-cooling. After the mixture was stirred for 30 minutes at room temperature, benzyl bromide (107 μL, 0.897 mmol) was added dropwise to the mixture at room temperature, and the resulting mixture was stirred for 24 hours. Water was added to the reaction mixture under ice-cooling, and the mixture was extracted with ethyl acetate. The organic layer was washed by water and brine, and was dried over anhydrous magnesium sulfate. The mixture was concentrated in vacuo and the resulting residue was purified by silica gel column chromatography (hexane-ethyl acetate).

The obtained compound (210 mg, 0.662 mmol) was dissolved in acetonitrile (3 mL). To the reaction mixture was added a solution of sodium periodate (425 mg, 1.985 mmol) in water (3 mL) at room temperature. 10% osmium tetroxide (168 mg, 0.066 mmol) was added to the mixture, and the resulting mixture was stirred for 6 hours and standed for 2 days. The reaction mixture was diluted by water (5 mL) and ethyl acetate (5 mL), and the insoluble was removed by filtration using Celite. The filtrate was extracted with ethyl acetate. The organic layer was washed by water and brine, and dried over anhydrous magnesium sulfate. The mixture was concentrated in vacuo and the resulting residue was purified by silica gel column chromatography (hexane-ethyl acetate) to give Compound iv-2 (117 mg, 2 steps, Yield 49%).

LC/MS (Condition B) RT=2.72, [M+H]$^+$=320.

Step 2

Under nitrogen atmosphere, Compound iv-2 (50 mg, 0.157 mmol) was dissolved in dichloromethane (2 mL), and DAST (46 µL, 0.344 mmol) was gradually added dropwise at −78° C. The reaction mixture was allowed to warm to room temperature gradually over 6 hours with stirring and left standing overnight. To the mixture was added saturated aqueous sodium bicarbonate, and the mixture was extracted with ethyl acetate. The organic layer was washed by water and brine, and dried over anhydrous magnesium sulfate. The mixture was concentrated in vacuo and the resulting residue was purified by silica gel column chromatography (hexane-ethyl acetate) to give Compound iv-3 (36 mg, Yield 68%).

Step 3

Compound iv-3 (35 mg, 0.103 mmol) was dissolved in ethanol (1 mL), and Pd(OH)$_2$ (10 mg) was added to the mixture. The mixture was stirred for 4 hours under hydrogen atmosphere at atmospheric pressure. After the reaction was completed, the insoluble was removed by filtration using Celite. The filtrate was concentrated in vacuo to give Compound IV-1 (26 mg, Yield 100%).

$^1$H-NMR (CDCl$_3$) δ: 5.94 (1H, tt, J=56.3, 4.4 Hz), 4.13-3.99 (1H, m), 3.81-3.59 (2H, m), 3.26-3.00 (2H, m), 2.36-2.19 (1H, m), 1.93-1.73 (2H, m), 1.46 (9H, s).

REFERENCE EXAMPLE 4 was added to the resulting mixture. The mixture was extracted with ethyl acetate. The organic layer was washed by brine, and dried over anhydrous magnesium sulfate. The mixture was concentrated in vacuo and the resulting residue was purified by silica gel column chromatography (hexane-ethyl acetate) to give Compound iv-4 (63 mg, Yield 99%).

Step 2

Compound iv-4 (60 mg, 0.187 mmol) was dissolved in dichloromethane (2 mL) under nitrogen atmosphere, and DAST (37 µL, 0.280 mmol) was added dropwise to the solution at −78° C. gradually. The reaction mixture was allowed to warm to room temperature gradually and stirred for 6 hours, and left standing overnight. Saturated aqueous sodium bicarbonate was added to the mixture and the resulting mixture was extracted with ethyl acetate. The organic layer was washed by water and brine, and dried over anhydrous magnesium sulfate. The mixture was concentrated in vacuo and the resulting residue was purified by silica gel column chromatography (hexane-ethyl acetate) to give Compound iv-5 (25 mg, Yield 41%).

Step 3

Compound iv-5 (24 mg, 0.074 mmol) was dissolved in ethanol (1 mL), and Pd(OH)$_2$ (10 mg) was added to the solution. The mixture was stirred for 15 hours under hydrogen atmosphere at atmospheric pressure. After the reaction was completed, the insoluble was removed by filtration using Celite. The filtrate was concentrated in vacuo to give Compound IV-2 (18 mg, Yield 100%).

$^1$H-NMR (CDCl$_3$) δ: 4.70-4.55 (1H, m), 4.55-4.40 (1H, m), 4.13-4.02 (1H, m), 3.78-3.55 (2H, m), 3.31-2.99 (2H, m), 2.26-2.11 (1H, m), 2.01-1.78 (2H, m), 1.46 (9H, s).

REFERENCE EXAMPLE 5

[Chemical Formula 66]

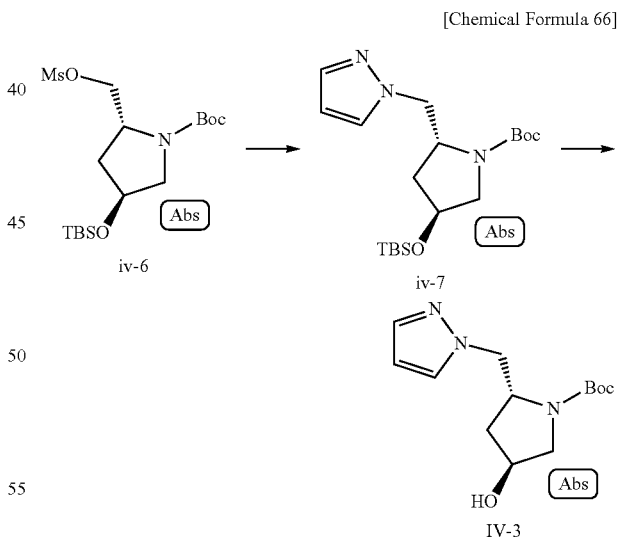

[Chemical Formula 65]

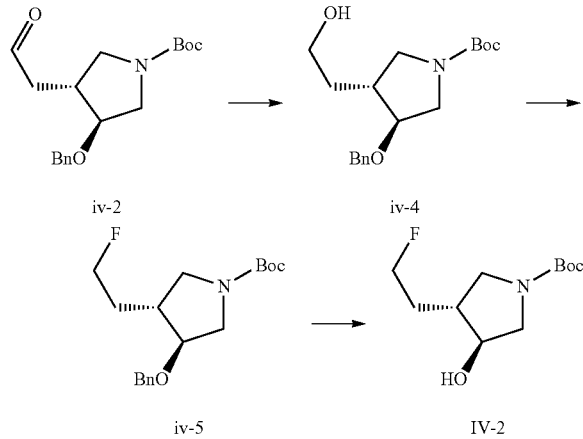

Step 1

Compound iv-2 (63 mg, 0.197 mmol) was dissolved in THF (2 mL) under nitrogen atmosphere, and sodium borohydride (8.95 mg, 0.237 mmol) was added to the solution at room temperature. The mixture was stirred for 2 hours at room temperature, and 1 mol/L aqueous hydrochloric acid Step 1

Pyrazole (37 mg, 0.536 mmol) was dissolved in DMF (1.5 mL) under ice-cooling. To a solution was added 60% sodium hydride (21 mg, 0.536 mmol), and the mixture was stirred for 10 minutes. To the reaction mixture, the solution of Compound iv-6 (146 mg, 0.357 mmol) which was synthesized in a similar manner as described in Medicinal Chemistry letters, 2011, vol. 2, no. 2 p. 142-147, in DMF (1.5 mL) was added dropwise, and the resulting mixture was stirred for 1.5 hours at 60° C. After the reaction mixture was allowed to cool to room temperature, water was added to the mixture, and the resulting mixture was extracted with ethyl acetate. The organic layer was washed by water and brine, dried over magnesium sulphate, and concentrated in vacuo. The resulting residue was purified by silica gel column chromatography (hexane-ethyl acetate) to give Compound iv-7 (136 mg, Yield 100%).

$^1$H-NMR (CDCl$_3$) δ: 7.48 (1H, s), 7.29 (1H, s), 6.25 (1H, s), 4.64-4.33 (1H, m), 4.29 (1H, dd, J=14.27, 2.69 Hz), 4.23-4.12 (1H, br m), 3.73-3.59 (1H, br m), 3.36-3.00 (2H, m), 2.16-1.96 (1H, m), 1.95-1.80 (1H, m), 1.54-1.47 (9H, m), 0.82 (9H, s), 0.00 (−0.03) (6H, m).

Step 2

Compound iv-7 (136 mg, 0.356 mmol) was dissolved in THF (2.5 mL). To a solution was added 1.0 mol/L tetrabutylammonium fluoride in THF (0.535 mL, 0.535 mmol) under ice-cooling, and the mixture was stirred for 4 hours at room temperature. To the reaction mixture was added water, and the mixture was extracted with ethyl acetate. The organic layer was washed by brine, and dried over sodium sulphate. The mixture was concentrated in vacuo and the resulting residue was purified by silica gel column chromatography (hexane-ethyl acetate) to give Compound IV-3 (92 mg, Yield 97%).

$^1$H-NMR (CDCl$_3$) δ: 7.52 (1H, d, J=1.85 Hz), 7.35 (1H, br s), 6.30 (1H, dd, J=2.18, 1.85 Hz), 4.72-4.35 (2H, m), 4.32-4.22 (1H, m), 4.06 (1H, br s), 3.61-3.30 (1H, br m), 3.11 (1H, dd, J=11.75, 4.36 Hz), 2.34-2.10 (1H, br m), 2.07-1.96 (1H, m), 1.56 (9H, s).

REFERENCE EXAMPLE 6

[Chemical Formula 67]

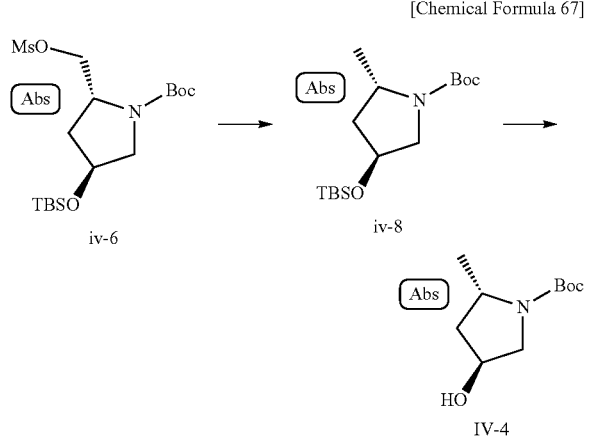

Step 1

Compound iv-6 (3.27 g, 7.98 mmol) was dissolved in THF (10 ml). To the solution was added 1 mol/L lithium triethylborohydride in THF (23.95 mL) under ice-cooling, and the mixture was stirred for 3 hours at room temperature. To the reaction mixture was added water, and the resulting mixture was extracted with ethyl acetate. The organic layer was washed by brine, and concentrated in vacuo to give Compound iv-8 (3 g, Yield 99%).

$^1$H-NMR (CDCl$_3$) δ: 4.34 (1H, t, J=4.88 Hz), 3.97-3.93 (1H, m), 3.43-3.39 (1H, m), 3.34-3.30 (1H, m), 2.01-1.98 (1H, m), 1.68-1.65 (1H, m), 1.46 (9H, d, J=1.37 Hz), 1.20 (3H, d, J=6.25 Hz), 0.87 (9H, d, J=1.53 Hz), 0.06 (6H, s).

Step 2

Compound iv-8 (2.52 g, 7.99 mmol) was dissolved in THF (13 mL). To the solution was added 1 mol/L tetra butylammonium fluoride in THF (15.97 mL, 15.97 mmol) under ice-cooling, and the mixture was stirred for 10 hours under ice-cooling. To the reaction mixture was added water, and the resulting mixture was extracted with ethyl acetate. The organic layer was washed by water and brine, and concentrated in vacuo to give Compound IV-4 (1.6 g, Yield 99.5%).

$^1$H-NMR (CDCl$_3$) δ: 4.42-4.39 (1H, m), 4.02-3.99 (1H, m), 3.49-3.46 (2H, m), 2.11-2.08 (1H, m), 1.76-1.73 (1H, br m), 1.57-1.53 (1H, m), 1.47 (9H, s), 1.24 (3H, t, J=5.26 Hz).

REFERENCE EXAMPLE 7

[Chemical Formula 68]

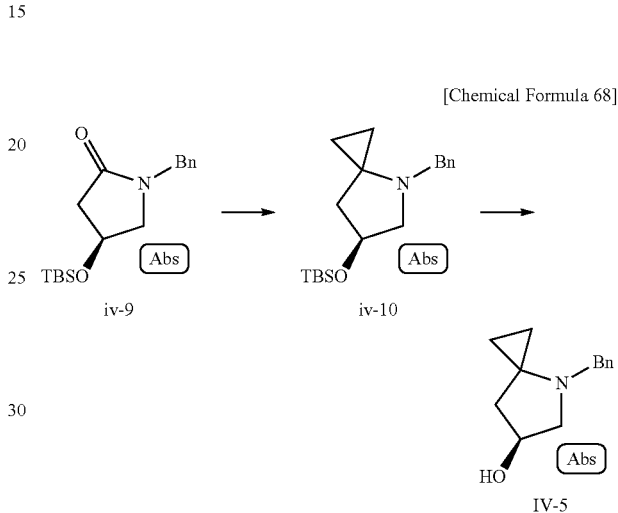

Step 1

Compound iv-9 (815 mg, 2.67 mmol) which was described in Heterocycles, 2000, vol. 53, No. 1, p. 173-182, was dissolved in THF (8 mL). To the solution were added 1.0 mol/L methyltriisopropoxytitanium in THF (3.21 mL, 3.21 mmol) and 3.0 mol/L ethylmagnesium bromide in diethyl ether (1.78 mL, 5.34 mmol), and the mixture was stirred for 24 hours at room temperature. To the reaction mixture were added diethyl ether (1.55 mL) and water (0.052 mL), and the resulting mixture was stirred for 4.5 hours at room temperature. After the precipitated solid was removed by filtration using Hy-flo-super cell, the filtrate was dried over sodium sulphate, and the filtrate was concentrated in vacuo. The residue was purified by silica gel column chromatography (hexane-ethyl acetate) to give Compound iv-10 (218 mg, Yield 26%).

$^1$H-NMR (CDCl$_3$) δ: 7.32-7.24 (5H, m), 4.52-4.42 (1H, m), 3.49 (1H, d, J=12.93 Hz), 3.42 (1H, d, J=12.93 Hz), 2.91 (1H, dd, J=10.83, 7.05 Hz), 2.62 (1H, dd, J=10.83, 4.11 Hz), 2.13 (1H, dd, J=13.01, 7.05 Hz), 1.90 (1H, dd, J=13.01, 4.11 Hz), 0.95-0.83 (10H, m), 0.75-0.65 (1H, m), 0.53-0.44 (1H, m), 0.40-0.31 (1H, m), 0.03-0.00 (6H, m).

Step 2

Compound iv-10 (218 mg, 0.686 mmol) was dissolved in THF (4 mL). To the solution was added 1.0 mol/L tetrabutylammonium fluoride in THF (1.03 mL, 1.03 mmol) under ice-cooling, and the mixture was stirred for 2 hours at room temperature and left standing overnight. The reaction mixture was concentrated, and water was added to the residue. After the mixture was extracted with ethyl acetate, the organic layer was washed by brine and dried over magnesium sulphate. The mixture was concentrated in vacuo and the resulting residue was purified by silica gel column chromatography (hexane-ethyl acetate) to give Compound IV-5 (105 mg, Yield 76%).

$^1$H-NMR (CDCl$_3$) δ: 7.38-7.24 (5H, m), 4.48-4.40 (1H, m), 3.50 (1H, d, J=13.09 Hz), 3.27 (1H, d, J=13.09 Hz), 2.87-2.75 (2H, m), 2.30 (1H, dd, J=13.76, 7.13 Hz), 1.97 (1H, dd, J=13.76, 2.27 Hz), 0.95-0.83 (2H, m), 0.59 (1H, dd, J=8.56, 5.71 Hz), 0.37 (1H, dd, J=8.39, 5.71 Hz).

REFERENCE EXAMPLE 8

[Chemical Formula 69]

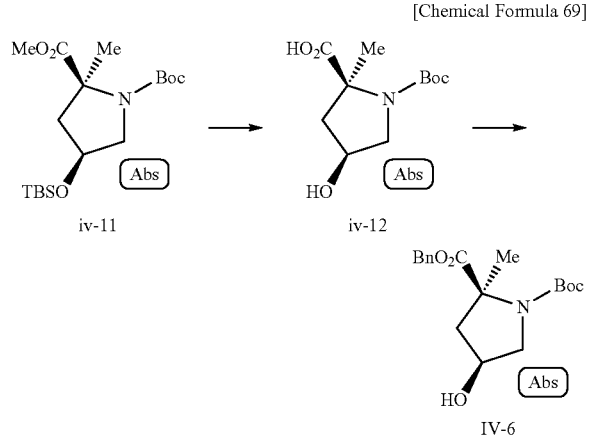

Step 1

Compound iv-11 (181 mg, 0.485 mmol) which was synthesized by the method in a similar manner as described in US2008/9497, was dissolved in THF (2 mL) and methanol (1 mL). To the solution was added 2 mol/L aqueous sodium hydroxide (0.97 mL, 1.94 mmol), and the mixture was stirred for 2.5 hours at room temperature. After the mixture was left standing overnight, to the mixture were added water and 10% aqueous citric acid. The resulting mixture was extracted with ethyl acetate. The organic layer was washed by brine, and dried over magnesium sulphate. The mixture was concentrated in vacuo, and the resulting residue was purified by silica gel column chromatography (chloroform-methanol) to give Compound iv-12 (101 mg, Yield 85%).

$^1$H-NMR (CDCl$_3$) δ: 4.40-4.26 (1H, m), 3.90-3.58 (1H, m), 3.47 (1H, dd, J=11.92, 3.86 Hz), 2.83-2.39 (1H, m), 2.15-1.90 (1H, m), 1.60 (3H, d, J=19.81 Hz), 1.51-1.43 (9H, m).

Step 2

Compound iv-12 (99 mg, 0.405 mmol) was dissolved in THF (2 mL). To the solution were added triethylamine (0.084 mL, 0.608 mmol) and benzyl bromide (0.072 mL, 0.608 mmol), and the mixture was stirred for 26.5 hours at room temperature. The reaction mixture was filtered and filtrate was concentrated in vacuo. The resulting residue was purified by silica gel column chromatography (hexane-ethyl acetate) to give Compound IV-6 (93 mg, Yield 68%).

$^1$H-NMR (CDCl$_3$) δ: 7.39-7.33 (5H, m), 5.31-5.12 (2H, m), 4.28-4.16 (1H, br m), 3.88-3.39 (3H, m), 2.33-2.20 (1H, m), 2.15-2.00 (1H, m), 1.63-1.53 (3H, m), 1.46-1.35 (9H, m).

REFERENCE EXAMPLE 9

[Chemical Formula 70]

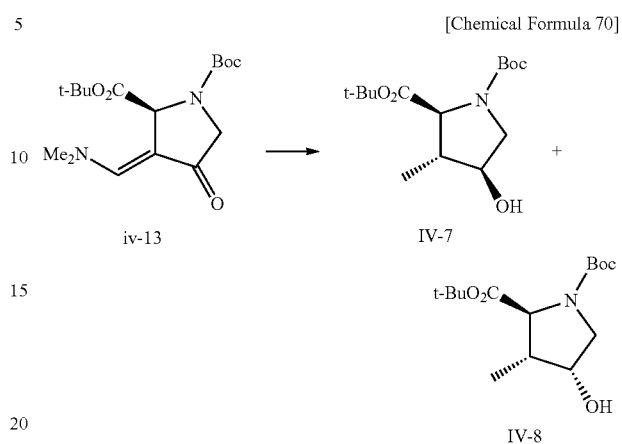

Compound iv-13 (2.83 g, 8.31 mmol) which is described in Tetrahedron, 2005, vol. 61, 2005, 3725-3731, was dissolved in 2-propanol (42 mL). To the solution was added Pd-Carbon (2.8 g), and the mixture was stirred for 47 hours under hydrogen atmosphere at atmospheric pressure. The reaction mixture was diluted with ethyl acetate and filtered using Celite The filtrate was concentrated in vacuo and the resulting residue was purified by silica gel column chromatography (hexane-ethyl acetate) to give Compound IV-7 (145.1 mg, Yield 5.8%) and Compound IV-8 (163.2 mg, Yield 6.5%).

Compound IV-7

$^1$H-NMR (CDCl$_3$) δ: 3.90-3.19 (5H, m), 2.33-2.24 (1H, m), 1.50-1.43 (18H, m), 1.13-1.08 (3H, m).

Compound IV-8

$^1$H-NMR (CDCl$_3$) δ: 4.23-4.17 (1H, br m), 4.03-3.49 (4H, m), 2.29-2.19 (1H, m), 1.50-1.46 (18H, m), 1.21-1.17 (3H, m).

Compound IV-9 and Compound IV-10 were synthesized by the method in a similar manner to the above.

[Chemical Formula 71]

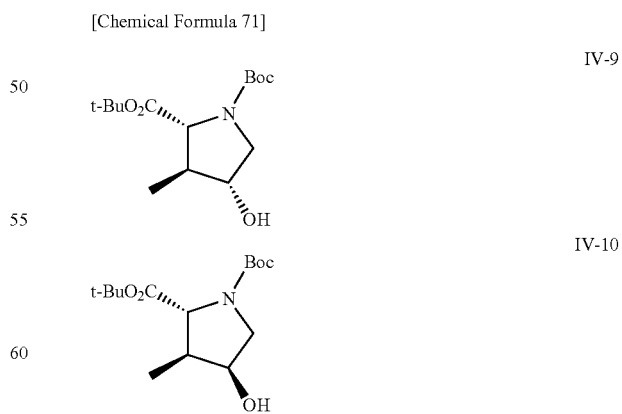

Compound IV-9

$^1$H-NMR (CDCl$_3$) δ: 3.90-3.20 (5H, m), 2.34-2.25 (1H, m), 1.50-1.44 (18H, m), 1.14-1.08 (3H, m).

Compound IV-10

$^1$H-1-NMR (CDCl$_3$) δ: 4.20 (1H, br s), 3.84-3.76 (1H, m), 3.67-3.49 (2H, m), 2.29-2.20 (1H, br m), 1.51-1.46 (18H, m), 1.22-1.17 (3H, m).

REFERENCE EXAMPLE 10

[Chemical Formula 72]

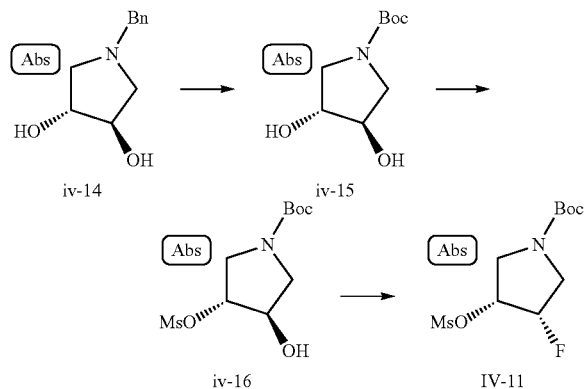

To a solution of Compound iv-14 (1.0 g, 5.17 mmol) in methanol (20 mL) were added 10% Pd-Carbon (wet 50%) (0.22 g) and Boc$_2$O (1.32 mL), and the mixture was stirred under hydrogen atmosphere. The reaction mixture was filtered using Celite, and the filtrate was concentrated in vacuo. The resulting residue was purified by silica gel column chromatography (methanol-chloroform) to give Compound iv-15 (0.42 g, Yield 40%).

To the mixture of Compound iv-15 (300 mg, 1.48 mmol) in dichloromethane (3 mL) and THF (6 mL) was added pyridine (0.239 mL, 2.95 mmol) and the mixture was added dropwise methanesulfonyl chloride (0.121 mL, 1.55 mmol) under ice-cooling. To the reaction mixture was added triethylamine (0.409 mL, 2.95 mmol), and the resulting mixture was stirred. To the reaction mixture was added water, and the resulting mixture was extracted with ethyl acetate. The organic layer was washed by aqueous citric acid, aqueous sodium bicarbonate, and brine, dried over anhydrous magnesium sulphate, and concentrated in vacuo. The resulting residue was purified by silica gel column chromatography to give Compound iv-16 (148 mg, Yield 30%).

To a solution of Compound iv-16 (90 mg, 0.32 mmol) in dichloromethane (1 mL), was added DAST (0.127 mL) under ice-cooling, and the mixture was stirred at room temperature. After aqueous sodium bicarbonate was added to the reaction mixture under ice-cooling, the resulting mixture was extracted with ethyl acetate. The organic layer was washed by aqueous sodium bicarbonate and brine, dried over anhydrous magnesium sulphate, and concentrated in vacuo. The resulting residue was purified by silica gel column chromatography (ethyl acetate-chloroform) to give crude product of Compound IV-11 (47 mg).

REFERENCE EXAMPLE 11

[Chemical Formula 73]

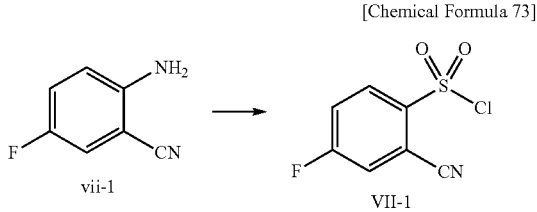

Step 1

Compound vii-1 (1.0 g, 7.35 mmol) was dissolved in acetonitrile (25 mL). To the solution was added concentrated hydrochloric acid (10 mL) at room temperature. The reaction mixture was allowed to cool to 0° C., and a solution of sodium nitrite (608 mg, 8.82 mmol) in water (1 mL) was added to the mixture. The reaction mixture was stirred for 1.5 hours at 0° C. To the reaction mixture was added acetic acid (12 mL), and the resulting mixture was stirred for 10 minutes at 0° C. In addition, sodium hydrogensulfate (7.64 g, 73.5 mmol) was added to the mixture and the resulting mixture was stirred for 5 minutes. Copper (II) chloride (988 mg, 7.35 mmol) and copper (I) chloride (72.7 mg, 0.735 mmol) were added to the mixture at the same timing. The resulting solution was allowed to warm to room temperature gradually from 0° C. and stirred for 3.5 hours. To the reaction mixture was added water, and the resulting mixture was extracted with ethyl acetate. The organic layer was washed by water and brine, and dried over anhydrous magnesium sulfate. The mixture was concentrated in vacuo, and the resulting residue was purified by silica gel column chromatography (hexane-ethyl acetate) to give Compound VII-1 (965 mg, Yield 60%).

$^1$H-NMR (CDCl$_3$) δ: 8.26 (1H, dd, J=9.0, 4.9 Hz), 7.69 (1H, dd, J=7.5, 2.6 Hz), 7.54 (1H, ddd, J=9.4, 6.8, 2.2 Hz).

LC/MS (Condition B) RT=1.80, [M+H]$^+$=220.

The following sulfonyl chloride derivatives were synthesized in a similar manner described in the above.

[Chemical Formula 74]

VII-2

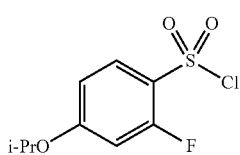

VII-3

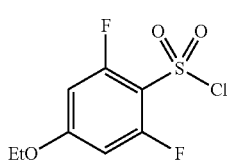

Compound VII-2

$^1$H-NMR (CDCl3) δ: 7.84 (1H, t, J=8.7 Hz), 6.77-6.71 (2H, m), 4.68-4.59 (1H, m), 1.40 (6H, d, J=6.1 Hz).

Compound VII-3

$^1$H-NMR (CDCl3) δ: 6.59-6.53 (2H, m), 4.11 (2H, q, J=6.9 Hz), 1.47 (3H, t, J=7.0 Hz).

REFERENCE EXAMPLE 12

[Chemical Formula 75]

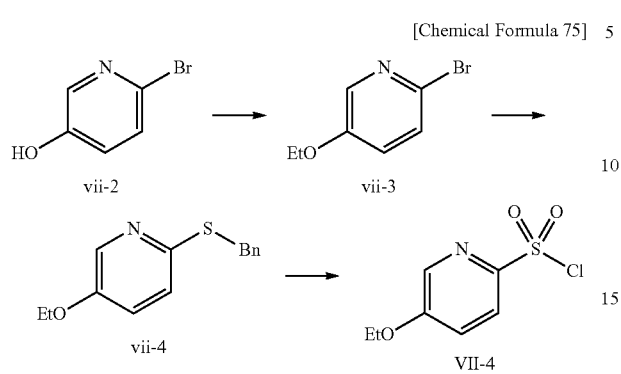

Step 1

To a solution of Compound vii-2 (2.0 g, 11.49 mmol) in DMF (20 mL) was added sodium hydride (0.644 g, 16.09 mmol) at room temperature, and the mixture was stirred for 30 minutes. Iodoethane (1.858 mL, 22.99 mmol) was added to the mixture and the resulting mixture was stirred for additional 3.5 hours at room temperature. To the reaction mixture was added water, and the mixture was extracted with ethyl acetate. The organic layer was washed by water and brine, dried over anhydrous magnesium sulphate, and concentrated in vacuo. The resulting residue was purified by silica gel column chromatography (hexane-ethyl acetate) to give Compound vii-3 (2.32 g, Yield 100%).

$^1$H-NMR (CDCl$_3$) δ: 8.03 (1H, d, J=2.75 Hz), 7.35 (1H, d, J=8.69 Hz), 7.07 (1H, dd, J=8.62, 2.97 Hz), 4.05 (2H, q, J=6.91 Hz), 1.43 (3H, t, J=6.94 Hz).

Step 2

To a solution of Compound vii-3 (1.5 g, 7.42 mmol) in toluene (15 mL) were added α-toluene thiol (0.966 ml, 8.17 mmol), DIPEA (2.85 mL, 16.33 mmol), Pd$_2$(dba)$_3$ (0.272 g, 0.297 mmol) and Xantphos (0.344 g, 0.594 mmol) under nitrogen atmosphere, and the mixture was stirred for 6.5 hours at 85° C. The reaction mixture was allowed to cool to room temperature, and diluted with ethyl acetate. The insoluble was removed by filtration by using Celite. The filtrate was concentrated, and the resulting residue was purified by silica gel column chromatography (hexane-ethyl acetate) to give Compound vii-4 (1.82 g, Yield 100%).

$^1$H-NMR (CDCl$_3$) δ: 8.18 (1H, s), 7.36-7.02 (7H, m), 4.36 (2H, s), 4.04 (2H, q, J=6.91 Hz), 1.42 (3H, t, J=7.02 Hz).

Step 3

To the mixture of Compound vii-4 (1.82 g, 7.42 mmol), acetic acid (12 mL), and purified water (4 mL), under nitrogen atmosphere was added N-chlorosuccinimide (3.73 g, 27.9 mmol) at room temperature, and the mixture was stirred for 3 hours. After the reaction mixture was concentrated in vacuo, water was added to the resulting mixture. The mixture was extracted with ethyl acetate. The organic layer was washed by brine, dried over anhydrous magnesium sulphate, and concentrated in vacuo. The resulting residue was purified by silica gel column chromatography (hexane-ethyl acetate) to give Compound VII-4 (1.34 g, Yield 80%).

$^1$H-1-NMR (CDCl$_3$) δ: 8.40 (1H, d, J=1.8 Hz), 8.04 (1H, d, J=8.7 Hz), 7.33 (1H, t, J=5.7 Hz), 4.21 (2H, ddd, J=14.0, 6.9, 1.1 Hz), 1.51 (3H, td, J=7.0, 1.2 Hz).

The following compound was synthesized by the method in a similar manner to the above.

[Chemical Formula 76]

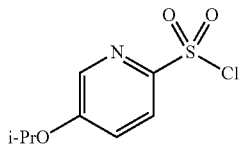

VII-5

Compound VII-5

LC/MS (Condition B) RT=2.10, [M+H]$^+$=236.

REFERENCE EXAMPLE 13

[Chemical Formula 77]

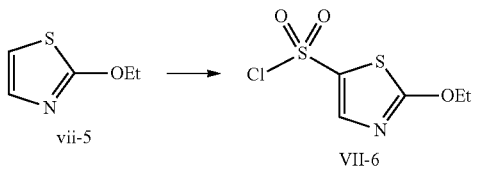

To a solution of 2-ethoxythiazole (2.0 g, 15.5 mmol) in THF (40 mL) was added dropwise 1.02 mol/L sec-butyl lithium in hexane (16.7 mL, 17.0 mmol) at −78° C. under nitrogen atmosphere, and the mixture was stirred for 1 hour at the same temperature. To the reaction mixture was added sulfur dioxide (9.92 g, 155 mmol), and the resulting mixture was stirred for 3 hours at room temperature. N-chlorosuccinimide (2.07 g, 15.5 mmol) was added to the mixture, and the resulting mixture was stirred for additional 1 hour at room temperature. To the reaction mixture was added 2 mol/L aqueous hydrochloric acid, and the resulting mixture was extracted with ethyl acetate. The organic layer was dried over anhydrous sodium sulphate, and concentrated in vacuo. The resulting residue was by purified by silica gel column chromatography (hexane-ethyl acetate) to give Compound VII-6 (2.27 g, Yield 65%).

REFERENCE EXAMPLE 14

[Chemical Formula 78]

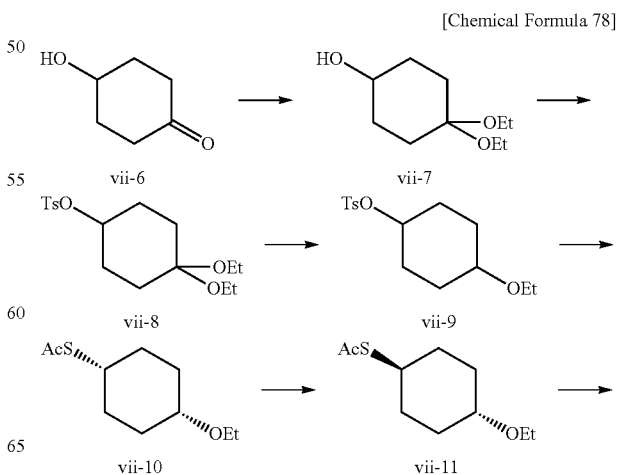

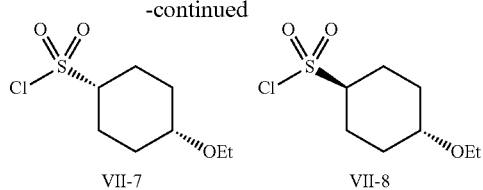

Step 1

To a solution of 4-hydroxycyclohexanone (2.0 g, 17.5 mmol) in ethanol (8 ml) were added triethyl orthoformate (8.78 ml, 52.6 mmol) and p-toluenesulfonic acid monohydrate (3.3 mg, 0.018 mmol), and the mixture was stirred overnight at room temperature. To the reaction mixture was added saturated aqueous sodium bicarbonate, and the resulting mixture was extracted with ethyl acetate. The organic layer was dried over anhydrous sodium sulphate, and concentrated in vacuo. The resulting residue was purified by silica gel column chromatography (hexane-ethyl acetate) to give Compound vii-7 (2.93 g, Yield 89%).

$^1$H-NMR (CDCl$_3$) δ: 1.15-1.21 (m, 6H), 1.49-1.60 (m, 4H), 1.76-1.81 (m, 2H), 1.93-2.00 (m, 2H), 3.43-3.50 (m, 4H), 3.77 (brs, 1H).

Step 2

To a solution of Compound vii-7 (2.93 g, 15.6 mmol) in dichloromethane (6 ml) were added triethylamine (6.48 ml, 46.7 mmol) and DMAP (0.571 g, 4.67 mmol) under ice-cooling. Then, a solution of TsCl (4.46 g, 23.4 mmol) in dichloromethane (9 ml) was added dropwise to the mixture, and the resulting mixture was stirred for 19 hours at room temperature. The mixture was concentrated in vacuo and the resulting residue was purified by silica gel column chromatography (hexane-ethyl acetate) to give Compound vii-8 (4.67 g, Yield 87%).

$^1$H-NMR (CDCl$_3$) δ: 1.11-1.18 (m, 6H), 1.58-1.89 (m, 8H), 2.45 (s, 3H), 3.37-3.45 (m, 4H), 4.60-4.65 (m, 1H), 7.33 (d, J=8.0 Hz, 2H), 7.79 (d, J=8.0 Hz, 2H).

Step 3

To the mixture of Compound vii-8 (1.04 g, 3.03 mmol) and triethylsilane (0.58 ml, 3.64 mmol) was added dropwise a solution of trimethylsilyl triflate (5.48 µl, 0.030 mmol) in dichloromethane (0.3 ml) under ice-cooling, and the mixture was stirred for 30 minutes. Then, the reaction mixture was stirred for 3 hours at room temperature. To the mixture was added aqueous sodium bicarbonate, and the resulting mixture was extracted with dichloromethane. The organic layer was dried over anhydrous sodium sulphate, and concentrated in vacuo. The resulting residue was purified by silica gel column chromatography (hexane-ethyl acetate) to give Compound vii-9 (0.88 g, Yield 98%) as a mixture of diastereomers (60:40).

$^1$H-NMR (CDCl$_3$) δ: 4.14-1.92 (m, 11H), 2.45 (s, 3H), 3.29-3.33 (m, 1H), 3.44 (t, J=6.8 Hz, 2H), 4.50-4.54 (m, 1H, minor isomer), 4.60-4.63 (m, 1H, major isomer), 7.33 (d, J=8.0 Hz, 2H, major isomer), 7.34 (d, J=8.0 Hz, 2H, minor isomer), 7.79 (d, J=8.0 Hz, 2H).

Step 4

To a solution of Compound vii-9 (0.88 g, 2.98 mmol) in DMF (3 ml) was added potassium thioacetate (0.85 g, 7.44 mmol), and the mixture was stirred for 1 hour at 80° C. To the reaction mixture was added water, and the resulting mixture was extracted with ethyl acetate. The organic layer was washed by water and brine, dried over anhydrous sodium sulphate, and concentrated in vacuo. The resulting residue was purified by silica gel column chromatography (hexane-ethyl acetate) to give Compound vii-10 (85.4 mg, Yield 14%) and Compound vii-11 (136 mg, Yield 23%).

Compound vii-10

$^1$H-NMR (CDCl$_3$) δ: 1.19 (t, J=6.8 Hz, 3H), 1.34-1.46 (m, 4H), 2.02-2.08 (m, 4H), 2.30 (s, 3H), 3.21-3.26 (m, 1H), 3.37-3.46 (m, 1H), 3.50 (q, J=6.8 Hz, 2H).

Compound vii-11

$^1$H-NMR (CDCl$_3$) δ: 1.19 (t, J=6.8 Hz, 3H), 1.66-1.88 (m, 8H), 2.30 (s, 3H), 3.40-3.52 (m, 1H), 3.47 (q, J=6.8 Hz, 2H), 3.59-3.63 (m, 1H).

Step 5

To a solution of Compound vii-10 (85.4 mg, 0.42 mmol) in acetonitrile (0.25 ml) were added 2 mol/L aqueous hydrochloric acid (0.05 ml) and N-chlorosuccinimide (225 mg, 1.69 mmol) under ice-cooling, and the mixture was stirred for 1 hour. To the reaction mixture was added water, and the mixture was extracted with diethyl ether. The organic layer was dried over anhydrous sodium sulphate, and concentrated in vacuo. The resulting residue was purified by silica gel column chromatography (hexane-ethyl acetate) to give Compound VII-7 (87.1 mg, Yield 91%).

$^1$H-NMR (CDCl$_3$) δ: 1.21 (t, J=6.8 Hz, 3H), 1.31-1.41 (m, 2H), 1.78-1.88 (m, 2H), 2.26-2.29 (m, 2H), 2.46-2.50 (m, 2H), 3.26-3.33 (m, 1H), 3.54 (q, J=6.8 Hz, 2H).

Compound VII-8 was synthesized by the method in a similar manner to the above.

REFERENCE EXAMPLE 15

[Chemical Formula 79]

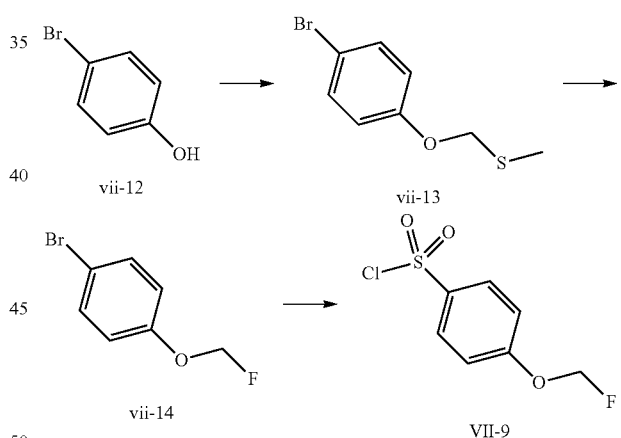

Step 1

To a solution of 4-bromophenol (7.00 g, 40.5 mmol) in DMF (140 ml) was added sodium hydride (60 wt %) (1.94 g, 48.6 mmol), and the mixture was stirred for 30 minutes at room temperature. To the reaction mixture was added (chloromethyl)methyl sulfide (4.01 ml, 48.6 mmol), and the mixture was stirred for 2.5 hours at 50° C. To the reaction mixture was added saturated aqueous ammonium chloride, and the resulting mixture was extracted with ethyl acetate. The organic layer was washed by water, dried over anhydrous sodium sulphate, and concentrated in vacuo. The resulting residue was purified by silica gel column chromatography (hexane-ethyl acetate) to give Compound vii-13 (8.84 g, Yield 94%).

$^1$H-NMR (CDCl$_3$) δ: 2.24 (s, 3H), 5.12 (s, 2H), 6.82-6.86 (m, 2H), 7.38-7.42 (m, 2H).

Step 2

To a solution of Compound vii-13 (1.00 g, 4.29 mmol) in dichloromethane (6 ml) was added sulfuryl chloride (0.35 ml, 4.29 mmol), and the mixture was stirred for 10 minutes at room temperature. The resulting mixture was concentrated in vacuo. To a solution of the resulting residue in dichloromethane (6 ml) was added dropwise 1.0 mol/L tetrabutylammonium fluoride in THF (8.58 mL, 8.58 mmol) under ice-cooling, and the mixture was stirred for 3 hours at room temperature. The reaction mixture was concentrated in vacuo, and the resulting residue was purified by silica gel column chromatography (hexane-ethyl acetate) to give Compound vii-14 (0.63 g, Yield 71%).

$^1$H-NMR (CDCl$_3$) δ: 5.68 (d, J$_{HF}$=54.5 Hz, 2H), 6.97 (d, J=8.8 Hz, 2H), 7.44 (d, J=8.8 Hz, 2H).

Step 3

Compound VII-9 was synthesized by the method described in the general procedures c) in the specification.

$^1$H-NMR (CDCl$_3$) δ: 5.81 (d, J$_{HF}$=53.2 Hz, 2H), 7.24-7.29 (m, 2H), 8.03-8.06 (m, 2H).

REFERENCE EXAMPLE 16

[Chemical Formula 80]

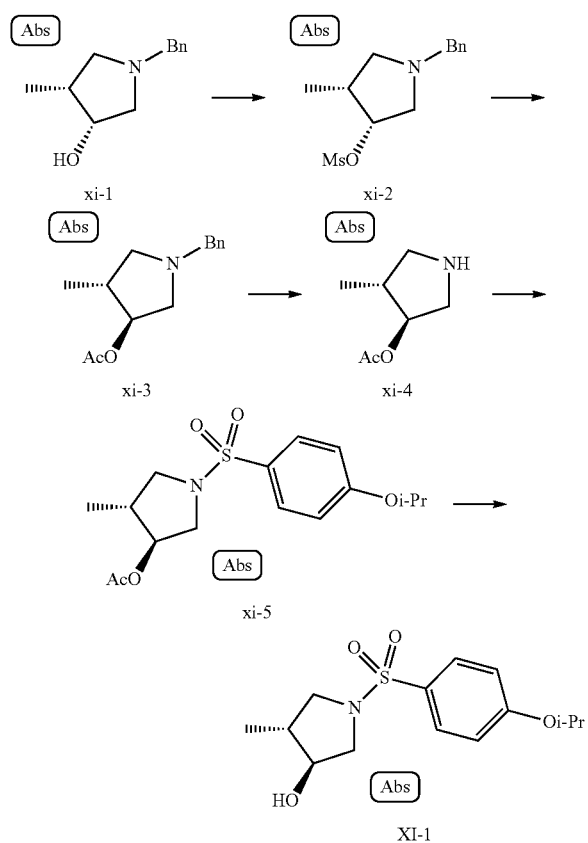

Steps 1 to 2

To a solution of Compound xi-1 (75 mg, 0.392 mmol), which was synthesized in a similar manner as described in EP0443498, in dichloromethane, were added dropwise triethylamine (0.109 mL, 0.784 mmol) and methanesulfonyl chloride (46 µL, 0.588 mmol) under nitrogen atmosphere under ice-cooling. After the reaction mixture was stirred for 30 minutes at room temperature, saturated aqueous sodium bicarbonate was added to the mixture, and the resulting mixture was extracted with ethyl acetate. The organic layer was washed by brine, and dried over anhydrous magnesium sulfate. The mixture was concentrated in vacuo to give Compound xi-2. Compound xi-2 was used in the next step without purification.

To a solution of the obtained compound xi-2 in DMA (2 mL) was added cesium acetate (226 mg, 1.176 mmol) under nitrogen atmosphere. The mixture was heated at 100° C., and stirred for 7.5 hours. To the reaction mixture was added water, and the resulting mixture was extracted with ethyl acetate. The organic layer was washed by brine, and dried over anhydrous magnesium sulfate. The mixture was concentrated in vacuo, and the resulting residue was purified by silica gel column chromatography (hexane-ethyl acetate) to give compound xi-3 (50 mg, Yield 55%).

$^1$H-NMR (CDCl$_3$) δ: 7.32-7.20 (5H, m), 4.74-4.70 (1H, m), 3.59 (2H, dd, J=35.0, 12.9 Hz), 3.04 (1H, t, J=8.2 Hz), 2.76 (2H, dd, J=10.7, 2.1 Hz), 2.65 (2H, dd, J=11.1, 6.3 Hz), 2.33-2.20 (1H, m), 2.04 (3H, s), 1.95 (1H, t, J=8.5 Hz), 1.11 (3H, d, J=7.2 Hz).

LC/MS (Condition B) RT=1.83, [M+H]$^+$=300.

Step 3

To a solution of Compound xi-3 (50 mg, 0.214 mmol) in ethanol (2 mL) was added Pd(OH)$_2$ (10 mg), and the mixture was stirred for 7 hours under hydrogen atmosphere at atmospheric pressure. After the reaction was completed, the insoluble was removed by filtration using Celite. The filtrate was concentrated in vacuo to give Compound xi-4.

Steps 4 to 5

To a solution of the obtained Compound xi-4 (4 mg, 0.028 mmol) in dichloromethane (1 mL) were added triethylamine (7.7 µL, 0.056 mmol) and 4-isopropoxybenzenesulfonyl chloride (7.2 mg, 0.031 mmol) under nitrogen atmosphere under ice-cooling. The mixture was stirred for 1 hour at room temperature. After the reaction was completed, the mixture was concentrated in vacuo. The resulting residue was dissolved in methanol (1 mL). To the mixture was added 2 mol/L aqueous sodium hydroxide (70 µL, 0.140 mmol) at room temperature. The reaction mixture was stirred for 30 minutes at room temperature, and 2 mol/L aqueous hydrochloric acid (70 µL, 0.140 mmol) and water were added to the mixture. The resulting mixture was extracted with ethyl acetate. The organic layer was washed by brine, and dried over anhydrous magnesium sulfate. The mixture was concentrated in vacuo, and the resulting residue was purified by silica gel column chromatography (hexane-ethyl acetate) to give Compound XI-1 (8.4 mg, Yield 100%).

LC/MS (Condition B) RT=1.83, [M+H]$^+$=300.

Compound XI-2 which is an enantiomer of Compound XI-1, and Compound XI-3 which is a racemic compound of Compound XI-1 were synthesized in a similar manner as described in the above.

[Chemical Formula 81]

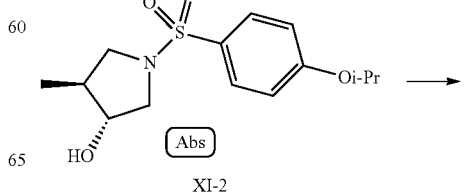

-continued

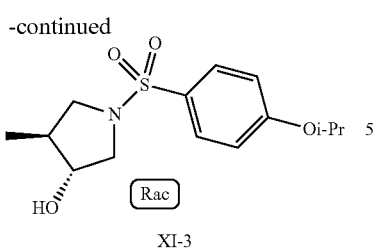

XI-3

Compound XI-2
LC/MS (Condition B) RT=1.83, [M+H]$^+$=300.
Compound XI-3
LC/MS (Condition B) RT=1.83, [M+H]$^+$=300.

REFERENCE EXAMPLE 17

[Chemical Formula 82]

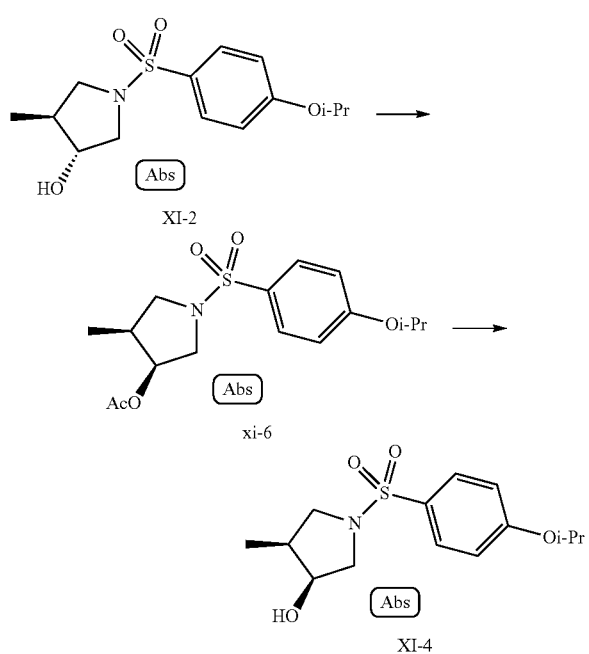

Step 1
Compound XI-2 (415 mg, 1.386 mmol) was treated in a similar manner as described in Steps 1-2 of Reference Example 8 to give Compound xi-6 (435 mg, Yield 92%).
LC/MS (Condition B) RT=2.21, [M+H]$^+$=342.
Step 2
To a solution of Compound xi-6 (430 mg, 1.259 mmol) in methanol (10 mL) was added 2 mol/L aqueous sodium hydroxide (1.259 mL, 2.52 mmol) at room temperature, and the mixture was stirred for 3.5 hours. After the reaction was completed, 2 mol/L aqueous hydrochloric acid (1.259 mL) and water were added to the mixture. The resulting mixture was extracted with ethyl acetate. The organic layer was washed by water and brine, and dried over anhydrous magnesium sulfate. The mixture was concentrated in vacuo, and the resulting residue was purified by silica gel column chromatography (hexane-ethyl acetate) to give Compound XI-4 (403 mg, Yield 100%).
$^1$H-NMR (CDCl$_3$) δ: 7.74 (2H, d, J=8.7 Hz), 6.94 (2H, d, J=8.8 Hz), 4.66-4.58 (1H, m), 4.12 (1H, t, J=3.4 Hz), 3.50-3.44 (2H, m), 3.32 (1H, d, J=11.3 Hz), 2.93 (1H, t, J=9.9 Hz), 2.21-2.03 (1H, m), 1.37 (6H, d, J=5.9 Hz), 0.99 (3H, d, J=6.9 Hz).
LC/MS (Condition B) RT=1.86, [M+H]$^+$=300.

Compound XI-5 which is an enantiomer of Compound XI-4, and Compound XI-6 which is a racemic compound of Compound XI-4 were synthesized in a similar manner as described in the above.

[Chemical Formula 83]

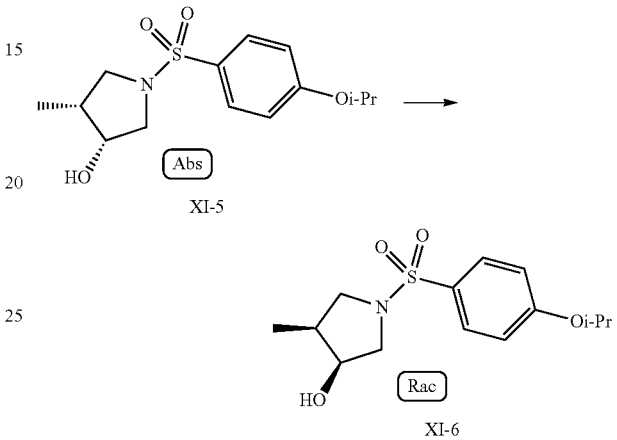

Compound XI-5
LC/MS (Condition B) RT=1.86, [M+H]$^+$=300.
Compound XI-6
LC/MS (Condition B) RT=1.86, [M+H]$^+$=300.

REFERENCE EXAMPLE 18

[Chemical Formula 84]

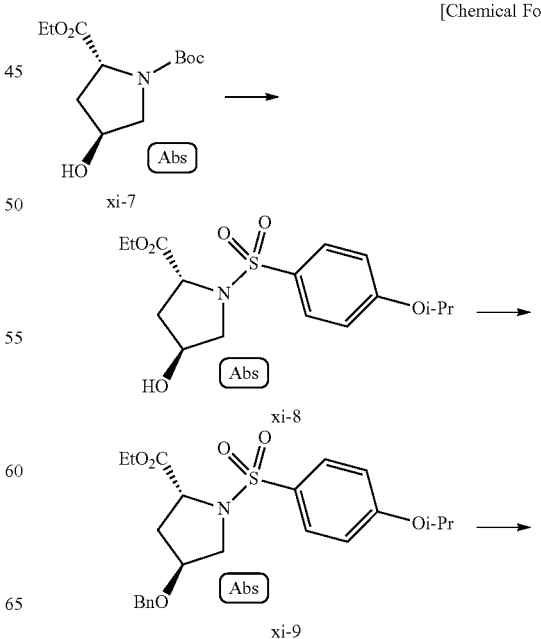

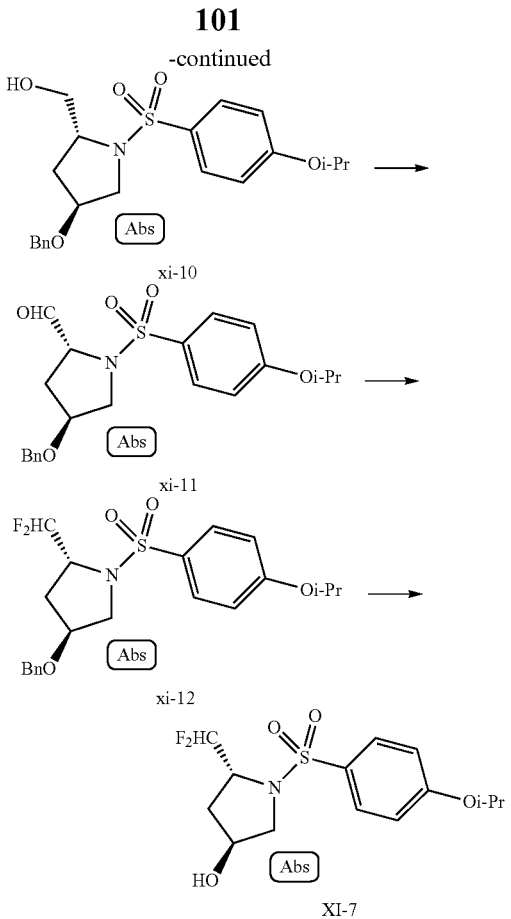

Step 1

To a solution of Compound xi-7 (1.03 g, 3.96 mmol), which is described in Organic and Biomolecular Chemistry, 2003, vol. 1, no. 19 p. 3277-3292, in ethyl acetate (10 mL), was added 4 mol/L hydrochloric acid in ethyl acetate (9.91 mL, 39.6 mmol). The mixture was stirred for 1.5 hours at room temperature. To the reaction mixture was added 4 mol/L hydrochloric acid in ethyl acetate (1.98 mL, 7.93 mmol), and the resulting mixture was stirred for additional 2 hours. The reaction mixture was concentrated in vacuo, and the resulting residue was dissolved in dichloromethane (10 mL). To the mixture was added triethylamine (1.37 mL, 9.91 mmol), and the resulting mixture was stirred for 5 minutes. To the mixture was added 4-isopropoxybenzene-sulfonyl chloride (1.02 g, 4.36 mmol) and the resulting mixture was stirred for 30 minutes at room temperature. After the reaction mixture was left standing overnight, water and 2 mol/L aqueous hydrochloric acid (1.2 mL) were added to the mixture. The resulting mixture was extracted with ethyl acetate. The organic layer was washed by saturated aqueous sodium bicarbonate and brine, dried over magnesium sulphate, and concentrated in vacuo. The resulting residue was purified by silica gel column chromatography (hexane-ethyl acetate) to give Compound xi-8 (1.25 g, Yield 88%).

$^1$H-NMR (CDCl$_3$) δ: 7.86 (2H, d, J=8.90 Hz), 6.99 (2H, d, J=8.90 Hz), 4.73-4.59 (1H, m), 4.53-4.41 (2H, m), 4.30-4.19 (2H, m), 3.63 (1H, dd, J=11.41, 4.03 Hz), 3.46-3.39 (1H, m), 2.33-2.22 (1H, m), 2.20-2.10 (1H, m), 1.41 (6H, d, J=6.04 Hz), 1.33 (3H, t, J=7.16 Hz).

Step 2

Compound xi-8 (500 mg, 1.399 mmol) was dissolved in DMF (10 mL). To the solution was added sodium hydride (67 mg, 1.679 mmol) under ice-cooling. The mixture was stirred for 15 minutes. To the reaction mixture was added benzyl bromide (0.249 mL, 2.098 mmol), and the resulting mixture was allowed to warm to room temperature and stirred for 8 hours. After the mixture was left standing overnight, water was added to the mixture under ice-cooling, and then, the resulting mixture was extracted with ethyl acetate. The organic layer was washed by water and brine, dried over sodium sulphate, and concentrated in vacuo. The resulting residue was purified by silica gel column chromatography (hexane-ethyl acetate) to give compound xi-9 (211 mg, Yield 34%).

$^1$H-NMR (CDCl$_3$) δ: 7.78 (2H, d, J=8.39 Hz), 7.30-7.23 (3H, m), 7.11-7.04 (2H, m), 6.88 (2H, d, J=8.39 Hz), 4.59-4.50 (1H, m), 4.31-4.17 (5H, m), 4.16-4.10 (1H, m), 3.63 (1H, dd, J=11.29, 4.27 Hz), 3.50 (1H, d, J=11.29 Hz), 2.35-2.23 (1H, m), 2.15-2.03 (1H, m), 1.36-1.23 (9H, m).

Step 3

Compound xi-9 (200 mg, 0.448 mmol) was dissolved in THF (4 mL). To the solution was added lithium borohydride (24 mg, 1.12 mmol) under ice-cooling, and the mixture was stirred for 8.5 hours at room temperature. To the reaction mixture was added lithium borohydride (24 mg, 1.12 mmol), and the resulting mixture was stirred for additional 1.5 hours. After the mixture was left standing overnight, iced-water was added to the mixture, and the resulting mixture was extracted with ethyl acetate. The organic layer was washed by 10% aqueous citric acid, saturated aqueous sodium bicarbonate and brine, dried over magnesium sulphate, and concentrated in vacuo. The resulting mixture was purified by silica gel column chromatography (hexane-ethyl acetate) to give Compound xi-10 (180 mg, Yield 99%).

$^1$H-NMR (CDCl$_3$) δ: 7.80 (2H, d, J=8.90 Hz), 7.34-7.29 (3H, m), 7.10-7.08 (2H, m), 6.90 (2H, d, J=8.90 Hz), 4.63-4.49 (1H, m), 4.27 (2H, s), 4.08-4.01 (1H, br m), 3.97-3.88 (1H, m), 3.80-3.54 (4H, m), 3.04-2.97 (1H, m), 2.07-1.90 (2H, m), 1.40-1.35 (6H, m).

Step 4

Compound xi-10 (121 mg, 0.299 mmol) was dissolved in dichloromethane (2.5 mL). To the solution was added Dess-Martin Periodinane (190 mg, 0.449 mmol) under ice-cooling, and the mixture was stirred for 9 hours at room temperature. The mixture was left standing overnight, 6% aqueous sodium thiosulfate and water were added to the mixture, and the resulting mixture was extracted with ethyl acetate. The organic layer was washed by saturated aqueous sodium bicarbonate and brine, dried over sodium sulphate, and concentrated in vacuo. The resulting residue was purified by silica gel column chromatography (hexane-ethyl acetate) to give Compound xi-11 (103 mg, Yield 85%).

$^1$H-NMR (CDCl$_3$) δ: 9.68 (1H, d, J=3.66 Hz), 7.74 (2H, d, J=8.69 Hz), 7.29-7.23 (3H, m), 7.02-6.96 (2H, m), 6.91 (2H, d, J=8.69 Hz), 4.60-4.51 (1H, m), 4.23 (2H, d, J=2.29 Hz), 4.10-4.04 (1H, br m), 4.00-3.92 (1H, m), 3.68 (1H, dd, J=11.59, 4.27 Hz), 3.48-3.41 (1H, m), 2.20-2.10 (1H, m), 2.09-1.98 (1H, m), 1.37-1.32 (6H, m).

Step 5

Compound xi-11 (102 mg, 0.253 mmol) was dissolved in dichloromethane (2 mL). To the solution was added DAST (0.074 mL, 0.557 mmol), and the mixture was allowed to warm to room temperature gradually and stirred for 1.5 hours. To the mixture was added saturated aqueous sodium bicarbonate, and the resulting mixture was extracted with ethyl acetate. The organic layer was washed by brine, dried over sodium sulphate, and concentrated in vacuo. The resulting residue was purified by silica gel column chromatography (hexane-ethyl acetate) to give Compound xi-12 (86 mg, Yield 82%).

$^1$H-NMR (CDCl$_3$) δ: 7.74 (2H, d, J=8.85 Hz), 7.32-7.24 (3H, m), 7.12-7.07 (2H, m), 6.87 (2H, d, J=8.85 Hz), 6.24 (1H, ddd, J=58.56, 56.58, 1.53 Hz), 4.58-4.49 (1H, m), 4.25 (2H, s), 4.16-4.08 (1H, m), 4.00-3.84 (1H, m), 3.56 (1H, dd, J=11.29, 4.42 Hz), 3.41-3.33 (1H, m), 2.34-2.24 (1H, m), 1.98-1.86 (1H, m), 1.34 (6H, d, J=6.25 Hz).

Step 6

Compound xi-12 (86 mg, 0.208 mmol) was dissolved in ethanol (1.5 mL) and ethyl acetate (0.5 mL). To the solution was added Pd(OH)$_2$ (18 mg), and the mixture was stirred for 3.5 hours under hydrogen atmosphere at room temperature. The reaction mixture was diluted with ethyl acetate, and filtrated by using Hyflo-super cell. The filtrate was concentrated in vacuo, and the resulting residue was purified by silica gel column chromatography (hexane-ethyl acetate) to give Compound XI-7 (68 mg, Yield 98%).

$^1$H-NMR (CDCl$_3$) δ: 7.82 (2H, d, J=8.90 Hz), 7.01 (2H, d, J=8.90 Hz), 6.23 (1H, ddd, J=58.50, 54.81, 1.59 Hz), 4.73-4.63 (1H, m), 4.53-4.44 (1H, m), 4.21-3.99 (1H, m), 3.56 (1H, dd, J=11.50, 4.28 Hz), 3.35-3.26 (1H, m), 2.39-2.28 (1H, m), 1.96-1.85 (1H, m), 1.42 (6H, d, J=6.04 Hz).

REFERENCE EXAMPLE 19

[Chemical Formula 85]

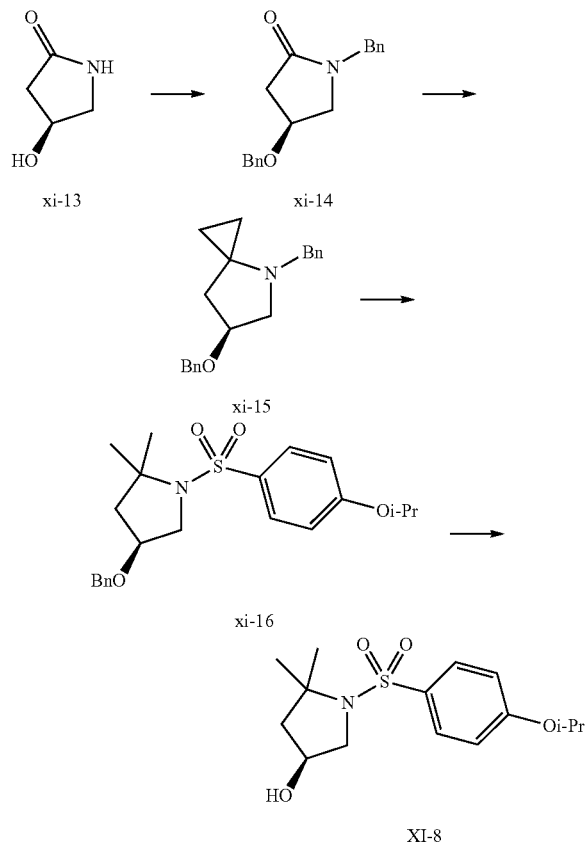

Step 1

Compound xi-13 (1.02 g, 10.09 mmol) was dissolved in DMF (10 mL). To the solution was added 60% sodium hydride (888 mg, 22.19 mmol) under ice-cooling, and the mixture was stirred for 10 minutes. Benzyl bromide (2.88 mL, 24.21 mmol) was added to the mixture, and the resulting mixture was allowed to warm to room temperature and stirred for 30 minutes. After the mixture was left standing overnight, water was added to the mixture, and the resulting mixture was extracted with ethyl acetate. The organic layer was washed by water and brine, dried over magnesium sulphate, and concentrated in vacuo. The resulting residue was purified by silica gel column chromatography (hexane-ethyl acetate) to give Compound xi-14 (1.79 g, Yield 63%).

$^1$H-NMR (CDCl$_3$) δ: 7.41-7.24 (10H, m), 4.57-4.45 (4H, m), 4.29-4.22 (1H, m), 3.51 (1H, dd, J=10.74, 6.38 Hz), 3.36 (1H, dd, J=10.74, 3.36 Hz), 2.75 (1H, dd, J=17.29, 6.38 Hz), 2.64 (1H, dd, J=17.29, 3.36 Hz).

Step 2

Compound xi-14 (164 mg, 0.584 mmol) was dissolved in THF (1.75 mL). To the solution were added 1.0 mol/L methyltriisopropoxytitanium in THF (0.70 mL, 0.700 mmol) and 0.90 mol/L ethylmagnesium bromide in THF (1.56 mL, 1.401 mmol), and the resulting mixture was stirred for 24 hours at room temperature. After the mixture was allowed to stand for 3 days, diethyl ether (1.75 mL) and water (0.058 mL) were added to the mixture, and the resulting mixture was stirred for 1 hour at room temperature. The precipitated solid was removed by filtration using Hyflo-super cell. To the filtrate was added water, and the mixture was extracted by diethyl ether. The organic layer was washed by brine, dried over sodium sulphate, and concentrated in vacuo. The resulting residue was purified by silica gel column chromatography (hexane-ethyl acetate) to give Compound xi-15 (49 mg, Yield 29%).

$^1$H-NMR (CDCl$_3$) δ: 7.34-7.24 (10H, m), 4.46 (2H, s), 4.28-4.19 (1H, m), 3.50 (1H, d, J=12.96 Hz), 3.39 (1H, d, J=12.96 Hz), 2.93 (1H, dd, J=11.29, 6.71 Hz), 2.83 (1H, dd, J=11.29, 3.58 Hz), 2.17 (1H, dd, J=13.27, 6.71 Hz), 2.06 (1H, dd, J=13.27, 3.58 Hz), 0.96-0.86 (1H, m), 0.82-0.72 (1H, m), 0.58-0.49 (1H, m), 0.42-0.33 (1H, m).

Step 3

After Compound xi-15 (48 mg, 0.163 mmol) was dissolved in ethanol (2 mL), Pd(OH)$_2$ (9 mg) was added to the solution under hydrogen atmosphere, and the resulting mixture was stirred for 21 hours at room temperature. The reaction mixture was diluted with ethyl acetate, filtered by using Hyflo-super cell, and concentrated in vacuo. The obtained compound was dissolved in dichloromethane (1.5 mL). To the solution were added triethylamine (0.045 mL, 0.326 mmol) and 4-isopropoxybenzenesulfonyl chloride (42.0 mg, 0.179 mmol), and the resulting mixture was stirred for 50 minutes at room temperature. The mixture was left standing overnight, and the reaction residue was purified by silica gel column chromatography (hexane-ethyl acetate) to give Compound xi-16 (31 mg, Yield 47%).

LC/MS (Condition B) RT=2.75, [M+H]$^+$=404.

Step 4

After Compound xi-16 (30 mg, 0.074 mmol) was dissolved in ethanol (1.5 mL), Pd(OH)$_2$ (9.0 mg) was added to the mixture, and the resulting mixture was stirred for 15 hours under hydrogen atmosphere at room temperature. Further, Pd(OH)$_2$ (9.0 mg) was added to the mixture, and the resulting mixture was stirred for 4.5 hours under hydrogen atmosphere at room temperature. The reaction mixture was diluted with ethyl acetate, and the mixture was filtered by using Hyflo-super cell and concentrated in vacuo. The resulting residue was purified by silica gel column chromatography (hexane-ethyl acetate) to give Compound XI-8 (17 mg, Yield 73%).

¹H-NMR (CDCl₃) δ: 7.74 (2H, d, J=8.85 Hz), 6.94 (2H, d, J=8.85 Hz), 4.68-4.58 (1H, m), 4.15-4.04 (1H, m), 3.60-3.50 (1H, m), 3.44 (1H, dd, J=11.74, 5.19 Hz), 3.31 (1H, dd, J=11.74, 5.19 Hz), 2.11-1.89 (2H, m), 1.78-1.62 (3H, m), 1.38 (6H, d, J=6.10 Hz), 0.94 (3H, t, J=7.47 Hz).

REFERENCE EXAMPLE 20

[Chemical Formula 86]

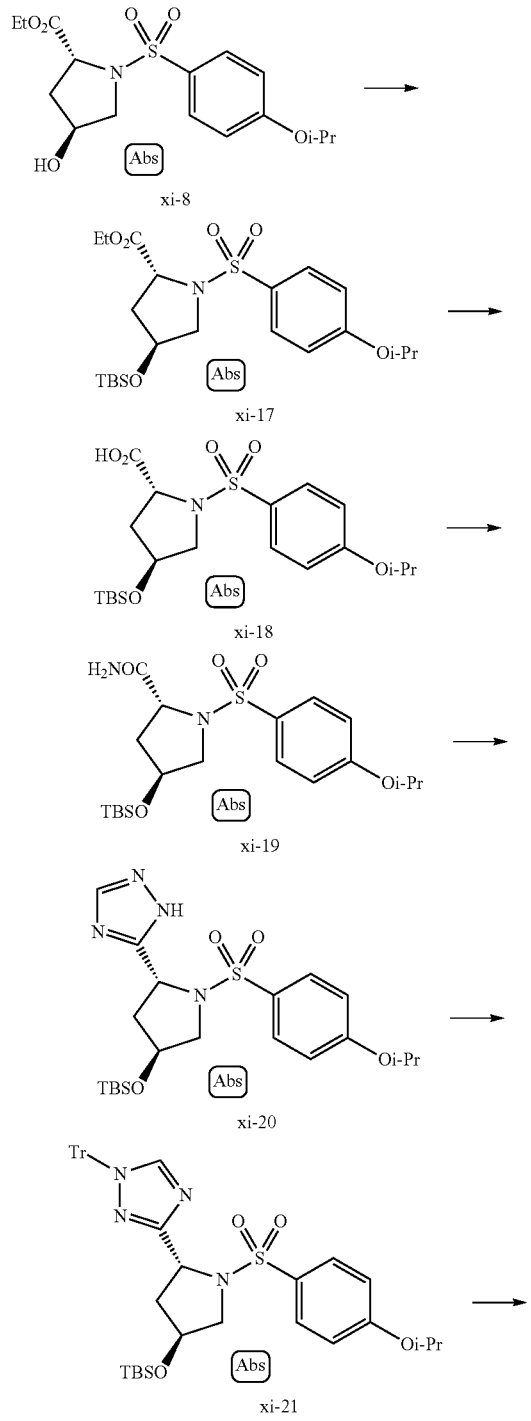

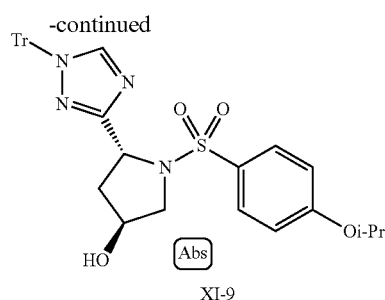

Step 1

Compound xi-8 (1.00 g, 2.80 mmol) was dissolved in DMF (15 mL). To the solution were added imidazole (381 mg, 5.60 mmol) and tert-butyldimethylsilyl chloride (464 mg, 3.08 mmol), and the mixture was stirred for 9 hours at room temperature. After the mixture was left standing overnight, water was added to the mixture, and the resulting mixture was extracted with ethyl acetate. The organic layer was washed by water and brine, dried over magnesium sulphate, and concentrated in vacuo. The resulting residue was purified by silica gel column chromatography (hexane-ethyl acetate) to give Compound xi-17 (1.22 g, Yield 93%).

¹H-NMR (CDCl₃) δ: 7.78 (2H, d, J=8.73 Hz), 6.92 (2H, d, J=8.73 Hz), 4.66-4.53 (1H, m), 4.42-4.35 (1H, br m), 4.30-4.18 (3H, m), 3.65 (1H, dd, J=10.58, 4.70 Hz), 3.17 (1H, dd, J=10.58, 2.35 Hz), 2.10-2.05 (2H, m), 1.39-1.23 (9H, m), 0.74 (9H, s), −0.05 (3H, s), −0.06 (3H, s).

Step 2

Compound xi-17 (1.20 g, 2.55 mmol) was dissolved in THF (12 mL) and ethanol (6 mL). To the solution was added 2 mol/L aqueous sodium hydroxide (2.55 mL, 5.10 mmol), and the mixture was stirred for 2.5 hours at room temperature. The mixture was neutralized by adding 2 mol/L aqueous hydrochloric acid (5.1 mL) and water, and the resulting mixture was extracted with ethyl acetate. The organic layer was washed by brine, dried over magnesium sulphate, and concentrated in vacuo. The resulting residue was purified by silica gel column chromatography (chloroform-methanol) to give Compound xi-18 (1.02 g, Yield 90%).

¹H-NMR (CDCl₃) δ: 7.78 (2H, d, J=8.90 Hz), 6.94 (2H, d, J=8.90 Hz), 4.66-4.56 (1H, m), 4.40-4.33 (1H, br m), 4.28-4.19 (1H, m), 3.67 (1H, dd, J=10.58, 4.45 Hz), 3.17 (1H, dd, J=10.58, 2.85 Hz), 2.30-1.99 (2H, m), 1.37 (6H, d, J=6.04 Hz), 0.74 (9H, s), −0.06 (6H, s).

Step 3

Compound xi-18 (150 mg, 0.338 mmol) was dissolved in THF (1.5 mL). To the solution were added HOBt (68.5 mg, 0.507 mmol) and EDC (52.5 mg, 0.338 mmol), and the mixture was stirred for 30 minutes at room temperature. To the reaction mixture was added 28% aqueous ammonia (0.470 mL, 3.38 mmol), and the mixture was stirred for 23.5 hours at room temperature. Additionally, 28% aqueous ammonia (0.470 mL, 3.38 mmol) was added to the mixture, and the resulting mixture was stirred for additional 10 hours at room temperature. After the mixture was left standing overnight, water was added to the mixture, and the resulting mixture was extracted with ethyl acetate. The organic layer was washed by water and brine, dried over magnesium sulphate, and concentrated in vacuo. The resulting residue was purified by silica gel column chromatography (hexane-ethyl acetate) to give Compound xi-19 (75.6 mg, Yield 51%).

¹H-NMR (CDCl₃) δ: 7.76 (2H, d, J=8.79 Hz), 6.96 (2H, d, J=8.79 Hz), 6.77 (1H, br s), 5.40 (1H, br s), 4.70-4.57 (1H, m), 4.34-4.25 (1H, m), 4.13-4.05 (1H, m), 3.69 (1H, dd, J=10.71, 4.67 Hz), 3.15 (1H, dd, J=10.71, 4.53 Hz), 2.27-2.16 (1H, m), 1.95-1.84 (1H, m), 1.40-1.35 (6H, m), 0.75 (9H, s), −0.05 (3H, s), −0.08 (3H, s).

Step 4

Compound xi-19 (75 mg, 0.170 mmol) was dissolved in dimethylformamide dimethyl acetal (0.75 mL), and the solution was heated at 100° C. for 2 hours. After the mixture was allowed to cool to room temperature, toluene was added to the mixture, and the resulting mixture was concentrated. The resulting residue was dissolved in acetic acid (1 ml). To the solution was added hydrazine monohydrate (0.017 mL, 0.341 mmol) under ice-cooling, and the mixture was heated at 90° C. and stirred for 1 hour. The mixture was allowed to cool to room temperature, and then, concentrated in vacuo. To the resulting residue were added ethyl acetate and saturated aqueous sodium bicarbonate, and the mixture was extracted with ethyl acetate. The organic layer was washed by water and brine, dried over magnesium sulphate, and concentrated in vacuo. The resulting residue was purified by silica gel column chromatography (hexane-ethyl acetate) to give Compound xi-20 (70 mg, Yield 88%).

$^1$H-NMR (CDCl$_3$) δ: 7.94 (1H, s), 7.75 (2H, d, J=9.06 Hz), 6.95 (2H, d, J=9.06 Hz), 4.90-4.83 (1H, m), 4.67-4.57 (1H, m), 4.43-4.35 (1H, m), 3.69 (1H, dd, J=10.58, 4.53 Hz), 3.24 (1H, dd, J=10.58, 4.36 Hz), 2.62-2.51 (1H, m), 2.18-2.08 (1H, m), 1.40-1.36 (6H, m), 0.78 (9H, s), −0.02 (3H, s), −0.05 (3H, s).

Step 5

Compound xi-20 (69 mg, 0.147 mmol) was dissolved in THF (1.5 mL). To the solution were added diisopropylethylamine (0.051 mL, 0.294 mmol) and trityl chloride (82 mg, 0.294 mmol), and the mixture was stirred for 1 hour 45 minutes at room temperature. The mixture was left standing overnight, and then, stirred for additional 10 hours. To the reaction mixture was added water, and the resulting mixture was extracted with ethyl acetate. The organic layer was washed by brine, dried over magnesium sulphate, and concentrated in vacuo. The resulting residue was purified by silica gel column chromatography (hexane-ethyl acetate) to give Compound xi-21 (42 mg, Yield 41%).

$^1$H-NMR (CDCl$_3$) δ: 7.88 (1H, s), 7.69 (2H, d, J=8.85 Hz), 7.38-7.31 (10H, m), 7.21-7.16 (5H, m), 6.80 (2H, d, J=8.85 Hz), 4.76-4.70 (1H, m), 4.58-4.50 (1H, m), 4.46-4.43 (1H, br m), 3.87 (1H, dd, J=10.83, 4.88 Hz), 3.30-3.24 (1H, m), 2.41-2.30 (1H, m), 2.11-1.99 (1H, m), 1.37-1.32 (6H, m), 0.73 (9H, s), −0.06 (3H, s), −0.06 (3H, s).

Step 6

Compound xi-21 (42 mg, 0.059 mmol) was dissolved in THF (1 mL). To the solution was added 1.0 mol/L tetrabutylammonium fluoride in THF (0.088 mL, 0.088 mmol), and the mixture was stirred for 1.5 hours at room temperature. To the reaction mixture was added water, and the resulting mixture was extracted with ethyl acetate. The organic layer was washed by brine, dried over magnesium sulphate, and concentrated in vacuo. The resulting residue was purified by silica gel column chromatography (hexane-ethyl acetate) to give Compound XI-9 (35 m, Yield 100%).

$^1$H-NMR (CDCl$_3$) δ: 7.84 (1H, s), 7.69 (2H, d, J=8.85 Hz), 7.37-7.31 (9H, m), 7.20-7.11 (6H, m), 6.78 (2H, d, J=8.85 Hz), 4.92-4.85 (1H, m), 4.59-4.50 (2H, m), 3.84 (1H, dd, J=11.59, 4.27 Hz), 3.49-3.42 (1H, m), 2.47-2.37 (1H, m), 2.25-2.16 (1H, m), 1.34 (6H, d, J=5.95 Hz).

REFERENCE EXAMPLE 21

[Chemical Formula 87]

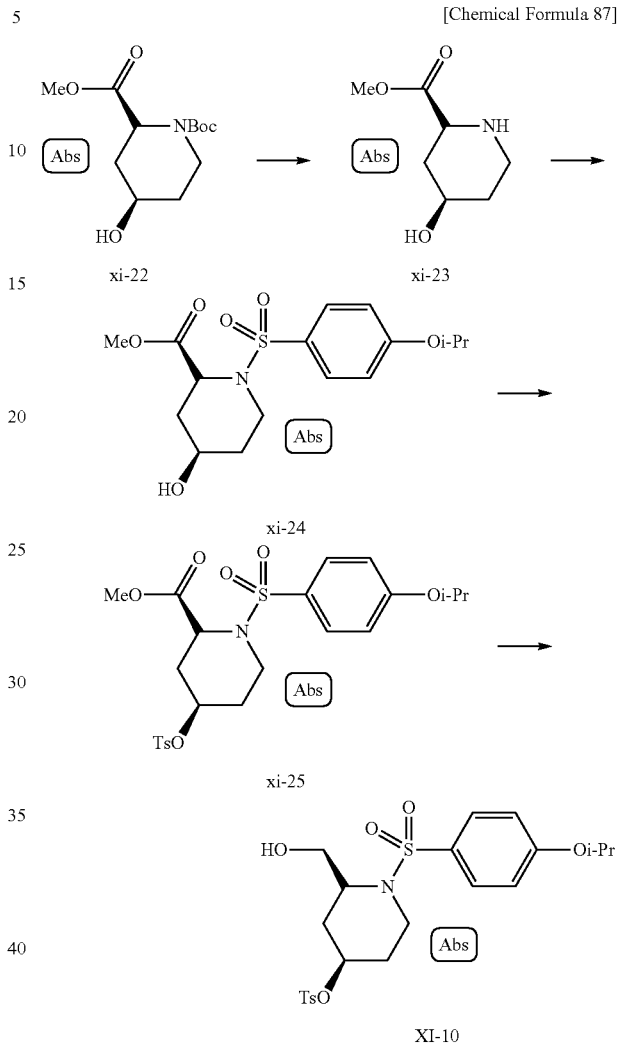

Step 1

Compound xi-22 (250 mg, 0.964 mmol) was dissolved in 2 mol/L hydrochloric acid in dioxane (2 mL), and the solution was stirred for 10 hours at room temperature. The mixture was concentrated in vacuo to give Compound xi-23 (190 mg, Yield 99%).

$^1$H-NMR (DMSO-d$_6$) δ: 9.14 (2H, s), 5.21 (1H, d, J=4.12 Hz), 4.18 (1H, d, J=7.69 Hz), 3.44-3.41 (1H, m), 2.93 (1H, d, J=8.79 Hz), 2.22 (1H, t, J=14.83 Hz), 1.89 (1H, d, J=14.01 Hz), 1.63-1.49 (2H, m).

Step 2

Compound xi-23 (190 mg, 0.971 mmol) was dissolved in dichloromethane (2 mL). To the solution were added 4-isopropoxybenzenesulfonyl chloride (274 mg, 1.165 mmol), and triethylamine (0.404 mL, 2.91 mmol), and the mixture was stirred for 1 hour at room temperature. To the reaction mixture was added water, and the resulting mixture was extracted with ethyl acetate. The organic layer was washed by brine and concentrated in vacuo. The resulting residue was purified by silica gel column chromatography (hexane-ethyl acetate) to give Compound xi-24 (364 mg, Yield 99%).

$^1$H-NMR (CDCl$_3$) δ: 7.73 (2H, d, J=8.79 Hz), 6.92 (2H, d, J=8.79 Hz), 4.70 (1H, d, J=6.59 Hz), 4.66-4.58 (1H, m), 4.12 (2H, d, J=7.14 Hz), 3.58 (3H, s), 3.53 (1H, dd, J=12.22, 7.28 Hz), 2.39 (1H, d, J=14.01 Hz), 1.98 (1H, dd, J=12.91, 5.49 Hz), 1.73-1.70 (2H, m), 1.65-1.62 (1H, m), 1.36 (6H, d, J=6.04 Hz).

Step 3

Compound xi-24 (274 mg, 0.767 mmol) was dissolved in pyridine (2 mL). To the solution was added p-tosyl chloride (219 mg, 1.15 mmol), and the mixture was stirred for 5 hours at room temperature. To the reaction mixture was added water, and the resulting mixture was extracted with ethyl acetate. The organic layer was washed by 10% aqueous citric acid and brine, and concentrated in vacuo. The resulting residue was purified by silica gel column chromatography (hexane-ethyl acetate) to give Compound xi-25 (148 mg, Yield 37.8%).

LC/MS (Condition B) RT=2.45, [M+H]$^+$=512.

Step 4

Compound xi-25 (187 mg, 0.366 mmol) was dissolved in THF (1 mL). To the solution was added lithium borohydride (20 mg, 0.914 mmol), and the resulting mixture was stirred for 20 hours at room temperature. To the reaction mixture was added water, and the resulting mixture was extracted with ethyl acetate. The organic layer was washed by 10% aqueous citric acid and brine, and concentrated in vacuo to give Compound XI-10 (2.7 g, Yield 99%).

$^1$H-NMR (CDCl$_3$) δ: 7.78-7.73 (5H, m), 7.33 (2H, d, J=8.08 Hz), 6.90 (2H, d, J=9.00 Hz), 4.76 (1H, s), 4.60 (1H, dd, J=12.12, 6.02 Hz), 3.98 (1H, s), 3.84 (1H, t, J=12.20 Hz), 3.67-3.59 (2H, m), 3.31 (1H, t, J=11.51 Hz), 2.45 (3H, d, J=4.58 Hz), 2.07 (1H, d, J=7.93 Hz), 1.94 (1H, d, J=16.93 Hz), 1.69 (2H, dd, J=25.16, 9.61 Hz), 1.36 (6H, d, J=6.10 Hz).

REFERENCE EXAMPLE 22

[Chemical Formula 88]

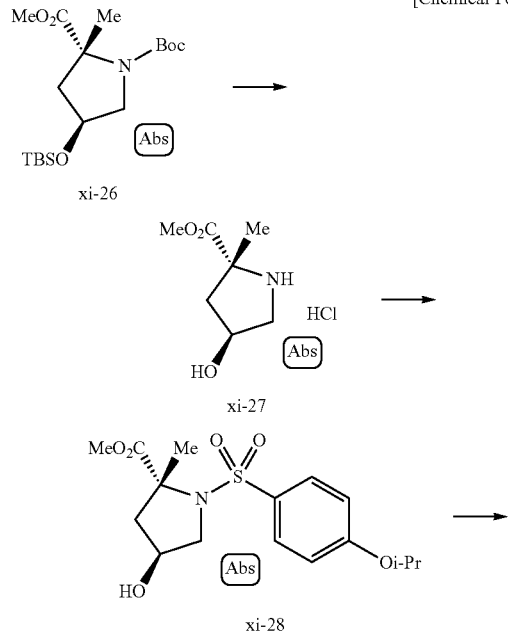

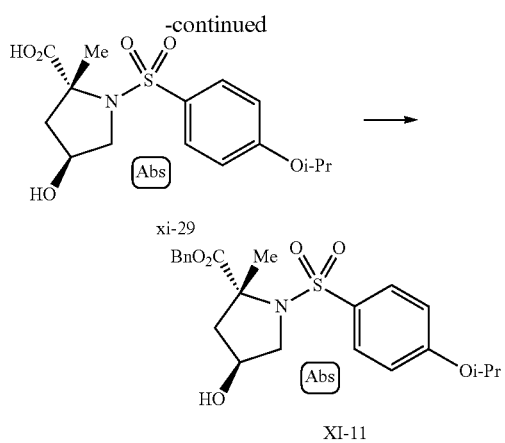

Step 1

Compound xi-26 (103 mg, 0.275 mmol) which was synthesized in a similar manner as described in US2008/9497, was dissolved in ethyl acetate (1 mL). To the solution was added 4 mol/L hydrochloric acid in ethyl acetate (1.0 mL, 4.00 mmol), and the mixture was stirred for 25 minutes at room temperature. After the mixture was left standing overnight, and the reaction mixture was concentrated in vacuo to give Compound xi-27. Compound xi-27 was used in the next step without purification.

Step 2

Compound xi-27 was dissolved in dichloromethane (2 mL). To the solution were added triethylamine (0.095 mL, 0.688 mmol) and p-isopropoxybenzenesulfonyl chloride (71 mg, 0.303 mmol), and the mixture was stirred for 2.5 hours at room temperature. The reaction mixture was purified by silica gel column chromatography (hexane-ethyl acetate) to give Compound xi-28 (66 mg, 2 steps, Yield 67%).

$^1$H-NMR (CDCl$_3$) δ: 7.85-7.79 (2H, m), 6.99-6.93 (2H, m), 4.71-4.61 (1H, m), 4.61-4.52 (1H, m), 3.85-3.78 (4H, m), 3.39 (1H, ddd, J=10.03, 3.23, 1.18 Hz), 2.52 (1H, dd, J=13.60, 5.88 Hz), 2.03 (1H, ddd, J=13.60, 4.36, 1.18 Hz), 1.82 (3H, s), 1.76 (1H, d, J=4.36 Hz), 1.41 (6H, d, J=6.04 Hz).

Step 3

Compound xi-28 (64 mg, 0.178 mmol) was dissolved in THF (1 mL) and methanol (0.5 mL). To the solution was added 2 mol/L aqueous sodium hydroxide (0.355 mL, 0.711 mmol), and the mixture was stirred for 1.5 hours at room temperature. After the mixture was left standing overnight, water and 2 mol/L aqueous hydrochloric acid (0.71 mL) were added to the mixture. The mixture was extracted with ethyl acetate. The organic layer was washed by brine, dried over magnesium sulphate, and concentrated in vacuo. The resulting residue was purified by silica gel column chromatography (chloroform-methanol) to give Compound xi-29 (58 mg, Yield 94%).

$^1$H-NMR (CDCl$_3$) δ: 7.85 (2H, d, J=8.90 Hz), 6.97 (2H, d, J=8.90 Hz), 4.72-4.55 (2H, m), 3.82 (1H, dd, J=10.41, 5.71 Hz), 3.37 (1H, dd, J=10.41, 3.36 Hz), 2.67 (1H, dd, J=13.60, 5.88 Hz), 2.10-2.01 (1H, m), 1.84 (3H, s), 1.41 (6H, d, J=6.04 Hz).

Step 4

Compound xi-29 (193 mg, 0.561 mmol) was dissolved in THF (3 mL). To the solution were added triethylamine (0.117 mL, 0.841 mmol) and benzyl bromide (0.100 mL, 0.841 mmol), and the mixture was stirred for 6.5 hours at room temperature. After the mixture was left standing overnight, the reaction mixture was filtered, and the filtrate was concentrated in vacuo. The resulting residue was purified by silica gel column chromatography (hexane-ethyl acetate) to give Compound XI-11 (204 mg, Yield 84%).

$^1$H-NMR (CDCl$_3$) δ: 7.79-7.73 (2H, m), 7.42-7.31 (5H, m), 6.91-6.85 (2H, m), 5.24 (1H, d, J=12.42 Hz), 5.11 (1H, d, J=12.42 Hz), 4.65-4.55 (1H, m), 4.52-4.43 (1H, m), 3.75 (1H, dd, J=10.07, 5.54 Hz), 3.33 (1H, ddd, J=10.07, 3.69, 1.18 Hz), 2.46 (1H, dd, J=13.43, 5.54 Hz), 1.97 (1H, ddd, J=13.43, 4.03, 1.18 Hz), 1.81 (3H, s), 1.36 (6H, d, J=6.04 Hz).

REFERENCE EXAMPLE 23

[Chemical Formula 89]

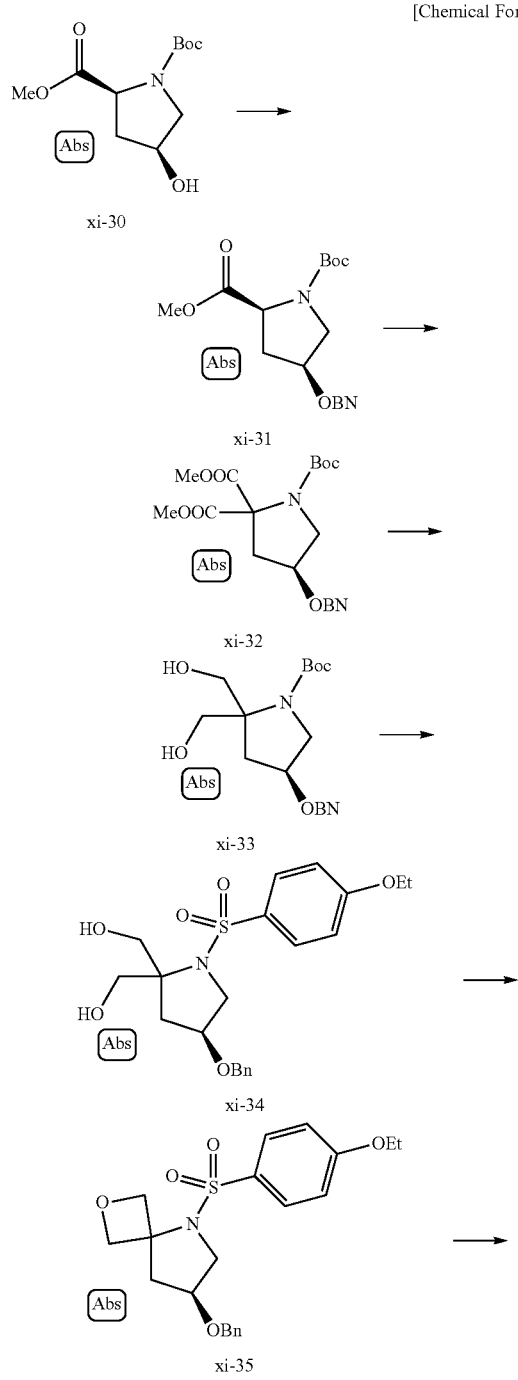

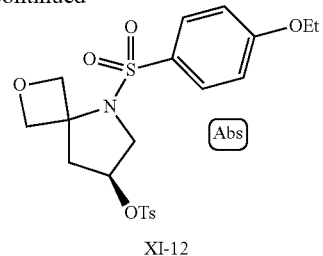

XI-12

Step 1

To a solution of Compound xi-30 (4.98 g, 20.3 mmol) in DMF (150 ml) was added sodium hydride (60 wt %) (0.974 g, 24.3 mmol) under ice-cooling, and the mixture was stirred for 10 minutes. Then, benzyl bromide (2.65 ml, 22.3 mmol) was added to the reaction, and the resulting mixture was stirred for 1 hour at room temperature. To the reaction mixture was added saturated aqueous ammonium chloride, and the resulting mixture was extracted with ethyl acetate. The organic layer was washed by water, dried over anhydrous sodium sulphate, and concentrated in vacuo. The resulting residue was purified by silica gel column chromatography (hexane-ethyl acetate) to give Compound xi-31 (6.81 g, Yield 78%).

Step 2

To a solution of DIPEA (6.87 ml, 48.9 mmol) in THF (50 ml) was added 1.65 mol/L n-butyllithium in hexane (28.7 mL, 47.3 mmol) at −78° C., and the mixture was stirred for 30 minutes at 0° C. The reaction mixture was allowed to cool to −78° C., and a solution of Compound xi-31 (5.29 g, 15.8 mmol) in THF (50 ml) was added dropwise over 1.5 hours. After the mixture was allowed to warm to −40° C., the resulting mixture was allowed to cool to −78° C. Then, methyl chloroformate (3.64 ml, 47.3 mmol) was added dropwise to the mixture over 30 minutes and the resulting mixture was stirred for 3.5 hours. To the reaction mixture was added saturated aqueous ammonium chloride, and the resulting mixture was extracted with ethyl acetate. The organic layer was washed by 10% aqueous citric acid and saturated aqueous sodium chloride, dried over anhydrous sodium sulphate, and concentrated in vacuo. The resulting residue was purified by silica gel column chromatography (hexane-ethyl acetate) to give Compound xi-32 (6.21 g, Yield 96%).

LC/MS (Condition B) RT=2.15, [M+H]$^+$=294.

Step 3

To a solution of lithium aluminium hydride (2.19 g, 57.7 mmol) in THF (30 ml) was added dropwise a solution of Compound xi-32 (5.68 g, 14.4 mmol) in THF (30 ml) over 40 minutes under ice-cooling. The reaction mixture was stirred for 1.5 hours at room temperature. Then, the mixture was diluted with water (8.8 ml) under ice-cooling, and 2 mol/L aqueous sodium hydroxide (2.2 ml) was added to the resulting mixture. The resulting mixture was stirred for 3 hours at room temperature. To the reaction suspension was added anhydrous magnesium sulphate, and mixture was filtered. The filtrate was concentrated in vacuo and the resulting residue was purified by silica gel column chromatography (hexane-ethyl acetate) to give Compound xi-33 (0.87 g, Yield 18%).

LC/MS (Condition B) RT=1.77, [M+H]$^+$=338.

Step 4

Compound xi-33 (0.87 g, 2.6 mmol) was cooled, and 4 mol/L hydrochloric acid in 1,4-dioxane (5 ml) was added.

The reaction mixture was stirred for 3.5 hours at room temperature. The resulting mixture was concentrated in vacuo, and the resulting residue was dissolved in dichloromethane (5 ml) To the mixture were added triethylamine (1.08 ml, 7.8 mmol) and 4-ethoxybenzenesulphonyl chloride (0.69 g, 3.1 mmol) under ice-cooling, and the resulting mixture was stirred for 1 hour at room temperature. The mixture was concentrated in vacuo and the resulting residue was purified by silica gel column chromatography (hexane-ethyl acetate) to give Compound xi-34 (0.62 g, Yield 57%).

LC/MS (Condition B) RT=1.93, [M+H]$^+$=422.

Step 5

To a solution of Compound xi-34 (0.59 g, 1.4 mmol) in THF (6 ml) were added 1.65 mol/L n-butyllithium in hexane (0.84 mL, 1.4 mmol) and a solution of TsCl (0.27 g, 1.4 mmol) in THF (6 ml) under ice-cooling, and the mixture was stirred for 1.5 hours at 0° C. To the reaction mixture was added 1.65 mol/L n-butyllithium in hexane (0.84 mL, 1.4 mmol), the resulting mixture was stirred for 30 minutes at 0° C. and for 1 hour at 60° C. To the reaction mixture was added saturated aqueous ammonium chloride, and the mixture was extracted with ethyl acetate. The organic layer was dried over anhydrous sodium sulphate, and concentrated in vacuo. The resulting residue was purified by silica gel column chromatography (hexane-ethyl acetate) to give Compound xi-35 (253 mg, Yield 45%).

$^1$H-NMR (CDCl$_3$)δ:1.43 (t, J=7.0 Hz, 3H), 2.26 (dd, J=13.6, 4.3 Hz, 1H), 2.75 (d, J=13.3 Hz, 1H), 3.48 (dd, J=10.7, 4.1 Hz, 1H), 3.59 (d, J=11.0 Hz, 1H), 4.03-4.08 (m, 3H), 4.41 (s, 2H), 4.46 (m, 2H), 5.22 (d, J=6.3 Hz, 1H), 5.56 (d, J=6.0 Hz, 1H), 6.90 (d, J=9.0 Hz, 2H), 7.17 (d, J=6.5 Hz, 2H), 7.28-7.34 (m, 3H), 7.79 (d, J=8.8 Hz, 2H).

LC/MS (Condition B) RT=2.16, [M+H]$^+$=404.

Step 6

To a solution of Compound xi-35 (253 mg, 0.63 mmol) in ethanol (2 ml) was added 10 wt % Pd(OH)$_2$ (44 mg), and mixture was stirred for 8.5 hours under hydrogen atmosphere. The mixture was filtered off, and the filtrate was concentrated in vacuo. The resulting residue was dissolved in dichloromethane (2 ml). To the mixture was added a mixture of triethylamine (0.22 mL, 1.58 mmol), trimethylamine hydrochloride (15 mg, 0.16 mmol), TsCl (165 mg, 0.87 mmol) and dichloromethane (2 ml) under ice-cooling, and the resulting mixture was stirred for 20 hours at room temperature. The reaction mixture was concentrated in vacuo, and the resulting residue was purified by silica gel column chromatography (hexane-ethyl acetate) to give Compound XI-12 (197 mg, Yield 80%).

LC/MS (Condition B) RT=2.11, [M+H]$^+$=468.

REFERENCE EXAMPLE 24

[Chemical Formula 90]

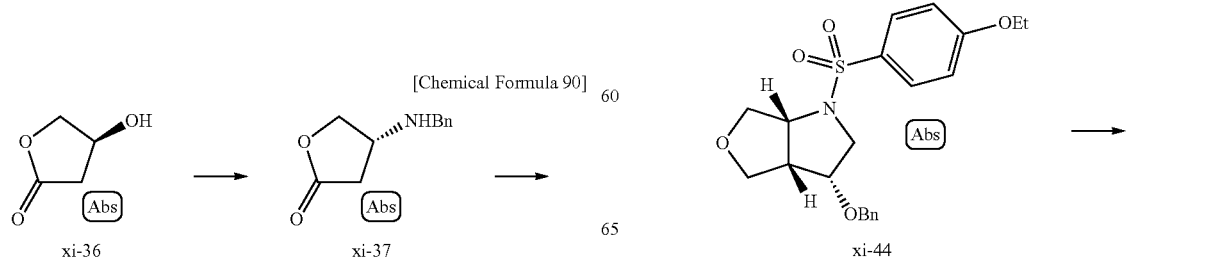

-continued

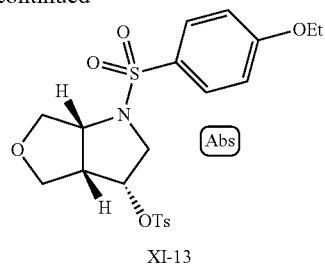

XI-13

Step 1

To a solution of Compound xi-36 (10.2 g, 100 mmol) in dichloromethane (100 ml) were added MsCl (12.5 ml, 160 mmol) and a mixture of triethylamine (21.8 ml, 150 mmol) and dichloromethane (30 ml) under ice-cooling, and the mixture was stirred for 1.5 hours at 0° C. To the reaction mixture was added water, and the resulting mixture was extracted with dichloromethane. The organic layer was washed by water, dried over anhydrous magnesium sulphate, and concentrated in vacuo. The resulting residue was purified by silica gel column chromatography (hexane-ethyl acetate).

To a solution of the obtained Compound in acetonitrile (170 ml) were added benzylamine (12.1 ml, 111 mmol) and DIPEA (14.3 ml, 111 mmol) under ice-cooling, and the mixture was stirred for 16 hours at room temperature. The mixture was concentrated in vacuo and the resulting residue was purified by silica gel column chromatography (hexane-ethyl acetate) to give Compound xi-37 (11.2 g, Yield 64%).

$^1$H-NMR (CDCl$_3$)δ:2.39 (dd, J=17.4, 4.6 Hz, 1H), 2.39 (dd, J=17.4, 4.6), 3.66-3.71 (m, 1H), 3.78 (d, J=13.6 Hz, 1H), 3.82 (d, J=13.6 Hz, 1H), 4.10-4.15 (m, 1H), 4.37 (dd, J=8.8, 6.0 Hz, 1H), 7.24-7.37 (m, 5H).

Step 2

To a solution of Compound xi-37 (2.16 g, 1.3 mmol) in acetonitrile (20 ml) were added DIPEA (7.90 ml, 45.2 mmol) and methyl bromoacetate (4.18 ml, 45.2 mmol) under ice-cooling, and the mixture was stirred for 24 hours at room temperature. To the reaction mixture was added water, and the resulting mixture was extracted with ethyl acetate. The organic layer was washed by water, dried over anhydrous sodium sulphate, and concentrated in vacuo. The resulting residue was purified by silica gel column chromatography (hexane-ethyl acetate) to give Compound xi-38 (2.34 g, Yield 79%).

$^1$H-NMR (CDCl$_3$)δ:2.61 (dd, J=17.5, 7.5 Hz, 1H), 2.61 (dd, J=17.4, 7.9 Hz, 1H), 3.33 (s, 2H), 3.69 (s, 3H), 3.77 (d, J=13.8 Hz, 1H), 3.85 (d, J=13.8 Hz, 1H), 3.99-4.06 (m, 1H), 4.23 (dd, J=9.2, 6.6 Hz, 1H), 4.45 (dd, J=8.2, 8.2 Hz, 1H), 7.28-7.36 (m, 5H).

LC/MS (Condition RT=1.60, [M+H]$^+$=264.

Step 3

To a solution of Compound xi-38 (10.9 g, 41 mmol) in toluene (110 ml) was added 1.0 mol/L potassium tert-butoxide in THF (49.5 mL, 50 mmol) under ice-cooling, and the mixture was stirred for 20 minutes at 0° C. The reaction mixture was added to 2 mol/L aqueous hydrochloric acid (25 ml, 50 mmol), and neutralized. To the mixture was added saturated aqueous sodium bicarbonate, and the resulting mixture was made alkaline. The mixture was extracted with ethyl acetate. The organic layer was dried over anhydrous sodium sulphate, and concentrated in vacuo. The resulting residue was purified by silica gel column chromatography (hexane-ethyl acetate) to give Compound xi-39 (6.06 g, Yield 64%).

$^1$H-NMR (DMSO-d6)δ:2.98 (d, J=16.6 Hz, 1H), 3.09 (d, J=16.8 Hz, 1H), 3.59 (d, J=13.3 Hz, 1H), 3.83 (d, J=6.3 Hz, 1H), 3.89-3.91 (m, 1H), 4.11 (d, J=13.3 Hz, 1H), 4.31 (dd, J=9.8, 3.3 Hz, 1H), 4.41 (d, J=10.0 Hz, 1H), 7.28-7.36 (m, 5H).

LC/MS (Condition B) RT=1.48, [M+H]$^+$=232.

Step 4

To a solution of Compound xi-39 (50 mg, 0.22 mmol) in methanol (1 ml) was added sodium borohydride (8.2 mg, 0.22 mmol) at −78° C., and the mixture was stirred for 5.5 hours. To the reaction mixture were added 2 mol/L aqueous hydrochloric acid (0.11 ml, 0.22 mmol) and water, and the mixture was extracted with ethyl acetate. The organic layer was dried over anhydrous sodium sulphate, and concentrated in vacuo. The resulting residue was purified by silica gel column chromatography (hexane-ethyl acetate) to give Compound xi-40 (31 mg, Yield 62%).

$^1$H-NMR (CDCl$_3$)δ:2.55 (dd, J=10.3, 4.5 Hz, 1H), 2.83 (d, J=4.0 Hz, 1H), 3.11 (d, J=10.3 Hz, 1H), 3.34 (dd, J=7.8, 7.8 Hz, 1H), 3.43 (dd, J=7.0, 7.0 Hz, 1H), 3.65 (d, J=12.8 Hz, 1H), 3.76 (d, J=13.1 Hz, 1H), 4.09 (d, J=9.8 Hz, 1H), 4.15 (dd, J=9.4, 5.4 Hz, 1H), 4.57-4.58 (m, 1H), 7.28-7.36 (m, 5H).

Step 5

To a solution of Compound xi-40 (0.65 g, 2.8 mmol) in ethanol (20 ml) was added 10 wt % Pd(OH)$_2$/C (65 mg), and the mixture was stirred for 21.5 hours under hydrogen atmosphere. The mixture was filtered off, and the filtrate was concentrated in vacuo. The resulting residue was dissolved in dichloromethane (20 ml). To the mixture were added triethylamine (0.78 mL, 5.6 mmol) and 4-ethoxybenzene-sulphonyl chloride (0.74 g, 3.4 mmol) under ice-cooling, and the resulting mixture was stirred for 2 hours at room temperature. The mixture was concentrated in vacuo, and the resulting residue was purified by silica gel column chromatography (hexane-ethyl acetate) to give Compound xi-41 (0.80 g, Yield 87%).

$^1$H-NMR (DMSO-d6)δ:1.36 (t, J=6.9 Hz, 3H), 2.99 (dd, J=9.9, 2.6 Hz, 1H), 3.26 (dd, J=9.9, 6.1 Hz, 1H), 3.40 (d, J=10.0 Hz, 1H), 4.13 (q, J=6.9 Hz, 2H), 4.19 (dd, J=8.8, 5.3 Hz, 1H), 4.28-4.34 (m, 2H), 4.50 (dd, J=8.3, 8.3 Hz, 1H), 5.83 (d, J=3.8 Hz, 1H), 7.15 (d, J=8.3 Hz, 2H), 7.74 (d, J=8.3 Hz, 2H).

LC/MS (Condition B) RT=1.37, [M+H]$^+$=328.

Step 6

To a solution of Compound xi-41 (100 mg, 0.31 mmol) in THF (0.5 ml) were added hexamethyldisiloxane (0.26 ml, 1.2 mmol), benzaldehyde (0.062 ml, 0.61 mmol), and trimethylsilyl triflate (0.083 ml, 0.46 mmol) at −20° C. After the mixture was stirred for 2 hours at −20° C., triethylsilane (0.15 ml, 0.92 mmol) was added to the mixture, and the resulting mixture was stirred for 1.5 hours (−20° C. to room temperature). To the reaction mixture was added saturated aqueous sodium bicarbonate, and the resulting mixture was extracted with ethyl acetate. The organic layer was dried over anhydrous sodium sulphate, and concentrated in vacuo. The resulting residue was purified by silica gel column chromatography (hexane-ethyl acetate) to give Compound xi-42 (101 mg, Yield 80%).

$^1$H-NMR (CDCl$_3$)δ:1.46 (t, J=7.0 Hz, 3H), 3.14 (dd, J=10.8, 3.8 Hz, 1H), 3.23 (dd, J=9.8, 6.3 Hz, 1H), 3.73 (d, J=10.8 Hz, 1H), 4.10 (q, J=7.3 Hz, 2H), 4.23 (brm, 1H), 4.39-4.47 (m, 2H), 4.56-4.62 (m, 3H), 6.99 (d, J=8.5 Hz, 2H), 7.29-7.36 (m, 5H), 7.74 (d, J=8.5 Hz, 2H).

LC/MS (Condition B) RT=2.09, [M+H]$^+$=418.

Step 7

To a solution of Compound xi-42 (665 mg, 1.59 mmol) in THF (7 ml) was added lithium aluminium hydride (121 mg, 3.19 mmol) under ice-cooling, and the mixture was stirred for 1 hour at 0° C. To the resulting mixture was added aqueous saturated potassium sodium tartrate, and the mixture was extracted with ethyl acetate. The organic layer was dried over anhydrous sodium sulphate, and concentrated in vacuo. The resulting residue was purified by silica gel column chromatography (hexane-ethyl acetate) to give Compound xi-43 (637 mg, Yield 95%).

$^1$H-NMR (CDCl$_3$)δ:1.45 (t, J=6.9 Hz, 3H), 2.00-2.03 (m, 1H), 2.50-2.53 (m, 1H), 3.14-3.17 (m, 2H), 3.73 (d, J=11.8 Hz, 1H), 3.76-3.81 (m, 1H), 3.85-3.93 (m, 4H), 4.02 (t, J=4.8 Hz, 1H), 4.09 (q, J=6.7 Hz, 2H), 4.35 (d, J=11.8 Hz, 1H), 4.65 (d, J=11.5 Hz, 1H), 6.97 (d, J=8.5 Hz, 2H), 7.31-7.37 (m, 5H), 7.77 (d, J=8.8 Hz, 2H).

LC/MS (Condition B) RT=1.83, [M+H]$^+$=422.

Step 8

To a solution of Compound xi-43 (562 mg, 1.33 mmol) in THF (10 ml) were added triphenylphosphine (770 mg, 2.94 mmol) and bis(2-methoxyethyl)azodicarboxylate (686 mg, 2.94 mmol) under ice-cooling, and the mixture was stirred for 1 hour. The mixture was concentrated in vacuo, and the resulting residue was dissolved in diethyl ether. The organic layer was washed by water, dried over anhydrous sodium sulphate, and concentrated in vacuo. The resulting residue was purified by silica gel column chromatography (hexane-ethyl acetate) to give Compound xi-44 (521 mg, Yield 97%).

$^1$H-NMR (CDCl$_3$)δ:1.46 (t, J=6.9 Hz, 3H), 2.83-2.90 (m, 1H), 3.19 (dd, J=9.7, 9.7 Hz, 1H), 3.51 (dd, J=9.7, 9.7 Hz, 1H), 3.61-3.66 (m, 2H), 3.71 (ddd, J=7.5, 7.5, 7.5 Hz, 1H), 4.04-4.11 (m, 3H), 4.24 (dd, J-9.4, 3.9 Hz, 1H), 4.33 (dd, J=5.9, 5.9 Hz, 1H), 4.39 (d, J=12.0 Hz, 1H), 4.44 (d, J=12.0 Hz, 1H), 6.94 (d, 8.3 Hz, 2H), 7.24-7.36 (m, 5H), 7.71 (d, J=8.3 Hz, 2H).

LC/MS (Condition B) RT=2.20, [M+H]$^+$=404.

Step 9

To a solution of Compound xi-44 (530 mg, 1.29 mmol) in THF (5 ml)-methanol (5 ml), was added 10 wt % Pd(OH)$_2$ (52 mg), and the mixture was stirred for 4.5 hours under hydrogen atmosphere. The mixture was filtered off, and the filtrate was concentrated in vacuo. The resulting residue was dissolved in dichloromethane (4 ml). To the mixture was added a mixture of triethylamine (0.35 mL, 2.49 mmol), trimethylamine hydrochloride (36 mg, 0.37 mmol), TsCl (355 mg, 1.86 mmol) and dichloromethane (2 ml) under ice-cooling, and the resulting mixture was stirred for 1 hour at 0° C. The mixture was concentrated in vacuo, and the resulting residue was purified by silica gel column chromatography (hexane-ethyl acetate) to give Compound XI-13 (529 mg, Yield 88%).

$^1$H-NMR (DMSO-d6)δ:1.37 (t, J=6.9 Hz, 3H), 2.44 (s, 3H), 2.94-2.97 (m, 1H), 3.18 (dd, J=11.8. 5.3 Hz, 1H), 3.24-3.29 (m, 2H), 3.54 (dd, J=9.7, 4.6 Hz, 1H), 3.81 (d, J=10.0 Hz, 1H), 3.91 (d, J=9.8 Hz, 1H), 4.00-4.03 (m, 1H), 4.14 (q, J=6.9 Hz, 2H), 4.49 (dd, J=11.7, 5.4 Hz, 1H), 7.12 (d, J=8.3 Hz, 2H), 7.49 (d, J=7.8 Hz, 2H), 7.70 (d, J=8.3 Hz, 2H), 7.75 (d, J=8.0 Hz, 2H).

LC/MS (Condition B) RT=2.16, [M+H]$^+$=468.

REFERENCE EXAMPLE 25

[Chemical Formula 91]

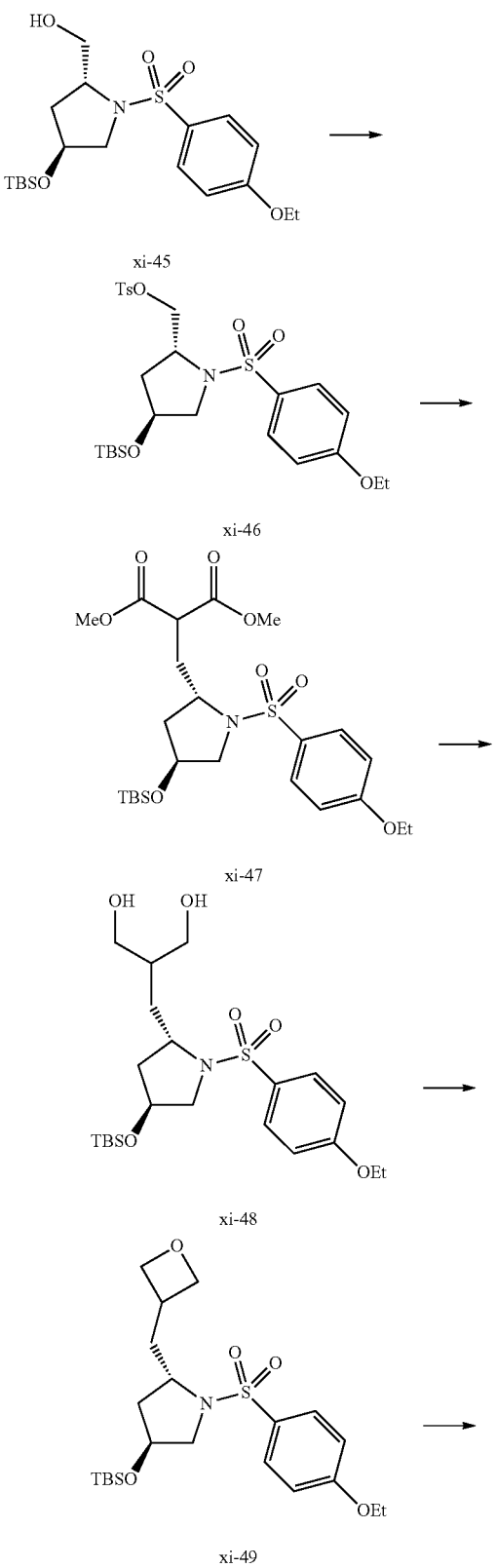

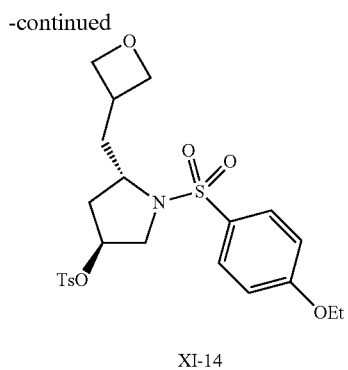

XI-14

Step 1

To a solution of Compound xi-45 (1.58 g, 3.81 mmol) in dichloromethane (20 mL) were added triethylamine (1.27 mL, 9.15 mmol), trimethylamine hydrochloride (109 mg, 1.14 mmol), and p-toluenesulfonyl chloride (1017 mg, 5.33 mmol) under ice-cooling, and the mixture was stirred for 4 hours at room temperature. To the reaction mixture was added 10% aqueous citric acid, and the resulting mixture was extracted with ethyl acetate. The organic layer was washed by brine, dried over anhydrous sodium sulphate, and concentrated in vacuo. The resulting residue was purified by silica gel column chromatography (hexane-ethyl acetate) to give Compound xi-46 (2.05 g, Yield 95%).

$^1$H-NMR (CDCl$_3$) δ: −0.09 (3H, s), −0.07 (3H, s), 0.73 (9H, s), 1.45 (3H, t, J=6.9 Hz), 1.76-1.85 (1H, m), 1.92-2.02 (1H, m), 2.46 (3H, s), 3.00 (1H, d, J=10.3 Hz), 3.51 (1H, dd, J=10.7, 4.0 Hz), 3.79 (1H, s), 4.02-4.10 (3H, m), 4.26-4.28 (1H, m), 4.42 (1H, d, J=9.8 Hz), 6.93 (2H, d, J=8.7 Hz), 7.37 (2H, d, J=7.8 Hz), 7.68 (2H, d, J=8.5 Hz), 7.82 (2H, d, J=8.0 Hz).

Step 2

Under nitrogen atmosphere, to a solution of dimethyl malonate (1.89 mL, 16.5 mmol) in DMF (20 mL) was added sodium hydride (658 mg, 16.5 mmol) under ice-cooling, and the resulting mixture was stirred for 1 hour at room temperature. To the reaction mixture was added a solution of Compound xi-46 (1.87 g, 3.29 mmol) in DMF (10 mL), and the resulting mixture was stirred for 5 hours at 100° C. After the mixture was cooled, to the reaction mixture was added saturated aqueous ammonium chloride. The mixture was extracted with ethyl acetate. The organic layer was washed by water and brine, dried over anhydrous sodium sulphate, and concentrated in vacuo. The resulting residue was purified by silica gel column chromatography (hexane-ethyl acetate) to give Compound xi-47 (1.40 g, Yield 80%).

$^1$H-NMR (CDCl$_3$) δ: −0.08 (3H, s), −0.05 (3H, s), 0.74 (9H, s), 1.26 (1H, t, J=7.0 Hz), 1.44 (3H, t, J=6.9 Hz), 1.49-1.56 (1H, m), 1.64-1.72 (1H, m), 2.09-2.19 (1H, m), 2.32-2.42 (1H, m), 3.04 (1H, dd, J=11.0, 4.3 Hz), 3.58 (1H, dd, J=11.0, 5.2 Hz), 3.70 (1H, t, J=7.3 Hz), 3.76 (3H, s), 3.77 (3H, s), 4.03-4.10 (2H, m), 4.31-4.34 (1H, m), 6.95 (2H, d, J=8.2 Hz), 7.73 (2H, d, J=8.3 Hz).

Step 3

Under nitrogen atmosphere, to a suspension of lithium aluminium hydride (401 mg, 10.6 mmol) in THF (15 mL) was added dropwise a solution of Compound xi-47 (1.40 g, 2.64 mmol) in THF (15 mL) over 20 minutes under ice-cooling. Then, the mixture was stirred for 2 hours at room temperature. To the reaction mixture was added aqueous saturated potassium sodium tartrate, and the mixture was extracted with ethyl acetate. The organic layer was washed by water and brine, dried over anhydrous sodium sulphate, and concentrated in vacuo. The resulting residue was purified by silica gel column chromatography (hexane-ethyl acetate) to give Compound xi-48 (739 mg, Yield 59%).

$^1$H-NMR (CDCl$_3$) δ: −0.07 (3H, s), −0.05 (3H, s), 0.75 (9H, s), 1.45 (3H, t, J=6.9 Hz), 1.66-1.85 (2H, m), 1.93-2.02 (1H, m), 2.33 (1H, t, J=5.1 Hz), 2.41 (1H, t, J=5.3 Hz), 3.08 (1H, dd, J=10.8, 3.6 Hz), 3.59 (1H, dd, J=10.9, 5.0 Hz), 3.68-3.86 (5H, m), 4.08 (2H, q, J=7.0 Hz), 4.27-4.34 (1H, m), 6.96 (2H, d, J=8.0 Hz), 7.74 (2H, d, J=7.8 Hz).

Step 4

Under nitrogen atmosphere, to a solution of Compound xi-48 (739 mg, 1.56 mmol) in THF (8 mL) was added 1.65 mol/L n-butyllithium in hexane (0.95 mL, 1.56 mmol) under ice-cooling, and the mixture was stirred for 30 minutes. To the mixture was added a solution of p-toluenesulfonyl chloride (297 mg, 1.56 mmol) in THF (8 mL), and the resulting mixture was allowed to warm to room temperature and stirred for 1 hour. To the reaction mixture was added 1.65 mol/L n-butyllithium in hexane (0.95 mL, 1.56 mmol) under ice-cooling, and the resulting mixture was stirred for 2 hours at 60° C. After the mixture was cooled, to the reaction mixture was added saturated aqueous ammonium chloride, and the resulting mixture was extracted with ethyl acetate. The organic layer was washed by brine, dried over anhydrous sodium sulphate, and concentrated in vacuo. The resulting residue was purified by silica gel column chromatography (hexane-ethyl acetate) to give Compound xi-49 (637 mg, Yield 90%).

$^1$H-NMR (CDCl$_3$) δ: −0.07 (3H, s), −0.06 (3H, s), 0.75 (9H, s), 1.45 (3H, t, J=6.9 Hz), 1.58-1.61 (1H, m), 1.93-2.02 (1H, m), 2.29-2.39 (1H, m), 3.08 (1H, dd, J=10.8, 3.8 Hz), 3.12-3.19 (1H, m), 3.50-3.60 (2H, m), 4.04-4.16 (3H, m), 4.24-4.30 (1H, m), 4.44-4.53 (2H, m), 4.76-4.83 (2H, m), 6.95 (2H, d, J=8.5 Hz), 7.71-7.79 (2H, m).

Step 5

To a solution of Compound xi-49 (342 mg, 0.749 mmol) in THF (7 mL) was added 1 mol/L tetra-butylammonium fluoride in THF (1.12 mL, 1.12 mmol) under ice-cooling, and the mixture was stirred for 1 hour at room temperature. To the reaction mixture was added saturated aqueous ammonium chloride, and the mixture was extracted with ethyl acetate. The organic layer was washed by brine, dried over anhydrous sodium sulphate, and concentrated in vacuo to give a crude product.

The obtained Compound was dissolved in dichloromethane (7 mL), and the solution was cooled under ice-cooling. To the reaction mixture were added triethylamine (0.54 mL, 3.90 mmol), trimethylamine hydrochloride (21 mg, 0.23 mmol), and p-toluenesulfonyl chloride (372 mg, 1.94 mmol), and the resulting mixture was stirred for 12 hours at room temperature. To the reaction mixture was added water, and the resulting mixture was extracted with ethyl acetate. The organic layer was washed by brine, dried over anhydrous sodium sulphate, and concentrated in vacuo. The resulting residue was purified by silica gel column chromatography (hexane-ethyl acetate) to give Compound XI-14 (263 mg, Yield 71%).

$^1$H-NMR (CDCl$_3$) δ: 1.46 (3H, t, J=6.9 Hz), 1.61-1.70 (1H, m), 1.88-1.99 (2H, m), 2.30-2.40 (1H, m), 2.46 (3H, s), 3.01-3.12 (1H, m), 3.47-3.56 (3H, m), 4.10 (2H, q, J =6.8 Hz), 4.39-4.48 (2H, m), 4.71-4.81 (3H, m), 6.95 (2H, d, J=8.5 Hz), 7.32 (2H, d, J =7.9 Hz), 7.56 (2H, d, J=7.9 Hz), 7.69 (2H, d, J=8.5 Hz).

REFERENCE EXAMPLE 26

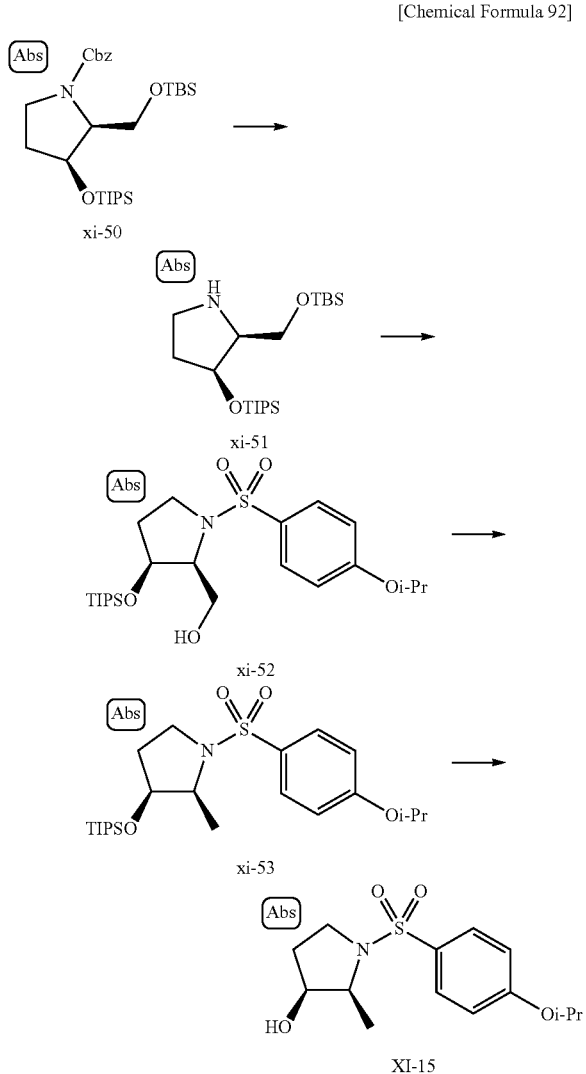

Step 1

To a solution of Compound xi-50 (3.43 g, 6.57 mmol) which was synthesized in a similar manner as described in Tetrahedron: Asymmetry, vol. 13, p. 1103-1113, in THF (35 mL), was added Pd/C (699 mg), and the mixture was stirred overnight under hydrogen atmosphere at room temperature. The reaction mixture was filtered using Celite, and the filtrate was washed by THF. The filtrate was concentrated in vacuo to give Compound xi-51 (2.53 g, Yield 99%).

$^1$H-NMR (CDCl$_3$) δ: 4.48 (1H, dd, J=10.4, 4.6 Hz), 3.80 (1H, dd, J=10.4, 5.1 Hz), 3.68-3.63 (1H, m), 3.17-3.09 (2H, m), 3.06-3.01 (2H, m), 2.88-2.82 (1H, m), 2.04-1.96 (1H, m), 1.86-1.72 (3H, m), 1.07-1.04 (18H, m), 0.89 (9H, s), 0.05 (6H, d, J=1.8 Hz).

Step 2

To a solution of Compound xi-51 (1 g, 2.58 mmol) in dichloromethane (10 mL) were added triethylamine (536 μL, 3.87 mmol) and 4-isopropoxybenzenesulfonyl chloride (726 mg, 3.09 mmol) under ice-cooling, and the mixture was stirred for 1 hour at room temperature. The reaction mixture was concentrated in vacuo. To the residue were added hydrochloric acid and water, and the mixture was extracted with ethyl acetate. The organic layer was washed by water and brine, dried over anhydrous magnesium sulphate, and concentrated in vacuo. The resulting residue was purified by silica gel column chromatography (hexane-ethyl acetate) to give a crude product (1.61 g).

To a solution of the obtained crude product (1.61 g) in THF (20 mL) was added 2 mol/L aqueous hydrochloric acid (4.12 mL, 8.24 mmol), and the mixture was stirred for 2 hours at 50° C. The reaction mixture was concentrated in vacuo. To the residue was added saturated aqueous sodium bicarbonate, and the mixture was extracted with ethyl acetate. The organic layer was washed by water and brine, dried over anhydrous magnesium sulphate, and concentrated in vacuo. The resulting residue was purified by silica gel column chromatography (hexane-ethyl acetate) to give Compound xi-52 (1.03 g, 2 Step Yield 85%).

$^1$H-NMR (CDCl$_3$) δ: 7.77 (2H, d, J=8.8 Hz), 6.96 (2H, d, J=8.8 Hz), 4.66-4.60 (1H, m), 4.10-4.04 (1H, m), 3.96-3.89 (1H, m), 3.83-3.77 (1H, m), 3.69-3.64 (1H, m), 3.57-3.51 (1H, m), 3.22-3.15 (1H, m), 2.87-2.83 (1H, m), 1.97-1.82 (2H, m), 1.37 (6H, d, J=6.0 Hz), 1.00 (21H, s).

Step 3

To a solution of Compound xi-52 (820 mg, 1.74 mmol) in dichloromethane (10 mL) were added triethylamine (361 μL, 2.61 mmol) and methanesulfonyl chloride (163 μL, 2.09 mmol) under ice-cooling, and the mixture was stirred for 30 minutes at room temperature. The reaction mixture was concentrated in vacuo. To the residue were added hydrochloric acid and water, and the mixture was extracted with ethyl acetate. The organic layer was washed by brine, dried over anhydrous magnesium sulphate, and concentrated in vacuo. The resulting residue was used in the next step without purification.

The resulting residue was dissolved in THF (10 mL). To the solution was added 1 mol/L lithium triethylborohydride in THF (8.69 mL, 8.69 mmol), and the mixture was heated at reflux at 2 hours. To the reaction mixture was added hydrochloric acid, and the mixture was extracted with ethyl acetate. The organic layer was washed by water and brine, dried over anhydrous magnesium sulphate, and concentrated in vacuo. The resulting residue was purified by silica gel column chromatography (hexane-ethyl acetate) to give Compound xi-53 (719 mg, 2 Steps Yield 91%).

$^1$H-NMR (CDCl$_3$) δ: 7.74 (2H, d, J=8.7 Hz), 6.94 (2H, d, J=8.7 Hz), 4.65-4.59 (1H, m), 3.94-3.88 (1H, m), 3.74-3.67 (1H, m), 3.48-3.42 (1H, m), 3.19-3.11 (1H, m), 1.89-1.78 (2H, m), 1.37 (6H, d, J=6.0 Hz), 1.23 (3H, d, J=6.8 Hz), 0.99 (21H, s).

Step 4

To a solution of Compound xi-53 (710 mg, 1.56 mmol) in THF (5 mL) was added 1 mol/L tetrabutylammonium fluoride in THF (1.87 mL, 1.87 mmol), and the mixture was stirred for 1 hour at room temperature. To the reaction mixture was added water, and the resulting mixture was extracted with ethyl acetate. The organic layer was washed by water and brine, dried over anhydrous magnesium sulphate, and concentrated in vacuo. The resulting residue was purified by silica gel column chromatography (hexane-ethyl acetate) to give Compound XI-15 (458 mg, Yield 98%).

$^1$H-NMR (CDCl$_3$) δ: 7.74 (2H, d, J=8.5 Hz), 6.95 (2H, d, J=8.5 Hz), 4.67-4.58 (1H, m), 4.07-4.01 (1H, m), 3.63-3.50 (2H, m), 3.31-3.24 (1H, m), 1.85-1.67 (2H, m), 1.37 (6H, d, J=6.0 Hz), 1.34 (3H, d, J=6.7 Hz).

REFERENCE EXAMPLE 27

[Chemical Formula 93]

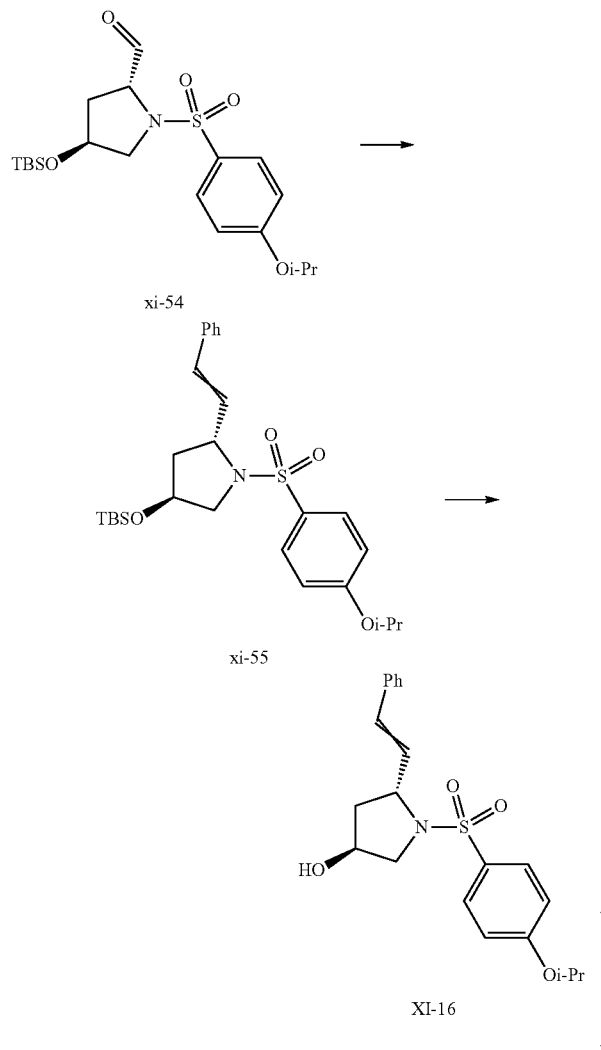

Step 1

Benzyltriphenylphosphonium chloride (100 mg, 0.257 mmol) was dissolved in THF (1.0 mL). To the solution was added NaOtBu (24.7 mg, 0.257 mmol), and the mixture was stirred for 30 minutes at −78° C. To the reaction mixture was added dropwise gradually a solution of Compound xi-54 (100 mg, 0.234 mmol) in THF (0.5 mL) at −78° C., and the mixture was stirred for 2 hours. To the reaction mixture was added water, and the resulting mixture was extracted with ethyl acetate. The organic layer was washed by water and brine and concentrated in vacuo. The resulting residue was purified by silica gel column chromatography (hexane-ethyl acetate) to give Compound xi-55 (83.1 mg, diastereomer ratio 3:1, Yield 71%).

$^1$H-NMR (CDCl$_3$) δ: 7.76 (2H, d, J=8.3 Hz), 7.38-7.30 (5H, m), 6.92 (2H, d, J=8.3 Hz), 6.51 (1H, d, J=15.8 Hz), 6.17 (1H, dd, J=15.9, 7.4 Hz), 4.63-4.57 (1H, m), 4.34 (1H, s), 4.26 (1H, dd, J=14.7, 7.2 Hz), 3.70 (1H, dd, J=10.9, 4.6 Hz), 3.30 (1H, d, J=11.3 Hz), 1.93 (2H, t, J=5.6 Hz), 1.38 (6H, d, J=5.8 Hz), 0.80 (9H, s), 0.01 (6H, d, J=8.3 Hz).

Step 2

Compound xi-55 (67 mg, 0.134 mmol) was dissolved in 2 mol/L hydrochloric acid in dioxane (0.5 mL), and the reaction mixture was stirred for 3 hours at room temperature. The reaction mixture was concentrated in vacuo to give Compound XI-16 (51.7 mg, Yield 100%).

LC/MS (Condition B) RT=2.14, [M+H]$^+$=388.

REFERENCE EXAMPLE 28

[Chemical Formula 94]

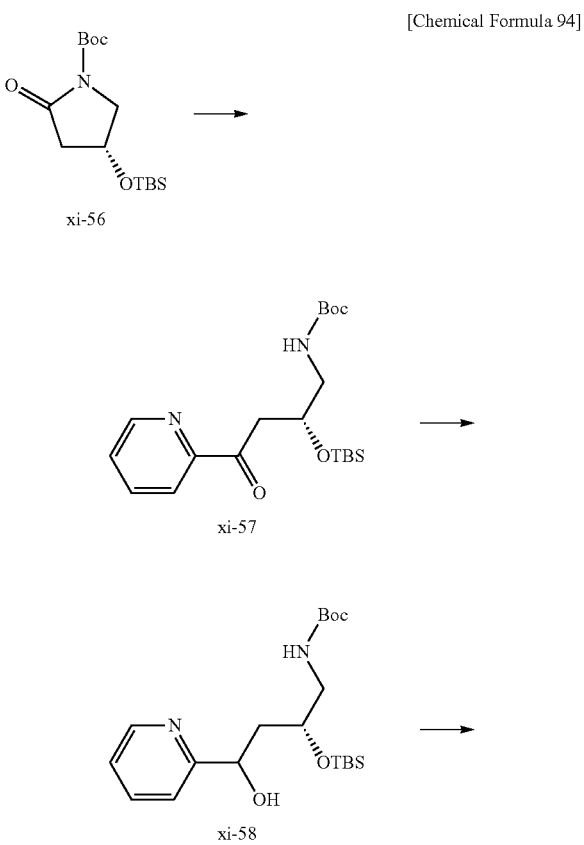

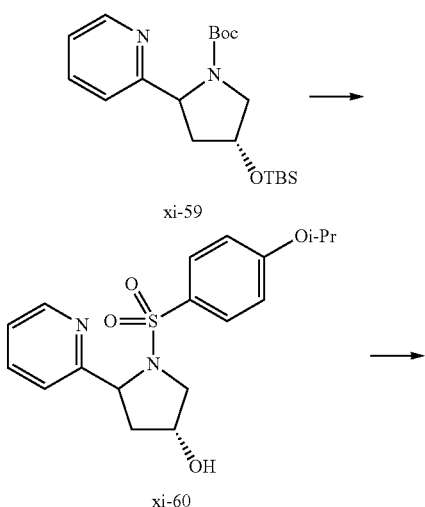

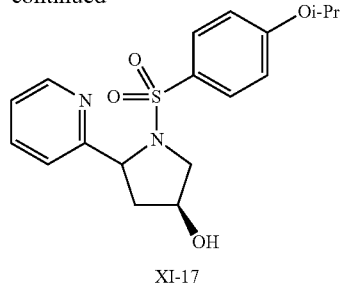

XI-17

Step 1

To a solution of 2-bromopyridine (0.647 mL, 6.75 mmol) in diethyl ether (40.0 mL) was added dropwise gradually 1.6 mol/L n-butyllithium in hexane (4.22 mL, 6.75 mmol) at −78° C., and the mixture was stirred for 30 minutes. To the reaction mixture was added dropwise gradually a solution of Compound xi-56 (2.13 g, 6.75 mmol) in THF (4.0 mL) at −78° C., and the mixture was stirred for 2 hours. To the reaction mixture was added 2 mol/L aqueous hydrochloric acid, and the mixture was extracted with ethyl acetate. The organic layer was washed by water and brine, and concentrated in vacuo to give crude product of Compound xi-57 (2.51 g).

$^1$H-NMR (CDCl$_3$) δ: 8.67 (1H, d, J=4.3 Hz), 8.03 (1H, d, J=7.8 Hz), 7.83 (1H, t, J=7.7 Hz), 7.46 (1H, t, J=6.0 Hz), 3.38 (2H, t, J=5.0 Hz), 3.27 (2H, d, J=5.8 Hz), 2.55 (1H, dd, J=9.9, 6.1 Hz), 2.41 (1H, dd, J=12.0, 7.3 Hz), 1.41 (9H, s), 0.87 (9H, s), 0.09 (6H, s).

Step 2

To a solution of Compound xi-57 (2.51 g, 6.36 mmol) in methanol (20.0 mL) was added sodium borohydride (289 mg, 7.63 mmol) at −10° C., and the mixture was stirred for 30 minutes. To the reaction mixture was added water, and the mixture was extracted with ethyl acetate. The organic layer was washed by water and brine, and concentrated in vacuo to give crude product of Compound xi-58 (2.46 g).

LC/MS (Condition B) RT=2.01, 2.06 [M+H]$^+$=397.

Step 3

To a solution of Compound xi-58 (2.46 g, 6.20 mmol) in dichloromethane (3.0 mL) were added methanesulfonyl chloride (0.58 mL, 7.44 mmol) and triethylamine (2.58 mL, 18.61 mmol) at 0° C., and the mixture was stirred for 1 hour at room temperature. To the reaction mixture was added water, and the mixture was extracted with ethyl acetate. The organic layer was washed by water and brine, and concentrated in vacuo to give crude product (2.70 g).

To a solution of the obtained compound (2.70 g) in DMF (30.0 mL) was added sodium hydride (0.25 mg, 6.26 mmol) at 0° C., and the mixture was stirred for 30 minutes at room temperature. To the reaction mixture was added water, and the mixture was extracted with ethyl acetate. The organic layer was washed by water and brine, and concentrated in vacuo to give crude product of Compound xi-59 (2.36 g).

LC/MSMS (Condition RT=2.30, 2.54 [M+H]$^+$=379.

Step 4

Compound xi-59 (2.15 g, 5.68 mmol) was dissolved in 2 mol/L hydrochloric acid in dioxane (22.5 mL), and the solution was stirred for 30 minutes at room temperature. The reaction mixture was concentrated in vacuo.

To a solution of the obtained Compound (1.14 g) in dichloromethane (11.0 mL) were added 4-isopropoxybenzenesulfonyl chloride (1.467 g, 6.25 mmol) and triethylamine (2.36 mL, 17.04 mmol), and the mixture was stirred for 1 hour at room temperature. To the reaction mixture was added water, and the mixture was extracted with ethyl acetate. The organic layer was washed by water and brine, and concentrated in vacuo to give crude product of Compound xi-60 (2.06 g).

LC/MSMS (Condition B) RT=1.25, 1.34 [M+H]$^+$=363.

Step 5

To a solution of Compound xi-60 (2.06 g) in dichloromethane (15.0 mL) were added methanesulfonyl chloride (0.53 mL, 6.82 mmol) and triethylamine (2.36 mL, 17.05 mmol), and the mixture was stirred for 1 hour at room temperature. To the reaction mixture was added water, and the mixture was extracted with ethyl acetate. The organic layer was washed by water and brine, and concentrated in vacuo.

The obtained compound (2.38 g) was dissolved in DMA (20.0 mL). To the solution was added cesium acetate (2.07 g, 10.79 mmol), and the mixture was stirred for 5 hours at 85° C. To the reaction mixture was added water, and the mixture was extracted with ethyl acetate. The organic layer was washed by water and brine, and concentrated in vacuo.

The obtained compound (1.95 g) was dissolved in methanol (20.0 mL). To the solution was added potassium carbonate (1.33 g, 9.65 mmol), and the mixture was stirred for 1 hour at room temperature. To the reaction mixture was added water, and the mixture was extracted with ethyl acetate. The organic layer was washed by water and brine, and concentrated in vacuo to give crude product of Compound XI-17 (1.39 g).

LC/MS (Condition B) RT=1.25, 1.35 [M+H]$^+$=363.

The following compound was synthesized by the method in a similar manner to the above.

[Chemical Formula 95]

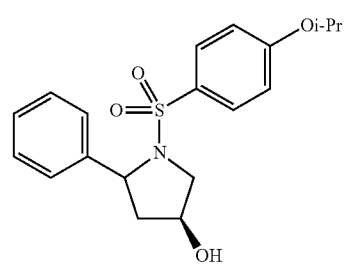

XI-18

REFERENCE EXAMPLE 29

[Chemical Formula 96]

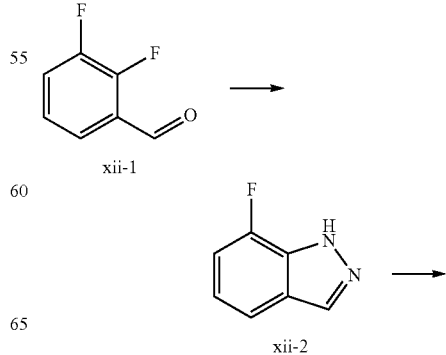

-continued

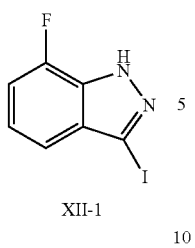

XII-1

Step 1

Hydrazine monohydrate (10 mL) was slowly added to Compound xii-1 (5 g, 35.2 mmol), and the mixture was stirred for 3 hours at 150° C. The reaction mixture was concentrated in vacuo, and water was added to the mixture. The precipitated solids were collected by filtration to give Compound xii-2 (1.98 g, Yield 41%).

$^1$H-NMR (CDCl$_3$) δ: 10.40 (1H, br s), 7.32-7.28 (1H, m), 7.18-7.12 (2H, m).

Step 2

Compound xii-2 (500 mg, 3.67 mmol) was dissolved in dimethylformamide (5 mL). To the solution were added potassium hydroxide (721 mg, 12.86 mmol) and iodine (1.63 g, 6.43 mmol), and the mixture was stirred for 1 hour at room temperature. To the reaction mixture was added water, and the resulting mixture was extracted with ethyl acetate. The organic layer was washed by water, aqueous sodium hydrogensulfate, and brine, and concentrated in vacuo. The resulting residue was purified by silica gel column chromatography (hexane-ethyl acetate) to give Compound XII-1 (852 mg, Yield 89%).

$^1$H-NMR (CDCl$_3$) δ: 10.20 (1H, s), 8.11 (1H, d, J=3.51 Hz), 7.54-7.50 (1H, m), 7.10-7.08 (2H, m).

The following indazole derivative was synthesized by the method in a similar manner described in the above.

[Chemical Formula 97]

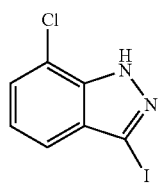

XII-2

Compound XII-2

$^1$H-NMR (CDCl$_3$) δ: 10.53 (1H, br s), 7.44 (2H, ddd, J=7.70, 6.25, 0.76 Hz), 7.18 (1H, dd, J=8.08, 7.47 Hz).

EXAMPLE 1

[Chemical Formula 98]

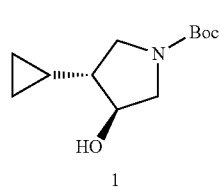

Step 1

Compound 1 (150 mg, 0.660 mmol) was dissolved in dichloromethane (2 mL) under nitrogen atmosphere. To the solution were added triethylamine (183 μL, 1.32 mmol) and methanesulfonyl chloride (77 μL, 0.990 mmol) under ice-cooling, and the mixture was stirred for 80 minutes at room temperature. To the reaction mixture was added saturated aqueous sodium bicarbonate, and the mixture was extracted with ethyl acetate. The organic layer was washed by brine, dried over anhydrous magnesium sulfate, and concentrated in vacuo. The resulting residue was used in Step 2 without purification.

Step 2

Compound III-1 (171 mg, 0.726 mmol) was dissolved in DMF (1 mL) under nitrogen atmosphere. To the solution was added 60% sodium hydride (29.0 mg, 0.726 mmol) under ice-cooling, and the mixture was stirred for 10 minutes. To the reaction mixture was added a solution of Compound 2 obtained in Step 1 in DMF (1 mL). The mixture was heated at 85° C. and stirred for 6 hours. After the reaction mixture was allowed to cool to room temperature, 1 mol/L aqueous hydrochloric acid was added to the mixture, and the resulting mixture was extracted with ethyl acetate. The organic layer was washed by water and brine, dried over anhydrous magnesium sulfate, and concentrated in vacuo. The resulting residue was purified by silica gel column chromatography (hexane-ethyl acetate) to give Compound 3 (88 mg, Yield 30%).

LC/MS (Condition B) RT=2.85, [M+H]$^+$=446.

Step 3

Compound 4 (85 mg, 0.191 mmol) was dissolved in ethyl acetate (2 mL) under nitrogen atmosphere. To the solution was added 4 mol/L hydrochloric acid in ethyl acetate (0.24 mL, 0.954 mmol) at room temperature, and the resulting mixture was stirred for 1 hour. After the reaction was completed, the mixture was concentrated in vacuo to give Compound 4 (73 mg).

LC/MS (Condition B) RT=1.43, [M+H]$^+$=346.

Step 4

Compound 4 (28 mg, 0.073 mmol) was dissolved in dichloromethane (2 mL) under nitrogen atmosphere. To the solution were added triethylamine (30 μL, 0.220 mmol) and 4-isopropoxybenzenesulfonyl chloride (18.9 mg, 0.081 mmol) under ice-cooling, and the mixture was stirred for 15 hours at room temperature. After the reaction mixture was concentrated until the amount of solvent was to be half amount, the resulting residue was purified by silica gel column chromatography (hexane-ethyl acetate) to give Compound 5 (40 mg, Yield 100%).

LC/MS (Condition B) RT=2.91, [M+H]$^+$=544.

Step 5

Compound 5 (40 mg, 0.074 mmol) was dissolved in DMSO (1 mL). To the solution was added 2 mol/L aqueous sodium hydroxide (74 μL, 0.147 mmol) at room temperature, and the mixture was stirred for 1 hour. After the reaction was completed, 2 mol/L aqueous hydrochloric acid (74 μL, 0.147 mmol) and distilled water (20 mL) were added dropwise gradually to the mixture. The precipitation was gathered by filtration and dried by heating to give Compound I-41 (33.2 mg, Yield 89%).

LC/MS (Condition B) RT=2.35, [M+H]$^+$=502.

EXAMPLE 2

[Chemical Formula 99]

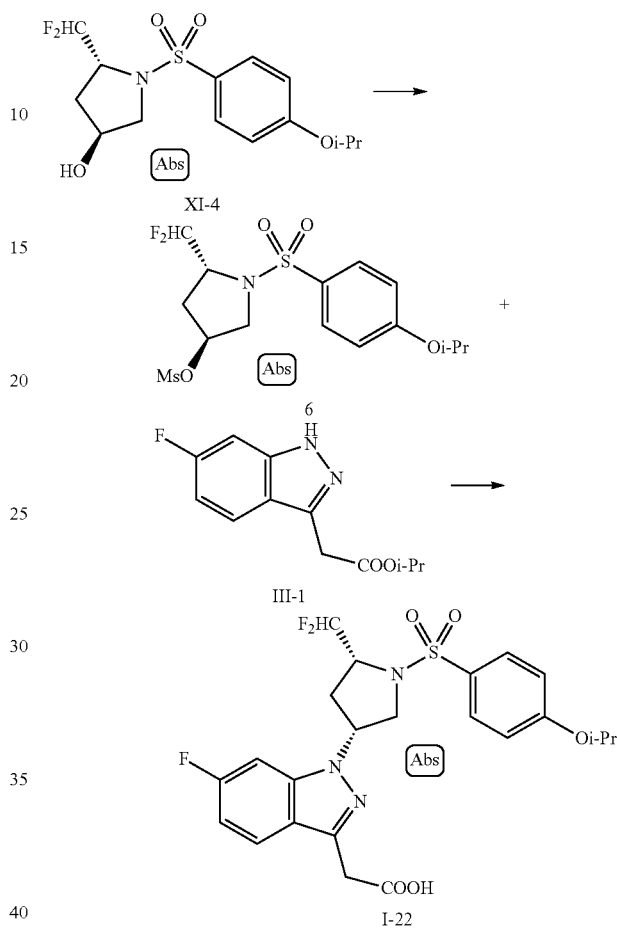

Step 1

Compound XI-4 (64 mg, 0.191 mmol) was dissolved in dichloromethane (1.5 mL). To the solution were added triethylamine (0.053 mL, 0.382 mmol) and methanesulfonyl chloride (0.022 mL, 0.287 mmol) under ice-cooling, and the mixture was stirred for 35 minutes. To the mixture was added saturated aqueous sodium bicarbonate, and the resulting mixture was extracted with ethyl acetate. The organic layer was washed by water and brine, dried over magnesium sulphate, and concentrated in vacuo. The obtained Compound 6 was used in next step without purification.

Step 2

Compound 6 (0.191 mmol) was dissolved in DMF (1.5 mL). To the solution were added Compound 9 (54 mg, 0.229 mmol) and cesium carbonate (125 mg, 0.382 mmol), and the mixture was heated and stirred at 80° C. for 2 hours. The mixture was allowed to cool to room temperature, and water was added to the mixture. The resulting mixture was extracted with ethyl acetate. The organic layer was washed by water and brine, dried over magnesium sulphate, and concentrated in vacuo. The resulting residue was purified by silica gel column chromatography (hexane-ethyl acetate). The obtained compound was hydrolyzed according to the method described in the general synthetic procedures to give Compound I-22 (18 mg, 2 steps, Yield 18%).

¹H-NMR (CDCl₃) δ: 7.83 (2H, d, J=8.90 Hz), 7.60 (1H, dd, J=8.73, 5.04 Hz), 7.05 (2H, d, J=8.90 Hz), 6.97-6.88 (1H, m), 6.75 (1H, dd, J=9.23, 1.68 Hz), 6.17 (1H, ddd, J=57.75, 56.07, 2.52 Hz), 4.75-4.62 (1H, m), 4.41-4.16 (2H, m), 4.01-3.86 (3H, m), 3.70-3.59 (1H, m), 2.87-2.73 (1H, m), 2.51-2.38 (1H, m), 1.41 (6H, dd, J=5.96, 1.43 Hz).

EXAMPLE 3

[Chemical Formula 100]

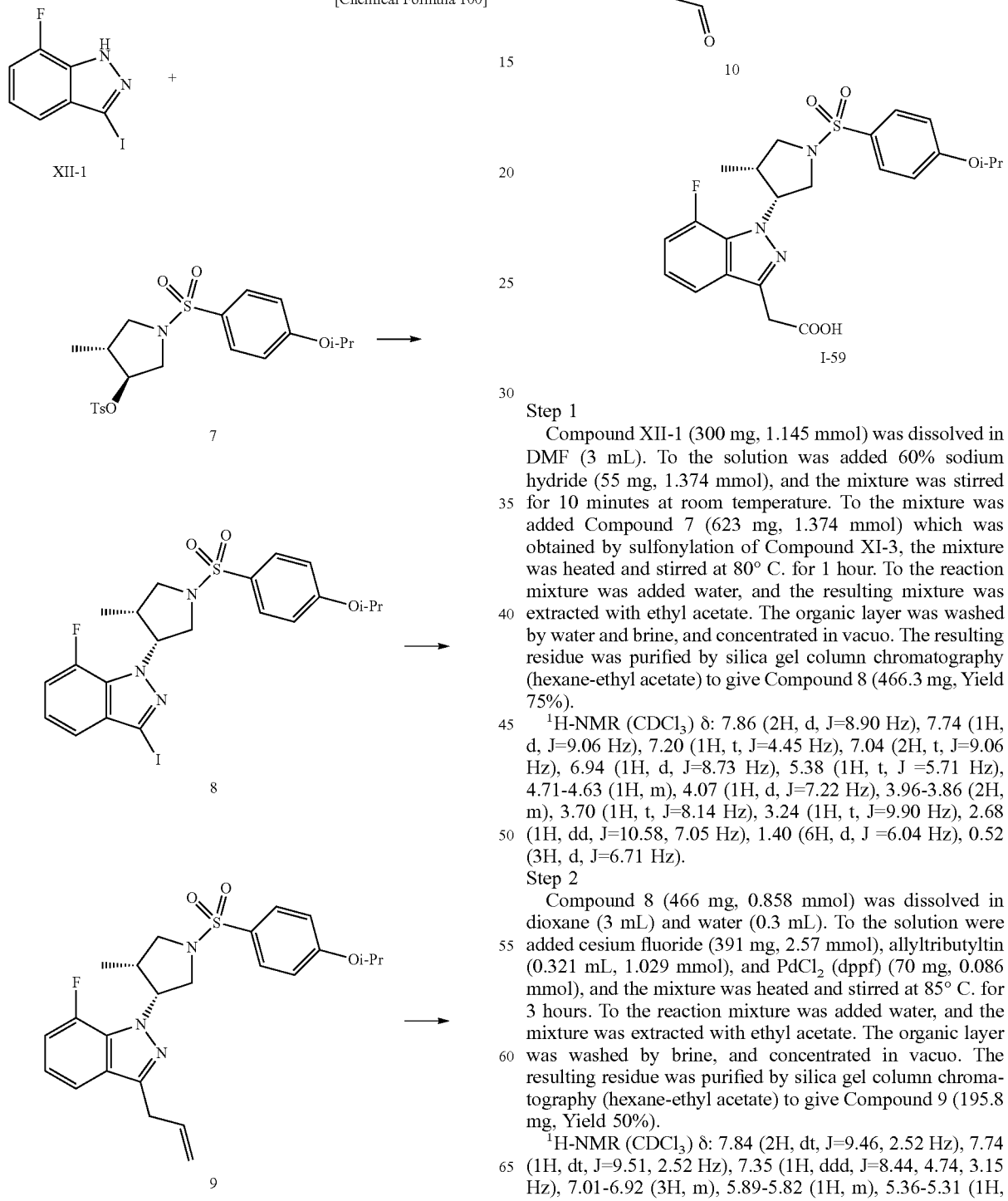

Step 1

Compound XII-1 (300 mg, 1.145 mmol) was dissolved in DMF (3 mL). To the solution was added 60% sodium hydride (55 mg, 1.374 mmol), and the mixture was stirred for 10 minutes at room temperature. To the mixture was added Compound 7 (623 mg, 1.374 mmol) which was obtained by sulfonylation of Compound XI-3, the mixture was heated and stirred at 80° C. for 1 hour. To the reaction mixture was added water, and the resulting mixture was extracted with ethyl acetate. The organic layer was washed by water and brine, and concentrated in vacuo. The resulting residue was purified by silica gel column chromatography (hexane-ethyl acetate) to give Compound 8 (466.3 mg, Yield 75%).

¹H-NMR (CDCl₃) δ: 7.86 (2H, d, J=8.90 Hz), 7.74 (1H, d, J=9.06 Hz), 7.20 (1H, t, J=4.45 Hz), 7.04 (2H, t, J=9.06 Hz), 6.94 (1H, d, J=8.73 Hz), 5.38 (1H, t, J =5.71 Hz), 4.71-4.63 (1H, m), 4.07 (1H, d, J=7.22 Hz), 3.96-3.86 (2H, m), 3.70 (1H, t, J=8.14 Hz), 3.24 (1H, t, J=9.90 Hz), 2.68 (1H, dd, J=10.58, 7.05 Hz), 1.40 (6H, d, J =6.04 Hz), 0.52 (3H, d, J=6.71 Hz).

Step 2

Compound 8 (466 mg, 0.858 mmol) was dissolved in dioxane (3 mL) and water (0.3 mL). To the solution were added cesium fluoride (391 mg, 2.57 mmol), allyltributyltin (0.321 mL, 1.029 mmol), and PdCl₂ (dppf) (70 mg, 0.086 mmol), and the mixture was heated and stirred at 85° C. for 3 hours. To the reaction mixture was added water, and the mixture was extracted with ethyl acetate. The organic layer was washed by brine, and concentrated in vacuo. The resulting residue was purified by silica gel column chromatography (hexane-ethyl acetate) to give Compound 9 (195.8 mg, Yield 50%).

¹H-NMR (CDCl₃) δ: 7.84 (2H, dt, J=9.46, 2.52 Hz), 7.74 (1H, dt, J=9.51, 2.52 Hz), 7.35 (1H, ddd, J=8.44, 4.74, 3.15 Hz), 7.01-6.92 (3H, m), 5.89-5.82 (1H, m), 5.36-5.31 (1H, m), 5.10-5.06 (1H, m), 5.03 (1H, t, J=1.59 Hz), 4.63 (1H, td, J=12.30, 6.15 Hz), 4.06-4.03 (1H, m), 3.95 (1H, s), 3.90 (1H, dd, J=11.08, 2.52 Hz), 3.70-3.64 (1H, m), 3.38 (2H, dt, J=6.38, 1.51 Hz), 3.25 (1H, dd, J=10.74, 8.73 Hz), 2.68-2.58 (0H, m), 1.39 (6H, d, J=6.04 Hz), 0.48 (3H, d, J=6.88 Hz).

Step 3

Compound 9 (190 mg, 0.415 mmol) was dissolved in acetonitrile (1.5 mL) and water (0.75 mL). To the solution were added sodium periodate (266 mg, 1.246 mmol) and 10% osmium tetroxide (106 mg, 0.042 mmol), and the mixture was stirred for 1 hour at room temperature. The reaction mixture was filtered by using Celite, and the filtrate was concentrated in vacuo. To the mixture was added water, and the resulting mixture was extracted with ethyl acetate. The organic layer was washed by brine, and concentrated in vacuo. The residue was used in the next step without purification.

$^1$H-NMR (CDCl$_3$) δ: 9.60 (1H, s), 7.83 (2H, t, J=4.39 Hz), 7.71 (1H, d, J=9.06 Hz), 7.05-6.94 (4H, m), 5.37 (1H, d, J=4.67 Hz), 4.69-4.62 (2H, m), 4.09 (1H, dd, J=16.48, 12.64 Hz), 3.91 (1H, dd, J=8.10, 5.63 Hz), 3.69 (2H, dt, J=15.20, 6.52 Hz), 3.23 (1H, t, J=10.03 Hz), 2.66 (1H, d, J=18.95 Hz), 1.40 (6H, d, J=6.04 Hz), 0.50 (3H, d, J=6.87 Hz).

Step 4

Compound 10 (190 mg, 0.415 mmol) was dissolved in tert-butanol (2 mL) and water (1 mL). To the solution were added sodium dihydrogenphosphate (50 mg, 0.416 mmol), 2-methylbutene (0.286 ml, 2.7 mmol), and sodium chlorite (132 mg, 1.455 mmol), and the mixture was stirred for 1 hour at room temperature. To the reaction mixture was added 2 mol/L aqueous hydrochloric acid, and the resulting mixture was extracted with ethyl acetate. The organic layer was washed by brine, and concentrated in vacuo. The resulting residue was purified by silica gel column chromatography (hexane-ethyl acetate) to give Compound I-59 (87.6 mg, Yield 44%).

$^1$H-NMR (CDCl$_3$) δ: 7.82 (2H, d, J=8.24 Hz), 7.37 (1H, s), 6.98 (4H, d, J=8.54 Hz), 5.35 (1H, s), 4.65 (1H, t, J=5.72 Hz), 4.13-4.01 (1H, m), 3.91 (1H, d, J=11.13 Hz), 3.71 (2H, s), 3.65 (1H, t, J=8.08 Hz), 3.22 (1H, t, J=9.30 Hz), 2.63 (1H, s), 1.38 (6H, d, J=5.64 Hz), 0.48 (3H, d, J=6.25 Hz).

EXAMPLE 4

[Chemical Formula 101]

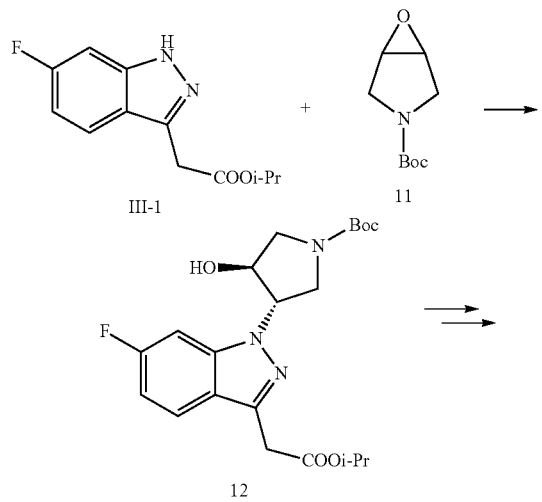

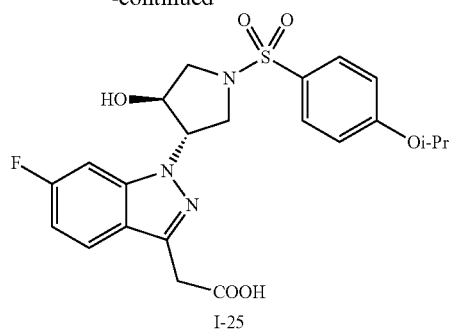

Step 1

60% sodium hydride (27.9 mg, 0.698 mmol) was suspended in DMF (1 mL) under nitrogen atmosphere. To the suspension was added a solution of Compound III-1 (150 mg, 0.635 mmol) in DMF (1 mL), and the mixture was stirred for 10 minutes at room temperature. To the reaction mixture was added Compound 11 (129 mg, 0.698 mmol), and the mixture was stirred for 4 hours at 60° C. The reaction mixture was allowed to cool to room temperature, saturated aqueous ammonium chloride was added to the mixture. The mixture was extracted with ethyl acetate. The organic layer was washed by water and brine, dried over anhydrous magnesium sulfate, and concentrated in vacuo. The resulting residue was purified by silica gel column chromatography (hexane-ethyl acetate) to give Compound 12 (41 mg, Yield 15%).

LC/MS (Condition B) RT=2.36, [M+H]$^+$=422.

Step 2 and after Step 2

Compound I-25 was obtained in a similar manner to those described in Steps 3 to 5 in Example 1.

$^1$H-NMR (DMSO-d6) δ: 7.69 (2H, d, J=8.8 Hz), 7.67 (1H, d, J=10.1 Hz), 7.46 (1H, dd, J=10.1, 2.0 Hz), 7.08 (2H, d, J=8.8 Hz), 6.99 (1H, dt, J=12.8, 4.6 Hz), 5.69-5.58 (1H, m), 5.01-4.91 (1H, m), 4.80-4.67 (1H, m), 4.38-4.25 (1H, m), 3.84-3.69 (1H, m), 3.76 (2H, s), 3.55 (1H, dd, J=10.3, 6.0 Hz), 3.49-3.40 (1H, m), 3.11 (1H, dd, J =10.2, 5.0 Hz), 1.31 (6H, d, J=6.1 Hz).

LC/MS (Condition B) RT=1.92, [M+H]$^+$=478.

EXAMPLE 5

[Chemical Formula 102]

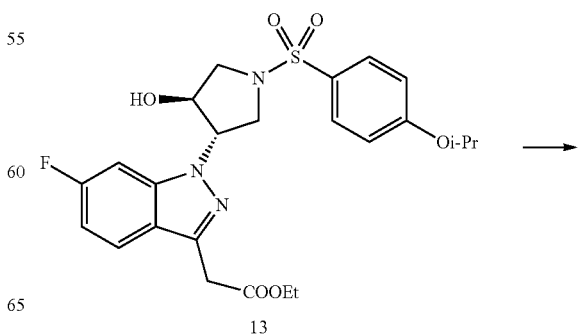

-continued

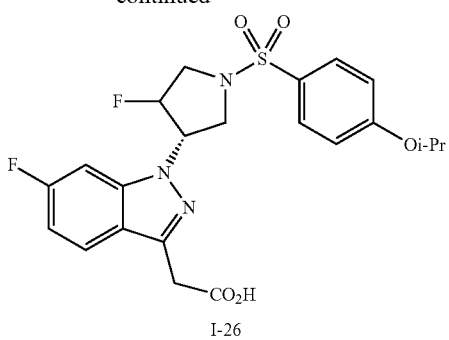

I-26

To a solution of Compound 13 (90 mg, 0.178 mmol) in dichloromethane (1 mL) was added DAST (35 μl, 0.267 mmol) dropwise at 0° C. under nitrogen atmosphere. The mixture was allowed to warm to room temperature gradually and stirred for 3.5 hours. To the mixture was added saturated aqueous sodium bicarbonate under ice-cooling, and the resulting mixture was extracted with ethyl acetate. The organic layer was washed by water and brine, dried over anhydrous magnesium sulfate, and concentrated in vacuo. The resulting residue was purified by silica gel column chromatography (hexane-ethyl acetate). The obtained compound (22 mg) was hydrolyzed according to the method described in the general synthetic procedures to give Compound I-26 (11 mg, 2 steps, Yield 14%).

$^1$H-NMR (CDCl3) δ: 7.73 (2H, d, J=8.7 Hz), 7.61 (1H, dd, J=9.0, 4.8 Hz), 7.02-6.89 (2H, m), 6.94 (2H, d, J=8.6 Hz), 5.33 (1H, dd, J=52.4, 2.5 Hz), 5.09-4.95 (1H, m), 4.70-4.58 (1H, m), 3.98 (1H, dd, J=10.7, 7.7 Hz), 3.86 (2H, s), 3.82 (1H, d, J=3.4 Hz), 3.75-3.62 (2H, m), 1.38 (6H, d, J=6.0 Hz).

LC/MS (Condition B) RT=2.16, [M+H]$^+$=480.

EXAMPLE 6

[Chemical Formula 103]

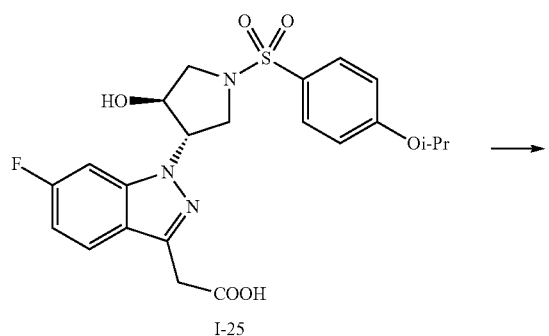

I-25

-continued

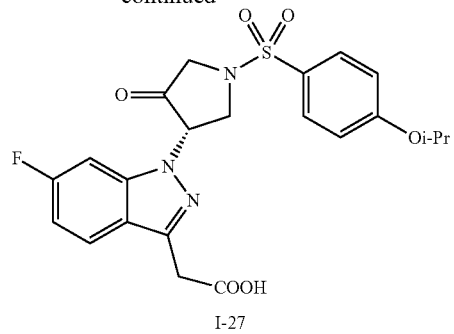

I-27

To a solution of Compound I-25 (23 mg, 0.048 mmol) in dichloromethane (2 mL) was added Dess-Martin Periodinane (30.6 mg, 0.072 mmol) at room temperature under nitrogen atmosphere, and the mixture was stirred for 4.5 hours. To the reaction mixture were added 1 mol/L aqueous sodium thiosulfate and 1 mol/L aqueous hydrochloric acid, and the resulting mixture was extracted with ethyl acetate. The organic layer was washed by water and brine, dried over anhydrous magnesium sulfate, and concentrated in vacuo. The resulting residue was purified by silica gel column chromatography (hexane-ethyl acetate) to give Compound I-27 (18 mg, Yield 80%).

$^1$H-NMR (CDCl3) δ: 7.79 (2H, d, J=8.7 Hz), 7.63 (1H, dd, J=8.9, 5.0 Hz), 7.03 (2H, d, J=8.7 Hz), 6.97 (1H, t, J=9.7 Hz), 6.88 (1H, d, J=9.1 Hz), 5.13 (1H, t, J=9.2 Hz), 4.71-4.63 (1H, m), 4.38 (1H, t, J=9.5 Hz), 4.10 (2H, d, J=17.6 Hz), 3.94 (2H, d, J=1.2 Hz), 3.73 (1H, t, J=10.2 Hz), 3.56 (1H, d, J=18.0 Hz), 1.40 (6H, d, J=6.0 Hz).

LC/MS (Condition B) RT=2.07, [M+H]$^+$=476.

EXAMPLE 7

[Chemical Formula 104]

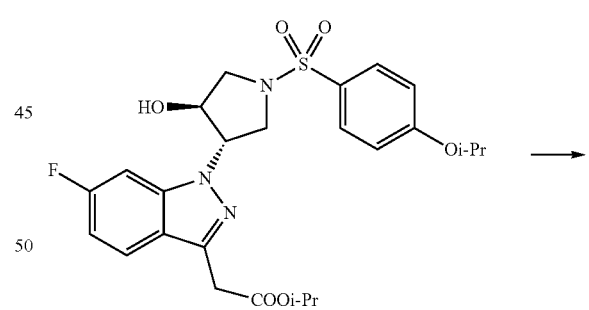

14

15

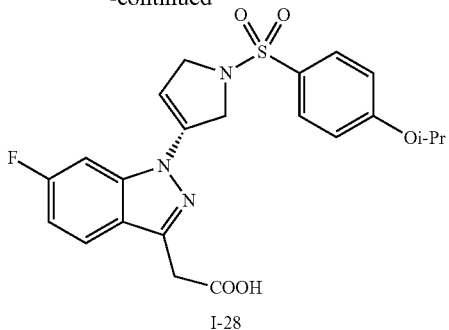

I-28

Step 1

To a solution of Intermediate 14 (25 mg, 0.048 mmol), which is an intermediate of the synthesis method of Compound I-25 described in Example 4, in dichloromethane (2 mL) were added triethylamine (13 μL, 0.096 mmol) and methanesulfonyl chloride (5.6 μL, 0.072 mmol) in turn under ice-cooling, and the resulting mixture was stirred for 30 minutes. To the mixture was added saturated aqueous sodium bicarbonate and the resulting mixture was extracted with ethyl acetate. The organic layer was washed by water and brine, dried over anhydrous magnesium sulfate, and concentrated in vacuo. The resulting residue was used in Step 2 without purification.

Step 2

To the resulting residue was added 1 mol/L sodium methoxide (0.481 mL, 0.481 mmol) at room temperature. After the residue was dissolved, the mixture was stirred for 2 hours at 60° C. The mixture was allowed to cool to room temperature, and 1 mol/L aqueous hydrochloric acid was added to the mixture. The resulting mixture was extracted with ethyl acetate. The organic layer was washed by water and brine, dried over anhydrous magnesium sulfate, and concentrated in vacuo. The resulting residue was purified by silica gel column chromatography (chloroform-methanol) to give Compound I-28 (8.7 mg, Yield 39%).

$^1$H-NMR (DMSO-d6) δ: 7.94-7.61 (4H, m), 7.26-7.04 (3H, m), 6.10-5.99 (1H, m), 4.78-4.51 (3H, m), 4.36-4.21 (2H, m), 4.03-3.88 (2H, m), 1.31-1.20 (6H, m).

LC/MS (Condition B) RT=2.19, [M+H]$^+$=460.

EXAMPLE 8

[Chemical Formula 105]

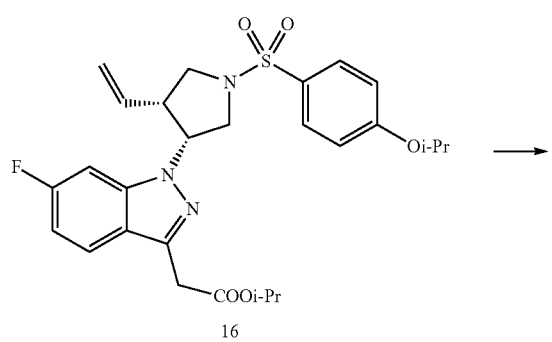

16

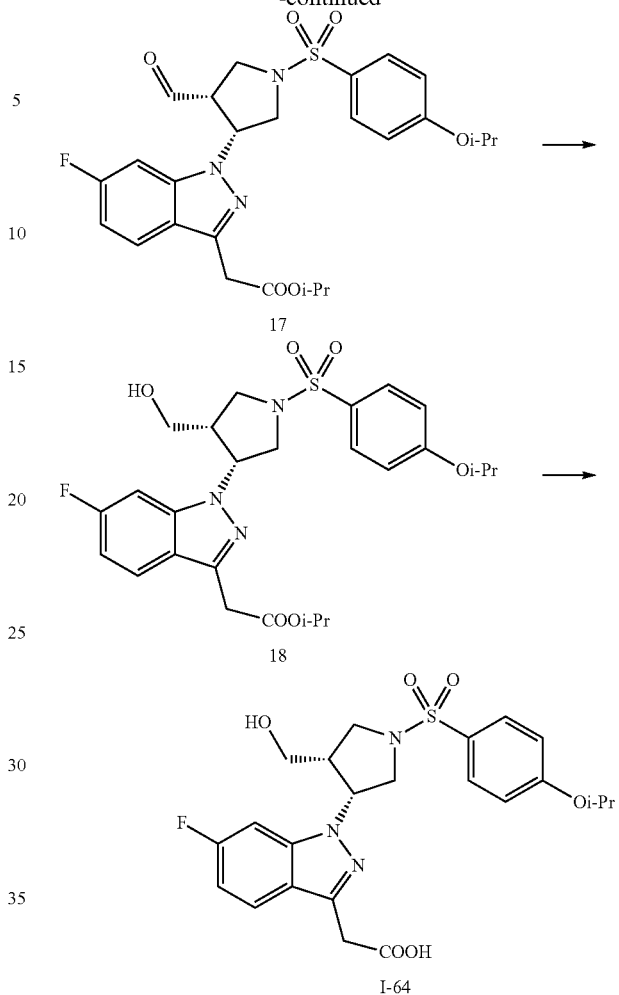

Step 1

Intermediate 16 (290 mg, 0.548 mmol) which is an intermediate of the synthesis method of Compound I-38 was dissolved in acetonitrile (3 mL). To the solution was added a solution of sodium periodate (351 mg, 1.643 mmol) in water (3 mL) at room temperature. Additionally, 10% osmium tetroxide (139 mg, 0.055 mmol) was added to the mixture, and the resulting mixture was stirred for 6 hours. The mixture was left standing for 1 day. After the reaction mixture was diluted by water (5 mL) and ethyl acetate (5 mL), the insoluble was removed by filtration using Celite. The filtrate was extracted with ethyl acetate. The organic layer was washed by water and brine, dried over anhydrous magnesium sulfate, and concentrated in vacuo. The obtained Compound 17 (280 mg) was used in the next step without purification.

Step 2

The obtained Compound 17 (200 mg) was dissolved in THF (4 mL). To the solution was added sodium borohydride (14.2 mg, 0.376 mmol) at room temperature. The mixture was stirred for 6 hours at room temperature, and left standing overnight. To the mixture was added 1 mol/L aqueous hydrochloric acid, and the resulting mixture was extracted with ethyl acetate. The organic layer was washed by brine, dried over anhydrous magnesium sulfate, and concentrated in vacuo. The resulting residue was purified by silica gel column chromatography (hexane-ethyl acetate) to give Compound 18 (74 mg).

LC/MS (Condition B) RT=2.44, [M+H]$^+$=534.

Step 3

The obtained Compound 18 was hydrolyzed by the method described in the general synthetic procedures to give Compound I-64.

LC/MS (Condition B) RT=1.93, [M+H]$^+$=492.

EXAMPLE 9

[Chemical Formula 106]

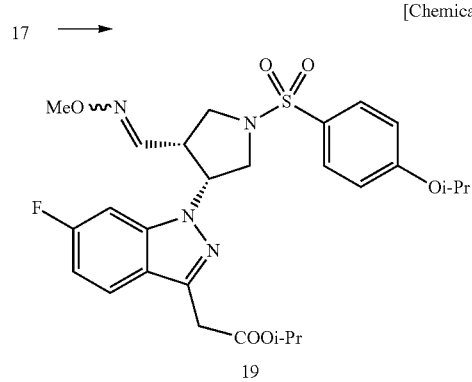

EXAMPLE 10

[Chemical Formula 107]

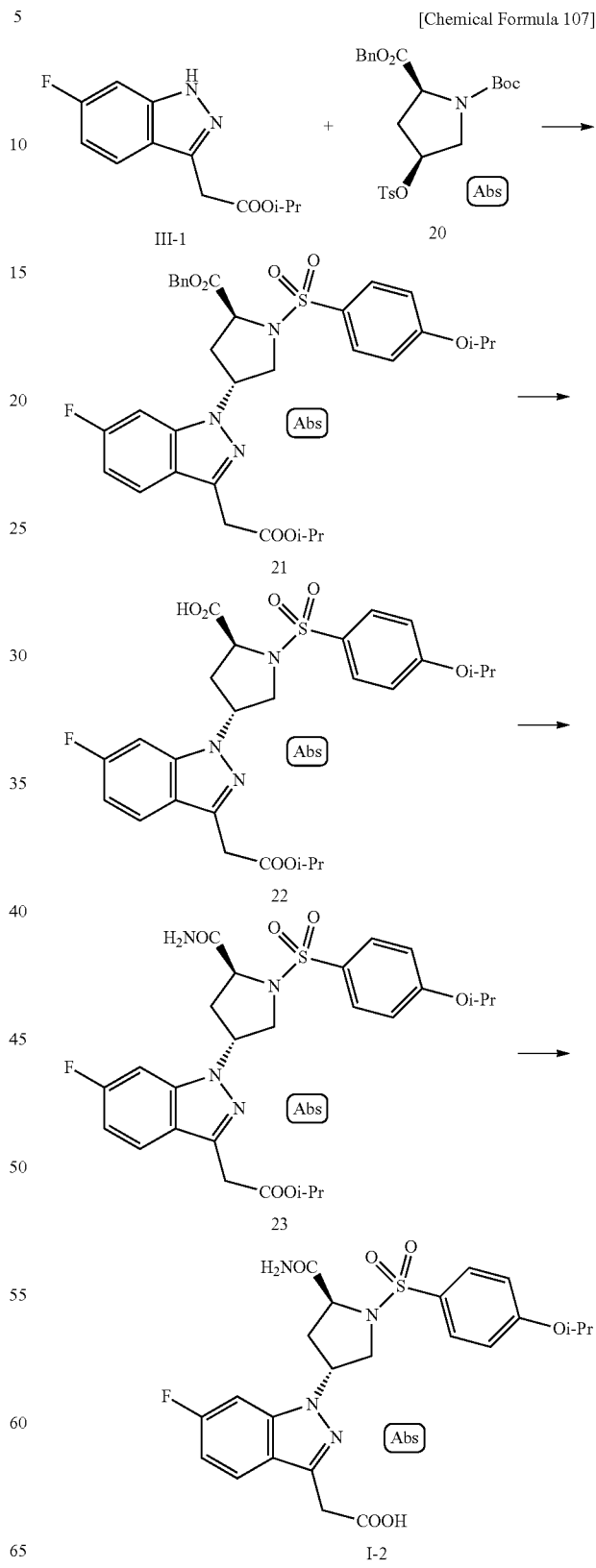

Step 1

Compound 17 (80 mg) was dissolved in ethanol (2 mL) under nitrogen atmosphere. To the solution were added methanolamine hydrochloride (15.1 mg, 0.181 mmol) and sodium acetate (14.8 mg, 0.181 mmol) at room temperature. After the mixture was stirred for 10 hours at room temperature, the mixture was left standing overnight. To the reaction mixture was added water, and the mixture was extracted with ethyl acetate. The organic layer was washed by brine, dried over anhydrous magnesium sulfate, and concentrated in vacuo. The resulting residue was purified by silica gel column chromatography (hexane-ethyl acetate) to give Compound 19 (34 mg).

LC/MS (Condition B) RT=2.70, [M+H]$^+$=561.

Step 2

Compound 19 was hydrolyzed by the method described in the general synthetic procedures to give Compound I-65.

LC/MS (Condition B) RT=2.20, [M+H]$^+$=519.

Step 1

Compound 20, which was synthesized in a similar manner as described in Tetrahedron, 1996, vol. 52, no. 47, p. 15017-15030, was reacted with Compound III-1 according to the similar manner described in the general method in the specification to give Compound 21.

$^1$H-NMR (CDCl$_3$) δ: 7.67 (2H, d, J=7.58 Hz), 7.61-7.54 (1H, m), 7.45-7.33 (5H, m), 6.93-6.79 (4H, m), 5.28 (1H, d, J=12.13 Hz), 5.21 (1H, d, J=12.13 Hz), 5.13-4.96 (2H, m), 4.66-4.54 (2H, m), 4.00-3.92 (1H, m), 3.78-3.66 (3H, m), 2.95-2.84 (1H, m), 2.44-2.35 (1H, m), 1.37 (6H, d, J=6.06 Hz), 1.22 (6H, d, J=6.06 Hz).

Step 2

Compound 21 (120 mg, 0.188 mmol) was dissolved in ethanol (2 mL). To the solution was added Pd-Carbon (12 mg) under hydrogen atmosphere at room temperature, and the mixture was stirred for 4 hours. After the reaction mixture was diluted with ethyl acetate, the mixture was filtered by using Celite. The filtrate was concentrated in vacuo. The resulting residue was purified by silica gel column chromatography (chloroform-methanol) to give Compound 22 (102.7 mg, Yield 100%).

$^1$H-NMR (CDCl$_3$) δ: 7.67 (2H, d, J=8.08 Hz), 7.56-7.49 (1H, m), 7.11-7.04 (1H, m), 6.88-6.76 (3H, m), 5.27-5.18 (1H, m), 5.06-4.95 (1H, m), 4.64-4.52 (2H, m), 4.17-4.02 (1H, m), 3.72 (2H, s), 3.67-3.60 (1H, m), 2.92-2.79 (1H, m), 2.72-2.62 (1H, m), 1.34 (6H, d, J=6.06 Hz), 1.20 (6H, d, J=6.06 Hz).

Step 3

Compound 22 (35 mg, 0.064 mmol) was dissolved in DMF (1 mL). To the solution were added diisopropylethylamine (0.056 mL, 0.320 mmol), HATU (36.5 mg, 0.096 mmol), and ammonium chloride (5.1 mg, 0.096 mmol), and the mixture was stirred for 5 hours at room temperature. To the mixture was added water, and the resulting mixture was extracted with ethyl acetate. The organic layer was washed by water and brine, dried over magnesium sulphate, and concentrated in vacuo. The resulting residue was purified by silica gel column chromatography (hexane-ethyl acetate) to give Compound 23 (29 mg, Yield 83%).

$^1$H-NMR (CDCl$_3$) δ: 7.72 (2H, d, J=8.59 Hz), 7.62-7.56 (1H, m), 7.01 (1H, br s), 6.95-6.87 (4H, m), 5.68-5.62 (1H, m), 5.08-4.96 (2H, m), 4.69-4.59 (1H, m), 4.38 (1H, d, J=6.06 Hz), 4.01-3.92 (1H, m), 3.80-3.73 (3H, m), 2.70-2.62 (1H, m), 2.57-2.46 (1H, m), 1.43-1.36 (6H, m), 1.23 (6H, d, J=6.06 Hz).

Step 4

Compound 23 was hydrolyzed by the method described in the general synthetic procedures in the specification to give Compound I-2.

$^1$H-NMR (DMSO-d$_6$) δ: 7.68-7.52 (4H, m), 7.42 (1H, d, J=10.61 Hz), 7.26-7.21 (1H, br m), 7.02-6.93 (1H, br m), 6.89 (2H, d, J=8.08 Hz), 5.30-5.22 (1H, m), 4.73-4.61 (1H, m), 4.37-4.29 (1H, m), 3.98-3.89 (1H, m), 3.72-3.15 (3H, m), 2.69-2.14 (2H, m), 1.33-1.19 (6H, m).

EXAMPLE 11

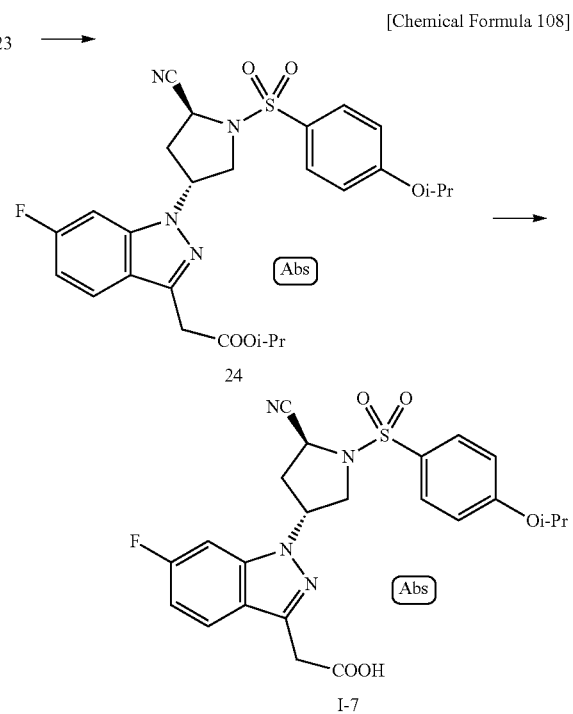

[Chemical Formula 108]

Step 1

Compound 23 (26 mg, 0.048 mmol) was dissolved in THF (1 mL). To the solution were added triethylamine (0.021 mL, 0.155 mmol) and trifluoroacetic anhydride (0.011 mL, 0.077 mmol) under ice-cooling, and the mixture was stirred for 1.5 hours. Additionally, triethylamine (0.021 mL, 0.155 mmol) and trifluoroacetic anhydride (0.011 mL, 0.077 mmol) were added to the mixture under ice-cooling, and the resulting mixture was stirred for 3 hours. To the reaction mixture was added water, and the resulting mixture was extracted with ethyl acetate. The organic layer was washed by water and brine, dried over sodium sulphate, and concentrated in vacuo. The resulting residue was purified by silica gel column chromatography (hexane-ethyl acetate) to give Compound 24 (19 mg, Yield 76%).

$^1$H-NMR (CDCl$_3$) δ: 7.69 (2H, d, J=8.59 Hz), 7.65-7.58 (1H, m), 6.99-6.90 (2H, m), 6.85 (2H, d, J=8.59 Hz), 5.16-4.99 (2H, m), 4.94-4.88 (1H, m), 4.65-4.56 (1H, m), 3.88-3.71 (4H, m), 3.18-3.09 (1H, m), 2.74-2.65 (1H, m), 1.38 (6H, d, J=4.55 Hz), 1.24 (6H, d, J=6.06 Hz).

Step 2

To a solution of Compound 24 (18 mg, 0.035 mmol) in THF was added 0.1 mol/L aqueous lithium hydroxide (0.348 mL, 0.035 mmol), and the mixture was stirred for 2 hours at room temperature. To the mixture was added 0.1 mol/L aqueous lithium hydroxide (0.174 mL, 0.017 mmol), and the resulting mixture was stirred for 1 hour at room temperature. Additionally, 0.1 mol/L aqueous lithium hydroxide (0.384 mL, 0.035 mmol) was added to the mixture. The reaction mixture was stirred for 6 hours and left standing overnight. To the mixture were added water and 10% aqueous citric acid, and the resulting mixture was extracted with ethyl acetate. The organic layer was washed by brine, dried over sodium sulphate, and concentrated in vacuo. The resulting residue was purified by silica gel column chromatography (chloroform-methanol) to give Compound I-7 (12 mg, Yield 71%).

$^1$H-NMR (DMSO-d$_6$) δ: 7.89-7.54 (4H, m), 7.20-6.92 (3H, m), 5.49-5.41 (1H, m), 5.06-4.99 (1H, m), 4.76-4.64 (1H, m), 3.96-3.61 (4H, m), 2.89-2.72 (2H, m), 1.31 (6H, d, J=5.56 Hz).

EXAMPLE 12

[Chemical Formula 109]

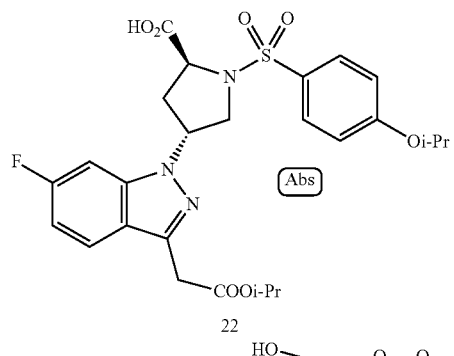

22

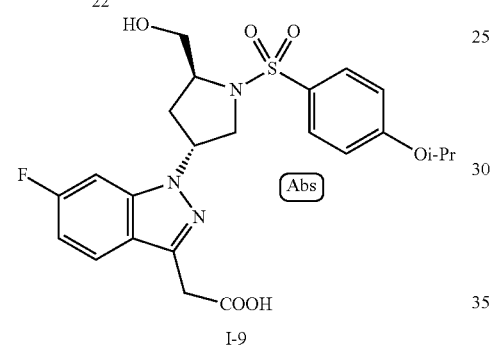

I-9

A solution of Compound 22 (21 mg, 0.038 mmol) in dichloromethane (1 mL) was cooled to −10° C. To the solution were added triethylamine (6.4 μL, 0.046 mmol) and ethyl chlorocarbonate (4.0 μL, 0.042 mmol), and the mixture was stirred for 35 minutes. Additionally, tetrabutylammonium bromide (1.2 mg, 3.8 μmol) and sodium borohydride (3.2 mg, 0.084 mmol) were added to the mixture, and the resulting mixture was stirred for 35 minutes at −5° C. vigorously. To the mixture were added 2 mol/L aqueous hydrochloric acid (0.070 mL), water, and ethyl acetate, and the resulting mixture was stirred for 30 minutes at −5° C. The reaction mixture was extracted with ethyl acetate. The organic layer was washed by saturated aqueous sodium bicarbonate and brine, dried over sodium sulphate, and concentrated in vacuo. The resulting residue was purified by silica gel column chromatography (hexane-ethyl acetate). The obtained compound was hydrolyzed by the method described in the general synthetic procedures in the specification to give Compound I-9 (14 mg, Yield 75%).

$^1$H-NMR (CDCl$_3$) δ: 7.61-7.51 (3H, m), 6.96-6.88 (2H, m), 6.78 (2H, d, J=8.59 Hz), 5.06-4.97 (1H, m), 4.63-4.54 (1H, m), 4.07-3.91 (3H, m), 3.82-3.66 (4H, m), 3.52-3.44 (1H, m), 2.68-2.57 (1H, m), 2.40-2.28 (1H, m), 1.40-1.34 (6H, m).

EXAMPLE 13

[Chemical Formula 110]

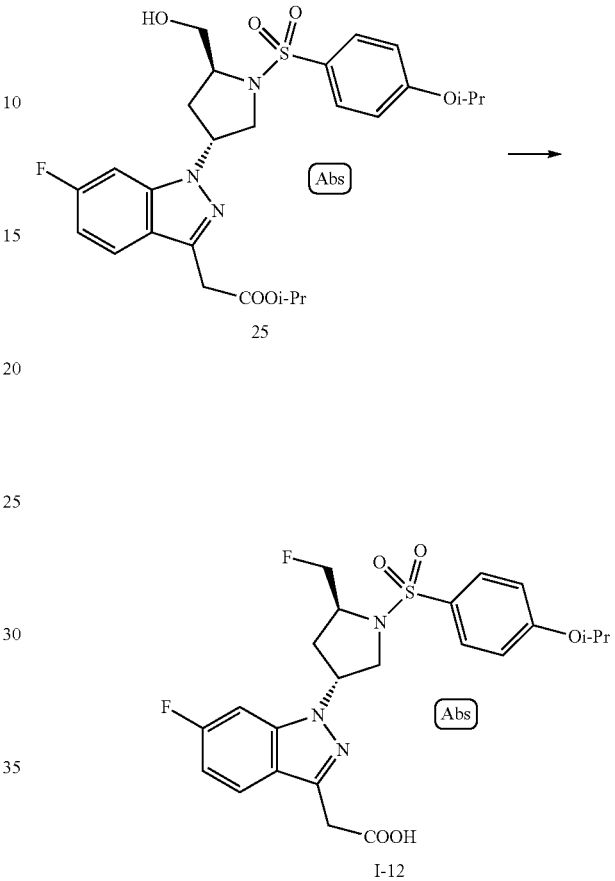

Intermediate 25 (25 mg, 0.047 mmol), which is an intermediate of the synthesis method of Compound I-9, was dissolved in dichloromethane (1 mL). To the solution was added DAST (6.2 μL, 0.047 mmol) under ice-cooling, and the mixture was stirred for 1 hour. To the mixture was added DAST (6.2 μL, 0.047 mmol), and the mixture was stirred for additional 20 minutes. The mixture was allowed to warm to room temperature gradually, and left standing overnight. To the mixture was added saturated aqueous sodium bicarbonate, and the resulting mixture was extracted with ethyl acetate. The organic layer was washed by brine, dried over sodium sulphate, and concentrated in vacuo. The resulting residue was purified by silica gel column chromatography (hexane-ethyl acetate). The obtained compound was hydrolyzed by the method described in the general synthetic procedures in the specification to give Compound I-12 (16 mg, Yield 74%).

$^1$H-NMR (CDCl$_3$) δ: 7.74-7.57 (3H, m), 7.06-6.89 (4H, m), 5.14-4.91 (1H, m), 4.82-4.70 (1H, m), 4.69-4.57 (1H, m), 4.26-4.15 (1H, m), 4.02-3.92 (3H, m), 2.91-2.61 (2H, m), 2.50-2.22 (2H, m), 1.38 (6H, d, J=5.56 Hz).

145
EXAMPLE 14

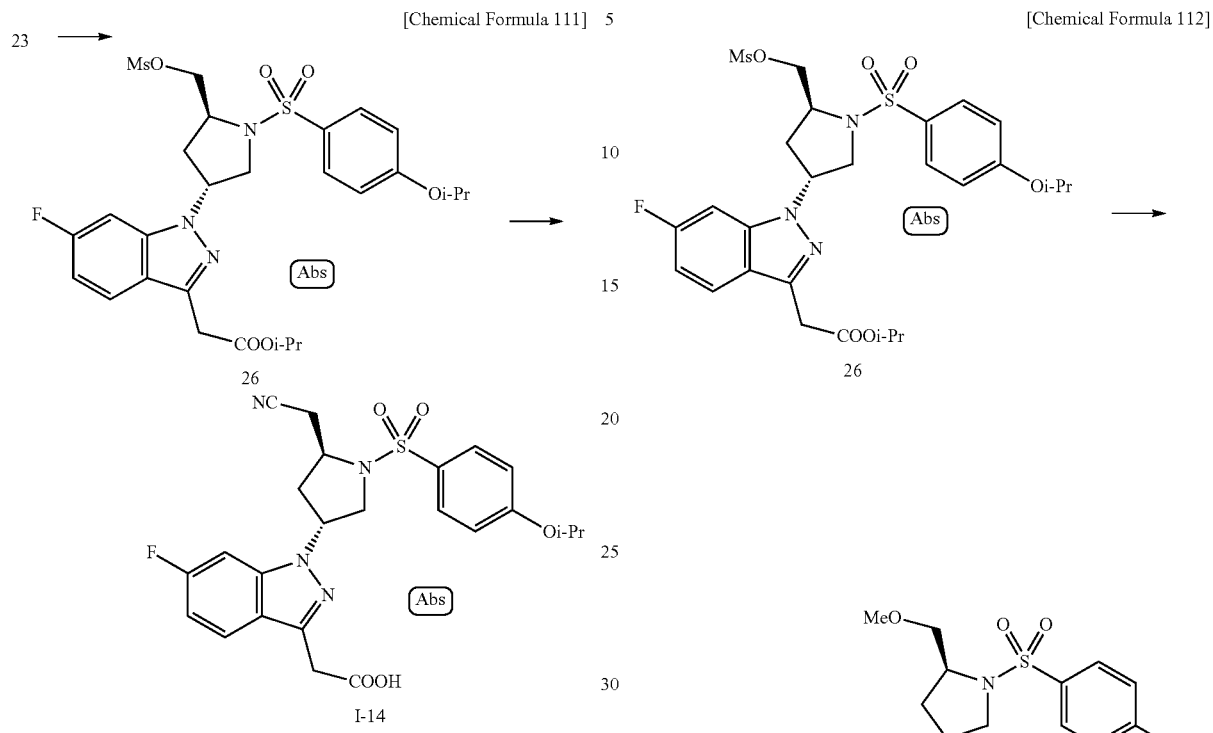

[Chemical Formula 111]

Step 1

Compound 23 (44 mg, 0.082 mmol) was dissolved in dichloromethane (1 mL). To the solution were added triethylamine (0.017 mL, 0.123 mmol) and methanesulfonyl chloride (7.6 µL, 0.098 mmol) under ice-cooling, and the mixture was stirred for 1 hour.

To the mixture was added saturated aqueous sodium bicarbonate, and the resulting mixture was extracted with ethyl acetate. The organic layer was washed by brine, dried over sodium sulphate, and concentrated in vacuo. The obtained Compound 26 was used in the next step without purification.

Step 2

Compound 26 was dissolved in DMSO (1.5 mL). To the solution was added sodium cyanide (12 mg, 0.240 mmol), and the mixture was heated at 90° C. and stirred for 5 hours. The mixture was allowed to cool to room temperature, and left standing overnight. The mixture was diluted with ethyl acetate, and water was added to the mixture. The resulting mixture was extracted with ethyl acetate. The organic layer was washed by water and brine, dried over sodium sulphate, and concentrated in vacuo. The resulting residue was purified by silica gel column chromatography (hexane-ethyl acetate). The obtained compound was hydrolyzed by the method described in the general synthetic procedures in the specification to give Compound I-14 (9.4 mg, Yield 23%).

LC/MS (Condition B) RT=2.04, [M+H]$^+$=501.

146
EXAMPLE 15

[Chemical Formula 112]

Compound 26 (0.058 mmol) was dissolved in methanol (1 mL). To the solution was added 1.02 mol/L sodium methoxide in methanol (0.285 mL, 0.291 mmol), and the mixture was stirred for 4 hours at reflux. After the mixture was allowed to cool to room temperature, 1.02 mol/L sodium methoxide in methanol (0.571 mL, 0.583 mmol) was added to the reaction mixture. Additionally, the mixture was stirred for 2.5 hours at reflux. After the reaction mixture was allowed to cool to room temperature, water and 2 mol/L aqueous hydrochloric acid were added to the mixture. The resulting mixture was extracted with ethyl acetate. The organic layer was washed by water and brine, dried over sodium sulphate, and concentrated in vacuo. The resulting residue was purified by silica gel column chromatography (chloroform-methanol) to give Compound I-16 (14 mg, Yield 47%).

$^1$H-NMR (CDCl$_3$) δ: 7.67 (2H, d, J=8.08 Hz), 7.61-7.52 (1H, m), 6.96-6.81 (4H, m), 5.18-5.07 (1H, m), 4.66-4.55 (1H, m), 4.16-3.99 (1H, m), 3.92-3.83 (3H, m), 3.73-3.56 (3H, m), 3.44 (3H, s), 2.58-2.46 (1H, m), 2.39-2.29 (1H, m), 1.38-1.34 (6H, m).

EXAMPLE 16

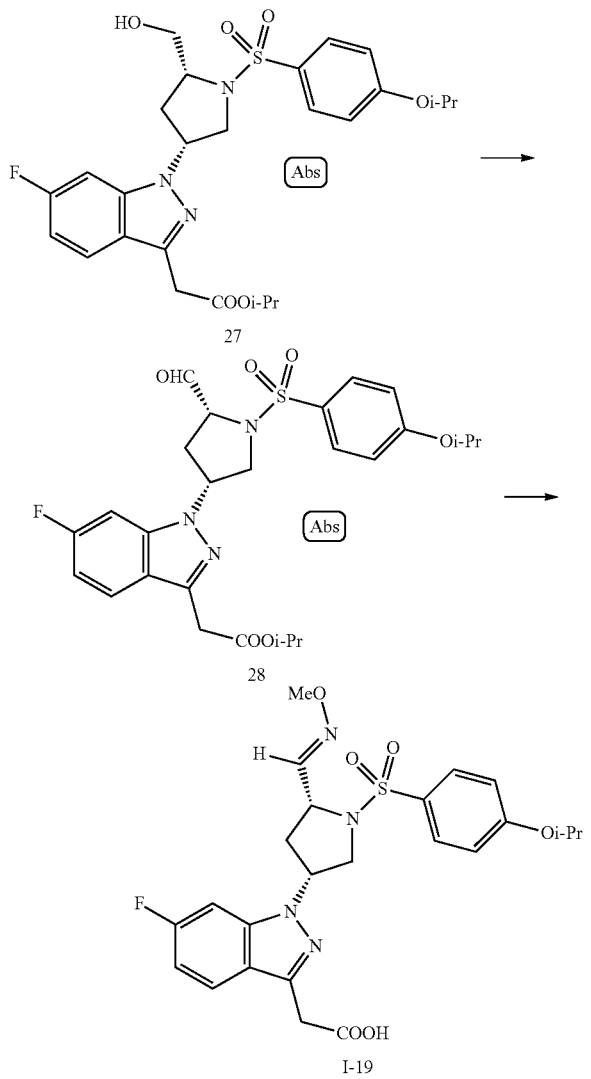

Step 1

Intermediate 27 (20 mg, 0.038 mmol), which is an intermediate of the synthesis method of Compound I-11 was dissolved in dichloromethane (1 mL). To the solution was added Dess-Martin Periodinane (24 mg, 0.057 mmol) under ice-cooling, and the mixture was stirred for 1 hour at room temperature. Dess-Martin Periodinane (24 mg, 0.057 mmol) was added to the mixture, and stirred for additional 5 hours at room temperature. The mixture was left standing overnight. To the mixture were added 6% aqueous sodium thiosulfate and water, and the resulting mixture was extracted with ethyl acetate. The organic layer was washed by saturated aqueous sodium bicarbonate and brine, dried over sodium sulphate, and concentrated in vacuo. The resulting residue was purified by silica gel column chromatography (hexane-ethyl acetate) to give Compound 28 (16 mg, Yield 79%).

$^1$H-NMR (CDCl$_3$) δ: 9.83 (1H, s), 7.80 (2H, d, J=8.08 Hz), 7.70-7.61 (1H, m), 7.06-6.81 (4H, m), 5.09-4.98 (1H, m), 4.84-4.75 (1H, m), 4.73-4.60 (1H, m), 4.09-4.01 (1H, m), 3.90-3.84 (3H, br m), 3.69-3.61 (1H, m), 2.81-2.70 (1H, m), 2.50-2.39 (1H, m), 1.40 (6H, d, J=5.56 Hz), 1.24 (6H, d, J=6.06 Hz).

Step 2

Compound 28 (16 mg, 0.030 mmol) was dissolved in ethanol (1 mL). To the solution was added methanolamine hydrochloride (3 mg, 0.036 mmol) under ice-cooling, and the mixture was stirred for 4 hours at room temperature. The mixture was left standing overnight. To the mixture was added water, and the resulting mixture was extracted with ethyl acetate. The organic layer was washed by water and brine, dried over sodium sulphate, and concentrated in vacuo. The resulting residue was purified by silica gel column chromatography (hexane-ethyl acetate). The obtained compound was hydrolyzed by the method described in the general synthetic procedures in the specification to give Compound I-19 (13 mg, Yield 87%).

LC/MS (Condition B) RT=2.24, [M+H]$^+$=519.

EXAMPLE 17

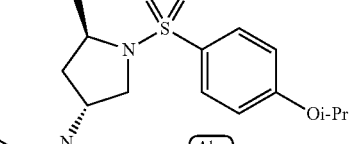

Step 1

Compound 27 (32 mg, 0.060 mmol) was dissolved in dichloromethane (1 mL). To the solution were added triethylamine (0.013 mL, 0.091 mmol) and p-toluenesulfonyl chloride (15 mg, 0.078 mmol) under ice-cooling, and the mixture was stirred for 1 hour. Triethylamine (0.013 mL, 0.091 mmol) and p-toluenesulfonyl chloride (15 mg, 0.078 mmol) were added to the mixture, and the resulting mixture was allowed to warm to room temperature and stirred for additional 55 minutes. DMAP (0.7 mg, 6.0 μmol) was added to the mixture, and the resulting mixture was stirred for additional 9 hours. To the reaction mixture was added saturated aqueous sodium bicarbonate, and the resulting mixture was extracted with ethyl acetate. The organic layer was washed by brine, dried over sodium sulphate, and concentrated in vacuo. The resulting mixture was purified by silica gel column chromatography (hexane-ethyl acetate) to give Compound 29 (20 mg, Yield 48%).

LC/MS (Condition B) RT=2.86, [M+H]$^+$=688.

Step 2

Imidazole (2.8 mg, 0.041 mmol) was dissolved in DMF (1 mL). To the solution was added sodium hydride (1.7 mg, 0.041 mmol), and the mixture was stirred for 10 minutes. A solution of Compound 29 (19 mg, 0.028 mmol) in DMF (1 mL) was added dropwise to the mixture, and the resulting mixture was stirred for 4 hours at 60° C. After the mixture was allowed to cool to room temperature, water and saturated aqueous ammonia were added to the mixture. The resulting mixture was extracted with ethyl acetate. The organic layer was washed by water and brine, dried over sodium sulphate, and concentrated in vacuo. The resulting residue was purified by silica gel column chromatography (hexane-ethyl acetate). The obtained compound was hydrolyzed by the method described in the general synthetic procedures in the specification to give Compound I-20 (5.5 mg, Yield 25%).

LC/MS (Condition B) RT=1.51, [M+H]$^+$=542.

EXAMPLE 18

[Chemical Formula 115]

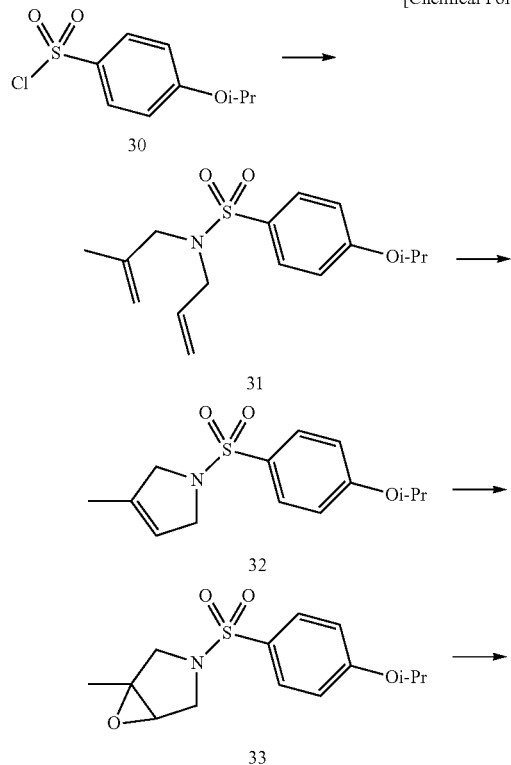

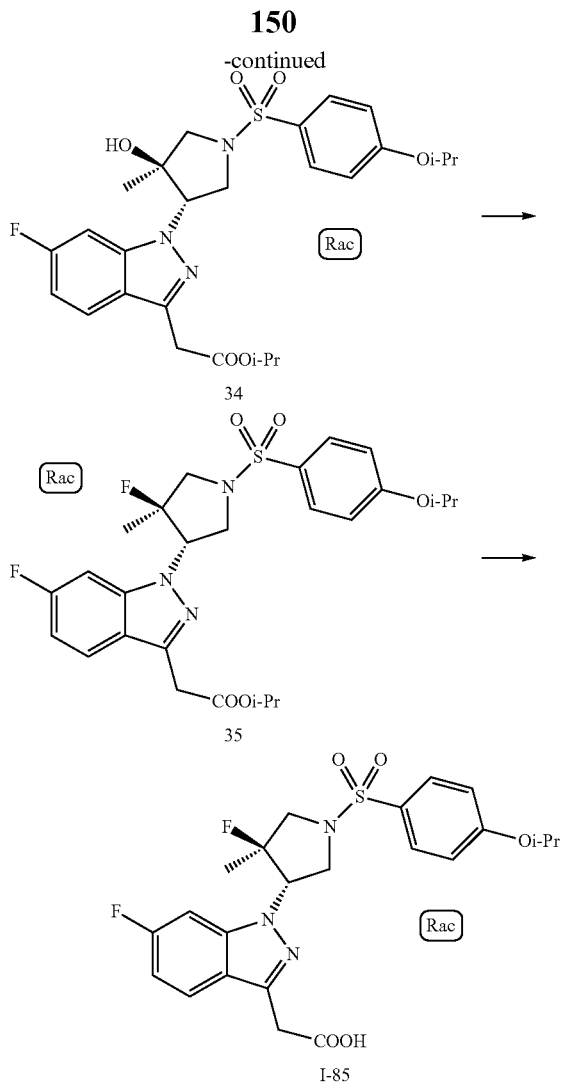

Step 1

To a solution of allylamine (3.35 mL, 44.7 mmol) in dichloromethane (50 mL) was added Compound 30 (5.0 g, 21.3 mmol) under ice-cooling, and the mixture was stirred under ice-cooling. The reaction mixture was washed by diluted hydrochloric acid, water, and brine, dried over sodium sulfate, and concentrated in vacuo to give oil (6.22 g). To a solution of the obtained oil (2.4 g) in DMF (20 mL) were added cesium carbonate (4.59 g, 14.1 mmol) and 3-bromo-2-methyl-1-propene (1.14 mL, 11.28 mmol), and the mixture was stirred for 4 hours. To the reaction mixture was added hydrochloric acid under ice-cooling, and the resulting mixture was extracted with ethyl acetate. The organic layer was washed by water and brine, dried over anhydrous magnesium sulfate, and concentrated in vacuo. The resulting crude product was purified by silica gel column chromatography (hexane-ethyl acetate) to give Compound 31 (2.81 g, Yield 20%) as colorless oil.

Step 2

To a solution of the obtained Compound 31 (3.8 g, 12.3 mmol) in dichloromethane (120 mL) was added (1,3-bis(2,4,6-trimethylphenyl)-2-imidazolidinylidene)dichloro(phenylmethylene)(tri-cyclohexyl phosphine)ruthenium (313 mg, 0.368 mmol) under nitrogen atmosphere, and the mixture was stirred for 1 hour at room temperature. The reaction mixture was filtered by using silica gel pad. The filtrate was concentrated in vacuo. The resulting residue was purified by silica gel column chromatography (hexane-ethyl acetate) to give Compound 32 (3.01 g, Yield 87%) as white solid.

Step 3

To a solution of Compound 32 (0.85 g, 3.02 mmol) in dichloromethane (8.5 mL) was added m-chloroperbenzoic acid (1.49 g, 6.04 mmol), and the mixture was stirred over night. To the reaction mixture was added aqueous sodium bicarbonate and the resulting mixture was extracted with ethyl acetate. The extract layer was washed by water and brine, dried over sodium sulfate, and concentrated in vacuo. The obtained crude product was purified by silica gel column chromatography (hexane-ethyl acetate) to give Compound 33 (608 mg, Yield 68%) as pale yellow solid.

$^1$H-NMR (CDCl$_3$) δ: 1.36 (6H, d, J=6.03 Hz), 1.45 (3H, s), 3.25 (1H, d, J=11.75 Hz), 3.35-3.40 (2H, m), 3.55 (2H, d, J=11.75 Hz), 3.65 (2H, d, J=11.75 Hz), 4.62 (1H, m), 6.91-6.96 (2H, m), 7.66-7.71 (2H, m).

Step 4

A suspension of Compound 33 (230 mg, 0.773 mmol), Compound III-1 (219 mg, 0.927 mmol), and cesium carbonate (605 mg, 1.856 mmol) in DMA (2 mL) was stirred for 5 hours at 120° C. under nitrogen atmosphere. The reaction mixture was allowed to cool to room temperature. To the mixture were added ethyl acetate and diluted hydrochloric acid, and the resulting mixture was extracted with ethyl acetate. The extract layer was washed by water and brine, dried over sodium sulfate, and concentrated in vacuo. The resulting residue was purified by silica gel column chromatography (chloroform-methanol) to give Compound 34 (183 mg, Yield 44%) as pale brown amorphous.

$^1$H-NMR (CDCl$_3$) δ: 1.21 (6H, dd, J=6.32, 3.85 Hz), 1.40 (6H, dd, J=6.04, 1.65 Hz), 1.54 (3H, s), 2.34 (1H, br s), 3.51 (2H, dd, J=22.25, 10.44 Hz), 3.65 (2H, dd, J=23.00, 16.00 Hz), 3.89 (1H, dd, J=11.12, 3.71 Hz), 4.17 (1H, dd, J=10.99, 7.97 Hz), 4.63-4.78 (2H, m), 4.97-5.05 (1H, m), 6.90 (1H, td, J=8.93, 2.11 Hz), 7.01 (2H, d, J=9.06 Hz), 7.05 (1H, dd, J=9.20, 1.79 Hz), 7.57 (1H, dd, J=8.93, 5.08 Hz), 7.82-7.87 (2H, m).

Step 5

To a solution of Compound 34 (50 mg, 0.094 mmol) in dichloromethane (1 mL) was added DAST (30 mg, 0.19 mmol) under ice-cooling. After the reaction mixture was stirred for 1.5 hours at room temperature, aqueous sodium bicarbonate was added to the reaction mixture under ice-cooling. The mixture was extracted with dichloromethane, and the extract layer was concentrated in vacuo. The resulting crude product was purified by silica gel column chromatography (chloroform-ethyl acetate) to give Compound 35 (37 mg, Yield 73%) as colorless oil.

LC/MS (Condition C) RT=2.63, [M+H]$^+$=536.

Step 6

To a solution of Compound 35 (37 mg, 0.069 mmol) in THF-methanol (1:1.2 mL) was added 4 mol/L aqueous lithium hydroxide (69 μL, 0.28 mmol). After the mixture was stirred at room temperature, diluted hydrochloric acid was added to the mixture. The resulting mixture was extracted with dichloromethane. The extract layer was concentrated in vacuo to give Compound I-85 (32.8 mg, Yield 96%) as pale brown amorphous.

LC/MS (Condition C) RT=2.15, [M+H]$^+$=494.

EXAMPLE 19

[Chemical Formula 116]

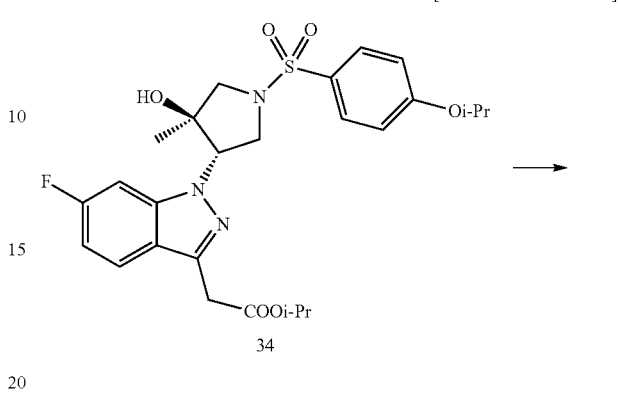

Compound 34 was hydrolyzed by the method described in the general synthetic procedures in the present specification to give Compound I-84.

EXAMPLE 20

[Chemical Formula 117]

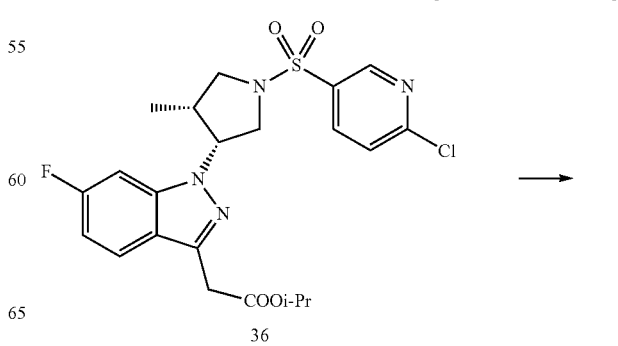

-continued

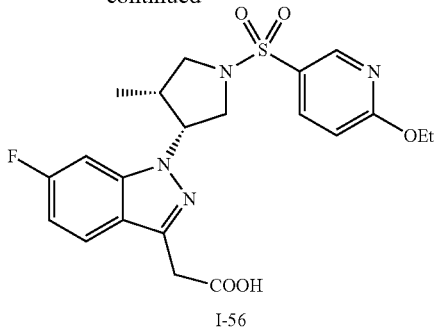

I-56

Compound 36 was synthesized by the method described in the general method in the specification by using Compound III-1 as a starting material. Compound 36 (50 mg, 0.10 mmol) and cesium carbonate (99 mg, 0.30 mmol) were dissolved in ethanol (2 mL), and the solution was stirred for 5 hours at reflux. To the reaction mixture were added water and 2 mol/L aqueous hydrochloric acid, and the resulting mixture was extracted with ethyl acetate. The organic layer was washed by brine, and concentrated in vacuo. The resulting residue was dissolved in ethyl acetate. The solution was filtered and concentrated to give Compound I-56 (31 mg, Yield 66.4%).

$^1$H-NMR (DMSO-d6) δ: 12.45 (1H, s), 8.63 (1H, d, J=2.01 Hz), 8.11 (1H, dd, J =8.73, 1.34 Hz), 7.65 (1H, dd, J=8.64, 5.29 Hz), 7.52 (1H, d, J=9.57 Hz), 6.94-7.01 (2H, m), 5.31 (1H, t, J=6.63 Hz), 4.43 (2H, q, J=7.05 Hz), 3.93 (1H, dd, J=11.58, 7.05 Hz), 3.48-3.65 (4H, m), 3.13 (1H, t, J=9.90 Hz), 2.54-2.62 (1H, m), 1.38 (3H, t, J =6.97 Hz), 0.32 (3H, d, J=6.55 Hz).

LC/MS (Condition A) RT=1.99, [M+H]$^+$=463.

EXAMPLE 21

[Chemical Formula 118]

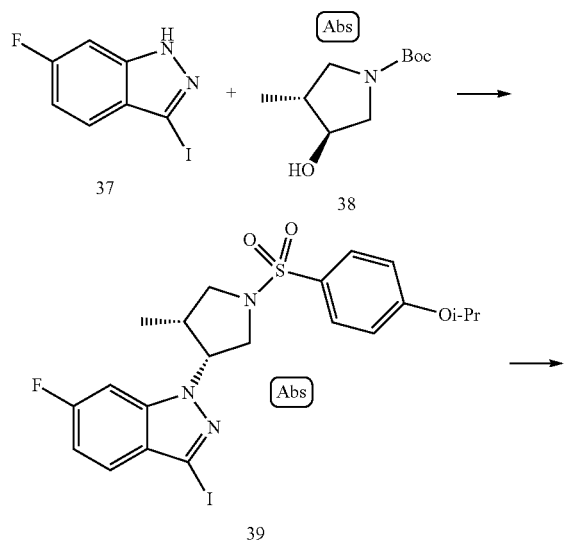

-continued

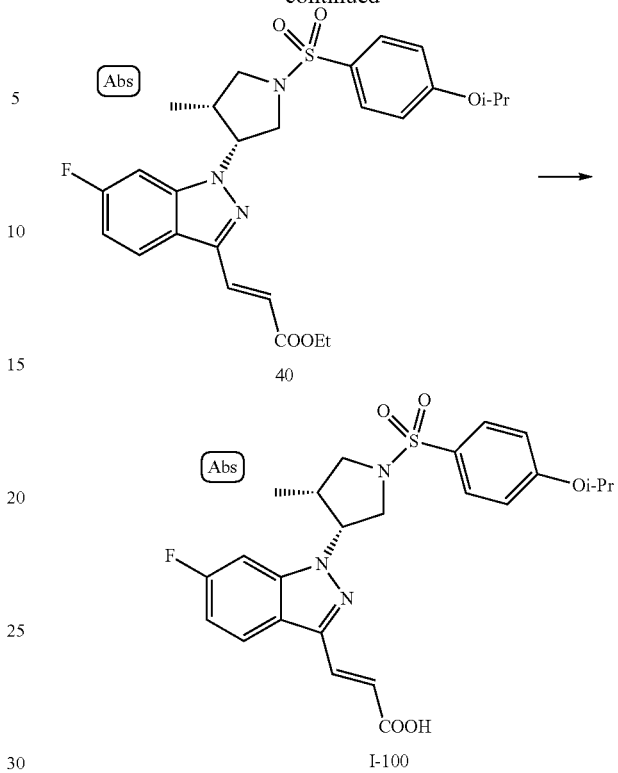

I-100

Step 1

Compound 38 was synthesized by the similar manner as described in WO2004/112793. Compound 38 (405 mg, 2.01 mmol) was dissolved in pyridine (4 mL). To the solution were added p-toluenesulfonyl chloride (460 mg, 2.42 mmol) and catalytic amount of DMAP, and the resulting mixture was stirred overnight at room temperature. The reaction mixture was concentrated in vacuo. To the residue was added water, and the mixture was extracted with ethyl acetate. The organic layer was washed by water and brine, dried over anhydrous magnesium sulfate, and concentrated in vacuo. The resulting residue was purified by silica gel column chromatography (hexane/ethyl acetate=80/20) to give sulfonyl derivative as colorless oil.

Commercially available Compound 37 (164 mg, 0.63 mmol) was dissolved in DMF (6 mL). To the solution were added the obtained sulfonyl derivative (340 mg, 0.75 mmol) and cesium carbonate (611 mg, 1.87 mmol), and the mixture was stirred for 3 hours at 100° C. The reaction mixture was poured into water, and the resulting mixture was extracted with ethyl acetate. The organic layer was washed by water and brine, dried over anhydrous magnesium sulfate, and concentrated in vacuo. The resulting residue was purified by silica gel column chromatography (hexane/ethyl acetate=80/20) to give Compound 39 (292 mg, Yield 86%) as colorless oil.

$^1$H-NMR (CDCl$_3$) δ: 7.86-7.82 (2H, m), 7.37 (1H, dd, J=8.7, 5.1 Hz), 7.04-6.92 (4H, m), 4.94 (1H, td, J=6.9, 2.7 Hz), 4.71-4.63 (1H, m), 4.13-4.04 (1H, m), 3.82 (1H, dd, J=11.3, 2.7 Hz), 3.71 (1H, t, J=8.1 Hz), 3.26 (1H, t, J=9.9 Hz), 2.74-2.64 (1H, m), 1.40 (6H, d, J=6.0 Hz), 0.50 (3H, d, J=6.9 Hz).

Step 2

(E)-ethyl-3-(4,4,5,5-tetramethyl-1,3,2-dioxaborolane2-yl)acrylate (182 mg, 0.81 mmol) was dissolved in DME (4 mL) and ethanol (1.5 mL). To the solution were added Compound 39 (292 mg, 0.54 mmol), PdCl$_2$ (dppf) (21.9 mg, 0.027 mmol), and 2 mol/L aqueous sodium carbonate (0.81 mL, 1.61 mmol), and the mixture was stirred for 2 hours at 80° C. The reaction mixture was poured into water, and the resulting mixture was extracted with ethyl acetate. The organic layer was washed by brine, dried over anhydrous magnesium sulfate, and concentrated in vacuo. The resulting residue was purified by silica gel column chromatography (hexane/ethyl acetate=75/25) to give Compound 40 (246 mg, Yield 89%) as colorless oil.

$^1$H-NMR (CDCl$_3$) δ: 7.87-7.79 (3H, m), 7.67 (1H, d, J=16.2 Hz), 7.05-6.97 (4H, m), 6.56 (1H, d, J=16.2 Hz), 5.03-4.92 (1H, m), 4.98 (1H, td, J=7.1, 3.0 Hz), 4.71-4.63 (1H, m), 4.32 (2H, q, J=7.2 Hz), 4.07 (1H, dd, J=11.3, 7.5 Hz), 3.83-3.72 (2H, m), 3.37 (1H, t, J=9.8 Hz), 2.78-2.66 (1H, m), 1.43-1.34 (9H, m), 0.51 (3H, d, J=6.9 Hz).

Step 3

Compound I-100 was synthesized from Compound 40 by the similar manner as described in the general synthetic procedures in the present specification.

$^1$H-NMR (DMSO-d$_6$) δ: 8.09 (1H, dd, J=8.9, 5.1 Hz), 7.78 (2H, d, J=8.7 Hz), 7.68 (1H, dd, J=9.8, 2.0 Hz), 7.54 (1H, d, J=16.3 Hz), 7.15-7.09 (3H, m), 6.57 (1H, d, J=16.3 Hz), 5.47-5.40 (1H, m), 4.80-4.70 (1H, m), 3.92-3.86 (1H, m), 3.65-3.59 (2H, m), 3.28-3.19 (1H, m), 2.63-2.51 (1H, m), 1.30 (6H, dd, J=7.6, 6.2 Hz), 0.36 (3H, d, J =6.7 Hz).

EXAMPLE 22

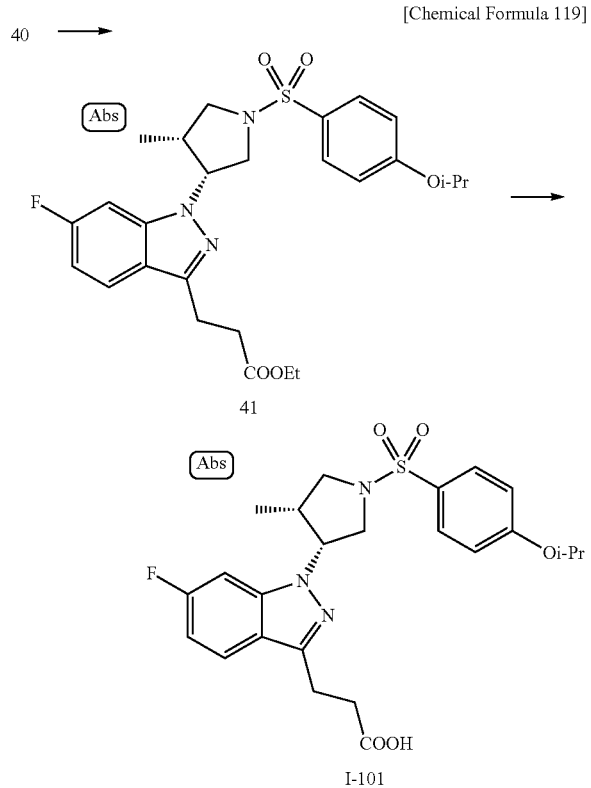

[Chemical Formula 119]

Step 1

Compound 40 (70 mg, 0.14 mmol) was dissolved in THF (1.5 mL) and ethanol (1.5 mL). To the solution was added Pd-Carbon (14 mg), and the mixture was stirred overnight under hydrogen atmosphere at atmospheric pressure. After the reaction was completed, the insoluble was removed by filtration using Celite. The filtrate was concentrated in vacuo to give Compound 41. Compound 41 was used in the next step without further purification.

Step 2

Compound I-101 was synthesized from the hydrolysis of Compound 41 by the similar manner as described in the general synthetic procedures in the specification.

$^1$H-NMR (DMSO-d$_6$) δ: 7.78-7.71 (3H, m), 7.48 (1H, dd, J=10.2, 2.0 Hz), 7.12 (2H, d, J=8.5 Hz), 6.94 (m, td, J=9.0, 1.8 Hz), 5.30-5.25 (1H, m), 4.79-4.71 (1H, m), 3.89-3.83 (1H, m), 3.62-3.52 (2H, m), 3.20-3.13 (1H, m), 3.05-2.95 (1H, m), 2.88-2.78 (1H, m), 2.54-2.40 (1H, m), 1.32 (6H, dd, J=6.0, 3.4 Hz), 0.29 (3H, d, J=6.6 Hz).

EXAMPLE 23

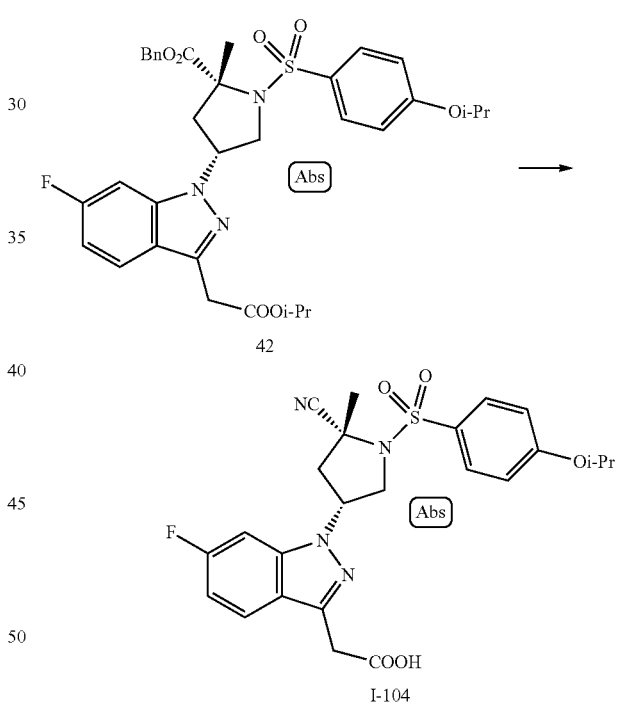

[Chemical Formula 120]

Compound 42 (15.5 mg, 0.024 mmol), which was synthesized from Compound III-1 and Compound XI-11 by the similar manner as described in the general synthetic procedures in the specification, was subjected to the same reactions described in Steps 2 and 3 of Example 10 and Example 11 in sequence to give Compound I-104 (2.8 mg, 6 steps, Yield 26%).

$^1$H-NMR (CDCl$_3$) δ: 7.83 (2H, d, J=8.85 Hz), 7.62-7.51 (1H, m), 6.92 (5H, d, J =8.85 Hz), 5.11-4.99 (1H, m), 4.67-4.57 (1H, m), 4.06-3.96 (1H, m), 3.84 (2H, s), 3.69-3.57 (1H, m), 3.28-3.15 (1H, m), 2.64-2.52 (1H, m), 2.01 (3H, s), 1.36 (6H, dd, J=6.10, 1.53 Hz).

EXAMPLE 24

[Chemical Formula 12]

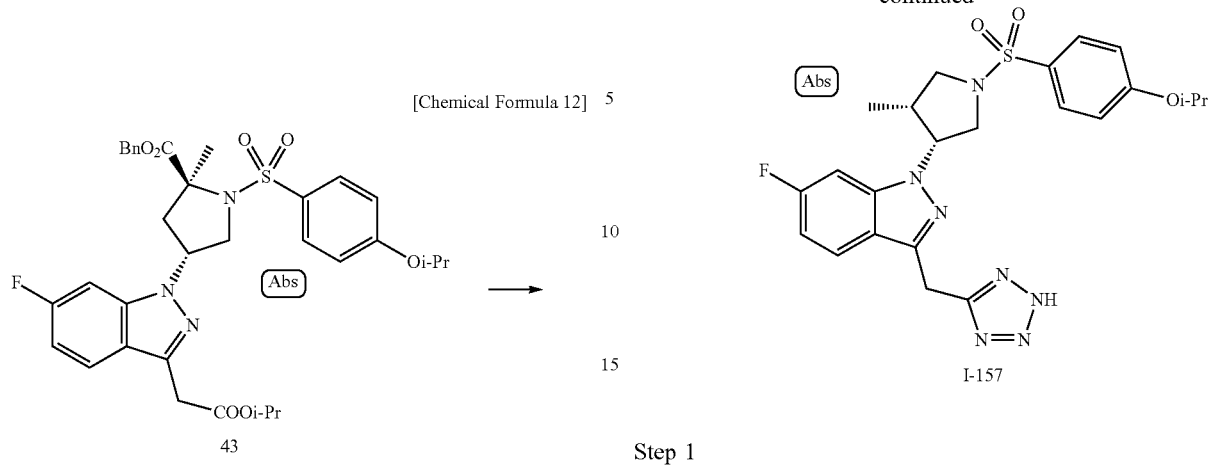

Compound 43, which was synthesized from Compound III-1 and Compound IV-6 by the similar manner as described in the general synthetic procedures in the specification, was subjected to the same reaction described in Example 23 to give Compound I-105 (7.5 mg, 7 steps, Yield 8.1%).

$^1$H-NMR (CDCl$_3$) δ: 7.84 (2H, d, J=9.06 Hz), 7.66-7.59 (1H, m), 7.03-6.89 (4H, m), 5.12-5.04 (1H, m), 4.69-4.60 (1H, m), 3.96 (2H, br s), 3.88-3.82 (2H, m), 2.92-2.84 (2H, m), 2.01 (3H, s), 1.38 (6H, d, J=6.04 Hz).

EXAMPLE 25

[Chemical Formula 122]

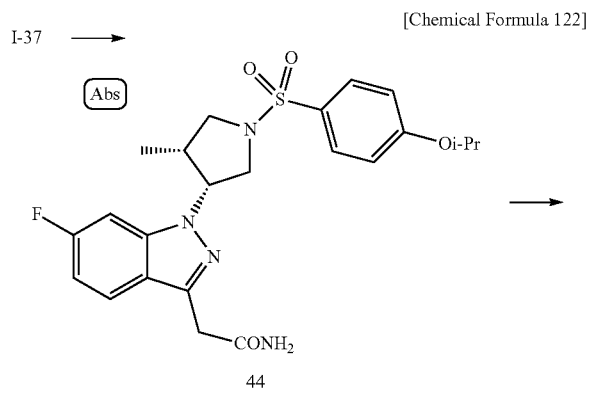

Step 1

To a solution of Compound I-37 (120 mg, 0.25 mmol) in DMF (2 mL) were added ammonium chloride (20.3 mg, 0.38 mmol), triethylamine (52 μL, 0.38 mmol), EDC (53 mg, 0.28 mmol), HOBt (43 mg, 0.28 mmol), and catalytic amount of DMAP under ice-cooling, and the mixture was stirred overnight at room temperature. To the reaction mixture was added water, and precipitated solid was filtered off. The obtained solid was well washed by water to give Compound 44 (120 mg, Yield 100%).

$^1$H-NMR (CDCl$_3$) δ: 7.85-7.81 (2H, m), 7.64 (1H, dd, J=8.8, 5.0 Hz), 7.02-6.90 (4H, m), 6.34 (1H, brs), 5.44 (1H, brs), 4.95-4.89 (1H, m), 4.72-4.63 (1H, m), 4.01-3.96 (1H, m), 3.90-3.85 (1H, m), 3.74-3.64 (3H, m), 3.27 (1H, t, J=9.9 Hz), 2.68-2.62 (1H, m), 1.42-1.38 (6H, m), 0.51 (3H, d, J=6.8 Hz).

Step 2

To a solution of Compound 44 (117 mg, 0.25 mmol) in dichloromethane (2 mL) and pyridine (0.2 mL) was added trifluoroacetic anhydride (84 μL, 0.60 mmol), and the mixture was stirred for 7 hours at room temperature. To the reaction mixture was added water, and the mixture was extracted with ethyl acetate. The organic layer was washed by water and brine, dried over anhydrous magnesium sulphate, and concentrated in vacuo. The resulting residue was purified by silica gel column chromatography (hexane-ethyl acetate).

To a solution of the obtained compound (93 mg, 0.20 mmol) in DMF (2 mL) were added sodium azide (66 mg, 1.02 mmol) and triethylamine hydrochloride (140 mg, 1.02 mmol), and the mixture was stirred for 8 hours at 110° C. To the reaction mixture was added hydrochloric acid under ice-cooling, and the mixture was extracted with ethyl acetate. The organic layer was washed by water and brine, dried over anhydrous magnesium sulphate, and concentrated in vacuo. The resulting residue was purified by silica gel column chromatography (chloroform -methanol) to give Compound I-157 (42 mg, Yield 42%).

$^1$H-NMR (DMSO-d$_6$) δ: 7.77 (2H, d, J=8.9 Hz), 7.58-7.49 (2H, m), 7.10 (2H, d, J =8.9 Hz), 6.97 (1H, td, J=9.1, 2.1 Hz), 5.33-5.29 (1H, m), 4.74-4.65 (1H, m), 4.40 (2H, s), 3.84 (1H, dd, J=11.2, 7.3 Hz), 3.69 (1H, dd, J=11.3, 2.5 Hz), 3.58 (1H, dd, J =9.3, 7.4 Hz), 3.17 (1H, t, J=10.0 Hz), 2.45-2.33 (1H, m), 1.27 (6H, d, J=5.3 Hz), 0.32 (3H, d, J=6.7 Hz).

EXAMPLE 26

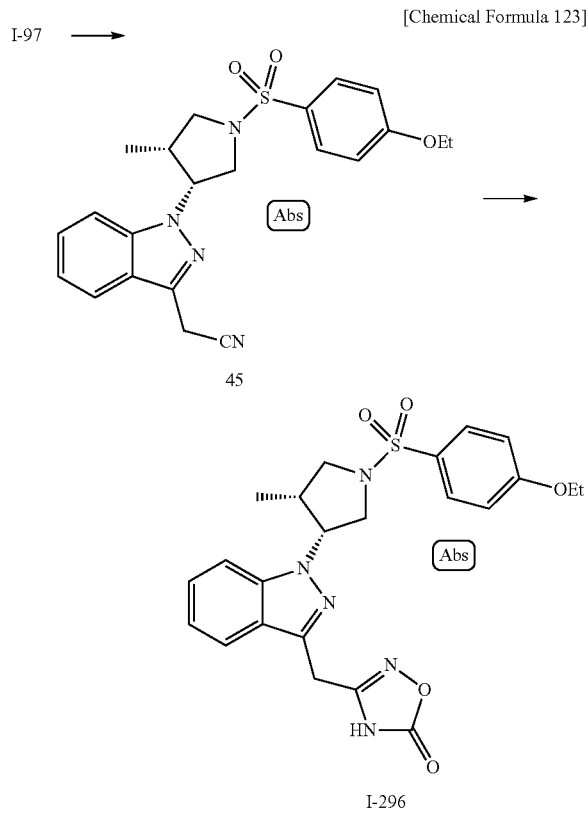

EXAMPLE 27

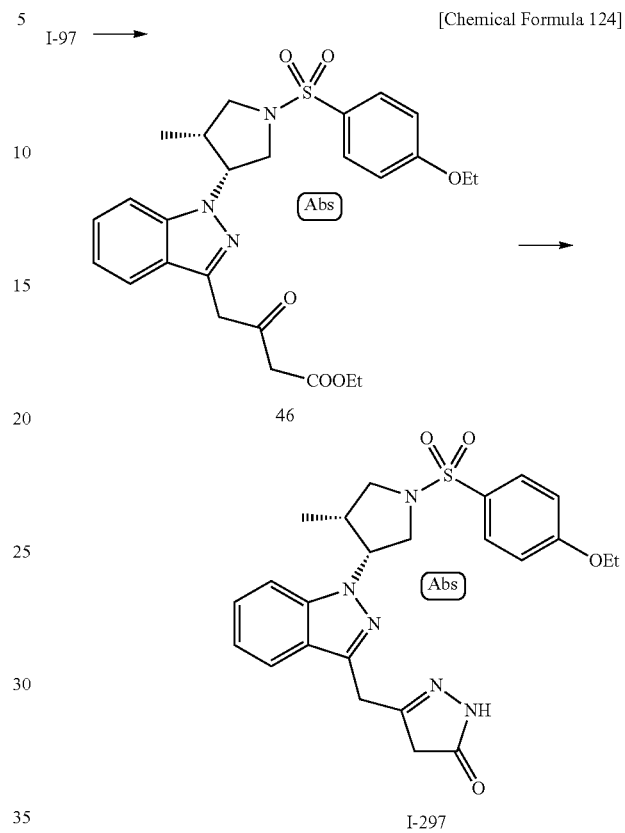

Step 1

Compound 45 was synthesized from Compound I-97 in a similar manner as described in Example 25.

$^1$H-NMR (DMSO-$d_6$) δ: 7.83-7.77 (3H, m), 7.69 (1H, d, J=8.7 Hz), 7.42 (1H, t, J =7.3 Hz), 7.20-7.16 (3H, m), 5.43-5.38 (1H, m), 4.20-4.04 (4H, m), 3.90-3.85 (1H, m), 3.65-3.57 (2H, m), 3.16 (1H, t, J=10.0 Hz), 2.51-2.43 (1H, m), 1.39 (3H, t, J=6.9 Hz), 0.28 (3H, d, J=6.8 Hz).

Step 2

To a suspension of Compound 45 (110 mg, 0.26 mmol), hydroxylamine hydrochloride (43.2 mg, 0.62 mmol) and ethanol (3 mL), 28% sodium methoxide in methanol (120 mg, 0.62 mmol) was added, and the mixture was stirred for 4 hours. To the reaction mixture was added water, and the mixture was extracted with ethyl acetate. The organic layer was washed by water and brine, dried over anhydrous magnesium sulphate, and concentrated in vacuo.

The resulting residue was dissolved in 1, 4-dioxane (2 mL). To the solution were added carbonyldiimidazole (35 mg, 0.22 mmol) and diazabicycloundecene (32 μL, 0.22 mmol), and the mixture was stirred for 2 hours at 105° C. Then, to the reaction mixture was added phenyl chlorocarbonate (27 μL, 0.22 mmol), and the mixture was stirred for 2 hours at 105° C. To the reaction mixture was added water, and the mixture was extracted with ethyl acetate. The organic layer was washed by water and brine, dried over anhydrous magnesium sulphate, and concentrated in vacuo. The resulting residue was purified by silica gel column chromatography (chloroform-methanol) to give Compound I-296 (22 mg, 2 Steps Yield 18%).

LC/MS (Condition B) RT=2.09, [M+H]$^+$=484.

Step 1

To a suspension of Compound I-97 (200 mg, 0.45 mmol) in dichloromethane were added catalytic amount of DMF and oxalyl chloride (47 μL, 0.54 mmol) under ice-cooling, and the mixture was stirred for 30 minutes at 0° C. The reaction mixture was concentrated in vacuo, and dichloromethane (2 mL) was added to the resulting residue. To the reaction mixture were added Meldrum's Acid (72 mg, 0.50 mmol) and N,N-diisopropylethylamine (173 μL, 0.99 mmol) under ice-cooling, and the mixture was stirred for 1 hour at room temperature. The reaction mixture was concentrated in vacuo. To the residue was added ethanol (4 mL), and the mixture was heated at reflux for 2 hours. The reaction mixture was concentrated in vacuo. To the residue was added hydrochloric acid, and the mixture was extracted with ethyl acetate. The organic layer was washed by brine, dried over anhydrous magnesium sulphate, and concentrated in vacuo. The resulting residue was purified by silica gel column chromatography (hexane-ethyl acetate) to give Compound 46 (43 mg, Yield 19%).

LC/MS (Condition B) RT=2.37, [M+H]$^+$=514.

Step 2

To a suspension of Compound 46 (40 mg, 0.078 mmol) in ethanol (1 mL) was added hydrazine monohydrate (5.7 μL, 0.12 mmol). The mixture was stirred for 1 hour at room temperature, and heated at reflux for 3 hours. To the reaction mixture was added water, and the resulting mixture was extracted with ethyl acetate. The organic layer was washed by brine, dried over anhydrous magnesium sulphate, and concentrated in vacuo. The resulting residue was purified by silica gel column chromatography (chloroform-methanol) to give Compound I-297 (27 mg, Yield 71%).

$^1$H-NMR (DMSO-D$_6$) δ: 11.44 (1H, brs), 9.35 (0.4H, brs), 7.81 (2H, d, J=8.9 Hz), 7.59 (1H, d, J=8.5 Hz), 7.47 (1H, d, J=8.2 Hz), 7.31 (1H, t, J=7.5 Hz), 7.13 (2H, d, J=8.8 Hz), 7.03 (1H, t, J=7.5 Hz), 5.37-5.32 (1H, m), 5.04 (1H, brs), 4.07 (2H, q, J=6.9 Hz), 3.92-3.81 (3H, m), 3.72-3.67 (1H, m), 3.61-3.56 (1H, m), 3.19 (1H, t, J=10.0 Hz), 2.51-2.42 (1H, m), 1.33 (3H, t, J=7.0 Hz), 0.28 (3H, d, J=6.8 Hz).

LC/MS (Condition B) RT=1.82, [M+H]$^+$=482.

EXAMPLE 28

I-97 ⟶ [Chemical Formula 125]

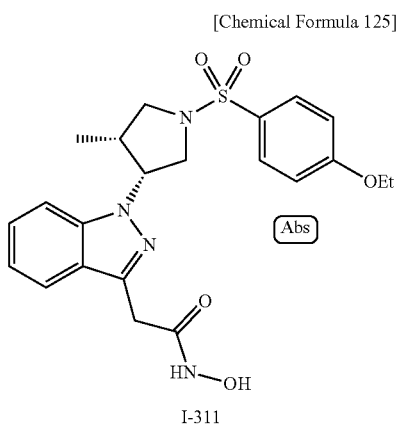

I-311

To a suspension of Compound I-97 (80 mg, 0.18 mmol) in dichloromethane (2 mL) were added catalytic amount of DMF and oxalyl chloride (19 μL, 0.22 mmol) under ice-cooling, and the mixture was stirred for 1 hour at 0° C. The reaction mixture was concentrated in vacuo.

To a solution of hydroxylamine hydrochloride (50 mg, 0.72 mmol) in water (0.5 mL) were added triethylamine (100 μL, 0.72 mmol) and acetonitrile (2.5 mL) under ice-cooling, and the mixture was stirred for 1 hour at 0° C. To the resulting reaction mixture was added a solution of the resulting residue of the above process in dichloromethane (2 mL), and the mixture was stirred for 1 hour at room temperature. To the reaction mixture was added water, and the mixture was extracted with ethyl acetate. The organic layer was washed by water and brine, dried over anhydrous magnesium sulphate, and concentrated in vacuo. The resulting residue was purified by silica gel column chromatography (chloroform-methanol) to give Compound I-311 (36 mg, Yield 43%).

$^1$H-NMR (DMSO-d$_6$) δ: 10.77 (1H, brs), 8.93 (1H, brs), 7.81 (2H, d, J=8.5 Hz), 7.72 (1H, d, J=8.2 Hz), 7.59 (1H, d, J=8.4 Hz), 7.34 (1H, t, J=7.5 Hz), 7.17-7.07 (3H, m), 5.35-5.30 (1H, m), 4.15 (2H, q, J=6.8 Hz), 3.87-3.82 (1H, m), 3.70-3.46 (4H, m), 3.20 (1H, t, J=9.9 Hz), 2.43-2.32 (1H, m), 1.38 (3H, t, J=6.8 Hz), 0.28 (3H, d, J=6.5 Hz).

LC/MS (Condition B) RT=1.78, [M+H]$^+$=459.

EXAMPLE 29

I-37 ⟶ [Chemical Formula 126]

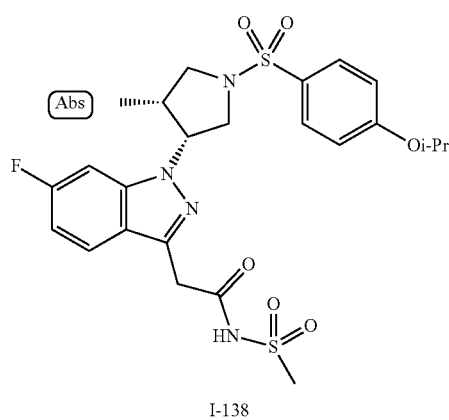

I-138

To a solution of Compound I-37 (100 mg, 0.210 mmol) in dichloromethane were added methanesulfonamide (40 mg, 0.421 mmol), DMAP (25.7 mg, 0.21 mmol) and DCC (47.7 mg, 0.231 mmol), and the mixture was stirred overnight. To the resulting suspension was added diluted hydrochloric acid, and the mixture was extracted with dichloromethane. The organic layer was concentrated in vacuo, and the resulting residue was purified by silica gel column chromatography (methanol-chloroform) to give Compound I-138 (106 mg).

$^1$H-NMR (DMSO-D6) δ: 1.32 (6H, br s), 2.35 (1H, m), 3.15-3.27 (2H, m), 3.25 (3H, s), 3.59 (1H, m), 3.68 (1H, m), 3.77-3.84 (1H, m), 3.84 (2H, s), 4.76 (1H, m), 5.39 (1H, m), 5.75 (1H, br s), 7.01 (1H, m), 7.09-7.17 (2H, m), 7.49-7.57 (1H, m), 7.66-7.75 (2H, m), 7.75-7.84 (2H, m).

EXAMPLE 30

[Chemical Formula 127]

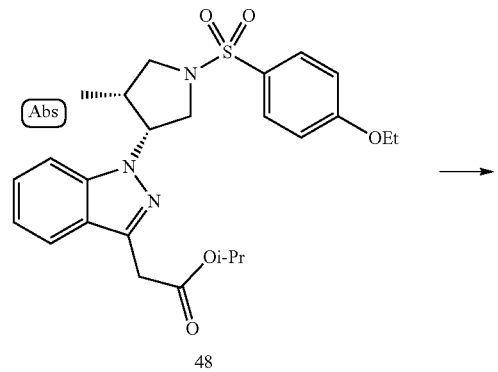

48

-continued

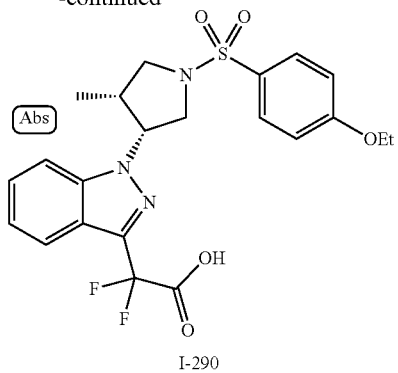

I-290

To a solution of Compound 48 (100 mg, 0.21 mmol) in THF (2 ml) was added 1.0 mol/L sodium bis(trimethylsilyl) amide in THF (0.41 ml, 0.41 mmol) at −78° C., and the mixture was stirred for 30 minutes at −78° C. To the resulting mixture was added N-fluorobenzenesulfonimide (130 mg, 0.41 mmol) at −78° C., and the mixture was allowed to warm gradually to room temperature from −78° C. over 1.5 hours. To the mixture was added 2 mol/L aqueous hydrochloric acid, and the resulting mixture was extracted with ethyl acetate. The organic layer was dried over anhydrous sodium sulphate and concentrated in vacuo.

To a solution of the resulting residue in DMSO (1 ml) was added 2 mol/L aqueous sodium hydroxide (0.19 ml, 0.38 mmol), and the mixture was stirred for 1 hour. To the mixture were added 2 mol/L aqueous hydrochloric acid (0.19 ml, 0.38 mmol) and water, and the resulting mixture was extracted with ethyl acetate. The organic layer was washed by water, dried over anhydrous sodium sulphate, and concentrated in vacuo. The resulting residue was purified by HPLC for isolation to give Compound I-290 (49.7 mg, Yield 50%).

$^1$H-NMR (DMSO-d$_6$) δ: 0.26 (d, J=6.8 Hz, 3H), 1.37 (t, J=6.8 Hz, 3H), 2.33-2.42 (m, 1H), 3.15-3.88 (m, 4H), 4.15 (q, J=6.8 Hz, 2H), 5.50-5.53 (m, 1H), 7.15 (d, J=8.8 Hz, 2H), 7.29 (d, J=7.6 Hz, 1H), 7.49 (d, J=7.6 Hz, 1H), 7.78-7.81 (m, 2H), 7.81 (d, J=8.8 Hz, 2H).

EXAMPLE 31

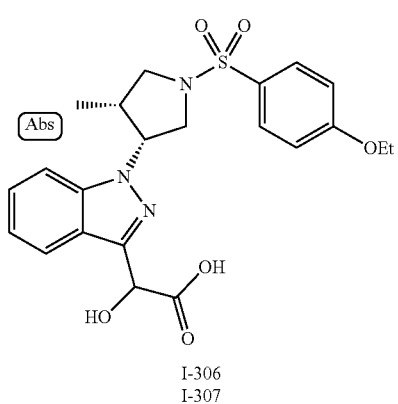

I-306
I-307

To a solution of Compound 48 (200 mg, 0.41 mmol) in THF (4 ml) was added 2.0 mol/L lithium diisopropylamide in THF (0.21 ml, 0.41 mmol) at −78° C., and the mixture was stirred for 30 minutes at −78° C. To the reaction mixture was added carbon tetrachloride (0.10 ml, 1.03 mmol), and the mixture was stirred for 1 hour at −78° C. To the reaction mixture was added saturated aqueous ammonium chloride, and the mixture was extracted with ethyl acetate. The organic layer was dried over anhydrous sodium sulphate, and concentrated in vacuo. To a solution of the resulting residue in DMSO (2 ml) was added 2 mol/L aqueous sodium hydroxide (0.82 ml, 1.65 mmol), and the mixture was stirred for 19 hours at room temperature. To the reaction mixture were added 2 mol/L aqueous hydrochloric acid (0.82 ml, 1.65 mmol) and water, and the mixture was extracted with ethyl acetate. The organic layer was washed by water, dried over anhydrous sodium sulphate, and concentrated in vacuo. The resulting residue was purified by preparative HPLC to give Compound I-306 (38.5 mg, Yield 20%) and Compound I-307 (12.3 mg, Yield 7%). The absolute configuration of these two compounds is not identified.

Compound I-306

$^1$H-NMR (DMSO-d6)δ:0.26 (d, J=6.8 Hz, 3H), 1.37 (t, J=6.9 Hz, 3H), 2.39-2.46 (m, 1H), 3.17 (dd, J=9.9, 9.9 Hz, 1H), 3.58 (dd, J=9.0, 7.5 Hz, 1H), 3.67 (dd, J=11.3, 2.5 Hz, 1H), 3.88 (dd, J=11.2, 7.4 Hz, 1H), 4.14 (q, J=6.9 Hz, 2H), 5.06 (s, 1H), 5.35-5.39 (m, 1H), 7.09 (dd, J=7.4, 7.4 Hz, 1H), 7.15 (d, J=8.8 Hz, 2H), 7.35 (dd, J=7.5, 7.5 Hz, 1H), 7.62 (d, J=8.5 Hz, 1H), 7.71 (d, J=8.0 Hz, 1H), 7.81 (d, J=8.8 Hz, 2H).

LC/MS (Condition B) RT=1.74, [M+H]$^+$=460.

Compound I-307

$^1$H-NMR (DMSO-d6)δ:0.24 (d, J=6.8 Hz, 3H), 1.38 (t, J=7.0 Hz, 3H), 2.33-2.44 (m, 1H), 3.17 (dd, J=9.9, 9.9 Hz, 1H), 3.57 (dd, J=8.4, 8.4 Hz, 1H), 3.69 (dd, J=11.0, 2.5 Hz, 1H), 3.87 (dd, J=11.2, 7.4 Hz, 1H), 4.13-4.19 (m, 2H), 5.09 (s, 1H), 5.35-5.38 (m, 1H), 7.09 (dd, J=7.5, 7.5 Hz, 1H), 7.16 (d, J=8.8 Hz, 2H), 7.34 (dd, J=7.7, 7.7 Hz, 1H), 7.62 (d, J=8.5 Hz, 1H), 7.75 (d, J=8.3 Hz, 1H), 7.81 (d, J=8.8 Hz, 2H).

LC/MS (Condition B) RT=1.75, [M+H]$^+$=460.

EXAMPLE 32

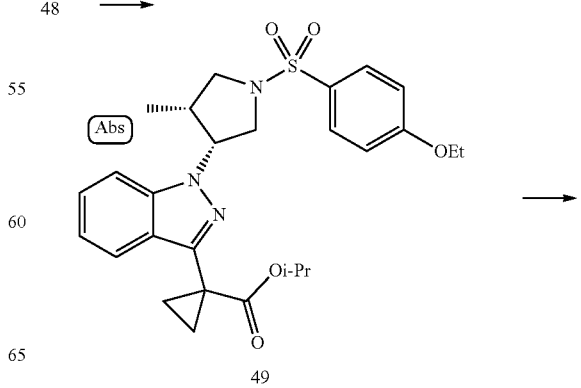

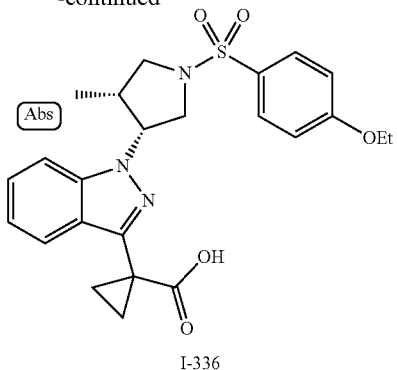

I-336

To a solution of Compound 48 (129.7 mg, 0.27 mmol) in THF (2 ml) was added 2.0 mol/L lithium diisopropylamide in THF (0.26 ml, 0.52 mmol) at −78° C., and the mixture was stirred for 30 minutes at −78° C. To the mixture was added 1,2-dibromoethane (0.138 ml, 1.60 mmol), and the resulting mixture was allowed gradually to room temperature from −78° C. To the reaction mixture was added saturated aqueous ammonium chloride, and the mixture was extracted with ethyl acetate. The organic layer was dried over anhydrous sodium sulphate, and concentrated in vacuo. The resulting residue was purified by preparative HPLC to give Compound 49 (44.7 mg, Yield 33%).

LC/MS (Condition B) RT=2.69, [M+H]$^+$=512.

Step 2

Compound 49 was hydrolyzed according to the method described in the general synthetic procedures to give Compound I-336.

$^1$H-NMR (DMSO-d6)δ:0.22 (d, J=6.8 Hz, 3H), 0.93 (dd, J=9.2, 4.1 Hz, 1H), 1.06-1.11 (m, 1H), 1.38 (t, J=6.9 Hz, 3H), 1.42-1.44 (m, 2H), 2.44-2.48 (m, 1H), 3.06 (t, J=9.9 Hz, 1H), 3.53-3.61 (m, 2H), 3.90 (dd, J=10.9, 7.7 Hz, 1H), 4.14 (q, J=6.9 Hz, 2H), 5.36-5.40 (m, 1H), 7.09 (dd, 7.7, 7.7 Hz, 1H), 7.15 (d, J=9.0 Hz, 2H), 7.34 (dd, J=7.7, 7.7 Hz, 1H), 7.61 (d, J=8.3 Hz, 2H), 7.79 (d, J=9.0 Hz, 2H), 12.37 (brs, 1H).

LC/MS (Condition B) RT=2.13, [M+H]$^+$=470.

EXAMPLE 33

[Chemical Formula 130]

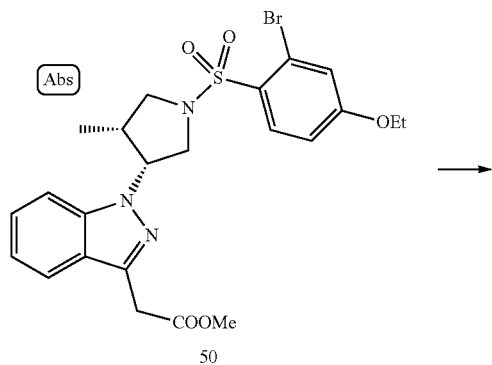

50

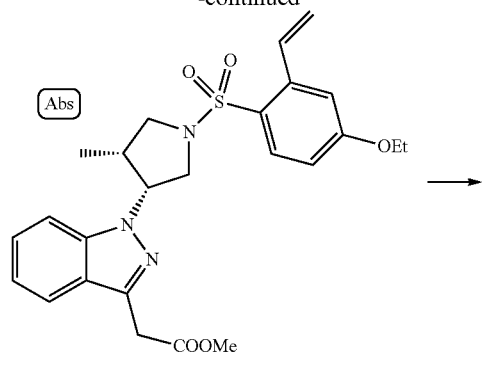

51

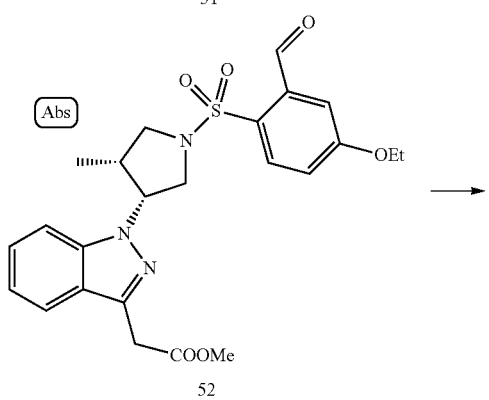

52

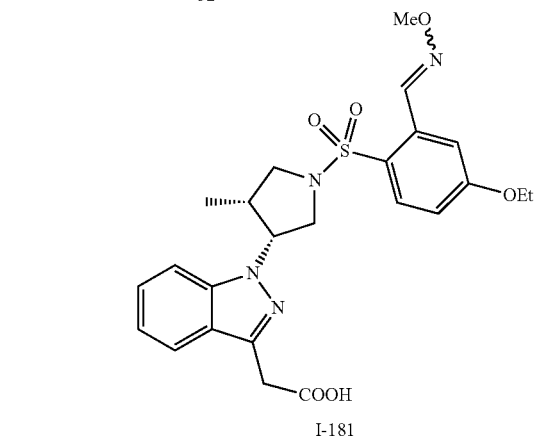

I-181

Step 1

To the mixture of Compound 50 (500 mg, 0.93 mmol), dimethoxyethane (8 mL), and ethanol (4 mL) were added 4,4,5,5-tetramethyl-2-vinyl-1,3,2-dioxaborolane (215 mg, 1.40 mmol), PdCl$_2$ (dppf) (68 mg, 0.093 mmol), and 2 mol/L aqueous sodium carbonate (1.40 ml, 2.80 mmol), and the resulting mixture was stirred for 8 hours at 80° C. To the reaction mixture was added water, and the mixture was extracted with ethyl acetate. The organic layer was washed by water and brine, dried over anhydrous magnesium sulphate, and concentrated in vacuo. The resulting residue was purified by silica gel column chromatography (hexane-ethyl acetate) to give Compound 51 (280 mg, Yield 62%).

LC/MS (Condition B) RT=2.51 [M+H]$^+$=484.

Step 2

To the mixture of Compound 51 (100 mg, 0.21 mmol), acetonitrile (3 mL), and water (0.75 mL) were added 7% osmium tetroxide (75 mg, 0.021 mmol) and sodium periodate (133 mg, 0.62 mmol), and the resulting mixture was heated with reflux at 4 hours. The reaction mixture was filtered, and washed by ethyl acetate. To the filtrate was added water, and the mixture was extracted with ethyl acetate. The organic layer was washed by water and brine, dried over anhydrous magnesium sulphate, and concentrated in vacuo. The resulting residue was purified by silica gel column chromatography (hexane-ethyl acetate) to give Compound 52 (35 mg, Yield 35%).

LC/MS (Condition B) RT=2.45 [M+H]$^+$=486.

Step 3

To a mixture of Compound 52 (100 mg, 0.072 mmol), THF (1 mL), and water (0.5 mL) were added O-methylhydroxylamine hydrochloride (9.0 mg, 0.11 mmol) and sodium acetate (8.9 mg, 0.11 mmol), and the mixture was stirred for 30 minutes at room temperature. To the reaction mixture was added water, and the mixture was extracted with ethyl acetate. The organic layer was washed by water and brine, dried over anhydrous magnesium sulphate, and concentrated in vacuo. The resulting residue was purified by silica gel column chromatography (hexane-ethyl acetate).

The obtained compound (33 mg, 0.064 mmol) was dissolved in THF (0.75 mL) and methanol (0.75 mL). To the solution was added 2 mol/L aqueous sodium hydroxide (192 μL, 0.38 mmol), and the mixture was stirred for 1 hour at room temperature. To the reaction mixture was added hydrochloric acid, and the resulting mixture was extracted with ethyl acetate. The organic layer was washed by brine, dried over anhydrous magnesium sulphate, and concentrated in vacuo. The resulting residue was purified by silica gel column chromatography (chloroform-methanol) to give Compound I-181 (18 mg, Yield 56%).

$^1$H-NMR (DMSO-D$_6$) δ: 8.88 (1H, s), 8.00 (1H, d, J=9.0 Hz), 7.64 (2H, t, J=9.4 Hz), 7.45 (1H, d, J=2.5 Hz), 7.35 (1H, t, J=7.5 Hz), 7.19 (1H, dd, J=8.9, 2.6 Hz), 7.09 (1H, t, J=7.4 Hz), 5.43-5.38 (1H, m), 4.17 (2H, q, J=6.9 Hz), 3.96-3.89 (4H, m), 3.70 (2H, d, J=2.8 Hz), 3.63-3.58 (2H, m), 3.16 (1H, t, J=9.7 Hz), 2.72-2.63 (1H, m), 1.38 (3H, t, J=6.9 Hz), 0.33 (3H, d, J=6.5 Hz).

LC/MS (Condition B) RT=2.27 [M+H]$^+$=501.

EXAMPLE 34

[Chemical Formula 131]

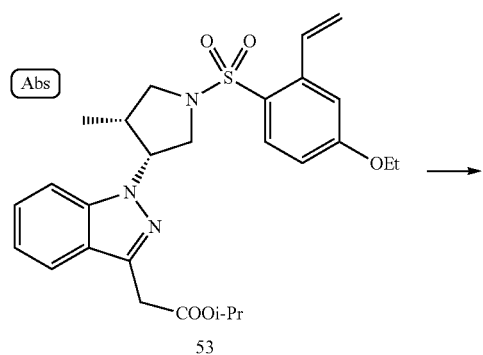

53

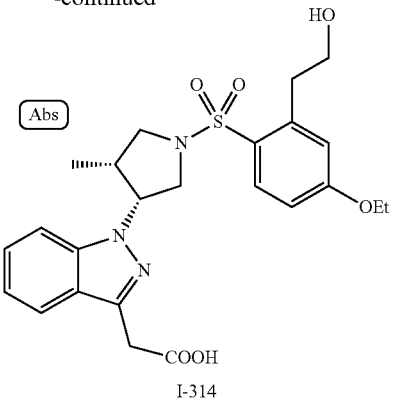

I-314

To a solution of Compound 53 (168 mg, 0.33 mmol) which was synthesized by the similar manner as described in Example 33 in THF (2 mL) was added 0.5 mol/L 9-borabicyclo[3.3.1]nonane in THF (0.99 mL, 0.49 mmol) under ice-cooling, and the mixture was stirred for 1 hour at room temperature. To the reaction mixture was added 2 mol/L dimethyl sulfide borane in toluene (0.25 mL, 0.49 mmol), and the mixture was stirred overnight at room temperature. Then, water (0.5 mL) and 30% hydrogen peroxide solution (0.5 mL) were added to the mixture, and the resulting mixture was stirred for 1 hour at room temperature. Further, 2 mol/L aqueous sodium hydroxide (0.49 mL, 0.99 mmol) was added to the mixture, and the resulting mixture was stirred for 1 hour at room temperature. To the reaction mixture was added 10% aqueous sodium hydrogensulfite, and the mixture was extracted with ethyl acetate. The organic layer was washed by water and brine, dried over anhydrous magnesium sulphate, and concentrated in vacuo. The resulting residue was purified by silica gel column chromatography (hexane-ethyl acetate).

The obtained compound (48 mg, 0.064 mmol) was dissolved in THF (1 mL) and methanol (1 mL). To the solution was added 2 mol/L aqueous sodium hydroxide (204 μL, 0.41 mmol), and the resulting mixture was stirred for 90 minutes at room temperature. The reaction mixture was back extracted with 0.1 mol/L aqueous sodium hydroxide. To the water layer was added hydrochloric acid and the mixture was made acidic. The resulting mixture was extracted with chloroform. The organic layer was dried over anhydrous magnesium sulphate, and concentrated in vacuo. The resulting residue was purified by silica gel column chromatography (chloroform-methanol) to give Compound I-314 (23.1 mg, 2 Steps Yield 16%).

$^1$H-NMR (DMSO-d$_6$) δ: 7.98 (1H, d, J=8.5 Hz), 7.71-7.63 (2H, m), 7.37 (1H, t, J =7.4 Hz), 7.11 (1H, t, J=7.3 Hz), 7.02 (1H, s), 6.96 (1H, d, J=8.3 Hz), 5.47-5.42 (1H, m), 4.16-4.09 (2H, m), 3.99-3.93 (1H, m), 3.80 (2H, s), 3.71-3.58 (4H, m), 3.25-3.11 (3H, m), 2.74-2.64 (1H, m), 1.36 (3H, t, J=6.5 Hz), 0.36 (3H, d, J=6.3 Hz).

LC/MS (Condition B) RT=1.87, [M+H]$^+$=488.

EXAMPLE 35

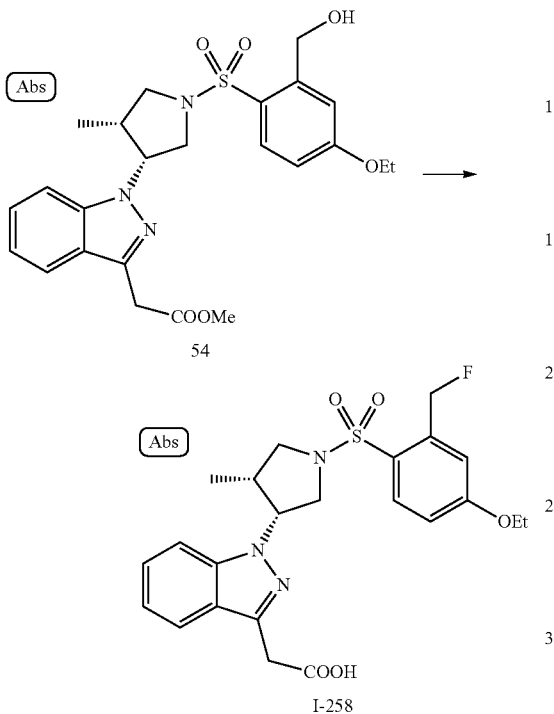

Step 1

To the mixture of Compound 52 (174 mg, 0.36 mmol), methanol (1.5 mL), and THF (1.5 mL) was added sodium borohydride (13.56 mg, 0.36 mmol) under ice-cooling, and the mixture was stirred for 15 minutes at 0° C. To the reaction mixture was added 2 mol/L aqueous hydrochloric acid, and the mixture was extracted with ethyl acetate. The organic layer was washed by brine, dried over anhydrous magnesium sulphate, and concentrated in vacuo to give crude product of Compound 54 (151 mg).

Step 2

To a solution of Compound 54 (48 mg, 0.098 mmol) in dichloromethane (1.5 mL) was added DAST (20 μL, 0.15 mmol) at −78° C., and the mixture was stirred for 1 hour at −78° C. To the reaction mixture was added saturated aqueous sodium bicarbonate, and the mixture was extracted with ethyl acetate. The organic layer was washed by brine, dried over anhydrous magnesium sulphate, and concentrated in vacuo.

The resulting residue was dissolved in THF (0.75 mL) and methanol (0.75 mL). To a solution was added 2 mol/L aqueous sodium hydroxide (140 μL, 0.28 mmol), and the mixture was stirred for 2 hours at room temperature. To the reaction mixture was added 2 mol/L aqueous hydrochloric acid, and the mixture was extracted with ethyl acetate. The organic layer was washed by brine, dried over anhydrous magnesium sulphate, and concentrated in vacuo. The resulting residue was purified by silica gel column chromatography (chloroform-methanol) to give Compound I-258 (15.6 mg, 2 Steps Yield 34%).

$^1$H-NMR (DMSO-$d_6$) δ: 7.96 (1H, d, J=8.8 Hz), 7.65 (2H, t, J=9.2 Hz), 7.36 (1H, t, J=7.7 Hz), 7.20 (1H, s), 7.14-7.08 (2H, m), 5.91 (1H, s), 5.79 (1H, s), 5.42 (1H, t, J=6.3 Hz), 4.17 (2H, q, J=6.8 Hz), 3.96-3.91 (1H, m), 3.76-3.58 (4H, m), 3.13 (1H, t, J=9.7 Hz), 2.72-2.64 (1H, m), 1.38 (3H, t, J=6.8 Hz), 0.34 (3H, d, J=6.7 Hz).

LC/MS (Condition B) RT=2.19 [M+H]$^+$=476.

EXAMPLE 36

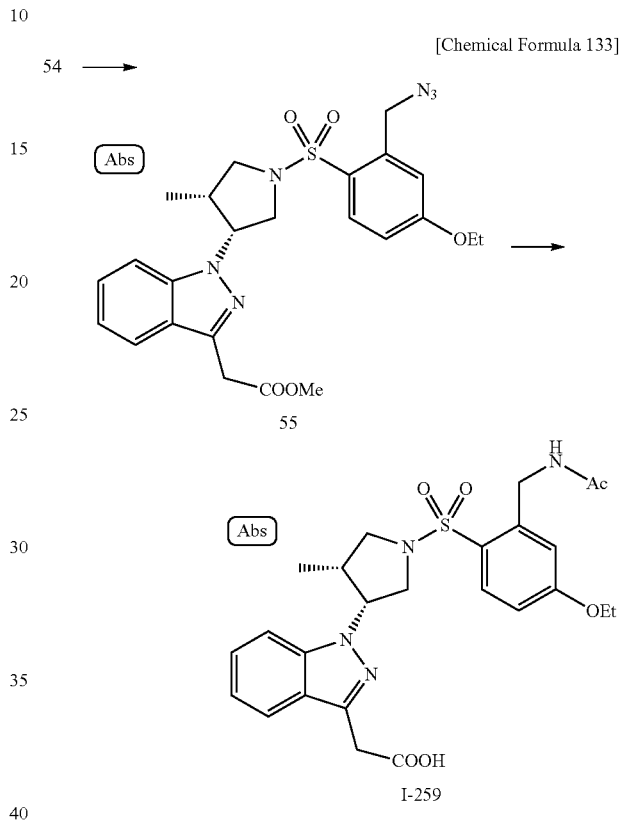

Step 1

To a solution of Compound 54 (40 mg, 0.082 mmol) in THF (1 mL) were added diphenylphosphoryl azide (43 μL, 0.196 mmol) and diazabicycloundecene (30 μL, 0.196 mmol), and the mixture was stirred for 2 days at room temperature. To the reaction mixture was added water, and the mixture was extracted with ethyl acetate. The organic layer was washed by brine, dried over anhydrous magnesium sulphate, and concentrated in vacuo. The resulting residue was purified by silica gel column chromatography (hexane-ethyl acetate) to give Compound 55 (63 mg).

LC/MS (Condition RT=2.59 [M+H]$^+$=513.

Step 2

To the mixture of Compound 55 (63 mg), THF (1 mL), and methanol (1 mL) was added Pd-Carbon (13 mg), and the mixture was stirred for 4 hours under hydrogen atmosphere at room temperature. The reaction mixture was filtered by using Celite, and washed by methanol. The filtrate was concentrated in vacuo.

The resulting residue was dissolved in dichloromethane (1.5 mL). To the solution were added triethylamine (30 μL, 0.22 mmol) and acetyl chloride (12.4 μL, 0.172 mmol) under ice-cooling, and the mixture was stirred for 2 hours at room temperature. To the reaction mixture was added water, and the mixture was extracted with ethyl acetate. The organic layer was washed by brine, dried over anhydrous magnesium sulphate, and concentrated in vacuo.

The resulting residue was dissolved in THF (1.5 mL) and methanol (1.5 mL). To the solution was added 2 mol/L aqueous sodium hydroxide (70 μL, 0.14 mmol), and the mixture was stirred overnight at room temperature. To the reaction mixture was added 2 mol/L aqueous hydrochloric acid, and the mixture was extracted with ethyl acetate. The organic layer was washed by brine, dried over anhydrous magnesium sulphate, and concentrated in vacuo. The resulting residue was purified by silica gel column chromatography (chloroform-methanol) to give Compound I-259 (18.5 mg, 4 Steps Yield 44%).

$^1$H-NMR (DMSO-d$_6$) δ: 8.39 (1H, brs), 7.99 (1H, d, J=8.8 Hz), 7.71-7.64 (2H, m), 7.37 (1H, t, J=7.5 Hz), 7.11 (1H, t, J=7.4 Hz), 7.01 (1H, dd, J=8.8, 2.5 Hz), 6.98-6.96 (1H, m), 5.48-5.42 (1H, m), 4.69 (2H, d, J=6.0 Hz), 4.12 (2H, q, J=6.9 Hz), 3.96 (1H, dd, J=10.7, 7.2 Hz), 3.82 (2H, s), 3.70 (1H, d, J=10.8 Hz), 3.62 (1H, t, J=8.2 Hz), 3.20 (1H, t, J=9.5 Hz), 2.74-2.65 (1H, m), 1.94 (3H, s), 1.36 (3H, t, J=6.9 Hz), 0.36 (3H, d, J=6.5 Hz).

LC/MS (Condition B) RT=1.81 [M+H]$^+$=515.

EXAMPLE 37

[Chemical Formula 134]

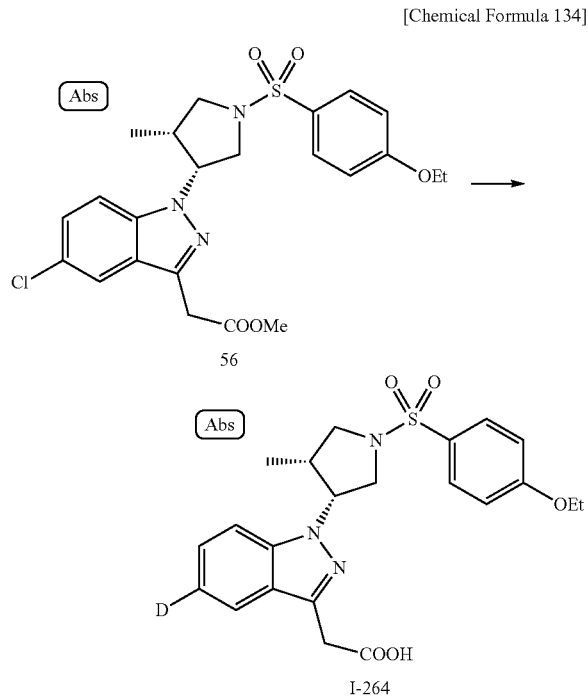

To a mixture of Compound 56 (95 mg, 0.193 mmol), THF (1.5 mL), and deuteromethanol (1.5 mL) was added dried 10% Pd-Carbon (62 mg), and the mixture was stirred overnight under deuterium atmosphere at room temperature. The reaction mixture was filtered by using Celite, and washed by ethanol. The filtrate was concentrated in vacuo, and the resulting residue was purified by silica gel column chromatography (acetonitrile including 0.1% formic acid −0.1% aqueous formic acid).

The obtained compound (8 mg, 0.017 mmol) was dissolved in THF (0.5 mL) and methanol (0.5 mL). To the solution was added 2 mol/L aqueous sodium hydroxide (52 μL, 0.104 mmol), and the mixture was stirred for 2 hours at room temperature. To the reaction mixture was added 2 mol/L aqueous hydrochloric acid, and the mixture was extracted with ethyl acetate. The organic layer was washed by brine, dried over anhydrous magnesium sulphate, and concentrated in vacuo. The resulting residue was purified by silica gel column chromatography (chloroform-methanol) to give Compound I-264 (7.8 mg, Yield 10%).

LC/MS (Condition B) RT=2.04 [M+H]$^+$=445.

EXAMPLE 38

[Chemical Formula 135]

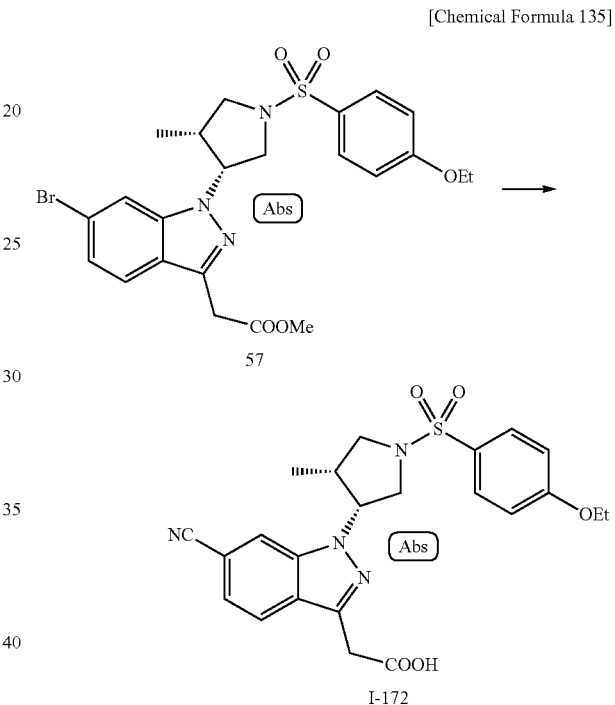

To a solution of Compound 57 (50 mg, 0.093 mmol) in NMP (2 mL) were added Zn(CN)$_2$ (10.94 mg, 0.093 mmol), Zn (1.22 mg, 0.019 mmol) and bis(tri-tert-butylphosphine) palladium (4.76 mg, 9.32 μmol) at room temperature, and the mixture was stirred for 30 minutes at 130° C. by using the microwave reactor. To the reaction mixture was added water, and the mixture was extracted with ethyl acetate. The organic layer was washed by water and brine, dried over anhydrous magnesium sulphate, and concentrated in vacuo. The resulting residue was purified by silica gel column chromatography (hexane-ethyl acetate).

The obtained compound was hydrolyzed according to the method described in the general synthetic procedures to give Compound I-172 (33 mg, 2 Steps Yield 80%).

$^1$H-NMR (DMSO-D$_6$) δ: 8.37 (1H, s), 7.85 (1H, d, J=8.4 Hz), 7.78 (2H, d, J=8.9 Hz), 7.43 (1H, dd, J=8.3, 1.2 Hz), 7.14 (2H, d, J=9.0 Hz), 5.46 (1H, t, J=5.8 Hz), 4.15 (2H, q, J=6.9 Hz), 3.90 (1H, dd, J=11.4, 7.4 Hz), 3.75-3.55 (4H, m), 3.10 (1H, t, J=10.0 Hz), 2.5 (1H, m), 1.39 (3H, t, J=7.0 Hz), 0.27 (3H, d, J=6.7 Hz).

LC/MS (Condition B) RT=1.98, [M+H]$^+$=469.

EXAMPLE 39

57 ⟶

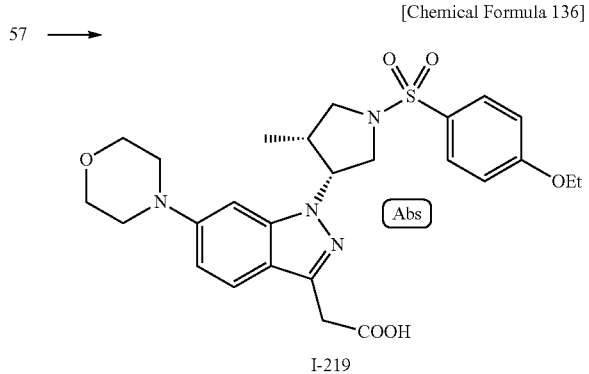

I-219

To a solution of Compound 57 (25 mg, 0.047 mmol) in toluene (2 mL) were added morpholine (0.012 ml, 0.140 mmol), cesium carbonate (45.6 mg, 0.140 mmol), BINAP (1.94 mg, 3.12 μmol) and palladium acetate (2.09 mg, 9.32 μmol) at room temperature, and the mixture was stirred for 7.5 hours under nitrogen atmosphere at 110° C. To the reaction mixture was added water, and the mixture was extracted with ethyl acetate. The organic layer was washed by water and brine, dried over anhydrous magnesium sulphate, and concentrated in vacuo. The resulting residue was purified by silica gel column chromatography (hexane-ethyl acetate).

The obtained compound was hydrolyzed according to the method described in the general synthetic procedures to give Compound I-219 (14.3 mg, 66%).

$^1$H-NMR (CDCl$_3$) δ: 7.83 (2H, d, J=8.9 Hz), 7.46 (1H, d, J=8.9 Hz), 7.02 (2H, d, J=8.9 Hz), 6.89 (1H, dd, J=9.0, 1.8 Hz), 6.64 (1H, d, J=1.6 Hz), 5.00 (1H, dt, J=10.2, 3.6 Hz), 4.13 (2H, ddd, J=14.1, 7.1, 2.6 Hz), 4.01 (1H, dd, J=11.1, 7.6 Hz), 3.89 (4H, t, J=4.8 Hz), 3.82-3.76 (3H, m), 3.69 (1H, dd, J=9.0, 7.4 Hz), 3.24-3.18 (5H, m), 2.66 (1H, ddd, J=15.4, 8.7, 5.4 Hz), 1.47 (3H, t, J=7.0 Hz), 0.50 (3H, d, J=6.8 Hz).

LC/MS (Condition B) RT=1.95, [M+H]$^+$=529.

EXAMPLE 40

57 ⟶

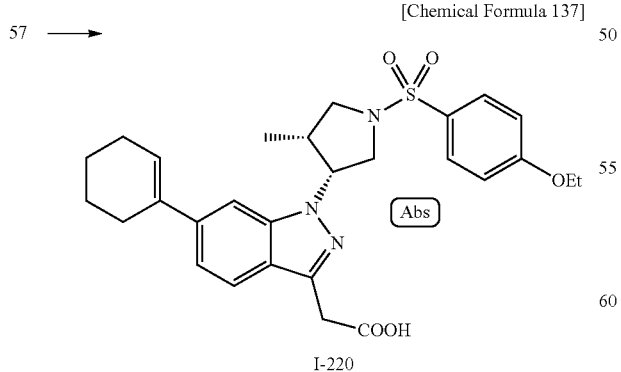

I-220

To the mixture of Compound 57 (25 mg, 0.047 mmol), toluene (2 mL), and purified water (0.1 mL) were added 2-cyclohexyl-4,4,5,5-tetramethyl-1,3,2-dioxyborolane (12.61 mg, 0.061 mmol), potassium phosphate (34.6 mg, 0.163 mmol), triphenylphosphine (1.22 mg, 4.66 μmol), and palladium acetate (0.523 mg, 2.330 μmol) at room temperature, and the resulting mixture was stirred for 7.5 hours under nitrogen atmosphere at 100° C. To the reaction mixture was added water, and the mixture was extracted with ethyl acetate. The organic layer was washed by water and brine, dried over anhydrous magnesium sulphate, and concentrated in vacuo. The resulting residue was purified by silica gel column chromatography (hexane-ethyl acetate).

The obtained compound was hydrolyzed according to the method described in the general synthetic procedures to give Compound I-220 (20.9 mg, 98%).

$^1$H-NMR (CDCl$_3$) δ: 7.84 (2H, d, J=8.9 Hz), 7.51 (1H, d, J=8.4 Hz), 7.26-7.23 (2H, m), 7.02 (2H, d, J=8.9 Hz), 6.19 (1H, s), 5.07 (1H, td, J=7.0, 2.8 Hz), 4.15-4.03 (3H, m), 3.82-3.68 (4H, m), 3.22 (1H, t, J=9.7 Hz), 2.68 (1H, dt, J=17.2, 6.9 Hz), 2.49-2.42 (2H, m), 2.27-2.21 (2H, m), 1.84-1.78 (2H, m), 1.71-1.65 (2H, q, J=6.0 Hz), 1.47 (3H, t, J=7.0 Hz), 0.47 (3H, d, J=6.9 Hz).

LC/MS (Condition B) RT=2.60, [M+H]$^+$=523.

EXAMPLE 41

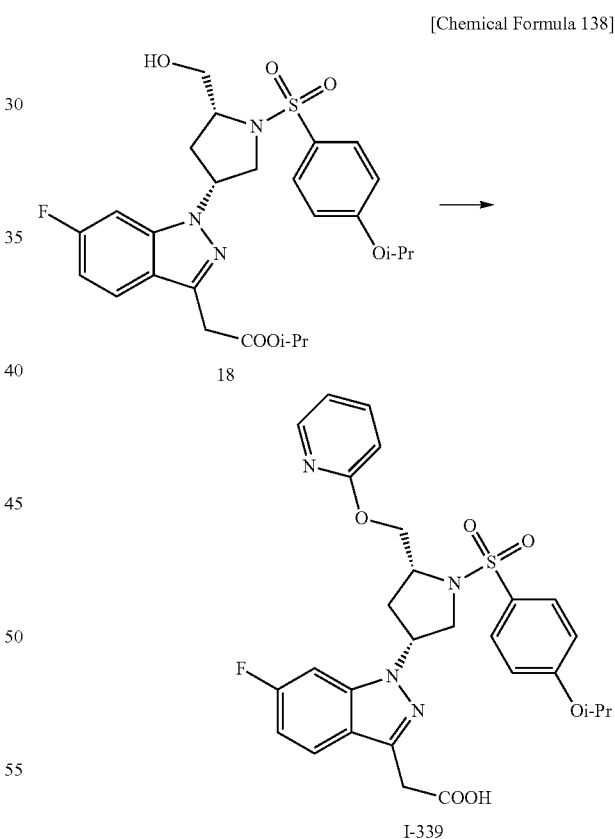

I-339

To a solution of Compound 18 (60.0 mg, 0.112 mmol) in THF (0.5 mL) were added pyridine 2-ol (26.7 mg, 0.281 mmol), 2.2 mol/L DEAD in toluene (0.051 mL, 0.112 mmol), and triphenylphosphine (29.5 mg, 0.112 mmol) at 0° C., and the mixture was stirred overnight at room temperature. To the reaction mixture was added water, and the mixture was extracted with ethyl acetate. The organic layer was washed by brine, and concentrated in vacuo. The resulting residue was purified by silica gel column chromatography (hexane-ethyl acetate).

The obtained compound was hydrolyzed according to the method described in the general synthetic procedures to give Compound I-339.

LC/MS (Condition B) RT=2.27, [M+H]$^+$=569.

EXAMPLE 42

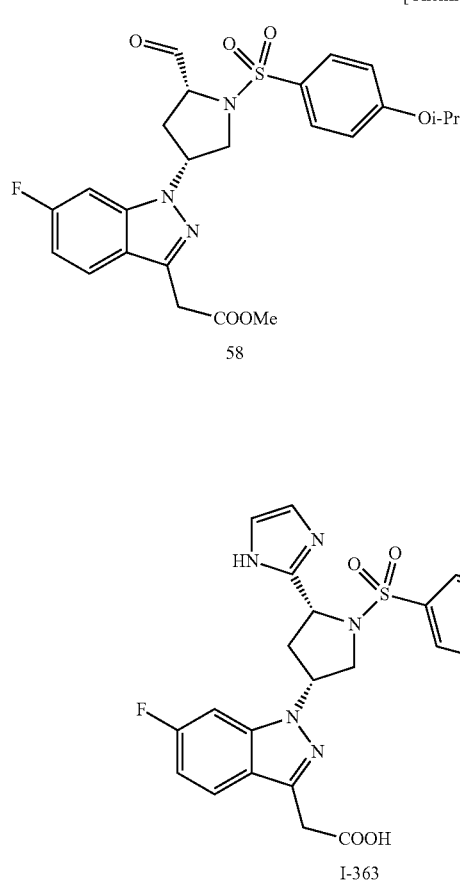

To a solution of Compound 58 (181 mg, 0.359 mmol) in methanol (2.0 mL) were added 8.8 mol/L aqueous glyoxal (0.41 mL, 3.59 mmol) and 28% aqueous ammonia (0.28 mL, 3.59 mmol), and the mixture was stirred for overnight at room temperature. To the reaction mixture was added water, and the mixture was extracted with ethyl acetate. The organic layer was washed by brine, and concentrated in vacuo. The resulting residue was purified by silica gel column chromatography (hexane-ethyl acetate).

The obtained compound was hydrolyzed according to the method described in the general synthetic procedures to give Compound I-363.

$^1$H-NMR (DMSO-D6) δ: 7.75-7.73 (4H, m), 7.34 (1H, d, J=9.8 Hz), 7.13 (2H, d, J=8.5 Hz), 7.03 (1H, t, J=9.2 Hz), 6.94 (1H, s), 4.81-4.77 (3H, m), 3.92 (3H, s), 3.80 (1H, t, J=9.9 Hz), 2.72 (2H, dt, J=22.8, 8.8 Hz), 1.33 (6H, d, J=5.8 Hz).

EXAMPLE 43

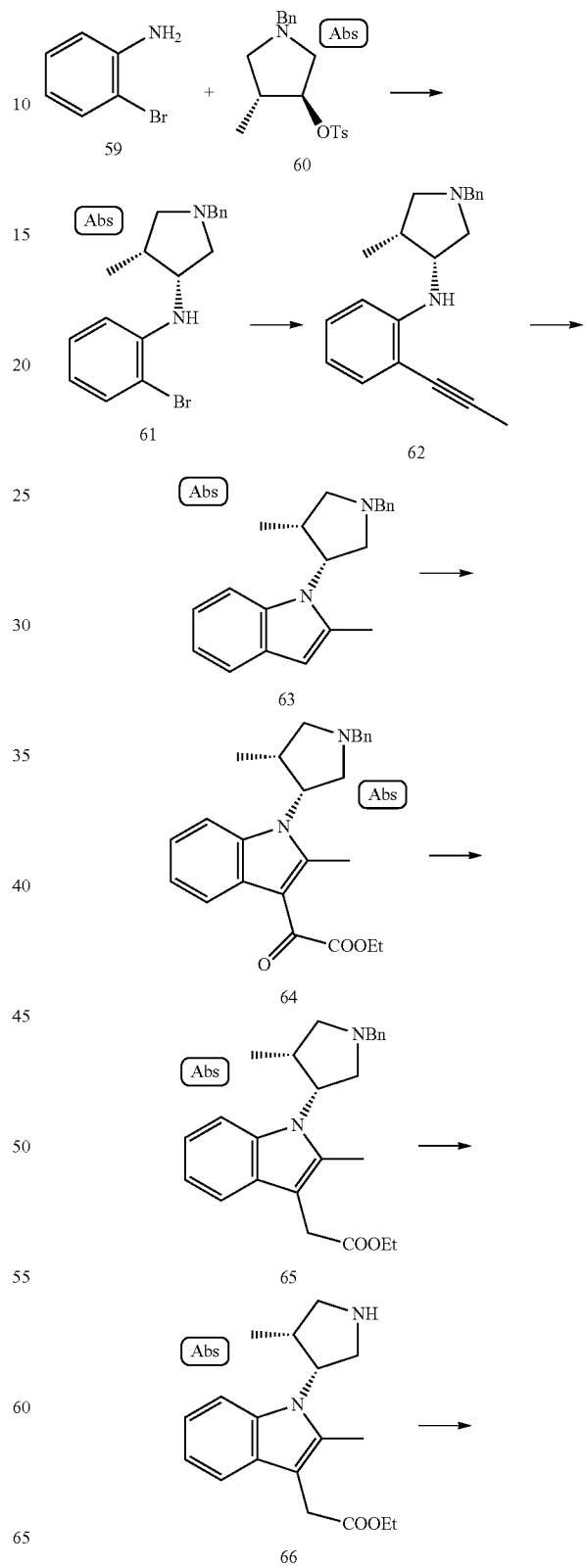

-continued

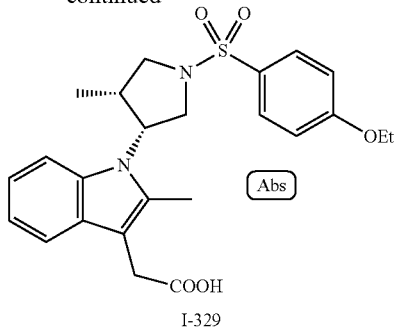

I-329

Step 1

To a solution of Compound 59 (996 mg, 5.79 mmol) in NMP (23 ml) was added sodium hydride (347 mg, 8.68 mmol) at 0° C., and the mixture was stirred for 30 minutes at room temperature. Then, Compound 60 (2 g, 5.79 mmol) was added to the mixture, and the resulting mixture was stirred for 2 hours at 80° C. The reaction mixture was diluted with ethyl acetate, and washed by brine. The organic layer was dried over anhydrous magnesium sulphate, and concentrated in vacuo. The resulting residue was purified by silica gel column chromatography (hexane-ethyl acetate) to give Compound 61 (1.05 g, Yield 53%).

LC/MS (Condition B) RT=1.54, [M+H]$^+$=345.

Step 2

The solution of Compound 61 (1 g, 2.90 mmol), (1-propynyl)tributylstannane (0.881 ml, 2.90 mmol) and tetrakis (triphenylphosphine) palladium (167 mg, 0.145 mmol) in toluene (10 ml) was stirred for 2 hours at 140° C. by using the microwave reactor. The reaction mixture was diluted with ethyl acetate, and washed by saturated aqueous potassium fluoride. The organic layer was dried over anhydrous magnesium sulphate, and concentrated in vacuo. The resulting residue was purified by silica gel column chromatography (hexane-ethyl acetate) to give Compound 62 (742 mg, Yield 84%).

LC/MS (Condition B) RT=1.58, [M+H]$^+$=305.

Step 3

The solution of Compound 62 (616 mg, 2.02 mmol) and copper iodide (39 mg, 0.20 mmol) in DMF (5 ml) was stirred for 4 hours at 160° C. by using the microwave reactor. The reaction mixture was diluted with ethyl acetate, and washed by brine. The organic layer was dried over anhydrous magnesium sulphate, and concentrated in vacuo. The resulting residue was purified by silica gel column chromatography (hexane-ethyl acetate) to give Compound 63 (322 mg, Yield 52%).

LC/MS (Condition B) RT=1.60, [M+H]$^+$=305.

Step 4

To a solution of Compound 63 (322 mg, 1.06 mmol) in THF (4 ml) was added oxalyl chloride (116 ml, 1.32 mmol) at 0° C., and the mixture was stirred for 1 hour at room temperature. To the mixture was added ethanol (1.2 ml, 21 mmol), and the resulting mixture was stirred for additional 1 hour at room temperature. To the reaction mixture was added saturated aqueous sodium hydrogencarbonate, and the resulting mixture was extracted with ethyl acetate. The organic layer was dried over anhydrous magnesium sulphate, and concentrated in vacuo. The resulting residue was purified by silica gel column chromatography (hexane-ethyl acetate) to give Compound 64 (335 mg, Yield 78%).

LC/MS (Condition B) RT=1.71, [M+H]$^+$=405.

Step 5

To a solution of Compound 64 (139 mg, 0.34 mmol) in dichloromethane (2 ml) were added triethylsilane (165 ml, 1.03 mmol) and trifluoroacetic acid (0.529 ml, 6.87 mmol), and the mixture was stirred for 3 hours at room temperature. To the reaction mixture was added saturated aqueous sodium hydrogencarbonate, and extracted with ethyl acetate. The organic layer was dried over anhydrous magnesium sulphate, and the concentrated in vacuo. The resulting residue was purified by silica gel column chromatography (hexane-ethyl acetate) to give Compound 65 (118 mg, Yield 88%).

LC/MS (Condition B) RT=1.69, [M+H]$^+$=391.

Step 6

To a solution of Compound 65 (118 mg, 0.30 mmol) in THF (4 ml) was added Pd-Carbon (32 mg), and the mixture was stirred for 5 hours under hydrogen atmosphere at atmospheric pressure. The insoleble was filtered off and the filtrate was concentrated in vacuo to give Compound 66 (90 mg, Yield 99%).

LC/MS (Condition A) RT=1.36, [M+H]$^+$=301.

Step 7

Compound I-329 was synthesized according to the method described in the general synthetic procedures from Compound 66.

$^1$H-NMR (DMSO-D$_6$) δ: 0.33 (d, J=7.0 Hz, 3H), 1.39 (t, J=7.0 Hz, 3H), 2.28 (s, 3H), 2.44-2.46 (m, 1H), 2.99 (t, J=10.0 Hz, 1H), 3.56 (s, 2H), 3.65 (dd, J=10.2, 8.2 Hz, 1H), 3.77-3.82 (m, 2H), 4.16-4.20 (m, 2H), 5.16-5.19 (m, 1H), 6.79 (t, J=7.7 Hz, 1H), 6.94-6.96 (m, 2H), 7.21 (d, J=9.0 Hz, 2H), 7.40 (d, J=7.8 Hz, 1H), 7.85 (d, J=8.8 Hz, 2H), 12.11 (s, 1H).

According to the similar manner as described in the above Examples or in the general synthetic procedures, the following Examples were synthesized by using the commercially available compounds or the intermediates described in the above Reference Examples. The chemical structures and physical properties of the Examples are shown in the Tables 1 to 81.

TABLE 1

| No. | compound | ¹H-NMR δ ppm | [M + H] | RT | LC/MS condition |
|---|---|---|---|---|---|
| I-1 | | (DMSO-d$_6$) δ: 7.85-7.71 (3H, m), 7.40 (1H, d, J = 8.4 Hz), 7.15 (2H, d, J = 8.5 Hz), 6.99 (1H, t, J = 8.8 Hz), 5.02 (1H, q, J = 6.7 Hz), 4.81-4.73 (1H, m), 3.97-3.79 (4H, m), 3.41-3.33 (2H, m), 1.99-1.93 (1H, m), 1.33 (6H, d, J = 6.0 Hz), 0.67 (3H, d, J = 6.3 Hz). | 476 | 2.21 | P |
| I-2 | | (DMSO-d$_6$) δ: 7.68-7.52 (4H, m), 7.42 (1H, d, J = 10.61 Hz), 7.26-7.21 (1H, br m), 7.02-6.93 (1H, br m), 6.89 (2H, d, J = 8.08 Hz), 5.30-5.22 (1H, m), 4.73-4.61 (1H, m), 4.37-4.29 (1H, m), 3.98-3.89 (1H, m), 3.72-3.15 (3H, m), 2.69-2.14 (2H, m), 1.33-1.19 (6H, m). | 505 | 1.74 | B |
| I-3 | | (CDCl$_3$) δ: 7.88 (2H, d, J = 8.59 Hz), 7.56-7.48 (1H, m), 7.47-7.40 (1H, m), 7.34-7.29 (1H, m), 7.04 (2H, d, J = 8.59 Hz), 6.93-6.82 (2H, m), 4.90-4.84 (1H, m), 4.75-4.67 (1H, m), 4.45-4.38 (1H, m), 4.31-4.24 (1H, m), 3.93-3.83 (1H, m), 3.80-3.73 (1H, m), 3.71-3.63 (1H, m), 2.67-2.59 (1H, m), 2.57-2.49 (1H, m), 1.44-1.38 (6H, m). | 505 | 1.87 | B |
| I-4 | | | 519 | 1.81 | B |

TABLE 1-continued
| No. | compound | ¹H-NMR δ ppm | [M + H] | RT | LC/MS condition |
|---|---|---|---|---|---|
| I-5 | 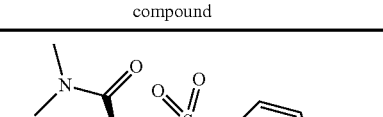 | | 533 | 1.84 | B |
TABLE 2
| No. | compound | ¹H-NMR δ ppm | [M + H] | RT | LC/MS condition |
|---|---|---|---|---|---|
| I-6 | | | 547 | 2.02 | B |
| I-7 | | (DMSO-d₆) δ: 7.89-7.54 (4H, m), 7.20-6.92 (3H, m), 5.49-5.41 (1H, m), 5.06-4.99 (1H, m), 4.76-4.64 (1H, m), 3.96-3.61 (4H, m), 2.89-2.72 (2H, m), 1.31 (6H, d, J = 5.56 Hz). | 487 | 2.09 | B |

TABLE 2-continued
| No. | compound | ¹H-NMR δ ppm | [M + H] | RT | LC/MS condition |
|---|---|---|---|---|---|
| I-8 | 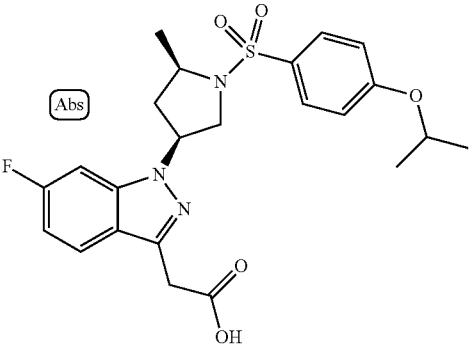 [SMILES: CC(C)Oc1ccc(S(=O)(=O)N2C[C@@H](n3nc(CC(=O)O)c4ccc(F)cc43)C[C@H]2C)cc1] | (CDCl₃) δ: 7.83 (2H, d, J = 8.08 Hz), 7.64-7.56 (1H, m), 7.02 (2H, d, J = 8.08 Hz), 6.96-6.88 (1H, m), 6.79 (1H, d, J = 8.08 Hz), 4.73-4.62 (1H, m), 4.41-4.29 (1H, m), 4.01-3.81 (4H, m), 3.75-3.66 (1H, m), 2.52-2.41 (1H, m), 2.36-2.25 (1H, m), 1.49 (3H, d, J = 5.56 Hz), 1.40 (6H, d, J = 5.56 Hz). | 476 | 2.26 | B |
| I-9 | 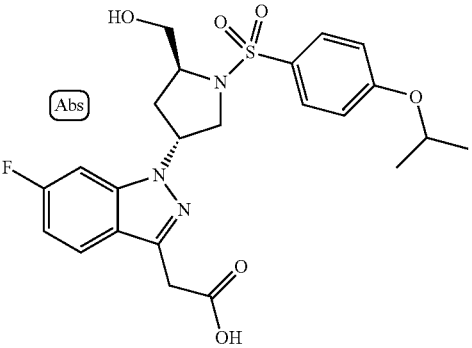 [SMILES: CC(C)Oc1ccc(S(=O)(=O)N2C[C@H](n3nc(CC(=O)O)c4ccc(F)cc43)C[C@H]2CO)cc1] | (CDCl₃) δ: 7.61-7.51 (3H, m), 6.96-6.88 (2H, m), 6.78 (2H, d, J = 8.59 Hz), 5.06-4.97 (1H, m), 4.63-4.54 (1H, m), 4.07-3.91 (3H, m), 3.82-3.66 (4H, m), 3.52-3.44 (1H, m), 2.68-2.57 (1H, m), 2.40-2.28 (1H, m), 1.40-1.34 (6H, m). | 492 | 1.87 | B |
| I-10 | 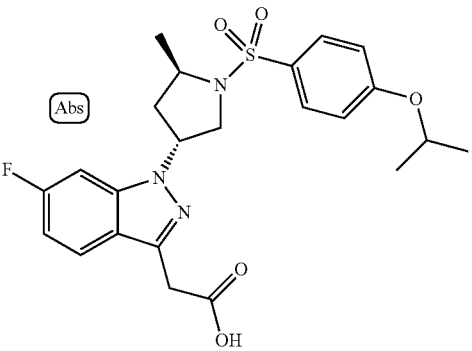 [SMILES: CC(C)Oc1ccc(S(=O)(=O)N2C[C@H](n3nc(CC(=O)O)c4ccc(F)cc43)C[C@H]2C)cc1] | (CDCl₃) δ: 7.62-7.50 (3H, m), 6.97-6.88 (2H, m), 6.78 (2H, d, J = 8.59 Hz), 5.01-4.91 (1H, m), 4.62-4.53 (1H, m), 4.06-3.98 (1H, m), 3.97-3.90 (1H, m), 3.83 (2H, s), 3.66-3.58 (1H, m), 3.53-3.44 (1H, m), 2.74-2.63 (1H, m), 2.09-2.00 (1H, m), 1.51 (3H, d, J = 6.06 Hz), 1.39-1.32 (6H, m). | 476 | 2.17 | B |

TABLE 3

| No. | compound | ¹H-NMR δ ppm | [M + H] | RT | LC/MS condition |
|---|---|---|---|---|---|
| I-11 | | (CDCl₃) δ: 7.83 (2H, d, J = 8.08 Hz), 7.63-7.56 (1H, m), 7.04 (2H, d, J = 8.08 Hz), 6.94-6.85 (1H, m), 6.76 (1H, d, J = 8.59 Hz), 4.73-4.64 (1H, m), 4.39-4.27 (1H, m), 3.98-3.67 (8H, m), 2.56-2.45 (1H, m), 2.44-2.32 (1H, m), 1.40 (6H, d, J = 5.56 Hz). | 492 | 2 | B |
| I-12 | | (CDCl₃) δ: 7.74-7.57 (3H, m), 7.06-6.89 (4H, m), 5.14-4.91 (1H, m), 4.82-4.70 (1H, m), 4.69-4.57 (1H, m), 4.26-4.15 (1H, m), 4.02-3.92 (3H, m), 2.91-2.61 (2H, m), 2.50-2.22 (2H, m), 1.38 (6H, d, J = 5.56 Hz). | 494 | 2.18 | B |
| I-13 | | (CDCl₃) δ: 7.84 (2H, d, J = 8.59 Hz), 7.63-7.57 (1H, m), 7.03 (2H, d, J = 8.59 Hz), 6.96-6.87 (1H, m), 6.78 (1H, d, J = 8.59 Hz), 4.71-4.58 (3H, m), 4.47-4.34 (1H, m), 4.24-4.08 (1H, m), 3.97 (2H, s), 3.91-3.82 (1H, m), 3.74-3.60 (1H, m), 2.70-2.57 (1H, m), 2.52-2.39 (1H, m), 1.40 (6H, d, J = 5.05 Hz). | 494 | 2.22 | B |
| I-14 | | | 501 | 2.04 | B |

TABLE 3-continued
| No. | compound | ¹H-NMR δ ppm | [M + H] | RT | LC/MS condition |
|---|---|---|---|---|---|
| I-15 | 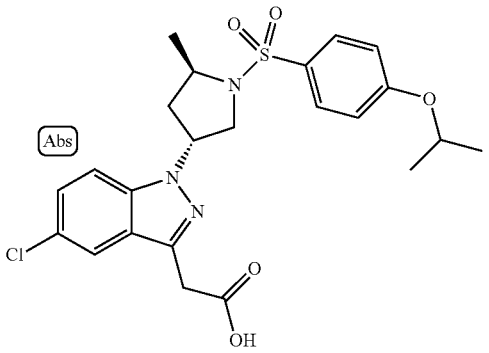 [SMILES: CC(C)Oc1ccc(S(=O)(=O)N2C[C@H](n3nc(CC(=O)O)c4cc(Cl)ccc43)C[C@H]2C)cc1] | (CDCl₃) δ: 7.61-7.51 (3H, m), 7.35-7.15 (2H, m), 6.74 (2H, d, J = 8.59 Hz), 5.05-4.94 (1H, m), 4.62-4.50 (1H, m), 4.07-3.89 (2H, m), 3.80 (2H, s), 3.66-3.58 (1H, m), 2.78-2.66 (1H, m), 2.10-1.98 (1H, m), 1.51 (3H, d, J = 6.06 Hz), 1.40-1.31 (6H, m). | 492 | 2.25 | B |
TABLE 4
| No. | compound | ¹H-NMR δ ppm | [M + H] | RT | LC/MS condition |
|---|---|---|---|---|---|
| I-16 | 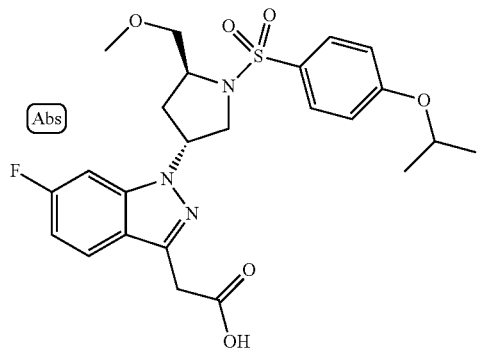 [SMILES: COC[C@@H]1C[C@@H](n2nc(CC(=O)O)c3ccc(F)cc32)CN1S(=O)(=O)c1ccc(OC(C)C)cc1] | (CDCl₃) δ: 7.67 (2H, d, J = 8.08 Hz), 7.61-7.52 (1H, m), 6.96-6.81 (4H, m), 5.18-5.07 (1H, m), 4.66-4.55 (1H, m), 4.16-3.99 (1H, m), 3.92-3.83 (3H, m), 3.73-3.56 (3H, m), 3.44 (3H, s), 2.58-2.46 (1H, m), 2.39-2.29 (1H, m), 1.38-1.34 (6H, m). | 506 | 2.15 | B |
| I-17 | 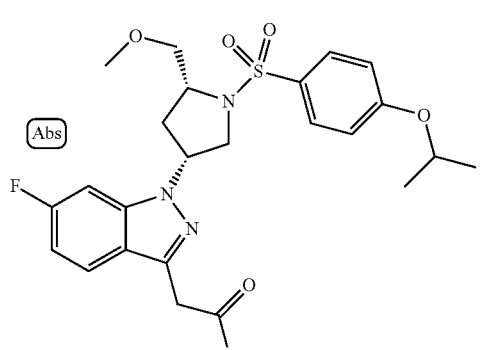 | (CDCl₃) δ: 7.83 (2H, d, J = 7.58 Hz), 7.64-7.54 (1H, m), 7.03 (2H, d, J = 7.58 Hz), 6.94-6.77 (2H, m), 4.73-4.62 (1H, m), 4.37-4.26 (1H, m), 4.16-3.53 (7H, m), 3.38 (3H, s), 2.62-2.50 (1H, m), 2.47-2.31 (1H, m), 1.39 (6H, d, J = 5.56 Hz). | 506 | 2.21 | B |

TABLE 4-continued
| No. | compound | ¹H-NMR δ ppm | [M + H] | RT | LC/MS condition |
|---|---|---|---|---|---|
| I-18 | 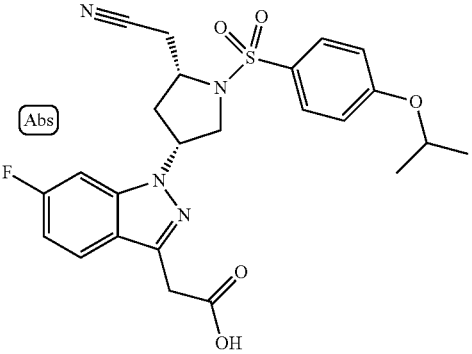 [SMILES: CC(C)Oc1ccc(S(=O)(=O)N2C[C@H](n3nc(CC(=O)O)c4ccc(F)cc43)C[C@@H]2CC#N)cc1] | | 501 | 2.05 | B |
| I-19 | 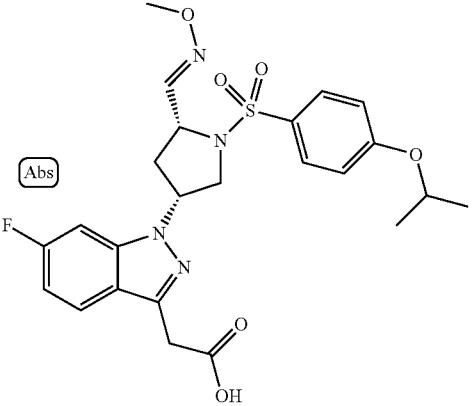 [SMILES: CO/N=C/[C@H]1C[C@@H](n2nc(CC(=O)O)c3ccc(F)cc32)CN1S(=O)(=O)c1ccc(OC(C)C)cc1] | | 519 | 2.24 | B |
| I-20 | 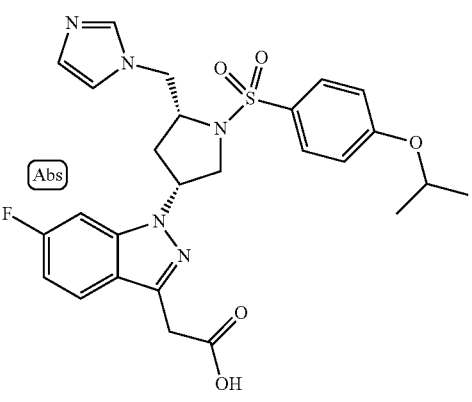 [SMILES: CC(C)Oc1ccc(S(=O)(=O)N2C[C@H](n3nc(CC(=O)O)c4ccc(F)cc43)C[C@@H]2Cn2ccnc2)cc1] | | 542 | 1.51 | B |

TABLE 5
| No. | compound | ¹H-NMR δ ppm | [M + H] | RT | LC/MS condition |
|---|---|---|---|---|---|
| I-21 | 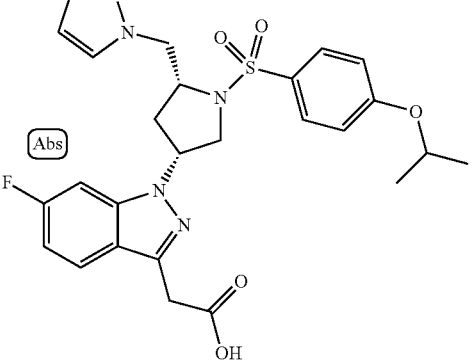 | (CDCl₃) δ: 7.84 (2H, d, J = 8.85 Hz), 7.62-7.50 (3H, m), 7.04 (2H, d, J = 8.85 Hz), 6.95-6.86 (1H, m), 6.64 (1H, dd, J = 9.15, 1.98 Hz), 6.29-6.26 (1H, m), 4.73-4.59 (3H, m), 4.40-4.17 (2H, m), 3.97 (2H, s), 3.85-3.74 (1H, m), 3.62-3.53 (1H, m), 2.55-2.43 (1H, m), 2.31-2.20 (1H, m), 1.42 (6H, d, J = 6.10 Hz). | 542 | 2.17 | B |
| I-22 | 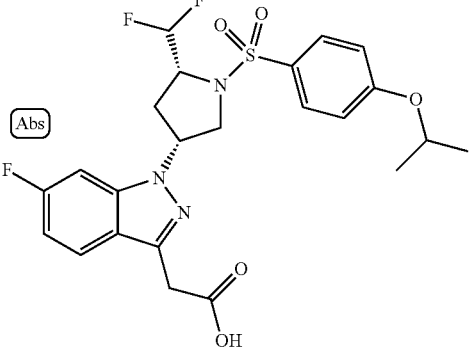 | (CDCl₃) δ: 7.83 (2H, d, J = 8.90 Hz), 7.60 (1H, dd, J = 8.73, 5.04 Hz), 7.05 (2H, d, J = 8.90 Hz), 6.97-6.88 (1H, m), 6.75 (1H, dd, J = 9.23, 1.68 Hz), 6.17 (1H, ddd, J = 57.75, 56.07, 2.52 Hz), 4.75-4.62 (1H, m), 4.41-4.16 (2H, m), 4.01-3.86 (3H, m), 3.70-3.59 (1H, m), 2.87-2.73 (1H, m), 2.51-2.38 (1H, m), 1.41 (6H, dd, J = 5.96, 1.43 Hz). | 512 | 2.29 | B |
| I-23 | 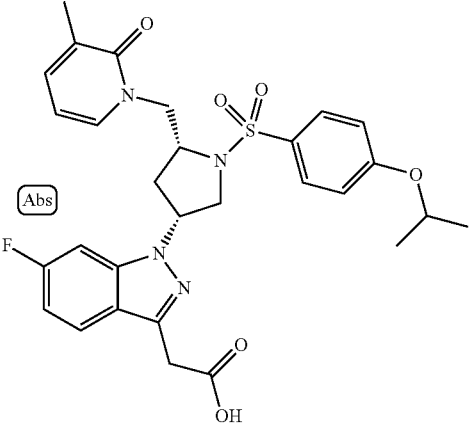 [SMILES: Cc1cccn(C[C@H]2C[C@@H](n3nc(CC(=O)O)c4ccc(F)cc43)CN2S(=O)(=O)c2ccc(OC(C)C)cc2)c1=O] | | 583 | 2.12 | B |
| I-24 | 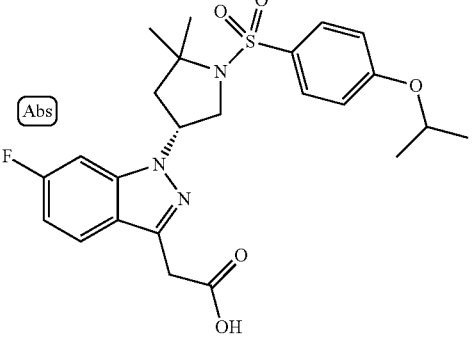 | (CDCl₃) δ: 7.67-7.57 (3H, m), 7.02-6.90 (2H, m), 6.84 (2H, d, J = 8.73 Hz), 5.05-4.94 (1H, m), 4.69-4.59 (1H, m), 3.97-3.87 (3H, m), 3.70 (1H, dd, J = 10.66, 5.96 Hz), 2.69-2.57 (1H, m), 2.23-2.05 (2H, m), 1.42 (6H, d, J = 6.04 Hz), 1.33-1.27 (3H, m), 1.09-1.01 (3H, m). | 490 | 2.29 | B |

TABLE 5-continued

| No. | compound | ¹H-NMR δ ppm | [M + H] | RT | LC/MS condition |
|---|---|---|---|---|---|
| I-25 | 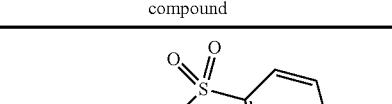 | (DMSO-d$_6$) δ: 7.69 (2H, d, J = 8.8 Hz), 7.67 (1H, d, J = 10.1 Hz), 7.46 (1H, dd, J = 10.1, 2.0 Hz), 7.08 (2H, d, J = 8.8 Hz), 6.99 (1H, dt, J = 12.8, 4.6 Hz), 5.69-5.58 (1H, m), 5.01-4.91 (1H, m), 4.80-4.67 (1H, m), 4.38-4.25 (1H, m), 3.84-3.69 (1H, m), 3.76 (2H, s), 3.55 (1H, dd, J = 10.3, 6.0 Hz), 3.49-3.40 (1H, m), 3.11 (1H, dd, J = 10.2, 5.0 Hz), 1.31 (6H, d, J = 6.1 Hz). | 478 | 1.92 | B |

TABLE 6

| No. | compound | ¹H-NMR δ ppm | [M + H] | RT | LC/MS condition |
|---|---|---|---|---|---|
| I-26 | | (CDCl$_3$) δ: 7.73 (2H, d, J = 8.7 Hz), 7.61 (1H, dd, J = 9.0, 4.8 Hz), 7.02-6.89 (2H, m), 6.94 (2H, d, J = 8.6 Hz), 5.33 (1H, dd, J = 52.4, 2.5 Hz), 5.09-4.95 (1H, m), 4.70-4.58 (1H, m), 3.98 (1H, dd, J = 10.7, 7.7 Hz), 3.86 (2H, s), 3.82 (1H, d, J = 3.4 Hz), 3.75-3.62 (2H, m), 1.38 (6H, d, J = 6.0 Hz). | 480 | 2.16 | B |
| I-27 | | (CDCl$_3$) δ: 7.79 (2H, d, J = 8.7 Hz), 7.63 (1H, dd, J = 8.9, 5.0 Hz), 7.03 (2H, d, J = 8.7 Hz), 6.97 (1H, t, J = 9.7 Hz), 6.88 (1H, d, J = 9.1 Hz), 5.13 (1H, t, J = 9.2 Hz), 4.71-4.63 (1H, m), 4.38 (1H, t, J = 9.5 Hz), 4.10 (2H, d, J = 17.6 Hz), 3.94 (2H, d, J = 1.2 Hz), 3.73 (1H, t, J = 10.2 Hz), 3.56 (1H, d, J = 18.0 Hz), 1.40 (6H, d, J = 6.0 Hz). | 476 | 2.07 | B |
| I-28 | | (DMSO-d$_6$) δ: 7.94-7.61 (4H, m), 7.26-7.04 (3H, m), 6.10-5.99 (1H, m), 4.78-4.51 (3H, m), 4.36-4.21 (2H, m), 4.03-3.88 (2H, m), 1.31-1.20 (6H, m). | 460 | 2.19 | B |

TABLE 6-continued
| No. | compound | ¹H-NMR δ ppm | [M + H] | RT | LC/MS condition |
|---|---|---|---|---|---|
| I-29 | | (DMSO-d₆) δ: 7.75 (2H, d, J = 8.5 Hz), 7.65 (1H, dd, J = 9.1, 5.4 Hz), 7.50 (1H, d, J = 9.8 Hz), 7.11 (2H, d, J = 8.1 Hz), 6.95 (1H, t, J = 9.1 Hz), 5.28 (1H, t, J = 5.9 Hz), 4.79-4.71 (1H, m), 3.85 (1H, dd, J = 11.0, 7.6 Hz), 3.61 (4H, dt, J = 31.7, 11.8 Hz), 3.11 (1H, t, J = 9.7 Hz), 1.33 (6H, d, J = 5.9 Hz), 0.29 (3H, d, J = 6.6 Hz). | 476 | 2.22 | B |
| I-30 | | (DMSO-d₆) δ: 7.80 (2H, d, J = 8.9 Hz), 7.69 (1H, dd, J = 8.7, 5.5 Hz), 7.49 (1H, d, J = 9.4 Hz), 7.14 (2H, d, J = 9.1 Hz), 7.02-6.95 (1H, m), 5.33-5.24 (1H, m), 4.83-4.71 (1H, m), 4.15-4.05 (1H, m), 3.86-3.69 (3H, m), 3.59 (1H, dd, J = 10.0, 5.3 Hz). | 492 | 2.07 | B |
TABLE 7
| No. | compound | ¹H-NMR δ ppm | [M + H] | RT | LC/MS condition |
|---|---|---|---|---|---|
| I-31 | 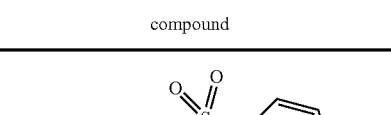 | (CDCl₃) δ: 7.75 (2H, d, J = 8.4 Hz), 7.59 (1H, dd, J = 8.6, 4.8 Hz), 7.00-6.85 (2H, m), 6.97 (2H, d, J = 8.4 Hz), 4.69-4.61 (1H, m), 4.41 (1H, q, J = 7.9 Hz), 3.92 (2H, s), 3.79 (1H, t, J = 8.8 Hz), 3.74-3.55 (2H, m), 3.06 (1H, t, J = 9.1 Hz), 2.85-2.71 (1H, m), 1.39 (6H, d, J = 5.9 Hz), 0.99 (3H, d, J = 6.7 Hz). | 476 | 2.23 | B |

TABLE 7-continued

| No. | compound | ¹H-NMR δ ppm | [M + H] | RT | LC/MS condition |
|---|---|---|---|---|---|
| I-32 | | (CDCl₃) δ: 7.80 (2H, d, J = 8.4 Hz), 7.56 (1H, dd, J = 8.8, 5.0 Hz), 7.00-6.86 (2H, m), 6.98 (2H, d, J = 8.7 Hz), 5.49 (1H, td, J = 16.8, 6.6 Hz), 4.97 (1H, t, J = 6.4 Hz), 4.86 (1H, d, J = 10.4 Hz), 4.73-4.60 (2H, m), 4.03 (1H, dd, J = 11.2, 7.2 Hz), 3.78-3.67 (2H, m), 3.75 (2H, s), 3.35 (1H, t, J = 9.8 Hz), 2.72-2.55 (1H, m), 1.70-1.57 (1H, m), 1.53-1.43 (1H, m), 1.39 (6H, dd, J = 5.9, 2.1 Hz). | 502 | 2.33 | B |
| I-33 | | (CDCl₃) δ: 7.81 (2H, d, J = 8.7 Hz), 7.53 (1H, d, J = 8.5 Hz), 7.33 (1H, s), 7.10 (1H, t, J = 4.3 Hz), 6.99 (2H, d, J = 8.8 Hz), 4.95 (1H, td, J = 7.1, 2.7 Hz), 4.72-4.60 (1H, m), 4.04 (1H, dd, J = 11.2, 7.2 Hz), 3.81 (1H, dd, J = 11.3, 2.9 Hz), 3.74 (2H, d, J = 2.1, Hz), 3.68 (1H, dd, J = 9.0, 7.3 Hz), 3.23 (1H, t, J = 9.6 Hz), 2.76-2.58 (1H, m), 1.39 (6H, dd, J = 6.1, 1.8 Hz), 0.47 (3H, d, J = 6.9 Hz). | 492 | 2.33 | B |
| I-34 | | (DMSO-d₆) δ: 7.75 (2H, d, J = 7.9 Hz), 7.64 (1H, dd, J = 9.0, 5.5 Hz), 7.50 (1H, d, J = 9.2 Hz), 7.10 (2H, d, J = 8.1 Hz), 6.95 (1H, t, J = 9.2 Hz), 5.33 (1H, t, J = 6.3 Hz), 4.80-4.68 (1H, m), 3.89-3.80 (1H, m), 3.70-3.15 (5H, m), 1.32 (6H, dd, J = 5.6, 3.4 Hz), 2.39-2.22 (1H, m), 1.13-0.62 (3H, m), 0.57 (3H, t, J = 7.4 Hz), 0.52-0.37 (1H, m). | 504 | 2.4 | B |
| I-35 | | (DMSO-d₆) δ: 7.78 (2H, d, J = 8.1 Hz), 7.62 (1H, dd, J = 12.6, 8.6 Hz), 7.34 (1H, t, J = 7.3 Hz), 7.19-7.04 (3H, m), 5.41-5.30 (1H, m), 4.83-4.69 (1H, m), 3.95-3.82 (1H, m), 3.73-3.50 (4H, m), 3.20-3.07 (1H, m), 2.39-2.10 (1H, m), 1.34 (6H, d, J = 5.6 Hz), 0.29 (3H, d, J = 6.6 Hz). | 458 | 2.16 | B |

TABLE 8

| No. | compound | ¹H-NMR δ ppm | [M + H] | RT | LC/MS condition |
|---|---|---|---|---|---|
| I-36 | | (DMSO-d₆) δ: 7.75 (2H, d, J = 8.4 Hz), 7.65 (1H, dd, J = 8.9, 5.4 Hz), 7.50 (1H, d, J = 9.9 Hz), 7.11 (2H, d, J = 8.4 Hz), 6.95 (1H, t, J = 8.9 Hz), 5.33-5.23 (1H, m), 4.82-4.67 (1H, m), 3.92-3.79 (1H, m), 3.73-3.49 (3H, m), 3.17-3.04 (1H, m), 2.52-2.35 (1H, m), 1.32 (6H, d, J = 5.6 Hz), 0.29 (3H, d, J = 6.4 Hz). | 476 | 2.23 | B |
| I-37 | | (DMSO-d₆) δ: 7.75 (2H, d, J = 8.8 Hz), 7.65 (1H, dd, J = 8.8, 5.3 Hz), 7.50 (1H, dd, J = 10.1, 2.1 Hz), 7.11 (2H, d, J = 8.8 Hz), 6.95 (1H, td, J = 9.0, 2.1 Hz), 5.32-5.22 (1H, m), 4.83-4.67 (1H, m), 3.90-3.80 (1H, m), 3.73-3.49 (4H, m), 3.17-3.05 (1H, m), 1.33 (6H, dd, J = 5.9, 1.8 Hz), 0.29 (3H, d, J = 6.7 Hz). | 476 | 2.23 | B |
| I-38 | | (CDCl₃) δ: 7.82 (2H, d, J = 8.7 Hz), 7.55 (1H, dd, J = 8.2, 4.8 Hz), 6.99 (2H, d, J = 9.0 Hz), 6.96-6.85 (2H, m), 5.08-4.96 (2H, m), 4.93-4.76 (2H, m), 4.74-4.60 (1H, m), 4.10-4.00 (1H, m), 3.83 (1H, dd, J = 11.8, 2.5 Hz), 3.74 (2H, d, J = 2.3 Hz), 3.70 (1H, d, J = 7.8 Hz). 3.48 (1H, t, J = 9.8 Hz), 3.28-3.13 (1H, m), 1.40 (6H, dd, J = 6.1, 2.3 Hz). | 488 | 2.27 | B |
| I-39 | | | 490 | 2.32 | B |

TABLE 8-continued
| No. | compound | ¹H-NMR δ ppm | [M + H] | RT | LC/MS condition |
|---|---|---|---|---|---|
| I-40 | 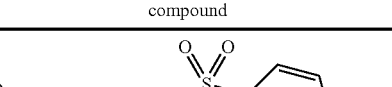 | | 506 | 1.94 | B |
TABLE 9
| No. | compound | ¹H-NMR δ ppm | [M + H] | RT | LC/MS condition |
|---|---|---|---|---|---|
| I-41 | | | 502 | 2.35 | B |
| I-42 | | | 494 | 2.17 | B |
| I-43 | | | 474 | 2.18 | B |

TABLE 9-continued

| No. | compound | ¹H-NMR δ ppm | [M + H] | RT | LC/MS condition |
|---|---|---|---|---|---|
| I-44 | | | 526 | 2.24 | B |
| I-45 | | | 508 | 2.21 | B |

TABLE 10

| No. | compound | ¹H-NMR δ ppm | [M + H] | RT | LC/MS condition |
|---|---|---|---|---|---|
| I-46 | | (CDCl$_3$) δ: 7.82 (2H, d, J = 8.69 Hz), 7.59 (1H, dd, J = 8.92, 5.11 Hz), 7.02 (2H, d, J = 8.85 Hz), 6.94 (1H, d, J = 7.02 Hz), 6.79 (1H, d, J = 9.00 Hz), 4.71-4.63 (1H, m), 4.35 (1H, t, J = 8.46 Hz), 4.00 (2H, s), 3.95 (1H, d, J = 7.47 Hz), 3.85 (1H, dd, J = 11.06, 7.24 Hz), 3.70 (1H, t, J = 10.45 Hz), 2.47 (1H, dd, J = 13.57, 7.02 Hz), 2.33 (1H, t, J = 9.07 Hz), 1.50 (3H, d, J = 6.25 Hz), 1.40 (6H, d, J = 6.10 Hz). | 476 | 2.24 | B |
| I-47 | | | 531 | 1.44 | B |

TABLE 10-continued

| No. | compound | ¹H-NMR δ ppm | [M + H] | RT | LC/MS condition |
|---|---|---|---|---|---|
| I-48 | | (DMSO-d₆) δ: 7.94 (2H, dd, J = 8.39, 5.04 Hz), 7.67 (1H, dd, J = 8.64, 5.12 Hz), 7.44-7.52 (3H, m), 6.97 (1H, t, J = 8.14 Hz), 5.28-5.33 (1H, m), 3.88-3.95 (1H, m), 3.65-3.53 (4H, m), 3.14 (1H, t, J = 10.16 Hz), 2.55-2.57 (1H, m), 0.31 (3H, d, J = 6.71 Hz). | 436 | 1.93 | A |
| I-49 | | (DMSO-d₆) δ: 12.40 (1H, s), 7.88 (2H, dd, J = 8.31, 1.43 Hz), 7.73-7.64 (3H, m), 7.51 (1H, d, J = 10.07 Hz), 6.96 (1H, t, J = 8.98 Hz), 5.30 (1H, t, J = 6.29 Hz), 3.88-3.95 (1H, m), 3.51-3.67 (4H, m), 3.14 (1H, t, J = 9.57 Hz), 2.53-2.58 (1H, m), 0.31 (3H, d, J = 6.71 Hz). | 452 | 2.03 | A |
| I-50 | | (DMSO-d₆) δ: 12.46 (1H, s), 7.78 (2H, d, J = 8.90 Hz), 7.66 (1H, dd, J = 8.73, 5.20 Hz), 7.50 (1H, d, J = 10.07 Hz), 7.13 (2H, d, J = 8.73 Hz), 6.96 (1H, dt, J = 12.48, 4.70 Hz), 5.28 (1H, t, J = 6.38 Hz), 4.15 (2H, q, J = 6.94 Hz), 3.86 (1H, dd, J = 11.16, 7.30 Hz), 3.52-3.63 (4H, m), 3.11 (1H, t, J = 9.82 Hz), 2.41-2.47 (1H, m), 1.29 (3H, q, J = 23.44 Hz), 0.29 (3H, d, J = 6.71 Hz). | 462 | 2.01 | A |

TABLE 11

| No. | compound | ¹H-NMR δ ppm | [M + H] | RT | LC/MS condition |
|---|---|---|---|---|---|
| I-51 | | (DMSO-d₆) δ: 12.44 (1H, s), 7.94 (2H, d, J = 8.23 Hz), 7.67 (1H, dd, J = 8.81, 5.46 Hz), 7.51 (1H, d, J = 10.07 Hz), 7.43 (1H, t, J = 72.52 Hz), 7.41 (2H, d, J = 8.73 Hz), 6.97 (1H, t, J = 8.64 Hz), 5.30 (1H, t, J = 6.13 Hz), 3.89 (1H, t, J = 5.62 Hz), 3.53-3.69 (4H, m), 3.15 (1H, t, J = 9.90 Hz), 2.54-2.56 (1H, m), 0.31 (3H, d, J = 6.71 Hz). | 484 | 2.02 | A |

TABLE 11-continued

| No. | compound | ¹H-NMR δ ppm | [M + H] | RT | LC/MS condition |
|---|---|---|---|---|---|
| I-52 | | (DMSO-d₆) δ: 12.43 (1H, s), 7.79 (1H, t, J = 8.64 Hz), 7.70 (1H, dd, J = 8.73, 5.20 Hz), 7.56 (1H, d, J = 9.90 Hz), 6.94-7.09 (3H, m), 5.37 (1H, t, J = 5.96 Hz), 4.85-4.76 (1H, m), 3.96 (1H, dd, J = 11.16, 7.30 Hz), 3.58-3.77 (4H, m), 3.25 (1H, t, J = 9.82 Hz), 2.65 (1H, dt, J = 17.63, 6.67 Hz), 1.36 (6H, d, J = 6.04 Hz), 0.38 (3H, d, J = 6.55 Hz). | 494 | 2.16 | A |
| I-53 | | (DMSO-d₆) δ: 12.48 (1H, s), 8.00 (1H, d, J = 8.23 Hz), 7.72 (1H, dd, J = 8.48, 5.46 Hz), 7.55 (1H, d, J = 10.07 Hz), 7.41 (1H, s), 7.23 (1H, d, J = 8.23 Hz), 6.99 (1H, t, J = 9.06 Hz), 5.38 (1H, t, J = 6.04 Hz), 4.04-3.95 (11H, m), 3.82-3.65 (4H, m), 2.73-2.60 (1H, m), 2.09-2.00 (1H, m), 1.09 (2H, d, J = 7.05 Hz), 0.86 (2H, d, J = 4.87 Hz), 0.39 (3H, d, J = 6.55 Hz). | 492 | 2.19 | A |
| I-54 | | (CDCl₃) δ: 7.90 (2H, d, J = 7.39 Hz), 7.69-7.58 (1H, m), 7.03 (2H, d, J = 7.39 Hz), 6.99-6.87 (2H, m), 5.07-4.91 (1H, m), 4.76-4.63 (1H, m), 4.30-4.12 (1H, m), 4.10-3.95 (3H, m), 2.14-1.86 (2H, m), 1.45-0.71 (10H, m). | 488 | 2.32 | B |
| I-55 | | | 529 | 1.85 | B |

TABLE 12

| No. | compound | ¹H-NMR δ ppm | [M + H] | RT | LC/MS condition |
|---|---|---|---|---|---|
| I-56 | | (DMSO-d₆) δ: 12.45 (1H, s), 8.63 (1H, d, J = 2.01 Hz), 8.11 (1H, dd, J = 8.73, 1.34 Hz), 7.65 (1H, dd, J = 8.64, 5.29 Hz), 7.52 (1H, d, J = 9.57 Hz), 6.94-7.01 (2H, m), 5.31 (1H, t, J = 6.63 Hz), 4.43 (2H, q, J = 7.05 Hz), 3.93 (1H, dd, J = 11.58, 7.05 Hz), 3.48-3.65 (4H, m), 3.13 (1H, t, J = 9.90 Hz), 2.54-2.62 (1H, m), 1.38 (3H, t, J = 6.97 Hz), 0.32 (3H, d, J = 6.55 Hz). | 463 | 1.99 | A |
| I-57 | | (DMSO-d₆) δ: 12.41 (1H, s), 8.63 (1H, s), 8.09 (1H, d, J = 8.90 Hz), 7.66 (1H, t, J = 6.80 Hz), 7.52 (1H, d, J = 10.24 Hz), 6.93-6.99 (2H, m), 5.29-5.41 (2H, m), 3.92 (1H, dd, J = 11.25, 6.88 Hz), 3.46-3.67 (4H, m), 3.13 (1H, t, J = 9.99 Hz), 2.54-2.65 (1H, m), 1.34-1.37 (6H, m), 0.33 (2.9H, d, J = 6.55 Hz). | 477 | 2.12 | A |
| I-58 | | (DMSO-d₆) δ: 12.46 (1H, s), 8.00 (1H, d, J = 7.22 Hz), 7.66-7.69 (2H, m), 7.54 (1H, d, J = 10.24 Hz), 7.42 (1H, d, J = 9.06 Hz), 6.98 (1H, t, J = 9.06 Hz), 5.35 (1H, t, J = 6.13 Hz), 4.90-4.83 (1H, m), 4.01 (1H, dd, J = 11.75, 7.05 Hz), 3.78 (1H, d, J = 11.08 Hz), 3.45-3.67 (3H, m), 3.22 (1H, t, J = 9.74 Hz), 2.63-2.77 (1H, m), 1.35 (6H, d, J = 5.88 Hz), 0.36 (3H, d, J = 5.88 Hz). | 501 | 2.11 | A |
| I-59 | | (CDCl₃) δ: 7.82 (2H, d, J = 8.24 Hz), 7.37 (1H, s), 6.98 (4H, d, J = 8.54 Hz), 5.35 (1H, s), 4.65 (1H, t, J = 5.72 Hz), 4.13-4.01 (1H, m), 3.91 (1H, d, J = 11.13 Hz), 3.71 (2H, s), 3.65 (1H, t, J = 8.08 Hz), 3.22 (1H, t, J = 9.30 Hz), 2.63 (1H, s), 1.38 (6H, d, J = 5.64 Hz), 0.48 (3H, d, J = 6.25 Hz). | 476 | 2.29 | B |

TABLE 12-continued
| No. | compound | ¹H-NMR δ ppm | [M + H] | RT | LC/MS condition |
|---|---|---|---|---|---|
| I-60 | 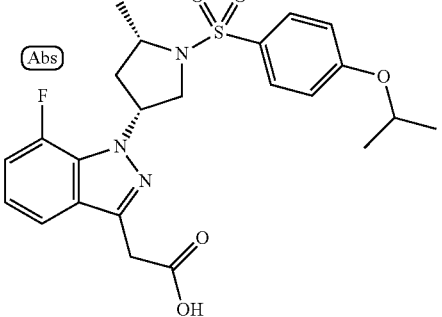 | (CDCl₃) δ: 7.81 (2H, d, J = 8.85 Hz), 7.40 (1H, d, J = 7.02 Hz), 7.01 (4H, t, J = 7.70 Hz), 4.76 (1H, s), 4.65 (1H, dd, J = 12.05, 6.10 Hz), 4.01 (2H, s), 3.96-3.90 (4H, m), 2.43 (1H, t, J = 12.58 Hz), 1.50 (3H, d, J = 6.25 Hz), 1.40 (6H, d, J = 5.95 Hz). | 476 | 2.3 | B |
TABLE 13
| No. | compound | ¹H-NMR δ ppm | [M + H] | RT | LC/MS condition |
|---|---|---|---|---|---|
| I-61 | 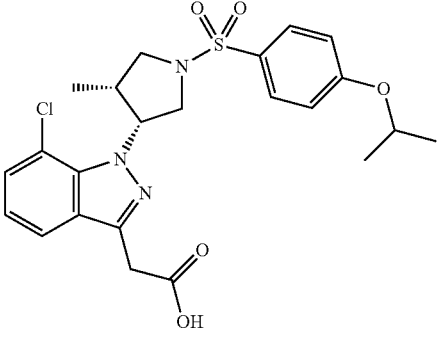 [SMILES: CC(C)Oc1ccc(S(=O)(=O)N2C[C@@H](C)[C@@H](n3nc(CC(=O)O)c4cccc(Cl)c43)C2)cc1] | (CDCl₃) δ: 7.82 (2H, d, J = 7.78 Hz), 7.51 (1H, d, J = 8.08 Hz), 7.32 (1H, d, J = 7.93 Hz), 7.05 (1H, d, J = 7.63 Hz), 6.98 (2H, d, J = 7.47 Hz), 6.04 (1H, s), 5.29 (2H, d, J = 1.37 Hz), 4.65 (1H, s), 3.99 (1H, t, J = 10.60 Hz), 3.71 (1H, s), 3.64 (2H, d, J = 7.47 Hz), 3.20 (1H, t, J = 9.61 Hz), 2.64 (1H, s), 1.38 (6H, d, J = 5.95 Hz), 0.47 (3H, d, J = 6.56 Hz). | 492 | 2.4 | B |
| I-62 | 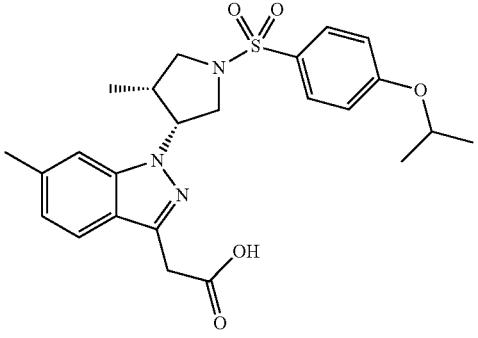 [SMILES: Cc1ccc2c(CC(=O)O)nn([C@H]3CN(S(=O)(=O)c4ccc(OC(C)C)cc4)C[C@H]3C)c2c1] | | 472 | 2.3 | B |
| I-63 | 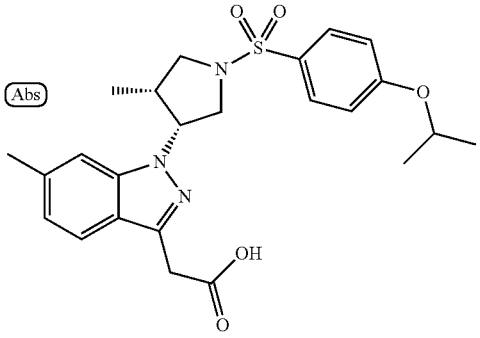 [SMILES: Cc1ccc2c(CC(=O)O)nn([C@H]3CN(S(=O)(=O)c4ccc(OC(C)C)cc4)C[C@H]3C)c2c1] | | 472 | 2.3 | B |

TABLE 13-continued

| No. | compound | ¹H-NMR δ ppm | [M + H] | RT | LC/MS condition |
|---|---|---|---|---|---|
| I-64 | | | 492 | 1.93 | B |
| I-65 | | | 519 | 2.2 | B |

TABLE 14

| No. | compound | ¹H-NMR δ ppm | [M + H] | RT | LC/MS condition |
|---|---|---|---|---|---|
| I-66 | | | 476 | 2.25 | B |
| I-67 | | | 458 | 2.09 | C |

TABLE 14-continued
| No. | compound | ¹H-NMR δ ppm | [M + H] | RT | LC/MS condition |
|---|---|---|---|---|---|
| I-68 | | | 494 | 2.15 | A |
| I-69 | | | 476 | 2.12 | A |
| I-70 | | (CDCl₃) δ: 7.75 (2H, d, J = 8.69 Hz), 7.38 (1H, dd, J = 13.95, 9.53 Hz), 7.05 (2H, t, J = 6.25 Hz), 6.96 (2H, d, J = 8.85 Hz), 4.83 (1H, q, J = 7.57 Hz), 4.69-4.61 (1H, m), 3.93 (2H, s), 3.87 (1H, t, J = 8.69 Hz), 3.67 (2H, t, J = 7.40 Hz), 3.08 (1H, t, J = 8.69 Hz), 2.80 (1H, t, J = 6.79 Hz), 1.39 (6H, t, J = 3.05 Hz), 1.01 (3H, d, J = 6.71 Hz). | 476 | 2.27 | B |
TABLE 15
| No. | compound | ¹H-NMR δ ppm | [M + H] | RT | LC/MS condition |
|---|---|---|---|---|---|
| I-71 | 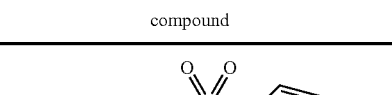 | | 488 | 2.23 | B |

TABLE 15-continued
| No. | compound | ¹H-NMR δ ppm | [M + H] | RT | LC/MS condition |
|---|---|---|---|---|---|
| I-72 | 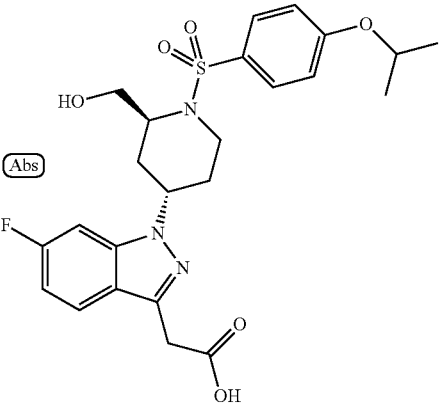 [SMILES: CC(C)Oc1ccc(S(=O)(=O)N2CC[C@H](n3nc(CC(=O)O)c4ccc(F)cc43)C[C@H]2CO)cc1] | (DMSO-d₆) δ: 7.79 (2H, d, J = 8.23 Hz), 7.69 (1H, s), 7.46 (1H, d, J = 10.74 Hz), 7.11 (2H, d, J = 8.73 Hz), 6.98 (1H, t, J = 8.48 Hz), 4.98 (1H, s), 4.78-4.75 (2H, m), 4.11-4.08 (1H, m), 3.84-3.81 (3H, m), 3.80-3.76 (2H, m), 3.59-3.49 (1H, m), 2.00-1.96 (1H, m), 1.94-1.80 (1H, m), 1.74-1.71 (1H, m), 1.31 (6H, d, J = 5.20 Hz). | 506 | 1.93 | B |
| I-73 | 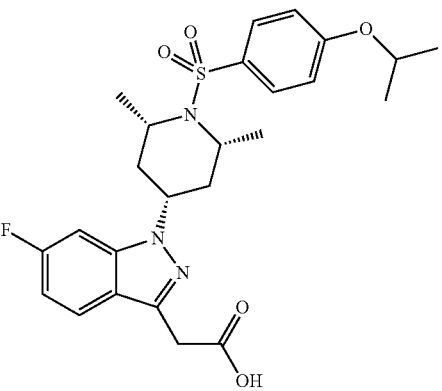 [SMILES: CC(C)Oc1ccc(S(=O)(=O)N2[C@H](C)C[C@H](n3nc(CC(=O)O)c4ccc(F)cc43)C[C@@H]2C)cc1] | | 504 | 2.32 | B |
| I-74 | 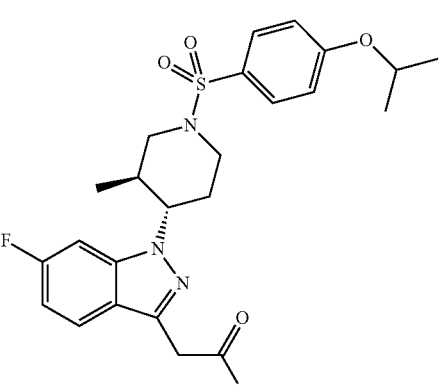 | | 490 | 2.31 | B |

TABLE 15-continued

| No. | compound | ¹H-NMR δ ppm | [M + H] | RT | LC/MS condition |
|---|---|---|---|---|---|
| I-75 | | | 490 | 2.3 | B |

TABLE 16

| No. | compound | ¹H-NMR δ ppm | [M + H] | RT | LC/MS condition |
|---|---|---|---|---|---|
| I-76 | | | 490 | 2.29 | B |
| I-77 | | | 450 | 2.08 | B |

TABLE 16-continued
| No. | compound | ¹H-NMR δ ppm | [M + H] | RT | LC/MS condition |
|---|---|---|---|---|---|
| I-78 | 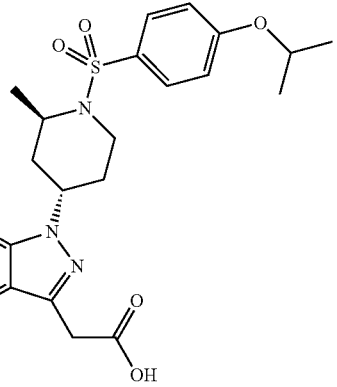 | | 490 | 2.27 | B |
| I-79 | 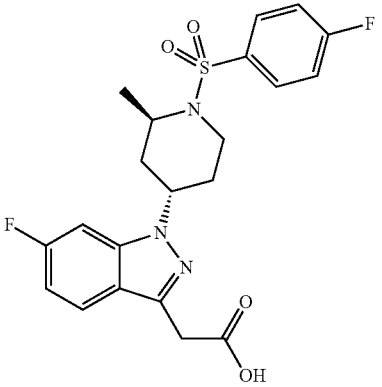 [SMILES: C[C@@H]1C[C@@H](n2nc(CC(=O)O)c3ccc(F)cc32)CCN1S(=O)(=O)c1ccc(F)cc1] | | 450 | 2.06 | B |
TABLE 17
| No. | compound | ¹H-NMR δ ppm | [M + H] | RT | LC/MS condition |
|---|---|---|---|---|---|
| I-80 | 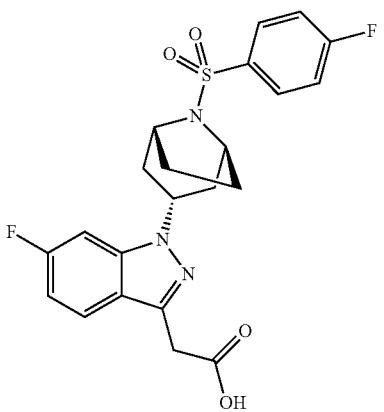 [SMILES: O=C(O)Cc1nn([C@@H]2C[C@H]3CC[C@@H](C2)N3S(=O)(=O)c2ccc(F)cc2)c2cc(F)ccc12] | | 462 | 2.1 | B |

TABLE 17-continued
| No. | compound | ¹H-NMR δ ppm [M + H] | RT | LC/MS condition |
|---|---|---|---|---|
| I-81 | 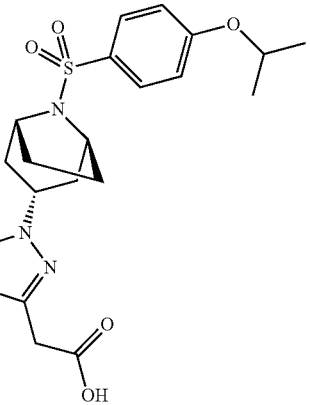 | 502 | 2.32 | B |
| I-82 | 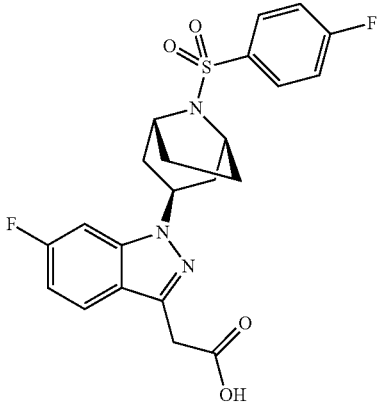 [SMILES: O=C(O)Cc1nn([C@H]2C[C@H]3CC[C@@H](C2)N3S(=O)(=O)c2ccc(F)cc2)c2cc(F)ccc12] | 462 | 2.15 | B |
| I-83 | 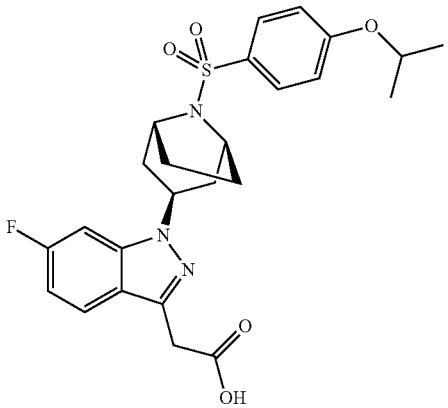 [SMILES: CC(C)Oc1ccc(S(=O)(=O)N2[C@@H]3CC[C@H]2C[C@@H](n2nc(CC(=O)O)c4ccc(F)cc42)C3)cc1] | 502 | 2.35 | B |

TABLE 18

| No. | compound | ¹H-NMR δ ppm | [M + H] | RT | LC/MS condition |
|---|---|---|---|---|---|
| I-84 | | | 492.45 | 1.86 | A |
| I-85 | (Rac) | | 494.26 | 2.15 | A |
| I-86 | | | 474.12 | 1.81 | A |
| I-87 | | | 488.15 | 1.9 | A |

TABLE 18-continued
| No. | compound | ¹H-NMR δ ppm | [M + H] | RT | LC/MS condition |
|---|---|---|---|---|---|
| I-88 | 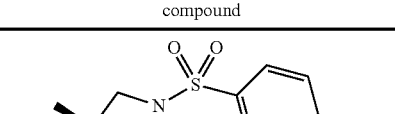 | | 476.16 | 2.09 | A |
TABLE 19
| No. | compound | ¹H-NMR δ ppm | [M + H] | RT | LC/MS condition |
|---|---|---|---|---|---|
| I-89 | | | 290.17 | 2.19 | A |
| I-90 | | | 494 | 2.26 | B |
| I-91 | | | 458 | 2.21 | B |

TABLE 19-continued
| No. | compound | ¹H-NMR δ ppm | [M + H] | RT | LC/MS condition |
|---|---|---|---|---|---|
| I-92 | 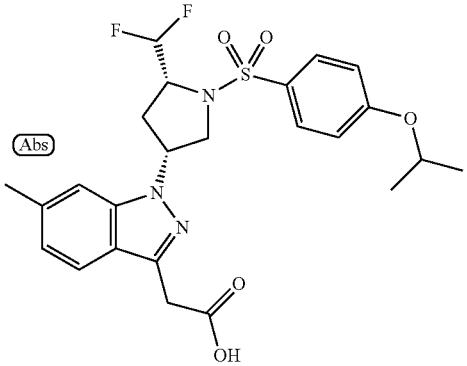 [SMILES: Cc1ccc2c(CC(=O)O)nn([C@@H]3C[C@H](C(F)F)N(S(=O)(=O)c4ccc(OC(C)C)cc4)C3)c2c1] | | 508 | 2.35 | B |
| I-93 | 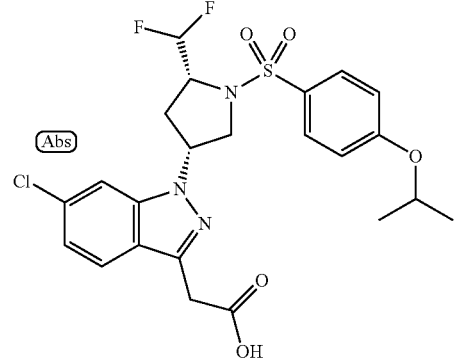 [SMILES: CC(C)Oc1ccc(S(=O)(=O)N2C[C@H](n3nc(CC(=O)O)c4ccc(Cl)cc43)C[C@@H]2C(F)F)cc1] | | 528 | 2.41 | B |
TABLE 20
| No. | compound | ¹H-NMR δ ppm | [M + H] | RT | LC/MS condition |
|---|---|---|---|---|---|
| I-94 | 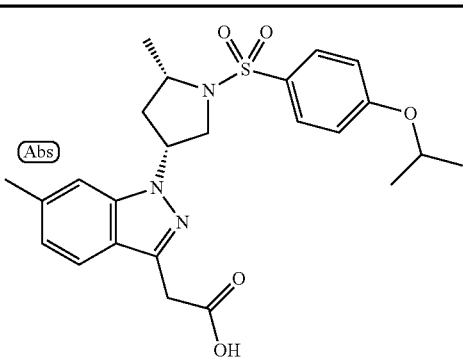 | | 472 | 2.32 | B |

TABLE 20-continued

| No. | compound | ¹H-NMR δ ppm | [M + H] | RT | LC/MS condition |
|---|---|---|---|---|---|
| I-95 | | | 492 | 2.39 | B |
| I-96 | | (DMSO-d₆) δ: 8.64 (1H, d, J = 1.8 Hz), 8.11 (1H, dd, J = 8.7, 1.4 Hz), 7.61 (2H, d, J = 8.4 Hz), 7.34 (1H, t, J = 7.7 Hz), 7.08 (1H, t, J = 7.7 Hz), 7.00 (1H, d, J = 8.9 Hz), 5.37 (1H, t, J = 6.0 Hz), 4.43 (2H, q, J = 7.0 Hz), 3.95 (1H, dd, J= 10.6, 7.1 Hz), 3.67-3.49 (4H, m), 3.19-3.11 (1H, m), 2.65-2.54 (1H, m), 1.39 (3H, t, J = 6.7 Hz), 0.29 (3H, d, J = 6.4 Hz). | 445.3 | 1.99 | P |
| I-97 | | (DMSO-d₆) δ: 7.79 (2H, d, J = 8.5 Hz), 7.61 (2H, t, J = 7.3 Hz), 7.33 (1H, t, J = 7.7 Hz), 7.15-7.05 (3H, m), 5.34 (2H, s), 4.16 (2H, q, J = 6.8 Hz), 3.93-3.86 (1H, m), 3.70-3.53 (4H, m), 3.17-3.10 (1H, m), 1.39 (3H, t, J = 6.7 Hz), 0.28 (3H, d, J = 6.6 Hz). | 444.3 | 2.03 | P |
| I-98 | | (DMSO-d₆) δ: 7.94 (2H, d, J = 8.7 Hz), 7.68-7.59 (2H, m), 7.43-7.31 (4H, m), 7.08 (1H, t, J = 7.5 Hz), 5.36 (1H, t, J = 5.9 Hz), 3.97-3.89 (1H, m), 3.70-3.54 (4H, m), 3.21-3.14 (1H, m), 0.29 (3H, d, J = 6.7 Hz). | 466.3 | 2.03 | P |

TABLE 21

| No. | compound | ¹H-NMR δ ppm | [M + H] | RT | LC/MS condition |
|---|---|---|---|---|---|
| I-99 | | (DMSO-d₆) δ: 8.63 (1H, d, J = 2.4 Hz), 8.09 (1H, dd, J = 8.8, 2.5 Hz), 7.61 (2H, d, J = 8.7 Hz), 7.34 (1H, t, J = 7.9 Hz), 7.08 (1H, t, J = 7.7 Hz), 6.95 (1H, d, J = 8.8 Hz), 5.41-5.33 (2H, m), 3.98-3.91 (1H, m), 3.68-3.47 (4H, m), 3.19-3.12 (1H, m), 2.65-2.53 (1H, m), 1.36 (6H, dd, J = 6.1, 3.4 Hz), 0.30 (3H, d, J = 6.7 Hz). | 459.3 | 2.14 | P |
| I-100 | | (DMSO-d₆) δ: 8.09 (1H, dd, J = 8.9, 5.1 Hz), 7.78 (2H, d, J = 8.7 Hz), 7.68 (1H, dd, J = 9.8, 2.0 Hz), 7.54 (1H, d, J = 16.3 Hz), 7.15-7.09 (3H, m), 6.57 (1H, d, J = 16.3 Hz), 5.47-5.40 (1H, m), 4.80-4.70 (1H, m), 3.92-3.86 (1H, m), 3.65-3.59 (2H, m), 3.28-3.19 (1H, m), 2.63-2.51 (1H, m), 1.30 (6H, dd, J = 7.6, 6.2 Hz), 0.36 (3H, d, J = 6.7 Hz). | 488.3 | 2.24 | P |
| I-101 | | (DMSO-d₆) δ: 7.78-7.71 (3H, m), 7.48 (1H, dd, J = 10.2, 2.0 Hz), 7.12 (2H, d, J = 8.5 Hz), 6.94 (1H, td, J = 9.0, 1.8 Hz), 5.30-5.25 (1H, m), 4.79-4.71 (1H, m), 3.89-3.83 (1H, m), 3.62-3.52 (2H, m), 3.20-3.13 (1H, m), 3.05-2.95 (1H, m), 2.88-2.78 (1H, m), 2.54-2.40 (1H, m), 1.32 (6H, dd, J = 6.0, 3.4 Hz), 0.29 (3H, d, J = 6.6 Hz). | 490.3 | 2.28 | P |
| I-102 | | (CDCl₃) δ: 7.87-7.81 (2H, m), 7.64 (1H, dd, J = 8.73, 5.04 Hz), 7.07-7.01 (2H, m), 7.00-6.88 (2H, m), 6.04-5.90 (1H, m), 5.33 (1H, d, J = 16.95 Hz), 5.18 (1H, d, J = 10.24 Hz), 4.78-4.55 (2H, m), 4.34 (1H, dd, J = 15.61, 7.72 Hz), 4.03-3.91 (3H, m), 3.77 (1H, dd, J = 11.25, 8.56 Hz), 2.64-2.47 (2H, m), 1.44 (6H, d, J = 6.21 Hz). | 488 | 2.29 | B |

TABLE 21-continued
| No. | compound | ¹H-NMR δ ppm | [M + H] | RT | LC/MS condition |
|---|---|---|---|---|---|
| I-103 | 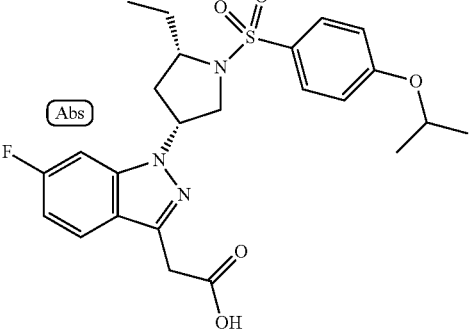 | (CDCl₃) δ: 7.87 (2H, d, J = 8.90 Hz), 7.67-7.57 (1H, br m), 7.07 (2H, d, J = 8.90 Hz), 6.96-6.85 (1H, br m), 6.74 (1H, d, J = 8.73 Hz), 4.78-4.67 (1H, m), 4.33-4.19 (1H, m), 4.02-3.82 (4H, m), 3.71-3.60 (1H, m), 2.51-2.24 (2H, m), 1.85-1.58 (2H, m), 1.45 (6H, dd, J = 6.04, 1.85 Hz), 1.04-0.83 (3H, m). | 490 | 2.37 | B |
TABLE 22
| No. | compound | ¹H-NMR δ ppm | [M + H] | RT | LC/MS condition |
|---|---|---|---|---|---|
| I-104 | 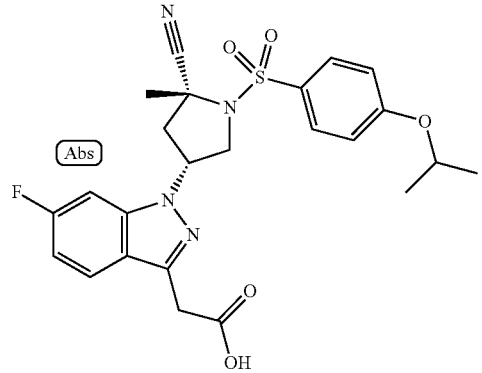 [SMILES: CC(C)Oc1ccc(S(=O)(=O)N2C[C@H](n3nc(CC(=O)O)c4ccc(F)cc43)C[C@]2(C)C#N)cc1] | (CDCl₃) δ: 7.83 (2H, d, J = 8.85 Hz), 7.62-7.51 (1H, m), 6.92 (5H, d, J = 8.85 Hz), 5.11-4.99 (1H, m), 4.67-4.57 (1H, m), 4.06-3.96 (1H, m), 3.84 (2H, s), 3.69-3.57 (1H, m), 3.28-3.15 (1H, m), 2.64-2.52 (1H, m), 2.01 (3H, s), 1.36 (6H, dd, J = 6.10, 1.53 Hz). | 501 | 2.15 | B |
| I-105 | 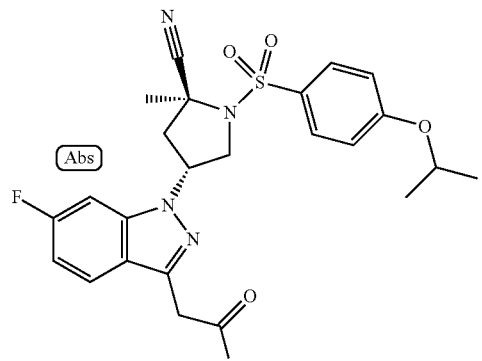 | (CDCl₃) δ: 7.84 (2H, d, J = 9.06 Hz), 7.66-7.59 (1H, m), 7.03-6.89 (4H, m), 5.12-5.04 (1H, m), 4.69-4.60 (1H, m), 3.96 (2H, br s), 3.88-3.82 (2H, m), 2.92-2.84 (2H, m), 2.01 (3H, s), 1.38 (6H, d, J = 6.04 Hz). | 501 | 2.24 | B |

TABLE 22-continued
| No. | compound | ¹H-NMR δ ppm | [M + H] | RT | LC/MS condition |
|---|---|---|---|---|---|
| I-106 | 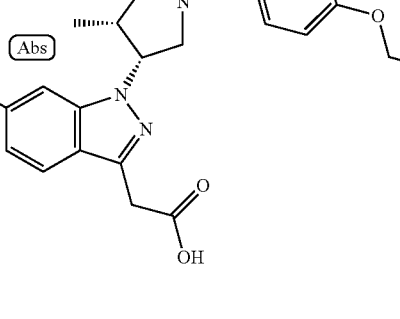 | | 462 | 2.12 | B |
| I-107 | 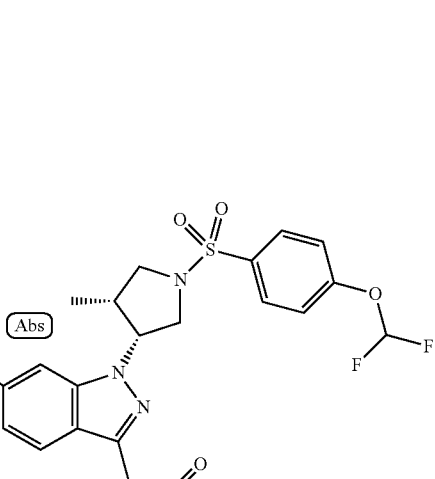 | | 484 | 2.11 | B |
| I-108 | 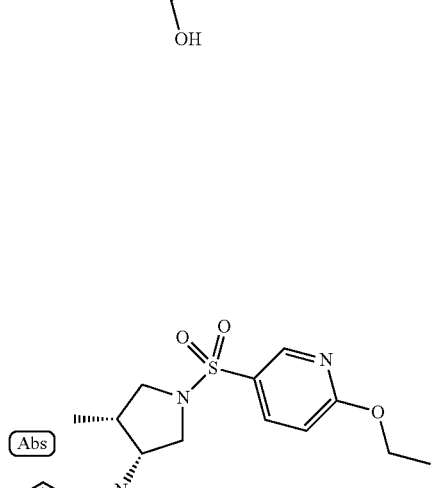 | | 463 | 2.09 | B |

TABLE 23
| No. | compound | ¹H-NMR δ ppm | [M + H] | RT | LC/MS condition |
|---|---|---|---|---|---|
| I-109 | 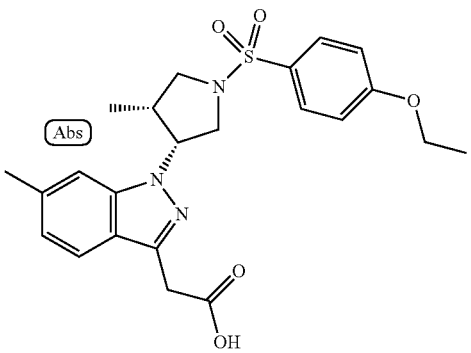 [SMILES: CCOc1ccc(S(=O)(=O)N2C[C@@H](C)[C@@H](n3nc(CC(=O)O)c4ccc(C)cc43)C2)cc1] | | 458 | 2.19 | B |
| I-110 | 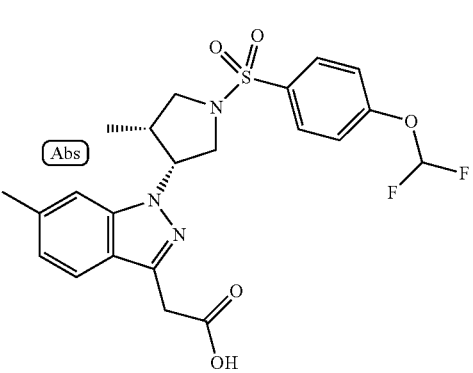 [SMILES: Cc1ccc2c(CC(=O)O)nn([C@H]3CN(S(=O)(=O)c4ccc(OC(F)F)cc4)C[C@H]3C)c2c1] | | 480 | 2.17 | B |
| I-111 | 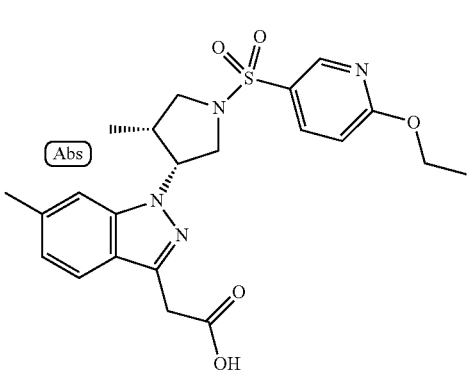 [SMILES: CCOc1ccc(S(=O)(=O)N2C[C@@H](C)[C@@H](n3nc(CC(=O)O)c4ccc(C)cc43)C2)cn1] | | 459 | 2.16 | B |
| I-112 | 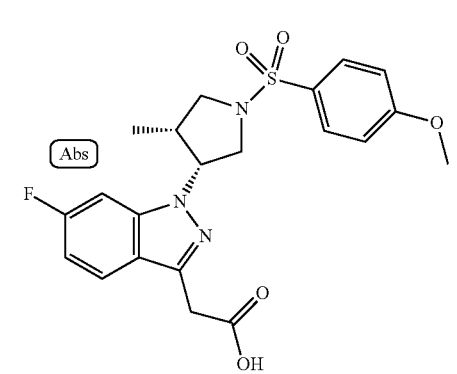 [SMILES: COc1ccc(S(=O)(=O)N2C[C@@H](C)[C@@H](n3nc(CC(=O)O)c4ccc(F)cc43)C2)cc1] | | 448 | 1.99 | B |

TABLE 23-continued
| No. | compound | ¹H-NMR δ ppm | [M + H] | RT | LC/MS condition |
|-----|----------|--------------|---------|-----|-----------------|
| I-113 | 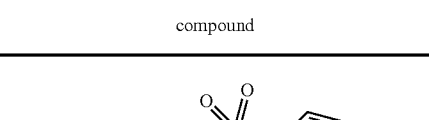 | | 458 | 2.2 | B |
TABLE 24
| No. | compound | ¹H-NMR δ ppm | [M + H] | RT | LC/MS condition |
|-----|----------|--------------|---------|-----|-----------------|
| I-114 | 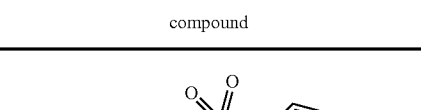 | | 472 | 2.3 | B |
| I-115 | 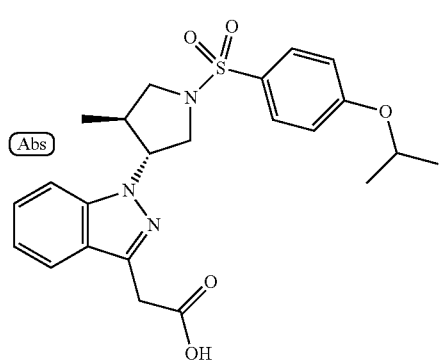 [SMILES: CC(C)Oc1ccc(S(=O)(=O)N2C[C@H](C)[C@@H](n3nc(CC(=O)O)c4ccccc43)C2)cc1] | | 458 | 2.2 | B |

TABLE 24-continued
| No. | compound | ¹H-NMR δ ppm [M + H] | RT | LC/MS condition |
|---|---|---|---|---|
| I-116 | 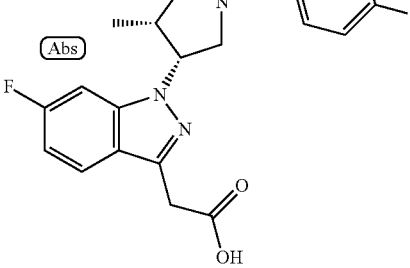 | 449 | 1.95 | B |
| I-117 | 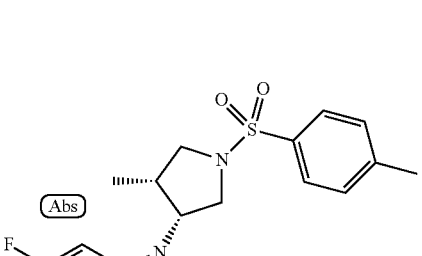 | 432 | 2.08 | B |
| I-118 | 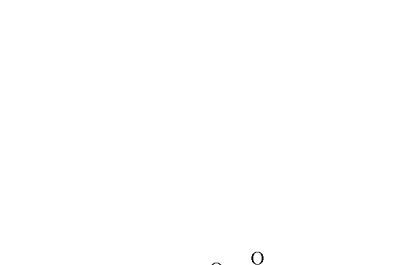 | 446 | 2.21 | B |

TABLE 25
| No. | compound | [M + H] | RT | LC/MS condition |
|---|---|---|---|---|
| I-119 | 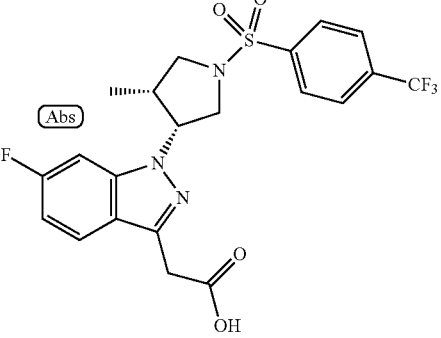 | 486 | 2.24 | B |
| I-120 | 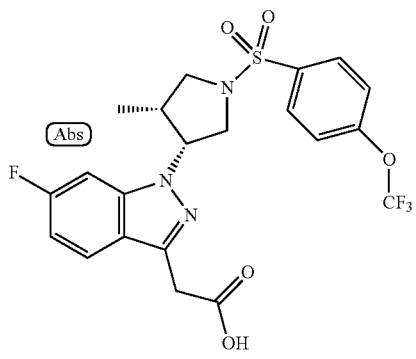 [SMILES: C[C@@H]1CN(S(=O)(=O)c2ccc(OC(F)(F)F)cc2)C[C@@H]1n1nc(CC(=O)O)c2ccc(F)cc21] | 502 | 2.28 | B |
| I-121 | 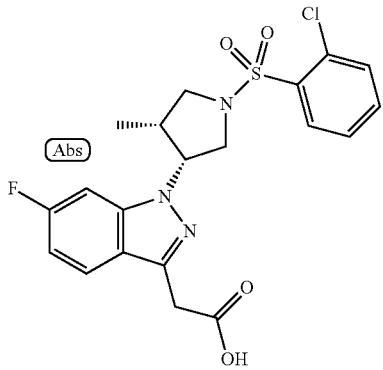 [SMILES: C[C@@H]1CN(S(=O)(=O)c2ccccc2Cl)C[C@@H]1n1nc(CC(=O)O)c2ccc(F)cc21] | 452 | 2.08 | B |
| I-122 | 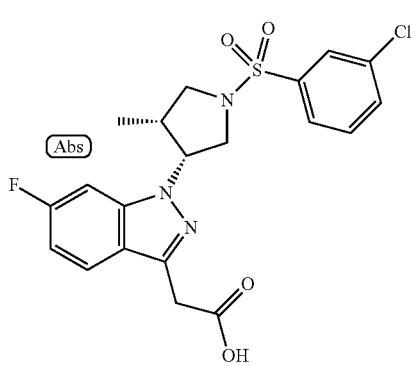 [SMILES: C[C@@H]1CN(S(=O)(=O)c2cccc(Cl)c2)C[C@@H]1n1nc(CC(=O)O)c2ccc(F)cc21] | 452 | 2.15 | B |

TABLE 25-continued
| No. | compound | ¹H-NMR δ ppm | [M + H] | RT | LC/MS condition |
|---|---|---|---|---|---|
| I-123 |  | | 477 | 2.23 | B |
TABLE 26
| No. | compound | ¹H-NMR δ ppm | [M + H] | RT | LC/MS condition |
|---|---|---|---|---|---|
| I-124 | | | 443 | 1.92 | B |
| I-125 | 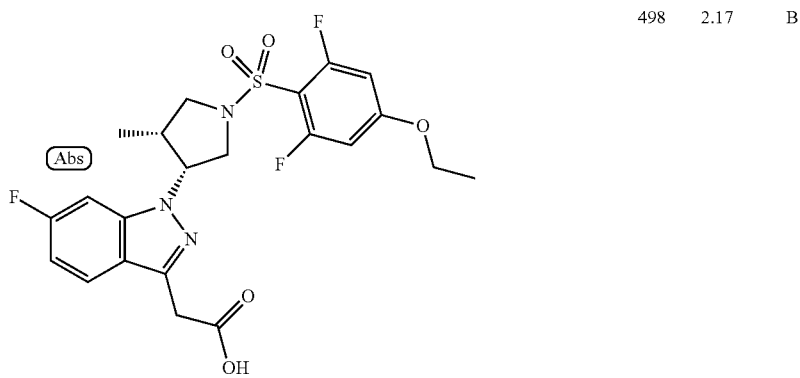 | | 498 | 2.17 | B |

TABLE 26-continued
| No. | compound | ¹H-NMR δ ppm | [M + H] | RT | LC/MS condition |
|-----|----------|--------------|---------|-----|-----------------|
| I-126 | 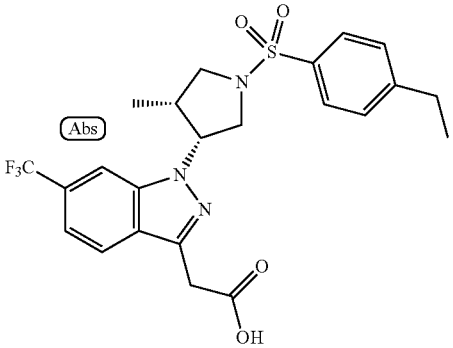 [SMILES: CCc1ccc(S(=O)(=O)N2C[C@@H](C)[C@@H](n3nc(CC(=O)O)c4ccc(C(F)(F)F)cc43)C2)cc1] | | 496 | 2.38 | B |
| I-127 | 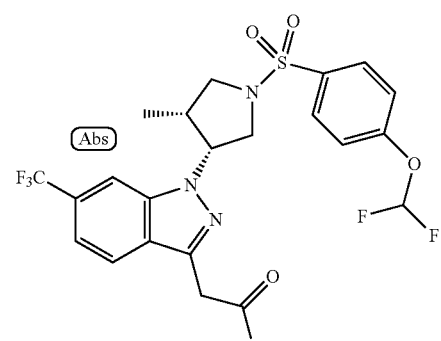 | | 534 | 2.28 | B |
| I-128 | 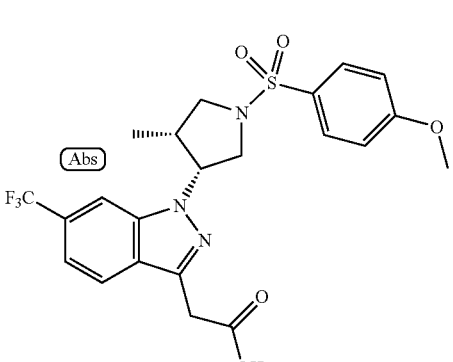 | | 498 | 2.19 | B |

TABLE 27
| No. | compound | ¹H-NMR δ ppm [M + H] | RT | LC/MS condition |
|---|---|---|---|---|
| I-129 | 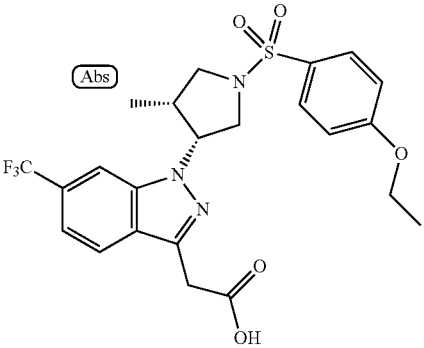 [SMILES: CCOc1ccc(S(=O)(=O)N2C[C@@H](C)[C@@H](n3nc(CC(=O)O)c4ccc(C(F)(F)F)cc43)C2)cc1] | 512 | 2.3 | B |
| I-130 | 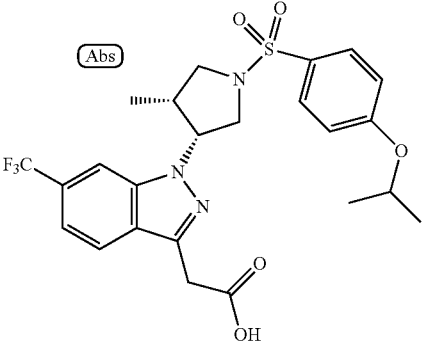 [SMILES: CC(C)Oc1ccc(S(=O)(=O)N2C[C@@H](C)[C@@H](n3nc(CC(=O)O)c4ccc(C(F)(F)F)cc43)C2)cc1] | 526 | 2.4 | B |
| I-131 | 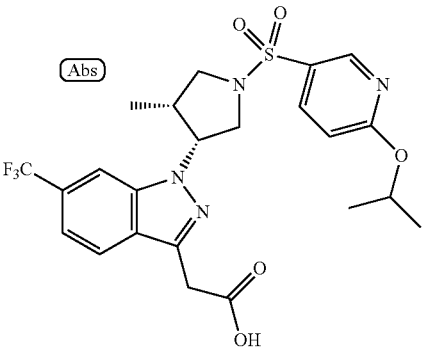 [SMILES: CC(C)Oc1ccc(S(=O)(=O)N2C[C@@H](C)[C@@H](n3nc(CC(=O)O)c4ccc(C(F)(F)F)cc43)C2)cn1] | 527 | 2.41 | B |
| I-132 | 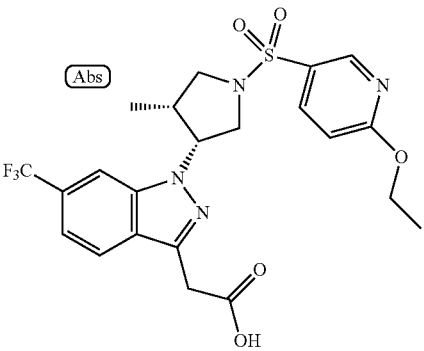 [SMILES: CCOc1ccc(S(=O)(=O)N2C[C@@H](C)[C@@H](n3nc(CC(=O)O)c4ccc(C(F)(F)F)cc43)C2)cn1] | 513 | 2.29 | B |

TABLE 28

| No. | compound | ¹H-NMR δ ppm | [M + H] | RT | LC/MS condition |
|---|---|---|---|---|---|
| I-133 | | (CDCl₃) δ: 8.00 (1H, d, J = 8.39 Hz), 7.84 (2H, t, J = 5.95 Hz), 7.42 (1H, d, J = 7.78 Hz), 7.04 (3H, d, J = 9.00 Hz), 6.20 (1H, t, J = 57.50 Hz), 4.92-4.89 (1H, m), 4.76-4.73 (1H, m), 4.69 (1H, t, J = 6.10 Hz), 4.24-4.07 (1H, m), 4.03 (2H, s), 3.79-3.70 (1H, m), 2.94-2.91 (1H, m), 2.46 (1H, s), 1.42 (6H, dd, J = 5.95, 0.76 Hz). | 512 | 2.3 | B |
| I-134 | | (CDCl₃) δ: 7.93 (2H, d, J = 8.54 Hz), 7.54 (1H, d ,J = 8.69 Hz), 7.31 (3H, t, J = 7.24 Hz), 7.10 (1H, d, J = 10.07 Hz), 6.68 (1H, t, J = 73.51 Hz), 4.99-4.95 (1H, m), 4.09 (1H, dd, J = 10.98, 6.86 Hz), 3.78 (1H, dd, J = 12.12, 9.84 Hz), 3.71 (1H, d, J = 7.93 Hz), 3.67 (2H, s), 3.24 (1H, t, J = 9.84 Hz), 2.75-2.71 (1H, m), 1.25-1.24 (1H, m), 0.47 (3H, d, J = 7.17 Hz). | 500 | 2.2 | B |
| I-135 | | (CDCl₃) δ: 7.81 (2H, d, J = 7.78 Hz), 7.53 (1H, d, J = 8.54 Hz), 7.33 (1H, s), 7.09 (1H, d, J = 8.39 Hz), 6.98 (2H, d, J = 7.93 Hz), 4.97-4.93 (1H, m), 4.67-4.63 (1H, m), 4.03 (1H, dd, J = 10.90, 7.55 Hz), 3.82 (1H, t, J = 7.17 Hz), 3.73 (2H, s), 3.68 (1H, t, J = 8.31 Hz), 3.23 (1H, t, J = 9.46 Hz), 2.68-2.64 (1H, m), 1.39 (6H, d, J = 6.25 Hz), 0.47 (3H, d, J = 6.86 Hz). | 492 | 2.33 | B |
| I-136 | | | 484 | 2.11 | B |

TABLE 29

| No. | compound | ¹H-NMR δ ppm | [M + H] | RT | LC/MS condition |
|---|---|---|---|---|---|
| I-137 | | | 478 | 2.23 | B |
| I-138 | | 1H-NMR (DMSO-D6) δ: 1.32 (6H, br s), 2.35 (1H, m), 3.15-3.27 (2H, m), 3.25 (3H, s), 3.59 (1H, m), 3.68 (1H, m), 3.77-3.84 (1H, m), 3.84 (2H, s), 4.76 (1H, m), 5.39 (1H, m), 5.75 (1H, br s), 7.01 (1H, m), 7.09-7.17 (2H, m), 7.49-7.57 (1H, m), 7.66-7.75 (2H, m), 7.75-7.84 (2H, m). | | | |
| I-139 | | 1H-NMR (DMSO-D6) δ: 0.31 (3H, d, J = 5.6 Hz), 1.32 (6H, s), 2.38 (1H, br s), 3.17-3.90 (m), 4.75 (1H, m), 5.31 (1H, br), 5.75 (1H, br s), 7.01 (1H, t, J = 8.6 Hz), 7.13 (2H, d, J = 7.6 Hz), 7.54 (1H, d, J = 9.6 Hz), 7.72 (1H, m), 7.79 (2H, d, J = 8.1 Hz). | | | |
| I-140 | | | 464 | 2.1 | B |

TABLE 29-continued
| No. | compound | ¹H-NMR δ ppm | [M + H] | RT | LC/MS condition |
|---|---|---|---|---|---|
| I-141 | 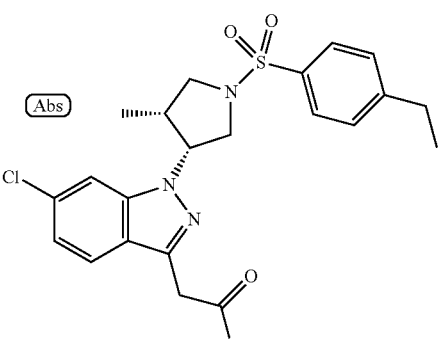 | | 462 | 2.31 | B |
TABLE 30
| No. | compound | ¹H-NMR δ ppm | [M + H] | RT | LC/MS condition |
|---|---|---|---|---|---|
| I-142 | 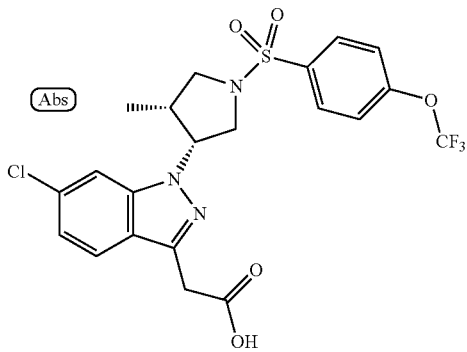 [SMILES: C[C@@H]1CN(S(=O)(=O)c2ccc(OC(F)(F)F)cc2)C[C@@H]1n1nc(CC(=O)O)c2ccc(Cl)cc21] | | 518 | 2.36 | B |
| I-143 | 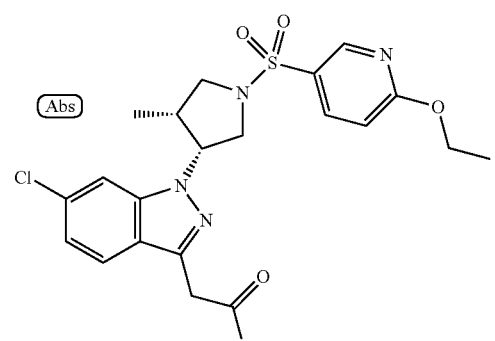 | | 479 | 2.19 | B |

TABLE 30-continued
| No. | compound | ¹H-NMR δ ppm | [M + H] | RT | LC/MS condition |
|---|---|---|---|---|---|
| I-144 | 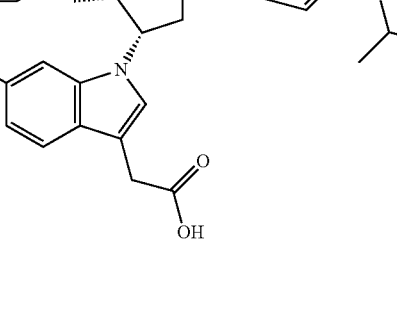 | 1H-NMR (CDCl3) δ: 0.51 (d, J = 6.9 Hz, 3H), 1.38 (s, 3H), 1.40 (s, 3H), 2.46-2.56 (m, 1H), 3.07 (t, J = 10.1 Hz, 1H), 3.60-3.66 (m, 3H), 3.73-3.83 (m, 2H), 4.62-4.71 (m, 1H), 4.74-4.78 (m, 1H), 6.67 (s, 1H), 6.88 (ddd, J = 18.0, 9.2, 2.0 Hz, 2H), 7.00-7.04 (m, 2H), 7.47 (dd, J = 8.6, 5.4 Hz, 1H), 7.81-7.84 (m, 2H). | | | |
| I-145 | 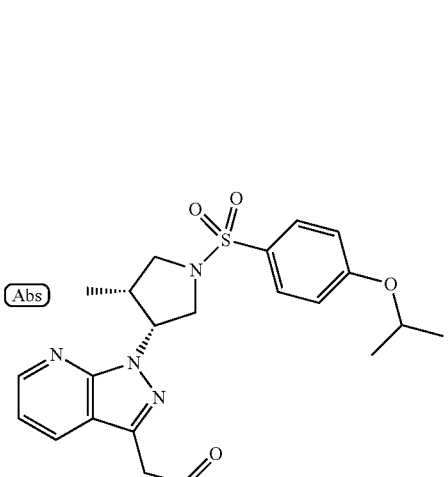 | ¹H-NMR (CDCl₃) δ: 8.48 (1H, d, J = 3.4 Hz), 8.05 (1H, d, J = 6.9 Hz), 7.86 (2H, d, J = 8.9 Hz), 7.15-7.08 (1H, m), 7.03 (2H, d, J = 8.9 Hz), 5.65-5.57 (1H, m), 4.75-4.66 (1H, m), 4.10-4.01 (1H, m), 3.88-3.79 (3H, m), 3.76-3.66 (1H, m), 3.39-3.30 (1H, m), 2.75-2.62 (1H, m), 1.46-1.41 (6H, m), 0.51 (3H, d, J = 6.7 Hz). | | | |
| I-146 | 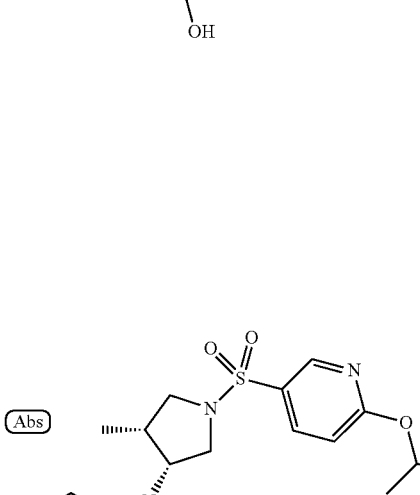 | 1H-NMR (CDCl3) δ: 8.76 (1H, t, J = 4.19 Hz), 8.05-7.99 (1H, m), 7.55 (1H, d, J = 8.54 Hz), 7.35 (1H, s), 7.10 (1H, d, J = 8.69 Hz), 6.80 (1H, d, J = 8.85 Hz), 5.39-5.35 (1H, m), 5.00 (1H, t, J = 5.49 Hz), 4.05 (1H, s), 3.87 (1H, d, J = 10.83 Hz), 3.74 (2H, s), 3.72-3.70 (1H, m), 3.27 (1H, t, J = 9.84 Hz), 2.75 (1H, dd, J = 10.68, 6.71 Hz), 1.40 (6H, d, J = 6.25 Hz), 0.49 (4H, d, J = 6.71 Hz). | | | |

TABLE 31

| No. | compound | ¹H-NMR δ ppm | [M + H] | RT | LC/MS condition |
|---|---|---|---|---|---|
| I-147 | | | | | |
| I-148 | | 1H-NMR (CDCl3) δ: 8.24 (1H, dd, J = 4.7, 1.5 Hz), 7.90 (1H, dd, J = 7.8, 1.5 Hz), 7.83 (2H, d, J = 8.6 Hz), 7.08-7.00 (3H, m), 6.91 (1H, s), 5.58-5.52 (1H, m), 4.72-4.62 (1H, m), 3.82-3.67 (4H, m), 3.60 (1H, dd, J = 9.9, 8.2 Hz), 3.12 (1H, dd, J = 9.9, 9.9 Hz), 2.60-2.48 (1H, m), 1.40 (6H, d, J = 6.0 Hz), 0.52 (3H, d, J = 6.9 Hz). | | | |
| I-149 | | | 477 | 2.06 | B |
| I-150 | | ¹H-NMR (DMSO-D₆) δ: 7.83-7.71 (2H, m), 7.78 (2H, d, J = 8.8 Hz), 7.48-7.44 (1H, m), 7.35-7.29 (1H, m), 7.14 (2H, d, J = 8.8 Hz), 6.84-6.79 (1H, m), 5.39-5.28 (1H, m), 4.14 (2H, q, J = 6.9 Hz), 3.92-3.82 (1H, m), 3.64-3.51 (3H, m), 3.10 (1H, t, J = 9.9 Hz), 1.39 (3H, t, J = 6.9 Hz), 0.29 (3H, t, J = 5.3 Hz). | 462 | 2.07 | B |

TABLE 31-continued

| No. | compound | ¹H-NMR δ ppm | [M + H] | RT | LC/MS condition |
|---|---|---|---|---|---|
| I-151 | | | 472 | 2.36 | B |

TABLE 32

| No. | compound | ¹H-NMR δ ppm | [M + H] | RT | LC/MS condition |
|---|---|---|---|---|---|
| I-152 | | | 456 | 2.16 | B |
| I-153 | | | 456 | 2.02 | B |

TABLE 32-continued
| No. | compound | ¹H-NMR δ ppm | [M + H] | RT | LC/MS condition |
|---|---|---|---|---|---|
| I-154 | 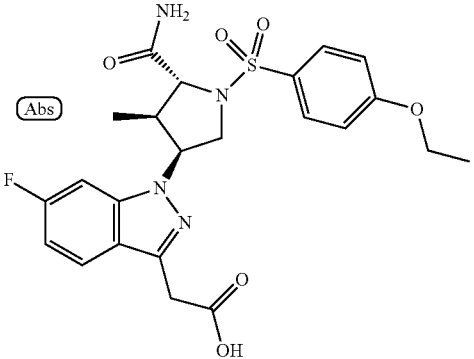 [SMILES: CCOc1ccc(S(=O)(=O)N2C[C@@H](n3nc(CC(=O)O)c4ccc(F)cc43)[C@@H](C)[C@@H]2C(N)=O)cc1] | ¹H-NMR (CDCl₃) δ: 7.87 (2H, d, J = 8.8 Hz), 7.60-7.51 (1H, m), 7.05 (2H, d, J = 8.8 Hz), 7.02-6.86 (2H, m), 5.87-5.82 (1H, m), 5.02-4.96 (1H, m), 4.32-4.25 (1H, m), 4.19-4.00 (3H, m), 3.81-3.61 (4H, m), 3.00-2.91 (1H, m), 1.47 (3H, t, J = 7.0 Hz), 0.26 (3H, d, J = 7.0 Hz). | 505 | 1.66 | B |
| I-155 | 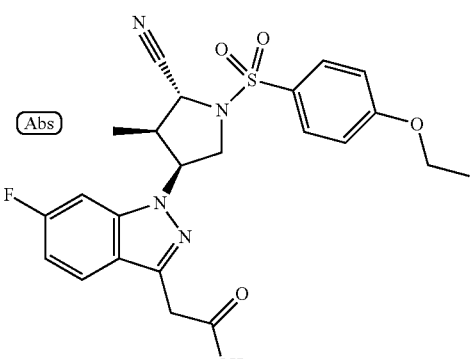 | ¹H-NMR (CDCl₃) δ: 7.86 (2H, d, J = 8.7 Hz), 7.62-7.56 (1H, m), 7.07-6.89 (4H, m), 4.98-4.91 (1H, m), 4.53 (1H, d, J = 9.4 Hz), 4.16-4.03 (3H, m), 4.02-3.85 (1H, m), 3.71-3.60 (2H, m), 3.07-2.94 (1H, m), 1.46 (3H, t, J = 6.8 Hz), 0.70 (3H, d, J = 6.8 Hz). | 487 | 2.05 | B |
| I-156 | 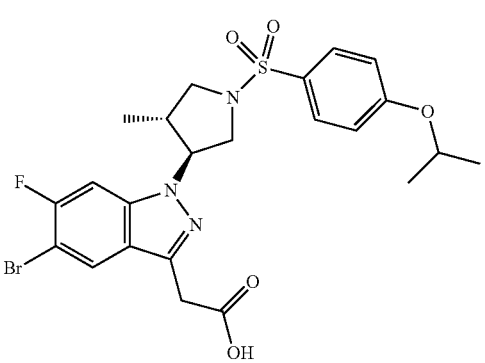 [SMILES: CC(C)Oc1ccc(S(=O)(=O)N2C[C@@H](C)[C@H](n3nc(CC(=O)O)c4cc(Br)c(F)cc43)C2)cc1] | 1H-NMR (CDCl3) δ: 7.82 (3H, d, J = 8.66 Hz), 7.09 (1H, d, J = 8.66 Hz), 7.00 (2H, d, J = 8.78 Hz), 4.91-4.88 (1H, m), 4.68-4.65 (1H, m), 4.05 (1H, dd, J = 10.98, 7.72 Hz), 3.83 (1H, d, J = 11.04 Hz), 3.70 (2H, s), 3.68-3.66 (1H, m), 3.21 (1H, t, J = 9.85 Hz), 2.64 (1H, s), 1.40 (6H, dd, J = 5.83, 2.57 Hz), 0.45 (3H, d, J = 6.78 Hz). | 554 556 | 2.38 | B |

TABLE 33

| No. | compound | $^1$H-NMR δ ppm | [M + H] | RT | LC/MS condition |
|---|---|---|---|---|---|
| I-157 | 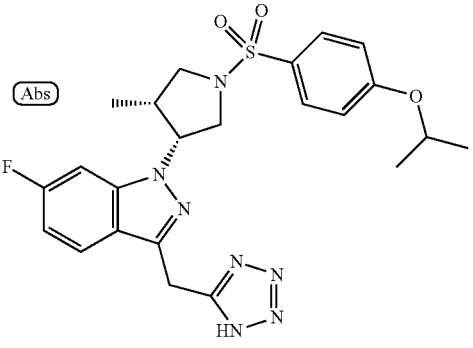 [SMILES: CC(C)Oc1ccc(S(=O)(=O)N2C[C@@H](C)[C@@H](n3nc(Cc4nnn[nH]4)c4ccc(F)cc43)C2)cc1] | $^1$H-NMR (DMSO-d$_6$) δ: 7.77 (2H, d, J = 8.9 Hz), 7.58-7.49 (2H, m), 7.10 (2H, d, J = 8.9 Hz), 6.97 (1H, td, J = 9.1, 2.1 Hz), 5.33-5.29 (1H, m), 4.74-4.65 (1H, m), 4.40 (2H, s), 3.84 (1H, dd, J = 11.2, 7.3 Hz), 3.69 (1H, dd, J = 11.3, 2.5 Hz), 3.58 (1H, dd, J = 9.3, 7.4 Hz), 3.17 (1H, t, J = 10.0 Hz), 2.45-2.33 (1H, m), 1.27 (6H, d, J = 5.3 Hz), 0.32 (3H, d, J = 6.7 Hz). | 500 | 2.46 | B |
| I-158 | 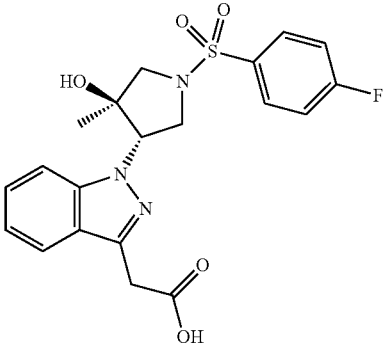 [SMILES: C[C@]1(O)CN(S(=O)(=O)c2ccc(F)cc2)C[C@@H]1n1nc(CC(=O)O)c2ccccc21] | 1H-NMR (DMSO-D6) δ: 7.96-7.91 (2H, m), 7.67-7.56 (2H, m), 7.48-7.33 (3H, m), 7.09 (1H, t, J = 7.5 Hz), 5.38 (1H, s), 5.03-4.97 (1H, m), 4.07-3.99 (1H, m), 3.70-3.62 (3H, m), 0.53 (3H, s). | | | C |
| I-159 | 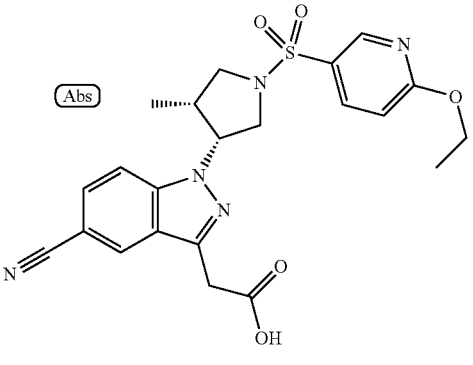 [SMILES: CCOc1ccc(S(=O)(=O)N2C[C@@H](C)[C@@H](n3nc(CC(=O)O)c4cc(C#N)ccc43)C2)cn1] | 1H-NMR (CDCl3) δ: 8.79 (1H, d, J = 2.01 Hz), 8.07 (1H, s), 8.05 (1H, dd, J = 8.53, 2.51 Hz), 7.59 (1H, dd, J = 8.78, 1.51 Hz), 7.45 (1H, d, J = 8.53 Hz), 6.88 (1H, d, J = 8.78 Hz), 5.13-5.11 (1H, m), 4.49 (2H, q, J = 6.94 Hz), 4.19 (1H, dd, J = 11.42, 7.15 Hz), 3.89 (1H, d, J = 11.29 Hz), 3.80 (2H, d, J = 3.76 Hz), 3.77-3.75 (1H, m), 3.27 (1H, t, J = 10.04 Hz), 2.82-2.79 (1H, m), 1.46 (3H, t, J = 7.03 Hz), 0.48 (3H, d, J = 6.78 Hz). | 470 | 1.93 | B |
| I-160 | 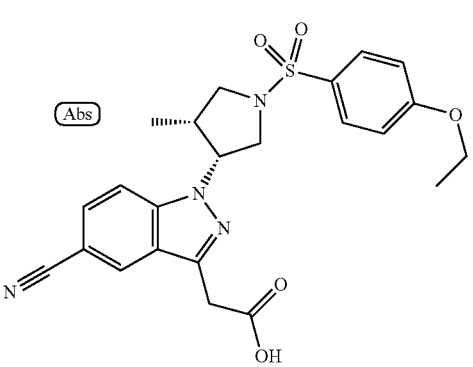 [SMILES: CCOc1ccc(S(=O)(=O)N2C[C@@H](C)[C@@H](n3nc(CC(=O)O)c4cc(C#N)ccc43)C2)cc1] | 1H-NMR (CDCl3) δ: 8.05 (1H, s), 7.84 (2H, d, J = 8.78 Hz), 7.56 (1H, dd, J = 8.78, 1.51 Hz), 7.42 (2H, d, J = 8.53 Hz), 7.02 (2H, d, J = 8.78 Hz), 5.06 (1H, d, J = 4.77 Hz), 4.14 (2H, q, J = 6.94 Hz), 4.07 (1H, dd, J = 11.54, 7.28 Hz), 3.82 (1H, dd, J = 11.54, 2.51 Hz), 3.75 (2H, s), 3.70 (1H, t, J = 8.16 Hz), 3.22 (1H, t, J = 10.04 Hz), 2.72-2.70 (1H, m), 1.48 (3H, t, J = 6.90 Hz), 0.45 (3H, d, J = 6.78 Hz). | 469 | 1.96 | B |

TABLE 34

| No. | compound | ¹H-NMR δ ppm | [M + H] | RT | LC/MS condition |
|---|---|---|---|---|---|
| I-161 | 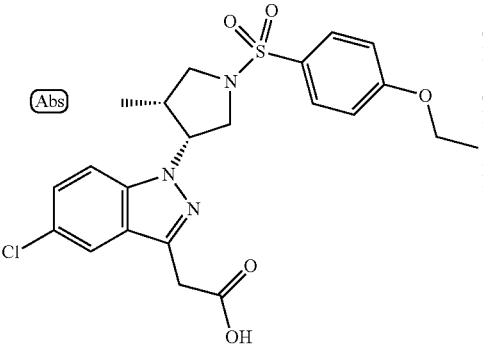 [SMILES: CCOc1ccc(S(=O)(=O)N2C[C@@H](C)[C@@H](n3nc(CC(=O)O)c4cc(Cl)ccc43)C2)cc1] | 1H-NMR (DMSO-d6) δ: 7.78 (2H, d, J = 8.8 Hz), 7.73 (1H, d, J = 1.8 Hz), 7.68 (1H, d, J = 9.0 Hz), 7.37 (1H, dd, J = 9.0, 1.9 Hz), 7.14 (2H, d, J = 8.9 Hz), 5.36 (1H, t, J = 5.8 Hz), 4.15 (2H, q, J = 6.9 Hz), 3.88 (1H, dd, J = 11.3, 7.4 Hz), 3.70-3.53 (4H, m), 3.09 (1H, t, J = 10.0 Hz), 1.39 (3H, t, J = 6.9 Hz), 0.25 (3H, d, J = 6.8 Hz). | 478 | 2.19 | B |
| I-162 | 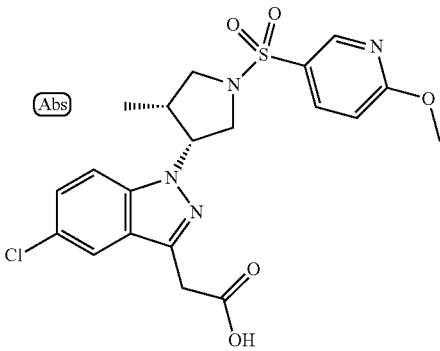 | 1H-NMR (DMSO-d6) δ: 8.64 (1H, d, J = 2.5 Hz), 8.12 (1H, dd, J = 8.7, 2.5 Hz), 7.73-7.68 (2H, m), 7.38 (1H, dd, J = 9.0, 1.9 Hz), 7.01 (1H, d, J = 8.7 Hz), 5.39 (1H, t, J = 6.0 Hz), 4.43 (2H, q, J = 7.0 Hz), 3.99-3.92 (1H, m), 3.66-3.50 (4H, m), 3.13-3.07 (1H, m), 2.65-2.55 (1H, m), 1.38 (3H, t, J = 7.0 Hz), 0.27 (3H, d, J = 6.8 Hz). | 479 | 2.16 | B |
| I-163 | 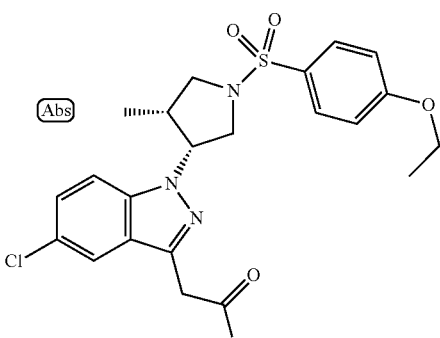 | 1H-NMR (DMSO-d6) δ: 7.78-7.67 (4H, m), 7.37 (1H, dd, J = 8.9, 1.9 Hz), 7.13 (2H, d, J = 8.9 Hz), 5.37 (1H, t, J = 5.8 Hz), 4.80-4.74 (1H, m), 3.90-3.85 (1H, m), 3.73-3.53 (4H, m), 3.10 (1H, t, J = 10.0 Hz), 1.34 (6H, dd, J = 6.0, 3.3 Hz), 0.26 (3H, d, J = 6.7 Hz). | 492 | 2.3 | B |
| I-164 | 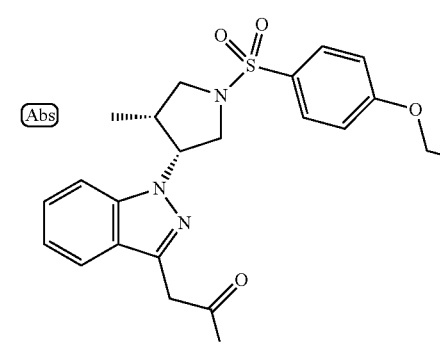 | 1H-NMR (DMSO-d6) δ: 0.31 (d, J = 6.7 Hz, 3H), 1.38 (t, J = 7.0 Hz, 3H), 2.43-2.45 (m, 1H), 2.93 (t, J = 10.0 Hz, 1H), 3.51 (s, 2H), 3.56-3.59 (m, 3H), 3.78 (dd, J = 11.4, 6.8 Hz, 1H), 4.16 (q, J = 6.9 Hz, 2H), 5.12-5.14 (m, 1H), 6.52 (s, 1H), 7.00 (t, J = 7.5 Hz, 1H), 7.11 (t, J = 7.5 Hz, 1H), 7.20 (d, J = 8.9 Hz, 2H), 7.46 (t, J = 6.7 Hz, 2H), 7.86 (d, J = 8.8 Hz, 2H). | 443 | 2.18 | P |

TABLE 34-continued

| No. | compound | ¹H-NMR δ ppm | [M + H] | RT | LC/MS condition |
|---|---|---|---|---|---|
| I-165 | (structure) | 1H-NMR (DMSO-d6) δ: 0.32 (d, J = 6.4 Hz, 3H), 1.33 (d, J = 5.6 Hz, 6H), 2.44 (t, J = 7.1 Hz, 1H), 2.94 (t, J = 9.8 Hz, 1H), 3.52-3.62 (m, 5H), 3.77 (dd, J = 10.9, 6.7 Hz, 1H), 4.77-4.80 (m, 1H), 5.14 (s, 1H), 6.61 (s, 1H), 7.00 (t, J = 7.3 Hz, 1H), 7.10 (t, J = 7.5 Hz, 1H), 7.18 (d, J = 7.7 Hz, 2H), 7.45 (t, J = 7.9 Hz, 2H), 7.84 (d, J = 7.7 Hz, 2H). | 457 | 2.3 | P |

TABLE 35

| No. | compound | ¹H-NMR δ ppm | [M + H] | RT | LC/MS condition |
|---|---|---|---|---|---|
| I-166 | (structure) | | 469 | 2.07 | B |
| I-167 | (structure) | 1H-NMR (CDCl3) δ: 8.01 (1H, d, J = 6.02 Hz), 7.81 (2H, d, J = 8.78 Hz), 7.13 (1H, d, J = 9.03 Hz), 7.00 (2H, d, J = 8.78 Hz), 4.92 (1H, t, J = 5.77 Hz), 4.70-4.64 (1H, m), 4.05 (1H, dd, J = 11.42, 7.40 Hz), 3.82 (1H, dd, J = 11.42, 2.38 Hz), 3.74 (2H, s), 3.69 (1H, t, J = 8.28 Hz), 3.21 (1H, t, J = 9.91 Hz), 2.68 (2H, dd, J = 11.04, 7.53 Hz), 1.40 (6H, dd, J = 6.02, 2.76 Hz), 0.48 (3H, d, J = 6.78 Hz). | 501 | 2.15 | B |
| I-168 | (structure) | | 451 | 2.01 | B |

TABLE 35-continued

| No. | compound | ¹H-NMR δ ppm | [M + H] | RT | LC/MS condition |
|---|---|---|---|---|---|
| I-169 | | | 468 | 2.12 | B |
| I-170 | | | 465 | 2.14 | B |

TABLE 36

| No. | compound | ¹H-NMR δ ppm | [M + H] | RT | LC/MS condition |
|---|---|---|---|---|---|
| I-171 | | | 464 | 2.19 | B |
| I-172 | | 1H-NMR (DMSO-D6) δ: 8.37 (1H, s), 7.85 (1H, d, J = 8.4 Hz), 7.78 (2H, d, J = 8.9 Hz), 7.43 (1H, dd, J = 8.3, 1.2 Hz), 7.14 (2H, d, J = 9.0 Hz), 5.46 (1H, t, J = 5.8 Hz), 4.15 (2H, q, J = 6.9 Hz), 3.90 (1H, dd, J = 11.4, 7.4 Hz), 3.75-3.55 (4H, m), 3.10 (1H, t, J = 10.0 Hz), 2.5 (1H, m), 1.39 (3H, t, J = 7.0 Hz), 0.27 (3H, d, J = 6.7 Hz). | 469 | 1.98 | B |

TABLE 36-continued

| No. | compound | ¹H-NMR δ ppm | [M + H] | RT | LC/MS condition |
|---|---|---|---|---|---|
| I-173 | | | 470 | 1.94 | B |
| I-174 | | | 502 | 2.1 | B |
| I-175 | | | 488 | 1.99 | B |

TABLE 37

| No. | compound | ¹H-NMR δ ppm | [M + H] | RT | LC/MS condition |
|---|---|---|---|---|---|
| I-176 | | | 489 | 2 | B |

TABLE 37-continued
| No. | compound | ¹H-NMR δ ppm | [M + H] | RT | LC/MS condition |
|---|---|---|---|---|---|
| I-177 | 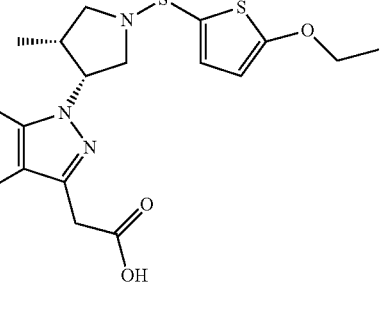 | | 450 | 2.07 | B |
| I-178 | 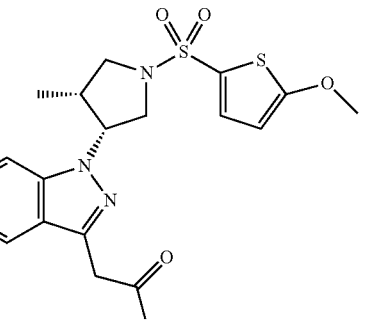 | | 436 | 1.93 | B |
| I-179 | 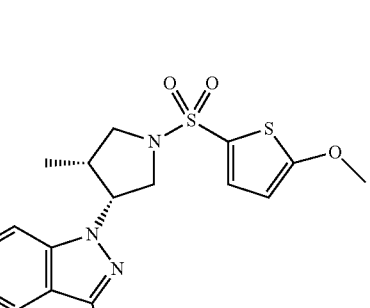 | | 454 | 1.98 | B |
| I-180 | 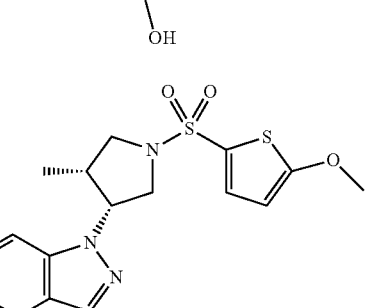 | | 450 | 2.06 | B |

TABLE 38

| No. | compound | ¹H-NMR δ ppm | [M + H] | RT | LC/MS condition |
|---|---|---|---|---|---|
| I-181 | | ¹H-NMR (DMSO-D₆) δ: 8.88 (1H, s), 8.00 (1H, d, J = 9.0 Hz), 7.64 (2H, t, J = 9.4 Hz), 7.45 (1H, d, J = 2.5 Hz), 7.35 (1H, t, J = 7.5 Hz), 7.19 (1H, dd, J = 8.9, 2.6 Hz), 7.09 (1H, t, J = 7.4 Hz), 5.43-5.38 (1H, m), 4.17 (2H, q, J = 6.9 Hz), 3.96-3.89 (4H, m), 3.70 (2H, d, J = 2.8 Hz), 3.63-3.58 (2H, m), 3.16 (1H, t, J = 9.7 Hz), 2.72-2.63 (1H, m), 1.38 (3H, t, J = 6.9 Hz), 0.33 (3H, d, J = 6.5 Hz). | 501 | 2.27 | B |
| I-182 | | 1H-NMR (DMSO-d6) δ: 7.94 (1H, d, J = 8.8 Hz), 7.67 (1H, d, J = 8.0 Hz), 7.63 (1H, d, J = 8.4 Hz), 7.43 (1H, d, J = 15.8 Hz), 7.36 (1H, t, J = 7.6 Hz), 7.24 (1H, s), 7.10 (1H, t, J = 7.4 Hz), 7.03 (1H, d, J = 8.5 Hz), 6.34 (1H, td, J = 10.5, 5.4 Hz), 5.41-5.37 (1H, m), 4.18 (2H, q, J = 6.8 Hz), 4.03-4.00 (2H, m), 3.92-3.86 (1H, m), 3.79-3.69 (3H, m), 3.59 (1H, t, J = 8.1 Hz), 3.24-3.19 (4H, m), 2.62-2.55 (1H, m), 1.38 (3H, t, J = 6.8 Hz), 0.32 (3H, d, J = 6.5 Hz). | 514 | 2.2 | B |
| I-183 | | ¹H-NMR (DMSO-d₆) δ: 7.97 (1H, d, J = 8.5 Hz), 7.71-7.64 (2H, m), 7.37 (1H, t, J = 7.6 Hz), 7.11 (1H, t, J = 7.3 Hz), 6.99-6.94 (2H, m), 5.48-5.43 (1H, m), 4.13 (2H, q, J = 6.8 Hz), 3.98-3.93 (1H, m), 3.79 (2H, s), 3.68 (1H, d, J = 10.9 Hz), 3.60 (1H, t, J = 7.9 Hz), 3.24-3.17 (4H, m), 2.99 (2H, t, J = 7.9 Hz), 2.73-2.64 (1H, m), 1.91-1.82 (2H, m), 1.36 (3H, t, J = 6.8 Hz), 0.36 (3H, d, J = 6.5 Hz). | 516 | 2.23 | B |

TABLE 38-continued

| No. | compound | ¹H-NMR δ ppm | [M + H] | RT | LC/MS condition |
|---|---|---|---|---|---|
| I-184 | (structure) | ¹H-NMR (DMSO-d$_6$) δ: 7.95 (1H, d, J = 8.8 Hz), 7.69-7.63 (2H, m), 7.36 (1H, t, J = 7.5 Hz), 7.21 (1H, s), 7.10 (1H, t, J = 7.3 Hz), 7.03 (1H, d, J = 7.0 Hz), 5.46-5.42 (1H, m), 4.83 (2H, s), 4.14 (2H, q, J = 6.9 Hz), 3.98-3.92 (1H, m), 3.80-3.59 (4H, m), 3.37 (3H, s), 3.16 (1H, t, J = 9.6 Hz), 2.72-2.63 (1H, m), 1.37 (3H, t, J = 6.9 Hz), 0.34 (3H, d, J = 6.7 Hz). | 488 | 2.16 | B |

TABLE 39

| No. | compound | ¹H-NMR δ ppm | [M + H] | RT | LC/MS condition |
|---|---|---|---|---|---|
| I-185 | (structure) | ¹H-NMR (DMSO-d$_6$) δ: 8.05-7.97 (2H, m), 7.65 (1H, d, J = 8.2 Hz), 7.58 (1H, d, J = 8.5 Hz), 7.52 (2H, d, J = 7.8 Hz), 7.45 (1H, s), 7.40-7.20 (7H, m), 7.10-7.05 (2H, m), 5.39-5.34 (1H, m), 4.22 (2H, q, J = 6.8 Hz), 3.93-3.88 (1H, m), 3.76-3.58 (5H, m), 3.23 (1H, t, J = 9.5 Hz), 2.61-2.53 (1H, m), 1.40 (3H, t, J = 7.0 Hz), 0.27 (3H, d, J = 6.7 Hz). | 546 | 2.52 | B |
| I-186 | (structure) | ¹H-NMR (DMSO-d$_6$) δ: 8.01 (1H, d, J = 8.8 Hz), 7.70-7.63 (2H, m), 7.36 (1H, t, J = 7.6 Hz), 7.29 (4H, m), 7.20-7.05 (3H, m), 6.98 (1H, d, J = 8.4 Hz), 5.48-5.43 (1H, m), 4.11 (2H, q, J = 6.8 Hz), 4.01-3.95 (1H, m), 3.78-3.59 (4H, m), 3.27-3.18 (3H, m), 2.97-2.90 (2H, m), 2.74-2.64 (1H, m), 1.35 (3H, t, J = 6.7 Hz), 0.35 (3H, d, J = 6.5 Hz). | 548 | 2.55 | B |

TABLE 39-continued

| No. | compound | ¹H-NMR δ ppm | [M + H] | RT | LC/MS condition |
|---|---|---|---|---|---|
| I-187 | (structure) | ¹H-NMR (DMSO-d₆) δ: 8.10 (1H, d, J = 8.9 Hz), 7.71 (1H, d, J = 8.2 Hz), 7.63 (1H, d, J = 8.5 Hz), 7.45-7.35 (6H, m), 7.16-7.09 (2H, m), 6.82 (1H, s), 5.31-5.24 (1H, m), 4.16 (2H, q, J = 6.8 Hz), 3.86 (2H, s), 3.53-3.45 (2H, m), 3.15 (1H, t, J = 8.0 Hz), 3.01 (1H, t, J = 9.6 Hz), 1.36 (3H, t, J = 6.8 Hz), 0.29 (3H, d, J = 6.7 Hz). | 520 | 2.4 | B |
| I-188 | (structure) | | 489 | 2.06 | B |

TABLE 40

| No. | compound | ¹H-NMR δ ppm | [M + H] | RT | LC/MS condition |
|---|---|---|---|---|---|
| I-189 | (structure) | | 474 | 1.9 | B |

TABLE 40-continued
| No. | compound | ¹H-NMR δ ppm | [M + H] | RT | LC/MS condition |
|---|---|---|---|---|---|
| I-190 | 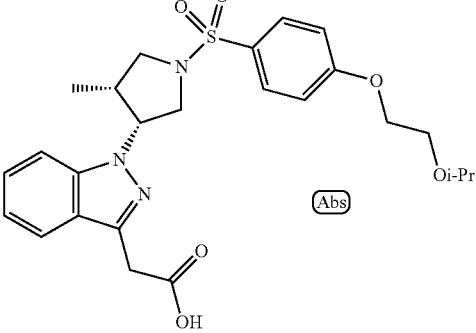 | | 502 | 2.17 | B |
| I-191 | 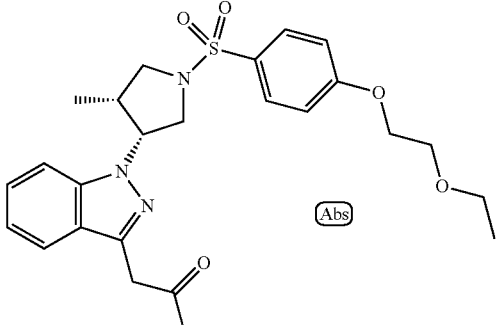 | | 488 | 2.04 | B |
| I-192 | 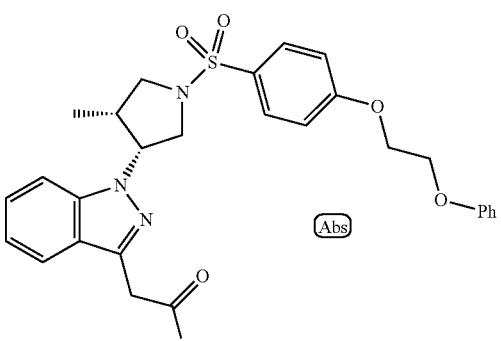 | | 536 | 2.31 | B |
| I-193 | 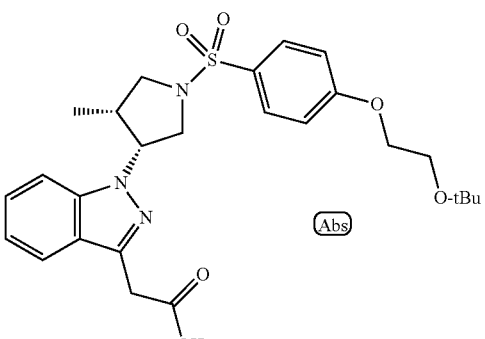 | | 516 | 2.29 | B |

TABLE 41

| No. | compound | ¹H-NMR δ ppm | [M + H] | RT | LC/MS condition |
|---|---|---|---|---|---|
| I-194 | | 1H-NMR (DMSO-d6) δ: 0.86 (d, J = 6.7 Hz, 3H), 2.55-2.59 (m, 1H), 2.97 (t, J = 9.2 Hz, 1H), 3.49 (dd, J = 9.7, 7.3 Hz, 1H), 3.70 (t, J = 8.6 Hz, 1H), 3.77 (t, J = 9.0 Hz, 1H), 3.84 (s, 2H), 4.97 (q, J = 7.7 Hz, 1H), 7.13 (t, J = 7.5 Hz, 1H), 7.29-7.47 (m, 4H), 7.61 (d, J = 8.5 Hz, 1H), 7.67 (t, J = 7.6 Hz, 1H), 7.93 (d, J = 8.5 Hz, 2H), 12.52 (s, 1H). | 466 | 2.02 | B |
| I-195 | | 1H-NMR (DMSO-d6) δ: 0.86 (d, J = 6.5 Hz, 3H), 2.55-2.59 (m, 1H), 2.97 (t, J = 9.2 Hz, 1H), 3.49 (t, J = 8.4 Hz, 1H), 3.70 (t, J = 8.6 Hz, 1H), 3.77 (t, J = 9.0 Hz, 1H), 3.84 (s, 2H), 4.97 (q, J = 7.5 Hz, 1H), 7.12 (t, J = 7.5 Hz, 1H), 7.29-7.47 (m, 4H), 7.60-7.69 (m, 2H), 7.93 (d, J = 8.4 Hz, 2H), 12.54 (s, 1H). | 466 | 2.02 | B |
| I-196 | | 1H-NMR (DMSO-d6) δ: 1.38 (t, J = 6.8 Hz, 6H), 2.08-2.11 (m, 1H), 2.43-2.46 (m, 1H), 3.65-3.70 (m, 2H), 3.81 (dd, J = 11.2, 7.7 Hz, 1H), 3.92 (s, 2H), 4.17 (q, J = 7.0 Hz, 2H), 4.64-4.72 (m, 1H), 7.13 (t, J = 7.1 Hz, 1H), 7.19 (d, J = 8.8 Hz, 2H), 7.36-7.40 (m, 2H), 7.70 (d, J = 8.0 Hz, 1H), 7.86 (d, J = 8.8 Hz, 2H), 12.53 (s, 1H). | 444 | 2.06 | B |
| I-197 | | 1H-NMR (DMSO-d6) δ: 0.85 (d, J = 6.7 Hz, 3H), 1.38 (t, J = 6.9 Hz, 3H), 2.93 (t, J = 9.2 Hz, 1H), 3.45 (dd, J = 9.9, 7.3 Hz, 2H), 3.65 (t, J = 8.7 Hz, 1H), 3.71 (t, J = 8.9 Hz, 1H), 3.84 (s, 2H), 4.15 (q, J = 6.9 Hz, 2H), 4.93 (q, J = 7.7 Hz, 1H), 7.11-7.15 (m, 3H), 7.36 (t, J = 7.7 Hz, 1H), 7.60 (d, J = 8.5 Hz, 1H), 7.68 (d, J = 8.0 Hz, 1H), 7.77 (d, J = 8.7 Hz, 2H). | 444 | 2.04 | B |

TABLE 41-continued

| No. | compound | ¹H-NMR δ ppm | [M + H] | RT | LC/MS condition |
|---|---|---|---|---|---|
| I-198 | | 1H-NMR (DMSO-d6) δ: 0.85 (d, J = 6.7 Hz, 3H), 1.38 (t, J = 7.0 Hz, 3H), 2.55 (d, J = 7.4 Hz, 1H), 2.93 (t, J = 9.2 Hz, 1H), 3.45 (dd, J = 9.9, 7.2 Hz, 2H), 3.65 (dd, J = 9.6, 7.7 Hz, 1H), 3.71 (dd, J = 9.6, 8.2 Hz, 1H), 3.84 (s, 2H), 4.15 (q, J = 6.9 Hz, 2H), 4.92-4.94 (m, 1H), 7.11-7.15 (m, 3H), 7.37 (t, J = 7.6 Hz, 1H), 7.60 (d, J = 8.5 Hz, 1H), 7.68 (d, J = 8.0 Hz, 1H), 7.77 (d, J = 8.8 Hz, 2H). | 444 | 2.04 | B |

TABLE 42

| No. | compound | ¹H-NMR δ ppm | [M + H] | RT | LC/MS condition |
|---|---|---|---|---|---|
| I-199 | | 1H-NMR (DMSO-d6) δ: 0.85 (d, J = 6.5 Hz, 3H), 1.33 (d, J = 5.9 Hz, 6H), 2.56-2.58 (m, 1H), 2.93 (t, J = 9.3 Hz, 1H), 3.45 (dd, J = 9.5, 7.4 Hz, 2H), 3.66 (t, J = 8.7 Hz, 1H), 3.71 (t, J = 9.0 Hz, 1H), 3.84 (s, 2H), 4.74-4.80 (m, 1H), 4.93 (q, J = 7.7 Hz, 1H), 7.11-7.14 (m, 3H), 7.36 (t, J = 7.7 Hz, 1H), 7.59 (d, J = 8.5 Hz, 1H), 7.68 (d, J = 8.2 Hz, 1H), 7.75 (d, J = 8.8 Hz, 2H). | 458 | 2.16 | B |
| I-200 | | ¹H-NMR (DMSO-d₆) δ: 8.02 (1H, d, J = 8.9 Hz), 7.70 (1H, d, J = 2.6 Hz), 7.63 (2H, d, J = 8.7 Hz), 7.43 (1H, dd, J = 8.9, 2.5 Hz), 7.36 (1H, t, J = 7.6 Hz), 7.09 (1H, t, J = 7.6 Hz), 5.41 (1H, t, J = 6.1 Hz), 4.23 (2H, q, J = 6.9 Hz), 4.05-4.01 (1H, m), 3.78 (1H, d, J = 11.2 Hz), 3.64 (1H, t, J = 7.8 Hz), 3.58-3.47 (2H, m), 3.22 (1H, t, J = 9.9 Hz), 2.75-2.67 (1H, m), 1.39 (3H, t, J = 6.9 Hz), 0.31 (3H, d, J = 6.8 Hz). | 469 | 2.02 | B |

TABLE 42-continued
| No. | compound | ¹H-NMR δ ppm | [M + H] | RT | LC/MS condition |
|---|---|---|---|---|---|
| I-201 | 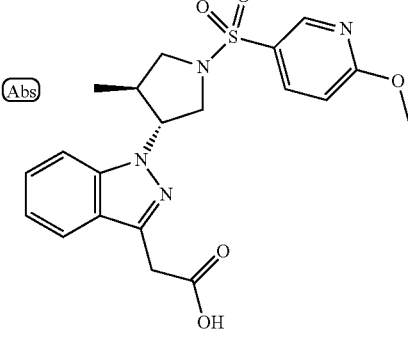 | 1H-NMR (DMSO-d6) δ: 0.89 (d, J = 6.5 Hz, 3H), 1.37 (t, J = 6.8 Hz, 3H), 2.55-2.57 (m, 1H), 2.99 (t, J = 9.0 Hz, 1H), 3.51 (t, J = 8.2 Hz, 1H), 3.70 (t, J = 8.4 Hz, 1H), 3.78-3.81 (m, 3H), 4.43 (q, J = 6.8 Hz, 2H), 4.99 (q, J = 7.2 Hz, 1H), 7.02 (d, J = 8.7 Hz, 1H), 7.12 (t, J = 7.3 Hz, 1H), 7.38 (t, J = 7.5 Hz, 1H), 7.62 (d, J = 8.4 Hz, 1H), 7.68 (d, J = 8.0 Hz, 1H), 8.11 (d, J = 8.3 Hz, 1H), 8.62 (s, 1H), 12.53 (s, 1H). | 445 | 2 | B |
| I-202 | 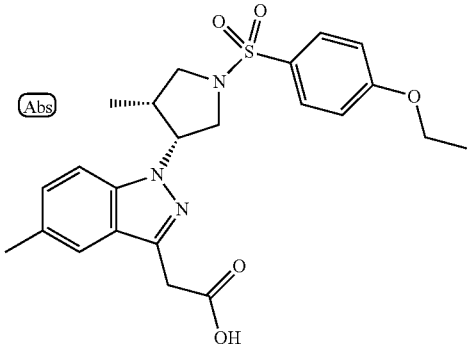 [SMILES: CCOc1ccc(S(=O)(=O)N2C[C@@H](C)[C@@H](n3nc(CC(=O)O)c4cc(C)ccc43)C2)cc1] | | 458 | 2.16 | B |
TABLE 43
| No. | compound | ¹H-NMR δ ppm | [M + H] | RT | LC/MS condition |
|---|---|---|---|---|---|
| I-203 | 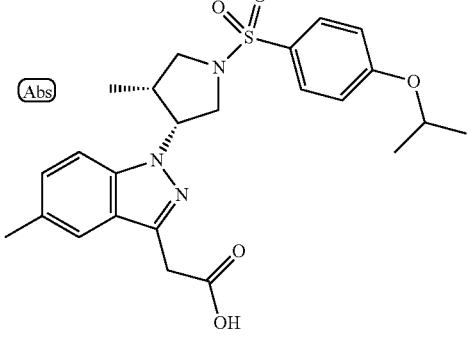 | | 472 | 2.26 | B |

TABLE 43-continued

| No. | compound | ¹H-NMR δ ppm | [M + H] | RT | LC/MS condition |
|---|---|---|---|---|---|
| I-204 | | | 488 | 2.15 | B |
| I-205 | | ¹H-NMR (DMSO-d₆) δ: 7.78 (2H, d, J = 8.8 Hz), 7.41 (1H, d, J = 8.5 Hz), 7.21-7.13 (3H, m), 6.80 (1H, d, J = 6.9 Hz), 5.34-5.28 (1H, m), 4.15 (2H, q, J = 6.9 Hz), 3.89 (1H, dd, J = 11.0, 7.5 Hz), 3.66-3.52 (4H, m), 3.11 (1H, t, J = 9.9 Hz), 1.39 (3H, t, J = 6.9 Hz), 0.25 (3H, d, J = 6.7 Hz). | 458 | 2.14 | B |
| I-206 | | 1H-NMR (DMSO-d6) δ: 8.65 (1H, d, J = 2.4 Hz), 8.12 (1H, dd, J = 8.8, 2.4 Hz), 7.42 (1H, d, J = 8.5 Hz), 7.20 (1H, t, J = 7.7 Hz), 7.00 (1H, d, J = 8.8 Hz), 6.81 (1H, d, J = 7.0 Hz), 5.37-5.31 (1H, m), 4.43 (2H, q, J = 7.0 Hz), 3.95 (1H, dd, J = 11.2, 7.3 Hz), 3.67-3.55 (4H, m), 3.12 (1H, t, J = 9.9 Hz), 2.68-2.55 (1H, m), 1.39 (3H, t, J = 7.0 Hz), 0.27 (3H, d, J = 6.8 Hz). | 459 | 2.11 | B |
| I-207 | | 1H-NMR (DMSO-D6) δ: 0.79 (3H, d, J = 21.6 Hz), 1.37 (3H, t, J = 7.0 Hz), 3.63-3.80 (2H, m), 4.04 (1H, dd, J = 10.9, 7.7 Hz), 4.43 (2H, q, J = 7.0 Hz), 5.43 (1H, dd, J = 12.9, 7.4 Hz), 7.01-7.10 (2.1H, m), 7.36 (1.1H, t, J = 7.7 Hz), 7.69 (2.2H, dd, J = 8.3, 3.5 Hz), 8.14 (1.1H, dd, J = 8.8, 2.8 Hz), 8.65 (1.0H, d, J = 2.3 Hz). | 463 | 2.02 | B |

TABLE 44

| No. | compound | ¹H-NMR δ ppm | [M + H] | RT | LC/MS condition |
|---|---|---|---|---|---|
| I-208 | (Rac) | 1H-NMR (DMSO-D6) δ: 0.77 (3H, d, J = 21.8 Hz), 3.51-3.81 (m), 3.99 (3H, s), 4.06 (1H, dd, J = 10.9, 7.7 Hz), 5.49 (1H, dd, J = 13.3, 7.0 Hz), 7.05 (1H, d, J = 8.8 Hz), 7.14 (1H, t, J = 7.4 Hz), 7.41 (1H, t, J = 7.3 Hz), 7.67 (1H, d, J = 8.3 Hz), 7.77 (1H, t, J = 9.0 Hz), 8.15 (1H, dd, J = 8.8, 2.5 Hz), 8.60 (1H, d, J = 2.5 Hz), 12.51 (1H, br s). | 449 | 1.87 | B |
| I-209 | (Abs) | 1H-NMR (CDCl3) δ: 1.48 (t, J = 6.9 Hz, 3H), 2.44-2.52 (m, 1H), 2.62-2.69 (m, 1H), 3.71 (dd, J = 11.4, 9.3 Hz, 1H), 3.91 (dd, J = 11.7, 7.4 Hz, 1H), 4.00 (s, 2H), 4.12-4.18 (m, 3H), 4.57-4.61 (m, 2H), 4.67-4.75 (m, 1H), 7.04 (d, J = 8.7 Hz, 2H), 7.17 (dd, J = 17.5, 8.2 Hz, 2H), 7.38 (t, J = 7.7 Hz, 1H), 7.66 (d, J = 8.0 Hz, 1H), 7.85 (d, J = 8.7 Hz, 2H). | 462 | 2.15 | P |
| I-210 | (Abs) | 1H-NMR (DMSO-d6) δ: 7.64 (1H, dd, J = 8.6, 5.2 Hz), 7.56 (2H, d, J = 8.5 Hz), 7.45 (1H, d, J = 9.8 Hz), 7.02-6.93 (3H, m), 4.94-4.89 (1H, m), 4.73-4.66 (1H, m), 3.74-3.53 (5H, m), 2.37-2.29 (1H, m), 2.10-2.02 (1H, m), 1.39 (3H, d, J = 6.3 Hz), 1.32 (6H, d, J = 5.9 Hz). | 476 | 2.14 | B |
| I-211 | (Abs) | 1H-NMR (CDCl3) δ: 1.47 (dd, J = 15.0, 6.8 Hz, 6H), 1.98-2.02 (m, 1H), 2.44-2.51 (m, 1H), 3.59 (dd, J = 11.5, 7.6 Hz, 1H), 3.78-3.82 (m, 4H), 4.13 (q, J = 6.9 Hz, 2H), 4.33-4.41 (m, 1H), 7.04-7.22 (m, 6H), 7.57 (d, J = 7.8 Hz, 1H), 7.84 (d, J = 8.5 Hz, 2H). | 443 | 2.28 | P |

TABLE 44-continued
| No. | compound | ¹H-NMR δ ppm | [M + H] | RT | LC/MS condition |
|---|---|---|---|---|---|
| I-212 | 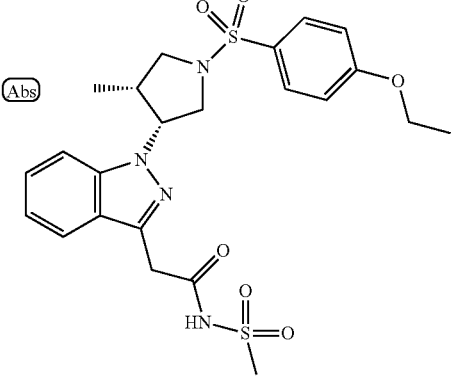 | | 521 | 2.03 | B |
TABLE 45
| No. | compound | ¹H-NMR δ ppm | [M + H] | RT | LC/MS condition |
|---|---|---|---|---|---|
| I-213 | 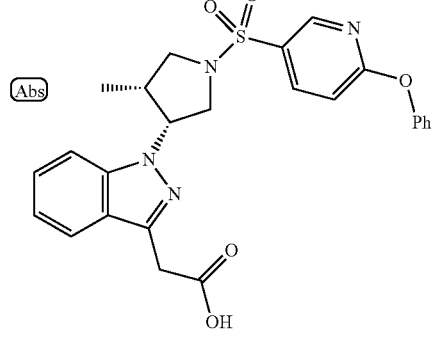 | | 493 | 2.15 | B |
| I-214 | 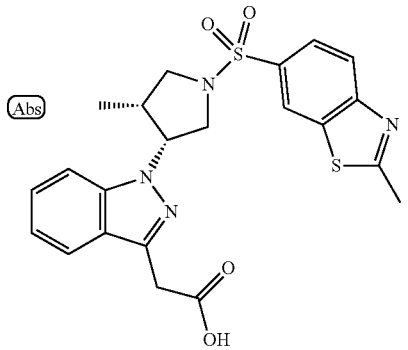 [SMILES: Cc1nc2ccc(S(=O)(=O)N3C[C@@H](C)[C@@H](n4nc(CC(=O)O)c5ccccc54)C3)cc2s1] | | 471 | 1.86 | B |

TABLE 45-continued
| No. | compound | ¹H-NMR δ ppm | [M + H] | RT | LC/MS condition |
|---|---|---|---|---|---|
| I-215 | 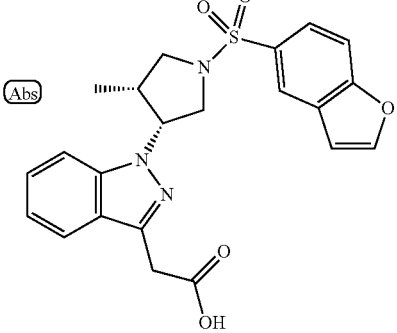 | | 440 | 1.94 | B |
| I-216 | 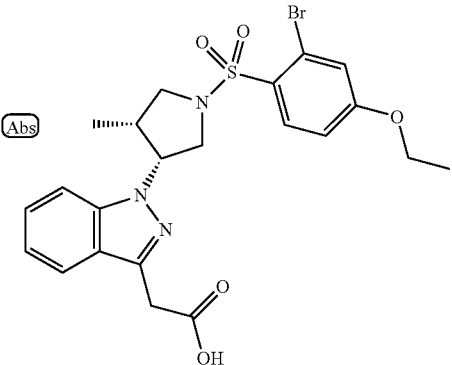 [SMILES: CCOc1ccc(S(=O)(=O)N2C[C@@H](C)[C@@H](n3nc(CC(=O)O)c4ccccc43)C2)c(Br)c1] | 1H-NMR (DMSO-d6) δ: 12.46 (1H, brs), 8.11 (1H, d, J = 8.8 Hz), 7.70-7.65 (2H, m), 7.42-7.36 (2H, m), 7.15-7.09 (2H, m), 5.45 (1H, t, J = 5.8 Hz), 4.17 (2H, q, J = 6.9 Hz), 4.03-3.98 (1H, m), 3.85-3.79 (3H, m), 3.68 (1H, t, J = 7.9 Hz), 3.39-3.33 (1H, m), 2.75-2.65 (1H, m), 1.36 (3H, t, J = 7.0 Hz), 0.37 (3H, d, J = 6.8 Hz). | 522 524 | 2.22 | B |
| I-217 | 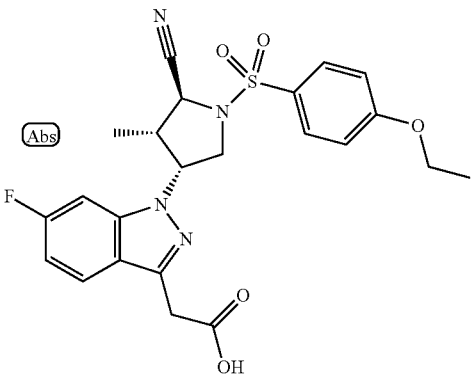 [SMILES: CCOc1ccc(S(=O)(=O)N2C[C@H](n3nc(CC(=O)O)c4ccc(F)cc43)[C@H](C)[C@H]2C#N)cc1] | ¹H-NMR (CDCl₃) δ: 7.86 (2H, d, J = 8.8 Hz), 7.59 (1H, dd, J = 8.8, 5.0 Hz), 7.07-6.89 (4H, m), 4.98-4.92 (1H, m), 4.53 (1H, d, J = 9.5 Hz), 4.18-3.86 (3H, m), 3.72-3.61 (3H, m), 3.03 (1H, dd, J = 15.9, 6.9 Hz), 1.48-1.43 (3H, m), 0.70 (3H, d, J = 6.8 Hz). | 487 | 2.04 | B |

TABLE 46
| No. | compound | ¹H-NMR δ ppm | [M + H] | RT | LC/MS condition |
|---|---|---|---|---|---|
| I-218 | 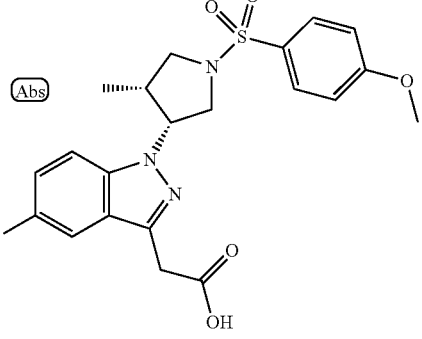 | 1H-NMR (DMSO-D6) δ: 7.80 (2H, d, J = 8.9 Hz), 7.74 (1H, d, J = 1.9 Hz), 7.68 (1H, d, J = 9.0 Hz), 7.37 (1H, dd, J = 8.9, 1.9 Hz), 7.16 (2H, d, J = 8.8 Hz), 5.40-5.33 (1H, m), 3.91-3.86 (5H, s), 3.70-3.53 (4H, m), 3.10 (1H, t, J = 10.0 Hz), 0.25 (3H, d, J = 6.8 Hz). | 464 | 2.06 | B |
| I-219 | 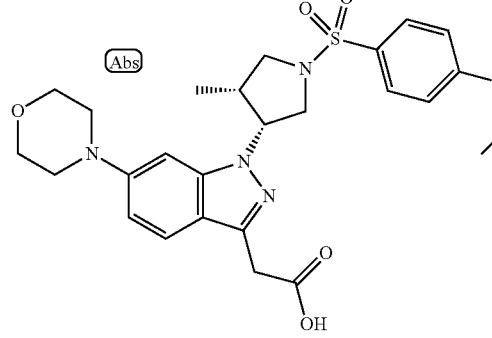 | 1H-NMR (CDCl3) δ: 7.83 (2H, d, J = 8.9 Hz), 7.46 (1H, d, J = 8.9 Hz), 7.02 (2H, d, J = 8.9 Hz), 6.89 (1H, dd, J = 9.0, 1.8 Hz), 6.64 (1H, d, J = 1.6 Hz), 5.00 (1H, dt, J = 10.2, 3.6 Hz), 4.13 (2H, ddd, J = 14.1, 7.1, 2.6 Hz), 4.01 (1H, dd, J = 11.1, 7.6 Hz), 3.89 (4H, t, J = 4.8 Hz), 3.82-3.76 (3H, m), 3.69 (1H, dd, J = 9.0, 7.4 Hz), 3.24-3.18 (5H, m), 2.66 (1H, ddd, J = 15.4, 8.7, 5.4 Hz), 1.47 (3H, t, J = 7.0 Hz), 0.50 (3H, d, J = 6.8 Hz). | 529 | 1.95 | B |
| I-220 | 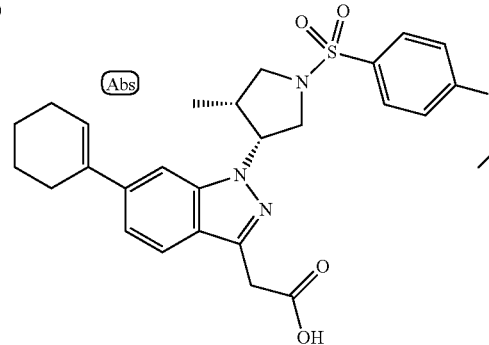 | 1H-NMR (CDCl3) δ: 7.84 (2H, d, J = 8.9 Hz), 7.51 (1H, d, J = 8.4 Hz), 7.26-7.23 (2H, m), 7.02 (2H, d, J = 8.9 Hz), 6.19 (1H, s), 5.07 (1H, td, J = 7 0, 2.8 Hz), 4.15-4.03 (3H, m), 3.82-3.68 (4H, m), 3.22 (1H, t, J = 9.7 Hz), 2.68 (1H, dt, J = 17.2, 6.9 Hz), 2.49-2.42 (2H, m), 2.27-2.21 (2H, m), 1.84-1.78 (2H, m), 1.71-1.65 (2H, q, J = 6.0 Hz), 1.47 (3H, t, J = 7.0 Hz), 0.47 (3H, d, J = 6.9 Hz). | 524 | 2.6 | B |
| I-221 | 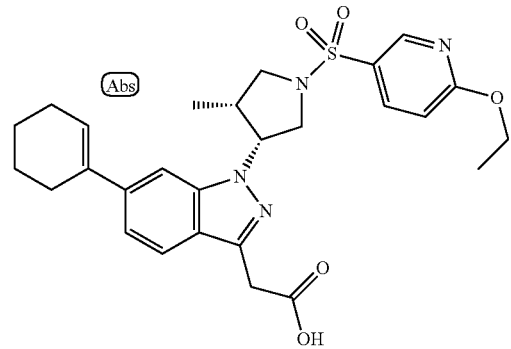 [SMILES: CCOc1ccc(S(=O)(=O)N2C[C@@H](C)[C@@H](n3nc(CC(=O)O)c4ccc(C5=CCCCC5)cc43)C2)cn1] | | 525 | 2.58 | B |

TABLE 47
| No. | compound | ¹H-NMR δ ppm | [M + H] | RT | LC/MS condition |
|---|---|---|---|---|---|
| I-222 | 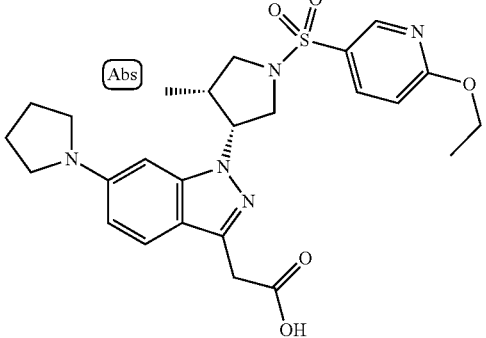 | | 514 | 2.33 | B |
| I-223 | 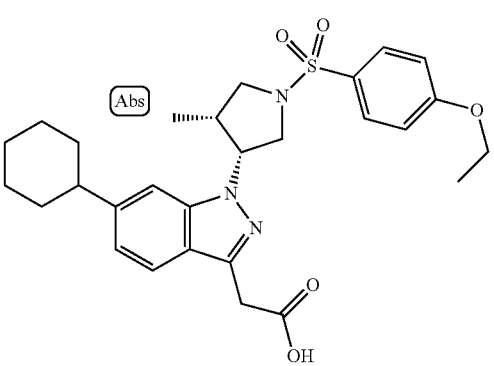 [SMILES: CCOc1ccc(S(=O)(=O)N2C[C@@H](C)[C@@H](n3nc(CC(=O)O)c4ccc(C5CCCCC5)cc43)C2)cc1] | 1H-NMR (CDCl3) δ: 7.83 (2H, d, J = 8.9 Hz), 7.51 (1H, d, J = 8.2 Hz), 7.14 (1H, s), 7.03 (3H, dd, J = 11.7, 8.7 Hz), 5.06 (1H, td, J = 7.0, 2.5 Hz), 4.13 (2H, q, J = 6.9 Hz), 4.05 (1H, dd, J = 11.2, 7.5 Hz), 3.82-3.68 (4H, m), 3.22 (1H, t, J = 9.7 Hz), 2.72-2.62 (2H, m), 1.91-1.76 (5H, m), 1.57-1.25 (5H, m), 1.47 (3H, t, J = 7.0 Hz), 0.49 (3H, t, J = 7.8 Hz). | 526 | 2.66 | B |
| I-224 | 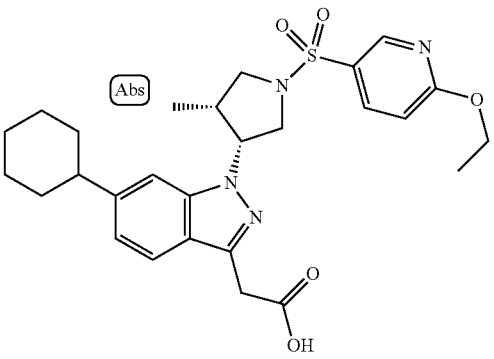 [SMILES: CCOc1ccc(S(=O)(=O)N2C[C@@H](C)[C@@H](n3nc(CC(=O)O)c4ccc(C5CCCCC5)cc43)C2)cn1] | | 527 | 2.65 | B |
| I-225 | 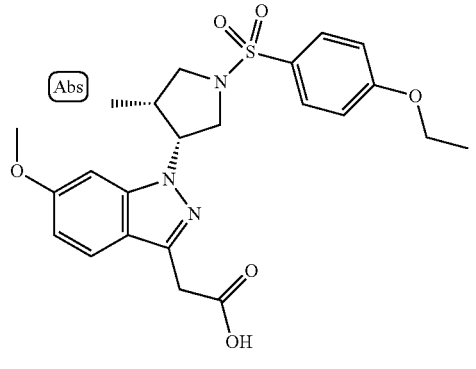 [SMILES: CCOc1ccc(S(=O)(=O)N2C[C@@H](C)[C@@H](n3nc(CC(=O)O)c4ccc(OC)cc43)C2)cc1] | 1H-NMR (CDCl₃) δ: 7.84 (2H, d, J = 8.8 Hz), 7.47 (1H, d, J = 8.8 Hz), 7.02 (2H, d, J = 8.8 Hz), 6.81 (1H, dd, J = 8.8, 1.9 Hz), 6.71 (1H, d, J = 1.9 Hz), 5.03-4.97 (1H, m), 4.14 (2H, q, J = 7.0 Hz), 4.03 (1H, dd, J = 11.2, 7.5 Hz), 3.88 (3H, s), 3.84-3.76 (3H, m), 3.73-3.61 (1H, m), 3.24-3.17 (1H, m), 2.72-2.63 (1H, m), 1.47 (3H, t, J = 7.0 Hz), 0.50 (3H, d, J = 6.9 Hz). | 474 | 2.03 | B |

TABLE 47-continued

| No. | compound | ¹H-NMR δ ppm | [M + H] | RT | LC/MS condition |
|---|---|---|---|---|---|
| I-226 | (Abs) structure | | 475 | 2.01 | B |

TABLE 48

| No. | compound | ¹H-NMR δ ppm | [M + H] | RT | LC/MS condition |
|---|---|---|---|---|---|
| I-227 | (Rac) structure | 1H-NMR (DMSO-D6) δ: 7.98-7.94 (2H, m), 7.76-7.65 (2H, m), 7.51-7.36 (3H, m), 7.13 (1H, t, J = 7.4 Hz), 5.52-5.43 (1H, m), 4.08-4.01 (1H, m), 3.81-3.50 (6H, m), 0.78 (3H, d, J = 21.7 Hz). | | | |
| I-228 | (Rac) structure | 1H-NMR (CDCl3) δ: 0.90 (3H, d, J = 21.6 Hz), 1.46 (3H, t, J = 7.0 Hz), 3.60 (1H, dd, J = 34.9, 11.5 Hz), 3.76-3.85 (3H, m), 3.89 (1H, dd, J = 11.0, 3.1 Hz), 4.08-4.17 (3H, m), 5, 04 (1H, ddd, J = 14.3, 7.6, 3.0 Hz), 6.98-7.04 (2H, m), 7.16-7.20 (1H, m), 7.39-7.44 (2H, m), 7.62-7.67 (1H, m), 7.80-7.86 (2H, m). | 462 | 2.05 | B |

TABLE 48-continued
| No. | compound | ¹H-NMR δ ppm | [M + H] | RT | LC/MS condition |
|---|---|---|---|---|---|
| I-229 | 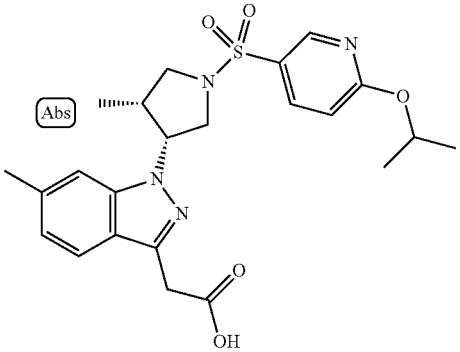 [SMILES: Cc1ccc2c(CC(=O)O)nn([C@H]3CN(S(=O)(=O)c4ccc(OC(C)C)nc4)C[C@H]3C)c2c1] | | 473 | 2.3 | B |
| I-230 | 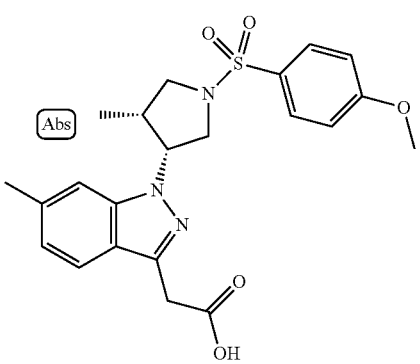 | | 444 | 2.06 | B |
| I-231 | 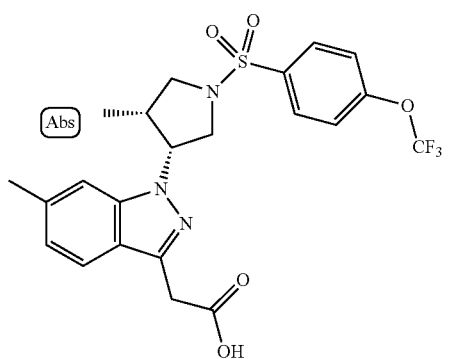 [SMILES: Cc1ccc2c(CC(=O)O)nn([C@H]3CN(S(=O)(=O)c4ccc(OC(F)(F)F)cc4)C[C@H]3C)c2c1] | | 498 | 2.34 | B |

TABLE 49

| No. | compound | ¹H-NMR δ ppm [M + H] | RT | LC/MS condition |
|---|---|---|---|---|
| I-232 | | 442 | 2.27 | B |
| I-233 | | 466 | 2.04 | B |
| I-234 | | 449 | 1.8 | B |
| I-235 | | 463 | 1.95 | B |

TABLE 49-continued
| No. | compound | ¹H-NMR δ ppm [M + H] | RT | LC/MS condition |
|---|---|---|---|---|
| I-236 | 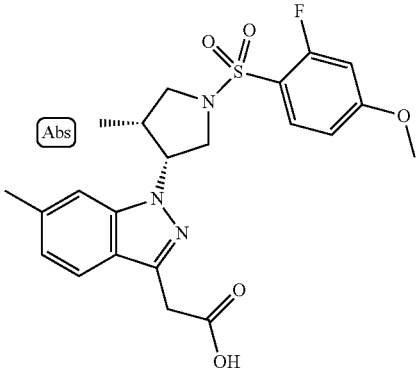 | 462 | 2.11 | B |
TABLE 50
| No. | compound | ¹H-NMR δ ppm [M + H] | RT | LC/MS condition |
|---|---|---|---|---|
| I-237 | 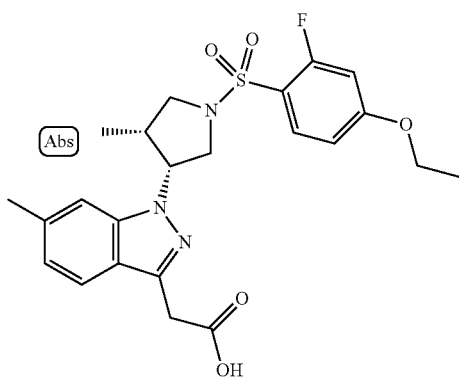 [SMILES: CCOc1ccc(S(=O)(=O)N2C[C@@H](C)[C@@H](n3nc(CC(=O)O)c4ccc(C)cc43)C2)c(F)c1] | 476 | 2.23 | B |
| I-238 | 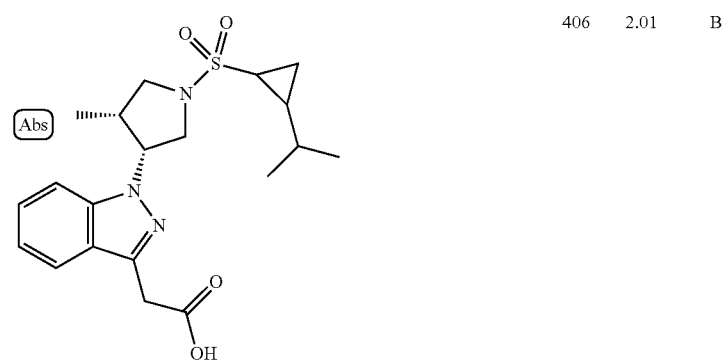 | 406 | 2.01 | B |

TABLE 50-continued
| No. | compound | ¹H-NMR δ ppm [M + H] | RT | LC/MS condition |
|---|---|---|---|---|
| I-239 | 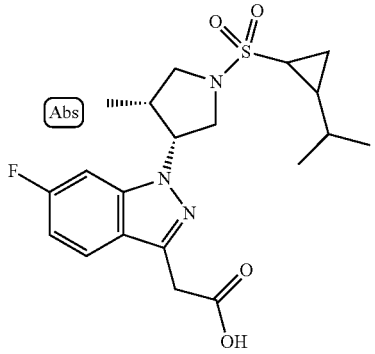 [SMILES: CC(C)C1CC1S(=O)(=O)N1C[C@@H](C)[C@@H](n2nc(CC(=O)O)c3ccc(F)cc32)C1] | 424 | 2.07 | B |
| I-240 | 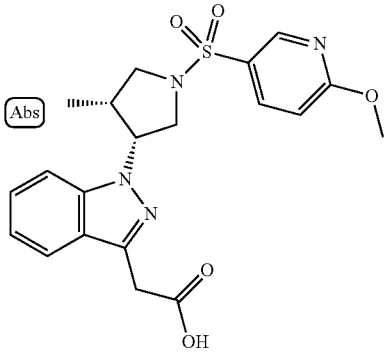 [SMILES: COc1ccc(S(=O)(=O)N2C[C@@H](C)[C@@H](n3nc(CC(=O)O)c4ccccc43)C2)cn1] | 431 | 1.88 | B |
| I-241 | 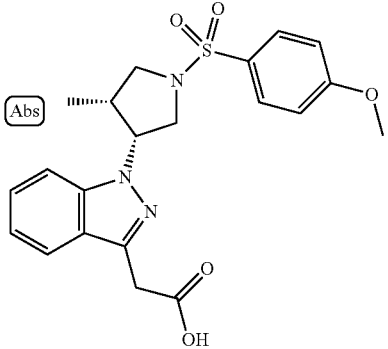 [SMILES: COc1ccc(S(=O)(=O)N2C[C@@H](C)[C@@H](n3nc(CC(=O)O)c4ccccc43)C2)cc1] | 430 | 1.92 | B |

TABLE 51
| No. | compound | ¹H-NMR δ ppm | [M + H] | RT | LC/MS condition |
|---|---|---|---|---|---|
| I-242 | 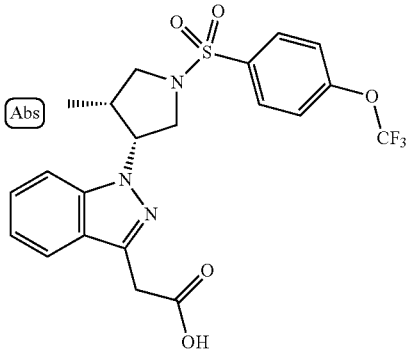 [SMILES: C[C@@H]1CN(S(=O)(=O)c2ccc(OC(F)(F)F)cc2)C[C@@H]1n1nc(CC(=O)O)c2ccccc21] | | 484 | 2.22 | B |
| I-243 | 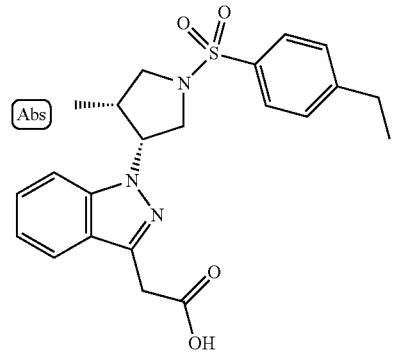 [SMILES: CCc1ccc(S(=O)(=O)N2C[C@@H](C)[C@@H](n3nc(CC(=O)O)c4ccccc43)C2)cc1] | | 428 | 2.15 | B |
| I-244 | 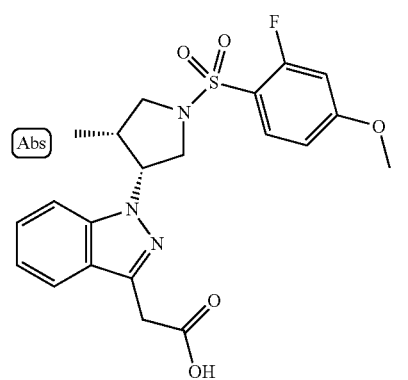 [SMILES: COc1ccc(S(=O)(=O)N2C[C@@H](C)[C@@H](n3nc(CC(=O)O)c4ccccc43)C2)c(F)c1] | | 448 | 1.98 | B |
| I-245 | 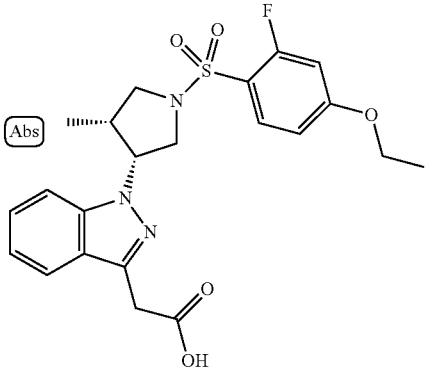 [SMILES: CCOc1ccc(S(=O)(=O)N2C[C@@H](C)[C@@H](n3nc(CC(=O)O)c4ccccc43)C2)c(F)c1] | | 462 | 2.12 | B |

TABLE 51-continued
| No. | compound | ¹H-NMR δ ppm | [M + H] | RT | LC/MS condition |
|---|---|---|---|---|---|
| I-246 | 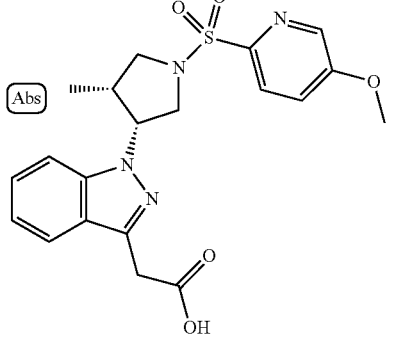 | | 431 | 1.74 | B |
TABLE 52
| No. | compound | ¹H-NMR δ ppm | [M + H] | RT | LC/MS condition |
|---|---|---|---|---|---|
| I-247 | 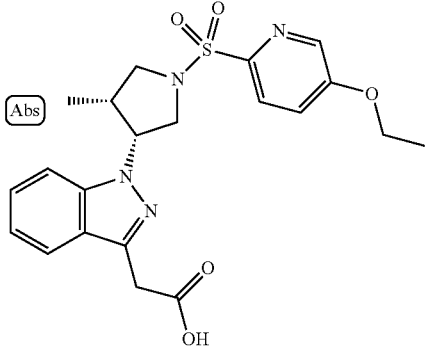 [SMILES: CCOc1ccc(S(=O)(=O)N2C[C@@H](C)[C@@H](n3nc(CC(=O)O)c4ccccc43)C2)nc1] | | 445 | 1.88 | B |
| I-248 | 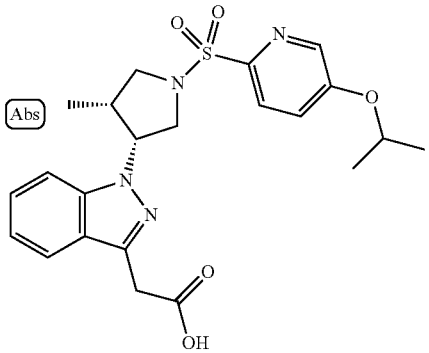 [SMILES: CC(C)Oc1ccc(S(=O)(=O)N2C[C@@H](C)[C@@H](n3nc(CC(=O)O)c4ccccc43)C2)nc1] | | 459 | 2.01 | B |

TABLE 52-continued
| No. | compound | ¹H-NMR δ ppm | [M + H] | RT | LC/MS condition |
|---|---|---|---|---|---|
| I-249 | 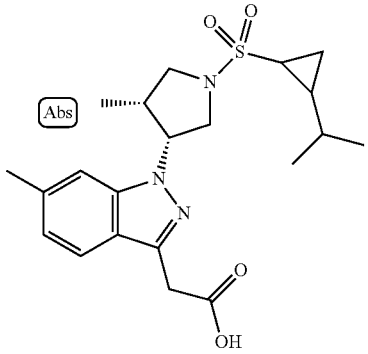 [SMILES: Cc1ccc2c(CC(=O)O)nn([C@H]3CN(S(=O)(=O)C4CC4C(C)C)C[C@H]3C)c2c1] | | 420 | 2.14 | B |
| I-250 | 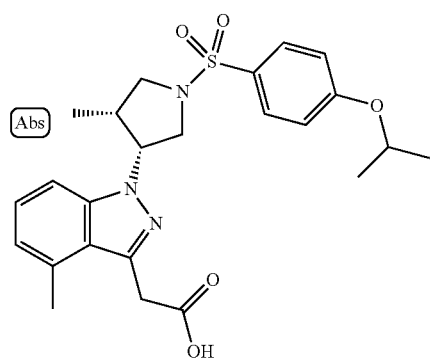 [SMILES: Cc1cccc2c1c(CC(=O)O)nn2[C@H]1CN(S(=O)(=O)c2ccc(OC(C)C)cc2)C[C@H]1C] | 1H-NMR (DMSO-d6) δ: 7.77 (2H, d, J = 8, 8 Hz), 7.41 (1H, d, J = 8.4 Hz), 7.19 (1H, t, J = 7.7 Hz), 7.12 (2H, d, J = 8.7 Hz), 6.81 (1H, d, J = 6.9 Hz), 5.32 (1H, t, J = 5.8 Hz), 4.79-4.73 (1H, m), 3.91-3.85 (1H, m), 3.75-3.52 (4H, m), 3.12 (1H, t, J = 9.9 Hz), 1.34 (6H, dd, J = 5.9, 1.9 Hz), 0.27 (3H, d, J = 6.8 Hz). | 472 | 2.23 | B |
| I-251 | 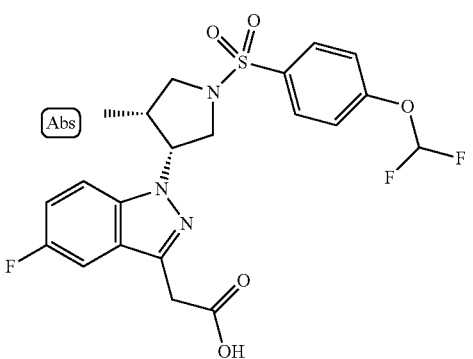 [SMILES: C[C@@H]1CN(S(=O)(=O)c2ccc(OC(F)F)cc2)C[C@@H]1n1nc(CC(=O)O)c2cc(F)ccc21] | 1H-NMR (DMSO-d6) δ: 0.27 (d, J = 6.8 Hz, 3H), 2.55-2.56 (m, 1H), 3.14 (t, J = 10.0 Hz, 1H), 3.58-3.63 (m, 4H), 3.92 (dd, J = 11.3, 7.3 Hz, 1H), 5.38 (t, J = 5.8 Hz, 1H), 7.25-7.28 (m, 1H), 7.41-7.46 (m, 4H), 7.64-7.70 (m, 1H), 7.95 (d, J = 8.8 Hz, 2H), 12.48 (s, 1H). | 484 | 2.05 | B |

TABLE 53

| No. | compound | ¹H-NMR δ ppm | [M + H] | RT | LC/MS condition |
|---|---|---|---|---|---|
| I-252 | | 1H-NMR (DMSO-d6) δ: 0.26 (d, J = 6.8 Hz, 3H), 1.39 (t, J = 7.0 Hz, 3H), 2.46-2.47 (m, 1H), 3.10 (t, J = 9.9 Hz, 1H), 3.53-3.67 (m, 4H), 3.88 (dd, J = 11.2, 7.3 Hz, 1H), 4.15 (q, J = 6.9 Hz, 2H), 5.34-5.38 (m, 1H), 7.14 (d, J = 8.8 Hz, 2H), 7.26 (td, J = 9.1, 2.4 Hz, 1H), 7.41 (dd, J = 9.1, 2.3 Hz, 1H), 7.67 (dd, J = 9.2, 4.1 Hz, 1H), 7.78 (d, J = 8.8 Hz, 2H), 12.47 (s, 1H). | 462 | 2.06 | B |
| I-253 | | | 518 | 1.91 | B |
| I-254 | | | 450 | 1.97 | B |
| I-255 | | | 450 | 1.92 | B |

TABLE 53-continued

| No. | compound | ¹H-NMR δ ppm | [M + H] | RT | LC/MS condition |
|---|---|---|---|---|---|
| I-256 | 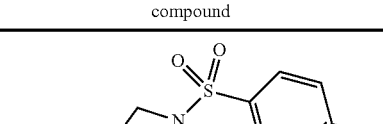 | 1H-NMR (DMSO-d6) δ: 0.32 (d, J = 6.9 Hz, 3H), 1.38 (t, J = 6.9 Hz, 3H), 2.42-2.46 (m, 1H), 2.95 (t, J = 9.9 Hz, 1H), 3.59-3.64 (m, 4H), 3.75 (dd, J = 11.5, 6.7 Hz, 1H), 4.16 (q, J = 6.9 Hz, 2H), 5.25 (td, J = 6.2, 2.7 Hz, 1H), 6.91 (s, 1H), 7.20 (d, J = 8.9 Hz, 2H), 7.36 (dd, J = 8.2, 1.2 Hz, 1H), 7.66 (d, J = 8.3 Hz, 1H), 7.86 (dd, J = 9.4, 2.4 Hz, 2H), 8.16 (s, 1H). | 468 | 2.16 | P |

TABLE 54

| No. | compound | ¹H-NMR δ ppm | [M + H] | RT | LC/MS condition |
|---|---|---|---|---|---|
| I-257 | 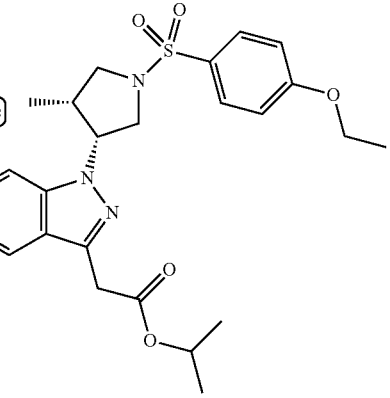 | 1H-NMR (DMSO-d6) δ: 7.79 (2H, d, J = 8.8 Hz), 7.62 (2H, d, J = 8.7 Hz), 7.35 (1H, t, J = 8.1 Hz), 7.16-7.07 (3H, m), 5.39-5.34 (1H, m), 4.92-4.85 (1H, m), 4.16 (2H, q, J = 7.0 Hz), 3.92-3.86 (1H, m), 3.77 (1H, d, J = 16.3 Hz), 3.66-3.54 (3H, m), 3.12 (1H, t, J = 10.0 Hz), 2.51-2.44 (1H, m), 1.40 (3H, t, J = 7.0 Hz), 1.15 (6H, dd, J = 8.3, 6.3 Hz). | 486 | 2.61 | B |
| I-258 | 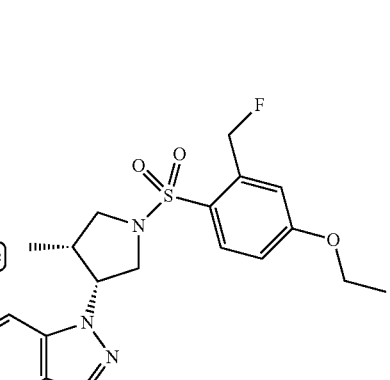 | 1H-NMR (DMSO-d6) δ: 7.96 (1H, d, J = 8.8 Hz), 7.65 (2H, t, J = 9.2 Hz), 7.36 (1H, t, J = 7.7 Hz), 7.20 (1H, s), 7.14-7.08 (2H, m), 5.91 (1H, s), 5.79 (1H, s), 5.42 (1H, t, J = 6.3 Hz), 4, 17 (2H, q, J = 6.8 Hz), 3.96-3.91 (1H, m), 3.76-3.58 (4H, m), 3.13 (1H, t, J = 9.7 Hz), 2.72-2.64 (1H, m), 1.38 (3H, t, J = 6.8 Hz), 0.34 (3H, d, J = 6.7 Hz). | 476 | 2.19 | B |

TABLE 54-continued

| No. | compound | ¹H-NMR δ ppm | [M + H] | RT | LC/MS condition |
|---|---|---|---|---|---|
| I-259 | | 1H-NMR (DMSO-d6) δ: 8.39 (1H, brs), 7.99 (1H, d, J = 8.8 Hz), 7.71-7.64 (2H, m), 7.37 (1H, t, J = 7.5 Hz), 7.11 (1H, t, J = 7.4 Hz), 7.01 (1H, dd, J = 8.8, 2.5 Hz), 6.98-6.96 (1H, m), 5.48-5.42 (1H, m), 4.69 (2H, d, J = 6.0 Hz), 4.12 (2H, q, J = 6.9 Hz), 3.96 (1H, dd, J = 10.7, 7.2 Hz), 3.82 (2H, s), 3.70 (1H, d, J = 10.8 Hz), 3, 62 (1H, t, J = 8.2 Hz), 3.20 (1H, t, J = 9.5 Hz), 2.74-2.65 (1H, m), 1.94 (3H, s), 1.36 (3H, t, J = 6.9 Hz), 0.36 (3H, d, J = 6.5 Hz). | 515 | 1.81 | B |
| I-260 | | 1H-NMR (DMSO-d6) δ: 7.97 (1H, d, J = 8.9 Hz), 7.89 (1H, brs), 7.70-7.64 (2H, m), 7.37 (1H, t, J = 7.3 Hz), 7.11 (1H, t, J = 7.4 Hz), 7.01 (1H, d, J = 2.5 Hz), 6.95 (1H, dd, J = 8.9, 2.5 Hz), 5.48-5.43 (1H, m), 4.13 (2H, q, J = 6.9 Hz), 3.97-3.92 (1H, m), 3.78 (2H, s), 3.69 (1H, d, J = 10.7 Hz), 3.59 (1H, t, J = 8.0 Hz), 3.19 (1H, t, J = 9.6 Hz), 3.08 (2H, dd, J = 12.8, 6.8 Hz), 2.96 (2H, t, J = 7.7 Hz), 2.73-2.64 (1H, m), 1.79-1.71 (5H, m), 1.36 (3H, t, J = 6.9 Hz), 0.35 (3H, d, J = 6.8 Hz). | 543 | 1.89 | B |

TABLE 55

| No. | compound | ¹H-NMR δ ppm | [M + H] | RT | LC/MS condition |
|---|---|---|---|---|---|
| I-261 | | 1H-NMR (DMSO-d6) δ: 7.74 (1H, d, J = 8.7 Hz), 7.70-7.64 (2H, m), 7.36 (1H, t, J = 7.6 Hz), 7.11 (1H, t, J = 7.4 Hz), 6.74 (1H, d, J = 2.0 Hz), 6.65 (1H, d, J = 8.8 Hz), 5.41-5.36 (1H, m), 4.15 (2H, q, J = 6.9 Hz), 3.95-3.75 (7H, m), 3.59 (1H, t, J = 8.3 Hz), 3.25 (1H, t, J = 9.9 Hz), 1.37 (3H, t, J = 6.9 Hz), 0.32 (3H, d, J = 6.7 Hz). | 474 | 2 | B |

TABLE 55-continued
| No. | compound | ¹H-NMR δ ppm | [M + H] | RT | LC/MS condition |
|---|---|---|---|---|---|
| I-262 | 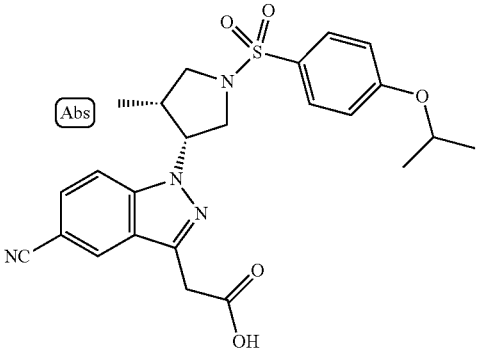 | 1H-NMR (CDCl3) δ: 8.06 (1H, s), 7.83 (2H, t, J = 4.52 Hz), 7.56 (1H, dd, J = 8.78, 1.25 Hz), 7.42 (1H, d, J = 9.03 Hz), 7.01 (2H, d, J = 9.03 Hz), 5.06 (1H, t, J = 7.40 Hz), 4.69 (1H, q, J = 6.02 Hz), 4.07 (1H, dd. J = 11.29, 7.28 Hz), 3.83 (1H, dd, J = 11.42, 2.64 Hz), 3.77 (2H, d, J = 2.26 Hz), 3.70 (1H, t, J = 8.28 Hz), 3.23 (1H, t, J = 9.79 Hz), 2.70 (1H, dd, J = 10.79, 7.03 Hz), 1.41 (6H, dd, J = 6.02, 2.51 Hz), 0.46 (3H, d, J = 7.03 Hz). | 483 | 2.07 | B |
| I-263 | 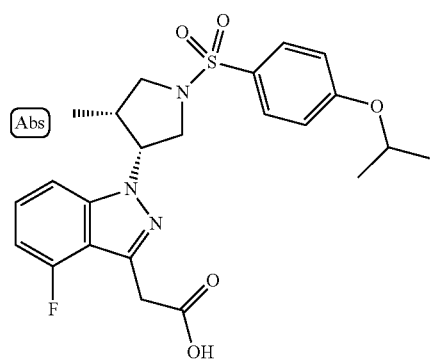 | 1H-NMR (DMSO-d6) δ: 12.50 (1H, s), 7.76 (2H, d, J = 8.9 Hz), 7.46 (1H, d, J = 8.5 Hz), 7.35-7.30 (1H, m), 7.13 (2H, d, J = 8.9 Hz), 6.82 (1H, dd, J = 10.5, 7.7 Hz), 5.37 (1H, t, J = 5.8 Hz), 4.78-4.72 (1H, m), 3.89 (1H, dd, J = 11.3, 7.4 Hz), 3.65-3.54 (4H, m), 3.10 (1H, t, J = 10.0 Hz), 1.34 (6H, dd, J = 6.0, 2.4 Hz), 0.29 (3H, d, J = 6.8 Hz). | 476 | 2.18 | B |
| I-264 | 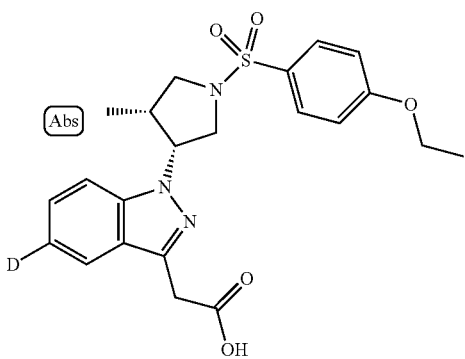 [SMILES: CCOc1ccc(S(=O)(=O)N2C[C@@H](C)[C@@H](n3nc(CC(=O)O)c4cc(F)ccc43)C2)cc1] |  | 445 | 2.04 | B |

TABLE 56

| No. | compound | ¹H-NMR δ ppm | [M + H] | RT | LC/MS condition |
|---|---|---|---|---|---|
| I-265 | | | 459 | 2.12 | B |
| I-266 | | | 406 | 2 | B |
| I-267 | | 1H-NMR (CDCl3) δ: 7.83 (2H, d, J = 8.78 Hz), 7.23 (1H, s), 7.05 (1H, t, J = 5.65 Hz), 7.00 (2H, d, J = 8.78 Hz), 6.92 (1H, d, J = 2.01 Hz), 5.01 (1H, s), 4.67 (1H, t, J = 6.02 Hz), 4.03 (1H, dd, J = 11.17, 7.40 Hz), 3.85 (1H, t, J = 3.01 Hz), 3.83 (3H, s), 3.79 (2H, d, J = 4.77 Hz), 3.69 (1H, t, J = 8.28 Hz), 3.22 (1H, t, J = 9.79 Hz), 2.67-2.64 (1H, m), 1.40 (6H, dd, J = 6.02, 2.76 Hz), 0.46 (3H, d, J = 6.78 Hz). | 488 | 2.15 | B |
| I-268 | | | 462 | 2.04 | B |

TABLE 57

| No. | compound | ¹H-NMR δ ppm | [M + H] | RT | LC/MS condition |
|---|---|---|---|---|---|
| I-269 | | | 466 | 1.97 | B |
| I-270 | | | 448 | 1.92 | B |
| I-271 | | 1H-NMR (DMSO-d6) δ: 0.32 (d, J = 6.8 Hz, 3H), 1.38 (t, J = 6.9 Hz, 3H), 2.37 (s, 3H), 2.42-2.46 (m, 1H), 2.92 (t, J = 9.9 Hz, 1H), 3.46 (s, 2H), 3.54-3.58 (m, 2H), 3.76 (dd, J = 11.3, 6.9 Hz, 1H), 4.16 (q, J = 6.9 Hz, 2H), 5.07-5.08 (m, 1H), 6.42 (s, 1H), 6.83 (d, J = 8.2 Hz, 1H), 7.20-7.23 (m, 3H), 7.34 (d, J = 8.0 Hz, 1H), 7.86 (d, J = 8.8 Hz, 2H), 12.20 (s, 1H). | 457 | 2.23 | B |
| I-272 | | 1H-NMR (DMSO-d6) δ: 0.37 (d, J = 6.8 Hz, 3H), 1.37 (t, J = 7.1 Hz, 3H), 2.38 (s, 3H), 2.44-2.46 (m, 1H), 3.02 (t, J = 9.7 Hz, 1H), 3.53 (s, 2H), 3.61-3.65 (m, 2H), 3.77 (dd, J = 11.1, 6.8 Hz, 1H), 4.43 (q, J = 7.0 Hz, 2H), 5.09 (dd, J = 9.0, 6.3 Hz, 1H), 6.80 (s, 1H), 6.85 (d, J = 8.0 Hz, 1H), 7.06 (d, J = 8.8 Hz, 1H), 7.26 (s, 1H), 7.36 (d, J = 8.2 Hz, 1H), 8.20 (dd, J = 8.8, 2.5 Hz, 1H), 8.70 (d, J = 2.3 Hz, 1H), 12.21 (s, 1H). | 458 | 2.2 | B |

TABLE 58
| No. | compound | ¹H-NMR δ ppm | [M + H] | RT | LC/MS condition |
|---|---|---|---|---|---|
| I-273 | 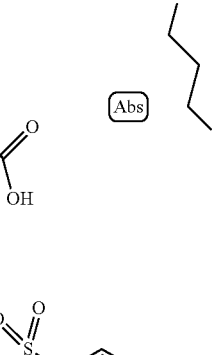 | | 502 | 2.16 | B |
| I-274 | 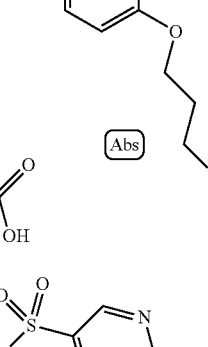 | | 488 | 2.03 | B |
| I-275 | 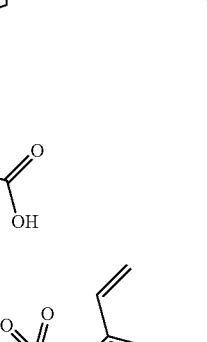 | 1H-NMR (DMSO-d6) δ: 1.38 (t, J = 7.0 Hz, 3H), 2.33-2.45 (m, 2H), 3.66 (t, J = 9.9 Hz, 1H), 3.86 (s, 2H), 3.97-4.08 (m, 2H), 4.45 (q, J = 7.0 Hz, 2H), 4.57 (dd, J = 13.6, 4.1 Hz, 1H), 4.69 (dd, J = 14.6, 4.0 Hz, 1H), 4.81 (t, J = 8.1 Hz, 1H), 7.06-7.14 (m, 2H), 7.35-7.42 (m, 2H), 7.71 (d, J = 8.0 Hz, 1H), 8.26 (d, J = 8.5 Hz, 1H), 8.74 (s, 1H). | 463 | 2.08 | P |
| I-276 | 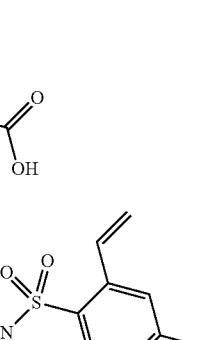 | 1H-NMR (DMSO-d6) δ: 12.48 (1H, brs), 7.96 (1H, d, J = 8.8 Hz), 7.68-7.54 (3H, m), 7.35 (1H, t, J = 7.7 Hz), 7.12-7.04 (2H, m), 5.85 (1H, d, J = 17.3 Hz), 5.44-5.38 (2H, m), 4.19 (2H, q, J = 6.9 Hz), 3.95-3.88 (1H, m), 3.78-3.70 (3H, m), 3.58 (1H, t, J = 8.0 Hz), 3.20 (1H, t, J = 9.7 Hz), 2.66-2.57 (1H, m), 1.38 (3H, t, J = 6.9 Hz), 0.32 (3H, d, J = 6.8 Hz). | 470 | 2.23 | B |

TABLE 59
| No. | compound | ¹H-NMR δ ppm | [M + H] | RT | LC/MS condition |
|---|---|---|---|---|---|
| I-277 | 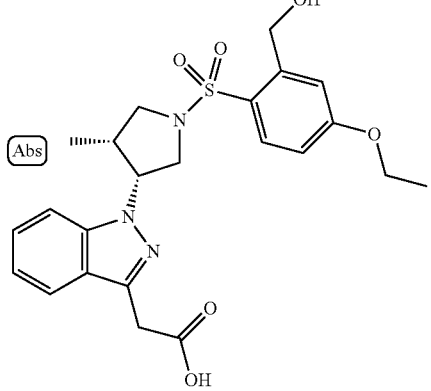 [SMILES: CCOc1ccc(S(=O)(=O)N2C[C@@H](C)[C@@H](n3nc(CC(=O)O)c4ccccc43)C2)c(OC)c1] | 1H-NMR (DMSO-d6) δ: 7.91 (1H, d, J = 8.8 Hz), 7.69-7.63 (2H, m), 7.37 (2H, t, J = 7.6 Hz), 7.10 (1H, t, J = 7.5 Hz), 6.96 (1H, d, J = 8.9 Hz), 5.46-5.40 (1H, m), 4.93 (2H, s), 4.14 (2H, q, J = 6.9 Hz), 3.95-3.89 (1H, m), 3.79 (2H, s), 3.65-3.57 (2H, m), 3.16 (1H, t, J = 9.6 Hz), 2.72-2.64 (1H, m), 1.37 (3H, t, J = 6.9 Hz), 0.36 (3H, d, J = 6.7 Hz). | 474 | 1.89 | B |
| I-278 | 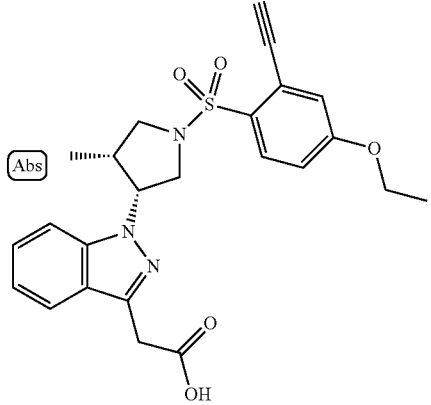 [SMILES: C#Cc1cc(OCC)ccc1S(=O)(=O)N1C[C@@H](C)[C@@H](n2nc(CC(=O)O)c3ccccc32)C1] | 1H-NMR (DMSO-d6) δ: 12.48 (1H, brs), 7.93 (1H, d, J = 8.8 Hz), 7.65 (2H, t, J = 8.4 Hz), 7.36 (1H, t, J = 7.5 Hz), 7.23 (1H, d, J = 2.8 Hz), 7.15 (1H, dd, J = 8.9, 2.6 Hz), 7.10 (1H, t, J = 7.5 Hz), 5.40 (1H, m), 4.55 (1H, s), 4.16 (2H, q, J = 6.9 Hz), 4.00-3.94 (1H, m), 3.86-3.81 (1H, m), 3.71-3.63 (3H, m), 3.32-3.26 (1H, m), 2.68-2.57 (1H, m), 1.37 (3H, t, J = 6.9 Hz), 0.32 (3H, d, J = 6.8 Hz). | 468 | 2.1 | B |
| I-279 | 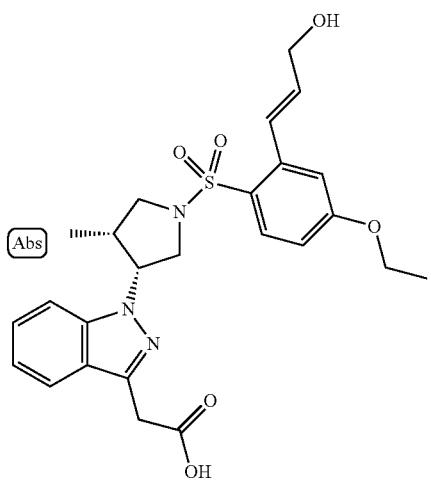 [SMILES: CCOc1ccc(S(=O)(=O)N2C[C@@H](C)[C@@H](n3nc(CC(=O)O)c4ccccc43)C2)c(/C=C/CO)c1] | 1H-NMR (DMSO-d6) δ: 7.93 (1H, d, J = 8.8 Hz), 7.68-7.62 (2H, m), 7.43 (1H, d, J = 15.6 Hz), 7.36 (1H, t, J = 7.7 Hz), 7.20 (1H, s), 7.10 (1H, t, J = 7.4 Hz), 7.00 (1H, d, J = 8.7 Hz), 6.41-6.33 (1H, m), 5.42-5.35 (1H, m), 4.17 (2H, q, J = 6.9 Hz), 4.10 (2H, s), 3.91-3.71 (4H, m), 3.59 (1H, t, J = 8.2 Hz), 3.22 (1H, t, J = 9.7 Hz), 1.37 (3H, t, J = 6.9 Hz), 0.32 (3H, d, J = 6.7 Hz). | 500 | 1.92 | B |

TABLE 59-continued

| No. | compound | ¹H-NMR δ ppm | [M + H] | RT | LC/MS condition |
|---|---|---|---|---|---|
| I-280 | 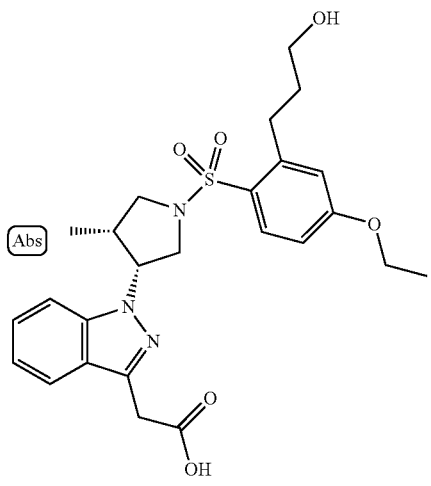 [SMILES: CCOc1ccc(S(=O)(=O)N2C[C@@H](C)[C@@H](n3nc(CC(=O)O)c4ccccc43)C2)c(CCCO)c1] | 1H-NMR (DMSO-d6) δ: 7.97 (1H, d, J = 8.5 Hz), 7.69 (1H, d, J = 8.0 Hz), 7.65 (1H, d, J = 8.5 Hz), 7.37 (1H, t, J = 7.5 Hz), 7.11 (1H, t, J = 7.5 Hz), 6.99-6.93 (2H, m), 5.48-5.42 (1H, m), 4.13 (2H, q, J = 6.9 Hz), 3.98-3.93 (1H, m), 3.80 (2H, s), 3.72-3.68 (1H, m), 3.60 (1H, t, J = 8.2 Hz), 3.45 (2H, t, J = 6.4 Hz), 3.20 (1H, t, J = 9.5 Hz), 2.99 (2H, t, J = 7.9 Hz), 2.72-2.63 (1H, m), 1.82-1.74 (2H, m), 1.36 (3H, t, J = 6.9 Hz), 0.36 (3H, d, J = 6.8 Hz). | 502 | 1.93 | B |

TABLE 60

| No. | compound | ¹H-NMR δ ppm | [M + H] | RT | LC/MS condition |
|---|---|---|---|---|---|
| I-281 | 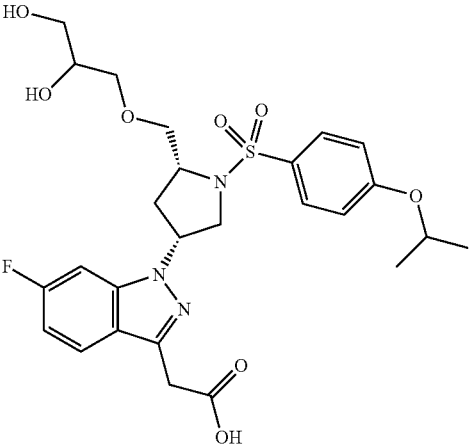 [SMILES: CC(C)Oc1ccc(S(=O)(=O)N2C[C@H](n3nc(CC(=O)O)c4ccc(F)cc43)C[C@@H]2COCC(O)CO)cc1] | 1H-NMR (CDCl3) δ: 7.77 (2H, d, J = 8.8 Hz), 7.61 (1H, t, J = 7.0 Hz), 7.45 (1H, d, J = 9.3 Hz), 6.98-6.95 (3H, m), 4.69-4.63 (3H, m), 4.00-3.93 (3H, m), 3.49-3.47 (2H, m), 3.40-3.37 (1H, m), 3.24-3.22 (1H, m), 3.10-3.08 (3H, m), 2.84-2.81 (1H, m), 2.11-2.08 (1H, m), 1.66-1.63 (1H, m), 1.37 (6H, d, J = 6.0 Hz). | 566 | 1.74 | B |
| I-282 | 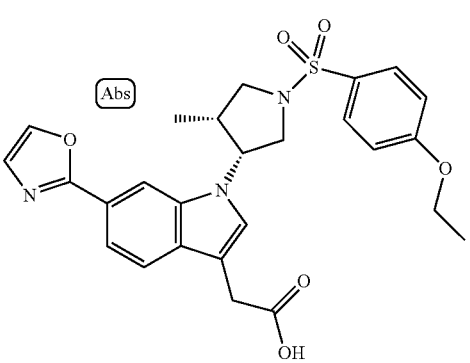 [SMILES: CCOc1ccc(S(=O)(=O)N2C[C@@H](C)[C@@H](n3cc(CC(=O)O)c4ccc(-c5ncco5)cc43)C2)cc1] | 1H-NMR (DMSO-D6) δ: 0.34 (d, J = 6.8 Hz, 3H), 1.39 (t, J = 7.0 Hz, 3H), 2.95 (t, J = 10.0 Hz, 1H), 3.58-3.63 (m, 4H), 3.78 (dd, J = 11.4, 6.8 Hz, 1H), 4.17 (q, J = 7.0 Hz, 2H), 5.31 (t, J = 5.1 Hz, 1H), 6.69 (s, 1H), 7.21 (d, J = 8.9 Hz, 2H), 7.34 (d, J = 0.8 Hz, 1H), 7.60 (d, J = 8.3 Hz, 1H), 7.68 (dd, J = 8.3, 1.3 Hz, 1H), 7.87 (d, J = 8.9 Hz, 2H), 8.12 (s, 1H), 8.18 (d, J = 0.8 Hz, 1H). | 510 | 2.14 | P |

TABLE 60-continued

| No. | compound | ¹H-NMR δ ppm | [M + H] | RT | LC/MS condition |
|---|---|---|---|---|---|
| I-283 | | 1H-NMR (CDCl3) δ: 0.44 (d, J = 6.8 Hz, 3H, minor), 0.47 (d, J = 6.8 Hz, 3H, major), 1.45-1.50 (m, mixture), 1.81 (s, 3H, minor), 1.85 (s, 3H, major), 2.65-2.73 (m, 1H, mixture), 3.16-3.33 (m, 1H, mixture), 3.59-3.67 (m, 1H, mixture), 3.74-3.78 (m, 1H, minor), 3.88-3.92 (m, 1H, major), 3.97-4.18 (m, 3H, mixture), 5.05-5.12 (m, 1H, mixture), 7.02 (d, J = 8.8 Hz, 2H, major), 7.05 (d, J = 8.8 Hz, 2H, minor), 7.16-7.21 (m, 1H, mixture), 7.32-7.35 (m, 1H, mixture), 7.38-7.42 (m, 1H, mixture), 7.84 (d, J = 8.8 Hz, 2H, major), 7.85 (d, J = 8.8 Hz, 2H, minor), 8.046-8.083 (m, 1H, mixture). | 474 | 1.89 | B |

TABLE 61

| No. | compound | ¹H-NMR δ ppm | [M + H] | RT | LC/MS condition |
|---|---|---|---|---|---|
| I-284 | | 1H-NMR (CDCl3) δ: 0.40-0.40 (m, 3H, mixture), 1.41-1.50 (m, 6H, mixture), 2.65-2.66 (m, 1H, mixture), 3.19-3.28 (m, 1H, mixture), 3.66-3.68 (m, 1H, mixture), 3.80-3.84 (m, 1H, mixture), 3.86-3.89 (m, 1H, major), 3.95-3.97 (m, 1H, minor), 4.04-4.15 (m, 3H, mixture), 5.04-5.09 (m, 1H, mixture), 7.00-7.02 (m, 2H, mixture), 7.09-7.12 (m, 1H, mixture), 7.32-7.34 (m, 2H, mixture), 7.67-7.71 (m, 1H, mixture), 7.83-7.85 (m, 2H, mixture). | 458 | 2.12 | B |
| I-285 [Abs] | | 1H-NMR (CDCl3) δ: 0.42 (d, J = 6.8 Hz, 3H), 1.47 (t, J = 6.9 Hz, 3H), 1.69 (s, 3H), 2.61-2.68 (m, 1H), 3.12 (s, 3H), 3.26 (dd, J = 9.8, 9.8 Hz, 1H), 3.69 (dd, J = 8.2, 8.2 Hz, 1H), 3.81 (dd, J = 10.8, 2.8 Hz, 1H), 4.06-4.15 (m, 3H), 5.13 (brm, 1H), 7.01 (d, J = 8.8 Hz, 2H), 7.13-7.15 (m, 1H), 7.33-7.40 (m, 2H), 7.77 (d, J = 8.3 Hz, 1H), 7.84 (d, J = 7.8 Hz, 2H). | 488 | 2.03 | B |
| I-286 [Abs] | | 1H-NMR (CDCl3) δ: 0.44 (d, J = 7.0 Hz, 3H), 1.45 (t, J = 6.9 Hz, 3H), 1.69 (s, 3H), 2.64-2.75 (m, 1H), 3.11 (s, 3H), 3.26 (dd, J = 9.7, 9.7 Hz, 1H), 3.71 (dd, J = 9.0, 7.3 Hz, 1H), 3.88 (dd, J = 10.9, 3.4 Hz, 1H), 4.06-4.15 (m, 3H), 5.11-5.16 (m, 1H), 7.02 (d, J = 8.8 Hz, 2H), 7.14-7.17 (m, 1H), 7.37-7.40 (m, 2H), 7.75 (d, J = 8.0 Hz, 1H), 7.84 (d, J = 8.8 Hz, 2H). | 488 | 2.04 | B |

TABLE 61-continued

| No. | compound | ¹H-NMR δ ppm | [M + H] | RT | LC/MS condition |
|---|---|---|---|---|---|
| I-287 | 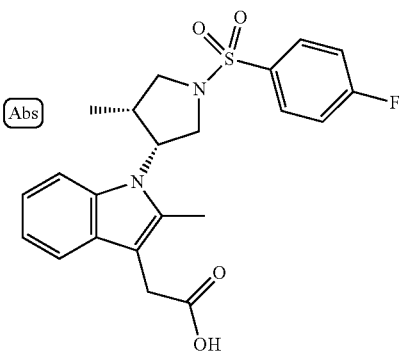 [SMILES: Cc1c(CC(=O)O)c2ccccc2n1[C@H]1CN(S(=O)(=O)c2ccc(F)cc2)C[C@H]1C] | 1H-NMR (DMSO-D6) δ: 0.34 (d, J = 6.9 Hz, 3H), 2.28 (s, 3H), 2.44-2.46 (m, 1H), 3.03 (t, J = 10.2 Hz, 1H), 3.57 (d, J = 0.9 Hz, 2H), 3.71 (dd, J = 10.4, 8.2 Hz, 1H), 3.84 (d, J = 6.3 Hz, 2H), 5.19 (dd, J = 14.0, 6.6 Hz, 1H), 6.80 (t, J = 7.5 Hz, 1H), 6.95 (t, J = 7.2 Hz, 2H), 7.41 (d, J = 7.5 Hz, 1H), 7.55-7.60 (m, 2H), 8.00-8.04 (m, 2H), 12.15 (br s, 1H). | 431 | 2.17 | P |

TABLE 62

| No. | compound | ¹H-NMR δ ppm | [M + H] | RT | LC/MS condition |
|---|---|---|---|---|---|
| I-288 | 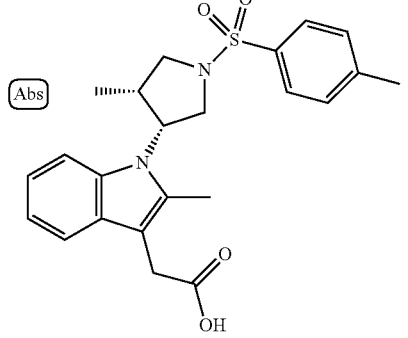 | 1H-NMR (DMSO-D6) δ: 0.32 (d, J = 7.0 Hz, 3H), 2.27 (s, 3H), 2.42-2.44 (m, 1H), 2.48 (s, 3H), 3.00 (t, J = 10.1 Hz, 1H), 3.56 (s, 2H), 3.67 (dd, J = 10.4, 8.2 Hz, 1H), 3.78-3.84 (m, 2H), 5.18 (dd, J = 12.7, 7.8 Hz, 1H), 6.77 (t, J = 7.6 Hz, 1H), 6.94 (t, J = 7.2 Hz, 2H), 7.40 (d, J = 7.5 Hz, 1H), 7.53 (d, J = 8.0 Hz, 2H), 7.82 (d, J = 8.2 Hz, 2H), 12.14 (br s, 1H). | 427 | 2.23 | P |
| I-289 | 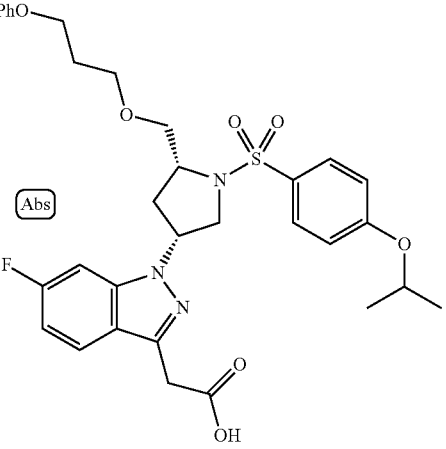 | 1H-NMR (CDCl3) δ: 7.76 (2H, d, J = 8.8 Hz), 7.61 (1H, dd, J = 8.8, 5.0 Hz), 7.46 (1H, d, J = 9.3 Hz), 7.26-7.24 (2H, m), 7.00-6.91 (4H, m), 6.81 (2H, d, J = 8.3 Hz), 4.79 (1H, dd, J = 14.6, 3.0 Hz), 4.59 (2H, td, J = 12.2, 6.2 Hz), 4.02 (2H, s), 3.92 (1H, d, J = 4.8 Hz), 3.76 (2H, t, J = 5.8 Hz), 3.57 (1H, t, J = 4.3 Hz), 3.33 (1H, dd, J = 11.3, 4.3 Hz), 3.25-3.19 (3H, m), 2.15-2.09 (1H, m), 1.78 (1H, s), 1.62 (1H, t, J = 6.1 Hz), 1.34 (6H, d, J = 5.8 Hz). | 626 | 2.52 | B |

TABLE 62-continued

| No. | compound | ¹H-NMR δ ppm | [M + H] | RT | LC/MS condition |
|-----|----------|--------------|---------|-----|-----------------|
| I-290 | | 1H-NMR (DMSO-d6) δ: 0.26 (d, J = 6.8 Hz, 3H), 1.37 (t, J = 6.8 Hz, 3H), 2.33-2.42 (m, 1H), 3.15-3.88 (m, 4H), 4.15 (q, J = 6.8 Hz, 2H), 5.50-5.53 (m, 1H), 7.15 (d, J = 8.8 Hz, 2H), 7.29 (d, J = 7.6 Hz, 1H), 7.49 (d, J = 7.6 Hz, 1H), 7.78-7.81 (m, 2H), 7.81 (d, J = 8.8 Hz, 2H). | 480 | 2.21 | B |
| I-291 | | | 594 | 2.07 | B |

TABLE 63

| No. | compound | ¹H-NMR δ ppm | [M + H] | RT | LC/MS condition |
|-----|----------|--------------|---------|-----|-----------------|
| I-292 | | 1H-NMR (CDCl3) δ: 7.80 (2H, d, J = 8.8 Hz), 7.66 (1H, dd, J = 9.0, 5.0 Hz), 6.95 (4H, d, J = 8.5 Hz), 6.91-6.87 (1H, m), 6.82-6.78 (3H, m), 4.65-4.59 (3H, m), 4.50 (1H, d, J = 9.5 Hz), 4.13 (2H, s), 3.99 (3H, ddd, J = 23.7, 14.7, 8.2 Hz), 2.70-2.62 (2H, m), 1.37 (6H, dd, J = 6.0, 4.0 Hz). | 584 | 2.32 | B |

TABLE 63-continued
| No. | compound | ¹H-NMR δ ppm | [M + H] | RT | LC/MS condition |
|---|---|---|---|---|---|
| I-293 | 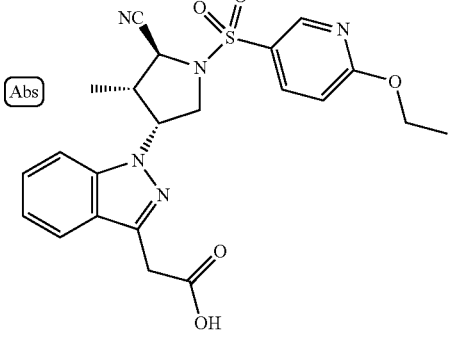 | 1H-NMR (CDCl3) δ: 8.74 (1H, d, J = 2.5 Hz), 8.04 (1H, dd, J = 8.8, 2.5 Hz), 7.65 (1H, d, J = 8.2 Hz), 7.44-7.38 (1H, m), 7.31 (1H, d, J = 8.5 Hz), 7.20-7.15 (1H, m), 6.84 (1H, d, J = 8.8 Hz), 5.11-5.06 (1H, m), 4.57 (1H, d, J = 9.9 Hz), 4.47 (2H, q, J = 7.0 Hz), 4.18-4.09 (1H, m), 3.96-3.91 (1H, m), 3.78-3.67 (2H, m), 3.12-3.01 (1H, m), 1.43 (3H, t, J = 7.0 Hz), 0.67 (3H, d, J = 6.9 Hz). | 470 | 1.93 | B |
| I-294 | 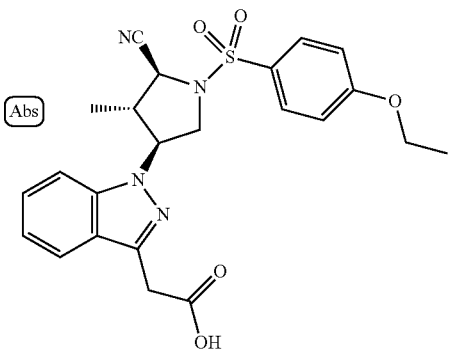 [SMILES: CCOc1ccc(S(=O)(=O)N2C[C@@H](n3nc(CC(=O)O)c4ccccc43)[C@H](C)[C@H]2C#N)cc1] | ¹H-NMR (CDCl₃) δ: 7.83 (2H, d, J = 8.9 Hz), 7.68 (1H, d, J = 8.0 Hz), 7.46-7.40 (1H, m), 7.38-7.30 (1H, m), 7.23-7.17 (1H, m), 7.00 (2H, d, J = 8.9 Hz), 4.87-4.78 (2H, m), 4.15-4.03 (2H, m), 3.99 (2H, s), 3.82-3.70 (2H, m), 3.21-3.11 (1H, m), 1.46 (3H, t, J = 7.0 Hz), 1.14 (3H, d, J = 6.8 Hz). | 469 | 2.01 | B |
| I-295 | 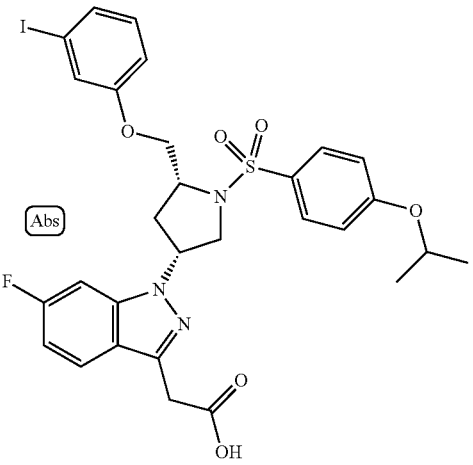 [SMILES: CC(C)Oc1ccc(S(=O)(=O)N2C[C@H](n3nc(CC(=O)O)c4ccc(F)cc43)C[C@@H]2COc2cccc(I)c2)cc1] | 1H-NMR (CDCl3) δ: 7.83 (2H, d, J = 9.0 Hz), 7.64 (2H, ddd, J = 18.5, 8.8, 5.1 Hz), 7.10 (1H, d, J = 8.8 Hz), 7.02-6.81 (8H, m), 4.68-4.61 (1H, m), 4.43 (1H, dd, J = 15.8, 8.0 Hz), 4.35 (1H, dd, J = 9.0, 3.8 Hz), 4.26-4.24 (1H, m), 4.06 (2H, s), 3.99 (2H, s), 3.92 (1H, dd, J = 11.4, 7.2 Hz), 3.80 (1H, dd, J = 11.5, 8.8 Hz), 2.72-2.65 (1H, m), 2.54 (1H, dd, J = 13.9, 6.9 Hz), 1.40 (6H, d, J = 6.0 Hz) | 694 | 2.66 | B |

TABLE 64
| No. | compound | ¹H-NMR δ ppm | [M + H] | RT | LC/MS condition |
|---|---|---|---|---|---|
| I-296 | 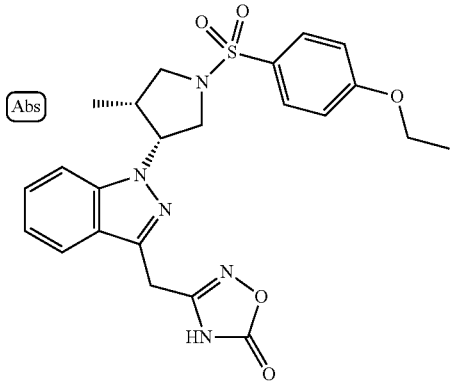 [SMILES: CCOc1ccc(S(=O)(=O)N2C[C@@H](C)[C@@H](n3nc(Cc4noc(=O)[nH]4)c4ccccc43)C2)cc1] | | 484 | 2.09 | B |
| I-297 | 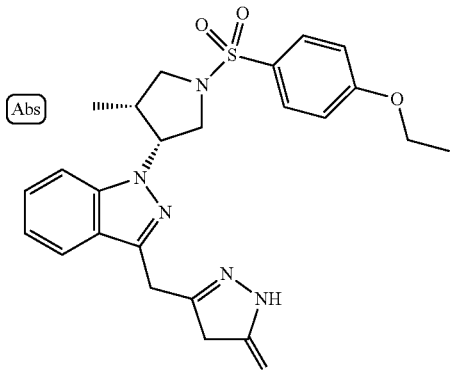 | 1H-NMR (DMSO-D6) δ: 11.44 (1H, brs), 9.35 (0.4H, brs). 7.81 (2H, d, J = 8.9 Hz), 7.59 (1H, d, J = 8.5 Hz), 7.47 (1H, d, J = 8.2 Hz), 7.31 (1H, t, J = 7.5 Hz), 7.13 (2H, d, J = 8.8 Hz), 7.03 (1H, t, J = 7.5 Hz), 5.37-5.32 (1H, m), 5.04 (1H, brs), 4.07 (2H, q, J = 6.9 Hz), 3.92-3.81 (3H, m), 3.72-3.67 (1H, m), 3.61-3.56 (1H, m), 3.19 (1H, t, J = 10.0 Hz), 2.51-2.42 (1H, m), 1.33 (3H, t, J = 7.0 Hz), 0.28 (3H, d, J = 6.8 Hz). | 482 | 1.82 | B |
| I-298 | 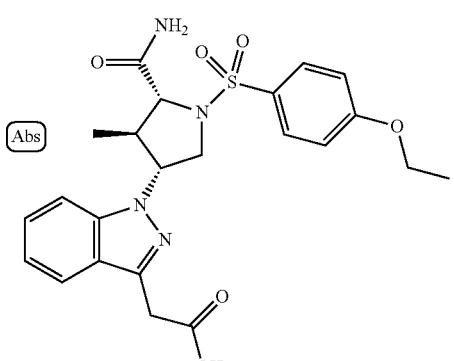 | ¹H-NMR (CDCl₃) δ: 7.74 (2H, d, J = 8.8 Hz), 7.71-7.06 (4H, m), 6.95 (2H, d, J = 8.8 Hz), 4.95-4.83 (1H, m), 4.33-4.24 (2H, m), 4.20-3.87 (5H, m), 3.86-3.75 (1H, m), 3.70-3.61 (1H, m), 2.97-2.86 (1H, m), 1.29-1.24 (3H, m), 0.93 (3H, d, J = 6.9 Hz). | 487 487 | 1.59 1.71 | B |
| I-299 | 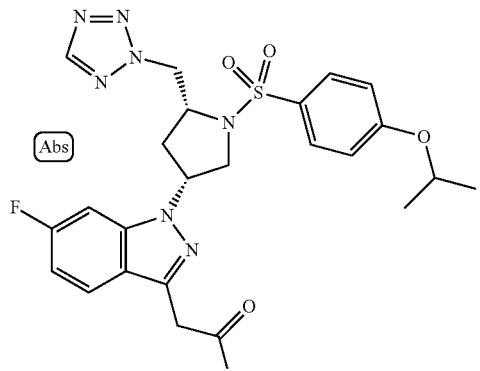 | 1H-NMR (CDCl3) δ: 8.52 (1H, s), 7.85 (2H, d, J = 8.9 Hz), 7.67-7.61 (2H, m), 7.04 (2H, d, J = 8.8 Hz), 6.77 (1H, d, J = 8.8 Hz), 5.23 (1H, d, J = 5.0 Hz), 5.16-5.14 (1H, m), 4.68-4.67 (1H, m), 4.54-4.52 (1H, m), 4.08 (1H, s), 4.01 (2H, s), 3.83-3.81 (1H, m), 3.76-3.74 (1H, m), 2.50-2.49 (1H, m), 2.37-2.35 (1H, m), 1.40 (6H, d, J = 6.0 Hz). | 544 | 2.05 | B |

TABLE 65

| No. | compound | ¹H-NMR δ ppm | [M + H] | RT | LC/MS condition |
|---|---|---|---|---|---|
| I-300 | 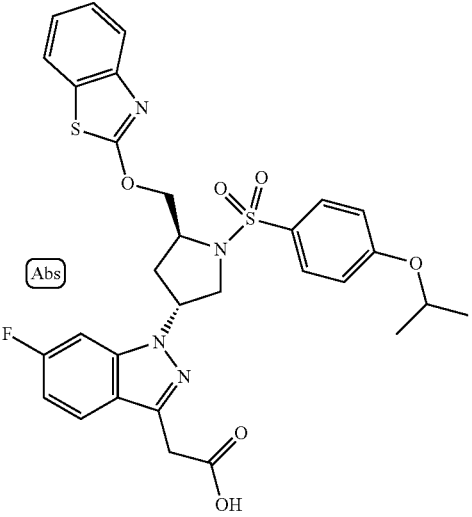 [SMILES: CC(C)Oc1ccc(S(=O)(=O)N2C[C@H](n3nc(CC(=O)O)c4ccc(F)cc43)C[C@H]2COc2nc3ccccc3s2)cc1] | 1H-NMR (CDCl3) δ: 7.71 (2H, d, J = 9.0 Hz), 7.62 (1H, d, J = 8.5 Hz), 7.55 (1H, dd, J = 8.8, 5.0 Hz), 7.48 (2H, t, J = 6.7 Hz), 7.25-7.23 (1H, m), 7.03 (1H, d, J = 7.3 Hz), 6.93 (1H, t, J = 8.9 Hz), 6.88 (2H, d, J = 8.8 Hz), 5.13-5.11 (1H, m), 4.61-4.60 (1H, m), 4.49 (1H, dd, J = 14.3, 9.8 Hz), 4.34-4.32 (1H, m), 4.27-4.25 (1H, m), 3.91 (1H, dd, J = 9.9, 6.9 Hz), 3.86 (2H, s), 3.67 (1H, t, J = 8.8 Hz), 2.48 (1H, s), 2.31 (1H, t, J = 10.8 Hz), 1.37 (6H, dd, J = 6.0, 4.3 Hz) | 625 | 2.37 | B |
| I-301 | 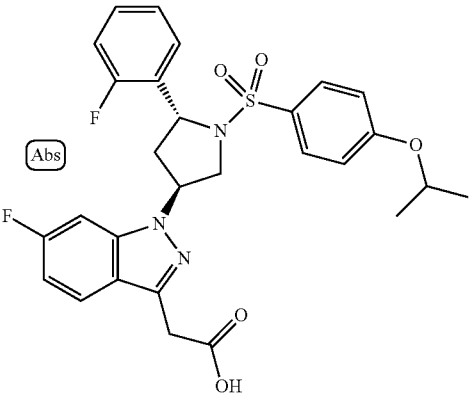 [SMILES: CC(C)Oc1ccc(S(=O)(=O)N2C[C@@H](n3nc(CC(=O)O)c4ccc(F)cc43)C[C@@H]2c2ccccc2F)cc1] | 1H-NMR (CDCl3) δ: 7.60-7.58 (4H, m), 7.32-7.29 (1H, m), 7.20 (1H, t, J = 7.3 Hz), 7.04 (1H, t, J = 9.7 Hz), 6.95 (1H, t, J = 8.9 Hz), 6.90 (1H, d, J = 9.0 Hz), 6.79 (2H, d, J = 8.8 Hz), 5.32 (1H, t, J = 6.5 Hz), 5.01 (1H, t, J = 6.3 Hz), 4.60 (1H, t, J = 6.0 Hz), 4.14 (1H, dd, J = 11.9, 6.7 Hz), 3.91 (2H, s), 3.88 (1H, t, J = 5.3 Hz), 2.98 (1H, dd, J = 13.4, 7.2 Hz), 2.39 (1H, t, J = 7.0 Hz), 1.38 (6H, d, J = 6.0 Hz). | 556 | 2.27 | B |
| I-302 | 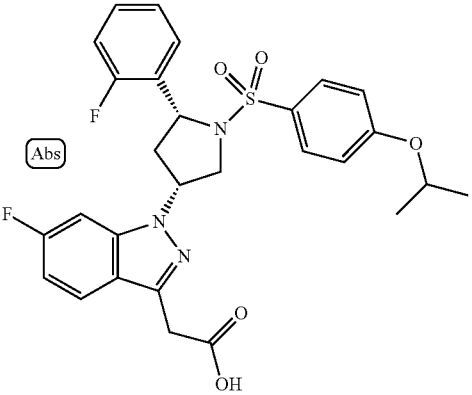 [SMILES: CC(C)Oc1ccc(S(=O)(=O)N2C[C@H](n3nc(CC(=O)O)c4ccc(F)cc43)C[C@@H]2c2ccccc2F)cc1] | 1H-NMR (CDCl3) δ: 7.71 (2H, d, J = 8.8 Hz), 7.60-7.55 (2H, m), 7.26-7.20 (1H, m), 7.11 (1H, t, J = 7.4 Hz), 6.95-6.91 (4H, m), 6.82 (1H, d, J = 9.0 Hz), 5.18 (1H, t, J = 8.5 Hz), 4.68-4.62 (1H, m), 4.52-4.47 (1H, m), 4.11 (1H, t, J = 8.4 Hz), 3.93-3.90 (1H, m), 3.93 (2H, s), 2.85-2.79 (1H, m), 2.66 (1H, dd, J = 22.7, 10.4 Hz), 1.39 (6H, d, J = 6.0 Hz). | 556 | 2.37 | B |

TABLE 65-continued
| No. | compound | ¹H-NMR δ ppm | [M + H] | RT | LC/MS condition |
|---|---|---|---|---|---|
| I-303 | 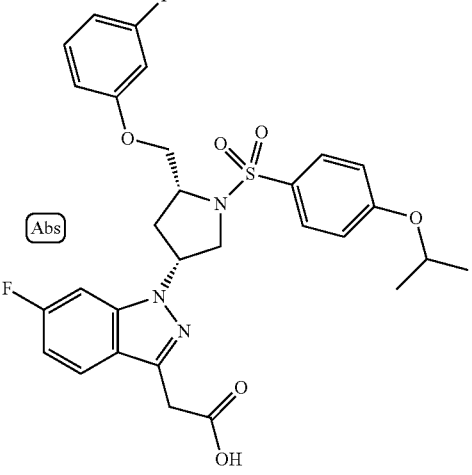 | 1H-NMR (CDCl3) δ: 7.83 (2H, d, J = 8.5 Hz), 7.60 (1H, t, J = 6.7 Hz), 7.21 (1H, t, J = 7.5 Hz), 7.01 (2H, d, J = 8.7 Hz), 6.92 (1H, t, J = 8.8 Hz), 6.81 (1H, d, J = 8.9 Hz), 6.68 (2H, t, J = 7.2 Hz), 6.62 (1H, t, J = 9.1 Hz), 4.67 (1H, q, J = 6.0 Hz), 4.43 (1H, t, J = 8.0 Hz), 4.36 (1H, d, J = 9.0 Hz), 4.26-4.24 (1H, m), 4.18-4.12 (1H, m), 3.96 (2H, s), 3.91 (1H, t, J = 9.3 Hz), 3.79 (1H, t, J = 10.4 Hz), 2.66 (1H, d, J = 8.3 Hz), 2.55 (1H, dd, J = 13.9, 6.7 Hz), 1.40 (6H, d, J = 5.9 Hz). | 586 | 2.47 | B |
TABLE 66
| No. | compound | ¹H-NMR δ ppm | [M + H] | RT | LC/MS condition |
|---|---|---|---|---|---|
| I-304 | 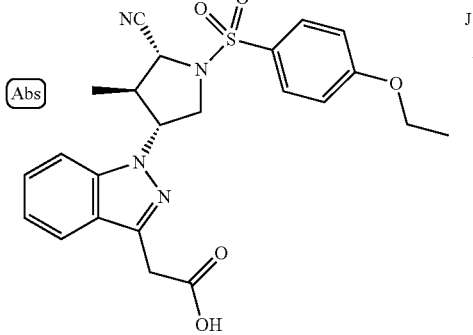 | ¹H-NMR (CDCl₃) δ: 7.83 (2H, d, J = 8.8 Hz), 7.72-7.67 (1H, m), 7.47-7.41 (1H, m), 7.39-7.31 (1H, m), 7.24-7.18 (1H, m), 7.01 (2H, d, J = 8.8 Hz), 4.88-4.79 (2H, m), 4.12 (2H, q, J = 7.0 Hz), 4.02-3.99 (2H, m), 3.80 (2H, d, J = 8.0 Hz), 3.20-3.10 (1H, m), 1.47 (3H, t, J = 6.9 Hz), 1.15 (3H, d, J = 6.8 Hz). | 469 | 2.04 | B |
| I-305 | 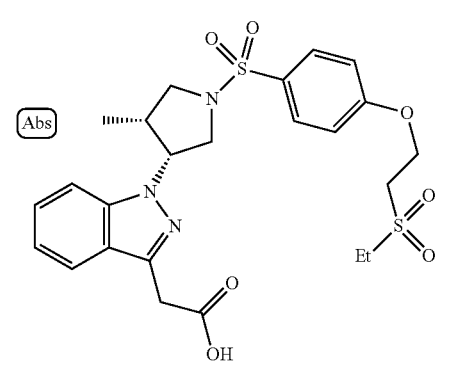 [SMILES: CCS(=O)(=O)CCOc1ccc(S(=O)(=O)N2C[C@@H](C)[C@@H](n3nc(CC(=O)O)c4ccccc43)C2)cc1] | | 536 | 1.78 | B |

TABLE 66-continued

| No. | compound | ¹H-NMR δ ppm | [M + H] | RT | LC/MS condition |
|---|---|---|---|---|---|
| I-306 | | 1H-NMR (DMSO-d6) δ: 0.26 (d, J = 6.8 Hz, 3H), 1.37 (t, J = 6.9 Hz, 3H), 2.39-2.46 (m, 1H), 3.17 (dd, J = 9.9, 9.9 Hz, 1H), 3.58 (dd, J = 9.0, 7.5 Hz, 1H), 3.67 (dd, J = 11.3, 2.5 Hz, 1H), 3.88 (dd, J = 11.2, 7.4 Hz, 1H), 4.14 (q, J = 6.9 Hz, 2H), 5.06 (s, 1H), 5.35-5.39 (m, 1H), 7.09 (dd, J = 7.4, 7.4 Hz, 1H), 7.15 (d, J = 8.8 Hz, 2H), 7.35 (dd, J = 7.5, 7.5 Hz, 1H), 7.62 (d, J = 8.5 Hz, 1H), 7.71 (d, J = 8.0 Hz, 1H), 7.81 (d, J = 8.8 Hz, 2H). | 460 | 1.74 | B |
| I-307 | | 1H-NMR (DMSO-d6) δ: 0.24 (d, J = 6.8 Hz, 3H), 1.38 (t, J = 7.0 Hz, 3H), 2.33-2.44 (m, 1H), 3.17 (dd, J = 9.9, 9.9 Hz, 1H), 3.57 (dd, J = 8.4, 8.4 Hz, 1H), 3.69 (dd, J = 11.0, 2.5 Hz, 1H), 3.87 (dd, J = 11.2, 7.4 Hz, 1H), 4.13-4.19 (m, 2H), 5.09 (s, 1H), 5.35-5.38 (m, 1H), 7.09 (dd, J = 7.5, 7.5 Hz, 1H), 7.16 (d, J = 8.8 Hz, 2H), 7.34 (dd, J = 7.7, 7.7 Hz, 1H), 7.62 (d, J = 8.5 Hz, 1H), 7.75 (d, J = 8.3 Hz, 1H), 7.81 (d, J = 8.8 Hz, 2H). | 460 | 1.75 | B |

TABLE 67

| No. | compound | ¹H-NMR δ ppm | [M + H] | RT | LC/MS condition |
|---|---|---|---|---|---|
| I-308 | | | 504 | 2.24 | B |
| I-309 | | | 462 | 2.07 | B |

TABLE 67-continued
| No. | compound | ¹H-NMR δ ppm | [M + H] | RT | LC/MS condition |
|---|---|---|---|---|---|
| I-310 | 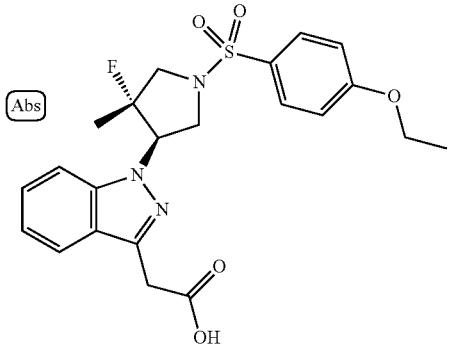 [SMILES: CCOc1ccc(S(=O)(=O)N2C[C@@H](n3nc(CC(=O)O)c4ccccc43)[C@](C)(F)C2)cc1] | | 462 | 2.07 | B |
| I-311 | 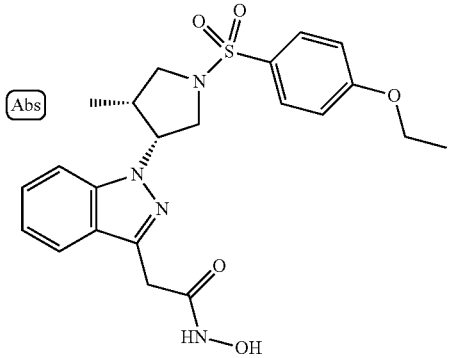 [SMILES: CCOc1ccc(S(=O)(=O)N2C[C@@H](C)[C@@H](n3nc(CC(=O)NO)c4ccccc43)C2)cc1] | 1H-NMR (DMSO-d6) δ: 10.77 (1H, brs), 8.93 (1H, brs), 7.81 (2H, d, J = 8.5 Hz), 7.72 (1H, d, J = 8.2 Hz), 7.59 (1H, d, J = 8.4 Hz), 7.34 (1H, t, J = 7.5 Hz), 7.17-7.07 (3H, m), 5.35-5.30 (1H, m), 4.15 (2H, q, J = 6.8 Hz), 3.87-3.82 (1H, m), 3.70-3.46 (4H, m), 3.20 (1H, t, J = 9.9 Hz), 2.43-2.32 (1H, m), 1.38 (3H, t, J = 6.8 Hz), 0.28 (3H, d, J = 6.5 Hz). | 459 | 1.78 | B |
| I-312 | 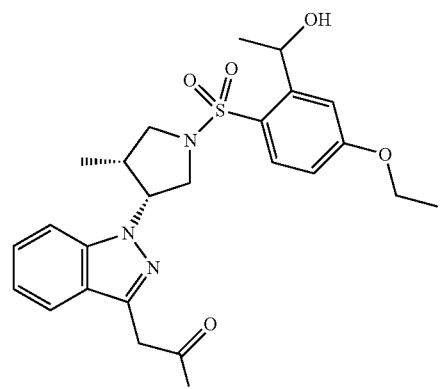 | | 488 | 1.96 | B |

TABLE 68
| No. | compound | ¹H-NMR δ ppm | [M + H] | RT | LC/MS condition |
|---|---|---|---|---|---|
| I-313 | 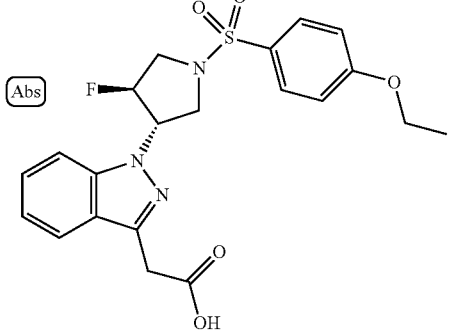 | 1H-NMR (CDCl3) δ: 1.24 (6H, d, J = 6.3 Hz), 1.49 (9H, d, J = 7.5 Hz), 3.72-3.85 (1H, m), 3.90-4.11 (5H (include 3.93 ppm (2H, s), m. ), 5.05 (1H, qq, J = 6.3 Hz, 6.3 Hz), 5.15-5.25 (1H, m), 5.36 (1H, d, J = 51.4 Hz), 7.19 (1H, m), 7.39-7.45 (2H, m), 7.69-7.75 (1.0H, m). | 448 | 1.99 | B |
| I-314 | 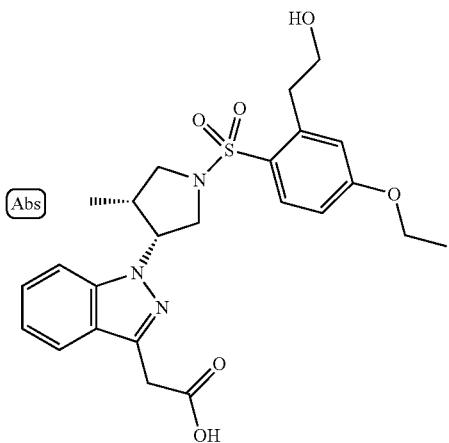 [SMILES: CCOc1ccc(S(=O)(=O)N2C[C@@H](C)[C@@H](n3nc(CC(=O)O)c4ccccc43)C2)c(CCO)c1] | 1H-NMR (DMSO-d6) δ: 7.98 (1H, d, J = 8.5 Hz), 7.71-7.63 (2H, m), 7.37 (1H, t, J = 7.4 Hz), 7.11 (1H, t, J = 7.3 Hz), 7.02 (1H, s), 6.96 (1H, d, J = 8.3 Hz), 5.47-5.42 (1H, m), 4.16-4.09 (2H, m), 3.99-3.93 (1H, m), 3.80 (2H, s), 3.71-3.58 (4H, m), 3.25-3.11 (3H, m), 2.74-2.64 (1H, m), 1.36 (3H, t, J = 6.5 Hz), 0.36 (3H, d, J = 6.3 Hz). | 488 | 1.87 | B |
| I-315 | 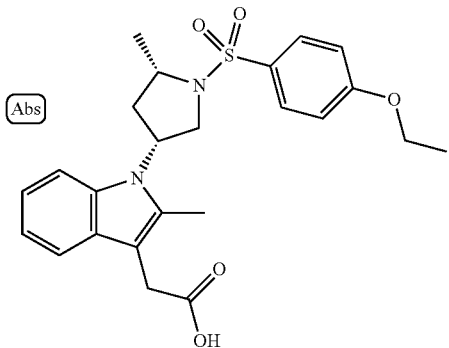 [SMILES: CCOc1ccc(S(=O)(=O)N2C[C@H](n3c(C)c(CC(=O)O)c4ccccc43)C[C@@H]2C)cc1] | | 457 | 2.3 | P |
| I-316 | 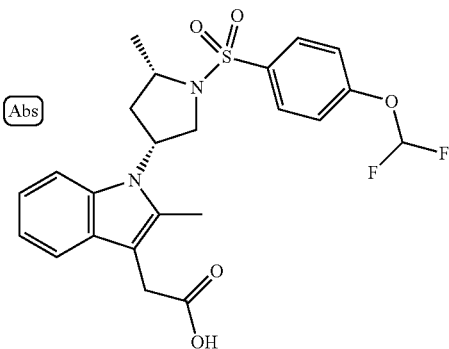 [SMILES: Cc1c(CC(=O)O)c2ccccc2n1[C@@H]1C[C@H](C)N(S(=O)(=O)c2ccc(OC(F)F)cc2)C1] | | 479 | 2.27 | P |

TABLE 69
| No. | compound | ¹H-NMR δ ppm | [M + H] | RT | LC/MS condition |
|---|---|---|---|---|---|
| I-317 | 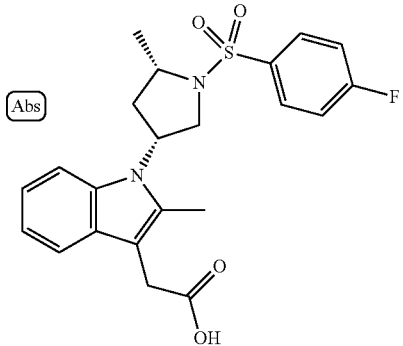 [SMILES: Cc1c(CC(=O)O)c2ccccc2n1[C@@H]1C[C@H](C)N(S(=O)(=O)c2ccc(F)cc2)C1] | | 431 | 2.19 | P |
| I-318 | 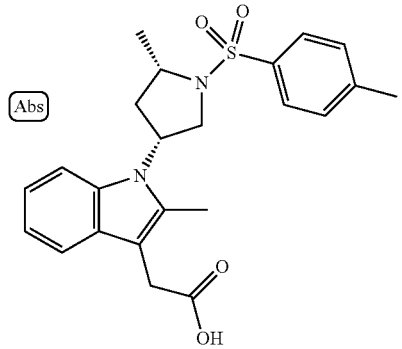 [SMILES: Cc1ccc(S(=O)(=O)N2C[C@H](n3c(C)c(CC(=O)O)c4ccccc43)C[C@@H]2C)cc1] | | 427 | 2.25 | P |
| I-319 | 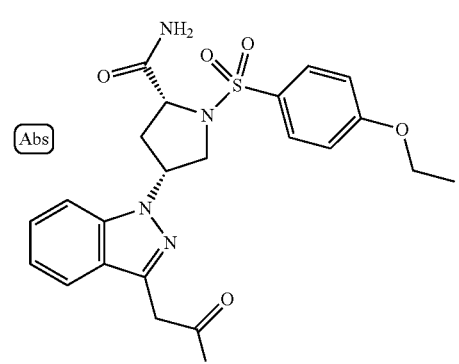 | ¹H-NMR (CDCl₃) δ: 7.92 (2H, d, J = 8.0 Hz), 7.71 (1H, d, J = 7.9 Hz), 7.60 (1H, s), 7.41-7.38 (2H, br m), 7.28-7.12 (4H, m), 4.69-4.59 (1H, m), 4.23-4.12 (3H, m), 3.94-3.86 (3H, m), 3.75-3.67 (1H, m), 2.56-2.47 (2H, m), 1.40 (3H, t, J = 6.7 Hz). | 473 | 1.62 | B |
| I-320 | 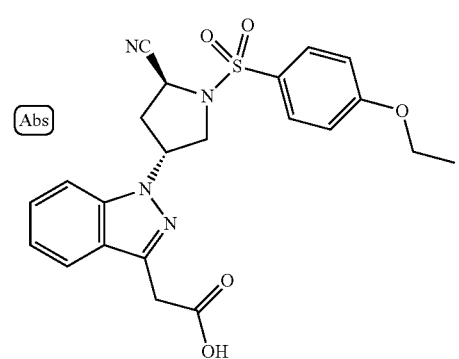 [SMILES: CCOc1ccc(S(=O)(=O)N2C[C@H](n3nc(CC(=O)O)c4ccccc43)C[C@H]2C#N)cc1] | ¹H-NMR (CDCl₃) δ: 7.92 (2H, d, J = 8.0 Hz), 7.71 (1H, d, J = 7.9 Hz), 7.60 (1H, s), 7.41-7.38 (2H, br m), 7.28-7.12 (4H, m), 4.69-4.59 (1H, m), 4.23-4.12 (3H, m), 3.94-3.86 (3H, m), 3.75-3.67 (1H, m), 2.56-2.47 (2H, m), 1.40 (3H, t, J = 6.7 Hz). | 455 | 1.84 | B |

TABLE 69-continued

| No. | compound | ¹H-NMR δ ppm | [M + H] | RT | LC/MS condition |
|---|---|---|---|---|---|
| I-321 | 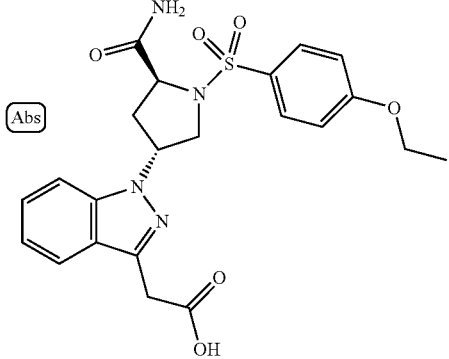 [SMILES: CCOc1ccc(S(=O)(=O)N2C[C@H](n3nc(CC(=O)O)c4ccccc43)C[C@H]2C(N)=O)cc1] | ¹H-NMR (CDCl₃) δ: 7.70 (2H, d, J = 8.8 Hz), 7.62 (1H, d, J = 7.8 Hz), 7.44-7.38 (1H, m), 7.21-7.16 (1H, m), 7.04 (1H, s), 6.93 (2H, d, J = 8.8 Hz), 5.69-5.63 (1H, m), 5.16-5.10 (1H, m), 4.40 (1H, d, J = 8.0 Hz), 4.17-4.08 (3H, m), 4.03-3.91 (3H, m), 3.80-3.73 (1H, m), 2.73-2.64 (1H, m), 2.50-2.40 (1H, m), 1.48 (3H, t, J = 7.0 Hz). | 473 | 1.47 | B |

TABLE 70

| No. | compound | ¹H-NMR δ ppm | [M + H] | RT | LC/MS condition |
|---|---|---|---|---|---|
| I-322 | 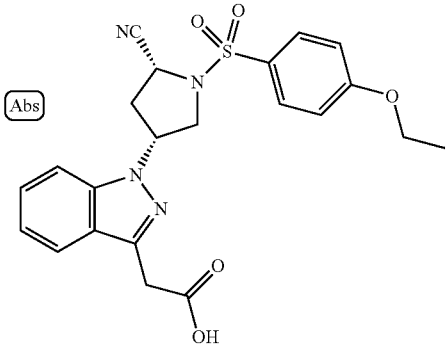 [SMILES: CCOc1ccc(S(=O)(=O)N2C[C@H](n3nc(CC(=O)O)c4ccccc43)C[C@@H]2C#N)cc1] | ¹H-NMR (CDCl₃) δ: 7.89 (2H, d, J = 8.8 Hz), 7.69 (1H, d, J = 7.9 Hz), 7.47-7.42 (1H, m), 7.35 (1H, d, J = 8.5 Hz), 7.29-7.19 (1H, m), 7.03 (2H, d, J = 8.8 Hz), 5.20-5.15 (1H, m), 4.91-4.85 (1H, m), 4.15-4.05 (3H, m), 4.00 (2H, s), 3.76 (1H, dd, J = 10.2, 6.7 Hz), 2.92 (2H, t, J = 6.7 Hz), 1.46 (3H, t, J = 7.0 Hz). | 455 | 1.86 | B |
| I-323 | 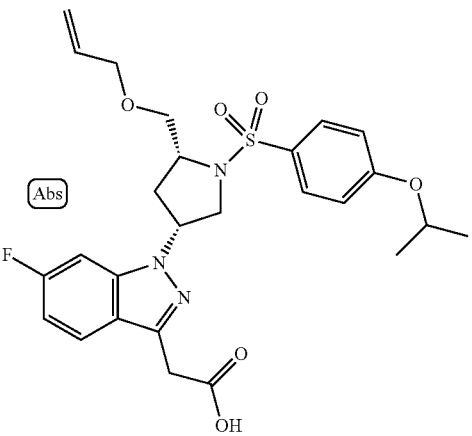 [SMILES: C=CCOC[C@H]1C[C@@H](n2nc(CC(=O)O)c3ccc(F)cc32)CN1S(=O)(=O)c1ccc(OC(C)C)cc1] | 1H-NMR (CDCl3) δ: 7.77 (2H, d, J = 8.8 Hz), 7.61 (1H, dd, J = 8.8, 5.0 Hz), 7.46 (1H, d, J = 7.3 Hz), 6.98 (1H, t, J = 5.6 Hz), 6.93 (2H, d, J = 8.8 Hz), 5.52 (1H, dt, J = 17.1, 5.3 Hz), 5.00 (2H, t, J = 11.5 Hz), 4.84 (1H, dd, J = 14.6, 2.8 Hz), 4.60 (2H, dt, J = 18.9, 6.5 Hz), 4.03 (2H, s), 3.96 (1H, d, J = 4.5 Hz), 3.68 (1H, d, J = 4.3 Hz), 3.56 (2H, t, J = 6.0 Hz), 3.35 (1H, dd, J = 11.2, 4.1 Hz), 3.18 (1H, d, J = 11.0 Hz), 2.15 (1H, dd, J = 15.9, 8.2 Hz), 1.80-1.77 (1H, m), 1.36 (6H, d, J = 6.0 Hz). | 532 | 2.24 | B |

TABLE 70-continued
| No. | compound | ¹H-NMR δ ppm | [M + H] | RT | LC/MS condition |
|---|---|---|---|---|---|
| I-324 | 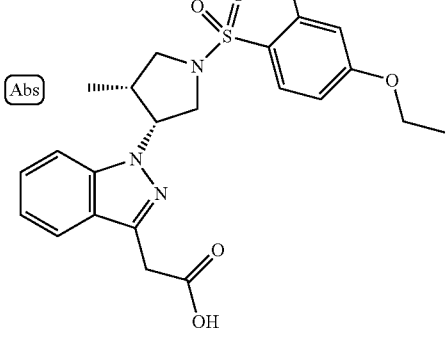 | 1H-NMR (DMSO-D6) δ: 8.07 (1H, d, J = 9.0 Hz), 7.66 (2H, d, J = 8.8 Hz), 7.59 (1H, d, J = 2.5 Hz), 7.39-7.34 (2H, m), 7.10 (1H, t, J = 7.7 Hz), 5.46-5.41 (1H, m), 4.22 (2H, q, J = 6.9 Hz), 4.03-3.98 (1H, m), 3.86 (1H, d, J = 10.7 Hz), 3.67-3.57 (4H, m), 2.75-2.66 (1H, m), 1.38 (3H, t, J = 7.0 Hz), 0.35 (3H, d, J = 6.7 Hz). | 489 | 2.13 | B |
| I-325 | 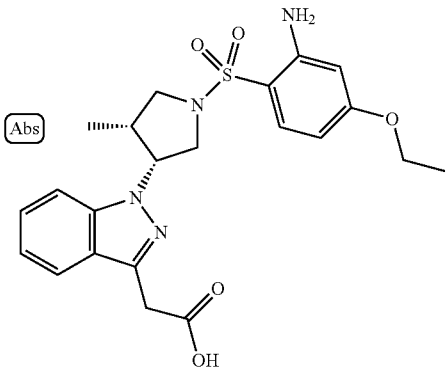 [SMILES: CCOc1ccc(S(=O)(=O)N2C[C@@H](C)[C@@H](n3nc(CC(=O)O)c4ccccc43)C2)c([N+](=O)[O-])c1] | 1H-NMR (DMSO-D6) δ: 7.64 (2H, t, J = 8.6 Hz), 7.45 (1H, d, J = 8.8 Hz), 7.35 (1H, t, J = 7.5 Hz), 7.09 (1H, t, J = 7.3 Hz), 6.39 (1H, d, J = 2.3 Hz), 6.26 (1H, dd, J = 9.1, 2.3 Hz), 6.06 (2H, brs), 5.41-5.35 (1H, m), 4.02 (2H, q, J = 7.0 Hz), 3.92-3.87 (1H, m), 3.81-3.71 (3H, m), 3.56 (1H, t, J = 8.2 Hz), 3.20 (1H, t, J = 9.7 Hz), 1.34 (3H, t, J = 6.9 Hz), 0.31 (3H, d, J = 6.8 Hz). | 459 | 1.93 | B |
TABLE 71
| No. | compound | ¹H-NMR δ ppm | [M + H] | RT | LC/MS condition |
|---|---|---|---|---|---|
| I-326 | 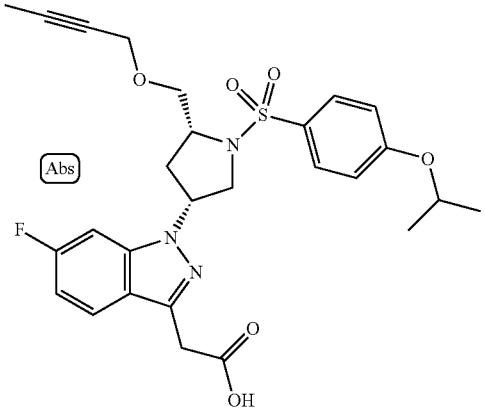 [SMILES: CC#CCOC[C@H]1C[C@@H](n2nc(CC(=O)O)c3ccc(F)cc32)CN1S(=O)(=O)c1ccc(OC(C)C)cc1] | | 544 | 2.23 | B |

TABLE 71-continued

| No. | compound | ¹H-NMR δ ppm | [M + H] | RT | LC/MS condition |
|---|---|---|---|---|---|
| I-327 | | 1H-NMR (CDCl3) δ: 7.78 (2H, d, J = 8.8 Hz), 7.66 (1H, ddd, J = 21.6, 8.8, 5.0 Hz), 7.44 (1H, d, J = 9.3 Hz), 7.10 (1H, d, J = 9.0 Hz), 6.94-6.93 (2H, m), 5.05 (2H, dt, J = 11.5, 4.6 Hz), 4.83 (1H, dd, J = 14.3, 3.0 Hz), 4.62-4.52 (2H, m), 3.94 (4H, d, J = 21.3 Hz), 3.64 (1H, s), 3.35 (1H, dd, J = 11.0, 4.5 Hz), 3.18 (1H, s), 3.01-2.94 (2H, m), 2.17 (2H, s), 1.36 (6H, dd, J = 6.0, 3.0 Hz), | 534 | 2.33 | B |
| I-328 | | 1H-NMR (DMSO-D6) δ: 0.36 (d, J = 6.8 Hz, 3H), 1.39 (t, J = 6.9 Hz, 3H), 2.94 (t, J = 9.9 Hz, 1H), 3.49 (s, 2H), 3.56-3.61 (m, 2H), 3.80-3.85 (m, 4H), 4.16 (q, J = 6.9 Hz, 2H), 5.18-5.19 (m, 1H), 6.46 (s, 1H), 7.21 (t, J = 7.8 Hz, 3H), 7.42 (d, J = 8.3 Hz, 1H), 7.70 (s, 1H), 7.86 (t, J = 8.3 Hz, 3H), 8.07 (s, 1H). | 523 | 2.04 | P |
| I-329 | | 1H-NMR (DMSO-D6) δ: 0.33 (d, J = 7.0 Hz, 3H), 1.39 (t, J = 7.0 Hz, 3H), 2.28 (s, 3H), 2.44-2.46 (m, 1H), 2.99 (t, J = 10.0 Hz, 1H), 3.56 (s, 2H), 3.65 (dd, J = 10.2, 8.2 Hz, 1H), 3.77-3.82 (m, 2H), 4.16-4.20 (m, 2H), 5.16-5.19 (m, 1H), 6.79 (t, J = 7.7 Hz, 1H), 6.94-6.96 (m, 2H), 7.21 (d, J = 9.0 Hz, 2H), 7.40 (d, J = 7.8 Hz, 1H), 7.85 (d, J = 8.8 Hz, 2H), 12.11 (s, 1H). | 457 | 2.27 | P |

TABLE 72

| No. | compound | ¹H-NMR δ ppm | [M + H] | RT | LC/MS condition |
|---|---|---|---|---|---|
| I-330 | | 1H-NMR (DMSO-D6) δ: 0.36 (d, J = 6.8 Hz, 3H), 1.38 (t, J = 7.0 Hz, 3H), 2.29 (s, 3H), 2.45-2.47 (m, 1H), 3.05 (t, J = 10.2 Hz, 1H), 3.57 (s, 2H), 3.72 (dd, J = 10.4, 8.2 Hz, 1H), 3.82-3.87 (m, 2H), 4.45 (q, J = 7.0 Hz, 2H), 5.20 (td, J = 8.0, 3.4 Hz, 1H), 6.85 (t, J = 7.5 Hz, 1H), 6.96 (t, J = 7.4 Hz, 1H), 7.09 (dd, J = 8.4, 3.9 Hz, 2H), 7.42 (d, J = 7.8 Hz, 1H), 8.20 (dd, J = 8.8, 2.5 Hz, 1H), 8.70 (d, J = 2.5 Hz, 1H). | 458 | 2.25 | P |
| I-331 | | 1H-NMR (CDCl3) δ: 7.84 (2H, d, J = 8.9 Hz), 7.55 (1H, dd, J = 8.9, 8.9 Hz), 7.03 (2H, d, J = 8.9 Hz), 6.98-6.88 (2H, m), 4.50 (1H, dd, J = 7.6, 3.8 Hz), 4.16-4.09 (2H, m), 4.05 (1H, dd, J = 11.0, 7.6 Hz), 3.90 (1H, dd, J = 11.0, 3.8 Hz), 3.75 (2H, d, J = 1.6 Hz), 3.35 (1H, d, J = 9.0 Hz), 3.29 (1H, d, J = 9.0 Hz), 1.47 (3H, t, J = 7.0 Hz), 1.22 (3H, s), 0.48 (3H, s). | 476 | 2.19 | P |
| I-332 | | 1H-NMR (CDCl3) δ: 7.87 (2H, d, J = 8.8 Hz), 7.65 (1H, d, J = 8.3 Hz), 7.45-7.39 (1H, m), 7.33 (1H, d, J = 8.8 Hz), 7.21-7.16 (1H, m), 7.02 (2H, d, J = 8.8 Hz), 5.13-5.07 (1H, m), 4.56 (1H, d, J = 9.5 Hz), 4.17-4.00 (3H, m), 3.97 (1H, dd, J = 11.0, 2.7 Hz), 3.81-3.71 (2H, m), 3.08-3.02 (1H, m), 1.48 (3H, t, J = 7.0 Hz), 0.70 (3H, d, J = 6.8 Hz). | 469 | 1.95 | B |
| I-333 | | 1H-NMR (CDCl3) δ: 7.99 (2H, d, J = 8.8 Hz), 7.69 (1H, d, J = 8.4 Hz), 7.45-7.39 (1H, m), 7.34 (1H, d, J = 8.4 Hz), 7.22-7.17 (1H, m), 7.06 (2H, d, J = 8.8 Hz), 5.20-5.15 (1H, m), 4.97 (1H, d, J = 8.7 Hz), 4.18-4.10 (3H, m), 4.03-3.98 (1H, m), 3.95 (2H, d, J = 4.0 Hz), 3.07-3.00 (1H, m), 1.46 (3H, t, J = 7.0 Hz), 0.77 (3H, d, J = 6.8 Hz). | 469 | 1.89 | B |

TABLE 73

| No. | compound | ¹H-NMR δ ppm | [M + H] | RT | LC/MS condition |
|---|---|---|---|---|---|
| I-334 | 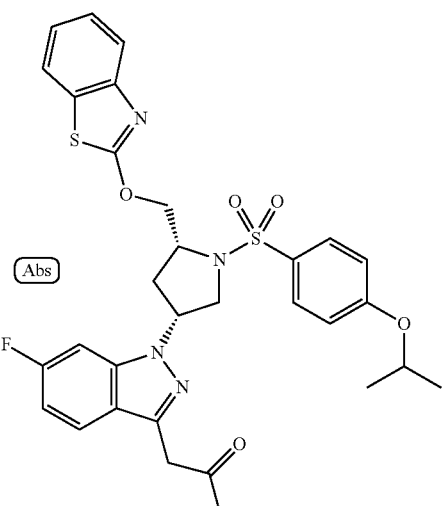 | 1H-NMR (CDCl3) δ: 7.78 (2H, d, J = 8.8 Hz), 7.63 (1H, dd, J = 8.8, 5.0 Hz), 7.48 (1H, d, J = 8.2 Hz), 7.39 (2H, dd, J = 17.3, 8.0 Hz), 7.19 (1H, t, J = 7.6 Hz), 6.98 (3H, d, J = 9.0 Hz), 6.74 (1H, d, J = 9.0 Hz), 4.65 (1H, t, J = 6.0 Hz), 4.44 (3H, dd, J = 13.6, 7.8 Hz), 4.33 (1H, s), 4.03 (2H, s), 3.89 (2H, d, J = 7.7 Hz), 2.51 (1H, d, J = 6.4 Hz), 2.41 (1H, s), 1.39 (6H, dd, J = 6.0, 1.6 Hz) | 625 | 2.37 | B |
| I-335 | 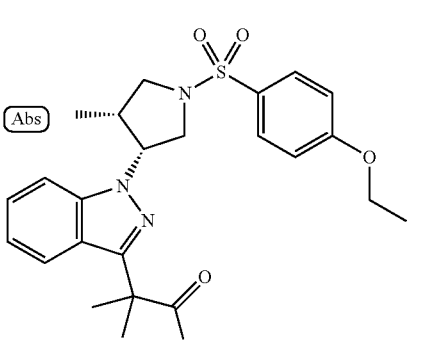 | 1H-NMR (DMSO-d6) δ: 0.23 (d, J = 6.8 Hz, 3H), 1.37 (s, 3H), 1.38 (t, J = 6.8 Hz, 3H), 1.39 (s, 3H), 2.46-2.54 (m, 1H), 3.11 (t, J = 9.8 Hz, 1H), 3.55-3.63 (m, 2H), 3.93 (dd, J = 10.8, 8.0 Hz, 1H), 4.13 (q, J = 6.8 Hz, 2H), 5.40-5.44 (m, 1H), 7.06 (dd, J = 7.5, 7.5 Hz, 1H), 7.14 (d, J = 8.8 Hz, 2H), 7.33 (dd, J = 7.5, 7.5 Hz), 7.59 (d, J = 9.3 Hz, 1H), 7.61 (d, J = 9.3 Hz, 1H), 7.79 (d, J = 8.8 Hz, 2H), 12.41 (brs, 1H). | 472 | 2.21 | B |
| I-336 | 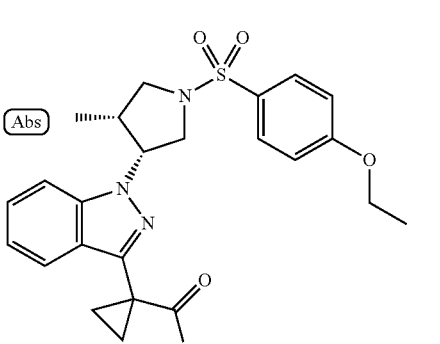 | 1H-NMR(DMSO-d6) δ: 0.22 (d, J = 6.8 Hz, 3H), 0.93 (dd, J = 9.2, 4.1 Hz, 1H), 1.06-1.11 (m, 1H), 1.38 (t, J = 6.9 Hz, 3H), 1.42-1.44 (m, 2H), 2.44-2.48 (m, 1H), 3.06 (t, J = 9.9 Hz, 1H), 3.53-3.61 (m, 2H), 3.90 (dd, J = 10.9, 7.7 Hz, 1H), 4.14 (q, J = 6.9 Hz, 2H), 5.36-5.40 (m, 1H), 7.09 (dd, 7.7, 7.7 Hz, 1H), 7.15 (d, J = 9.0 Hz, 2H), 7.34 (dd, J = 7.7, 7.7 Hz, 1H), 7.61 (d, J = 8.3 Hz, 2H), 7.79 (d, J = 9.0 Hz, 2H), 12.37 (brs, 1H). | 470 | 2.13 | B |
| I-337 | 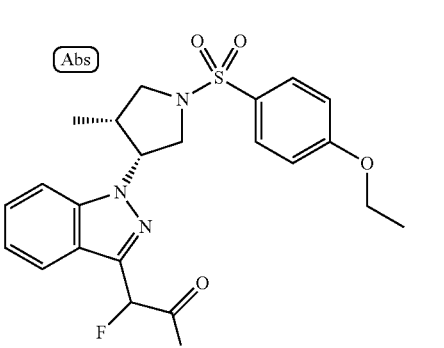 | 1H-NMR (DMSO-d6) δ: 0.25 (d, J = 6.8 Hz, 3H), 1.38 (t, J = 6.9 Hz, 3H), 2.47-2.55 (m, 1H), 3.15 (t, J = 9.9 Hz, 1H), 3.60 (dd, J = 8.9, 7.7 Hz, 1H), 3.66 (dd, J = 11.3, 2.3 Hz, 1H), 3.91 (dd, J = 11.3, 7.3 Hz, 1H), 4.14 (q, J = 6.9 Hz, 2H), 5.44-5.46 (m, 1H), 5.82 (d, JHF = 47.4 Hz, 1H), 7.17 (d, J = 8.8 Hz, 2H), 7.21 (dd, J = 7.5, 7.5 Hz, 1H), 7.43 (dd, J = 7.7, 7.7 Hz, 1H), 7.65 (d, 8.0 Hz, 1H), 7.73 (d, J = 8.5 Hz, 1H), 7.81 (d, J = 8.8 Hz, 2H). | 462 | 1.96 | B |

TABLE 74
| No. | compound | ¹H-NMR δ ppm | [M + H] | RT | LC/MS condition |
|---|---|---|---|---|---|
| I-338 | 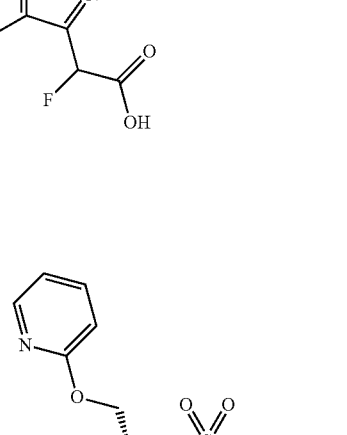 | 1H-NMR (DMSO-d6) δ: 0.25 (d, J = 6.8 Hz, 3H), 1.37 (t, J = 6.9 Hz, 3H), 2.45-2.47 (m, 1H), 3.15 (t, J = 10.0 Hz, 1H), 3.59-3.67 (m, 2H), 3.89 (dd, J = 11.4, 7.4 Hz, 1H), 4.14 (q, J = 6.9 Hz, 2H), 5.45-5.48 (m, 1H), 5.87 (d, JHF = 47.7 Hz, 1H), 7.16 (d, J = 8.8 Hz, 2H), 7.20 (dd, J = 7.7, 7.7 Hz, 1H), 7.43 (dd, J = 7.8, 7.8 Hz, 1H), 7.66 (d, J = 8.3 Hz, 1H), 7.74 (d, J = 8.8 Hz, 1H), 7.82 (d, J = 9.0 Hz, 2H). | 462 | 1.99 | B |
| I-339 | 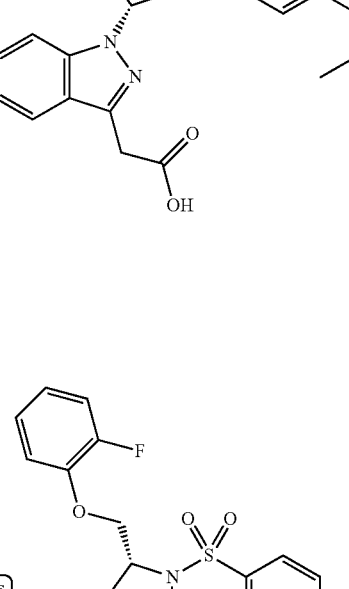 | | 569 | 2.27 | B |
| I-340 | 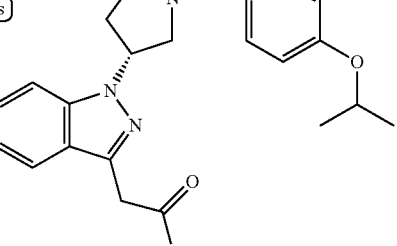 | | 586 | 2.44 | B |

TABLE 74-continued

| No. | compound | ¹H-NMR δ ppm | [M + H] | RT | LC/MS condition |
|---|---|---|---|---|---|
| I-341 | | 1H-NMR (CDCl3) δ: 7.86-7.82 (2H, m), 7.52 (1H, d, J = 8.2 Hz), 7.38-7.32 (2H, m), 7.13-7.09 (1H, m), 7.01-6.97 (2H, m), 5.47 (1H, s), 5.09-5.03 (1H, m), 4.12-4.02 (3H, m), 3.97 (2H, s), 3.84 (1H, dd, J = 11.2, 2.6 Hz), 3.70 (1H, t, J = 8.0 Hz), 3.24 (1H, dd, J = 10.6, 9.0 Hz), 2.74-2.65 (1H, m), 1.44 (3H, t, J = 7.0 Hz), 0.44 (3H, d, J = 6.9 Hz). | 483 | 2.07 | B |

TABLE 75

| No. | compound | ¹H-NMR δ ppm | [M + H] | RT | LC/MS condition |
|---|---|---|---|---|---|
| I-342 | | | 550 | 1.93 | B |
| I-343 | | 1H-NMR (CDCl3) δ: 7.65 (2H, s), 7.43 (2H, s), 7.16 (3H, s), 6.95 (2H, s), 6.71-6.63 (3H, m), 4.65-4.62 (1H, m), 4.13 (2H, br s), 3.83 (2H, br s), 3.73 (3H, br s), 2.70 (2H, br s), 2.57 (2H, brs), 2.35 (1H, s), 1.92 (1H, s), 1.38 (6H, s). | 566 | 2.53 | B |

TABLE 75-continued
| No. | compound | ¹H-NMR δ ppm | [M + H] | RT | LC/MS condition |
|---|---|---|---|---|---|
| I-344 | 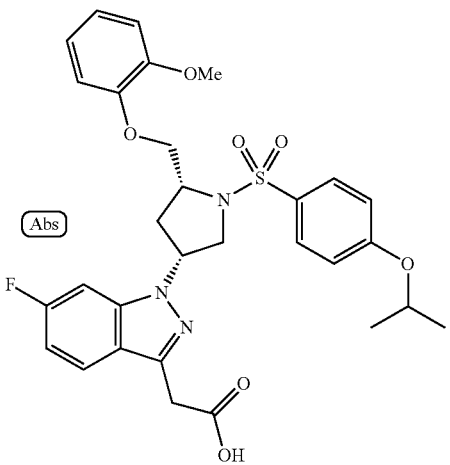 [SMILES: COc1ccccc1OC[C@H]1C[C@@H](n2nc(CC(=O)O)c3ccc(F)cc32)CN1S(=O)(=O)c1ccc(OC(C)C)cc1] | | 598 | 2.4 | B |
| I-345 | 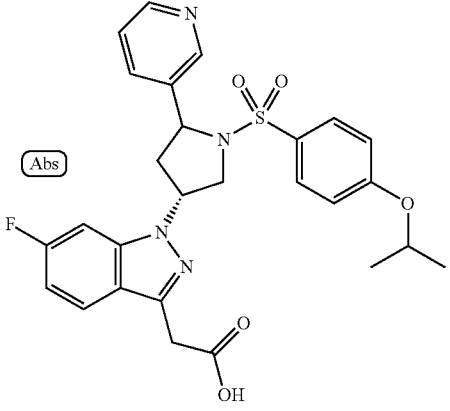 [SMILES: CC(C)Oc1ccc(S(=O)(=O)N2C[C@H](n3nc(CC(=O)O)c4ccc(F)cc43)CC2c2cccnc2)cc1] | | 539 | 1.6 | B |
TABLE 76
| No. | compound | ¹H-NMR δ ppm | [M + H] | RT | LC/MS condition |
|---|---|---|---|---|---|
| I-346 | 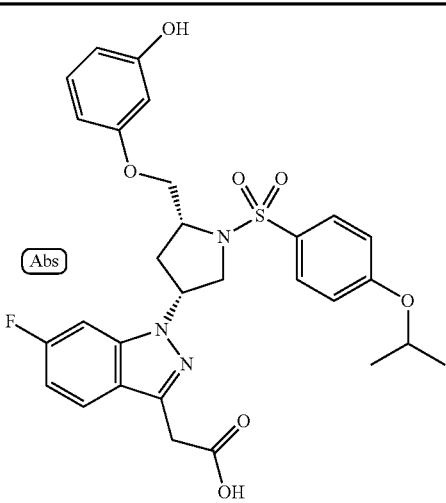 | | 584 | 2.18 | B |

| No. | compound | ¹H-NMR δ ppm | [M + H] | RT | LC/MS condition |
|---|---|---|---|---|---|
| I-347 | 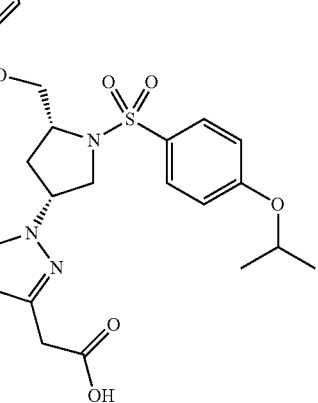 | | 584 | 2.13 | B |
| I-348 | 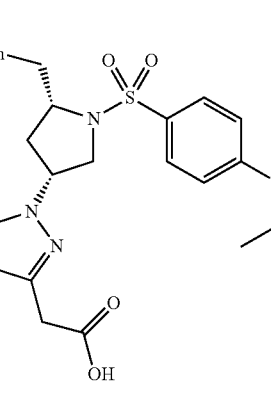 | 1H-NMR (DMSO-D6) δ: 7.91 (2H, d, J = 8.4 Hz), 7.74 (1H, dd, J = 8.7, 5.2 Hz), 7.29-7.25 (2H, m), 7.22-7.12 (6H, m), 7.01 (1H, t, J = 8.9 Hz), 4.83-4.76 (1H, m), 4.61-4.52 (1H, m), 3.92 (2H, s), 3.90-3.83 (2H, m), 3.74-3.68 (1H, m), 3.31-3.25 (2H, m), 2.94 (1H, t, J = 11.5 Hz), 2.08-2.03 (2H, m), 1.33 (6H, d, J = 5.9 Hz). | 552 | 2.47 | B |
| I-349 | 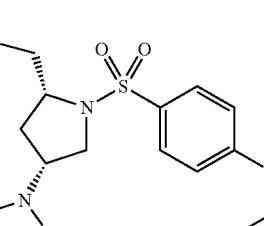 | 1H-NMR (DMSO-D6) δ: 7.92 (2H, d, J = 8.4 Hz), 7.70 (1H, d, J = 8.2 Hz), 7.34-7.10 (10H, m), 4.85-4.77 (1H, m), 4.61-4.53 (1H, m), 3.93-3.84 (4H, m), 3.72-3.67 (1H, m), 3.30-3.25 (1H, m), 2.95 (1H, t, J = 11.5 Hz), 2.12-2.07 (2H, m), 1.33 (6H, d, J = 5.9 Hz). | 534 | 2.43 | B |

TABLE 77
| No. | compound | ¹H-NMR δ ppm | [M + H] | RT | LC/MS condition |
|---|---|---|---|---|---|
| I-350 | 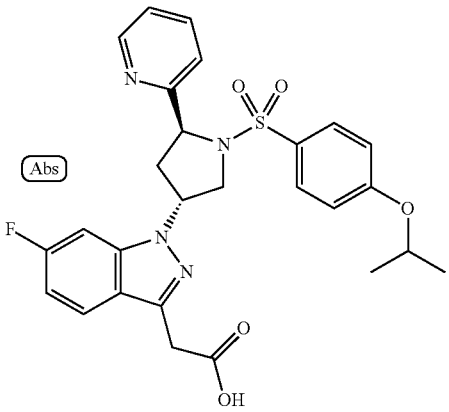 [SMILES: CC(C)Oc1ccc(S(=O)(=O)N2C[C@H](n3nc(CC(=O)O)c4ccc(F)cc43)C[C@H]2c2ccccn2)cc1] | 1H-NMR (CDCl3) δ: 8.59 (1H, d, J = 4.8 Hz), 7.81 (1H, t, J = 7.7 Hz), 7.74 (2H, t, J = 7.4 Hz), 7.62 (1H, dd, J = 8.8, 5.0 Hz), 7.53 (2H, d, J = 8.5 Hz), 6.91 (1H, t, J = 9.0 Hz), 6.85 (1H, d, J = 9.0 Hz), 6.74 (2H, d, J = 8.5 Hz), 5.28 (1H, t, J = 6.8 Hz), 5.10-5.03 (1H, m), 4.61-4.55 (1H, m), 4.09 (1H, dd, J = 10.8, 6.0 Hz), 3.88 (2H, d, J = 8.0 Hz), 3.09-3.02 (1H, m), 2.43-2.36 (1H, m), 1.39 (6H, dd, J = 11.0, 6.0 Hz). | | | |
| I-351 | 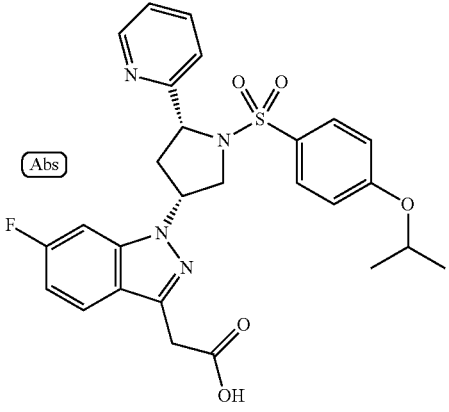 [SMILES: CC(C)Oc1ccc(S(=O)(=O)N2C[C@H](n3nc(CC(=O)O)c4ccc(F)cc43)C[C@@H]2c2ccccn2)cc1] | 1H-NMR (CDCl3) δ: 8.53 (1H, d, J = 5.0 Hz), 7.90 (2H, d, J = 7.5 Hz), 7.79 (2H, d, J = 8.5 Hz), 7.60 (1H, dd, J = 8.8, 5.0 Hz), 7.35 (1H, d, J = 5.8 Hz), 7.01 (2H, d, J = 8.8 Hz), 6.88 (1H, t, J = 9.0 Hz), 6.76 (1H, d, J = 9.0 Hz), 5.22 (1H, t, J = 8.0 Hz), 4.71-4.65 (1H, m), 4.46 (1H, dd, J = 15.3, 7.5 Hz), 3.97 (1H, t, J = 9.7 Hz), 3.90 (1H, t, J = 5.8 Hz), 3.86 (2H, s), 2.80-2.73 (2H, m), 1.41 (6H, d, J = 5.8 Hz). | | | |
| I-352 | 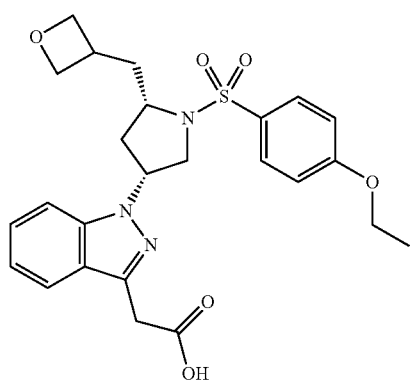 [SMILES: CCOc1ccc(S(=O)(=O)N2C[C@H](n3nc(CC(=O)O)c4ccccc43)C[C@@H]2CC2COC2)cc1] | | 500 | 1.89 | B |

TABLE 77-continued

| No. | compound | ¹H-NMR δ ppm | [M + H] | RT | LC/MS condition |
|---|---|---|---|---|---|
| I-353 | 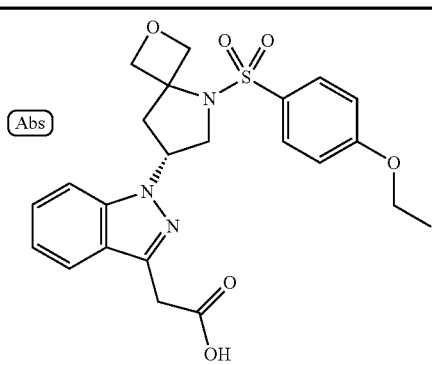 | 1H-NMR(CDCl3) δ: 1.43 (t, J = 6.9 Hz, 3H), 2.79 (dd, d = 13.3, 6.3 Hz, 1H), 3.06 (dd, J = 13.3, 5.0 Hz, 1H), 3.73 (dd, J = 10.2, 4.4 Hz, 1H), 3.81 (d, J = 16.7 Hz, 1H), 3.86 (d, J = 16.7 Hz, 1H), 4.06 (dd, J = 10.2, 6.4 Hz, 1H), 4.06 (q, J = 6.9 Hz, 2H), 4.44 (d, J = 6.8 Hz, 1H), 4.55 (d, J = 6.0 Hz, 1H), 5.00-5.06 (m, 1H), 5.34 (d, J = 6.8 Hz, 1 H), 5.56 (d, J = 6.0 Hz, 1H), 6.88 (d, J = 8.5 Hz, 2H), 7.16 (dd, J = 7.4, 7.4 Hz, 1H), 7.32 (d, J = 8.5 Hz, 1H), 7.39 (dd, J = 7.7, 7.7 Hz, 1H), 7.65 (d, J = 8.0 Hz, 1H), 7.75 (d, J = 8.5 Hz, 2H). | 472 | 1.78 | B |

TABLE 78

| No. | compound | ¹H-NMR δ ppm | [M + H] | RT | LC/MS condition |
|---|---|---|---|---|---|
| I-354 | 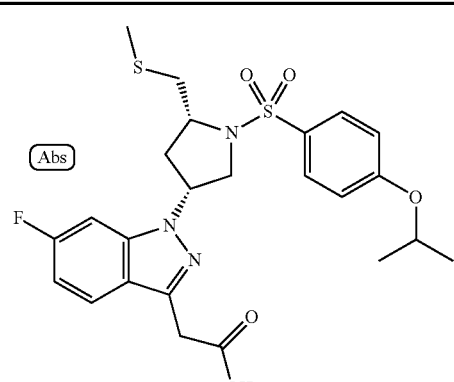 | 1H-NMR (DMSO-D6) δ: 7.87 (2H, d, J = 8.4 Hz), 7.77-7.72 (1H, m), 7.21-7.16 (3H, m), 7.02 (1H, t, J = 8.9 Hz), 4.85-4.76 (1H, m), 4.60-4.52 (1H, m), 3.93-3.82 (4H m), 3.71-3.66 (1H, m), 3.00-2.85 (2H, m), 2.48-2.41 (1H, m), 2.33-2.24 (1H, m), 2.11 (3H, s), 1.33 (6H, d, J = 5.8 Hz). | 522 | 2.28 | B |
| I-355 | 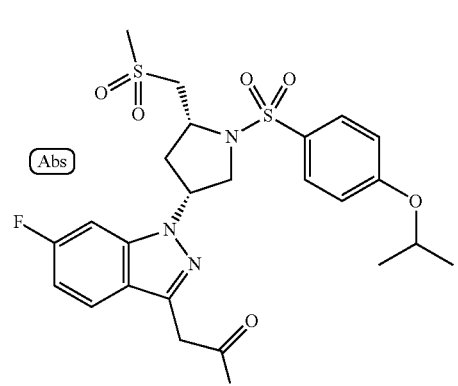 | 1H-NMR (DMSO-D6) δ: 7.76-7.58 (3H, m), 7.44 (1H, d, J = 9.7 Hz), 7.04-6.99 (3H, m), 6.08 (1H, dd, J = 15.4, 7.3 Hz), 5.77-5.69 (1H, m), 5.29 (1H, q, J = 6.9 Hz), 4.72-4.65 (1H, m), 3.94-3.80 (5H, m), 2.84 (3H, s), 1.28 (6H, d, J = 5.9 Hz). | 554 | 1.76 | B |

TABLE 78-continued

| No. | compound | ¹H-NMR δ ppm | [M + H] | RT | LC/MS condition |
|---|---|---|---|---|---|
| I-356 | | | 458 | 2.09 | B |
| I-357 | | | 539 | 1.49 | B |

TABLE 79

| No. | compound | ¹H-NMR δ ppm | [M + H] | RT | LC/MS condition |
|---|---|---|---|---|---|
| I-358 | | | 539 | 1.6 | B |

TABLE 79-continued

| No. | compound | ¹H-NMR δ ppm | [M + H] | RT | LC/MS condition |
|---|---|---|---|---|---|
| I-359 | | | 538 | 2.3 | P |
| I-360 | | 1H-NMR (CDCl3) δ: 7.60 (3H, d, J = 8.4 Hz), 7.37 (2H, d, J = 7.5 Hz), 7.30 (3H, t, J = 7.4 Hz), 6.96-6.89 (4H, m), 4.97 (1H, t, J = 8.5 Hz), 4.65 (2H, dd, J = 15.4, 9.3 Hz), 4.20-4.12 (1H, m), 3.98 (2H, s), 3.88 (1H, t, J = 10.4 Hz), 2.85-2.78 (1H, m), 2.71 (1H, dd, J = 22.2, 11.0 Hz), 1.39 (6H, d, J = 5.9 Hz). | 538 | 2.37 | P |
| I-361 | | 1H-NMR (CDCl3) δ: 8.59 (2H, s), 7.61 (2H, d, J = 8.0 Hz), 7.49 (3H, t, J = 6.0 Hz), 6.90 (1H, t, J = 8.4 Hz), 6.82 (1H, d, J = 8.8 Hz), 6.72 (2H, d, J = 8.3 Hz), 5.11-5.09 (1H, m), 4.88 (1H, s), 4.55 (1H, t, J = 5.9 Hz), 4.11 (1H, dd, J = 12.5, 5.8 Hz), 3.85 (1H, d, J = 11.3 Hz), 3.82 (2H, s), 3.06 (1H, s), 2.20 (1H, t, J = 6.5 Hz), 1.36 (6H, s). | 539 | 1.4 | B |

TABLE 80
| No. | compound | ¹H-NMR δ ppm | [M + H] | RT | LC/MS condition |
|---|---|---|---|---|---|
| I-362 | 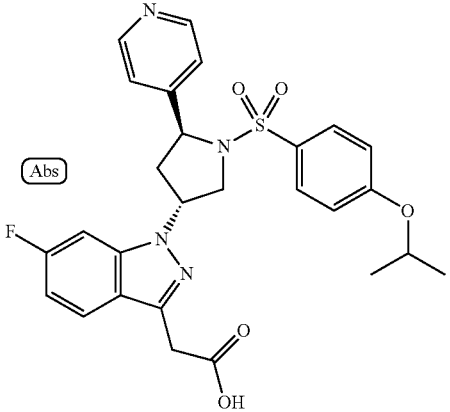 [SMILES: CC(C)Oc1ccc(S(=O)(=O)N2C[C@H](n3nc(CC(=O)O)c4ccc(F)cc43)C[C@H]2c2ccncc2)cc1] | 1H-NMR (CDCl3) δ: 8.47 (2H, s), 7.72 (2H, d, J = 7.3 Hz), 7.63 (1H, s), 7.39 (2H, s), 6.97 (2H, d, J = 7.5 Hz), 6.89 (1H, s), 6.80 (1H, d, J = 7.8 Hz), 4.98 (2H, s), 4.66 (2H, s), 4.05 (2H, s), 3.86 (2H, s), 2.75 (1H, s), 2.60 (1H, s), 1.38 (6H, s) | 539 | 1.52 | B |
| I-363 | 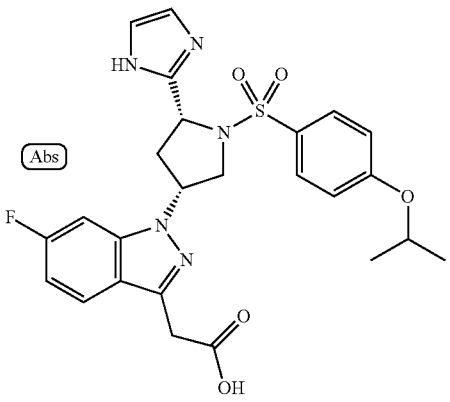 [SMILES: CC(C)Oc1ccc(S(=O)(=O)N2C[C@H](n3nc(CC(=O)O)c4ccc(F)cc43)C[C@@H]2c2ncc[nH]2)cc1] | 1H-NMR (DMSO-D6) δ: 7.75-7.73 (4H, m), 7.34 (1H, d, J = 9.8 Hz), 7.13 (2H, d, J = 8.5 Hz), 7.03 (1H, t, J = 9.2 Hz), 6.94 (1H, s), 4.81-4.77 (3H, m), 3.92 (3H, s), 3.80 (1H, t, J = 9.9 Hz), 2.72 (2H, dt, J = 22.8, 8.8 Hz), 1.33 (6H, d, J = 5.8 Hz). | 528 | 1.37 | B |
| I-364 | 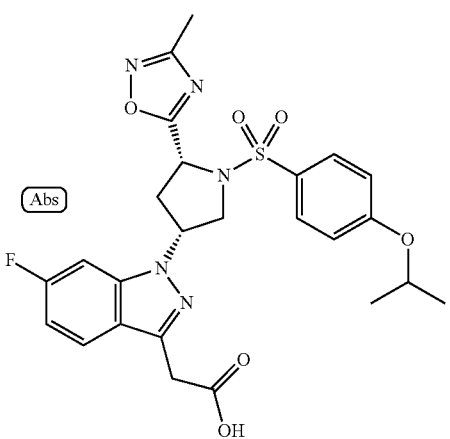 [SMILES: Cc1noc([C@H]2C[C@@H](n3nc(CC(=O)O)c4ccc(F)cc43)CN2S(=O)(=O)c2ccc(OC(C)C)cc2)n1] | 1H-NMR (CDCl3) δ: 7.62 (2H, t, J = 6.4 Hz), 7.58 (1H, t, J = 4.4 Hz), 7.00-6.93 (2H, m), 6.83 (2H, d, J = 8.8 Hz), 5.34 (1H, dd, J = 8.0, 5.0 Hz), 5.28 (1H, t, J = 6.0 Hz), 4.61 (1H, td, J = 12.3, 6.2 Hz), 4.09 (1H, dd, J = 10.4, 6.7 Hz), 3.85 (2H, s), 3.08-3.01 (1H, m), 2.62-2.56 (1H, m), 2.42 (3H, s), 1.38 (6H, d, J = 6.5 Hz). | 544 | 2.01 | B |

TABLE 80-continued

| No. | compound | ¹H-NMR δ ppm | [M + H] | RT | LC/MS condition |
|---|---|---|---|---|---|
| I-365 | [structure, Abs] | 1H-NMR (CDCl3) δ: 7.83 (2H, d, J = 8.4 Hz), 7.59 (1H, t, J = 6.8 Hz), 7.28 (3H, t, J = 6.9 Hz), 7.01-6.90 (5H, m), 6.81 (1H, d, J = 9.0 Hz), 4.66 (1H, t, J = 6.0 Hz), 4.41 (2H, d, J = 8.5 Hz), 4.26 (1H, s), 4.18 (1H, t, J = 8.7 Hz), 3.95 (2H, s), 3.89 (1H, d, J = 7.2 Hz), 3.80 (1H, t, J = 10.5 Hz), 2.73-2.67 (1H, m), 2.58-2.52 (1H, m), 1.40 (6H, d, J = 5.8 Hz). | 568 | 2.46 | B |

TABLE 81

| No. | compound | ¹H-NMR δ ppm | [M + H] | condition | LC/MS RT |
|---|---|---|---|---|---|
| I-366 | [structure, Abs] | 1H-NMR (CDCl3) δ: 7.82 (2H, d, J = 8.3 Hz), 7.60 (1H, dd, J = 8.8, 5.0 Hz), 7.01-6.81 (8H, m), 4.68-4.62 (1H, m), 4.42 (1H, dd, J = 16.3, 8.3 Hz), 4.34 (1H, dd, J = 9.0, 3.5 Hz), 4.26 (1H, d, J = 7.5 Hz), 4.14 (1H, dd, J = 14.9, 7.4 Hz), 3.96 (2H, s), 3.91 (1H, dd, J = 11.8, 7.3 Hz), 3.79 (1H, t, J = 10.3 Hz), 2.73-2.66 (1H, m), 2.57-2.49 (1H, m), 1.39 (6H, d, J = 6.0 Hz). | 586 | 2.46 | B |
| I-367 | [structure, Abs] | 1H-NMR(CDCl3) δ: 1.47 (t, J = 6.9 Hz, 3H), 3.37 (t, J = 9.0 Hz, 1H), 3.46-3.54 (m, 2H), 3.68 (dd, J = 10.3, 5.0 Hz, 1H), 33.85-3.92 (m, 2H), 3.94 (s. 2H), 4.11 (q, J = 6.9 Hz, 2H), 4.19-4.23 (m, 1H), 4.43 (m, 1H), 4.93-4.99 (m, 1H), 6.95 (d, J = 8.3 Hz, 2H), 7.17-7.20 (m, 1H), 7.39-7.45 (m, 2H), 7.65 (d, J = 8.0 Hz, 1H), 7.69 (d, J = 8.5 Hz, 2H). | 472 | 1.81 | B |

According to the similar manner as described in the above Examples or in the general synthetic procedures, the compounds in the following Table 82 to 97 can be synthesized by using the commercially available compounds or the intermediates described in the art.

TABLE 82

| No. | compound |
|---|---|
| II-1 | |
| II-2 | |
| II-3 | |
| II-4 | |

TABLE 82-continued

| No. | compound |
|---|---|
| II-5 | |
| II-6 | |
| II-7 | |
| II-8 | |
| II-9 | |

TABLE 82-continued
| No. | compound |
|---|---|
| II-10 | 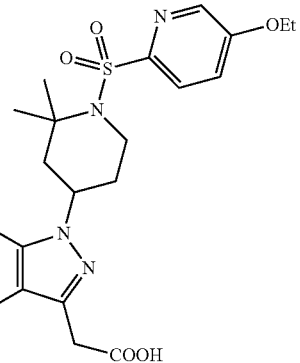 |
TABLE 83
| No. | compound |
|---|---|
| II-11 | 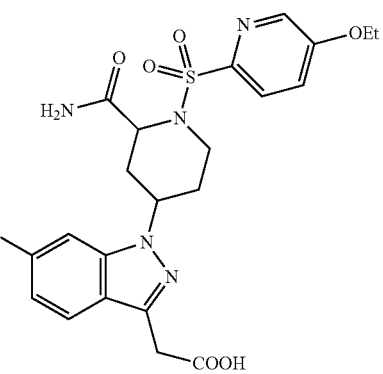 |
| II-12 | 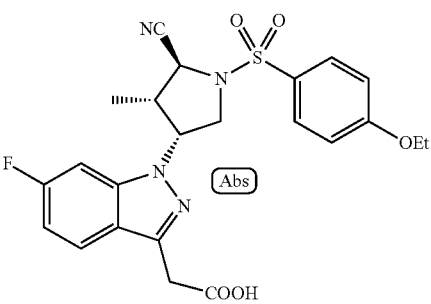 [SMILES: CCOc1ccc(S(=O)(=O)N2C[C@H](n3nc(CC(=O)O)c4ccc(F)cc43)[C@H](C)[C@H]2C#N)cc1] |
| II-13 | 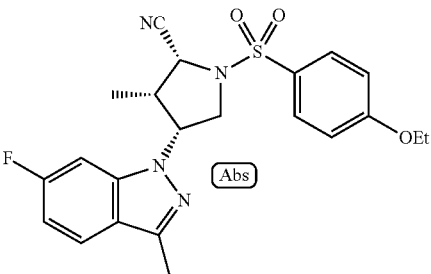 |
TABLE 83-continued
| No. | compound |
|---|---|
| II-14 | 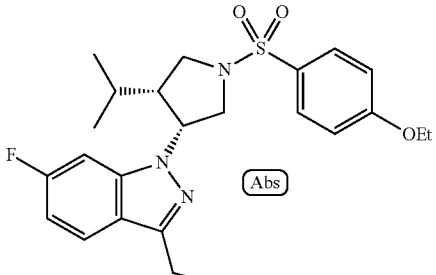 |
| II-15 | 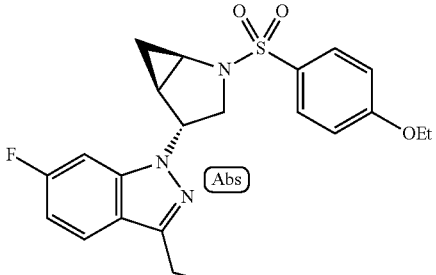 |
| II-16 | 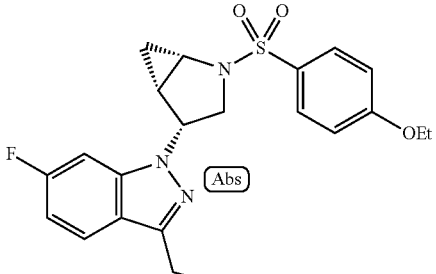 |
| II-17 | 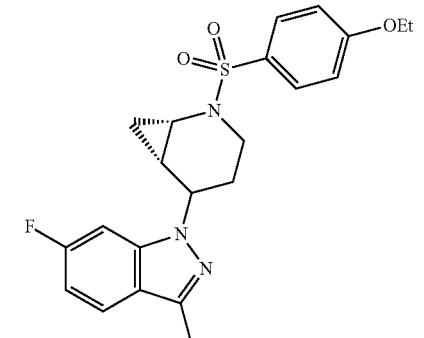 |
| II-18 | 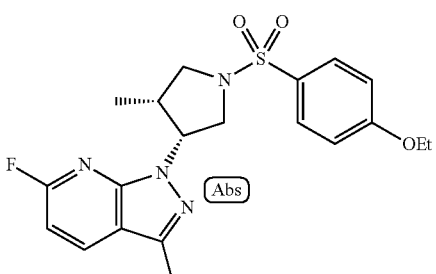 |

TABLE 83-continued
| No. | compound |
|---|---|
| II-19 | 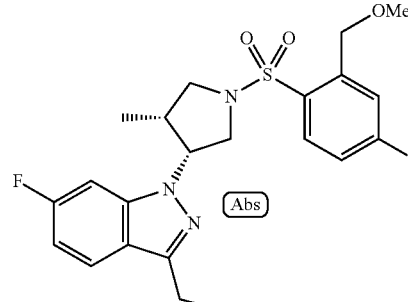 |
| II-20 | 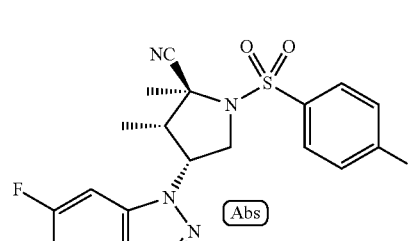 |
TABLE 84
| No. | compound |
|---|---|
| II-21 | 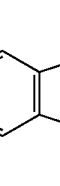 |
| II-22 |  |
TABLE 84-continued
| No. | compound |
|---|---|
| II-23 |  |
| II-24 | 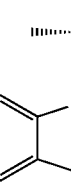 |
| II-25 |  |
| II-26 | |
| II-27 | |

TABLE 84-continued
| No. | compound |
|---|---|
| II-28 | 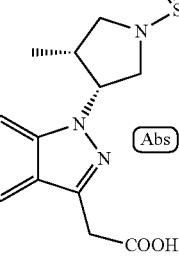 |
| II-29 | 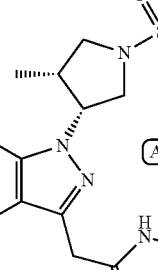 |
| II-30 | 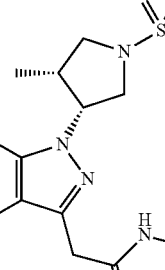 |
TABLE 85
| No. | compound |
|---|---|
| II-31 | 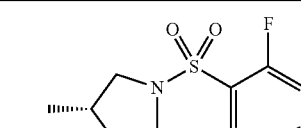 |
| II-32 | 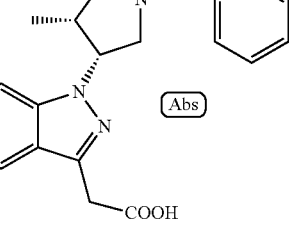 |
| II-33 | 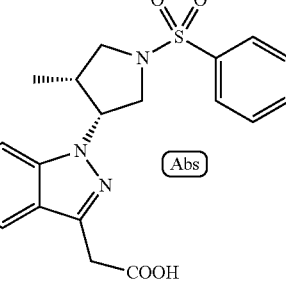 |
| II-34 | 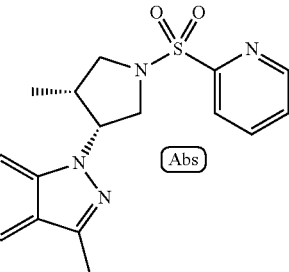 |
| II-35 | 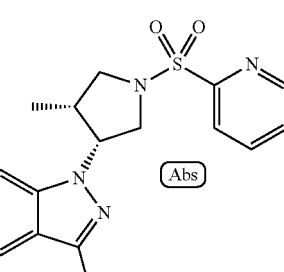 |
| II-36 | |

TABLE 85-continued
| No. | compound |
|---|---|
| II-37 | 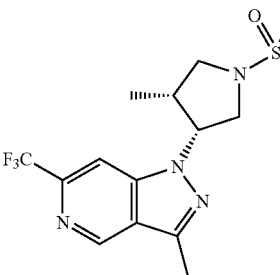 |
| II-38 | 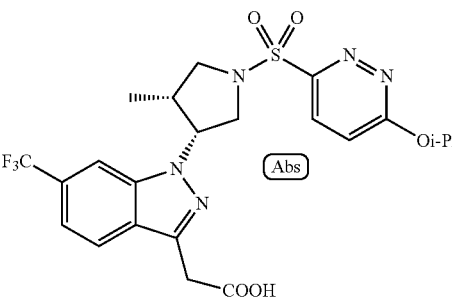 |
| II-39 | 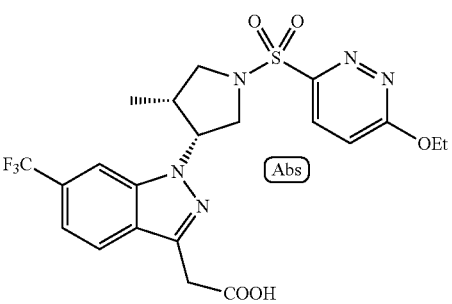 [SMILES: CCOc1ccc(S(=O)(=O)N2C[C@@H](C)[C@@H](n3nc(CC(=O)O)c4ccc(C(F)(F)F)cc43)C2)nn1] |
| II-40 | 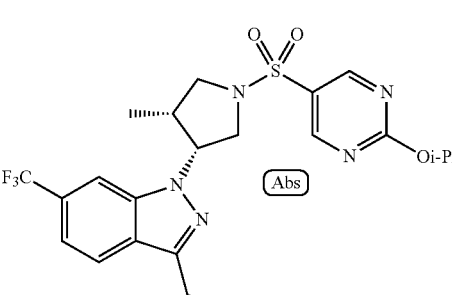 |
TABLE 86
| No. | compound |
|---|---|
| II-41 | 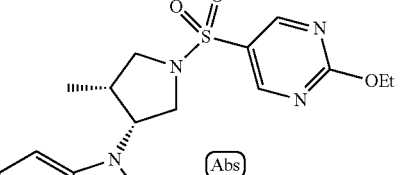 |
| II-42 | 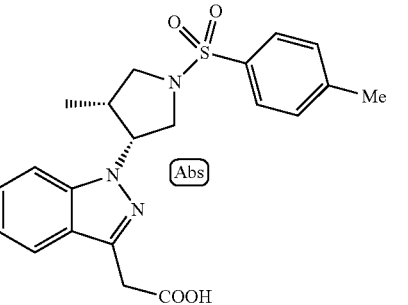 |
| II-43 | 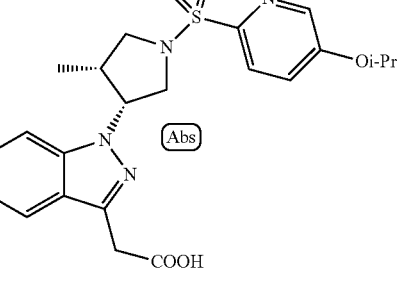 |
| II-44 | 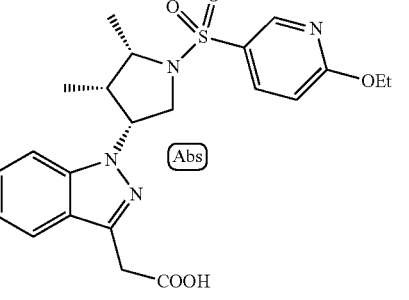 |
| II-45 | 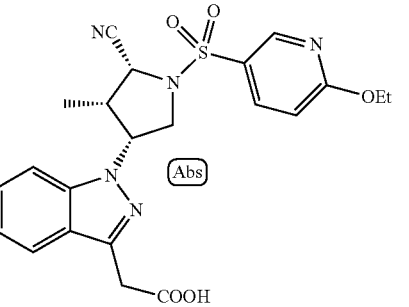 |

TABLE 86-continued

| No. | compound |
|---|---|
| II-46 | (structure) |
| II-47 | (structure) |
| II-48 | (structure) |
| II-49 | (structure) |

TABLE 86-continued

| No. | compound |
|---|---|
| II-50 | (structure) |

TABLE 87

| No. | compound |
|---|---|
| II-51 | (structure) |
| II-52 | (structure) |
| II-53 | (structure) |

TABLE 87-continued

| No. | compound |
|---|---|
| II-54 | (6-Cl-indazole, pyrrolidine-Me, SO2-C6H4-4-OMe) CH2COOH |
| II-55 | (6-Cl-indazole, pyrrolidine-Me, SO2-C6H4-4-Et) CH2COOH |
| II-56 | (6-Cl-indazole, pyrrolidine-Me, SO2-C6H4-4-OCF3) CH2COOH |
| II-57 | (6-Cl-indazole, pyrrolidine-Me, SO2-pyridine-OEt) CH2COOH |
| II-58 | (6-Cl-indazole, pyrrolidine-Me, SO2-pyridine-Oi-Pr) CH2COOH |

TABLE 87-continued

| No. | compound |
|---|---|
| II-59 | (6-Me-indazole, pyrrolidine-Me, SO2-C6H4-4-OMe) CH2COOH |
| II-60 | (6-Me-indazole, pyrrolidine-Me, SO2-C6H4-4-Et) CH2COOH |

TABLE 88

| No. | compound |
|---|---|
| II-61 | (6-Me-indazole, pyrrolidine-Me, SO2-C6H4-4-Me) CH2COOH |
| II-62 | (6-Me-indazole, pyrrolidine-Me, SO2-C6H4-4-OCF3) CH2COOH |

TABLE 88-continued

| No. | compound |
|---|---|
| II-63 | (structure) |
| II-64 | (structure) |
| II-65 | (structure) |
| II-66 | (structure) |
| II-67 | (structure) |

TABLE 88-continued

| No. | compound |
|---|---|
| II-68 | (structure) |
| II-69 | (structure) |
| II-70 | (structure) |

TABLE 89

| No. | compound |
|---|---|
| II-71 | (structure) |

TABLE 89-continued

| No. | compound |
|-----|----------|
| II-72 | |
| II-73 | [Abs] |
| II-74 | [Abs] |
| II-75 | [Abs] |
| II-76 | |
| II-77 | |
| II-78 | |
| II-79 | |
| II-80 | [Abs] |

TABLE 90

| No. | compound |
|---|---|
| II-81 | (structure) |
| II-82 | (structure) |
| II-83 | (structure) |
| II-84 | (structure) |
| II-85 | (structure) |

TABLE 90-continued

| No. | compound |
|---|---|
| II-86 | (structure) |
| II-87 | (structure) |
| II-88 | (structure) |
| II-89 | (structure) |
| II-90 | (structure) |

TABLE 91

| No. | compound |
|---|---|
| II-91 | (structure: 4-methoxyphenylsulfonyl pyrrolidine-indazole acetic acid) |
| II-92 | (structure: 4-OCF3-phenylsulfonyl pyrrolidine-indazole acetic acid) |
| II-93 | (structure: 6-Oi-Pr-pyridin-3-ylsulfonyl pyrrolidine-indazole acetic acid) |
| II-94 | (structure: 5-Oi-Pr-pyridin-2-ylsulfonyl pyrrolidine-indazole acetic acid) |
| II-95 | (structure: 5-OEt-pyridin-2-ylsulfonyl pyrrolidine-indazole acetic acid) |

TABLE 91-continued

| No. | compound |
|---|---|
| II-96 | (structure: 2,3-dihydrobenzofuran-5-ylsulfonyl pyrrolidine-indazole acetic acid) |
| II-97 | (structure: 2-methylbenzofuran-5-ylsulfonyl pyrrolidine-indazole acetic acid) |
| II-98 | (structure: 4-Oi-Pr-phenylsulfonyl dimethyl-pyrrolidine-indazole acetic acid) |
| II-99 | (structure: 4-Oi-Pr-phenylsulfonyl CN-pyrrolidine-indazole acetic acid) |
| II-100 | (structure: 4-Oi-Pr-phenylsulfonyl bicyclic pyrrolidine-indazole acetic acid) |

TABLE 92

| No. | compound |
|---|---|
| II-101 | |
| II-102 | |
| II-103 | |
| II-104 | |

TABLE 92-continued

| No. | compound |
|---|---|
| II-105 | |
| II-106 | |
| II-107 | |
| II-108 | |

TABLE 92-continued

| No. | compound |
|---|---|
| II-109 | (pyrrolidine with methyl, N-sulfonyl-pyridazine-Oi-Pr, linked to indazole-CH2COOH) (Abs) |
| II-110 | (pyrrolidine with methyl, N-sulfonyl-pyridazine-OEt, linked to indazole-CH2COOH) (Abs) |

TABLE 93

| No. | compound |
|---|---|
| II-111 | (pyrrolidine with methyl, N-sulfonyl-pyrimidine-Oi-Pr, linked to indazole-CH2COOH) (Abs) |
| II-112 | (pyrrolidine with methyl, N-sulfonyl-pyrimidine-OEt, linked to indazole-CH2COOH) (Abs) |

TABLE 93-continued

| No. | compound |
|---|---|
| II-113 | (pyrrolidine with methyl, N-sulfonyl-phenyl-OCH2F, linked to indazole-CH2COOH) (Abs) |
| II-114 | (pyrrolidine with CF3, N-sulfonyl-phenyl-Oi-Pr, linked to indazole-CH2COOH) (Abs) |
| II-115 | (pyrrolidine with methyl, N-sulfonyl-(2-Me,4-Oi-Pr)phenyl, linked to indazole-CH2COOH) (Abs) |
| II-116 | (pyrrolidine with methyl, N-sulfonyl-phenyl-Oi-Pr, linked to azaindazole-CH2COOH) (Abs) |
| II-117 | (pyrrolidine with methyl, N-sulfonyl-phenyl-Oi-Pr, linked to 6-MeO-indazole-CH2COOH) (Abs) |

TABLE 93-continued
| No. | compound |
|---|---|
| II-118 | 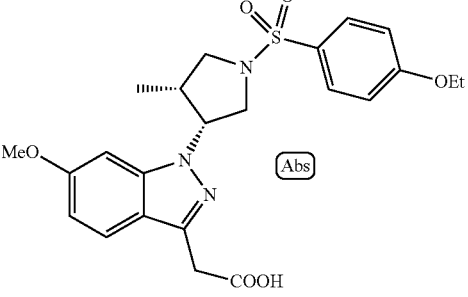 |
| II-119 | 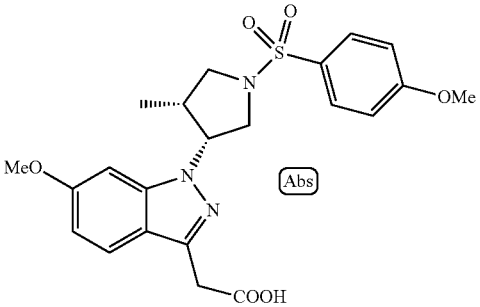 [SMILES: COc1ccc(S(=O)(=O)N2C[C@@H](C)[C@@H](n3nc(CC(=O)O)c4ccc(OC)cc43)C2)cc1] |
| II-120 | 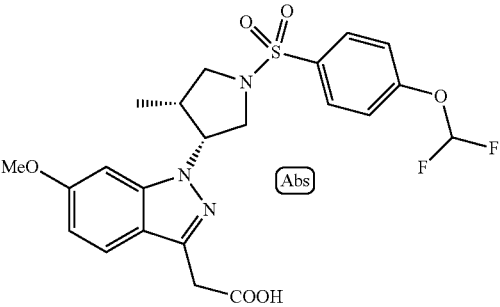 [SMILES: COc1ccc2c(CC(=O)O)nn([C@H]3CN(S(=O)(=O)c4ccc(OC(F)F)cc4)C[C@H]3C)c2c1] |
TABLE 94
| No. | compound |
|---|---|
| II-121 | 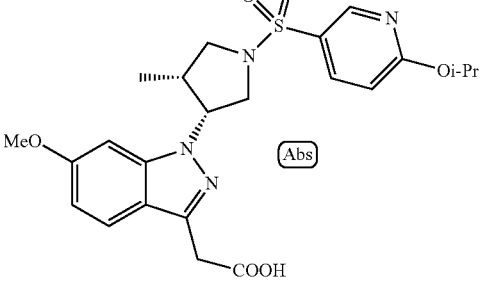 |
TABLE 94-continued
| No. | compound |
|---|---|
| II-122 | 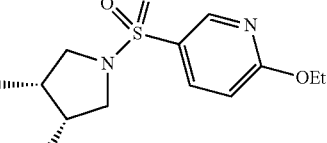 |
| II-123 | 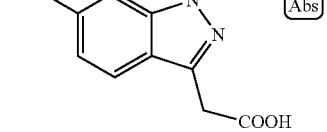 |
| II-124 | 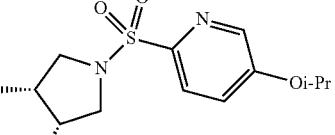 |
| II-125 | 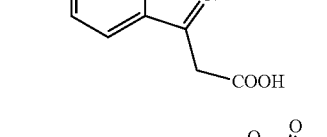 |
| II-126 | 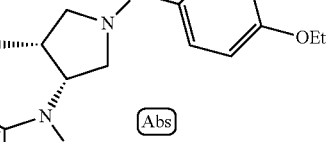 |

TABLE 94-continued
| No. | compound |
|---|---|
| II-127 | 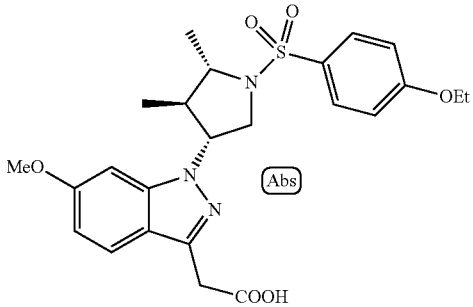 [SMILES: CCOc1ccc(S(=O)(=O)N2C[C@H](n3nc(CC(=O)O)c4ccc(OC)cc43)[C@@H](C)[C@@H]2C)cc1] |
| II-128 | 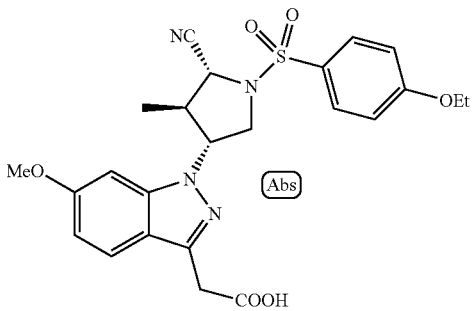 [SMILES: CCOc1ccc(S(=O)(=O)N2C[C@H](n3nc(CC(=O)O)c4ccc(OC)cc43)[C@@H](C)[C@@H]2C#N)cc1] |
| II-129 | 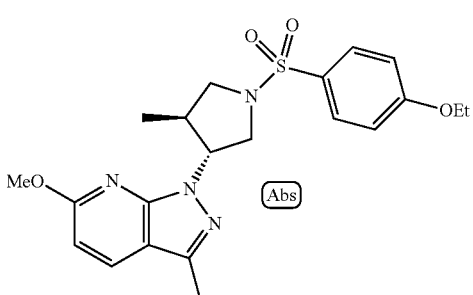 |
| II-130 | 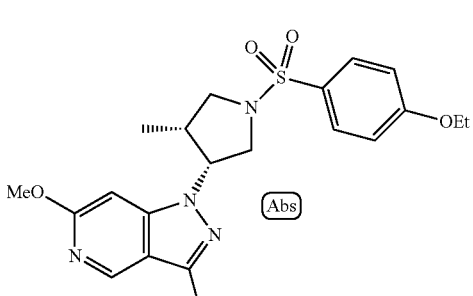 |
TABLE 95
| No. | compound |
|---|---|
| II-131 | 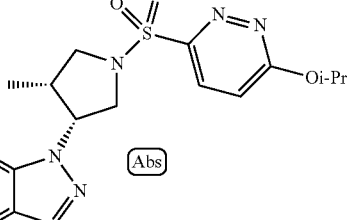 |
| II-132 | 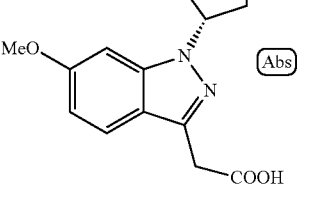 |
| II-133 | 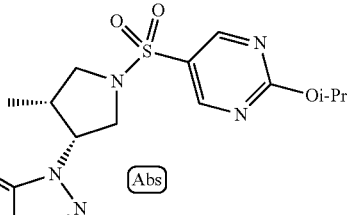 |
| II-134 | 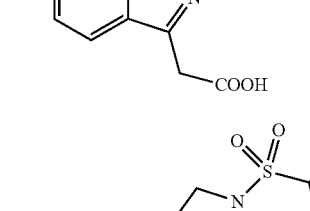 |
| II-135 | 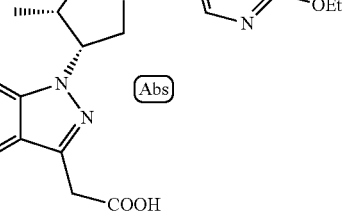 |

TABLE 95-continued
| No. | compound |
|---|---|
| II-136 | 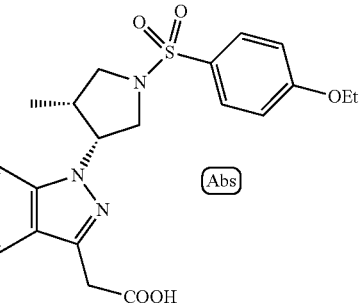 |
| II-137 | 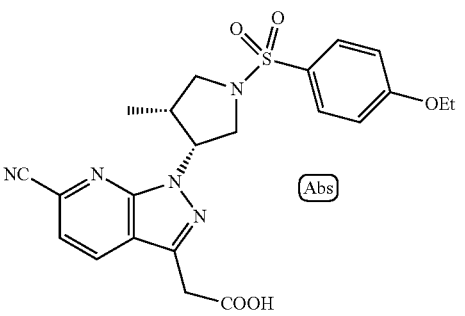 [SMILES: CCOc1ccc(S(=O)(=O)N2C[C@@H](C)[C@@H](n3nc(CC(=O)O)c4ccc(C#N)nc43)C2)cc1] |
| II-138 | 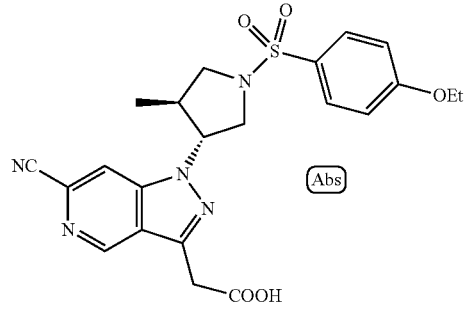 [SMILES: CCOc1ccc(S(=O)(=O)N2C[C@H](C)[C@@H](n3nc(CC(=O)O)c4cnc(C#N)cc43)C2)cc1] |
| II-139 | 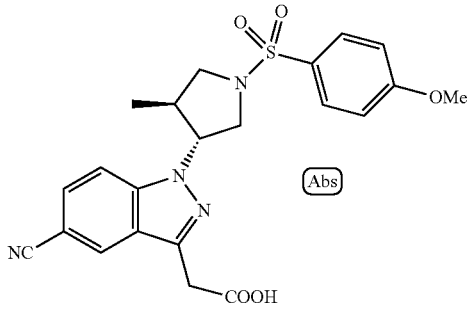 [SMILES: COc1ccc(S(=O)(=O)N2C[C@H](C)[C@@H](n3nc(CC(=O)O)c4cc(C#N)ccc43)C2)cc1] |
| II-140 | 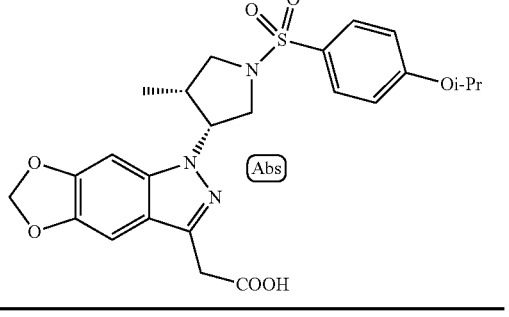 |
TABLE 96
| No. | compound |
|---|---|
| II-141 | 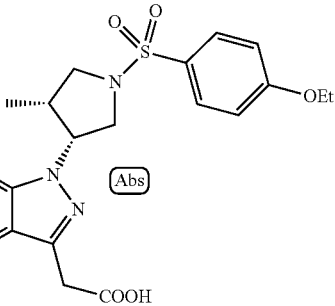 |
| II-142 | 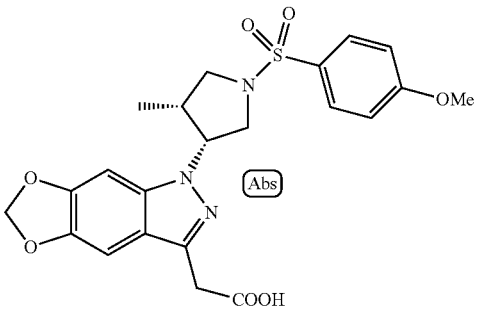 [SMILES: COc1ccc(S(=O)(=O)N2C[C@@H](C)[C@@H](n3nc(CC(=O)O)c4cc5c(cc43)OCO5)C2)cc1] |
| II-143 | 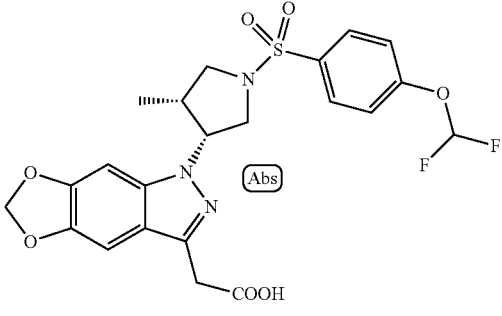 [SMILES: C[C@@H]1CN(S(=O)(=O)c2ccc(OC(F)F)cc2)C[C@@H]1n1nc(CC(=O)O)c2cc3c(cc21)OCO3] |
| II-144 | 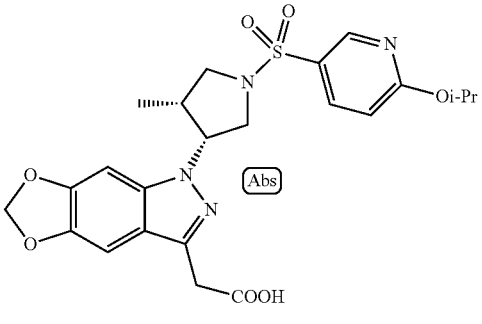 |
| II-145 | 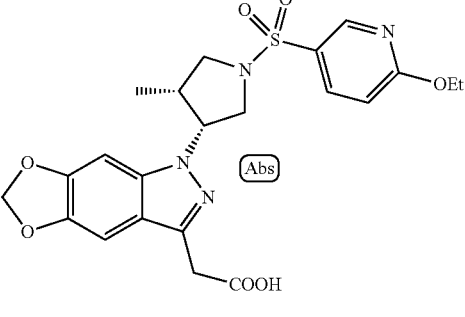 |

TABLE 96-continued

| No. | compound |
|---|---|
| II-146 | |
| II-147 | |
| II-148 | |
| II-149 | |
| II-150 | |

TABLE 97

| No. | compound |
|---|---|
| II-151 | |
| II-152 | |
| II-153 | |
| II-154 | |
| II-155 | |

TABLE 97-continued

| No. | compound |
|---|---|
| II-156 | 6-F, 5-NC-indazole, N1-(pyrrolidine with SO2-pyrimidine-OiPr), 3-CH2COOH (Abs) |
| II-157 | 6-F, 5-NC-indazole, N1-(pyrrolidine with SO2-pyrimidine-OEt), 3-CH2COOH (Abs) |
| II-158 | 6-Me, 5-NC-indazole, N1-(pyrrolidine with SO2-phenyl-OiPr), 3-CH2COOH (Abs) |
| II-159 | 6-Me, 5-NC-indazole, N1-(pyrrolidine with SO2-phenyl-OEt), 3-CH2COOH (Abs) |

TEST EXAMPLE 1

In Vitro DP Inhibitory Activity

1) DP Inhibitory Activity in Human Platelets

Thirty milliliter of blood was drown from healthy human into a syringe preloaded with ⅑ volume of 3.8% citrate sodium. The blood was centrifuged with 180 g for 10 min at room temperature and the upper plasma layer was collected as platelet rich plasma (PRP). The PRP was transferred to plate and treated with 3-isobutyl-1-methylxanthin (IBMX; 0.5 nM) for 5 min. Then the compounds of the present invention were added to the plate and after 10 min, 300 nM of PGD2 was added. The reaction was stopped with 1 mmol/l hydrogenchlolide after 2 min of PGD2 addition, and platelet was lysed by adding 12% Triton X-100. The concentration of cAMP in the supernatant of the platelet lysate was quantified using homogenous time resolved fluorescence (HTRF). Inhibition ratio was defined by cAMP increase with and without compound, and 1050 for each compound was calculated from inhibitory curve. Results were shown in Table 98.

2) Human DP1 Inhibitory Activity in DP1-Expressing Cell

Human DP1 receptor expressing Jurkut cell was suspended in buffer (HBSS, 20 mM HEPES buffer pH 7.4, 0.1 mM IBMX, 0.2 mM (4-(3-butoxy-4-methoxy-benzyl) imidazolidone (RO 20-1724)) at concentration of $1.2 \times 10^6$ cells/ml. Compounds of the present invention was added to the cell suspension and the mixture was incubated for 10 min at 37° C. PGD2 was added at final concentration of 60 nM, and the mixture was incubated for 60 min at 37° C. The concentration of cAMP in the cell lysate was measured using the cAMP dynamic 2 kit (Cisbio Bioassays, France) according to the manufacturer's instructions. Inhibition ratio was defined by cAMP increase with and without compound, and IC50 for each compound was calculated from inhibitory curve Results were shown in Table 98 as cAMP (nM). Compounds were categorized as AA (cAMP is less than 100 nM) and A (cAMP is more than 100 nM and less than 5000 nM) as shown in Table 99 and 100.

3) DP Receptor Binding Inhibitory Activity

Cell membrane was prepared from DP-expressing cells by homogenization and ultracentrifuge. Compounds of the present invention and [$^3$H]-PGD2 were mixed in plate, then cell membrane was added and the mixture was incubated on ice for 2 hr. The concentration of [$^3$H]-PGD2 was determined as equal to Kd calculated from Scatchard plot. Using cell harvester, the membrane was collected with glass fiber filter, washed 8 times and dried up, and radio activity on the filter was measured with scintillation counter (MicroBeta). Specific binding was defined as difference between total and non-specific binding (radio activity with 10 μM PGD2). Ki values for each compound were calculated from displacement curve.

TABLE 98

| Compound No. | cAMP (nM) | PRP (nM) |
|---|---|---|
| I-3 | 350 | |
| I-7 | 23 | 26 |
| I-11 | 99 | |
| I-19 | 56 | 260 |
| I-21 | 59 | 180 |
| I-37 | 10 | 71 |
| I-85 | 19 | 210 |
| I-96 | 40 | 68 |
| I-123 | 31 | 120 |
| I-130 | 10 | 240 |
| I-131 | 31 | 190 |
| I-142 | 9.9 | 92 |
| I-144 | 4.7 | 82 |
| I-150 | 20 | 41 |
| I-156 | 3 | 110 |
| I-159 | 140 | 68 |
| I-164 | 13 | 43 |
| I-166 | 32 | 55 |
| I-174 | 99 | |
| I-177 | 58 | 44 |
| I-205 | 13 | 70 |
| I-220 | 32 | |

TABLE 98-continued

| Compound No. | cAMP (nM) | PRP (nM) |
|---|---|---|
| I-222 | 95 | 140 |
| I-245 | 27 | 68 |
| I-284 | 50 | 130 |
| I-288 | 100 | |
| I-316 | 110 | |
| I-322 | 29 | 12 |
| I-325 | 24 | 210 |
| I-336 | 35 | 180 |
| I-353 | 120 | 37 |

TABLE 99

| Compound No. | cAMP |
|---|---|
| I-1 | A |
| I-2 | A |
| I-3 | A |
| I-4 | A |
| I-5 | A |
| I-6 | A |
| I-7 | AA |
| I-8 | A |
| I-9 | A |
| I-10 | A |
| I-11 | AA |
| I-12 | A |
| I-13 | AA |
| I-14 | A |
| I-15 | A |
| I-16 | A |
| I-17 | AA |
| I-18 | A |
| I-19 | AA |
| I-20 | A |
| I-21 | AA |
| I-22 | AA |
| I-23 | A |
| I-24 | A |
| I-25 | A |
| I-26 | A |
| I-27 | A |
| I-28 | AA |
| I-29 | AA |
| I-30 | A |
| I-31 | AA |
| I-32 | AA |
| I-33 | AA |
| I-34 | AA |
| I-35 | AA |
| I-36 | A |
| I-37 | AA |
| I-38 | AA |
| I-39 | AA |
| I-40 | A |
| I-41 | A |
| I-42 | A |
| I-43 | A |
| I-44 | A |
| I-45 | A |
| I-46 | AA |
| I-47 | A |
| I-48 | A |
| I-49 | A |
| I-50 | AA |
| I-51 | AA |
| I-52 | AA |
| I-53 | AA |
| I-54 | A |
| I-55 | A |
| I-56 | AA |
| I-57 | AA |
| I-58 | AA |
| I-59 | A |
| I-60 | AA |
| I-61 | A |
| I-62 | AA |
| I-63 | AA |
| I-64 | A |
| I-65 | A |
| I-66 | AA |
| I-67 | AA |
| I-68 | AA |
| I-69 | AA |
| I-72 | A |
| I-73 | AA |
| I-74 | AA |
| I-75 | AA |
| I-76 | AA |
| I-77 | A |
| I-78 | A |
| I-79 | A |
| I-80 | A |
| I-81 | A |
| I-82 | A |
| I-83 | AA |
| I-84 | A |
| I-85 | AA |
| I-86 | A |
| I-87 | A |
| I-88 | AA |
| I-89 | AA |
| I-90 | AA |
| I-91 | AA |
| I-92 | AA |
| I-93 | AA |
| I-94 | AA |
| I-95 | AA |
| I-96 | AA |
| I-97 | AA |
| I-98 | AA |
| I-99 | AA |
| I-100 | A |
| I-101 | A |
| I-102 | AA |
| I-103 | AA |
| I-104 | AA |
| I-105 | AA |
| I-106 | AA |
| I-107 | AA |
| I-108 | AA |
| I-109 | AA |
| I-110 | AA |
| I-111 | AA |
| I-112 | AA |
| I-113 | AA |
| I-114 | AA |
| I-115 | AA |
| I-116 | A |
| I-117 | A |
| I-118 | AA |
| I-119 | A |
| I-120 | AA |
| I-121 | A |
| I-122 | A |
| I-123 | AA |
| I-124 | A |
| I-125 | A |
| I-126 | AA |
| I-127 | AA |
| I-128 | AA |
| I-129 | AA |
| I-130 | AA |
| I-131 | AA |
| I-132 | AA |
| I-133 | A |
| I-134 | AA |
| I-135 | AA |
| I-136 | A |
| I-137 | AA |
| I-138 | A |
| I-139 | AA |
| I-140 | AA |

TABLE 99-continued

| Compound No. | cAMP |
|---|---|
| I-141 | AA |
| I-142 | AA |
| I-143 | AA |
| I-144 | AA |
| I-145 | A |
| I-146 | AA |
| I-147 | AA |
| I-148 | A |
| I-149 | A |
| I-150 | AA |
| I-151 | AA |
| I-152 | A |
| I-153 | AA |
| I-154 | A |
| I-155 | A |
| I-156 | AA |
| I-157 | A |
| I-158 | A |
| I-159 | A |
| I-160 | AA |
| I-161 | AA |
| I-162 | AA |
| I-163 | AA |
| I-164 | AA |
| I-165 | AA |
| I-166 | AA |
| I-167 | AA |
| I-168 | AA |
| I-169 | AA |
| I-170 | AA |
| I-171 | AA |
| I-172 | AA |
| I-173 | A |
| I-174 | AA |
| I-175 | A |
| I-176 | A |
| I-177 | AA |
| I-178 | A |
| I-179 | AA |
| I-180 | A |
| I-181 | A |
| I-182 | A |
| I-183 | A |
| I-184 | A |
| I-185 | A |
| I-186 | A |
| I-187 | A |
| I-188 | A |
| I-189 | A |
| I-190 | A |
| I-191 | A |
| I-192 | A |
| I-193 | A |
| I-194 | A |
| I-195 | A |
| I-196 | AA |
| I-197 | A |
| I-198 | A |
| I-199 | A |
| I-200 | AA |
| I-201 | A |
| I-202 | AA |
| I-203 | AA |
| I-204 | AA |
| I-205 | AA |
| I-206 | AA |
| I-207 | A |
| I-208 | A |
| I-209 | AA |
| I-210 | A |
| I-211 | AA |
| I-212 | A |
| I-213 | A |
| I-214 | AA |
| I-215 | A |
| I-216 | AA |
| I-217 | AA |
| I-218 | AA |
| I-219 | A |
| I-220 | AA |
| I-221 | AA |
| I-222 | AA |
| I-223 | A |
| I-224 | A |
| I-225 | AA |
| I-226 | A |

TABLE 100

| Compound No. | cAMP |
|---|---|
| I-227 | A |
| I-228 | AA |
| I-229 | AA |
| I-230 | AA |
| I-231 | AA |
| I-232 | AA |
| I-233 | AA |
| I-234 | A |
| I-235 | A |
| I-236 | AA |
| I-237 | AA |
| I-238 | A |
| I-239 | A |
| I-240 | A |
| I-241 | AA |
| I-242 | AA |
| I-243 | AA |
| I-244 | AA |
| I-245 | AA |
| I-246 | A |
| I-247 | A |
| I-248 | A |
| I-249 | A |
| I-250 | AA |
| I-251 | AA |
| I-252 | AA |
| I-253 | A |
| I-254 | A |
| I-255 | A |
| I-256 | AA |
| I-257 | A |
| I-258 | AA |
| I-259 | A |
| I-260 | A |
| I-261 | A |
| I-262 | AA |
| I-263 | AA |
| I-264 | AA |
| I-265 | AA |
| I-266 | A |
| I-267 | AA |
| I-268 | AA |
| I-269 | AA |
| I-270 | AA |
| I-271 | AA |
| I-272 | AA |
| I-273 | A |
| I-274 | A |
| I-275 | A |
| I-276 | AA |
| I-277 | AA |
| I-278 | A |
| I-279 | A |
| I-280 | A |
| I-281 | A |
| I-282 | A |
| I-283 | AA |
| I-284 | AA |
| I-285 | A |
| I-286 | AA |
| I-287 | A |
| I-288 | A |

TABLE 100-continued

| Compound No. | cAMP |
|---|---|
| I-289 | A |
| I-290 | AA |
| I-291 | A |
| I-292 | AA |
| I-293 | A |
| I-294 | A |
| I-295 | AA |
| I-296 | A |
| I-297 | A |
| I-298 | A |
| I-299 | A |
| I-300 | A |
| I-301 | A |
| I-302 | A |
| I-303 | AA |
| I-304 | AA |
| I-305 | A |
| I-306 | A |
| I-307 | A |
| I-308 | AA |
| I-309 | AA |
| I-310 | A |
| I-311 | A |
| I-312 | AA |
| I-313 | A |
| I-314 | A |
| I-315 | AA |
| I-316 | A |
| I-317 | A |
| I-318 | A |
| I-319 | A |
| I-320 | AA |
| I-321 | A |
| I-322 | AA |
| I-323 | A |
| I-324 | AA |
| I-325 | AA |
| I-326 | A |
| I-327 | A |
| I-328 | A |
| I-329 | AA |
| I-330 | AA |
| I-331 | AA |
| I-332 | A |
| I-333 | AA |
| I-334 | AA |
| I-335 | AA |
| I-336 | AA |
| I-337 | A |
| I-338 | AA |
| I-339 | A |
| I-340 | A |
| I-341 | A |
| I-342 | A |
| I-343 | AA |
| I-344 | AA |
| I-345 | A |
| I-346 | AA |
| I-347 | AA |
| I-348 | AA |
| I-349 | AA |
| I-350 | A |
| I-351 | A |
| I-352 | A |
| I-353 | A |
| I-354 | AA |
| I-355 | A |
| I-356 | A |
| I-357 | A |
| I-358 | A |
| I-359 | A |
| I-360 | AA |
| I-361 | A |
| I-362 | A |
| I-363 | A |
| I-364 | A |
| I-365 | AA |
| I-366 | AA |

TEST EXAMPLE 2

In Vitro CRTH2 Inhibitory Activity

1) CRTH2 Receptor Binding Inhibitory Activity

Cell membrane was prepared from CRTH2-expressing K562 cell. The cell membrane (20 µg/well) was mixed with reaction buffer (50 mM Tris/HCl, pH 7.4, 10 mM MgCl2). Then, [$^3$H]-PGD$_2$ was added to the mixture and incubated for 60 min at room temperature. The concentration of [$^3$H]-PGD$_2$ was determined as equal to Kd calculated from Scatchard plot. Then, the mixture was filtrated with glass paper immediately. The filter paper was washed several times and radio activity on the filter was measured. Specific binding was defined as difference between total and non-specific binding (radio activity with 10 µM PGD$_2$). Ki values for each compound were calculated from displacement curve.

Results were shown in Table 101 as Ki (nM). Compounds were categorized to AAAA (Ki is less than 100 nM) and AAA (Ki is more than 100 nM and less than 5000 nM) as shown in Table 102 and 103.

TABLE 101

| Compound No. | Ki (nM) |
|---|---|
| I-4 | 320 |
| I-9 | 6.2 |
| I-10 | 8.2 |
| I-15 | 56 |
| I-19 | 62 |
| I-21 | 10 |
| I-30 | 140 |
| I-33 | 2.1 |
| I-34 | 77 |
| I-37 | 2.4 |
| I-47 | 16 |
| I-49 | 0.59 |
| I-52 | 5.1 |
| I-57 | 3.8 |
| I-59 | 23 |
| I-63 | 3.1 |
| I-74 | 680 |
| I-77 | 48 |
| I-85 | 2.8 |
| I-96 | 37 |
| I-97 | 13 |
| I-104 | 16 |
| I-113 | 17 |
| I-117 | 1.6 |
| I-122 | 2.5 |
| I-123 | 4.3 |
| I-130 | 4.7 |
| I-131 | 7.4 |
| I-138 | 65 |
| I-139 | 32 |
| I-142 | 11 |
| I-144 | 3.1 |
| I-145 | 3.1 |
| I-148 | 5.6 |
| I-149 | 4.8 |
| I-150 | 99 |
| I-152 | 56 |
| I-153 | 65 |
| I-157 | 270 |

TABLE 101-continued

| Compound No. | Ki (nM) |
|---|---|
| I-164 | 16 |
| I-166 | 12 |
| I-173 | 11 |
| I-174 | 50 |
| I-177 | 15 |
| I-210 | 10 |
| I-215 | 22 |
| I-219 | 230 |
| I-220 | 8.1 |
| I-222 | 100 |
| I-239 | 4.4 |
| I-247 | 15 |
| I-255 | 390 |
| I-260 | 21 |
| I-280 | 7.8 |
| I-282 | 10 |
| I-284 | 55 |
| I-288 | 40 |
| I-316 | 220 |
| I-322 | 270 |
| I-325 | 28 |
| I-336 | 440 |
| I-353 | 400 |
| I-360 | 30 |
| I-363 | 170 |
| I-367 | 100 |

TABLE 102

| Compound No. | Ki |
|---|---|
| I-1 | AAA |
| I-2 | AAA |
| I-3 | AAA |
| I-4 | AAA |
| I-5 | AAA |
| I-6 | AAA |
| I-7 | AAAA |
| I-8 | AAAA |
| I-9 | AAAA |
| I-10 | AAAA |
| I-11 | AAA |
| I-12 | AAAA |
| I-13 | AAAA |
| I-14 | AAAA |
| I-15 | AAAA |
| I-16 | AAAA |
| I-17 | AAAA |
| I-18 | AAAA |
| I-19 | AAAA |
| I-20 | AAAA |
| I-21 | AAAA |
| I-22 | AAAA |
| I-23 | AAAA |
| I-24 | AAAA |
| I-25 | AAAA |
| I-26 | AAAA |
| I-27 | AAAA |
| I-28 | AAA |
| I-29 | AAAA |
| I-30 | AAA |
| I-31 | AAAA |
| I-32 | AAAA |
| I-33 | AAAA |
| I-34 | AAAA |
| I-35 | AAAA |
| I-36 | AAAA |
| I-37 | AAAA |
| I-38 | AAAA |
| I-39 | AAAA |
| I-40 | AAAA |
| I-41 | AAAA |
| I-42 | AAAA |
| I-43 | AAAA |
| I-44 | AAAA |
| I-45 | AAAA |
| I-46 | AAAA |
| I-47 | AAAA |
| I-48 | AAAA |
| I-49 | AAAA |
| I-50 | AAAA |
| I-51 | AAAA |
| I-52 | AAAA |
| I-53 | AAAA |
| I-54 | AAAA |
| I-55 | AAA |
| I-56 | AAAA |
| I-57 | AAAA |
| I-58 | AAAA |
| I-59 | AAAA |
| I-60 | AAA |
| I-61 | AAAA |
| I-62 | AAAA |
| I-63 | AAAA |
| I-64 | AAAA |
| I-65 | AAAA |
| I-66 | AAAA |
| I-67 | AAAA |
| I-68 | AAAA |
| I-69 | AAA |
| I-70 | AAAA |
| I-72 | AAA |
| I-73 | AAA |
| I-74 | AAA |
| I-75 | AAA |
| I-76 | AAA |
| I-77 | AAAA |
| I-78 | AAA |
| I-79 | AAA |
| I-80 | AAA |
| I-81 | AAA |
| I-82 | AAA |
| I-83 | AAA |
| I-84 | AAAA |
| I-85 | AAAA |
| I-86 | AAAA |
| I-87 | AAAA |
| I-88 | AAAA |
| I-89 | AAAA |
| I-90 | AAA |
| I-91 | AAAA |
| I-92 | AAA |
| I-93 | AAA |
| I-94 | AAAA |
| I-95 | AAAA |
| I-96 | AAAA |
| I-97 | AAAA |
| I-98 | AAAA |
| I-99 | AAAA |
| I-100 | AAAA |
| I-101 | AAA |
| I-102 | AAAA |
| I-103 | AAAA |
| I-104 | AAAA |
| I-105 | AAAA |
| I-106 | AAAA |
| I-107 | AAAA |
| I-108 | AAAA |
| I-109 | AAAA |
| I-110 | AAAA |
| I-111 | AAAA |
| I-112 | AAAA |
| I-113 | AAAA |
| I-114 | AAAA |
| I-115 | AAAA |
| I-116 | AAAA |
| I-117 | AAAA |
| I-118 | AAAA |
| I-119 | AAAA |
| I-120 | AAAA |
| I-121 | AAAA |
| I-122 | AAAA |

TABLE 102-continued

| Compound No. | Ki |
|---|---|
| I-123 | AAAA |
| I-124 | AAAA |
| I-125 | AAAA |
| I-126 | AAAA |
| I-127 | AAAA |
| I-128 | AAAA |
| I-129 | AAAA |
| I-130 | AAAA |
| I-131 | AAAA |
| I-132 | AAAA |
| I-133 | AAA |
| I-134 | AAAA |
| I-135 | AAAA |
| I-136 | AAA |
| I-137 | AAAA |
| I-138 | AAAA |
| I-139 | AAAA |
| I-140 | AAAA |
| I-141 | AAAA |
| I-142 | AAAA |
| I-143 | AAAA |
| I-144 | AAAA |
| I-145 | AAAA |
| I-146 | AAAA |
| I-147 | AAAA |
| I-148 | AAAA |
| I-149 | AAAA |
| I-150 | AAAA |
| I-151 | AAAA |
| I-152 | AAAA |
| I-153 | AAAA |
| I-155 | AAA |
| I-156 | AAA |
| I-157 | AAA |
| I-158 | AAAA |
| I-159 | AAA |
| I-160 | AAA |
| I-161 | AAA |
| I-162 | AAA |
| I-163 | AAA |
| I-164 | AAAA |
| I-165 | AAAA |
| I-166 | AAAA |
| I-167 | AAA |
| I-168 | AAAA |
| I-169 | AAAA |
| I-170 | AAAA |
| I-171 | AAAA |
| I-172 | AAAA |
| I-173 | AAAA |
| I-174 | AAAA |
| I-175 | AAAA |
| I-176 | AAAA |
| I-177 | AAAA |
| I-178 | AAAA |
| I-179 | AAAA |
| I-180 | AAAA |
| I-181 | AAA |
| I-182 | AAAA |
| I-183 | AAAA |
| I-184 | AAAA |
| I-185 | AAAA |
| I-186 | AAAA |
| I-187 | AAAA |
| I-188 | AAA |
| I-189 | AAAA |
| I-190 | AAAA |
| I-191 | AAAA |
| I-192 | AAAA |
| I-193 | AAA |
| I-194 | AAAA |
| I-195 | AAAA |
| I-196 | AAAA |
| I-197 | AAA |
| I-198 | AAAA |
| I-199 | AAA |
| I-200 | AAAA |
| I-201 | AAAA |
| I-202 | AAA |
| I-203 | AAA |
| I-204 | AAAA |
| I-205 | AAA |
| I-206 | AAA |
| I-207 | AAAA |
| I-208 | AAAA |
| I-209 | AAA |
| I-210 | AAAA |
| I-211 | AAA |
| I-212 | AAA |
| I-213 | AAA |
| I-214 | AAA |
| I-215 | AAAA |
| I-216 | AAAA |
| I-217 | AAAA |
| I-218 | AAA |
| I-219 | AAA |
| I-220 | AAAA |
| I-221 | AAAA |
| I-222 | AAA |
| I-223 | AAAA |
| I-224 | AAAA |
| I-225 | AAAA |
| I-226 | AAAA |

TABLE 103

| Compound No. | Ki |
|---|---|
| I-227 | AAAA |
| I-228 | AAAA |
| I-229 | AAAA |
| I-230 | AAAA |
| I-231 | AAAA |
| I-232 | AAAA |
| I-233 | AAAA |
| I-234 | AAAA |
| I-235 | AAAA |
| I-236 | AAAA |
| I-237 | AAAA |
| I-238 | AAAA |
| I-239 | AAAA |
| I-240 | AAAA |
| I-241 | AAAA |
| I-242 | AAAA |
| I-243 | AAA |
| I-244 | AAAA |
| I-245 | AAAA |
| I-246 | AAAA |
| I-247 | AAAA |
| I-248 | AAAA |
| I-249 | AAAA |
| I-250 | AAA |
| I-251 | AAAA |
| I-252 | AAAA |
| I-253 | AAA |
| I-254 | AAA |
| I-255 | AAA |
| I-256 | AAAA |
| I-258 | AAAA |
| I-259 | AAAA |
| I-260 | AAAA |
| I-261 | AAA |
| I-262 | AAA |
| I-263 | AAAA |
| I-264 | AAAA |
| I-265 | AAAA |
| I-266 | AAA |
| I-267 | AAA |
| I-268 | AAAA |
| I-269 | AAAA |
| I-270 | AAAA |
| I-271 | AAAA |
| I-272 | AAAA |

TABLE 103-continued

| Compound No. | Ki |
|---|---|
| I-273 | AAA |
| I-274 | AAAA |
| I-275 | AAA |
| I-276 | AAAA |
| I-277 | AAAA |
| I-278 | AAAA |
| I-279 | AAAA |
| I-280 | AAAA |
| I-282 | AAAA |
| I-283 | AAA |
| I-284 | AAAA |
| I-285 | AAA |
| I-287 | AAAA |
| I-288 | AAAA |
| I-289 | AAA |
| I-290 | AAA |
| I-291 | AAA |
| I-292 | AAA |
| I-293 | AAA |
| I-294 | AAA |
| I-295 | AAA |
| I-296 | AAA |
| I-297 | AAA |
| I-298 | AAA |
| I-299 | AAA |
| I-300 | AAAA |
| I-301 | AAA |
| I-302 | AAA |
| I-303 | AAA |
| I-304 | AAAA |
| I-305 | AAA |
| I-306 | AAA |
| I-307 | AAA |
| I-308 | AAAA |
| I-309 | AAAA |
| I-310 | AAA |
| I-311 | AAA |
| I-312 | AAAA |
| I-313 | AAAA |
| I-314 | AAAA |
| I-315 | AAA |
| I-316 | AAA |
| I-317 | AAA |
| I-318 | AAA |
| I-319 | AAA |
| I-320 | AAAA |
| I-322 | AAA |
| I-323 | AAA |
| I-324 | AAAA |
| I-325 | AAAA |
| I-326 | AAA |
| I-327 | AAA |
| I-328 | AAA |
| I-329 | AAAA |
| I-330 | AAAA |
| I-331 | AAAA |
| I-332 | AAAA |
| I-333 | AAAA |
| I-334 | AAA |
| I-336 | AAA |
| I-338 | AAA |
| I-341 | AAA |
| I-342 | AAA |
| I-343 | AAAA |
| I-344 | AAA |
| I-345 | AAA |
| I-346 | AAAA |
| I-347 | AAA |
| I-348 | AAAA |
| I-349 | AAA |
| I-350 | AAAA |
| I-351 | AAA |
| I-352 | AAA |
| I-353 | AAA |
| I-354 | AAA |
| I-355 | AAA |
| I-356 | AAAA |
| I-357 | AAA |
| I-358 | AAA |
| I-359 | AAAA |
| I-360 | AAAA |
| I-361 | AAA |
| I-362 | AAA |
| I-363 | AAA |
| I-364 | AAA |
| I-365 | AAA |
| I-366 | AAA |
| I-367 | AAA |

2) CRTH2 Inhibitory Activity in CRTH2-Expressing Cells

CRTH2 inhibitory activities of compounds were determined as inhibition activity of intra-cellular calcium concentration increase induced by PGD2 in CRTH2-expressing cells.

CRTH2-expressing K562 cells were suspended at concentration of $2 \times 10^6$ cells/ml in buffer (10 mM HEPES, pH 7.4, 0.1% Bovine serum albumin). Cells were incubated with Fura-3 AM (4 µM) for 30 min at room temperature. Cells were washed, resuspended and mixed with various concentration of compounds of the present invention. After 2 min, cells were treated with 200 nM of $PGD_2$. Then intracellular calcium concentration was measured using intracellular ion analyzer (FDSS3000). Inhibition ratio was defined by comparing intracellular calcium concentration increase with and without compound, and IC50 for each compound was calculated from inhibitory curve.

(Result)
Compound No. I-7:33 nM
Compound No. I-37:50 nM
Compound No. I-49:86 nM
Compound No. I-52:140 nM
Compound No. I-57:210 nM
Compound No. I-85:140 nM
Compound No. I-96:230 nM
Compound No. I-97:92 nM
Compound No. I-123:91 nM
Compound No. I-130:73 nM
Compound No. I-131:210 nM 3) CRTH2 Inhibitory Activity in Human Eosinophil CRTH2 inhibitory activity in human eosinophil was determined as inhibitory activity of PGD2 induced eosinophil shape change.

Human peripheral blood was mixed with compounds of the present invention at 37° C. After 5 min, the blood was treated with 40 nM of PGD2 for 10 min and fixed. The blood was hemolyzed and centrifuged. Blood cells were resuspended in PBS and measured forward scatter (FS) using flow cytometer (FACSAria). Inhibition ratio was defined by comparing FS with and without compound, and IC50 for each compound was calculated from inhibitory curve.

(Result)
Compound No. I-7: 34 nM
Compound No. I-31: 13 nM
Compound No. I-37: 15 nM
Compound No. I-85: 33 nM
Compound No. I-96: 270 nM
Compound No. I-97:68 nM
Compound No. I-123:60 nM
Compound No. I-130:46 nM
The others of Test Examples are shown below.

TEST EXAMPLE 3

CYP Inhibition Test

Using commercially available pooled human hepatic microsome, and employing, as markers, 7-ethoxyresorufin O-deethylation (CYP1A2), tolbutamide methyl-hydroxylation (CYP2C9), mephenyloin 4'-hydroxylation (CYP2C19), dextromethorphan O-demethylation (CYP2D6), and terfenedine hydroxylation as typical substrate metabolism reactions of human main five CYP enzyme forms (CYP1A2, 2C9, 2C19, 2D6, 3A4), an inhibitory degree of each metabolite production amount by a compound of the present compound was assessed.

The reaction conditions were as follows: substrate, 0.5 µmol/L ethoxyresorufin (CYP1A2), 100 µmol/L tolbutamide (CYP2C9), 50 µmol/L S-mephenyloin (CYP2C19), 5 µmol/L dextromethorphan (CYP2D6), 1 µmol/L terfenedine (CYP3A4); reaction time, 15 minutes; reaction temperature, 37° C.; enzyme, pooled human hepatic microsome 0.2 mg protein/mL; concentration of a compound of the present invention, 1, 5, 10, 20 µmol/L (four points).

Each five kinds of substrates, human hepatic microsome, or a compound of the present invention in 50 mM Hepes buffer as a reaction mixture was added to a 96-well plate at the composition as described above, NADPH, as a cofactor was added to initiate metabolism reactions as markers and. After the incubation at 37° C. for 15 minutes, a methanol/acetonitrile=1/1 (v/v) solution was added to stop the reaction. After the centrifugation at 3000 rpm for 15 minutes, resorufin (CYP1A2 metabolite) in the supernatant was quantified by a fluorescent multilabel counter and tolbutamide hydroxide (CYP2C9 metabolite), mephenyloin 4' hydroxide (CYP2C19 metabolite), dextrorphan (CYP2D6 metabolite), and terfenadine alcohol (CYP3A4 metabolite) were quantified by LC/MS/MS.

Addition of only DMSO being a solvent dissolving a the compound of the present invention to a reaction system was adopted as a control (100%), remaining activity (%) was calculated at each concentration of a compound of the present invention added as the solution and IC50 was calculated by reverse presumption by a logistic model using a concentration and an inhibition rate.

(Result)
Compound No. I-7: five kinds >20 µmol/L
Compound No. I-9: five kinds >20 µmol/L
Compound No. I-37: five kinds >20 µmol/L
Compound No. I-49: five kinds >20 µmol/L
Compound No. I-52: five kinds >20 µmol/L
Compound No. I-57: five kinds >20 µmol/L
Compound No. I-74: five kinds >20 µmol/L
Compound No. I-96: five kinds >20 µmol/L

TEST EXAMPLE 4

BA Test

An experimental material and a method for examining oral absorbability
(1) Animals used: rats or mice were used.
(2) Breeding condition: chow and sterilized tap water were allowed to be taken in freely.
(3) Setting of a dosage and grouping: a predetermined dosage was administered orally or intravenously. Groups were formed as shown below. (A dosage varied depending on each compound)
Oral administration 1-30 mg/kg (n=2 to 3)
Intravenous administration 0.5-10 mg/kg (n=2 to 3)
(4) Preparation of administered liquid: In oral administration, a solution or suspension was administered. In intravenous administration, after solubilization, the administration was performed.
(5) Method of Administration: In oral administration, compulsory administration to the stomach was conducted using an oral probe.
In intravenous administration, administration from the caudal vein was conducted using a syringe with an injection needle.
(6) Evaluation item: Blood was chronologically collected, and then the concentration of a compound of the present invention blood plasma was measured using a LC/MS/MS.
(7) Statistical analysis: With regard to a shift in plasma concentration, the plasma concentration-time area under the curve (AUC) was calculated using a nonlinear least-squares program WinNonlin®. Bioavailability (BA) was calculated from the AUCs of the oral administration group and the intravenous administration group, respectively.
(Result) Rats, Oral administration 1 mg/kg
Compound No. I-37: 71%
Compound No. I-96: 82%

TEST EXAMPLE 5

Metabolism Stability Test

Using a commercially available pooled human hepatic microsomes, a compound of the present invention was reacted for a constant time, a remaining rate was calculated by comparing a reacted sample and an unreacted sample, thereby, a degree of metabolism in liver was assessed.

A reaction was performed (oxidative reaction) at 37° C. for 0 minute or 30 minutes in the presence of 1 mmol/L NADPH in 0.2 mL of a buffer (50 mmol/L Tris-HCl pH 7.4, 150 mmol/L potassium chloride, 10 mmol/L magnesium chloride) containing 0.5 mg protein/mL of human liver microsomes. After the reaction, 50 µL of the reaction mixture was added to 100 µL of a methanol/acetonitrile=1/1 (v/v), mixed and centrifuged at 3000 rpm for 15 minutes. The compound of the present invention in the supernatant was quantified by LC/MS/MS, and a remaining amount of the compound of the present invention after the reaction was calculated, letting a compound amount at 0 minute reaction time to be 100%. Glucuronidation reaction was in the presence of 5 mM UDP-glucuronic acid in place of NADPH, followed by similar operations.

(Result) % inhibition was shown at 0.5 µmol/L of the compound.
Compound No. I-9: 98.7%
Compound No. I-47: 91.8%
Compound No. I-49: 94.7%
Compound No. I-52: 97.2%
Compound No. I-57: 86.9%
Compound No. I-75: 99.2%
Compound No. I-96: 99.3%

TEST EXAMPLE 6

CYP3A4 Fluorescent MBI Test

The CYP3A4 fluorescent MBI test is a test of investigating enhancement of CYP3A4 inhibition of a compound by a metabolism reaction, and the test was performed using, as CYP3A4 enzyme expressed in *Escherichia coli* and employing, as an index, a reaction in which 7-benzyloxytrifluoromethylcoumarin (7-BFC) is debenzylated by the CYP3A4 enzyme to produce a metabolite, 7-hydroxytrifluoromethylcoumarin (HFC) emitting fluorescent light.

The reaction conditions were as follows: substrate, 5.6 μmol/L 7-BFC; pre-reaction time, 0 or 30 minutes; reaction time, 15 minutes; reaction temperature, 25° C. (room temperature); CYP3A4 content (expressed in *Escherichia coli*), at pre-reaction 62.5 μmol/mL, at reaction 6.25 μmol/mL (at 10-fold dilution); concentration of a compound of the present, 0.625, 1.25, 2.5, 5, 10, 20 μmol/L (six points).

An enzyme in a K-Pi buffer (pH 7.4) and a compound solution of the present invention as a pre-reaction mixture were added to a 96-well plate at the composition of the pre-reaction, a part of it was transferred to another 96-well plate so that it was 1/10 diluted by a substrate in a K-Pi buffer, NADPH as a co-factor was added to initiate a reaction as an index (without preincubation) and, after a predetermined time of a reaction, acetonitrile/0.5 mol/L Tris(trishydroxyaminomethane)=4/1 (V/V) was added to stop the reaction. In addition, NADPH was added to a remaining preincubation solution to initiate a preincubation (with preincubation) and, after a predetermined time of a preincubation, a part was transferred to another plate so that it was 1/10 diluted with a substrate and a K-Pi buffer to initiate a reaction as an index. After a predetermined time of a reaction, acetonitrile/0.5 mol/L Tris(trishydroxyaminomethane)=4/1 (V/V) was added to stop the reaction. For the plate on which each index reaction had been performed, a fluorescent value of 7-HFC which is a metabolite was measured with a fluorescent plate reader. (Ex=420 nm, Em=535 nm).

Addition of only DMSO which is a solvent dissolving a compound of the present invention to a reaction system was adopted as a control (100%), remaining activity (%) was calculated at each concentration of a compound of the present invention added as the solution, and IC50 was calculated by reverse-presumption by a logistic model using a concentration and an inhibition rate. When a difference between IC50 values is 5 μM or more, this was defined as (+) and, when the difference is 3 μM or less, this was defined as (−).

(Result)
Compound No. I-7: (−)
Compound No. I-9: (−)
Compound No. I-37: (−)
Compound No. I-52: (−)
Compound No. I-57: (−)
Compound No. I-75: (−)
Compound No. I-96: (−)
Compound No. I-256: (−)
Compound No. I-287: (−)
Compound No. I-329: (−)

TEST EXAMPLE 7

Fluctuation Ames Test

20 μL of freezing-stored rat typhoid *bacillus* (*Salmonella typhimurium* TA98 strain, TA100 strain) was inoculated on 10 mL of a liquid nutrient medium (2.5% Oxoid nutrient broth No. 2), and this was cultured before shaking at 37° C. for 10 hours. 9 mL of a bacterial solution of the TA98 strain was centrifuged (2000×g, 10 minutes) to remove a culturing solution. The bacteria was suspended in 9 mL of a Micro F buffer ($K_2HPO_4$: 3.5 g/L, $KH_2PO_4$: 1 g/L, $(NH_4)_2SO_4$: 1 g/L, trisodium citrate dehydrate: 0.25 g/L, $MgSO_4 \cdot 7H_2O$: 0.1 g/L), the suspension was added to 110 mL of an Exposure medium (Micro F buffer containing Biotin: 8 μg/mL, histidine: 0.2 μg/mL, glucose: 8 mg/mL). The TA100 strain was added to 120 mL of the Exposure medium relative to 3.16 mL of the bacterial solution to prepare a test bacterial solution. Each 12 μL of a DMSO solution of the compound of the present invention (8 stage dilution from maximum dose 50 mg/mL at 2-fold ratio), DMSO as a negative control, 50 μg/mL of 4-nitroquinoline-1-oxide DMSO solution for the TA98 strain, 0.25 μg/mL of 2-(furyl)-3-(5-nitro-2-furyl) acrylamide DMSO solution for the TA100 strain under the non-metabolism activating condition, 40 μg/mL of 2-aminoanthracene DMSO solution for the TA98 strain, 20 μg/mL of 2-aminoanthracene DMSO solution for the TA100 strain under the metabolism activating condition as a positive control, and 588 μL of the test bacterial solution (a mixed solution of 498 μl of the test bacterial solution and 90 μL of S9 mix under the metabolism activating condition) were mixed, and this was shaking-cultured at 37° C. for 90 minutes. 460 μL of the bacterial solution exposed to the compound of the present invention was mixed with 2300 μL of an Indicator medium (Micro F buffer containing biotin: 8 μg/mL, histidine: 0.2 μg/mL, glucose: 8 mg/mL, Bromo Cresol Purple: 37.5 μg/mL), each 50 μL was dispensed into microplate 48 wells/dose, and this was subjected to stationary culturing at 37° C. for 3 days. Since a well containing a bacterium which has obtained the proliferation ability by mutation of an amino acid (histidine) synthesizing enzyme gene turns from purple to yellow due to a pH change, the bacterium proliferation well which has turned to yellow in 48 wells per dose is counted, and was assessed by comparing with a negative control group.

(−) means that mutagenicity is negative and (+) is positive.

(Result)
Compound No. I-37: (−)

TEST EXAMPLE 8 hERG Test

For the purpose of assessing risk of an electrocardiogram QT interval prolongation, effects on delayed rectifier K+ current ($I_{Kr}$), which plays an important role in the ventricular repolarization process of the compound of the present invention, was studied using HEK293 cells expressing human ether-a-go-go related gene (hERG) channel.

After a cell was retained at a membrane potential of −80 mV by whole cell patch clamp method using an automated patch clamp system (PatchXpress 7000A, Axon Instruments Inc.) and given leakage potential at −50 mV, $I_{Kr}$ induced by depolarization pulse stimulation at +40 mV for 2 seconds and, further, repolarization pulse stimulation at −50 mV for 2 seconds was recorded. After the generated current was stabilized, extracellular solution (NaCl: 135 mmol/L, KCl: 5.4 mmol/L, $NaH_2PO_4$: 0.3 mmol/L, $CaCl_2 \cdot 2H_2O$: 1.8 mmol/L, $MgCl_2 \cdot 6H_2O$: 1 mmol/L, glucose: 10 mmol/L, HEPES (4-(2-hydroxyethyl)-1-piperazineethanesulfonic acid): 10 mmol/L, pH=7.4) in which a compound of the present invention had been dissolved at an objective concentration was applied to the cell under the room temperature condition for 10 minutes. From the recording $I_{Kr}$, an absolute value of the tail peak current was measured based on the current value at the resting membrane potential using an analysis software (DataXpress ver. 2, Molecular Devices Corporation). Further, the % inhibition relative to the tail peak current before application of the compound of the present invention was calculated, and compared with the vehicle-applied group (0.1% dimethyl sulfoxide solution) to assess influence of the compound of the present invention on $I_{Kr}$.

(Result) % inhibition was shown at 1 μmol/L of the compound.

Compound No. I-37: 7.1%

TEST EXAMPLE 9

Solubility Test

The solubility of each compound of the present invention is determined under 1% DMSO addition conditions. A 10 mmol/L solution of the compound of the present invention is prepared with DMSO, and 6 μL of the compound solution is added to 594 μL of an artificial intestinal juice (water and 118 mL of 0.2 mol/L NaOH reagent are added to 250 mL of 0.2 mol/L potassium dihydrogen phosphate reagent to reach 1000 mL) with a pH of 6.8. The mixture is left standing for 16 hours at 25° C., and the mixture is vacuum-filtered. The filtrate is two-fold diluted with methanol/water=1/1 (V/V), and the compound concentration in the filtrate is measured with HPLC or LC/MS/MS by the absolute calibration method.

(Result)
Compound No. I-7: >50 μmol/L
Compound No. I-9: >50 μmol/L
Compound No. I-37: >50 μmol/L
Compound No. I-49: >50 μmol/L
Compound No. I-52: >50 μmol/L
Compound No. I-57: >50 μmol/L
Compound No. I-74: >50 μmol/L
Compound No. I-85: >50 μmol/L
Compound No. I-96: >50 μmol/L

TEST EXAMPLE 10

Powder Solubility Test

Appropriate amounts of the compound of the present invention is put into vials and 200 μL of JP-1st Fluid (water is added to 2.0 g of sodium chloride in 7.0 mL of hydrochloride acid to reach 1000 mL), JP-2nd Fluid (water is added to 500 mL of phosphate buffer solution with a pH of 6.8) and 20 mmol/L sodium taurocholate (TCA) /JP-2nd Fluid (JP-2nd Fluid is added to 1.08 g of TCA in JP-2nd Fluid to reach 100 mL) is added to each vial. When the compound is completely dissolved, appropriate amount of compound is added. After shaken for 1 hour at 37° C., the mixture is filtered and 100 μL of methanol is added to 100 μL of each filtrate (double dilution). Dilution magnification is changed if necessary. After it is confirmed whether there are air bubbles and precipitates in the vials, the vials are shaken with tight stopper. The compound concentration is determined with HPLC by the absolute calibration method.

FORMULATION EXAMPLE

The following formulating examples 1-8 are just for illustrative purposes and not intended to limit the range of the present invention. The term of "active ingredient" means the compounds of the present invention or pharmaceutically acceptable salt thereof.

FORMULATION EXAMPLE 1

A hard-gelatin capsule is prepared with the following ingredients;

|  | Amount (mg/capsule) |
| --- | --- |
| active ingredient | 250 |
| starch (dried) | 200 |
| magnesium stearate | 10 |
| Total | 460 mg |

FORMULATION EXAMPLE 2

A tablet is prepared with the following ingredients;

|  | Amount (mg/tablet) |
| --- | --- |
| active ingredient | 250 |
|  | 253 |
| cellulose(micro crystalline) | 400 |
| silicon dioxide (fume) | 10 |
| stearic acid | 5 |
| Total | 665 mg |

The ingredients above are mixed and compressed to give a tablet weighing 665 mg/tablet.

FORMULATION EXAMPLE 3

An aerosol solution is prepared with the following ingredients;

|  | weight |
| --- | --- |
| active ingredient | 0.25 |
| ethanol | 25.75 |
| propellant 22(chlorodifluoroethane) | 74.00 |
| Total | 100.00 |

The active ingredient and ethanol are mixed and the mixture is added to a part of propellant 22, and the resulting solution is transferred to a filling apparatus after being cooled to −30° C. Next, the necessary amount is provided to a stainless-steel vessel and the content is diluted with the remaining propellant. A valve unit is fitted to the vessel.

FORMULATION EXAMPLE 4

A tablet containing 60 mg of an active ingredient is prepared as follows;

| active ingredient | 60 mg |
| --- | --- |
| starch | 45 mg |
| microcrystalline cellulose | 35 mg |
| polyvinylpyrrolidone (10% aq. solution) | 4 mg |
| sodium carboxymethylstarch | 4.5 mg |
| magnesium stearate | 0.5 mg |
| talc | 1 mg |
| Total | 150 mg |

The active ingredient, starch and cellulose are put through a sieve of No. 45 mesh US and mixed sufficiently. The

445 resulting powder is mixed with a solution containing polyvinylpyrrolidone and the mixture is put through a sieve of No. 14 mesh US. The granulated powder is dried at 50° C. and put through a sieve of No. 18 mesh US. Sodium carboxymethylstarch, magnesium stearate and talc are put through a sieve of No. 60 mesh US in advance and added to the granulated powder, mixed and compressed by a tableting machine to give a tablet weighing 150 mg/tablet.

FORMULATION EXAMPLE 5

A capsule containing 80 mg of an active ingredient is prepared as follows;

| active ingredient | 80 mg |
|---|---|
| starch | 59 mg |
| microcrystalline cellulose | 59 mg |
| magnesium stearate | 2 mg |
| Total | 200 mg |

The active ingredient, starch, cellulose and magnesium stearate are mixed, put through a sieve of No. 45 mesh US and filled in hard-gelatin capsules to give a capsule formulation containing 200 mg/capsule.

FORMULATION EXAMPLE 6

A suppository containing 225 mg of an active ingredient is prepared as follows;

| active ingredient | 225 mg |
|---|---|
| saturated fatty acid gliceride | 2000 mg |
| Total | 2225 mg |

The active ingredient is put through a sieve of No. 60 mesh US and suspended in the saturated fatty acid gliceride melted by the least amount of heating. Then, the mixture was cooled in a mold of 2 g in appearance.

FORMULATION EXAMPLE 7

A suspension containing 50 mg of an active ingredient is prepared as follows;

| active ingredient | 50 mg |
|---|---|
| sodium carboxymethylcellulose | 50 mg |
| syrup | 1.25 ml |
| solution of benzoic acid | 0.10 ml |
| flavor | q.v. |
| pigment | q.v. |
| Total (adding purified water) | 5 ml |

The active ingredient is put through a sieve of No. 45 mesh US and mixed with sodium carboxymethylcellulose and syrup to give a smooth paste. The solution of benzoic acid and flavor are diluted with a part of water and added to the paste and stirred. A necessary amount of water is added to give the objective suspension.

446

FORMULATION EXAMPLE 8

A formulation for i.v. injection is prepared as follows;

| active ingredient | 100 mg |
|---|---|
| saturated fatty acid gliceride | 1000 ml |

The solution containing the active ingredient above is usually injected intravenously to a patient at a rate of 1 ml/min.

INDUSTRIAL APPLICABILITY

The present inventors found that novel heterocyclic derivatives have PGD2 receptor antagonistic activity (DP receptor antagonistic activity, CRTH2 receptor antagonistic activity, and/or, antagonistic activity against both the DP receptor and CRTH2 receptor). These compounds are thought to be effective for treating allergic diseases.

The invention claimed is:

1. A compound of general formula (I) or a pharmaceutically acceptable salt thereof:

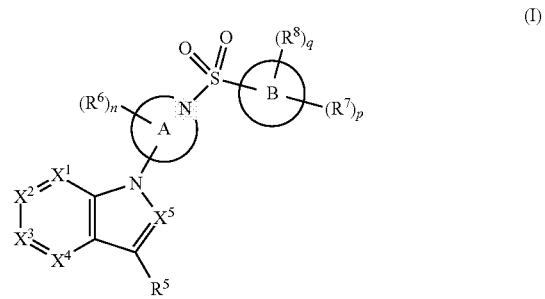

(I)

wherein ring A is a formula of:

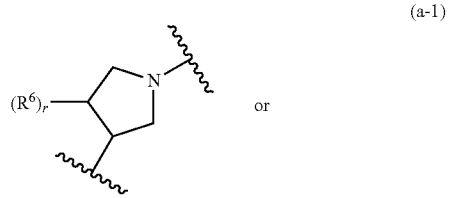

(a-1)

or

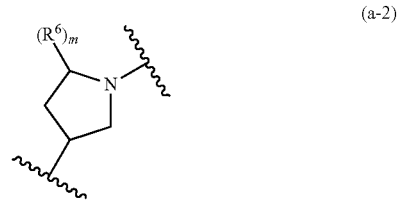

(a-2)

wherein m and r are independently 1 or 2; and
wherein each $R^6$ is independently a halogen, cyano, substituted alkyl or unsubstituted alkyl;

wherein ring B is:

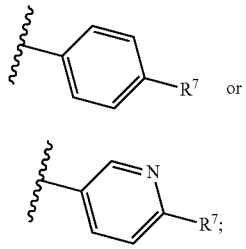

wherein R⁷ is halogen, substituted or unsubstituted alkyl, substituted or unsubstituted alkyloxy, substituted or unsubstituted non-aromatic carbocyclyl, substituted or unsubstituted aromatic carbocyclyl oxy or substituted or unsubstituted non-aromatic carbocyclyl oxy;
wherein —X¹= is —C(R¹)=;
wherein —X²= is —C(R²)=;
wherein —X³= is —C(R³)=;
wherein —X⁴= is —C(R⁴)=;
wherein —X⁵= is —N=; and
wherein R⁵ of the following formula (i) is formula: -L-R⁹; such that:

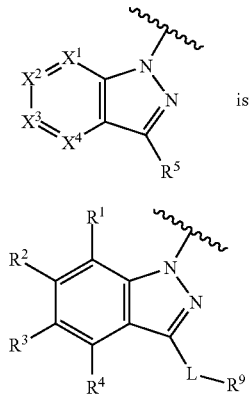

wherein R¹ of formula (i-1) is a hydrogen atom or halogen;
wherein R² of formula (i-1) is a hydrogen atom, halogen, substituted alkyl or unsubstituted alkyl;
wherein R³ of formula (i-1) is a hydrogen atom, halogen, substituted alkyl or unsubstituted alkyl;
wherein R⁴ of formula (i-1) is a hydrogen atom;
wherein -L- of formula (i-1) is substituted or unsubstituted methylene; and
wherein R⁹ of formula (i-1) is carboxy;
wherein n is 1 or 2;
wherein q is 0; and
wherein p is 0 or 1.

2. A pharmaceutical composition comprising the compound of claim 1 or the pharmaceutically acceptable salt thereof.

3. The compound or the pharmaceutically acceptable salt thereof according to claim 1, which is represented by one of the following structural formulas:

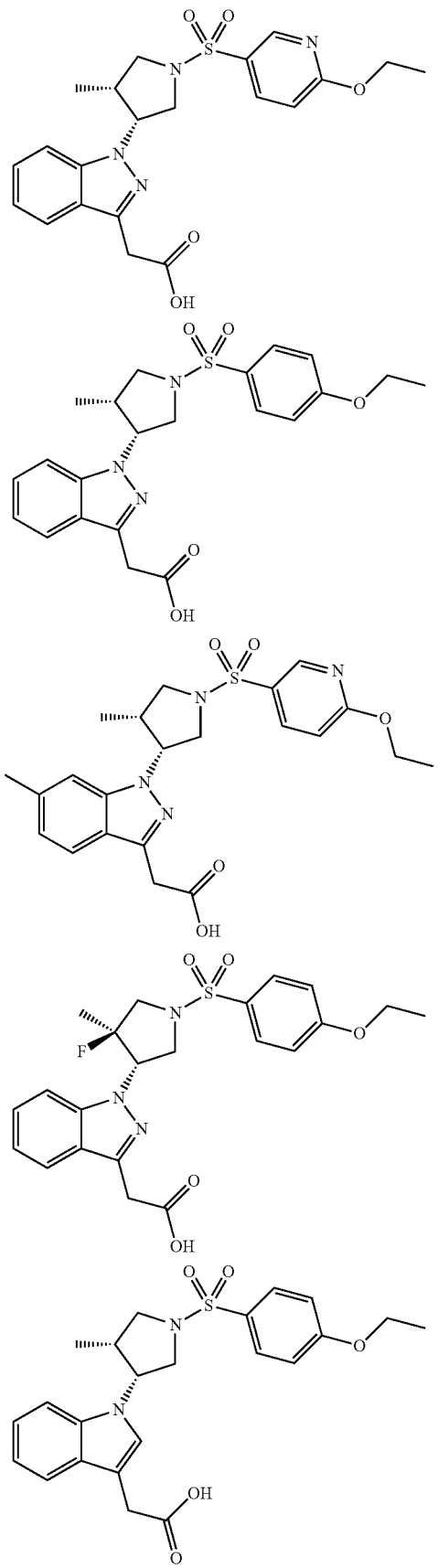

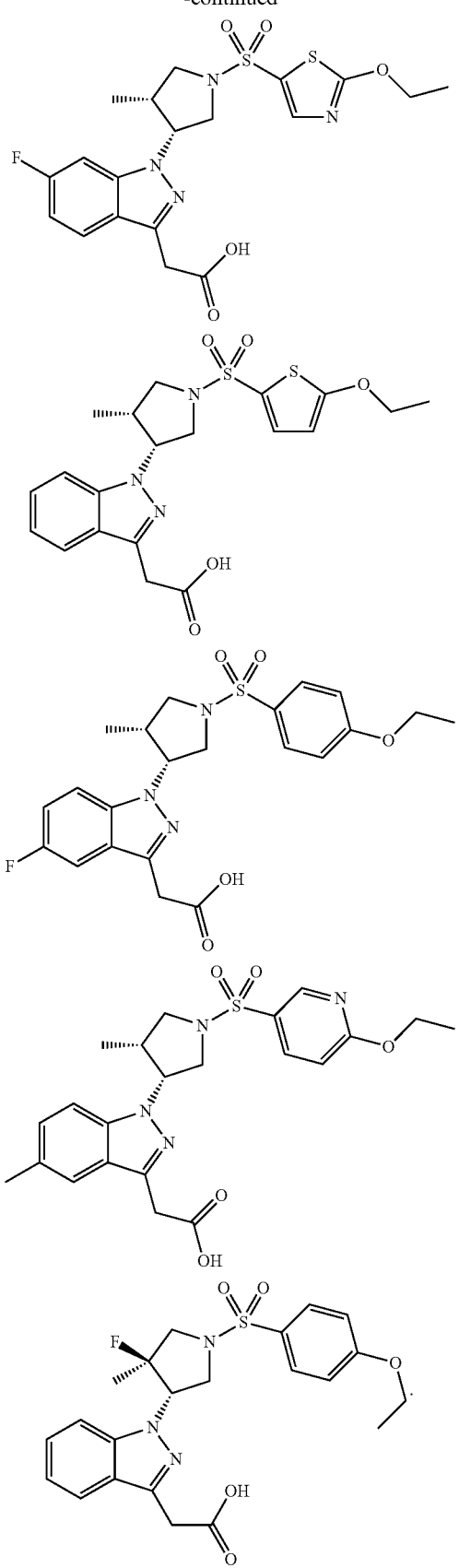

4. A pharmaceutical composition comprising the compound or the pharmaceutically acceptable salt thereof of claim 3.

5. The compound or the pharmaceutically acceptable salt thereof according to claim 1, which is represented by the following structural formula:

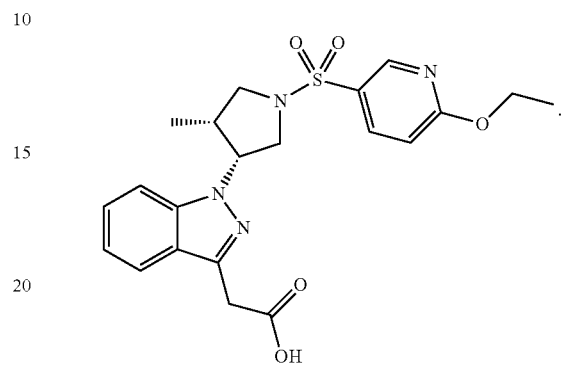

6. The compound or the pharmaceutically acceptable salt thereof according to claim 1, which is represented by the following structural formula:

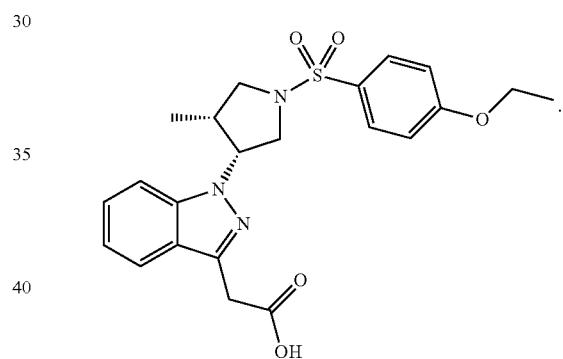

7. The compound or the pharmaceutically acceptable salt thereof according to claim 1, which is represented by the following structural formula:

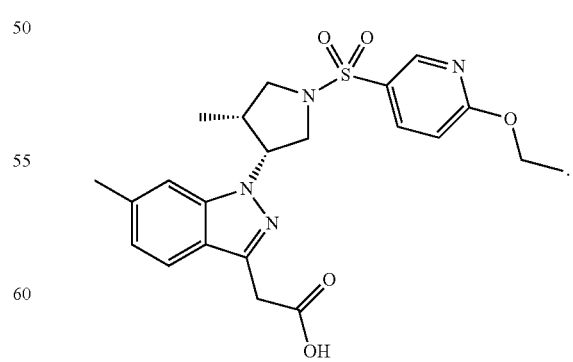

8. The compound or the pharmaceutically acceptable salt thereof according to claim 1, which is represented by the following structural formula:

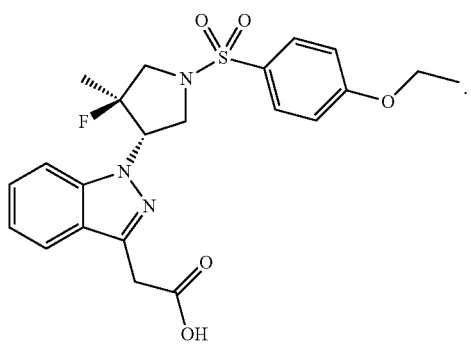 [SMILES: CCOc1ccc(S(=O)(=O)N2C[C@H](n3nc(CC(=O)O)c4ccccc43)[C@@](C)(F)C2)cc1]

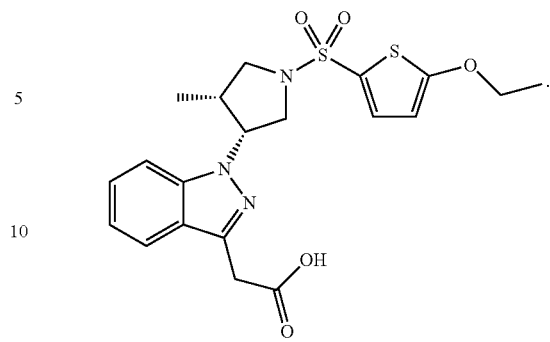

9. The compound or the pharmaceutically acceptable salt thereof according to claim 1, which is represented by the following structural formula:

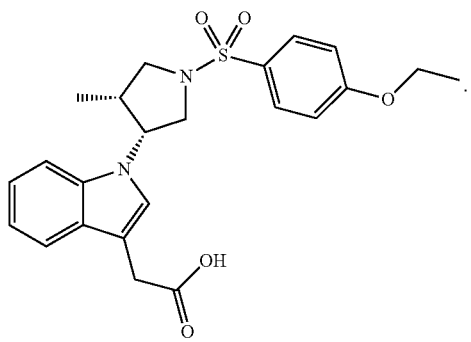 [SMILES: CCOc1ccc(S(=O)(=O)N2C[C@@H](C)[C@@H](n3cc(CC(=O)O)c4ccccc43)C2)cc1]

12. The compound or the pharmaceutically acceptable salt thereof according to claim 1, which is represented by the following structural formula:

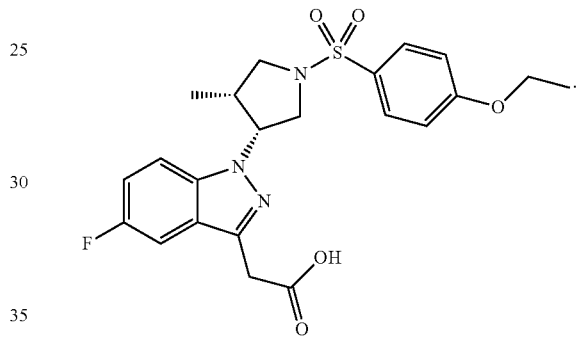

10. The compound or the pharmaceutically acceptable salt thereof according to claim 1, which is represented by the following structural formula:

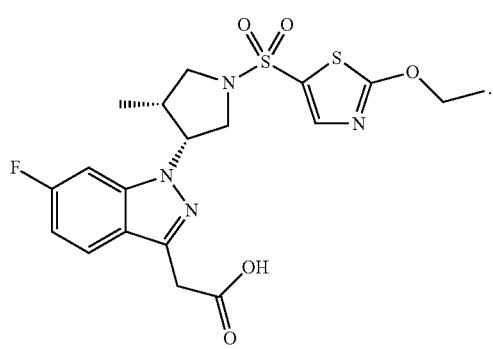 [SMILES: CCOc1ncc(S(=O)(=O)N2C[C@@H](C)[C@@H](n3nc(CC(=O)O)c4ccc(F)cc43)C2)s1]

13. The compound or the pharmaceutically acceptable salt thereof according to claim 1, which is represented by the following structural formula:

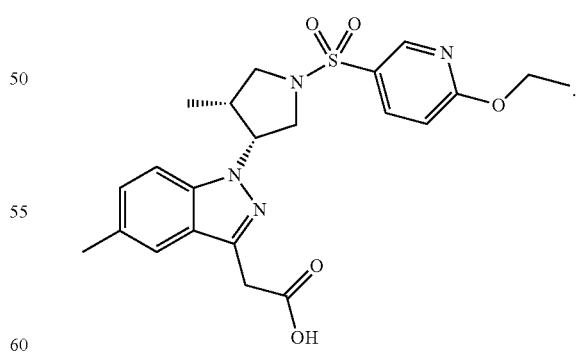

11. The compound or the pharmaceutically acceptable salt thereof according to claim 1, which is represented by the following structural formula:

14. The compound or the pharmaceutically acceptable salt thereof according to claim 1, which is represented by the following structural formula:

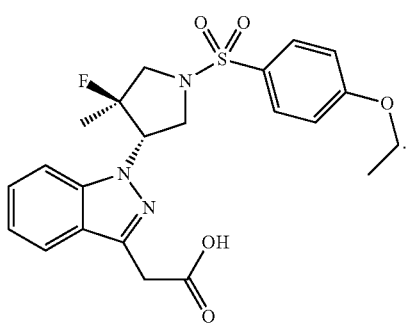 [SMILES: CCOc1ccc(S(=O)(=O)N2C[C@H](n3nc(CC(=O)O)c4ccccc43)[C@@](C)(F)C2)cc1]

15. A pharmaceutical composition comprising the compound or the pharmaceutically acceptable salt thereof of claim 5.

16. A pharmaceutical composition comprising the compound or the pharmaceutically acceptable salt thereof of claim 6.

17. A pharmaceutical composition comprising the compound or the pharmaceutically acceptable salt thereof of claim 7.

18. A pharmaceutical composition comprising the compound or the pharmaceutically acceptable salt thereof of claim 8.

19. A pharmaceutical composition comprising the compound or the pharmaceutically acceptable salt thereof of claim 9.

20. A pharmaceutical composition comprising the compound or the pharmaceutically acceptable salt thereof of claim 10.

21. A pharmaceutical composition comprising the compound or the pharmaceutically acceptable salt thereof of claim 11.

22. A pharmaceutical composition comprising the compound or the pharmaceutically acceptable salt thereof of claim 12.

23. A pharmaceutical composition comprising the compound or the pharmaceutically acceptable salt thereof of claim 13.

24. A pharmaceutical composition comprising the compound or the pharmaceutically acceptable salt thereof of claim 14.

* * * * *